United States Patent

Martin et al.

(10) Patent No.: US 8,163,771 B2
(45) Date of Patent: Apr. 24, 2012

(54) 11 β-HSD1 MODULATORS

(75) Inventors: Richard Martin, San Diego, CA (US);
Brenton T. Flatt, Poway, CA (US);
Jackline Eve Dalgard, Del Mar, CA (US); Venkataiah Bollu, San Diego, CA (US); Ping Huang, Mountain View, CA (US); Raju Mohan, Encinitas, CA (US); Edwin Schweiger, San Diego, CA (US); Tie-Lin Wang, San Diego, CA (US)

(73) Assignee: Exelixis, Inc., South San Francisco, CA (US)

( * ) Notice: Subject to any disclaimer, the term of this patent is extended or adjusted under 35 U.S.C. 154(b) by 456 days.

(21) Appl. No.: 12/381,682

(22) Filed: Mar. 13, 2009

(65) Prior Publication Data

US 2009/0247515 A1 Oct. 1, 2009
US 2010/0105675 A2 Apr. 29, 2010

Related U.S. Application Data

(60) Provisional application No. 61/069,648, filed on Mar. 14, 2008, provisional application No. 61/203,720, filed on Dec. 23, 2008.

(51) Int. Cl.
*A10N 43/42* (2006.01)
*A61K 31/44* (2006.01)
*C07D 451/00* (2006.01)

(52) U.S. Cl. ........................................ 514/304; 546/127
(58) Field of Classification Search .................. 514/304; 546/127

See application file for complete search history.

(56) References Cited

FOREIGN PATENT DOCUMENTS

WO  WO 2009007115 A1  *  1/2009

* cited by examiner

*Primary Examiner* — Sreeni Padmanabhan
*Assistant Examiner* — Kendra D Carter
(74) *Attorney, Agent, or Firm* — McDonnell Boehnen Hulbert & Berghoff LLP

(57) ABSTRACT

A compound according to Formula I:

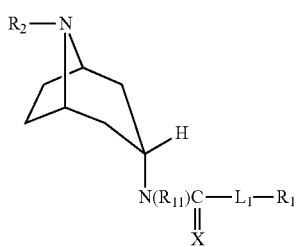

or a pharmaceutically acceptable salt thereof, wherein $R_1$, $R_2$, $R_{11}$, $L_1$ and X are as defined in the specification, pharmaceutical compositions thereof, and methods of use thereof.

40 Claims, No Drawings

11 β-HSD1 MODULATORS

CROSS-REFERENCE TO RELATED APPLICATIONS

This application claims priority to U.S. provisional application 61/069,648, filed Mar. 14, 2008, and U.S. provisional application 61/203,720 filed on Dec. 23, 2008, both of which are incorporated by reference in its entirety.

FIELD OF THE INVENTION

This disclosure relates to compounds, compositions thereof, and methods of use thereof. More particularly, this disclosure relates to hydroxysteroid dehydrogenase modulators, such as 11 β-HSD1 modulators, compositions thereof, and methods of treating diseases associated with the modulation of hydroxysteroid dehydrogenases, such as diabetes and obesity.

BACKGROUND OF THE INVENTION

Hydroxysteroid dehydrogenases (HSDs) regulate the occupancy and activation of steroid hormone receptors by converting steroid hormones into their inactive metabolites.

There exist numerous classes of HSDs. The 11 β-hydroxysteroid dehydrogenases catalyze the interconversion of active glucocorticoids (such as cortisol and corticosterone) into their inert forms (such as cortisone and 11-dehydrocorticosterone). The isoform 11-beta-hydroxysteroid dehydrogenase type 1 (11 β-HSD1) is expressed in liver, adipose tissue, brain, lung and other glucocorticoid tissue. 11 β-HSD1 is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

Glucocorticoids play a role in the development of diabetes. Glucocorticoids enable the effect of glucagon on the liver. Long et al., J. Exp. Med. 1936, 63: 465-490; and Houssay, Endocrinology 1942, 30: 884-892. In addition, it has been well substantiated that 11 β-HSD1 plays an important role in the regulation of local glucocorticoid effect and of glucose production in the liver. Jamieson et al., J. Endocrinol. 2000, 165:685-692.

Using 11 β-HSD1 inhibitors in the treatment of diabetes has been supported by various experiments conducted in mice and rats. These studies showed that the mRNA levels and activities of two key enzymes in hepatic glucose production, phosphoenolpyruvate carboxykinase (PEPCK) and glucose-6-phosphatase (G6Pase), were reduced upon administration of HSD inhibitors. In addition, blood glucose levels and hepatic glucose production were shown to be reduced in 11β-HSD1 knockout mice. Kotelevtsev et al., Proc. Natl. Acad. Sci. USA 1997, 94: 14924-14929.

HSDs also play a role in obesity. Obesity is an important factor in Syndrome X as well as type II (non-insulin dependent) diabetes. Omental fat appears to be of central importance in the development of both of these diseases, as abdominal obesity has been linked with glucose intolerance, hyperinsulinemia, hypertriglyceridemia, and other factors of Syndrome X (e.g., raised blood pressure, decreased levels of HDL and increased levels of VLDL). Montague et al., Diabetes 2000, 49:883-888, 2000. It has also been reported that inhibition of the 11β-HSD1s in pre-adipocytes (stromal cells) resulted in a decreased rate of differentiation into adipocytes. This is predicted to result in diminished expansion (possibly reduction) of the omental fat depot, which may lead to reduced central obesity. Bujalska et al., Lancet 1997, 349: 1210-1213.

Inhibition of 11 β-HSD1s in mature adipocytes is expected to attenuate secretion of the plasminogen activator inhibitor 1 (PAI-1), which is an independent cardiovascular risk factor, as reported in Halleux et al., J. Clin. Endocrinol. Metab. 1999, 84:4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases. Walker et al., Hypertension 1998, 31:891-895; and Fraser et al., Hypertension 1999, 33:1364-1368.

HSDs have also been implicated in the process of appetite control and therefore are believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1s in the brain may increase satiety, thus resulting in a decreased food intake. Woods et al., Science 1998, 280:1378-1383.

Another possible therapeutic effect associated with modulation of HSDs is that which is related to various pancreatic ailments. It is reported that inhibition of 11 β-HSD1s in murine pancreatic β-cells results in increased insulin secretion. Davani et al., J. Biol. Chem. 2000, 275:34841-34844. This follows from the discovery that glucocorticoids were previously found to be responsible for reduced pancreatic insulin release in vivo, Billaudel et al., Horm. Metab. Res. 1979, 11:555-560. Thus, it is suggested that inhibition of 11 β-HSD1 would yield other beneficial effects in the treatment of diabetes other than the predicted effects on the liver and fat reduction.

11 β-HSD1 also regulates glucocorticoid activity in the brain and thus contributes to neurotoxicity. Rajan et al., Neuroscience 1996, 16:65-70; and Seckl et al., Neuroendocrinol. 2000, 18:49-99. Stress and/or glucocorticoids are known to influence cognitive function (de Quervain et al., Nature 1998, 394:787-790). These reports, in addition to the known effects of glucocorticoids in the brain, suggest that inhibiting HSDs in the brain may have a positive therapeutic effect against anxiety and related conditions. Tronche et al., Nature Genetics 1999, 23:99-103. 11β-HSD1 reactivates 11-DHC to corticosterone in hippocampal cells and can potentiate kinase neurotoxicity, resulting in age-related learning impairments. Therefore, selective inhibitors of 11 β-HSD1 are believed to protect against hippocampal function decline with age. Yau et al., Proc Natl. Acad. Sci. USA 2001, 98:4716-4721. Thus, it has been hypothesized that inhibition of 11β-HSD 1 in the human brain would protect against deleterious glucocorticoid-mediated effects on neuronal function, such as cognitive impairment, depression, and increased appetite.

HSDs are believed to play a role in immunomodulation based on the general perception that glucocorticoids suppress the immune system. There is known to be a dynamic interaction between the immune system and the HPA (hypothalamo-pituitary-adrenal) axis (Rook, Baillier's Clin. Endocrinol. Metab. 2000, 13: 576-581). Glucocorticoids help balance between cell-mediated responses and humoral responses. Increased glucocorticoid activity, which may be induced by stress, is associated with a humoral response and as such, the inhibition of 11 β-HSD1 may result in shifting the response towards a cell-based reaction. In certain disease states, such as tuberculosis, leprosy, and psoriasis, the immune reaction is typically biased towards a humoral response when a cell-based response might be more appropriate.

Recent reports suggest that the levels of glucocorticoid target receptors and of HSDs are connected with the risks of developing glaucoma. Stokes et al., Invest. Opthalmol. 2000, 41:1629-1638. Further, a connection between inhibition of 11β-HSD1 and a lowering of the intraocular pressure was reported. Walker et al., poster P3-698 at the Endocrine society meeting Jun. 12-15, 1999, San Diego. It was shown that administration of the nonspecific 11β-HSD1 inhibitor, carbenoxolone, resulted in the reduction of the intraocular pressure by 20% in normal patients. In the eye, 11 β-HSD1 is expressed exclusively in the basal cells of the corneal epithelium, the non-pigmented epithelialium of the cornea (the site of aqueous production), ciliary muscle, and the sphincter and dilator muscles of the iris. No HSDs have been found at the trabecular meshwork, which is the site of drainage. Therefore, 11 β-HSD1 is suggested to have a role in aqueous production.

Glucocorticoids also play an essential role in skeletal development and function but are detrimental to such development and function when present in excess. Glucocorticoid-induced bone loss is partially derived from suppression of osteoblast proliferation and collagen synthesis, as reported in Kim et al., J. Endocrinol. 1999, 162:371 379. It has been reported that the detrimental effects of glucocorticoids on bone nodule formation can be lessened by administration of carbenoxolone, which is a non-specific 11 β-HSD1 inhibitor. Bellows et al., Bone 1998, 23:119-125. Additional reports suggest that 11-HSD1 may be responsible for providing increased levels of active glucocorticoid in osteoclasts, and thus in augmenting bone resorption. Cooper et al., Bone 2000, 27:375-381. This data suggests that inhibition of 11 β-HSD1 may have beneficial effects against osteoporosis via one or more mechanisms which may act in parallel.

There remains a need for inhibitors of 11 β-HSD1 for the treatment of 11 β-HSD 1-mediated conditions.

SUMMARY OF THE INVENTION

One aspect of the invention relates to a compound according to Formula I:

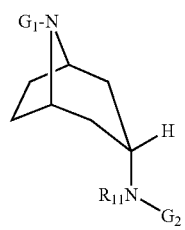

or a pharmaceutically acceptable salt thereof, wherein $R_{11}$, $G_1$ and $G_2$ are as defined in the specification.

All compounds of Formula I disclosed herein are endo-isomers in respect to the 8-azabicyclo[3.2.1]oct-8-yl moiety of Formula I.

Another aspect of this disclosure relates to a method of inhibiting 11β-HSD1 in a cell, comprising contacting the cell, in which inhibition of 11 β-HSD1 is desired, with a compound according Formula I, or a pharmaceutically acceptable salt thereof.

Another aspect of this disclosure relates to a method of inhibiting 11β-HSD1 in a cell, comprising contacting a cell in which inhibition of 11 β-HSD1 is desired with a pharmaceutical composition, comprising the compound according to Formula I, or a pharmaceutically acceptable salt thereof, and a pharmaceutically acceptable carrier, excipient, or diluent.

Another aspect of this disclosure relates to a method of treating one of the diseases or conditions disclosed herein that involves 11 β-HSD 1, wherein the method comprises administering to an animal, in need of the treatment, the compound according to Formula I, or a pharmaceutically acceptable salt thereof, optionally in combination with the one or more additional therapeutic agents or therapies disclosed herein.

There are many different aspects of the compounds, pharmaceutical compositions thereof, and methods of use thereof, as described hereinbelow, and each aspect is non-limiting in regard to the scope of the invention. The transitional term "comprising" as used herein, which is synonymous with "including," "containing," or "characterized by," is inclusive or open-ended and does not exclude additional, unrecited elements or method steps.

DETAILED DESCRIPTION OF THE INVENTION

One aspect of the invention relates to a compound according to Formula A:

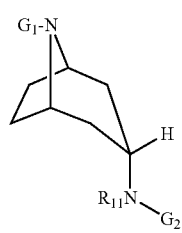

or a pharmaceutically acceptable salt thereof, wherein
$G_1$ is $R_2$, and $G_2$ is —N($R_{11}$)C(=X)-$L_1$-$R_1$, or
$G_1$ is —N($R_{11}$)C(=X)-$L_1$-$R_1$, and $G_2$ is $R_2$;
$R_1$ is selected from:

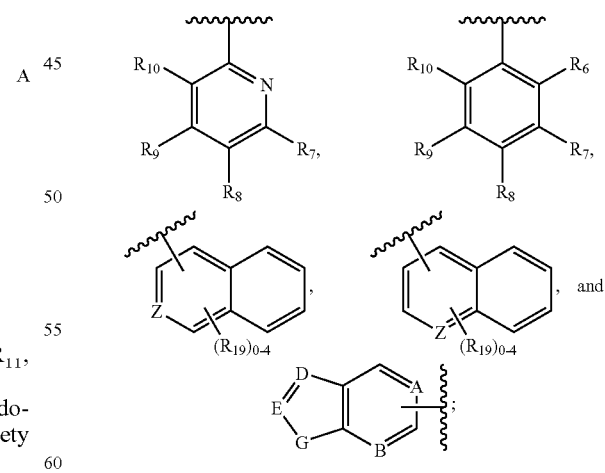

$R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl and 5-6 membered heteroaryl can each be unsubstituted or substituted with 1, 2, 3 or 4 groups selected from —C(O)—N(H)-$L_2$, —C(O)—O-$L_3$, —C(O)-$L_7$, —$CF_3$, —CN, $NH_2$, —N(H)S $(O)_2$-alkyl, —$S(O)_2$-alkyl, —$S(O)_2$—$N(L_5)L_6$, —N(H)C(O)-$L_4$, heteroaryl optionally substituted with halo or —$CF_3$, —N(H)C(O)N(H)-alkyl-$CF_3$, —OH, alkoxy, and halo; wherein the alkyl portion of —N(H)S$(O)_2$-alkyl, —S$(O)_2$-alkyl, and —N(H)C(O)N(H)-alkyl-$CF_3$ is optionally substituted with 1, 2, 3, 4 or 5 halo, and wherein any alkyl portion of any $R_2$ group described above is optionally substituted with hydroxyalkyl, aminoalkyl, alkoxyalkyl or alkoxyalkoxy;

$R_6$, $R_7$, $R_8$, $R_9$, and $R_{10}$ are each independently selected from H, halo, alkyl optionally substituted with 1-5 halo, alkynyl, —OH, —$NH_2$, alkenyl optionally substituted with 1-5 halo, phenyl, aminocarbonylalkoxy, aminocarbonylalkyl, carboxyalkoxy, carboxyalkyl, aminocarbonyl, —S$(O)_2$-alkyl, —S$(O)_2$—$NH_2$, —S$(O)_2$—N(H)-alkyl, —S$(O)_2$—N(alkyl)$_2$, cycloalkyl, cycloalkyalkoxy, heterocycloalkyl, heterocycloalkylalkoxy, alkynyl optionally substituted with 1-5 halo, —C(O)OH, —C(O)O—$NH_2$, —C(O)O-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkyalkoxy, heterocycloalkyl, heterocycloalkylalkoxy, heteroaryl, and heteroarylalkoxy is optionally substituted with 1, 2 or 3 groups selected from halo, —$CF_3$, —$(C_1$-$C_3)$alkyl, OH and alkoxy, and wherein any alkyl portion of any $R_6$, $R_7$, $R_8$, $R_9$ and $R_{10}$ group described above is optionally substituted with hydroxyl, hydroxyalkyl, aminoalkyl, alkoxyalkyl or alkoxyalkoxy;

$R_{11}$ is hydrogen, alkyl, alkenyl or alkynyl;

$R_{12}$ is selected from hydrogen, alkenyl, alkynyl, halo or alkyl;

$R_{13}$ is halo, alkyl, alkenyl or alkynyl; or $R_{12}$ and $R_{13}$, together with the carbon atom to which they are both attached, join to form a 3-6 membered cycloalkyl;

$R_{19}$, when $R_{19}$ is present, is selected from H, halo, alkyl optionally substituted with 1-5 halo, alkenyl, alkynyl —OH, —$NH_2$, alkenyl optionally substituted with 1-5 halo, phenyl, —S$(O)_2$-alkyl, —S$(O)_2$—$NH_2$, —S$(O)_2$—N(H)-alkyl, —S$(O)_2$—N(alkyl)$_2$, cycloalkyl, cycloalkyalkoxy, heterocycloalkyl, heterocycloalkylalkoxy, alkynyl optionally substituted with 1-5 halo, —C(O)OH, —C(O)O—$NH_2$, —C(O)O-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkyalkoxy, heterocycloalkyl, heterocycloalkylalkoxy, heteroaryl, and heteroarylalkoxy is optionally substituted with 1, 2 or 3 groups selected from halo, —$CF_3$, OH and alkoxy, and wherein any alkyl portion of $R_{19}$ described above is optionally substituted with hydroxyalkyl, aminoalkyl, alkoxyalkyl or alkoxyalkoxy;

A is N or CH;

B is N or CH;

D and E are each selected from CH and N, and G is selected from NH and $CH_2$, wherein one of D, E and G is optionally substituted with —N(H)—$R^{15}$, provided that no more than two of D, E and G are nitrogen;

$L_1$ is selected from —C($R_{12}$)($R_{13}$)—, —C($R_{12}$)($R_{13}$)—O—, —C($R_{12}$)($R_{13}$)—$CH_2$—O—, —C($R_{12}$)($R_{13}$)—S— and —C($R_{12}$)($R_{13}$)—S$(O)_2$—;

$L_2$ is selected from alkyl optionally substituted with 1-5 halo, alkyl optionally substituted with 1-2 hydroxyl, alkyl optionally substituted with 1-2 alkoxy, hydroxyalkyl optionally substituted with a spirocycloalkyl, heteroaryl, alkyl optionally substituted with 1-5 halo and with 1-2 hydroxyl, heterocycloalkylalkyl optionally substituted with —$CF_3$ at the alkyl portion of the heterocycloalkylalkyl, —$CH_2$—C(O)—$CF_3$, halo, alkenyl, alkynyl, cycloalkyl optionally substituted with 1-5 halo, heterocycloalkyl, heterocycloalkylalkyl optionally substituted with 1-2 oxo at the heterocycloalkyl portion of the heterocycloalkylalkyl, heteroarylalkyl, hydroxyalkyl, dialkylaminoalkyl, hydrogen, alkoxyalkyl, and —$CF_3$, wherein any alkyl portion of $L_2$ can be substituted with hydroxyl;

$L_3$ is selected from hydrogen, alkyl optionally substituted with hydroxyalkyl, aminoalkyl, alkoxyalkyl or alkoxyalkoxy, alkenyl and alkynyl;

$L_4$ is selected from —$CF_3$, alkyl optionally substituted with 1-5 halo, alkenyl and alkynyl, wherein any alkyl portion of $L_4$ is optionally substituted with hydroxyalkyl, aminoalkyl, alkoxyalkyl or alkoxyalkoxy;

$L_5$ is selected from hydrogen, alkyl, alkenyl and alkynyl, wherein any alkyl portion of $L_5$ is optionally substituted with hydroxyalkyl, aminoalkyl, alkoxyalkyl or alkoxyalkoxy;

$L_6$ is selected from hydrogen, —$CF_3$, alkyl optionally substituted with 1-5 halo, alkenyl and alkynyl, wherein any alkyl portion of $L_6$ is optionally substituted with hydroxyalkyl, aminoalkyl, alkoxyalkyl or alkoxyalkoxy;

$L_7$ is selected from hydrogen, heterocycloalkyl optionally substituted with 1-2 groups selected from hydroxyl and hydroxyalkyl, alkyl, alkenyl and alkynyl, wherein any alkyl portion of $L_7$ is optionally substituted with hydroxyalkyl, aminoalkyl, alkoxyalkyl or alkoxyalkoxy;

X is O or S; and

Z is N or CH.

In another embodiment of Formula I, $R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-$L_2$, —C(O)—O-$L_3$, —C(O)-$L_7$, —$CF_3$, —CN, —$NH_2$, —N(H)S$(O)_2$-alkyl, —S$(O)_2$-alkyl, —S$(O)_2$—$N(L_5)L_6$, —N(H)C(O)-$L_4$, heteroaryl optionally substituted with halo or —$CF_3$, —N(H)C(O)N(H)-alkyl-$CF_3$, —OH, alkoxy, and halo; wherein the alkyl portion of —N(H)S$(O)_2$-alkyl, —S$(O)_2$-alkyl, and —N(H)C(O)N(H)-alkyl-$CF_3$ is optionally substituted with 1 2, 3, 4 or 5 halo, and wherein any alkyl portion of any $R_2$ group desribed above is optionally substituted with hydroxyalkyl, aminoalkyl, alkoxyalkyl or alkoxyalkoxy;

$R_6$, $R_7$, $R_8$, $R_9$, and $R_{10}$ are each independently selected from H, halo, alkyl optionally substituted with 1-5 halo, —OH, —$NH_2$, alkenyl optionally substituted with 1-5 halo, phenyl, —S$(O)_2$-alkyl, —S$(O)_2$—$NH_2$, —S$(O)_2$—N(H)-alkyl, —S$(O)_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—$NH_2$, —C(O)O-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —$CF_3$, OH and alkoxy, and wherein any alkyl portion of any $R_6$, $R_7$, $R_8$, $R_9$ and $R_{10}$ group described above is optionally substituted with hydroxyl, hydroxyalkyl, aminoalkyl, alkoxyalkyl or alkoxyalkoxy;

$R_{11}$ is hydrogen or alkyl;

$R_{12}$ is selected from hydrogen, halo or alkyl;

$R_{13}$ is halo or alkyl;

or $R_{12}$ and $R_{13}$, together with the carbon atom to which they are both attached, join to form a 3-6 membered cycloalkyl;

$R_{19}$, when $R_{19}$ is present, is selected from H, halo, alkyl optionally substituted with 1-5 halo, —OH, —$NH_2$, alkenyl optionally substituted with 1-5 halo, phenyl, —S$(O)_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of R$_{19}$ described above is optionally substituted with hydroxyalkyl, aminoalkyl, alkoxyalkyl or alkoxyalkoxy;

A is N or CH;

B is N or CH;

L$_1$ is selected from —C(R$_{12}$)(R$_{13}$)—O—, —C(R$_{12}$)(R$_{13}$)—CH$_2$—O—, —C(R$_{12}$)(R$_{13}$)—S— and —C(R$_{12}$)(R$_{13}$)—S(O)$_2$—;

L$_2$ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF$_3$;

L$_3$ is selected from hydrogen and alkyl optionally substituted with hydroxyalkyl, aminoalkyl, alkoxyalkyl or alkoxyalkoxy;

L$_4$ is selected from —CF$_3$ and alkyl optionally substituted with 1-5 halo, wherein any alkyl portion of L$_4$ is optionally substituted with hydroxyalkyl, aminoalkyl, alkoxyalkyl or alkoxyalkoxy;

L$_5$ is selected from hydrogen and alkyl optionally substituted with hydroxyalkyl, aminoalkyl, alkoxyalkyl or alkoxyalkoxy;

L$_6$ is selected from hydrogen, —CF$_3$, and alkyl optionally substituted with 1-5 halo, wherein any alkyl portion of L$_6$ is optionally substituted with hydroxyalkyl, aminoalkyl, alkoxyalkyl or alkoxyalkoxy;

L$_7$ is selected from hydrogen and alkyl optionally substituted with hydroxyalkyl, aminoalkyl, alkoxyalkyl or alkoxyalkoxy;

X is O or S; and

Z is N or CH

In another embodiment of Formula I,

R$_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-L$_2$, —C(O)-L$_7$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl optionally substituted with halo or —CF$_3$, —N(H)C(O)N(H)-alkyl-CF$_3$, —OH, alkoxy, and halo; wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and wherein any alkyl portion of any R$_2$ group desribed above is optionally substituted with hydroxyalkyl, aminoalkyl, alkoxyalkyl or alkoxyalkoxy;

R$_6$, R$_7$, R$_8$, R$_9$, and R$_{10}$ are each independently selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of any R$_6$, R$_7$, R$_8$, R$_9$ and R$_{10}$ group described above is optionally substituted with hydroxyl, hydroxyalkyl, aminoalkyl, alkoxyalkyl or alkoxyalkoxy;

R$_{11}$ is hydrogen or alkyl;

R$_{12}$ is selected from hydrogen, halo or alkyl;

R$_{13}$ is halo or alkyl;

or R$_{12}$ and R$_{13}$, together with the carbon atom to which they are both attached, join to form a 3-6 membered cycloalkyl;

R$_{19}$, when R$_{19}$ is present, is selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of R$_{19}$ described above is optionally substituted with hydroxyalkyl, aminoalkyl, alkoxyalkyl or alkoxyalkoxy;

A is N or CH;

B is N or CH;

L$_1$ is selected from —C(R$_{12}$)(R$_{13}$)—O—, —C(R$_{12}$)(R$_{13}$)—CH$_2$—O—, —C(R$_{12}$)(R$_{13}$)—S— and —C(R$_{12}$)(R$_{13}$)—S(O)$_2$—;

L$_2$ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF$_3$;

L$_3$ is selected from hydrogen and alkyl optionally substituted with hydroxyalkyl, aminoalkyl, alkoxyalkyl or alkoxyalkoxy;

L$_4$ is selected from —CF$_3$ and alkyl optionally substituted with 1-5 halo, wherein any alkyl portion of L$_4$ is optionally substituted with hydroxyalkyl, aminoalkyl, alkoxyalkyl or alkoxyalkoxy;

L$_5$ is selected from hydrogen and alkyl optionally substituted with hydroxyalkyl, aminoalkyl, alkoxyalkyl or alkoxyalkoxy;

L$_6$ is selected from hydrogen, —CF$_3$, and alkyl optionally substituted with 1-5 halo, wherein any alkyl portion of L$_6$ is optionally substituted with hydroxyalkyl, aminoalkyl, alkoxyalkyl or alkoxyalkoxy;

L$_7$ is selected from hydrogen and alkyl optionally substituted with hydroxyalkyl, aminoalkyl, alkoxyalkyl or alkoxyalkoxy;

X is O or S; and

Z is N or CH.

In another embodiment of the compound of Formula A, G$_1$ is R$_2$, and G$_2$ is —N(R$_{11}$)C(=X)-L$_1$-R$_1$.

In another embodiment of the compound of formula A, G$_1$ is —N(R$_{11}$)C(=X)-L$_1$-R$_1$, and G$_2$ is R$_2$.

Another aspect of the invention relates to a compound according to Formula I:

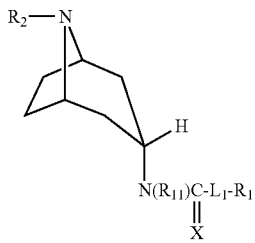

or a pharmaceutically acceptable salt thereof, wherein:
$R_1$ is selected from:

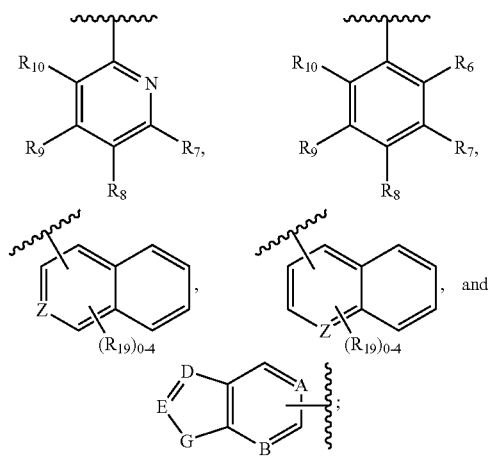

$R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl and 5-6 membered heteroaryl can each be unsubstituted or substituted with 1, 2, 3 or 4 groups selected from —C(O)—N(H)-$L_2$, —C(O)—O-$L_3$, —C(O)-$L_7$, —$CF_3$, —CN, —$NH_2$, —N(H)S(O)$_2$-alkyl, —S(O)$_2$-alkyl, —S(O)$_2$—N($L_5$)$L_6$, —N(H)C(O)-$L_4$, heteroaryl optionally substituted with halo or —$CF_3$, —N(H)C(O)N(H)-alkyl-$CF_3$, —OH, alkoxy, and halo; wherein the alkyl portion of —N(H)S(O)$_2$-alkyl, —S(O)$_2$-alkyl, and —N(H)C(O)N(H)-alkyl-$CF_3$ is optionally substituted with 1, 2, 3, 4 or 5 halo, and wherein any alkyl portion of any $R_2$ group desribed above is optionally substituted with hydroxyalkyl, aminoalkyl, alkoxyalkyl or alkoxyalkoxy;

$R_6$, $R_7$, $R_R$, $R_9$, and $R_{10}$ are each independently selected from H, halo, alkyl optionally substituted with 1-5 halo, alkynyl, —OH, —$NH_2$, alkenyl optionally substituted with 1-5 halo, phenyl, aminocarbonylalkoxy, aminocarbonylalkyl, carboxyalkoxy, carboxyalkyl, aminocarbonyl, —S(O)$_2$-alkyl, —S(O)$_2$—$NH_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—$NH_2$, —C(O)O-alkyl, —$CF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —$CF_3$, —(C$_1$-C$_3$)alkyl, OH and alkoxy, and wherein any alkyl portion of any $R_6$, $R_7$, $R_8$, $R_9$ and $R_{10}$ group described above is optionally substituted with hydroxyl, hydroxyalkyl, aminoalkyl, alkoxyalkyl or alkoxyalkoxy;

$R_{11}$ is hydrogen, alkyl, alkenyl or alkynyl;
$R_{12}$ is selected from hydrogen, alkenyl, alkynyl, halo or alkyl;
$R_{13}$ is halo, alkyl, alkenyl or alkynyl;
or $R_{12}$ and $R_{13}$, together with the carbon atom to which they are both attached, join to form a 3-6 membered cycloalkyl;

$R_{19}$, when $R_{19}$ is present, is selected from H, halo, alkyl optionally substituted with 1-5 halo, alkenyl, alkynyl —OH, —$NH_2$, alkenyl optionally substituted with 1-5 halo, phenyl, —S(O)$_2$-alkyl, —S(O)$_2$—$NH_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—$NH_2$, —C(O)O-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —$CF_3$, OH and alkoxy, and wherein any alkyl portion of $R_{19}$ described above is optionally substituted with hydroxyalkyl, aminoalkyl, alkoxyalkyl or alkoxyalkoxy;

A is N or CH;
B is N or CH;
D and E are each selected from CH and N, and G is selected from NH and $CH_2$, wherein one of D, E and G is optionally substituted with —N(H)—$R^{15}$, provided that no more than two of D, E and G are nitrogen;

$L_1$ is selected from —C($R_{12}$)($R_{13}$)—, —C($R_{12}$)($R_{13}$)—O—, —C($R_{12}$)($R_{13}$)—$CH_2$—O—, —C($R_{12}$)($R_{13}$)—S— and —C($R_{12}$)($R_{13}$)—S(O)$_2$—;

$L_2$ is selected from alkyl optionally substituted with 1-5 halo, alkyl optionally substituted with 1-2 hydroxyl, alkyl optionally substituted with 1-2 alkoxy, halo alkenyl, alkynyl, cycloalkyl optionally substituted with 1-5 halo, heterocycloalkyl, heterocycloalkylalkyl optionally substituted with 1-2 oxo, heteroarylalkyl, hydroxyalkyl, dialkylaminoalkyl, hydrogen, alkoxyalkyl, and —$CF_3$, wherein any alkyl portion of $L_2$ can be substituted with hydroxyl;

$L_3$ is selected from hydrogen, alkyl optionally substituted with hydroxyalkyl, aminoalkyl, alkoxyalkyl or alkoxyalkoxy, alkenyl and alkynyl;

$L_4$ is selected from —$CF_3$, alkyl optionally substituted with 1-5 halo, alkenyl and alkynyl, wherein any alkyl portion of $L_4$ is optionally substituted with hydroxyalkyl, aminoalkyl, alkoxyalkyl or alkoxyalkoxy;

$L_5$ is selected from hydrogen, alkyl, alkenyl and alkynyl, wherein any alkyl portion of $L_5$ is optionally substituted with hydroxyalkyl, aminoalkyl, alkoxyalkyl or alkoxyalkoxy;

$L_6$ is selected from hydrogen, —$CF_3$, alkyl optionally substituted with 1-5 halo, alkenyl and alkynyl, wherein any alkyl portion of $L_6$ is optionally substituted with hydroxyalkyl, aminoalkyl, alkoxyalkyl or alkoxyalkoxy;

$L_7$ is selected from hydrogen, heterocycloalkyl optionally substituted with 1-2 groups selected from hydroxyl and hydroxyalkyl, alkyl, alkenyl and alkynyl, wherein any alkyl portion of $L_7$ is optionally substituted with hydroxyalkyl, aminoalkyl, alkoxyalkyl or alkoxyalkoxy;

X is O or S; and
Z is N or CH.
In another embodiment of Formula I,
$R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-L$_2$, —C(O)—O-L$_3$, —C(O)-L7, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl optionally substituted with halo or —CF3, —N(H)C(O)N(H)-alkyl-CF$_3$, —OH, alkoxy, and halo; wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and wherein any alkyl portion of any R$_2$ group desribed above is optionally substituted with hydroxyalkyl, aminoalkyl, alkoxyalkyl or alkoxyalkoxy;

R$_6$, R7, R$_8$, K$_9$, and R$_{10}$ are each independently selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of any R$_6$, R$_7$, R$_8$, R$_9$ and R$_{10}$ group described above is optionally substituted with hydroxyl, hydroxyalkyl, aminoalkyl, alkoxyalkyl or alkoxyalkoxy;

R$_{11}$ is hydrogen or alkyl;
R$_{12}$ is selected from hydrogen, halo or alkyl;
R$_{13}$ is halo or alkyl;
or R$_{12}$ and R$_{13}$, together with the carbon atom to which they are both attached, join to form a 3-6 membered cycloalkyl;
R$_{19}$, when R$_{19}$ is present, is selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of R$_{19}$ described above is optionally substituted with hydroxyalkyl, aminoalkyl, alkoxyalkyl or alkoxyalkoxy;

A is N or CH;
B is N or CH;
L$_1$ is selected from —C(R$_{12}$)(R$_{13}$)—, —C(R$_{12}$)(R$_{13}$)—O—, —C(R$_{12}$)(R$_{13}$)—CH$_2$—O—, —C(R$_{12}$)(R$_{13}$)—S— and —C(R$_{12}$)(R$_{13}$)—S(O)$_2$—;
L$_2$ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF$_3$;
L$_3$ is selected from hydrogen and alkyl optionally substituted with hydroxyalkyl, aminoalkyl, alkoxyalkyl or alkoxyalkoxy;

L$_4$ is selected from —CF$_3$ and alkyl optionally substituted with 1-5 halo, wherein any alkyl portion of L$_4$ is optionally substituted with hydroxyalkyl, aminoalkyl, alkoxyalkyl or alkoxyalkoxy;
L$_5$ is selected from hydrogen and alkyl optionally substituted with hydroxyalkyl, aminoalkyl, alkoxyalkyl or alkoxyalkoxy;
L$_6$ is selected from hydrogen, —CF$_3$, and alkyl optionally substituted with 1-5 halo, wherein any alkyl portion of L$_6$ is optionally substituted with hydroxyalkyl, aminoalkyl, alkoxyalkyl or alkoxyalkoxy;
L$_7$ is selected from hydrogen and alkyl optionally substituted with hydroxyalkyl, aminoalkyl, alkoxyalkyl or alkoxyalkoxy;
X is O or S; and
Z is N or CH.

In another embodiment of Formula I,

R$_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-L$_2$, —C(O)—O-L$_3$, —C(O)-L$_7$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl optionally substituted with halo or —CF$_3$, —N(H)C(O)N(H)-alkyl-CF$_3$, —OH, alkoxy, and halo; wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and wherein any alkyl portion of any R$_2$ group desribed above is optionally substituted with hydroxyalkyl, aminoalkyl, alkoxyalkyl or alkoxyalkoxy;

R$_6$, R$_7$, R$_K$, R$_9$, and R$_{10}$ are each independently selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of any R$_6$, R$_7$, R$_8$, R$_9$ and R$_{10}$ group described above is optionally substituted with hydroxyl, hydroxyalkyl, aminoalkyl, alkoxyalkyl or alkoxyalkoxy;

R$_{11}$ is hydrogen or alkyl;
R$_{12}$ is selected from hydrogen, halo or alkyl;
R$_{13}$ is halo or alkyl;
or R$_{12}$ and R$_{13}$, together with the carbon atom to which they are both attached, join to form a 3-6 membered cycloalkyl;
R$_{19}$, when R$_{19}$ is present, is selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF₃, OH and alkoxy, and wherein any alkyl portion of R₁₉ described above is optionally substituted with hydroxyalkyl, aminoalkyl, alkoxyalkyl or alkoxyalkoxy;

A is N or CH;
B is N or CH;
L₁ is selected from —C(R₁₂)(R₁₃)—O—, —C(R₁₂)(R₁₃)—CH₂—O—, —C(R₁₂)(R₁₃)—S— and —C(R₁₂)(R₁₃)—S(O)₂—;
L₂ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF₃;
L₃ is selected from hydrogen and alkyl optionally substituted with hydroxyalkyl, aminoalkyl, alkoxyalkyl or alkoxyalkoxy;
L₄ is selected from —CF₃ and alkyl optionally substituted with 1-5 halo, wherein any alkyl portion of L₄ is optionally substituted with hydroxyalkyl, aminoalkyl, alkoxyalkyl or alkoxyalkoxy;
L₅ is selected from hydrogen and alkyl optionally substituted with hydroxyalkyl, aminoalkyl, alkoxyalkyl or alkoxyalkoxy;
L₆ is selected from hydrogen, —CF₃, and alkyl optionally substituted with 1-5 halo, wherein any alkyl portion of L₆ is optionally substituted with hydroxyalkyl, aminoalkyl, alkoxyalkyl or alkoxyalkoxy;
L₇ is selected from hydrogen and alkyl optionally substituted with hydroxyalkyl, aminoalkyl, alkoxyalkyl or alkoxyalkoxy;
X is O or S; and
Z is N or CH.

All of the compounds disclosed herein include either their free base form or their pharmaceutically acceptable salts whether it is stated in the specification that these compounds can exist as their pharmaceutically acceptable salt or not. So, for instance, for any given embodiment of the compound of Formula I (including embodiments relating to the compounds themselves or method of use thereof), this embodiment includes either its free base form or any of its pharmaceutically acceptable salts, whether this is stated within this embodiment or not.

The positions of attachment of the chemical groups in this disclosure are from left to right. For example, when L₁ is —C(R₁₂)(R₁₃)—O—, its position of attachment within Formula I is represented by the following structure:

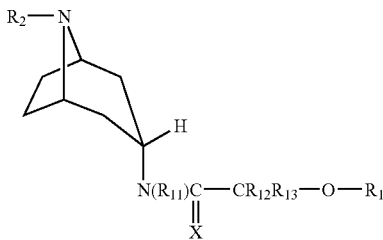

wherein R₁₂, R₁₃ and —O—R₁ are each attached to the one carbon on the left side. In addition, when a chemical group has a point of attachment in this disclosure, this point of attachment exists whether or not this point of attachment is represented by one or more dashes. For example, —OH and OH mean exactly the same thing. In another example, within the definition of Z, N or —N= would have exactly the same meaning.

In another embodiment of the compound of Formula I, R₂ selected from phenyl, —C(O)-phenyl, and a 5-6 membered heteroaryl that can contain 1, 2 or 3 heteroatoms, wherein the phenyl, —C(O)-phenyl or 5-6 membered heteroaryl can each be unsubstituted or substituted with 1, 2, 3 or 4 groups selected from —C(O)—N(H)-L₂, —C(O)—O-L₃, —C(O)-L₇, —CF₃, —CN, —NH₂, —N(H)S(O)₂-alkyl, —S(O)₂-alkyl, —S(O)₂—N(L₅)L₆, —N(H)C(O)-L₄, heteroaryl optionally substituted with halo or —CF₃, —N(H)C(O)N(H)-alkyl-CF₃, —OH, alkoxy, and halo, wherein the alkyl portion of —N(H)S(O)₂-alkyl, —S(O)₂-alkyl, and —N(H)C(O)N(H)-alkyl-CF₃ is optionally substituted with 1, 2, 3, 4 or 5 halo, and wherein any alkyl portion of any R₂ group described above is optionally substituted with hydroxyalkyl, aminoalkyl, alkoxyalkyl or alkoxyalkoxy.

In another embodiment of the compound of Formula I, R₂ is selected from phenyl and a 5-6 membered heteroaryl that can contain 1, 2 or 3 heteroatoms, wherein the phenyl, or 5-6 membered heteroaryl can each be unsubstituted or substituted with 1, 2, 3 or 4 groups selected from —C(O)—N(H)-L₂, —C(O)—O-L₃, —C(O)-L₇, —CF₃, —CN, —NH₂, —N(H)S(O)₂-alkyl, —S(O)₂-alkyl, —S(O)₂—N(L₅)L₆, —N(H)C(O)-L₄, heteroaryl optionally substituted with halo or —CF₃, —N(H)C(O)N(H)-alkyl-CF₃, —OH, alkoxy, and halo; wherein the alkyl portion of —N(H)S(O)₂-alkyl, —S(O)₂-alkyl, and —N(H)C(O)N(H)-alkyl-CF₃ is optionally substituted with 1, 2, 3, 4 or 5 halo, and wherein any alkyl portion of any R₂ group desribed above is optionally substituted with hydroxyalkyl, aminoalkyl, alkoxyalkyl or alkoxyalkoxy.

In another embodiment of the compound of Formula I, R₂ is pyridinyl or phenyl, wherein the pyridinyl or phenyl is substituted with one or two groups selected from —C(O)NH₂, —C(O)N(H)-cyclopropyl optionally substituted with 1 or 2 halo at any position on the cyclopropyl ring, —N(H)—S(O)₂-CH₃, —S(O)₂—NH₂, —S(O)₂-CH₃, —C(O)N(H)(C₁-C₃)alkyl-CF₃, and —C(O)N(H)(C₁-C₃)alkyl-OCH₃.

In another embodiment of the compound of Formula I, X is O.

In another embodiment of the compound of Formula I, R₂ is selected from N-cyclopropylpyridine-3-carboxamide, pyridine-3-carboxamide, 1-methylethyl)pyridine-3-carboxamide, 2,2,2-trifluoroethylpyridine-3-carboxamide, 2,2,2-trifluoroethylbenzamide, 3-chloro-2,2,2-trifluoroethylbenzamide, 3-fluoro-2,2,2-trifluoroethylbenzamide 5-[(methylsulfonyl)amino]pyridin-2-yl, 5-aminopyridin-2-yl, 2-(methyloxy)ethylpyridine-3-carboxamide, (trifluoroacetyl)aminophenyl, {[1-(4-chlorophenyl)cyclopropyl]carbonyl}amino, cyclopropylbenzamide, 3-chlorocyclopropylbenzamide, cyclopropyl-2-fluorobenzamide, 4-(methylsulfonyl)phenyl, 2,2,3,3,3-pentafluoropropyl)pyridine-3-carboxamide, 3-fluoro-(2,2,2-trifluoroethyl)benzamide, 2-chloro-(2,2,2-trifluoroethyl)benzamide, cyclopropyl-3-fluorobenzamide, 5-(aminosulfonyl)pyridin-2-yl, 5-fluoro-(2,2,2-trifluoroethyl)pyridine-3-carboxamide, 5-(methylsulfonyl)pyridin-2-yl, oxetan-3-ylpyridine-3-carboxamide, 2,2-difluorocyclopropyl)pyridine-3-carboxamide, pyridine-3-carboxylate, 5-cyanopyridin-2-yl, 4-cyanopyridin-2-yl, pyridine-3-carboxylic acid, 5-acetylpyridin-2-yl, 5-(acetylamino)pyridin-2-yl, 8-pyrazin-2-yl, 8-pyridin-3-yl, 5-(1H-tetrazol-5-yl, acetylamino)phenyl, 2-chloro-4-({[(2,2,2-trifluoroethyl)amino]carbonyl}amino)phenyl, 5-({[(2,2,2-trifluoroethyl)amino]carbonyl}amino)pyridin-2-yl, 4-({[(2,2,2-trifluoroethyl)amino]carbonyl}amino)phenyl, 2-chloro-4-({[(2,2,2-trifluoroethyl)amino]carbonyl}amino)phenyl, 2-fluoro-4-({[(2,2,2-trifluoroethyl)amino]carbonyl}amino)phenyl, 3-(methylsulfonyl)phenyl, (methylsulfonyl)amino]pyridin-2-yl, 6-(1H-tetrazol-5-yl)pyridin-3- yl, 5-(trifluoromethyl)-1,2,4-oxadiazol-3-yl]pyridin-2-yl and 5-[3-(trifluoromethyl)-1H-1,2,4-triazol-5-yl]pyridin-2-yl.

In another embodiment of the compound of Formula I, $R_2$ is selected from N-cyclopropylpyridine-3-carboxamide, pyridine-3-carboxamide, 1-methylethyl)pyridine-3-carboxamide, 2,2,2-trifluoroethylpyridine-3-carboxamide, 2,2,2-trifluoroethylbenzamide, 3-chloro-2,2,2-trifluoroethylbenzamide, 3-fluoro-2,2,2-trifluoroethylbenzamide 5-[(methylsulfonyl)amino]pyridin-2-yl, 5-aminopyridin-2-yl, 2-(methyloxy)ethylpyridine-3-carboxamide, (trifluoroacetyl)aminophenyl, {[1-(4-chlorophenyl)cyclopropyl]carbonyl}amino, cyclopropylbenzamide, 3-chloro-cyclopropylbenzamide, cyclopropyl-2-fluorobenzamide, 4-(methylsulfonyl)phenyl, 2,2,3,3,3-pentafluoropropyl)pyridine-3-carboxamide, 3-fluoro-(2,2,2-trifluoroethyl)benzamide, 2-chloro-(2,2,2-trifluoroethyl)benzamide, cyclopropyl-3-fluorobenzamide, 5-(aminosulfonyl)pyridin-2-yl, 5-fluoro-(2,2,2-trifluoroethyl)pyridine-3-carboxamide, 5-(methylsulfonyl)pyridin-2-yl, oxetan-3-ylpyridine-3-carboxamide and 2,2-difluorocyclopropyl)pyridine-3-carboxamide.

In another embodiment of the compound of Formula I, $R_1$ is selected from 2,4-dichlorophenyl, 3,4-dichlorophenyl, 4-fluorophenyl, 4-chlorophenyl, 4-methylphenyl, 2-chlorophenyl, 3-chlorophenyl, 3,4-difluorophenyl, 2,4-difluorophenyl, trifluoromethylphenyl, 4-cyanophenyl, 3-fluorophenyl, 4-chloro-2-fluorophenyl, 3,4-dichlorophenyl, 4-chloro-3-fluorophenyl, 4-(methyloxy)phenyl, 2-chloro-4-fluorophenyl, 2-chloro-5-fluorophenyl, 2,5-dichlorophenyl, 2-chloro-4,5-difluorophenyl, 2,4-dichloro-5-fluorophenyl, 3-chloro-4-fluorophenyl, 2,3-dichloro-4-fluorophenyl, 2,5-dichloro-4-fluorophenyl, 3,5-dichloropyridin-2-yl, 5-chloropyridin-2-yl, 5-fluoropyridin-2-yl, 4-(trifluoromethyl)phenyl, 2-(trifluoromethyl)phenyl, 5-chloro-3-fluoropyridin-2-yl, 4-[(trifluoromethyl)oxy]phenyl, 4-chloro-2-(trifluoromethyl)phenyl, 4-fluoro-2-(trifluoromethyl)phenyl, 3-chloro-5-(trifluoromethyl)pyridin-2-yl, 5-(trifluoromethyl)pyridin-2-yl, 2,5-dichloro-4-fluorophenyl, 2-chloro-4-fluorophenyl), 2,6-dichloro-4-fluorophenyl, 2-chloro-4-fluoro-6-(trifluoromethyl)phenyl, 2-chloro-4-(trifluoromethyl)phenyl, 4-chloro-3-(trifluoromethyl)phenyl, 2-fluoro-5-(trifluoromethyl)phenyl, 2,4,5-trichlorophenyl, 2-chloro-4-methylphenyl, 2,4,5-trifluorophenyl, 4-fluoro-2-methylphenyl, 4-fluoro-2-(methyloxy)phenyl, 2-chloro-4-(methyloxy)phenyl, 2,4,6-trifluorophenyl, 5-fluoro-2-(trifluoromethyl)phenyl, 1-chloronaphthalen-2-yl, 4-fluoro-3-(trifluoromethyl)phenyl, 5-chloro-3-(trifluoromethyl)pyridin-2-yl, 4-chloronaphthalen-1-yl, quinolin-2-yl, quinolin-4-yl, 4-chloro-2-(1-methylethyl)phenyl, phenyl, 3-chlorobiphenyl-4-yl, 4-fluoro-2-(methylsulfonyl)phenyl, 5-chloro-4'-fluorobiphenyl-2-yl, 4-chloro-2-cyclohexylphenyl, 2-(methylsulfonyl)phenyl, 4-chloro-2-(methylsulfonyl)phenyl, 2-[(3-chloro-4'-fluorobiphenyl-4-yl, 3-(methylsulfonyl)phenyl, 2-(methylsulfonyl)phenyl, 4-chloro-2-cyclopentylphenyl, and 5-chlorobiphenyl-2-yl.

In another embodiment of the compound of Formula I, $R_1$ is selected from 2,4-dichlorophenyl, 3,4-dichlorophenyl, 4-fluorophenyl, 4-chlorophenyl, 4-methylphenyl, 2-chlorophenyl, 3-chlorophenyl, 3,4-difluorophenyl, 2,4-difluorophenyl, trifluoromethylphenyl, 4-cyanophenyl, 3-fluorophenyl, 4-chloro-2-fluorophenyl, 3,4-dichlorophenyl, 4-chloro-3-fluorophenyl, 4-(methyloxy)phenyl, 2-chloro-4-fluorophenyl, 2-chloro-5-fluorophenyl, 2,5-dichlorophenyl, 2-chloro-4,5-difluorophenyl, 2,4-dichloro-5-fluorophenyl, 3-chloro-4-fluorophenyl, 2,3-dichloro-4-fluorophenyl, 2,5-dichloro-4-fluorophenyl, 3,5-dichloropyridin-2-yl, 5-chloropyridin-2-yl, 5-fluoropyridin-2-yl, 4-(trifluoromethyl)phenyl, 2-(trifluoromethyl)phenyl, 5-chloro-3-fluoropyridin-2-yl, 4-[(trifluoromethyl)oxy]phenyl, 4-chloro-2-(trifluoromethyl)phenyl, 4-fluoro-2-(trifluoromethyl)phenyl, 3-chloro-5-(trifluoromethyl)pyridin-2-yl, 5-(trifluoromethyl)pyridin-2-yl, 2,5-dichloro-4-fluorophenyl, 2-chloro-4-fluorophenyl), 2,6-dichloro-4-fluorophenyl, 2-chloro-4-fluoro-6-(trifluoromethyl)phenyl, 2-chloro-4-(trifluoromethyl)phenyl, 4-chloro-3-(trifluoromethyl)phenyl, 2-fluoro-5-(trifluoromethyl)phenyl, 2,4,5-trichlorophenyl, 2-chloro-4-methylphenyl, 2,4,5-trifluorophenyl, 4-fluoro-2-methylphenyl, 4-fluoro-2-(methyloxy)phenyl, 2-chloro-4-(methyloxy)phenyl, 2,4,6-trifluorophenyl, 5-fluoro-2-(trifluoromethyl)phenyl, 1-chloronaphthalen-2-yl, 4-fluoro-3-(trifluoromethyl)phenyl, 5-chloro-3-(trifluoromethyl)pyridin-2-yl, 4-chloronaphthalen-1-yl, quinolin-2-yl, quinolin-4-yl, 4-chloro-2-(1-methylethyl)phenyl, phenyl, 3-chlorobiphenyl-4-yl, 4-fluoro-2-(methylsulfonyl)phenyl, 5-chloro-4'-fluorobiphenyl-2-yl, 4-chloro-2-cyclohexylphenyl, 2-(methylsulfonyl)phenyl, 4-chloro-2-(methylsulfonyl)phenyl, 2-[(3-chloro-4'-fluorobiphenyl-4-yl, 3-(methylsulfonyl)phenyl, 2-(methylsulfonyl)phenyl, 4-chloro-2-cyclopentylphenyl, and 5-chlorobiphenyl-2-yl; and $R_2$ is selected from N-cyclopropylpyridine-3-carboxamide, pyridine-3-carboxamide, 1-methylethyl)pyridine-3-carboxamide, 2,2,2-trifluoroethylpyridine-3-carboxamide, 2,2,2-trifluoroethylbenzamide, 3-chloro-2,2,2-trifluoroethylbenzamide, 3-fluoro-2,2,2-trifluoroethylbenzamide 5-[(methylsulfonyl)amino]pyridin-2-yl, 5-aminopyridin-2-yl, 2-(methyloxy)ethylpyridine-3-carboxamide, (trifluoroacetyl)aminophenyl, {[1-(4-chlorophenyl)cyclopropyl]carbonyl}amino, cyclopropylbenzamide, 3-chloro-cyclopropylbenzamide, cyclopropyl-2-fluorobenzamide, 4-(methylsulfonyl)phenyl, 2,2,3,3,3-pentafluoropropyl)pyridine-3-carboxamide, 3-fluoro-(2,2,2-trifluoroethyl)benzamide, 2-chloro-(2,2,2-trifluoroethyl)benzamide, cyclopropyl-3-fluorobenzamide, 5-(aminosulfonyl)pyridin-2-yl, 5-fluoro-(2,2,2-trifluoroethyl)pyridine-3-carboxamide, 5-(methylsulfonyl)pyridin-2-yl, oxetan-3-ylpyridine-3-carboxamide, 2,2-difluorocyclopropyl)pyridine-3-carboxamide, pyridine-3-carboxylate, 5-cyanopyridin-2-yl, 4-cyanopyridin-2-yl, pyridine-3-carboxylic acid, 5-acetylpyridin-2-yl, 5-(acetylamino)pyridin-2-yl, 8-pyrazin-2-yl, 8-pyridin-3-yl, 5-(1H-tetrazol-5-yl, acetylamino)phenyl, 2-chloro-4-({[(2,2,2-trifluoroethyl)amino]carbonyl}amino)phenyl, 5-({[(2,2,2-trifluoroethyl)amino]carbonyl}amino)pyridin-2-yl, 4-({[(2,2,2-trifluoroethyl)amino]carbonyl}amino)phenyl, 2-chloro-4-({[(2,2,2-trifluoroethyl)amino]carbonyl}amino)phenyl, 2-fluoro-4-({[(2,2,2-trifluoroethyl)amino]carbonyl}amino)phenyl, 3-(methylsulfonyl)phenyl, (methylsulfonyl)amino]pyridin-2-yl, 6-(1H-tetrazol-5-yl)pyridin-3-yl, 5-(trifluoromethyl)-1,2,4-oxadiazol-3-yl]pyridin-2-yl and 5-[3-(trifluoromethyl)-1H-1,2,4-triazol-5-yl]pyridin-2-yl.

In another embodiment of the compound of Formula I, $L_1$ is a methylene group substituted with a spiro-cyclopropyl group represented by the following structure:

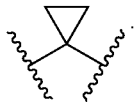

In another embodiment of the compound of Formula I, $L_1$ is an oxymethylene group substituted with a spiro-cyclopropyl group represented by the following structure:

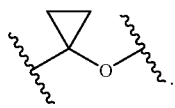

In another embodiment of the compound of Formula I, $L_1$ is selected from —CH(CH$_3$)—, —CH(CH$_3$)—O—, —C(CH$_3$)$_2$—, —C(CH$_3$)$_2$—O—, —C(CH$_3$)$_2$—CH$_2$—O—, —C(CH$_3$)$_2$—S—, —C(CH$_3$)$_2$—S(O)$_2$—,

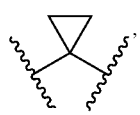 and 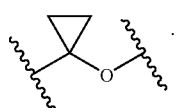

In another embodiment of the compound of Formula I, $L_1$ is selected from —CH(CH$_3$)—, —CH(CH$_3$)—O—, —C(CH$_3$)$_2$—, —C(CH$_3$)$_2$—O—, —C(CH$_3$)$_2$—CH$_2$—O—,

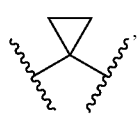 and 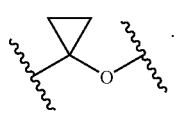

In another embodiment of the compound of Formula I, $L_1$ is —CH(CH$_3$)— or —C(CH$_3$)$_2$—.

In another embodiment of the compound of Formula I, $L_1$ is —CH(CH$_3$)— or —CH(CH$_3$)—O—.

In another embodiment of the compound of Formula I, $L_1$ is —C(CH$_3$)$_2$— or —C(CH$_3$)$_2$—O—.

In another embodiment of the compound of Formula I, $L_1$ is —CH(CH$_3$)—O— or —C(CH$_3$)$_2$—O—.

In another embodiment of the compound of Formula I, $L_1$ is selected from —CH(CH$_3$)—, —C(CH$_3$)$_2$— and

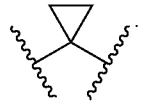

In another embodiment of the compound of Formula I, $L_1$ is selected from —CH(CH$_3$)—O—, —C(CH$_3$)$_2$—O—, and

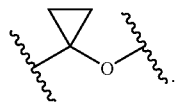

In another embodiment of the compound of Formula I, $L_1$ is —CH(CH$_3$)—.

In another embodiment of the compound of Formula I, $L_1$ is —CH(CH$_3$)—O—.

In another embodiment of the compound of Formula I, $L_1$ is —C(CH$_3$)$_2$—.

In another embodiment of the compound of Formula I, $L_1$ is —C(CH$_3$)$_2$—O—.

In another embodiment of the compound of Formula I, $L_1$ is —C(CH$_3$)$_2$—CH$_2$—O—.

In another embodiment of the compound of Formula I, $L_1$ is —C(R$_{12}$)(R$_{13}$)—S— or —C(R$_{12}$)(R$_{13}$)—S(O)$_2$—.

In another embodiment of the compound of Formula I, $L_2$ is selected from H, cyclopropyl, gem-difluorocyclopropyl, —(C$_1$-C$_3$)alkyl, —(C$_1$-C$_3$)alkyl-CF$_3$, —(C$_1$-C$_3$)alkyl-CF$_2$—CF$_3$, —(C$_1$-C$_3$)alkyl-(C$_1$-C$_3$)alkoxy, and -(4-6 membered) heterocycloalkyl, wherein any alkyl portion of $L_2$ is optionally substituted with hydroxyl, hydroxyalkyl, aminoalkyl, alkoxyalkyl or alkoxyalkoxy.

In another embodiment of the compound of Formula I, $L_2$ is selected from H, cyclopropyl, gem-difluorocyclopropyl, 1-methylethyl, —CH$_2$—CF$_3$, —CH$_2$—CHF$_2$, —CH$_2$—CH(OH)CF$_3$, —CH$_2$—C(CH$_3$)$_2$—OH, —CH$_2$—CF$_2$—CF$_3$, —CH$_2$—CH$_2$—O—CH$_3$ and oxetanyl.

In another embodiment of the compound of Formula I, $L_2$ is selected from H, cyclopropyl, gem-difluorocyclopropyl, 1-methylethyl, —CH$_2$—CF$_3$, and oxetanyl.

In another embodiment of the compound of Formula I, $L_2$ is H.

In another embodiment of the compound of Formula I, $L_2$ is cyclopropyl.

In another embodiment of the compound of Formula I, $L_2$ is gem-difluorocyclopropyl.

In another embodiment of the compound of Formula I, $L_2$ is 1-methylethyl.

In another embodiment of the compound of Formula I, $L_2$ is —CH$_2$—CHF$_2$.

In another embodiment of the compound of Formula I, $L_2$ is —CH$_2$—CH(OH)CF$_3$.

In another embodiment of the compound of Formula I, $L_2$ is —CH$_2$—C(CH$_3$)$_2$—OH.

In another embodiment of the compound of Formula I, $L_2$ is —CH$_2$—CF$_3$.

In another embodiment of the compound of Formula I, $L_2$ is —CH$_2$—CF$_2$—CF$_3$.

In another embodiment of the compound of Formula I, $L_2$ is —CH$_2$—CH$_2$—O—CH$_3$.

In another embodiment of the compound of Formula I, L$_2$ is oxetanyl.

In another embodiment of the compound of Formula I, L$_3$ is H or —(C$_1$-C$_3$)alkyl optionally substituted with hydroxyalkyl, aminoalkyl, alkoxyalkyl or alkoxyalkoxy.

In another embodiment of the compound of Formula I, L$_3$ is —CH$_3$ or H.

In another embodiment of the compound of Formula I, L$_3$ is —CH$_3$.

In another embodiment of the compound of Formula I, L$_3$ is H.

In another embodiment of the compound of Formula I, L$_4$ is —(C$_1$-C$_3$)alkyl, —(C$_1$-C$_3$)alkyl-CF$_3$, or CF$_3$, wherein any alkyl portion of L$_4$ is optionally substituted with hydroxyalkyl, aminoalkyl, alkoxyalkyl or alkoxyalkoxy.

In another embodiment of the compound of Formula I, L$_4$ is —CH$_3$, —CH$_3$—CF$_3$, or —CF$_3$.

In another embodiment of the compound of Formula I, L$_4$ is —CH$_3$.

In another embodiment of the compound of Formula I, L$_4$ is —CH$_3$—CF$_3$.

In another embodiment of the compound of Formula I, L$_4$ is —CF$_3$.

In another embodiment of the compound of Formula I, L$_5$ is —(C$_1$-C$_3$)alkyl or H, wherein any alkyl portion of L$_5$ is optionally substituted with hydroxyalkyl, aminoalkyl, alkoxyalkyl or alkoxyalkoxy.

In another embodiment of the compound of Formula I, L$_6$ is —(C$_1$-C$_3$)alkyl or H, wherein any alkyl portion of L$_6$ is optionally substituted with hydroxyalkyl, aminoalkyl, alkoxyalkyl or alkoxyalkoxy.

In another embodiment of the compound of Formula I, L$_5$ and L$_6$ are both H.

In another embodiment of the compound of Formula I, L$_7$ is —(C1-C$_3$)alkyl optionally substituted with hydroxyalkyl, aminoalkyl, alkoxyalkyl or alkoxyalkoxy.

In another embodiment of the compound of Formula I, L$_7$ is —CH$_3$.

In another embodiment of the compound of Formula I, R$_2$ is

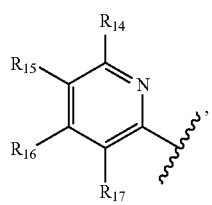

wherein R$_{14}$, R$_{15}$, R$_{16}$ and R$_{17}$ are each selected from hydrogen, —C(O)—N(H)-L$_2$, —C(O)-L$_7$, —C(O)—O-L$_3$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of L$_2$, L$_3$, L$_4$, L$_5$, L$_6$ and L$_7$ are as defined in any of the definitions above for each of these variables, including the definition in Formula I.

In another embodiment of the compound of Formula I, R$_2$ is

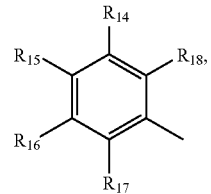

wherein R$_{14}$, R$_{15}$, R$_{16}$, R$_{17}$ and R$_{18}$ are each selected from hydrogen, —C(O)—N(H)-L$_2$, —C(O)-L$_7$, —C(O)—O-L$_3$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of L$_2$, L$_3$, L$_4$, L$_5$, L$_6$ and L$_7$ are as defined in any of the definitions above for each of these variables, including the definition in Formula I.

In another embodiment of the compound of Formula I, R$_2$ is

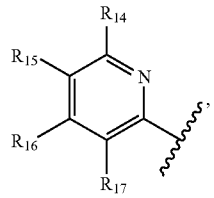

wherein three of R$_{14}$, R$_{15}$, R$_{16}$ and R$_{17}$ are hydrogen, one of R$_{14}$, R$_{15}$, R$_{16}$ and R$_{17}$ is selected from —C(O)—N(H)-L$_2$, —C(O)-L$_7$, —C(O)—O-L$_3$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of L$_2$, L$_3$, L$_4$, L$_5$, L$_6$ and L$_7$ are as defined in any of the definitions above for each of these variables, including the definition in Formula I.

In another embodiment of the compound of Formula I, R$_2$ is

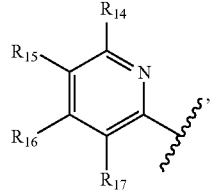

wherein two of R$_{14}$, R$_{15}$, R$_{16}$ and R$_{17}$ are hydrogen, two of R$_{14}$, R$_{15}$, R$_{16}$ and R$_{17}$ are selected from —C(O)—N(H)-L$_2$, —C(O)-L$_7$, —C(O)—O-L$_3$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I $R_2$ is

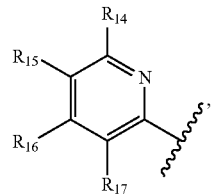

wherein one of $R_{14}$, $R_{15}$, $R_{16}$ and $R_{17}$ is hydrogen, three of $R_{14}$, $R_{15}$, $R_{16}$ and $R_{17}$ are selected from —C(O)—N(H)-$L_2$, —C(O)-$L_7$, —C(O)—O-$L_3$, —CF$_3$, —CN, —NH$_2$, —N(H)S(O)$_2$-alkyl, —S(O)$_2$-alkyl, —S(O)$_2$—N($L_5$)$L_6$, —N(H)C(O)-$L_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I, $R_2$ is

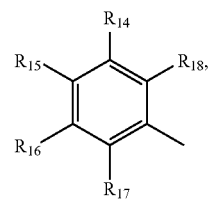

wherein four of $R_{14}$, $R_{15}$, $R_{16}$, $R_{17}$ and $R_{18}$ are hydrogen, one of $R_{14}$, $R_{15}$, $R_{16}$, $R_{17}$ and $R_{18}$ is selected from —C(O)—N(H)-$L_2$, —C(O)-$L_7$, —C(O)—O-$L_3$, —CF$_3$, —CN, —NH$_2$, —N(H)S(O)$_2$-alkyl, —S(O)$_2$-alkyl, —S(O)$_2$—N($L_5$)$L_6$, —N(H)C(O)-$L_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, —N(H)C(O)N(H)-alkyl-CF$_3$ and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I, $R_2$ is

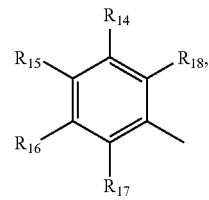

wherein three of $R_{14}$, $R_{15}$, $R_{16}$ and $R_{17}$ are hydrogen, two of $R_{14}$, $R_{15}$, $R_{16}$ and $R_{17}$ are selected from —C(O)—N(H)-$L_2$, —C(O)-$L_7$, —C(O)—O-$L_3$, —CF$_3$, —CN, —NH$_2$, —N(H)S(O)$_2$-alkyl, —S(O)$_2$-alkyl, —S(O)$_2$—N($L_5$)$L_6$, —N(H)C(O)-$L_4$, heteroaryl, —N(H)C(O)N(H)-alkyl-CF$_3$, —OH, alkoxy, and halo, wherein the alkyl portion of N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I, $R_2$ is

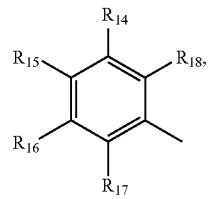

wherein two of $R_{14}$, $R_{15}$, $R_{16}$ and $R_{17}$ are hydrogen, three of $R_{14}$, $R_{15}$, $R_{16}$ and $R_{17}$ are selected from —C(O)—N(H)-$L_2$, —C(O)-$L_7$, —C(O)—O-$L_3$, —CF$_3$, —CN, —NH$_2$, —N(H)S(O)$_2$-alkyl, —S(O)$_2$-alkyl, —S(O)$_2$—N($L_5$)$L_6$, —N(H)C(O)-$L_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I, $R_2$ is

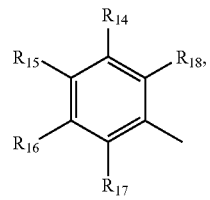

wherein one of $R_{14}$, $R_{15}$, $R_{16}$ and $R_{17}$ is hydrogen, four of $R_{14}$, $R_{15}$, $R_{16}$ and $R_{17}$ are selected from —C(O)—N(H)-$L_2$, —C(O)-$L_7$, —C(O)—O-$L_3$, —CF$_3$, —CN, —NH$_2$, —N(H)S(O)$_2$-alkyl, —S(O)$_2$-alkyl, —S(O)$_2$—N($L_5$)$L_6$, —N(H)C(O)-$L_4$, heteroaryl, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_3$, $L_4$, $L_5$, $L_6$ and $L_7$ are as defined in any of the definitions above for each of these variables, including the definition in Formula I.

In another embodiment of the compound of Formula I, $R_2$ is

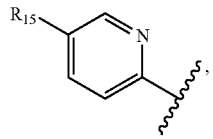

wherein $R_{15}$ is selected from —C(O)—N(H)-$L_2$, —N(H)S(O)$_2$-alkyl, —S(O)$_2$-alkyl, —S(O)$_2$—N($L_5$)$L_6$, —N(H)C(O)-$L_4$, and —N(H)C(O)N(H)-alkyl-CF$_3$, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and each of $L_2$, $L_4$, $L_5$, and $L_6$ are as defined in any of the definitions above for each of these variables, including the definition in Formula I.

In another embodiment of the compound of Formula I, $R_2$ is

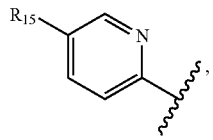

wherein $R_{15}$ is selected from —C(O)NH$_2$, —C(O)N(H)-cyclopropyl optionally substituted with 1 or 2 halo at any position on the cyclopropyl ring, —NH)—S(O)$_2$—CH$_3$, —S(O)$_2$—CH$_3$, —S(O)$_2$—N($L_5$)$L_6$, —C(O)N(H)(C$_1$-C$_3$)alkyl-CF$_3$, and —C(O)N(H)(C$_1$-C$_3$)alkyl-OCH$_3$.

In another embodiment of the compound of Formula I, $R_2$ is

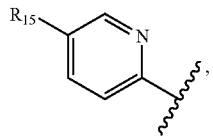

wherein $R_{15}$ is —C(O)NH$_2$.

In another embodiment of the compound of Formula I, $R_2$ is

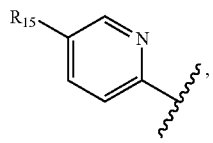

wherein $R_{15}$ is —C(O)N(H)-cyclopropyl optionally substituted with 1 or 2 halo at any position on the cyclopropyl ring.

In another embodiment of the compound of Formula I, $R_2$ is

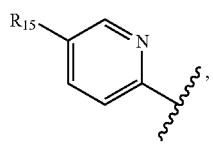

wherein $R_{15}$ is —N(H)—S(O)$_2$—CH$_3$.

In another embodiment of the compound of Formula I, $R_2$ is

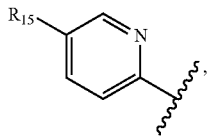

wherein $R_{15}$ is —S(O)$_2$—CH$_3$.

In another embodiment of the compound of Formula I, $R_2$ is

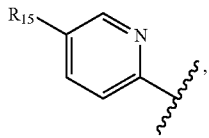

wherein $R_{15}$ is —C(O)N(H)(C$_1$-C$_3$)alkyl-CF$_3$.

In another embodiment of the compound of Formula I, $R_2$ is

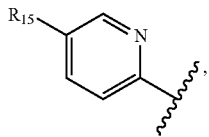

wherein $R_{15}$ is —C(O)N(H)(C$_1$-C$_3$)alkyl-C(H)F$_2$.

In another embodiment of the compound of Formula I, $R_2$ is

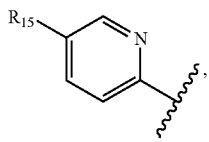

wherein $R_{15}$ is —N(H)C(O)-3-oxetane or —N(H)C(O)-2,2-difluorocyclopropyl.

In another embodiment of the compound of Formula I, $R_2$ is

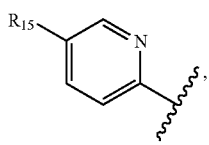

wherein $R_{15}$ is —C(O)N(H)(C$_1$-C$_3$)alkyl-OCH$_3$.

In another embodiment of the compound of Formula I, $R_2$ is

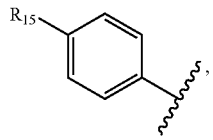

wherein $R_{15}$ is selected from —C(O)—N(H)-$L_2$, —N(H)S(O)$_2$-alkyl, —S(O)$_2$-alkyl, —S(O)$_2$—N($L_5$)$L_6$, —N(H)C(O)-$L_4$, and —N(H)C(O)N(H)-alkyl-CF$_3$, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and $L_2$, $L_4$, $L_5$, and $L_6$ are as defined above in the compound of Formula I.

In another embodiment of the compound of Formula I, $R_2$ is

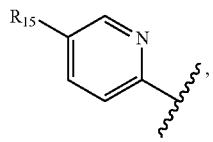

wherein $R_{15}$ is selected from —C(O)NH$_2$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —C(O)N(H)(C$_1$-C$_3$)alkyl-CF$_3$, —C(O)N(H)(C$_1$-C$_3$)alkyl-C(H)F$_2$, and —C(O)N(H)(C$_1$-C$_3$)alkyl-OCH$_3$.

In another embodiment of the compound of Formula I, $R_2$ is

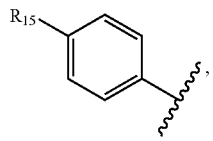

wherein $R_{15}$ is —C(O)NH$_2$.

In another embodiment of the compound of Formula I, $R_2$ is

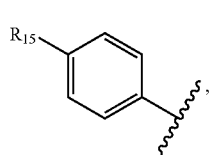

wherein $R_{15}$ is —C(O)N(H)-cyclopropyl optionally substituted with 1 or 2 halo at any position on the cyclopropyl ring.

In another embodiment of the compound of Formula I, $R_2$ is

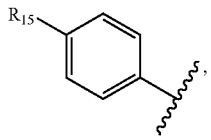

wherein $R_{15}$ is —N(H)—S(O)$_2$—CH$_3$.

In another embodiment of the compound of Formula I, $R_2$ is

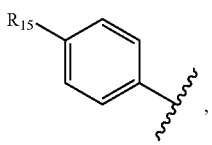

wherein $R_{15}$ is —N(H)C(O)-3-oxetane or —N(H)C(O)-2,2-difluorocyclopropyl.

In another embodiment of the compound of Formula I, $R_2$ is

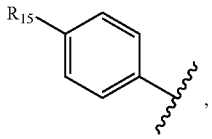

wherein $R_{15}$ is —S(O)$_2$—CH$_3$.

In another embodiment of the compound of Formula I, $R_2$ is

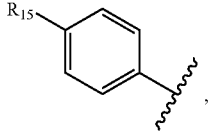

wherein $R_{15}$ is —C(O)N(H)(C$_1$-C$_3$)alkyl-CF$_3$.

In another embodiment of the compound of Formula I, $R_2$ is

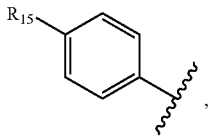

wherein $R_{15}$ is —C(O)N(H)(C$_1$-C$_3$)alkyl-C(H)F$_2$,

In another embodiment of the compound of Formula I, $R_2$ is

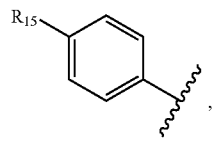

wherein $R_{15}$ is —C(O)N(H)($C_1$-$C_3$)alkyl-OCH$_3$.

In another embodiment of the compound of Formula I, $R_6$, $R_7$, $R_8$, $R_9$ and $R_{10}$ are each independently selected from H, halo, alkyl optionally substituted with 1-5 halo, phenyl optionally substituted with 1-3 halo, —S(O)$_2$—CH$_3$, cyclohexyl, cyclopentyl, —CF$_3$, —OCF$_3$, —CN, and alkoxy.

In another embodiment of the compound of Formula I, $R_6$, $R_7$, $R_8$, $R_9$ and $R_{10}$ are each independently selected from H, chloro, fluoro, methyl, phenyl optionally substituted with 1-3 halo, —S(O)$_2$—CH$_3$, cyclohexyl, cyclopentyl, —CF$_3$, —OCF$_3$, —CN, and methoxy.

In another embodiment of the compound of Formula I, $R_6$, $R_7$, $R_8$, $R_9$ and $R_{10}$ are each independently selected from H, chloro, fluoro, methyl, —CF$_3$, —OCF$_3$, —CN, and methoxy.

In another embodiment of the compound of Formula I, $R_6$, $R_7$, $R_8$, $R_9$, and $R_{10}$ are each independently selected from H, chloro, fluoro, —CF$_3$, —OCF$_3$, and methoxy.

In another embodiment of the compound of Formula I, $R_{19}$, when $R_{19}$ is present, is independently selected from H, halo, alkyl optionally substituted with 1-5 halo, phenyl optionally substituted with 1-3 halo, —S(O)$_2$—CH$_3$, cyclohexyl, cyclopentyl, —CF$_3$, —OCF$_3$, —CN, and alkoxy.

In another embodiment of the compound of Formula I, $R_{19}$, when $R_{19}$ is present, is selected from H, chloro, fluoro, methyl, phenyl optionally substituted with 1-3 halo, —S(O)$_2$—CH$_3$, cyclohexyl, cyclopentyl, —CF$_3$, —OCF$_3$, —CN, and methoxy.

In another embodiment of the compound of Formula I, $R_{19}$, when $R_{19}$ is present, is selected from H, chloro, fluoro, methyl, —CF$_3$, —OCF$_3$, —CN, and methoxy.

In another embodiment of the compound of Formula I, $R_{19}$, when $R_{19}$ is present, is selected from H, chloro, fluoro, —CF$_3$, —OCF$_3$, and methoxy.

In another embodiment of Formula I, $R_{11}$ is hydrogen or —CH$_3$.

In another embodiment of Formula I, $R_{11}$ is hydrogen.

In another embodiment of Formula I, $R_{12}$ is selected from halo or methyl.

In another embodiment of Formula I, $R_{13}$ is selected from halo or methyl.

In another embodiment of Formula I, or $R_{12}$ and $R_{13}$, together with the carbon atom to which they are both attached, join to form a 3-4 membered cycloalkyl.

In another embodiment of Formula I, A is N.
In another embodiment of Formula I, A is CH.
In another embodiment of Formula I, B is N.
In another embodiment of Formula I, B is CH.
In another embodiment of Formula I, X is O.
In another embodiment of Formula I, X is S.
In another embodiment of Formula I, Z is N.
In another embodiment of Formula I, Z is CH.

All compounds of Formula I disclosed above include any of the disclosed alternative aspects or embodiments for each of $R_1$, $R_2$, $R_6$, $R_7$, $R_8$, $R_9$, $R_{10}$, $R_{19}$, $R_{11}$, $R_{12}$, $R_{13}$, A, B, $L_1$, $L_2$, $L_3$, $L_4$, $L_5$, $L_6$, $L_7$, X and Z in combination with any other of the disclosed alternative aspects or embodiments of $R_1$, $R_2$, $R_6$, $R_7$, $R_8$, $R_9$, $R_{10}$, $R_{19}$, $R_{11}$, $R_{12}$, $R_{13}$, A, B, $L_1$, $L_2$, $L_3$, $L_4$, $L_5$, $L_6$, $L_7$, X and Z, as well as any pharmaceutically acceptable salt and stereoisomer of any such combination.

In Formula I of this disclosure, it is to be understood that $R_2$ cannot be substituted by more than one group that contains a cycloalkyl group, an aryl group, a heterocycloalkyl group, or a heteroaryl group. For instance the —C(O)-phenyl, benzyl, and a 5-6 membered heteroaryl of $R_2$ cannot be substituted with more than one heteroaryl group.

In Formula I in this disclosure, it is to be understood that $R_1$ cannot be substituted by more than one group that contains a cycloalkyl group, an aryl group, a heterocycloalkyl group, or a heteroaryl group. In otherwords, for any $R_1$ group, not more than one of $R_6$, $R_7$, $R_8$, $R_9$, $R_{10}$ and $R_{19}$ can be phenyl, cycloalkyl, cycloalkyalkoxy, heterocycloalkyl, heterocycloalkylalkoxy, heteroaryl, heteroarylalkoxy.

Other embodiments of the compound of Formula I include any combination of one or more of the following compounds selected from Formulae I(A), I(B), I(C), I(D), I(E), I(F), I(G), I(H), I(I), I(J), I(K), I((L), I(M) and I(N):

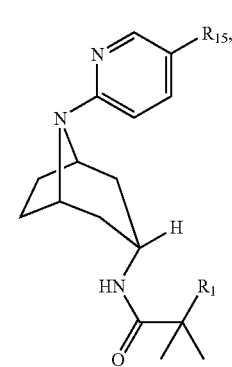

I(A)

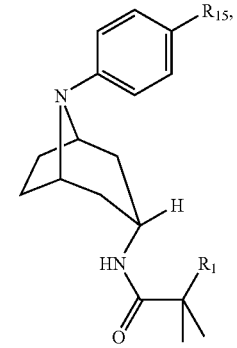

I(B)

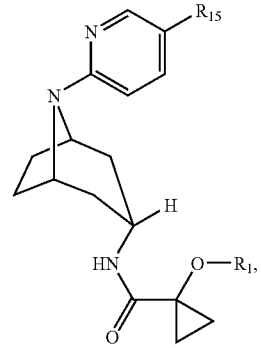

I(C)

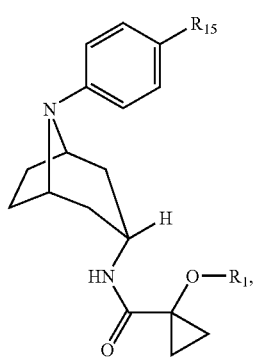 I(D)
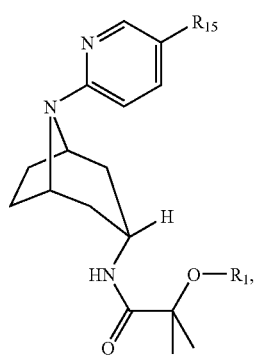 I(E)
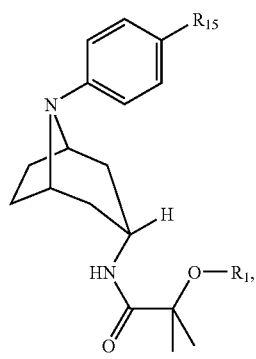 I(F)
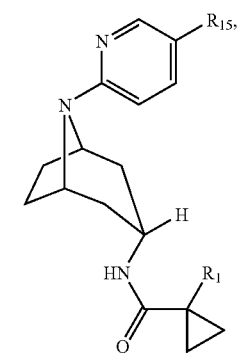 I(G)
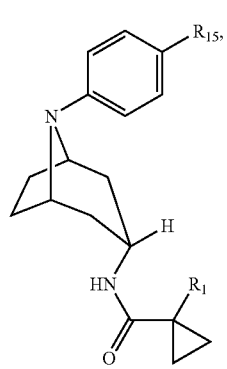 I(H)
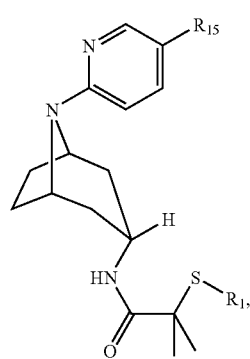 I(I)
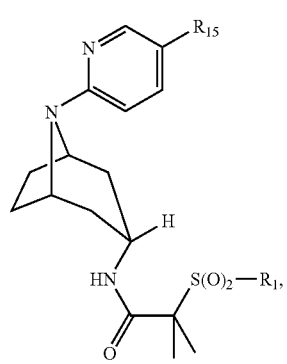 I(J)
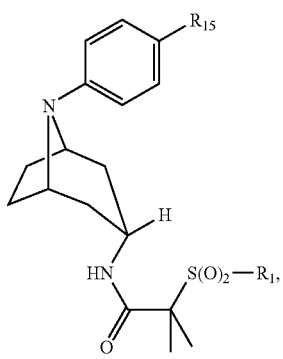 I(K)

I(L)

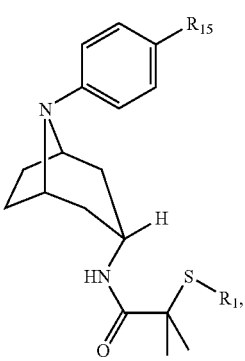

I(M)

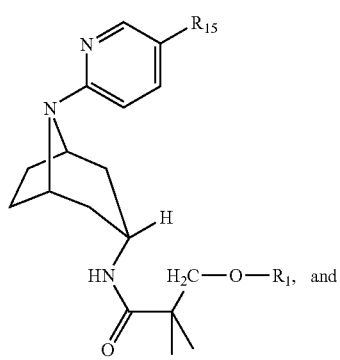

I(N)

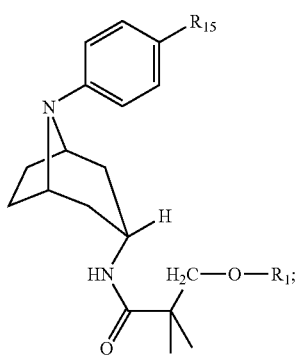

wherein $R_{15}$ is selected from —C(O)NH$_2$, —C(O)—CH$_3$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —S(O)$_2$—NH$_2$, —C(O)N(H)(C$_1$-C$_3$)alkyl-C(H)F$_2$, —C(O)N(H)(C$_1$-C$_3$)alkyl-CF$_3$, and —C(O)N(H)(C$_1$-C$_3$)alkyl-OCH$_3$; and $R_1$ is selected from

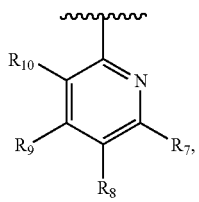

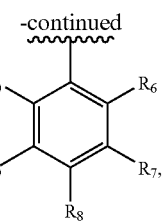

1-naphthyl optionally substituted with 1-4 $R_{19}$ groups, 2-quinolinyl optionally substituted with 1-4 $R_{19}$ groups, 2-naphthyl optionally substituted with 1-4 $R_{19}$ groups, and 4-quinolinyl optionally substituted with 1-4 $R_{19}$ groups, wherein $R_6$, $R_7$, $R_8$, $R_9$, $R_{10}$ and $R_{19}$ are each independently selected from H, halo, alkyl optionally substituted with 1-5 halo, alkyl optionally substituted with 1-2 —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)ON, —C(O)O—NH$_2$, —C(O)O-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, —OH and alkoxy.

When any of the embodiments in this specification refers to a any combination of one or more compounds of Formula I(A), I(B), I(C), I(D), I(E), I(F), I(G), I(H), I(I), I(J), I(K), I((L), I(M), or I(N), this is meant to mean that this embodiment includes each of Formula I(A), I(B), I(C), I(D), I(E), I(F), I(G), I(H), I(I), I(J), I(K), I((L), I(M), or I(N), individually or in any combination of each other. For instance, when any of the embodiments in this specification refers to a compound of Formula I(A), I(B), I(C), I(D), I(E), I(F), I(G), I(H), I(I), I(J), I(K), I((L), I(M), or I(N), this can be interpreted to include only compounds having Formula I(A), or only compounds having Formula I(B), or only compounds having Formula I(C), or only compounds having Formula I(D), or only compounds having Formula I(E), or a combination of any two of Formula I(A), I(B), I(C), I(D), I(E), I(F), I(G), I(H), I(I), I(J), I(K), I((L), I(M), or I(N), (such as, for example, a compound of Formula I(E) or I(F), or a compound of Formula I(J) or I(K), wherein all variables $R_1$ and $R_{15}$ are as defined above) or a combination of any three of Formula I(A), I(B), I(C), I(D), I(E), I(F), I(G), I(H), I(I), I(J), I(K), I((L), I(M), or I(N), or a combination of any four of Formula I(A), I(B), I(C), I(D), I(E), I(F), I(G), I(H), I(I), I(J), I(K), I((L), I(M), or I(N), or a combination of any five of Formula I(A), I(B), I(C), I(D), I(E), I(F), I(G), I(H), I(I), I(J), I(K), I((L), I(M), or I(N), or a combination of any six of Formula I(A), I(B), I(C), I(D), I(E), I(F), I(G), I(H), I(I), I(J), I(K), I((L), I(M), or I(N), or a combination of any seven of Formula I(A), I(B), I(C), I(D), I(E), I(F), I(G), I(H), I(I), I(J), I(K), I((L), I(M), or I(N), or a combination of any eight of Formula I(A), I(B), I(C), I(D), I(E), I(F), I(G), I(H), I(I), I(J), I(K), I((L), I(M), or I(N), or a combination of any nine of Formula I(A), I(B), I(C), I(D), I(E), I(F), I(G), I(H), I(I), I(J), I(K), I((L), I(M), or I(N), or a combination of any ten of Formula I(A), I(B), I(C), I(D), I(E), I(F), I(G), I(H), I(I), I(J), I(K), I((L), I(M), or I(N), or a combination of any eleven of Formula I(A), I(B), I(C), I(D), I(E), I(F), I(G), I(H), I(I), I(J), I(K), I((L), I(M), or I(N), or a combination of any twelve of Formula I(A), I(B), I(C), I(D), I(E), I(F), I(G), I(H), I(I), I(J), I(K), I((L), I(M), or I(N), or a combination of any thirteen of Formula I(A), I(B), I(C), I(D), I(E), I(F), I(G), I(H), I(I), I(J), I(K), I((L), I(M), or I(N), or all of Formulae or a combination of any ten of Formula I(A), I(B), I(C), I(D), I(E), I(F), I(G), I(H), I(I), I(J), I(K), I((L), I(M), and I(N).

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)NH$_2$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from halo, alkyl optionally substituted with 1-5 halo, —OH, —NH$_2$, alkenyl optionally substituted with 1-5 halo, phenyl optionally substituted with 1, 2 or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(O), I(H), I(I), I(J), I(K), I((L), I(M), or I(N), $R_{15}$ is —C(O)N(H)-cyclopropyl optionally substituted with 1 or 2 halo at any position on the cyclopropyl ring; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2 or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—CH$_3$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$ or —C(O)N(H)(C$_1$-C$_3$)alkyl-CF$_3$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-OCH$_3$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH₂, —C(O)O-alkyl, —CF₃, —OCF₃, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)NH₂; and $R_1$ is

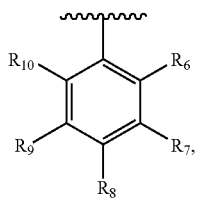

wherein $R_6$, $R_7$, $R_8$, $R_9$ and $R_{10}$ are each independently selected from H, halo, alkyl optionally substituted with 1-5 halo, —OH, —NH₂, alkenyl optionally substituted with 1-5 halo, phenyl optionally substituted with 1, 2, or 3 groups selected from halo and CF₃, —S(O)₂-alkyl, —S(O)₂—NH₂, —S(O)₂—N(H)-alkyl, —S(O)₂—N(alkyl)₂, cycloalkyl, heterocycloalkyl, alkynyl optionally substituted with 1-5 halo, —C(O)OH, —C(O)O—NH₂, —C(O)O-alkyl, —CF₃, —OCF₃, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)NH₂; and $R_1$ is

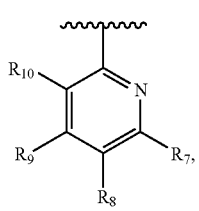

wherein $R_7$, $R_8$, $R_9$ and $R_{10}$ are each independently selected from H, halo, alkyl optionally substituted with 1-5 halo, alkyl optionally substituted with 1-2 —OH, —OH, —NH₂, alkenyl optionally substituted with 1-5 halo, phenyl optionally substituted with 1, 2, or 3 groups selected from halo and —CF₃, —S(O)₂-alkyl, —S(O)₂—NH₂, —S(O)₂—N(H)-alkyl, —S(O)₂—N(alkyl)₂, cycloalkyl, heterocycloalkyl, alkynyl optionally substituted with 1-5 halo, —C(O)OH, —C(O)O— NH₂, —C(O)O-alkyl, —CF₃, —OCF₃, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and $R_1$ is

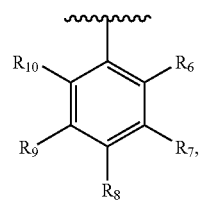

wherein $R_6$, $R_7$, $R_8$, $R_9$ and $R_{10}$ are each independently selected from H, halo, alkyl optionally substituted with 1-5 halo, —OH, —NH₂, alkenyl optionally substituted with 1-5 halo, phenyl optionally substituted with 1, 2, or 3 groups selected from halo and —CF₃, —S(O)₂-alkyl, —S(O)₂— NH₂, —S(O)₂—N(H)-alkyl, —S(O)₂—N(alkyl)₂, cycloalkyl, heterocycloalkyl, alkynyl optionally substituted with 1-5 halo, —C(O)OH, —C(O)O—NH₂, —C(O)O-alkyl, —CF₃, —OCF₃, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and $R_1$ is

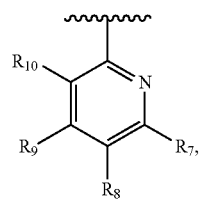

wherein $R_7$, $R_8$, $R_9$ and $R_{10}$ are each independently selected from H, halo, alkyl optionally substituted with 1-5 halo, alkyl optionally substituted with 1-2 —OH, —OH, —NH₂, alkenyl optionally substituted with 1-5 halo, phenyl optionally substituted with 1, 2, or 3 groups selected from halo and —CF₃, —S(O)₂-alkyl, —S(O)₂—NH₂, —S(O)₂—N(H)-alkyl, —S(O)₂—N(alkyl)₂, cycloalkyl, heterocycloalkyl, alkynyl optionally substituted with 1-5 halo, —C(O)OH, —C(O)O— NH₂, —C(O)O-alkyl, —CF₃, —OCF₃, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substited with 1 or 2 halo at any position on the cyclopropyl ring; and $R_1$ is

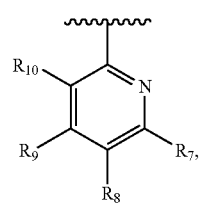

wherein $R_7$, $R_8$, $R_9$, and $R_{10}$, are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$alkyl, —S(O)$_2$—N(H)-alkyl, —S(O)$_2$—N(alkyl)$_2$, cycloakyl, heterocycoalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and $R_1$ is

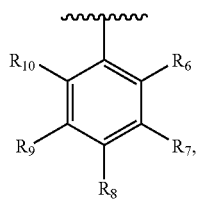

wherein $R_6$, $R_7$, $R_8$, $R_9$ and $R_{10}$ are each independently selected from H, halo, alkyl optionally substituted with 1-5 halo, —OH, —NH$_2$, alkenyl optionally substituted with 1-halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and $R_1$ is

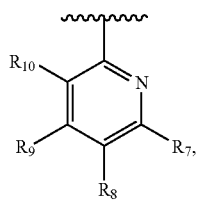

wherein $R_7$, $R_8$, $R_9$ and $R_{10}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—CH$_3$; and $R_1$ is

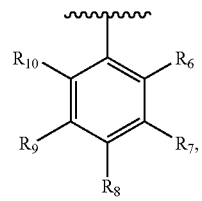

wherein $R_6$, $R_7$, $R_8$, $R_9$ and $R_{10}$ are each independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$—S(O)$_2$—CH$_3$; and $R_1$ is

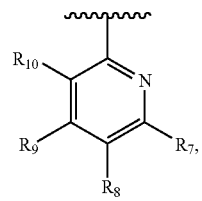

wherein $R_7$, $R_8$, $R_9$ and $R_{10}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and $R_1$ is

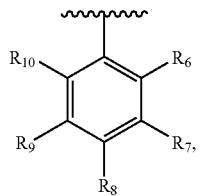

wherein $R_6$, $R_7$, $R_8$, $R_9$ and $R_{10}$ are each independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$—S(O)$_2$—NH$_2$; and $R_1$ is

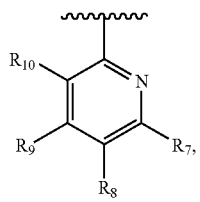

wherein $R_7$, $R_8$, $R_9$ and $R_{10}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$ or —C(O)N(H)(C$_1$-C$_3$)alkyl-CF$_3$; and $R_1$ is

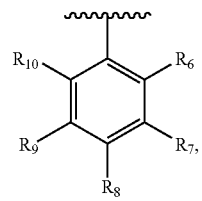

wherein $R_6$, $R_7$, $R_8$, $R_9$ and $R_{10}$ are each independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$ or —C(O)N(H)(C$_1$-C$_3$)alkyl-CF$_3$; and $R_1$ is

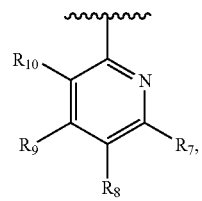

wherein $R_7$, $R_8$, $R_9$ and $R_{10}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-OCH$_3$; and $R_1$ is

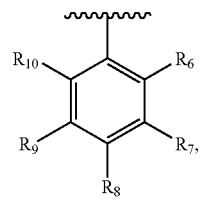

wherein $R_6$, $R_7$, $R_8$, $R_9$ and $R_{10}$ are each independently selected from H, halo, alkyl optionally substituted with 1-5 halo, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-OCH$_3$; and
$R_1$ is

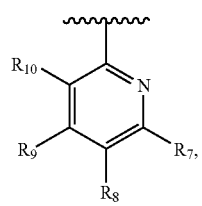

wherein $R_7$, $R_8$, $R_9$ and $R_{10}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl optionally substituted with 1, 2, or 3 groups selected from halo and —CF$_3$, —S(O)$_2$-alkyl, —S(O)$_2$—NH$_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)O—NH$_2$, —C(O)O-alkyl, —CF$_3$, —OCF$_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

In other separate embodiments for any combination of one or more of Formula I(A), I(B), I(C), I(D), I(E), I(F), I(G), I(H), I(I), I(J), I(K), I((L), I(M), or I(N), $R_{15}$ is selected from —C(O)NH$_2$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —S(O)$_2$—NH$_2$, —C(O)N(H)(C$_1$-C$_3$)alkyl-CF$_3$, and —C(O)N(H)(C$_1$-C$_3$)alkyl-OCH$_3$; and
$R_1$ is

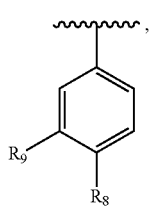

wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)NH$_2$; and
$R_1$ is

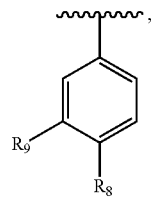

wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and
$R_1$ is

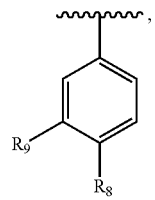

wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and
$R_1$ is

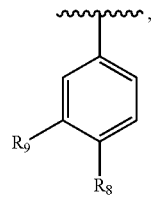

wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—CH$_3$; and
$R_1$ is

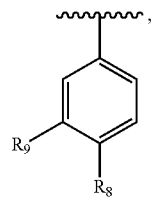

wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and
$R_1$ is

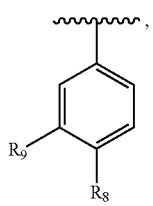, wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$ or —C(O)N(H)(C$_1$-C$_3$)alkyl-CF$_3$; and
$R_1$ is

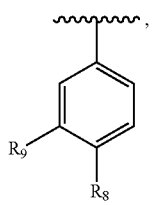, wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-OCH$_3$; and
$R_1$ is

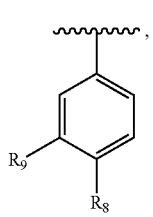, wherein $R_8$ and $R_9$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)NH$_2$; and
$R_1$ is

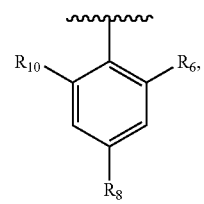

wherein $R_6$, $R_8$ and $R_{10}$ are each independently selected from Cl, F, hydroxyalkyl and —CF$_3$.

In other separate embodiments for each of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and
$R_1$ is

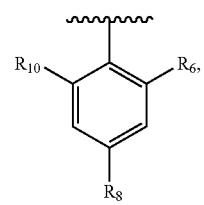

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and
$R_1$ is

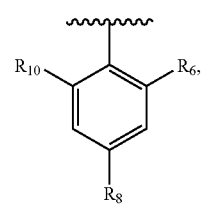

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—CH$_3$; and
$R_1$ is

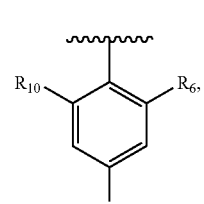

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and
$R_1$ is

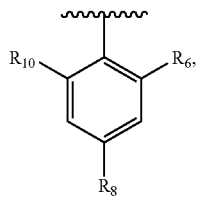

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$ or —C(O)N(H)(C$_1$-C$_3$)alkyl-CF$_3$; and
$R_1$ is

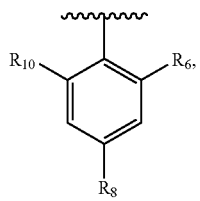

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is selected from —C(O)N(H)(C$_1$-C$_3$)alkyl-OCH$_3$; and
$R_1$ is

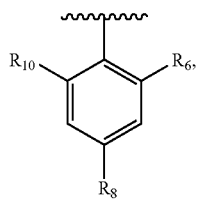

wherein $R_6$, $R_8$ and $R_{10}$ are each independently selected from Cl, F, hydroxyalkyl and —CF$_3$.

In other separate embodiments for any combination of one or more of Formula I(A), I(B), I(C), I(O), I(E), I(F), I(O), I(H), I(I), I(J), I(K), I((L), I(M), or I(N), $R_{15}$ is selected from —C(O)NH$_2$, —C(O)N(H)-cyclopropyl optionally substituted with 1 or 2 halo at any position on the cyclopropyl ring, —N(H)—S(O)$_2$—CH, —S(O)$_2$—CH$_3$, —S(O)$_2$—NH$_2$, —C(O)N(H)(C$_1$-C$_3$)alkyl-C(H)F$_2$, —C(O)N(H)(C$_1$-C$_3$)alkyl-CF$_3$, and —C(O)N(H)(C$_1$-C$_3$)alkyl-OCH$_3$; and
$R_1$ is

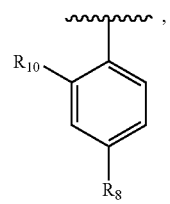

wherein $R_8$ and $R_{10}$ are each independently selected from Cl, F, hydroxyalkyl and —CF$_3$.

In other separate embodiments for any combination of one or more of Formula I(A), I(B), I(C), I(O), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and
$R_1$ is

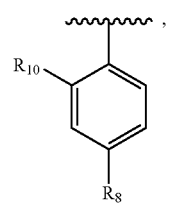

wherein $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and
$R_1$ is

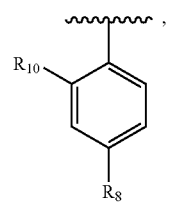

wherein $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—CH$_3$; and
$R_1$ is

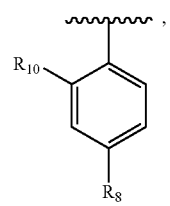

wherein $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N),
R$_{15}$ is —S(O)$_2$—NH$_2$; and
R$_1$ is

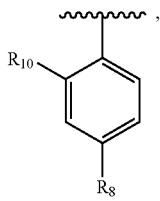

wherein R$_8$ and R$_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N),
R$_{15}$ is —C(O)N(H)(C$_1$-C$_3$)alkyl-C(H)F$_2$ or —C(O)N(H)(C$_1$-C$_3$)alkyl-CF$_3$; and
R$_1$ is

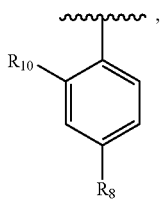

wherein R$_8$ and R$_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N),
R$_{15}$ is selected from —C(O)N(H)(C$_1$-C$_3$)alkyl-OCH$_3$; and
R$_1$ is

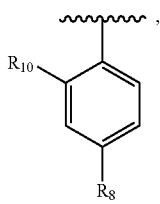

wherein R$_8$ and R$_{10}$ are each independently selected from Cl, F, hydroxyalkyl and —CF$_3$.

In other separate embodiments for any combination of one or more of Formula I(A), I(B), I(C), I(D), I(E), I(F), I(O), I(H), I(I), I(J), I(K), I((L), I(M), or I(N),
R$_{15}$ is selected from —C(O)NH$_2$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —S(O)$_2$—NH$_2$, —C(O)N(H)(C$_1$-C$_3$)alkyl-C(H)F$_2$, —C(O)N(H)(C$_1$-C$_3$)alkyl-CF$_3$, and —C(O)N(H)(C$_1$-C$_3$)alkyl-OCH$_3$; and
R$_1$ is

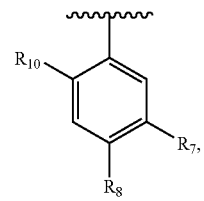

wherein R$_7$, R$_8$ and R$_{10}$ are each independently selected from Cl, F, hydroxyalkyl and In other separate embodiments for any combination of one or more of Formula I(A), I(B), I(C), I(D), I(E), I(F), I(G), I(H), I(I), I(J), I(K), I((L), I(M), or I(N),
R$_{15}$ is —C(O)N(H)-cyclopropyl optionally substituted with 1 or 2 halo at any position on the cyclopropyl ring; and
R$_1$ is

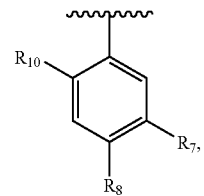

wherein R$_7$, R$_8$ and R$_{10}$ are each independently selected from H, Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N),
R$_{15}$ is —N(H)—S(O)$_2$—CH$_3$; and
R$_1$ is

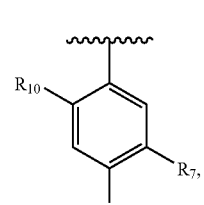

wherein R$_7$, R$_8$ and R$_{10}$ are each independently selected from Cl, F, hydroxyalkyl and —CF$_3$.

In other separate embodiments for each of Formula I(A), I(B), I(C), I(D), I(E), I(F), I(G), I(H), I(I), I(J), I(K), I((L), I(M), or I(N),
R$_{15}$ is —S(O)$_2$—CH$_3$; and
R$_1$ is wherein R$_7$, R$_8$ and R$_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and $R_1$ is

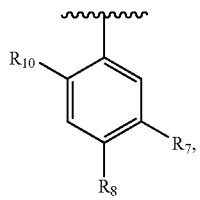

wherein $R_7$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)(C$_1$-C$_3$)alkyl-C(H)F$_2$, or —C(O)N(H)(C$_1$-C$_3$)alkyl-CF$_3$; and $R_1$ is

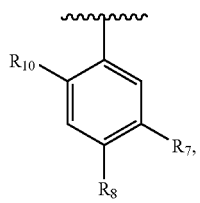

wherein $R_7$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is selected from —C(O)N(H)(C$_1$-C$_3$)alkyl-OCH$_3$; and $R_1$ is

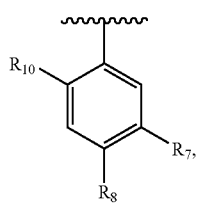

wherein $R_7$, $R_8$ and $R_{10}$ are each independently selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is selected from —C(O)NH$_2$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —S(O)$_2$—NH$_2$, —C(O)N(H)(C$_1$-C$_3$)alkyl-C(H)F$_2$, —C(O)N(H)(C$_1$-C$_3$)alkyl-CF$_3$, and —C(O)N(H)(C$_1$-C$_3$)alkyl-OCH$_3$; and $R_1$ is

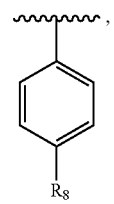

wherein $R_8$ is selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)-cyclopropyl optionally substituted with 1 or 2 halo at any position on the cyclopropyl ring; and $R_1$ is

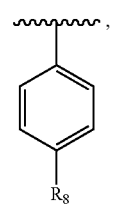

wherein $R_x$ is selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —N(H)—S(O)$_2$—CH$_3$; and $R_1$ is

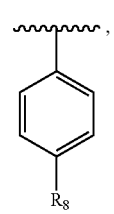

wherein $R_8$ is selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —S(O)$_2$—NH$_2$; and $R_1$ is

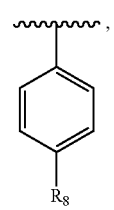

wherein $R_8$ is selected from Cl, F, hydroxyalkyl and —CF$_3$.

In other separate embodiments for any combination of one or more of Formula I(A), I(B), I(C), I(D), I(E), I(F), I(G), I(H), I(I), I(J), I(K), I((L), I(M), or I(N), $R_{15}$ is —C(O)N(H)($C_1$-$C_3$)alkyl-C(H)$F_2$ or —C(O)N(H)($C_1$-$C_3$)alkyl-$CF_3$; and
$R_1$ is

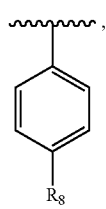

wherein $R_8$ is selected from Cl, F, hydroxyalkyl and —$CF_3$.

In other separate embodiments for any combination of one or more of Formula I(A), I(B), I(C), I(D), I(E), I(F), I(G), I(H), I(I), I(J), I(K), I((L), I(M), of I(N),
$R_{15}$ is selected from —C(O)N(H)($C_1$-$C_3$)alkyl-$OCH_3$; and
$R_1$ is

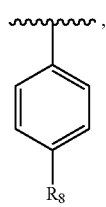

wherein $R_8$ is selected from Cl, F, hydroxyalkyl and —$CF_3$.

In other embodiments, any of the alkyl groups referred to in any of the above embodiments, including alkyl portions attached to other groups, can be a —($C_1$-$C_6$)alkyl group.

In other embodiments, any of the alkyl groups referred to in any of the above embodiments, including alkyl portions attached to other groups, can be a —($C_1$-$C_3$)alkyl group.

In other embodiments, any of the alkoxy groups referred to in any of the above embodiments, including alkoxy portions attached to other groups, can be a —($C_1$-$C_6$)alkoxy group.

In other embodiments, any of the alkoxy groups referred to in any of the above embodiments, including alkoxy portions attached to other groups, can be a —($C_1$-$C_3$)alkoxy group.

In other embodiments, any of the heterocycloalkyl groups referred to in any of the above embodiments, including heterocycloalkyl portions attached to other groups, can be a (4-6 membered) heterocycloalkyl group.

In other embodiments, any of the cycloalkyl groups referred to in any of the above embodiments, can be a —($C_3$-$C_6$)cycloalkyl group.

In another embodiment, the compound of Formula I, or its pharmaceutically acceptable salt, is selected from one of the following compounds from Table I (the activity for each of these compounds, listed underneath the name of each compound, is categorized as A, B or C, which are each defined below Table I):

TABLE I

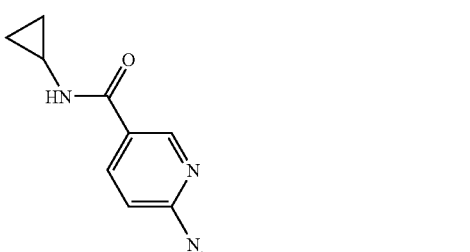

| No. | Name/Activity | Structure |
|---|---|---|
| 1 | 6-[3-endo-({[1-(4-chlorophenyl)cyclopropyl]carbonyl}amino)-8-azabicyclo[3.2.1]oct-8-yl]-N-cyclopropylpyridine-3-carboxamide<br>ACTIVITY = A | 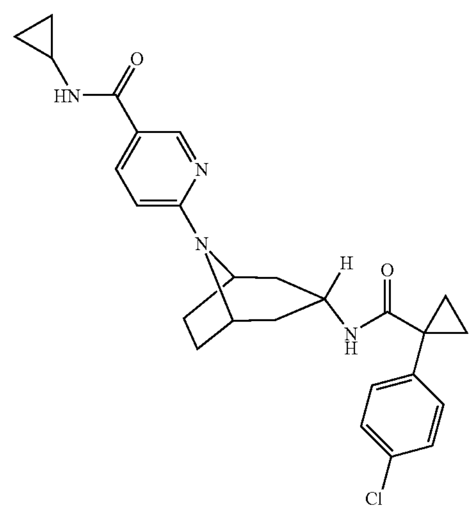 |

TABLE I-continued

| No. | Name/Activity | Structure |
|---|---|---|
| 2 | 2-[3-endo-({[1-(4-chlorophenyl)cyclopropyl]carbonyl}amino)-8-azabicyclo[3.2.1]oct-8-yl]pyridine-3-carboxamide<br>ACTIVITY = B | 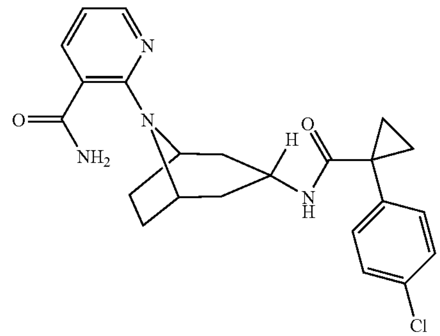 |
| 3 | methyl 6-[3-endo-({[1-(4-chlorophenyl)cyclopropyl]carbonyl}amino)-8-azabicyclo[3.2.1]oct-8-yl]pyridine-3-carboxylate<br>ACTIVITY = A | 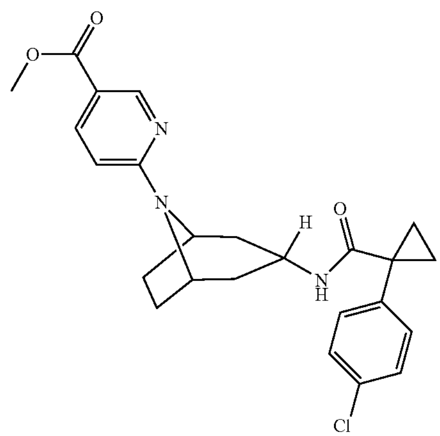 |
| 4 | 6-[3-endo-({[1-(4-chlorophenyl)cyclopropyl]carbonyl}amino)-8-azabicyclo[3.2.1]oct-8-yl]pyridine-3-carboxamide<br>ACTIVITY = A | 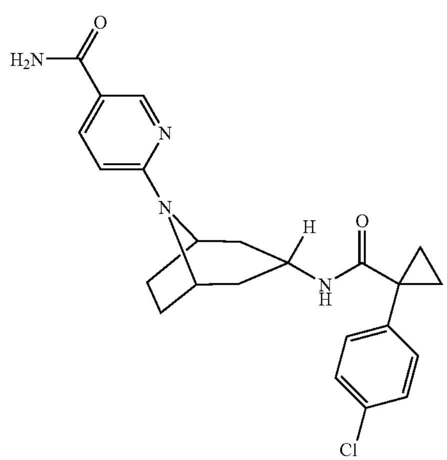 |
| 5 | 1-(4-chlorophenyl)-N-{8-[3-(trifluoromethyl)pyridin-2-yl]-8-azabicyclo[3.2.1]oct-3-yl}cyclopropanecarboxamide<br>ACTIVITY = B | 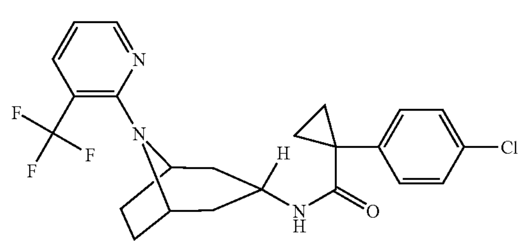 |

TABLE I-continued

| No. | Name/ Activity | Structure |
|---|---|---|
| 6 | 1-(4-chlorophenyl)-N-[8-(5-cyanopyridin-2-yl)-8-azabicyclo[3.2.1]oct-3-endo-yl]cyclopropanecarboxamide ACTIVITY = A | 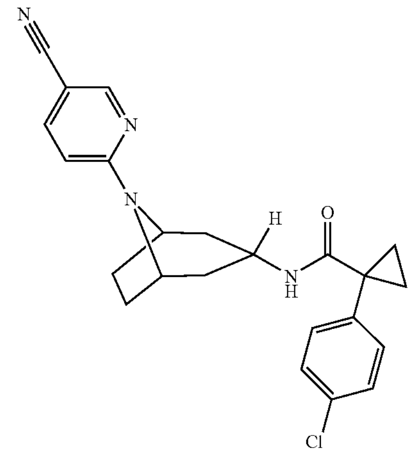 |
| 7 | 6-[3-({[1-(4-chlorophenyl)cyclopentyl]carbonyl}amino)-8-azabicyclo[3.2.1]oct-8-yl]-N-cyclopropylpyridine-3-carboxamide ACTIVITY = A | 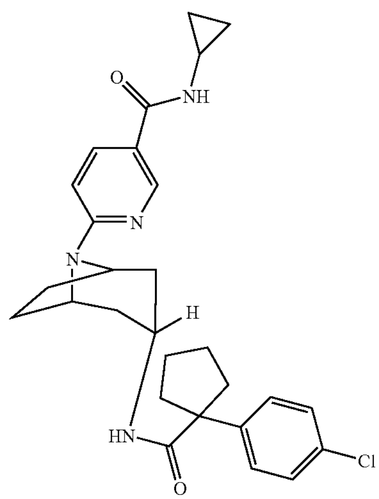 |
| 8 | N-cyclopropyl-6-[3-endo-({[1-(2,4-dichlorophenyl)cyclopropyl]carbonyl}amino)-8-azabicyclo[3.2.1]oct-8-yl]pyridine-3-carboxamide ACTIVITY = A | 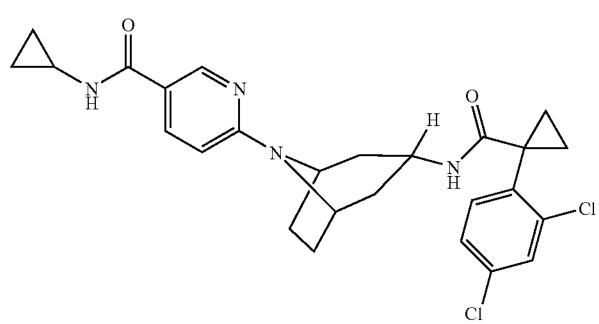 |
| 9 | N-cyclopropyl-6-(3-endo-{[(1-phenylcyclopropyl)carbonyl]amino}-8-azabicyclo[3.2.1]oct-8-yl)pyridine-3-carboxamide ACTIVITY = A | 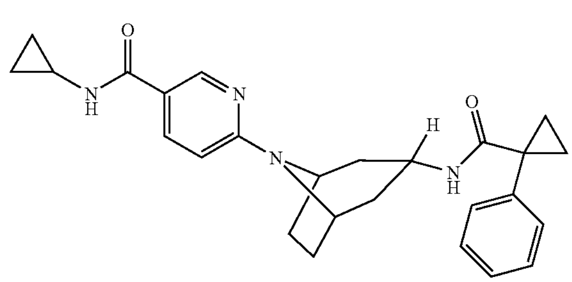 |

TABLE I-continued

| No. | Name/Activity | Structure |
|-----|---------------|-----------|
| 10 | N-cyclopropyl-6-[3-endo-({[1-(3,4-dichlorophenyl)cyclopropyl]carbonyl}amino)-8-azabicyclo[3.2.1]oct-8-yl]pyridine-3-carboxamide<br>ACTIVITY = A | 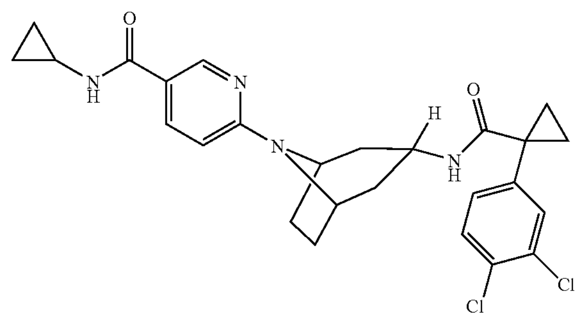 |
| 11 | N-cyclopropyl-6-[3-endo-({[1-(4-fluorophenyl)cyclopropyl]carbonyl}amino)-8-azabicyclo[3.2.1]oct-8-yl]pyridine-3-carboxamide<br>ACTIVITY = A | 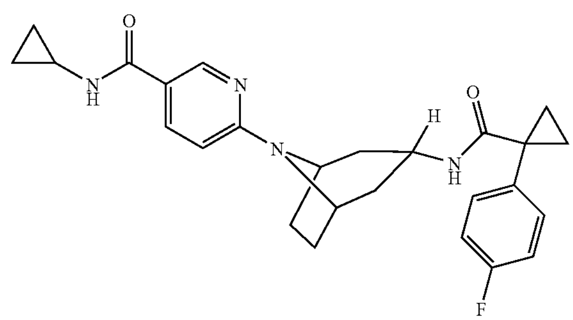 |
| 12 | 6-[3-endo-({[1-(4-chlorophenyl)cyclopropyl]carbonyl}amino)-8-azabicyclo[3.2.1]oct-8-yl]-N-(1-methylethyl)pyridine-3-carboxamide<br>ACTIVITY = A | 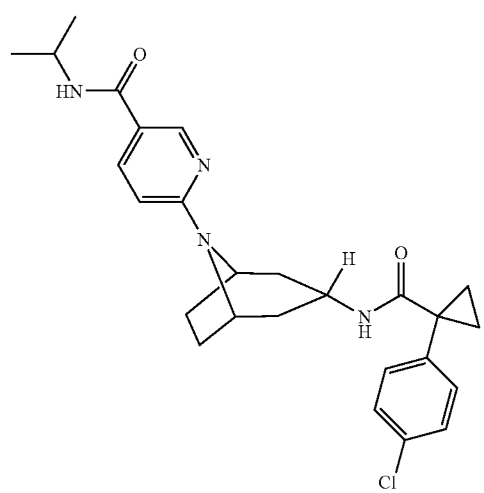 |
| 13 | 6-[3-endo-({2-[(4-chlorophenyl)oxy]-2-methylpropanoyl}amino)-8-azabicyclo[3.2.1]oct-8-yl]-N-cyclopropylpyridine-3-carboxamide<br>ACTIVITY = A | 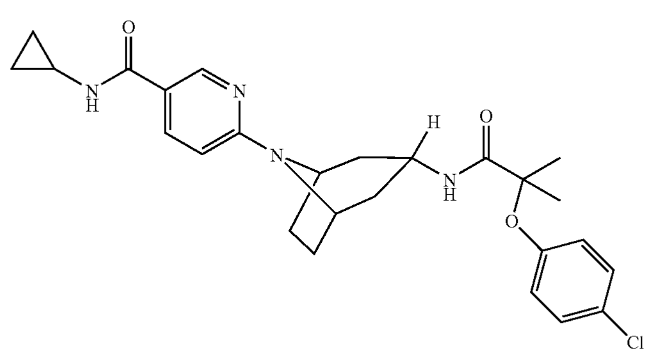 |

TABLE I-continued

| No. | Name/Activity | Structure |
|---|---|---|
| 14 | 6-[3-endo-({2-[(3-chlorophenyl)oxy]-2-methylpropanoyl}amino)-8-azabicyclo[3.2.1]oct-8-yl]-N-cyclopropylpyridine-3-carboxamide<br>ACTIVITY = A | 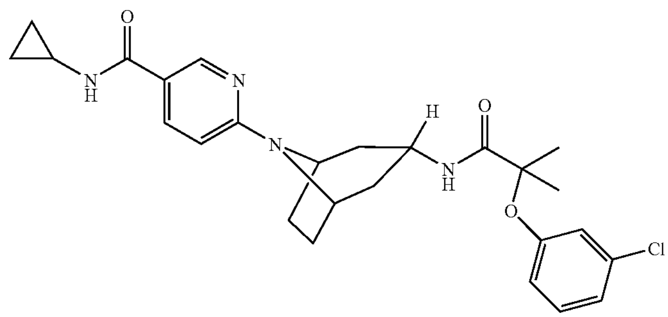 |
| 15 | N-cyclopropyl-6-(3-endo-{[2-methyl-2-(phenyloxy)propanoyl]amino}-8-azabicyclo[3.2.1]oct-8-yl)pyridine-3-carboxamide<br>ACTIVITY = A | 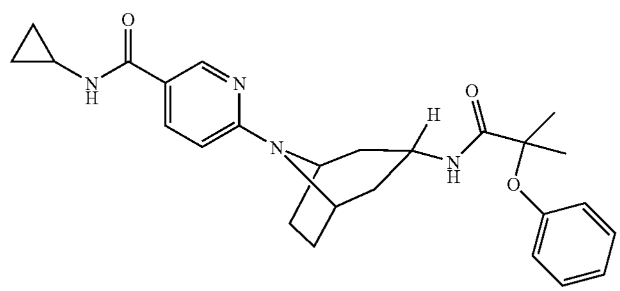 |
| 16 | 6-[3-endo-({[1-(3-chlorophenyl)cyclopropyl]carbonyl}amino)-8-azabicyclo[3.2.1]oct-8-yl]-N-cyclopropylpyridine-3-carboxamide<br>ACTIVITY = A | 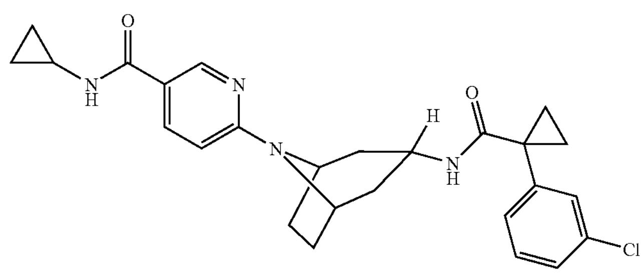 |
| 17 | 6-[3-endo-({[1-(2-chlorophenyl)cyclopropyl]carbonyl}amino)-8-azabicyclo[3.2.1]oct-8-yl]-N-cyclopropylpyridine-3-carboxamide<br>ACTIVITY = A | 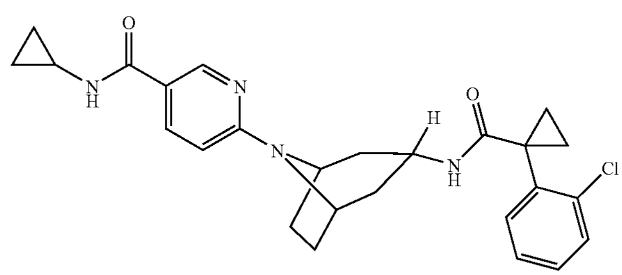 |
| 18 | 1-(4-chlorophenyl)-N-[8-(4-cyanopyridin-2-yl)-8-azabicyclo[3.2.1]oct-3-endo-yl]cyclopropanecarboxamide<br>ACTIVITY = B | 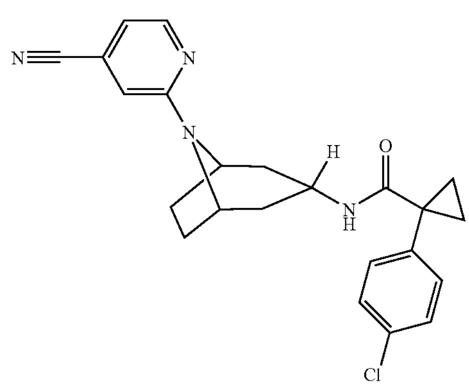 |

TABLE I-continued

| No. | Name/Activity | Structure |
|---|---|---|
| 19 | 6-[3-endo-({[1-(4-chlorophenyl)cyclopropyl]carbonyl}amino)-8-azabicyclo[3.2.1]oct-8-yl]pyridine-3-carboxylic acid<br>ACTIVITY = B | 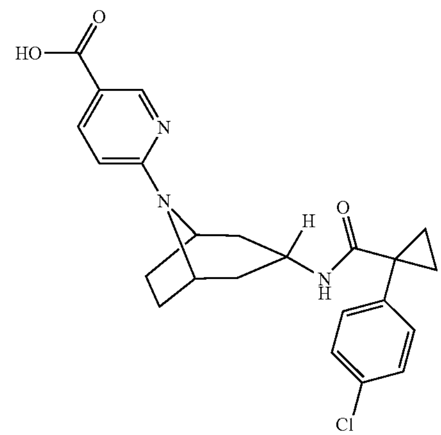 |
| 20 | 6-(3-endo-{[2-(4-chlorophenyl)-2-methylpropanoyl]amino}-8-azabicyclo[3.2.1]oct-8-yl)-N-cyclopropylpyridine-3-carboxamide<br>ACTIVITY = A | 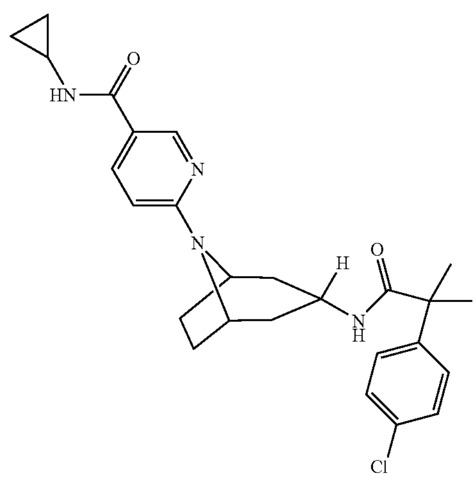 |
| 21 | N-cyclopropyl-6-{3-endo-[(2-methyl-2-phenylpropanoyl)amino]-8-azabicyclo[3.2.1]oct-8-yl}pyridine-3-carboxamide<br>ACTIVITY = A | 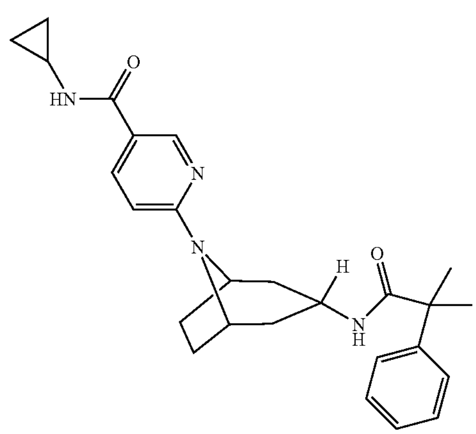 |

TABLE I-continued

| No. | Name/Activity | Structure |
|---|---|---|
| 22 | 6-[3-endo-({[1-(4-chlorophenyl)cyclopropyl]carbonyl}amino)-8-azabicyclo[3.2.1]oct-8-yl]-N-(2,2,2-trifluoroethyl)pyridine-3-carboxamide<br>ACTIVITY = A | 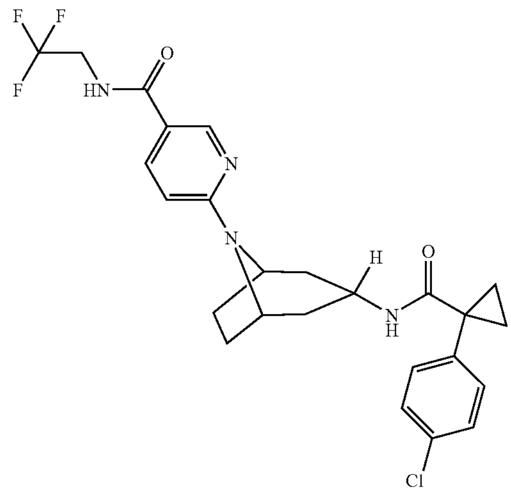 |
| 23 | N-cyclopropyl-6-[3-endo-({[1-(4-methylphenyl)cyclopropyl]carbonyl}amino)-8-azabicyclo[3.2.1]oct-8-yl]pyridine-3-carboxamide<br>ACTIVITY = A | 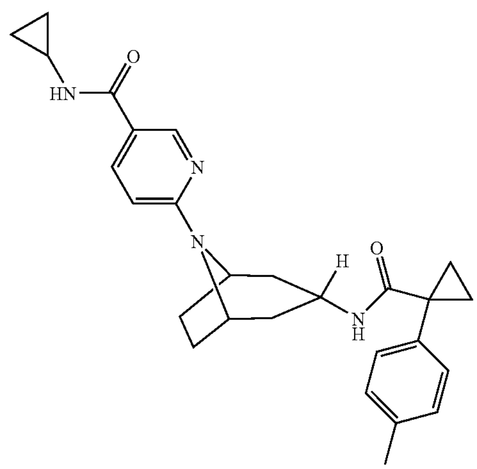 |
| 24 | 6-[3-endo-({2-[(2-chlorophenyl)oxy]-2-methylpropanoyl}amino)-8-azabicyclo[3.2.1]oct-8-yl]-N-cyclopropylpyridine-3-carboxamide<br>ACTIVITY = A | 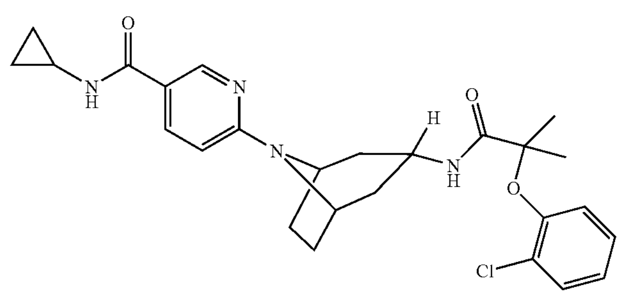 |
| 25 | 6-(3-endo-{[2-(3-chlorophenyl)-2-methylpropanoyl]amino}-8-azabicyclo[3.2.1]oct-8-yl)-N-cyclopropylpyridine-3-carboxamide<br>ACTIVITY = A | 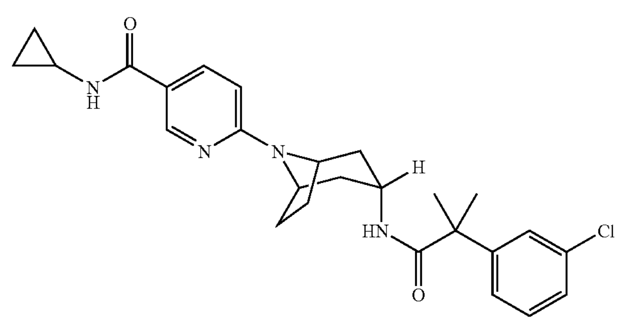 |

TABLE I-continued

| No. | Name/Activity | Structure |
|---|---|---|
| 26 | 6-(3-endo-{[2-(4-chlorophenyl)-2-methylpropanoyl]amino}-8-azabicyclo[3.2.1]oct-8-yl)-N-(2,2,2-trifluoroethyl)pyridine-3-carboxamide<br>ACTIVITY = A | 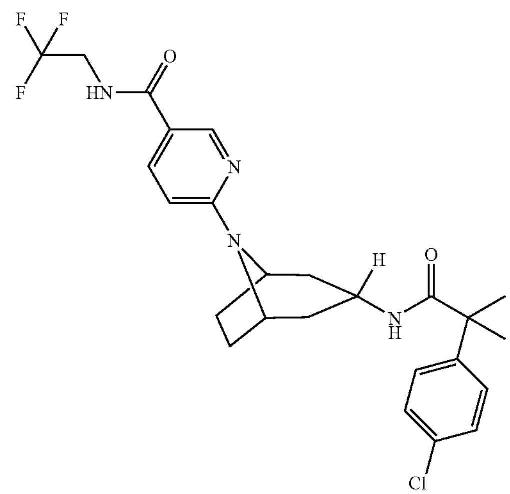 |
| 27 | 6-[3-endo-({2-[(4-chlorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 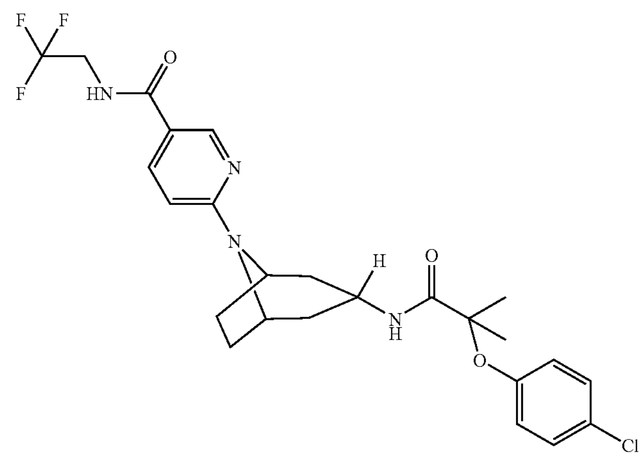 |
| 28 | N-cyclopropyl-6-[3-endo-({[1-(3,4-difluorophenyl)cyclopropyl]carbonyl}amino)-8-azabicyclo[3.2.1]oct-8-yl]pyridine-3-carboxamide<br>ACTIVITY = A | 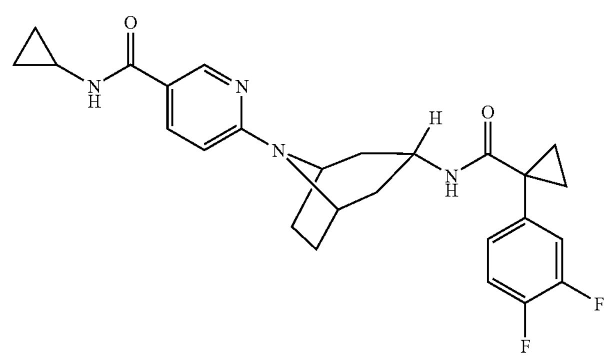 |

TABLE I-continued

| No. | Name/Activity | Structure |
|---|---|---|
| 29 | 6-[3-endo-({2-[(2-chlorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 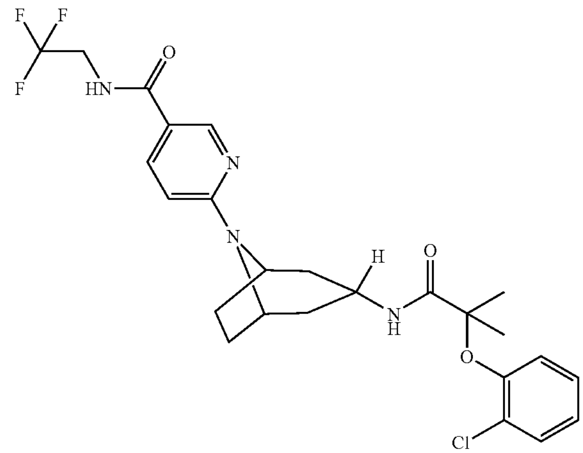 |
| 30 | 6-[3-endo-({2-[(4-chlorophenyl)oxy]-2-methylpropanoyl}amino)-8-azabicyclo[3.2.1]oct-8-yl]-N-(1-methylethyl)pyridine-3-carboxamide<br>ACTIVITY = A | 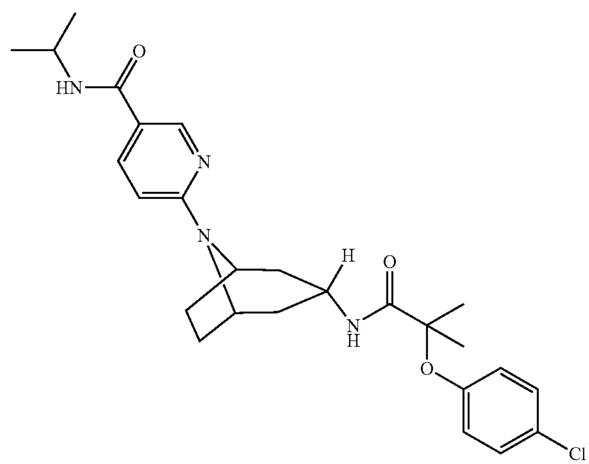 |
| 31 | N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide<br>ACTIVITY = A | 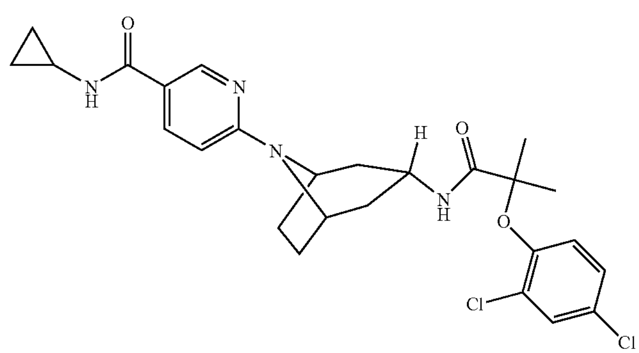 |

TABLE I-continued

| No. | Name/Activity | Structure |
|---|---|---|
| 32 | 2-[(4-chlorophenyl)oxy]-N-[8-(5-cyanopyridin-2-yl)-8-azabicyclo[3.2.1]oct-3-endo-yl]-2-methylpropanamide<br>ACTIVITY = A | 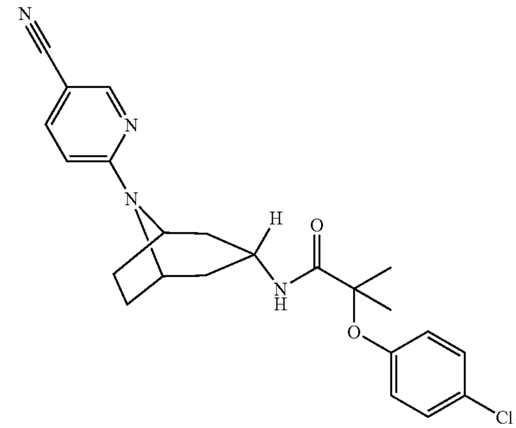 |
| 33 | N-cyclopropyl-6-[3-endo-({2-[(3,4-difluorophenyl)oxy]-2-methylpropanoyl}amino)-8-azabicyclo[3.2.1]oct-8-yl]pyridine-3-carboxamide<br>ACTIVITY = A | 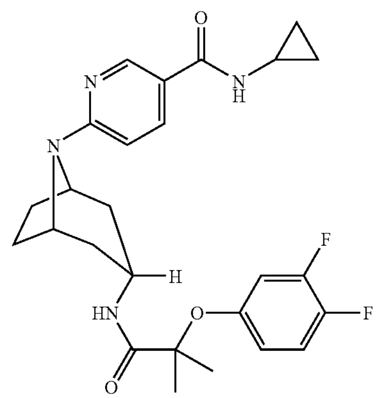 |
| 34 | 6-(3-endo-{[2-(2-chlorophenyl)-2-methylpropanoyl]amino}-8-azabicyclo[3.2.1]oct-8-yl)-N-cyclopropylpyridine-3-carboxamide<br>ACTIVITY = A | 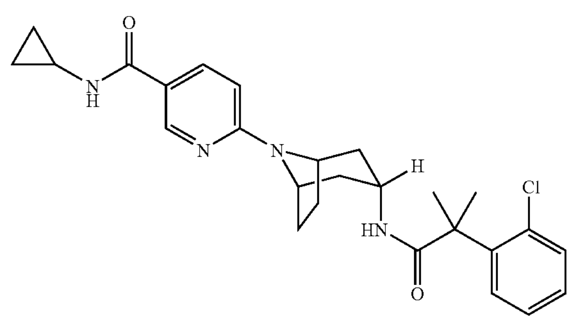 |
| 35 | N-cyclopropyl-6-[3-endo-({2-[(2,4-difluorophenyl)oxy]-2-methylpropanoyl}amino)-8-azabicyclo[3.2.1]oct-8-yl]pyridine-3-carboxamide<br>ACTIVITY = A | 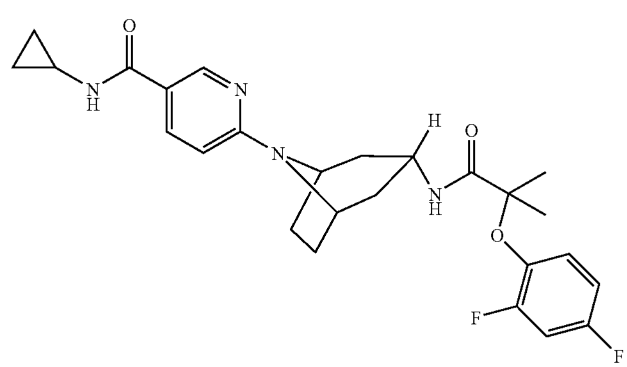 |

TABLE I-continued

| No. | Name/ Activity | Structure |
|---|---|---|
| 36 | 2-[3-endo-({2-[(4-chlorophenyl)oxy]-2-methylpropanoyl}amino)-8-azabicyclo[3.2.1]oct-8-yl]-N-cyclopropylpyrimidine-5-carboxamide<br>ACTIVITY = A | 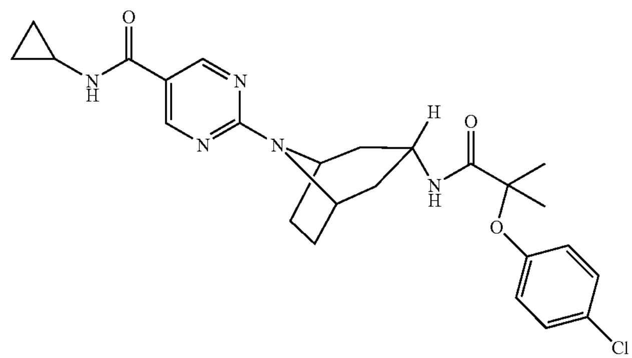 |
| 37 | N-cyclopropyl-6-{3-endo-[(2-methyl-2-{[4-(trifluoromethyl)phenyl]oxy}propanoyl)amino]-8-azabicyclo[3.2.1]oct-8-yl}pyridine-3-carboxamide<br>ACTIVITY = A | 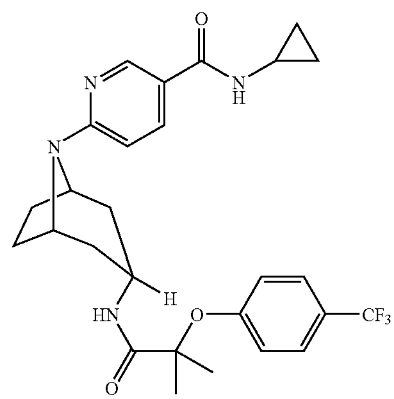 |
| 38 | 6-[3-endo-({2-[(4-cyanophenyl)oxy]-2-methylpropanoyl}amino)-8-azabicyclo[3.2.1]oct-8-yl]-N-cyclopropylpyridine-3-carboxamide<br>ACTIVITY = A | 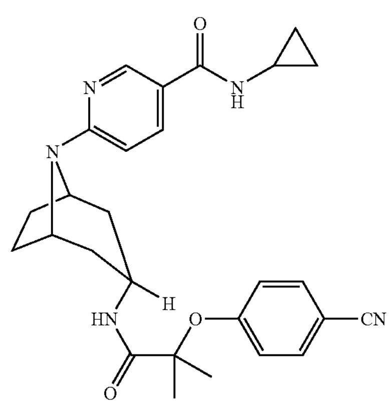 |
| 39 | N-cyclopropyl-6-[3-endo-({[1-(3-fluorophenyl)cyclopropyl]carbonyl}amino)-8-azabicyclo[3.2.1]oct-8-yl]pyridine-3-carboxamide<br>ACTIVITY = A | 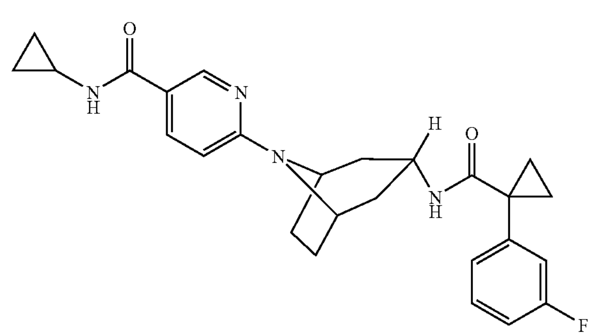 |

TABLE I-continued

| No. | Name/Activity | Structure |
|---|---|---|
| 40 | 6-[3-endo-({2-[(4-chlorophenyl)oxy]-2-methylpropanoyl}amino)-8-azabicyclo[3.2.1]oct-8-yl]-N-cyclopropyl-5-methylpyridine-3-carboxamide<br>ACTIVITY = A | 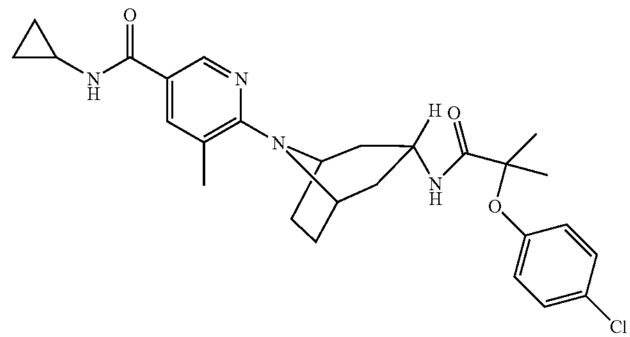 |
| 41 | 6-[3-endo-({2-[(4-chloro-2-fluorophenyl)oxy]-2-methylpropanoyl}amino)-8-azabicyclo[3.2.1]oct-8-yl]-N-cyclopropylpyridine-3-carboxamide<br>ACTIVITY = A | 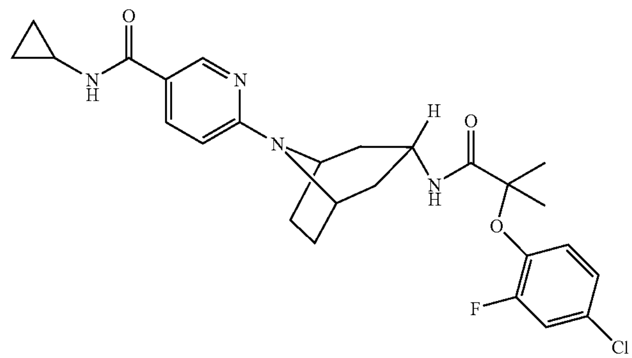 |
| 42 | N-cyclopropyl-6-[3-endo-({2-[(3,4-dichlorophenyl)oxy]-2-methylpropanoyl}amino)-8-azabicyclo[3.2.1]oct-8-yl]pyridine-3-carboxamide<br>ACTIVITY = A | 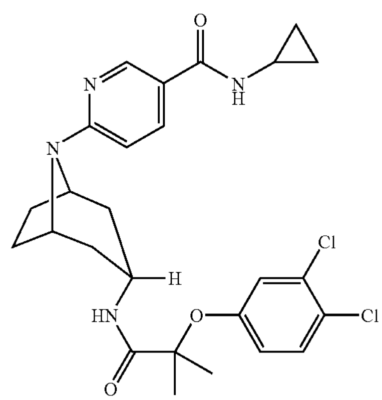 |
| 43 | 6-[3-endo-({2-[(4-chloro-3-fluorophenyl)oxy]-2-methylpropanoyl}amino)-8-azabicyclo[3.2.1]oct-8-yl]-N-cyclopropylpyridine-3-carboxamide<br>ACTIVITY = A | 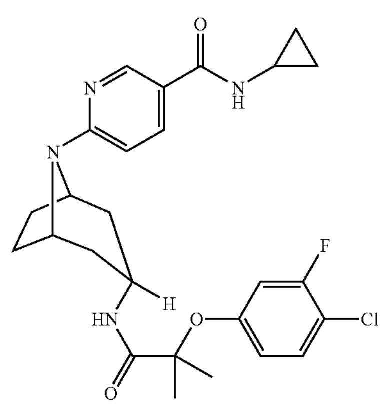 |

TABLE I-continued

| No. | Name/Activity | Structure |
|---|---|---|
| 44 | N-cyclopropyl-6-{3-endo-[(2-methyl-2-{[4-(methyloxy)phenyl]oxy}propanoyl)amino]-8-azabicyclo[3.2.1]oct-8-yl}pyridine-3-carboxamide<br>ACTIVITY = A | 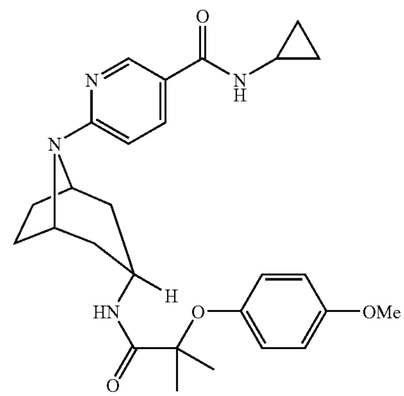 |
| 45 | N-cyclopropyl-6-[3-endo-({[1-(phenyloxy)cyclopropyl]carbonyl}amino)-8-azabicyclo[3.2.1]oct-8-yl]pyridine-3-carboxamide<br>ACTIVITY = A | 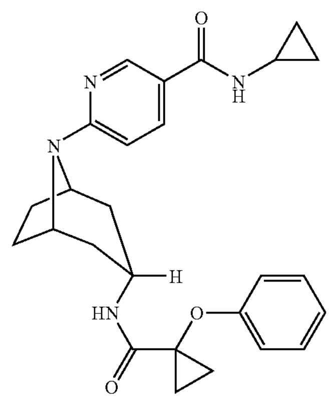 |
| 46 | N-cyclopropyl-6-[3-endo-({[1-(phenyloxy)cyclobutyl]carbonyl}amino)-8-azabicyclo[3.2.1]oct-8-yl]pyridine-3-carboxamide<br>ACTIVITY = A | 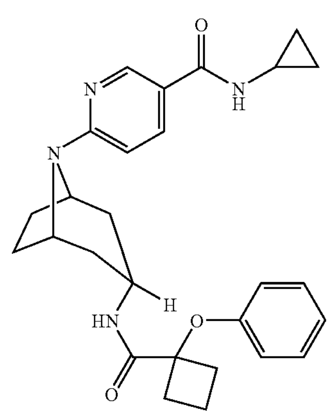 |

TABLE I-continued

| No. | Name/Activity | Structure |
|---|---|---|
| 47 | 6-{3-endo-[({1-[(4-chlorophenyl)oxy]cyclobutyl}carbonyl)amino]-8-azabicyclo[3.2.1]oct-8-yl}-N-cyclopropylpyridine-3-carboxamide<br>ACTIVITY = A | 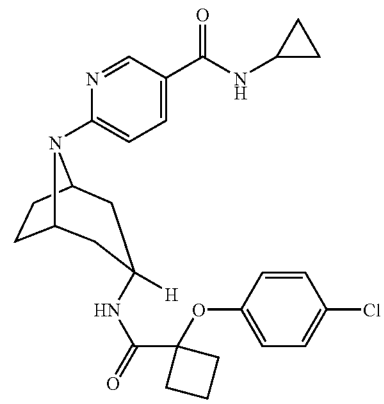 |
| 48 | N-cyclopropyl-6-(3-endo-{[2-(phenyloxy)propanoyl]amino}-8-azabicyclo[3.2.1]oct-8-yl)pyridine-3-carboxamide<br>ACTIVITY = B | 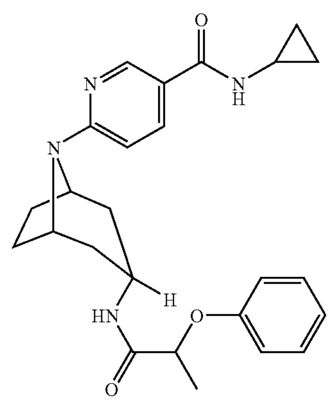 |
| 49 | 6-[3-endo-({2-[(4-chlorophenyl)oxy]propanoyl}amino)-8-azabicyclo[3.2.1]oct-8-yl]-N-cyclopropylpyridine-3-carboxamide<br>ACTIVITY = B | 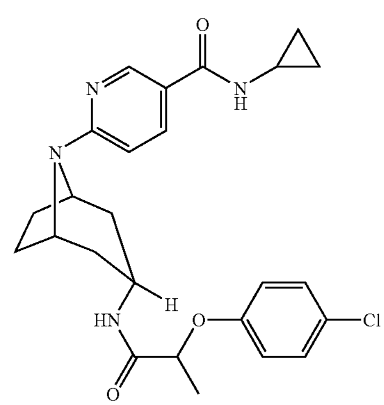 |

TABLE I-continued

| No. | Name/Activity | Structure |
|---|---|---|
| 50 | 6-[3-endo-({[1-(4-chlorophenyl)cyclobutyl]carbonyl}amino)-8-azabicyclo[3.2.1]oct-8-yl]-N-cyclopropylpyridine-3-carboxamide<br>ACTIVITY = A | 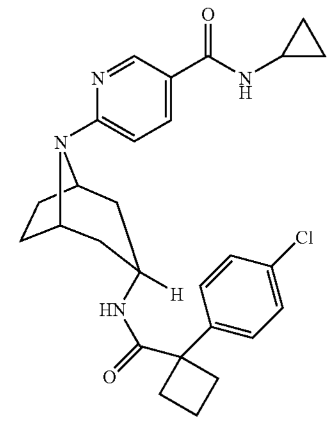 |
| 51 | 6-[3-endo-({2-[(4-chlorophenyl)oxy]-2-methylpropanoyl}amino)-8-azabicyclo[3.2.1]oct-8-yl]-N-cyclopropyl-2-methylpyridine-3-carboxamide<br>ACTIVITY = B | 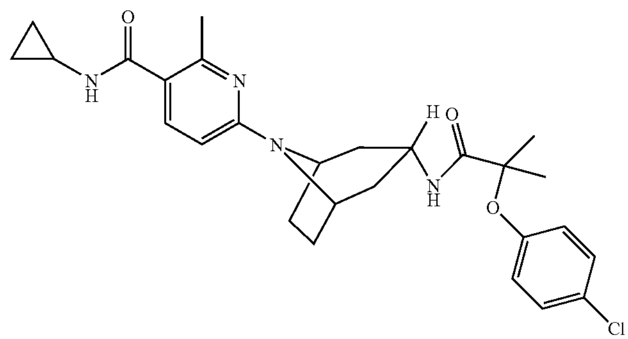 |
| 52 | 6-[3-endo-({2-[(2-chloro-4-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 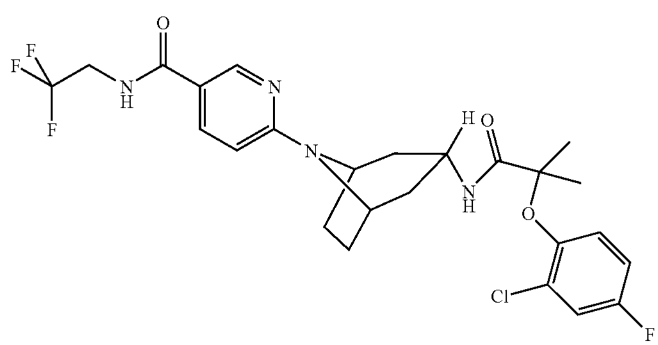 |
| 53 | 2-[(2,4-dichlorophenyl)oxy]-N-{8-[5-(1-hydroxy-1-methylethyl)pyridin-2-yl]-8-azabicyclo[3.2.1]oct-3-endo-yl}-2-methylpropanamide<br>ACTIVITY = B | 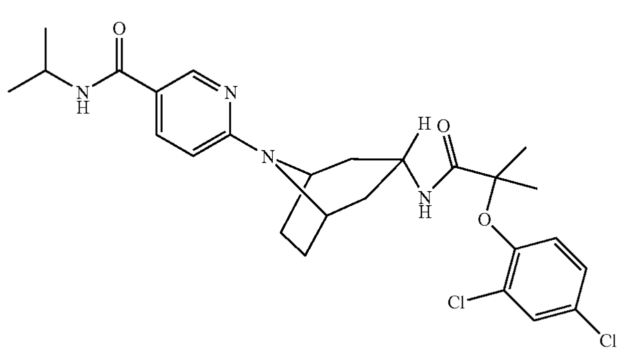 |

TABLE I-continued

| No. | Name/Activity | Structure |
|---|---|---|
| 54 | 6-[3-endo-({2-[(2,4-dichlorophenyl)oxy]-2-methylpropanoyl}amino)-8-azabicyclo[3.2.1]oct-8-yl]-N-(1-methylethyl)pyridine-3-carboxamide<br>ACTIVITY = A | 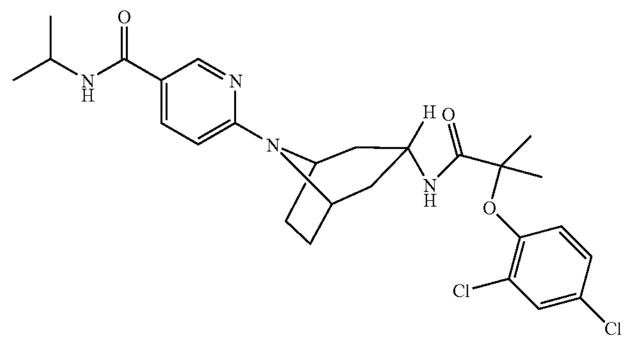 |
| 55 | N-[8-(5-cyanopyridin-2-yl)-8-azabicyclo[3.2.1]oct-3-endo-yl]-2-[(2,4-dichlorophenyl)oxy]-2-methylpropanamide<br>ACTIVITY = A | 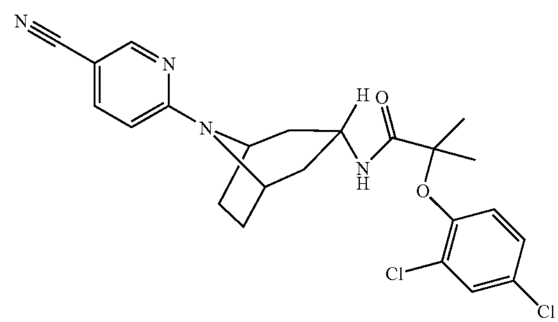 |
| 56 | 6-[3-endo-({2-[(2,4-dichlorophenyl)oxy]-2-methylpropanoyl}amino)-8-azabicyclo[3.2.1]oct-8-yl]pyridine-3-carboxamide<br>ACTIVITY = A | 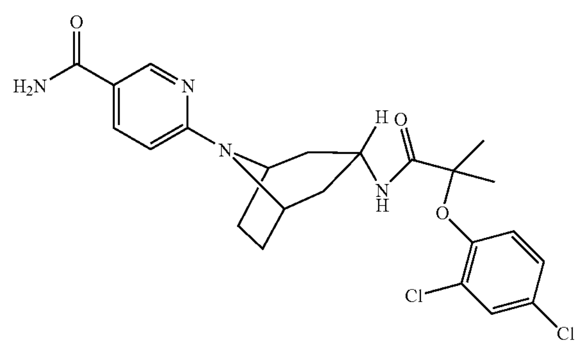 |
| 57 | N-[8-(5-acetylpyridin-2-yl)-8-azabicyclo[3.2.1]oct-3-endo-yl]-1-(4-chlorophenyl)cyclopropanecarboxamide<br>ACTIVITY = A | 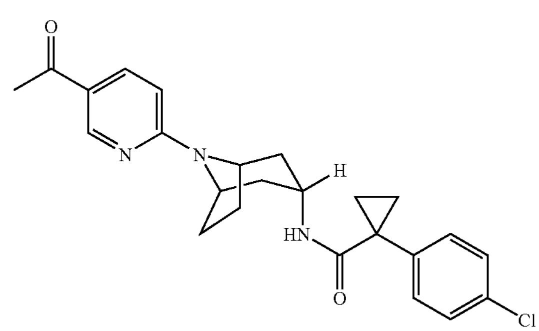 |

TABLE I-continued

| No. | Name/Activity | Structure |
|---|---|---|
| 58 | N-{8-[5-(acetylamino)pyridin-2-yl]-8-azabicyclo[3.2.1]oct-3-endo-yl}-1-(4-chlorophenyl)cyclopropane carboxamide<br>ACTIVITY = A | 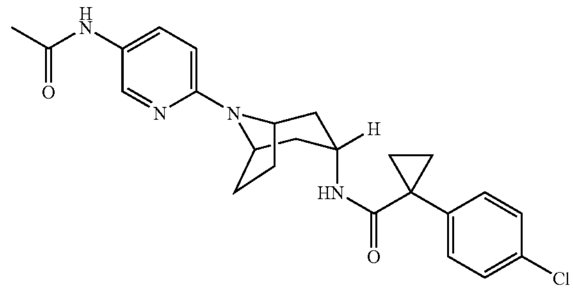 |
| 59 | 1-(4-chlorophenyl)-N-(8-{5-[(cyclopropylcarbonyl)amino]pyridin-2-yl}-8-azabicyclo[3.2.1]oct-3-endo-yl)cyclopropanecarboxamide<br>ACTIVITY = A | 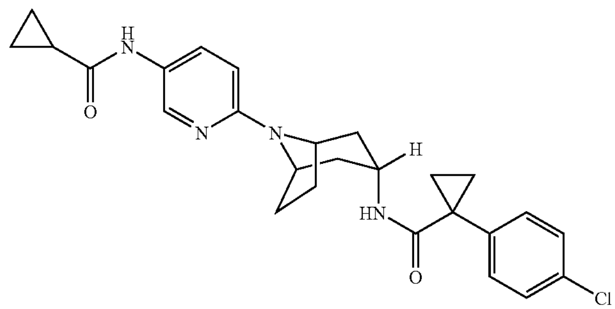 |
| 60 | 1-(4-chlorophenyl)-N-(8-{5-[(methylsulfonyl)amino]pyridin-2-yl}-8-azabicyclo[3.2.1]oct-3-endo-yl)cyclopropanecarboxamide<br>ACTIVITY = A | 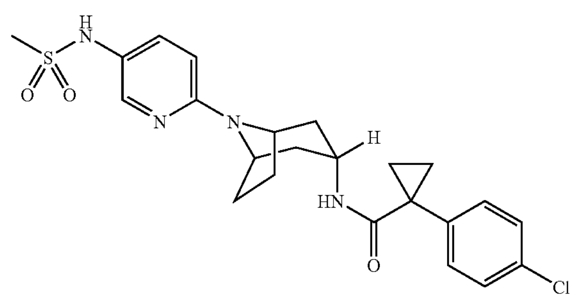 |
| 61 | N-[8-(5-aminopyridin-2-yl)-8-azabicyclo[3.2.1]oct-3-endo-yl]-1-(4-chlorophenyl)cyclopropane carboxamide<br>ACTIVITY = A | 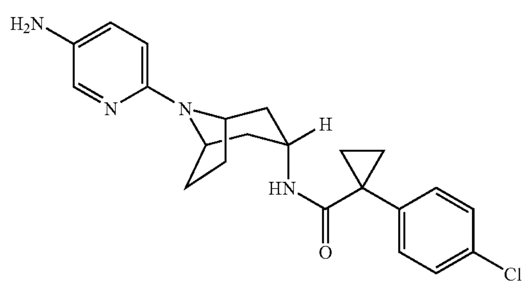 |
| 62 | 4-[3-endo-({[1-(4-chlorophenyl)cyclopropyl]carbonyl}amino)-8-azabicyclo[3.2.1]oct-8-yl]-N-cyclopropylbenzamide<br>ACTIVITY = A | 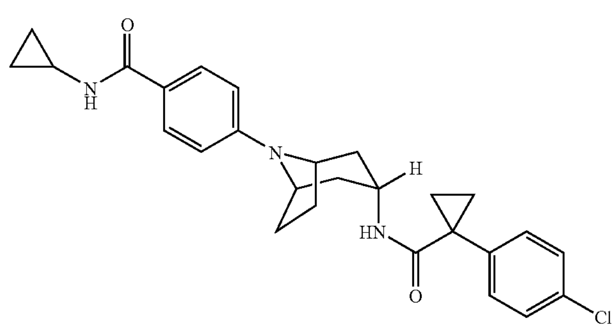 |

TABLE I-continued

| No. | Name/Activity | Structure |
|---|---|---|
| 63 | 2-chloro-4-[3-endo-({[1-(4-chlorophenyl)cyclopropyl]carbonyl}amino)-8-azabicyclo[3.2.1]oct-8-yl]-N-cyclopropylbenzamide<br>ACTIVITY = A | 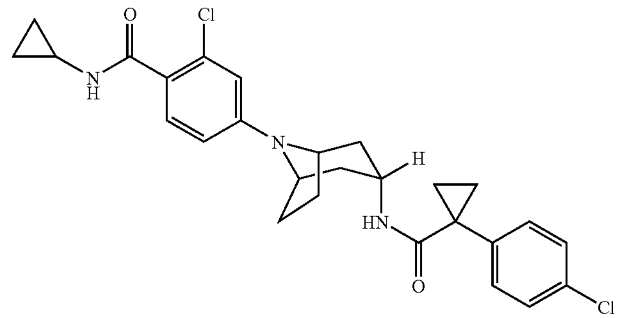 |
| 64 | 6-{3-endo-[({1-[(4-chlorophenyl)oxy]cyclopropyl}carbonyl)amino]-8-azabicyclo[3.2.1]oct-8-yl}-N-cyclopropylpyridine-3-carboxamide<br>ACTIVITY = A | 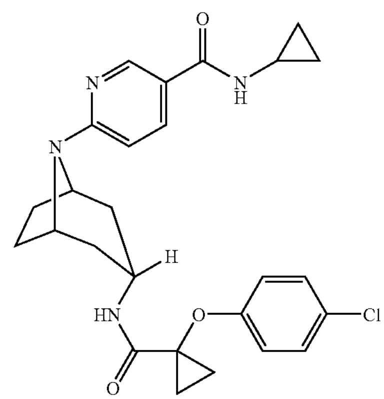 |
| 65 | 6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 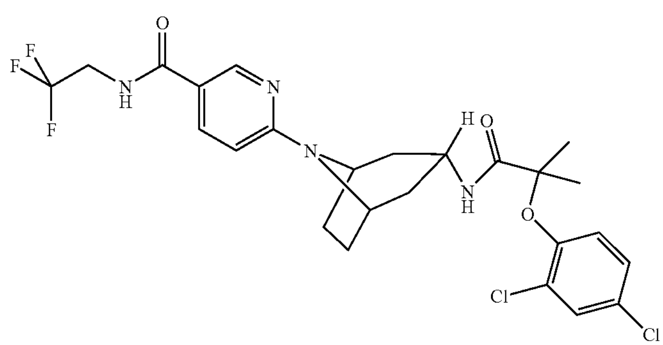 |
| 66 | 2-[(4-chlorophenyl)oxy]-2-methyl-N-(8-pyrazin-2-yl-8-azabicyclo[3.2.1]oct-3-endo-yl)propanamide<br>ACTIVITY = A | 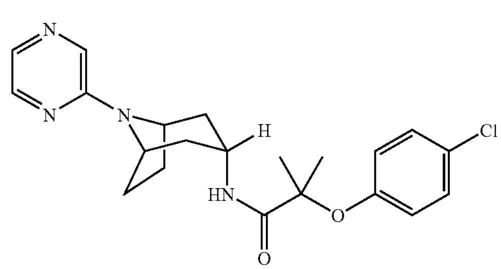 |

TABLE I-continued

| No. | Name/Activity | Structure |
|---|---|---|
| 67 | 6-[3-endo-({2-[(4-chlorophenyl)oxy]propanoyl}amino)-8-azabicyclo[3.2.1]oct-8-yl]-N-[2-(methyloxy)ethyl]pyridine-3-carboxamide<br>ACTIVITY = C | 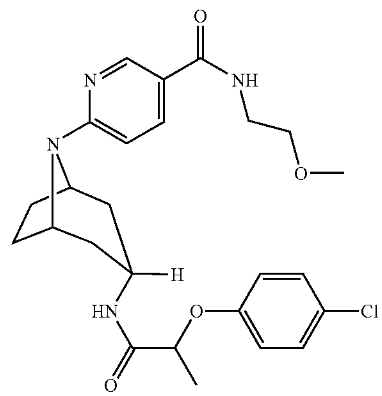 |
| 68 | 6-[3-endo-({2-[(2,4-dichlorophenyl)oxy]propanoyl}amino)-8-azabicyclo[3.2.1]oct-8-yl]-N-[2-(methyloxy)ethyl]pyridine-3-carboxamide<br>ACTIVITY = B | 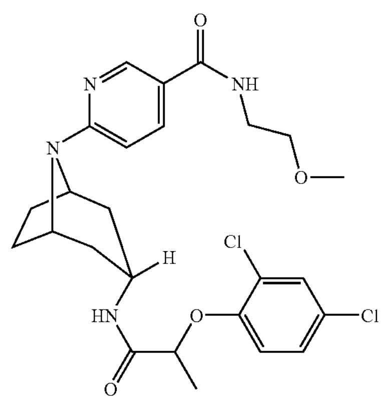 |
| 69 | 6-[3-endo-({2-[(2-chloro-5-fluorophenyl)oxy]-2-methylpropanoyl}amino)-8-azabicyclo[3.2.1]oct-8-yl]-N-cyclopropylpyridine-3-carboxamide<br>ACTIVITY = A | 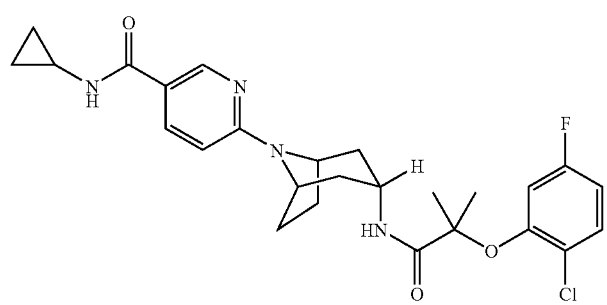 |
| 70 | 6-[3-endo-({2-[(2-chloro-4-fluorophenyl)oxy]-2-methylpropanoyl}amino)-8-azabicyclo[3.2.1]oct-8-yl]-N-(1-methylethyl)pyridine-3-carboxamide<br>ACTIVITY = A | 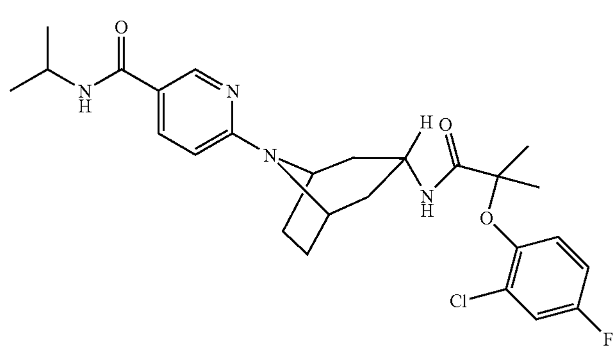 |

TABLE I-continued

| No. | Name/Activity | Structure |
|---|---|---|
| 71 | N-cyclopropyl-6-[3-endo-({2-[(2,5-dichlorophenyl)oxy]-2-methylpropanoyl}amino)-8-azabicyclo[3.2.1]oct-8-yl]pyridine-3-carboxamide<br>ACTIVITY = A | 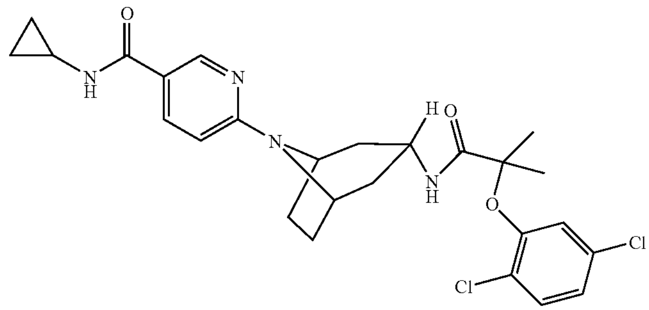 |
| 72 | 6-[3-endo-({2-[(2,5-dichlorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 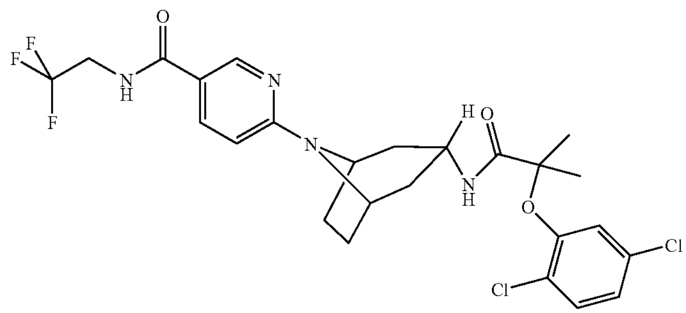 |
| 73 | 6-[3-endo-({2-[(2-chloro-5-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 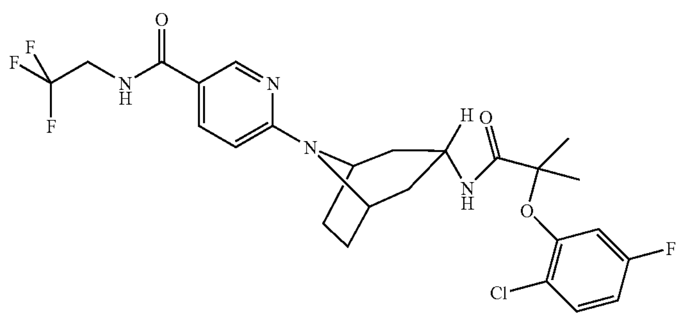 |
| 74 | 6-[3-endo-({2-[(2-chloro-4-fluorophenyl)oxy]-2-methylpropanoyl}amino)-8-azabicyclo[3.2.1]oct-8-yl]pyridine-3-carboxamide<br>ACTIVITY = A | 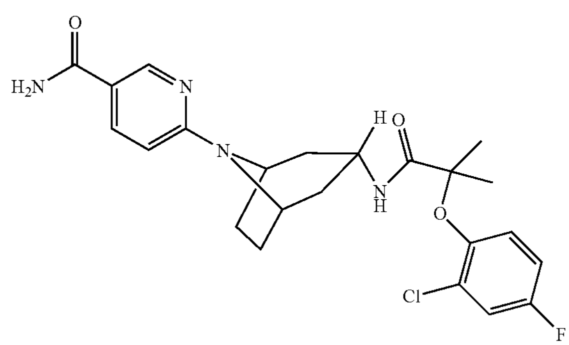 |
| 75 | 6-[3-endo-({2-[(2-chloro-4,5-difluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 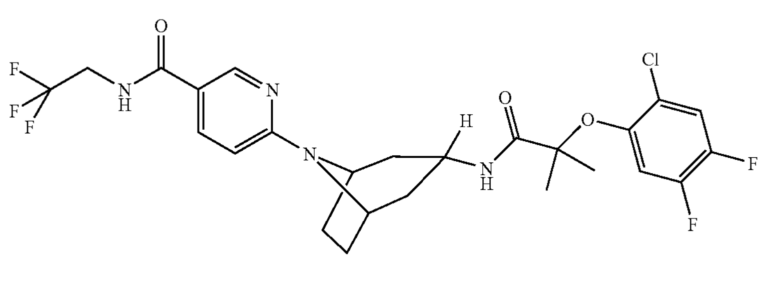 |

TABLE I-continued

| No. | Name/Activity | Structure |
|---|---|---|
| 76 | 6-[3-endo-({2-[(2,4-dichloro-5-fluorophenyl)oxy]-2-methylpropanoyl}amino)-8-azabicyclo[3.2.1]oct-8-yl]pyridine-3-carboxamide<br>ACTIVITY = A | 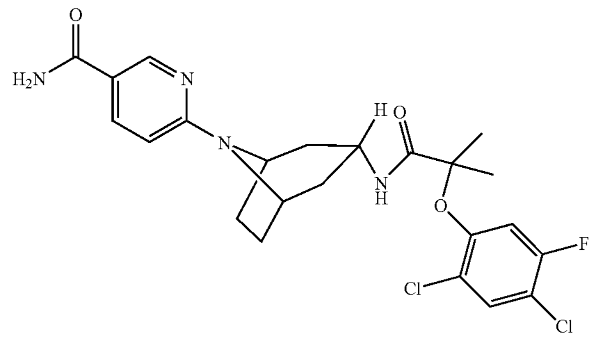 |
| 77 | 6-[3-endo-({2-[(4-chloro-3-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 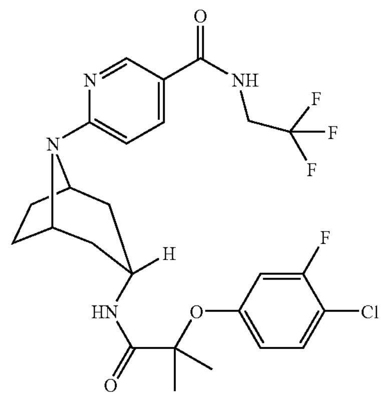 |
| 78 | 6-[3-endo-({2-[(3,4-difluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 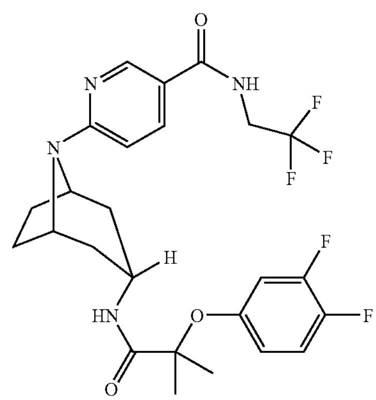 |
| 79 | 6-[3-endo-({2-[(3,4-dichlorophenyl)oxy]-2-methylpropanoyl}amino)-8-azabicycio[3.2.1]oct-8-yl]-N-(1-methylethyl)pyridine-3-carboxamide<br>ACTIVITY = A | 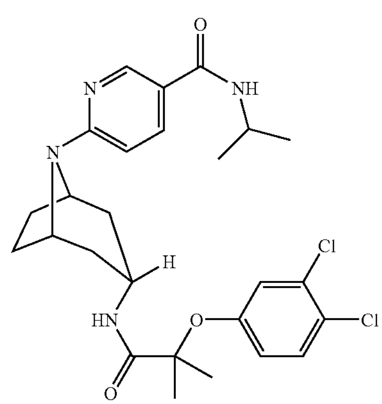 |

TABLE I-continued

| No. | Name/Activity | Structure |
|---|---|---|
| 80 | 6-[3-endo-({2-[(2,4-dichlorophenyl)oxy]-2-methylpropanoyl}amino)-8-azabicyclo[3.2.1]oct-8-yl]-N-[2-(methyloxy)ethyl]pyridine-3-carboxamide<br>ACTIVITY = A | 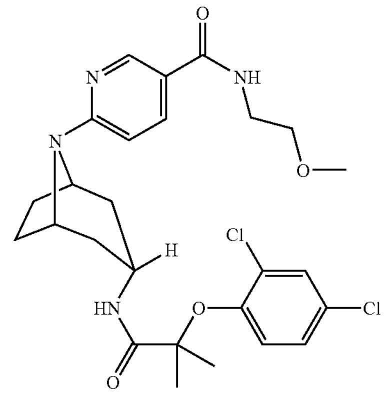 |
| 81 | 6-[3-endo-({2-[(4-chlorophenyl)oxy]butanoyl}amino)-8-azabicyclo[3.2.1]oct-8-yl]-N-[2-(methyloxy)ethyl]pyridine-3-carboxamide<br>ACTIVITY = B | 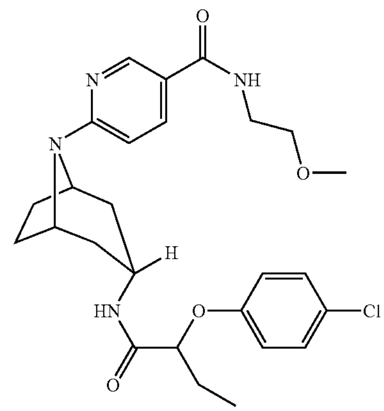 |
| 82 | N-cyclopropyl-6-[3-endo-({2-[(2,4-dichlorophenyl)oxy]propanoyl}amino)-8-azabicyclo[3.2.1]oct-8-yl]pyridine-3-carboxamide<br>ACTIVITY = A | 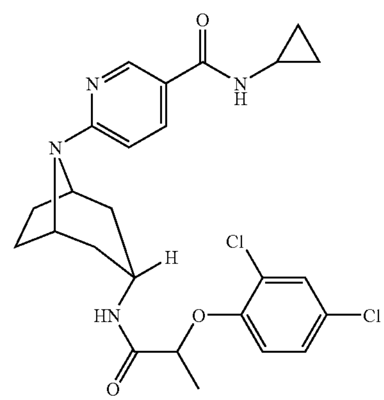 |
| 83 | 6-[3-endo-({2-[(3,4-dichlorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 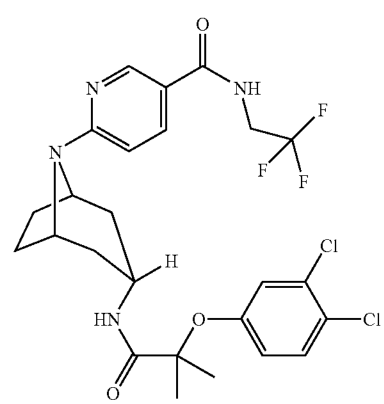 |

TABLE I-continued

| No. | Name/Activity | Structure |
|---|---|---|
| 84 | 6-[3-endo-({2-[(4-chloro-3-fluorophenyl)oxy]-2-methylpropanoyl}amino)-8-azabicyclo[3.2.1]oct-8-yl]-N-(1-methylethyl)pyridine-3-carboxamide<br>ACTIVITY = A | 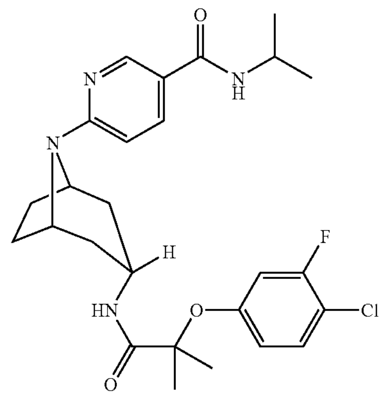 |
| 85 | 6-[3-endo-({2-[(3,4-difluorophenyl)oxy]-2-methylpropanoyl}amino)-8-azabicyclo[3.2.1]oct-8-yl]-N-(1-methylethyl)pyridine-3-carboxamide<br>ACTIVITY = B | 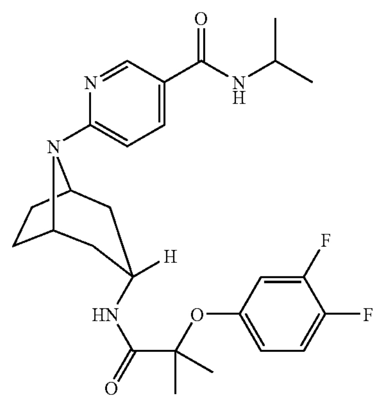 |
| 86 | 5-chloro-N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide<br>ACTIVITY = A | 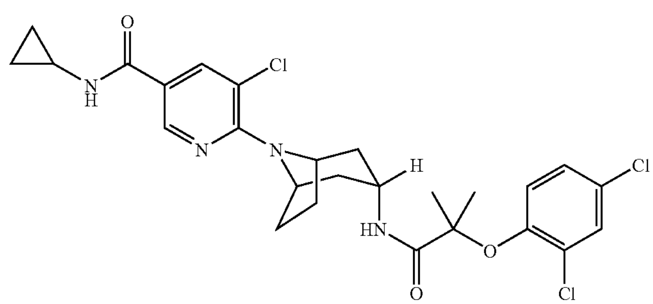 |
| 87 | N-[8-(5-acetylpyridin-2-yl)-8-azabicyclo[3.2.1]oct-3-endo-yl]-2-[(2,4-dichlorophenyl)oxy]-2-methylpropanamide<br>ACTIVITY = A | 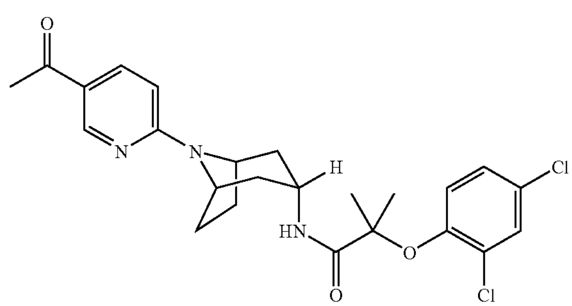 |

TABLE I-continued

| No. | Name/ Activity | Structure |
|---|---|---|
| 88 | N-[8-(5-aminopyridin-2-yl)-8-azabicyclo[3.2.1]oct-3-endo-yl]-2-[(2,4-dichlorophenyl)oxy]-2-methylpropanamide<br>ACTIVITY = A | 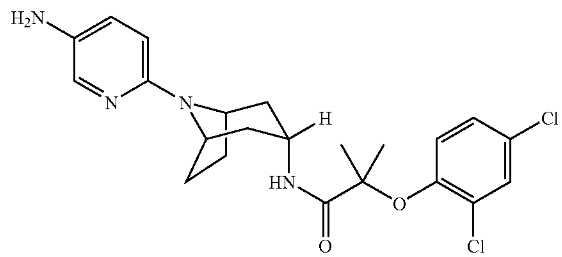 |
| 89 | 6-[3-endo-({2-[(4-chlorophenyl)oxy]-2-methylpropanoyl}amino)-8-azabicyclo[3.2.1]oct-8-yl]-N-[2-(methyloxy)ethyl]pyridine-3-carboxamide<br>ACTIVITY = A | 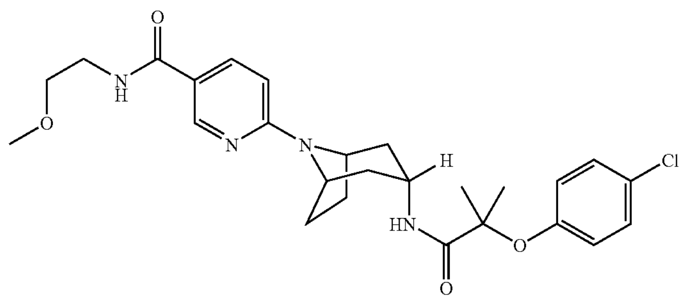 |
| 90 | 6-[3-endo-({2-[(2,4-dichloro-5-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 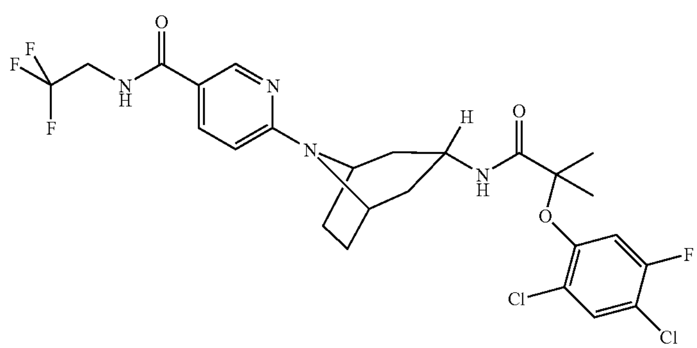 |
| 91 | N-cyclopropyl-6-[3-endo-({2-[(2,4-dichloro-5-fluorophenyl)oxy]-2-methylpropanoyl}amino)-8-azabicyclo[3.2.1]oct-8-yl]pyridine-3-carboxamide<br>ACTIVITY = A | 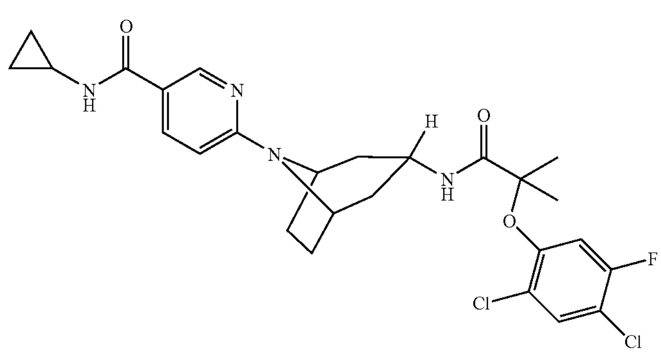 |

TABLE I-continued

| No. | Name/Activity | Structure |
|---|---|---|
| 92 | N-{6-[3-endo-({2-[(2,4-dichlorophenyl)oxy]-2-methylpropanoyl}amino)-8-azabicyclo[3.2.1]oct-8-yl]pyridin-3-yl}cyclopropanecarboxamide<br>ACTIVITY = A | 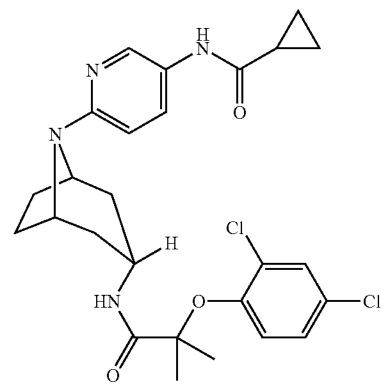 |
| 93 | 6-[3-endo-({2-[(3-chloro-4-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 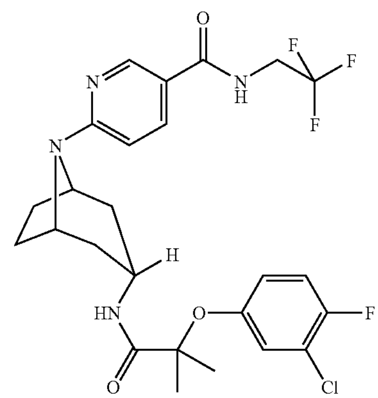 |
| 94 | N-{8-[5-(acetylamino)pyridin-2-yl]-8-azabicyclo[3.2.1]oct-3-endo-yl}-2-[(2,4-dichlorophenyl)oxy]-2-methylpropanamide<br>ACTIVITY = A | 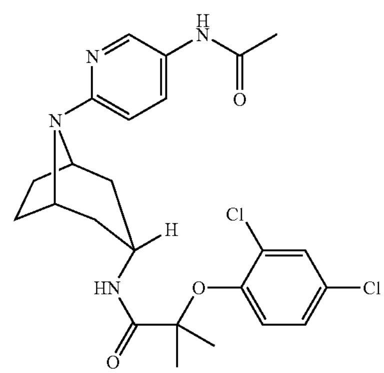 |
| 95 | 6-[3-endo-({2-[(3-chloro-4-fluorophenyl)oxy]-2-methylpropanoyl}amino)-8-azabicyclo[3.2.1]oct-8-yl]-N-(1-methylethyl)pyridine-3-carboxamide<br>ACTIVITY = A | 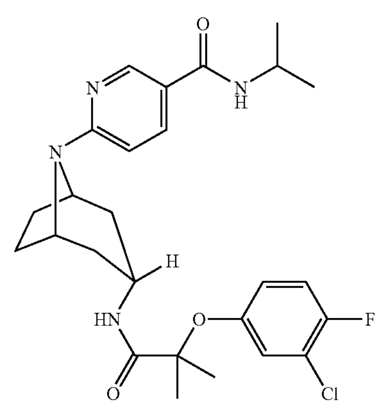 |

TABLE I-continued

| No. | Name/Activity | Structure |
|---|---|---|
| 96 | 6-[3-endo-({2-[(2-chloro-4,5-difluorophenyl)oxy]-2-methylpropanoyl}amino)-8-azabicyclo[3.2.1]oct-8-yl]pyridine-3-carboxamide<br>ACTIVITY = A | 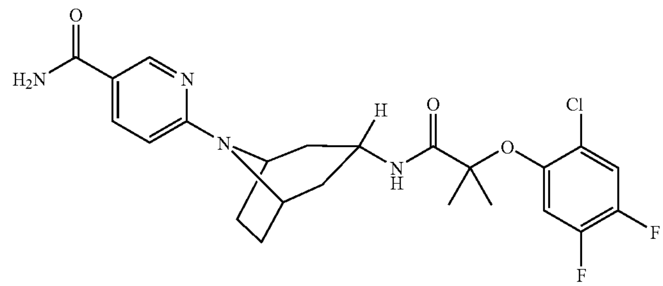 |
| 97 | 6-[3-endo-({2-[(2,3-dichloro-4-fluorophenyl)oxy]-2-methylpropanoyl}amino)-8-azabicyclo[3.2.1]oct-8-yl]pyridine-3-carboxamide<br>ACTIVITY = A | 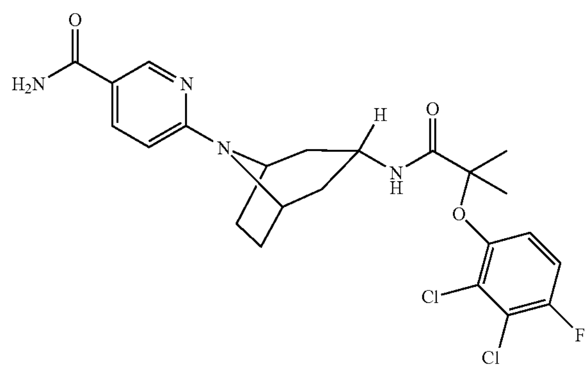 |
| 98 | 6-[3-endo-({2-[(2,5-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 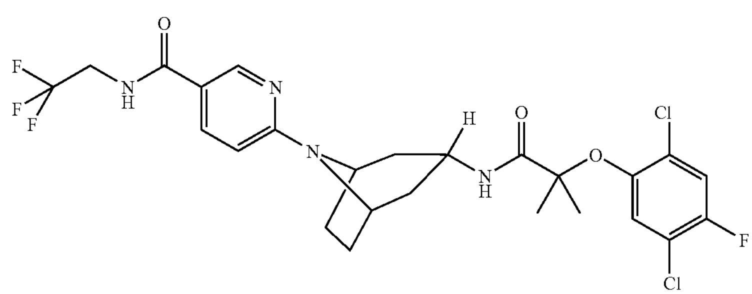 |
| 99 | 6-[3-endo-({2-[(2,5-dichloro-4-fluorophenyl)oxy]-2-methylpropanoyl}amino)-8-azabicyclo[3.2.1]oct-8-yl]pyridine-3-carboxamide<br>ACTIVITY = A | 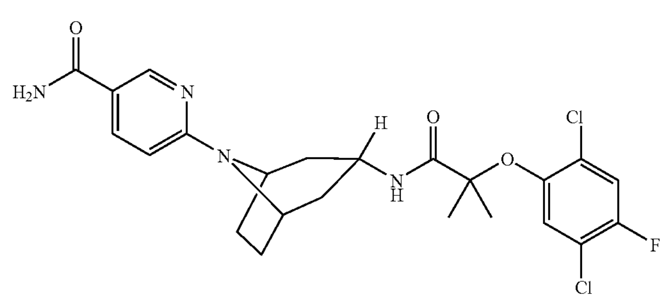 |

TABLE I-continued

| No. | Name/Activity | Structure |
|---|---|---|
| 100 | 6-[3-endo-({2-[(2,3-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 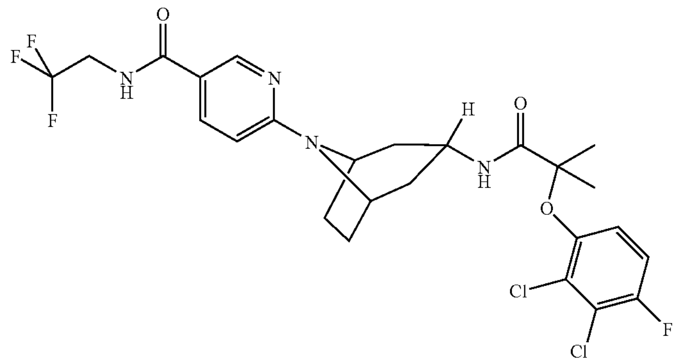 |
| 101 | 2-[(2,4-dichlorophenyl)oxy]-2-methyl-N-(8-{5-[(methylsulfonyl)amino]pyridin-2-yl}-8-azabicyclo[3.2.1]oct-3-endo-yl)propanamide<br>ACTIVITY = A | 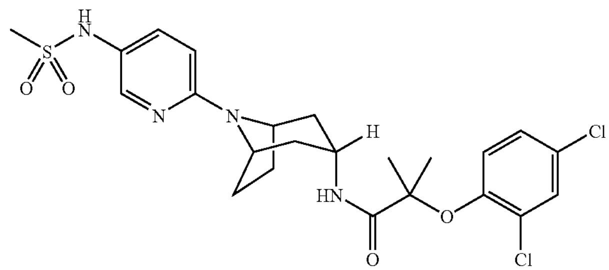 |
| 102 | 6-[3-endo-({[1-(3-chlorophenyl)cyclopropyl]carbonyl}amino)-8-azabicyclo[3.2.1]oct-8-yl]pyridine-3-carboxamide<br>ACTIVITY = A | 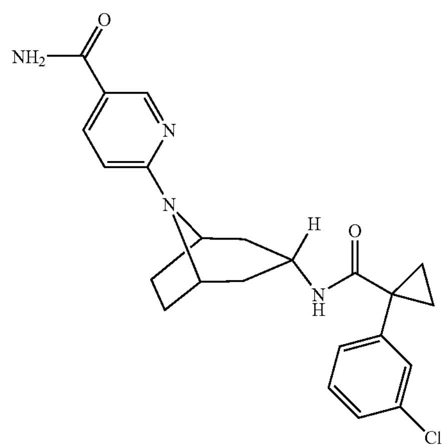 |
| 103 | 6-[3-endo-({[1-(3,4-dichlorophenyl)cyclopropyl]carbonyl}amino)-8-azabicyclo[3.2.1]oct-8-yl]pyridine-3-carboxamide<br>ACTIVITY = A | 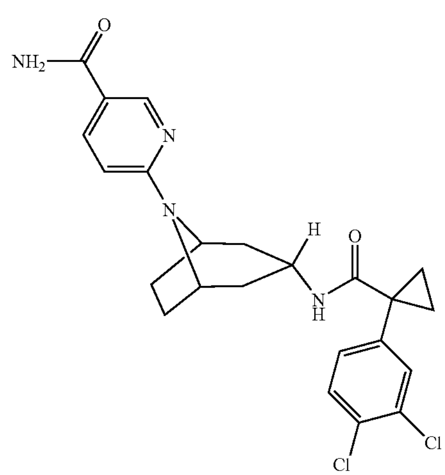 |

TABLE I-continued

| No. | Name/Activity | Structure |
|---|---|---|
| 104 | 6-[3-endo-({[1-(3-fluorophenyl)cyclopropyl]carbonyl}amino)-8-azabicyclo[3.2.1]oct-8-yl]pyridine-3-carboxamide<br>ACTIVITY = A | 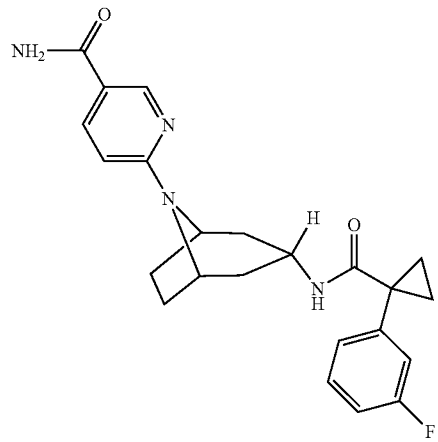 |
| 105 | 6-[3-endo-({2-[(4-chloro-2-fluorophenyl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 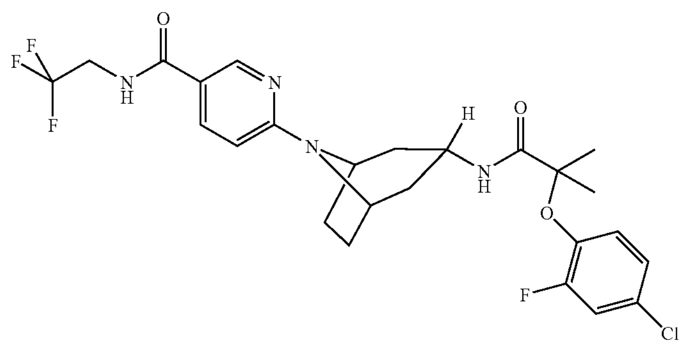 |
| 106 | 2-[(2,4-dichlorophenyl)oxy]-2-methyl-N-(8-pyridin-3-yl-8-azabicyclo[3.2.1]oct-3-endo-yl)propanamide<br>ACTIVITY = A | 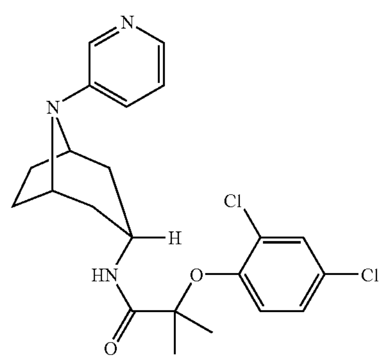 |
| 107 | 6-[3-endo-({2-[(3,5-dichloropyridin-2-yl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 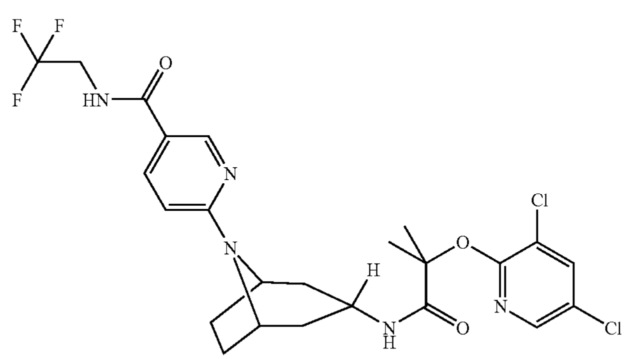 |

TABLE I-continued

| No. | Name/Activity | Structure |
|---|---|---|
| 108 | 6-[3-endo-({2-[(5-chloropyridin-2-yl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 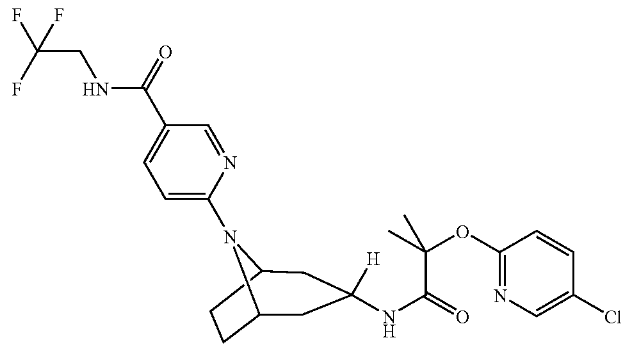 |
| 109 | 6-[3-endo-({2-[(5-fluoropyridin-2-yl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 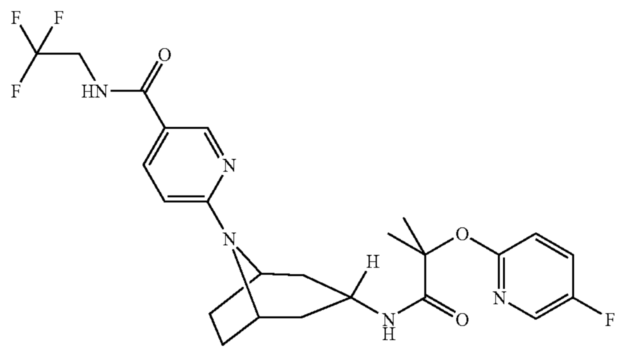 |
| 110 | 4-[3-endo-({2-[(2,4-dichlorophenyl)oxy]-2-methylpropanoyl}amino)-8-azabicyclo[3.2.1]oct-8-yl]-N-(2,2,2-trifluoroethyl)benzamide<br>ACTIVITY = A | 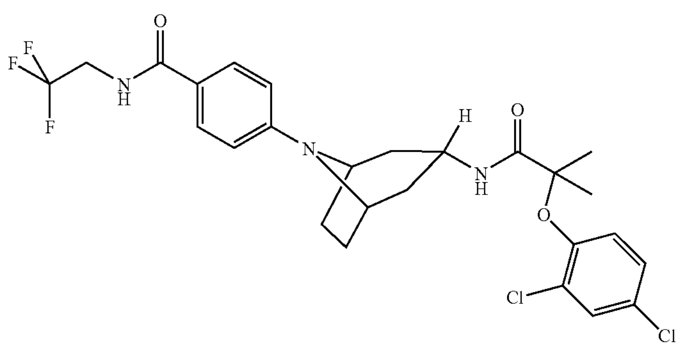 |
| 111 | 6-{3-endo-[(2-methyl-2-{[4-(trifluoromethyl)phenyl]oxy}propanoyl)amino]-8-azabicyclo[3.2.1]oct-8-yl}-N-(2,2,2-trifluoroethyl)pyridine-3-carboxamide<br>ACTIVITY = A | 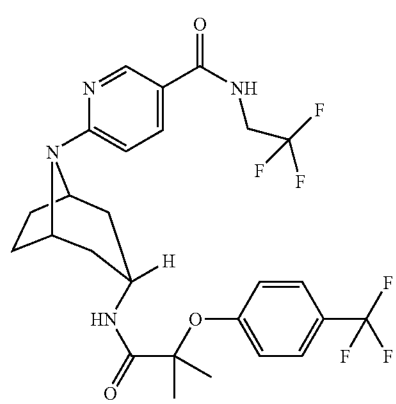 |

TABLE I-continued

| No. | Name/Activity | Structure |
|---|---|---|
| 112 | 6-{3-endo-[(2-methyl-2-{[2-(trifluoromethyl)phenyl]oxy}propanoyl)amino]-8-azabicyclo[3.2.1]oct-8-yl}-N-(2,2,2-trifluoroethyl)pyridine-3-carboxamide<br>ACTIVITY = A | 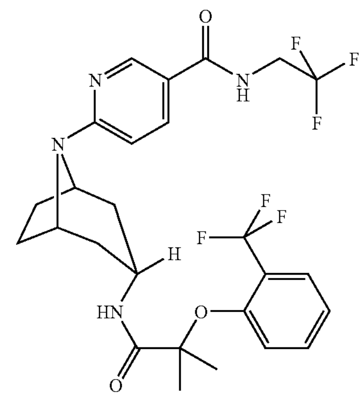 |
| 113 | N-cyclopropyl-6-{3-endo-[(2-methyl-2-{[2-(trifluoromethyl)phenyl]oxy}propanoyl)amino]-8-azabicyclo[3.2.1]oct-8-yl}pyridine-3-carboxamide<br>ACTIVITY = A | 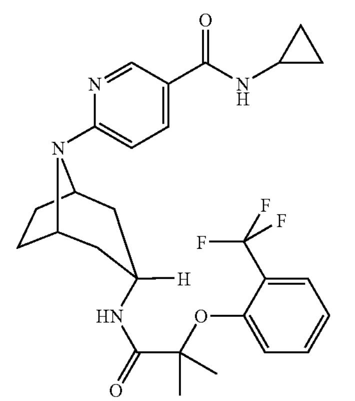 |
| 114 | 2-[(2,4-dichlorophenyl)oxy]-2-methyl-N-{8-[5-(1H-tetrazol-5-yl)pyridin-2-yl]-8-azabicyclo[3.2.1]oct-3-endo-yl}propanamide<br>ACTIVITY = A | 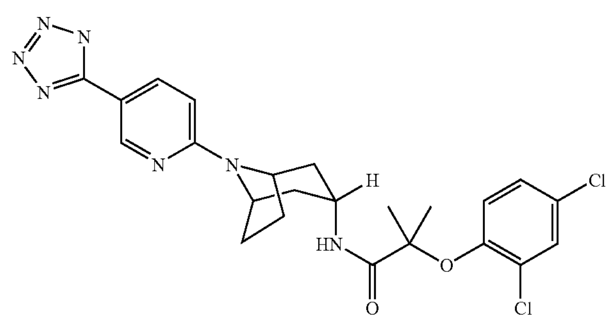 |
| 115 | N-{8-[4-(acetylamino)phenyl]-8-azabicyclo[3.2.1]oct-3-endo-yl}-2-[(2,4-dichlorophenyl)oxy]-2-methylpropanamide<br>ACTIVITY = A | 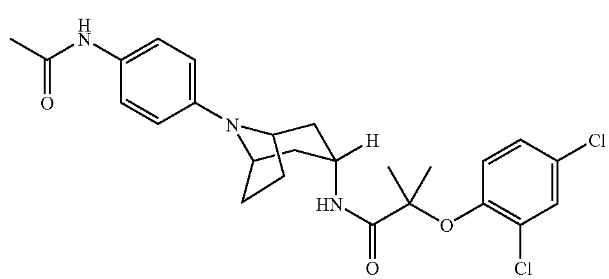 |

TABLE I-continued

| No. | Name/Activity | Structure |
|---|---|---|
| 116 | 2-[(2,4-dichlorophenyl)oxy]-2-methyl-N-(8-{4-[(trifluoroacetyl)amino]phenyl}-8-azabicyclo[3.2.1]oct-3-endo-yl)propanamide ACTIVITY = A | 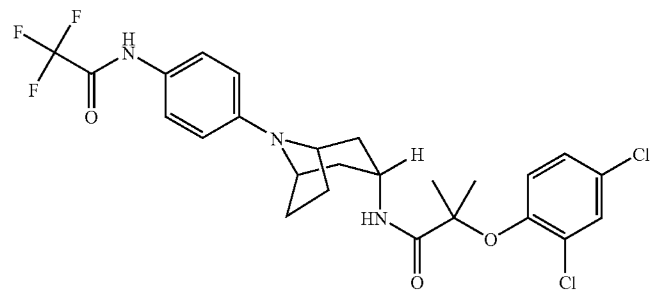 |
| 117 | 3-chloro-4-[3-endo-({2-[(2,4-dichlorophenyl)oxy]-2-methylpropanoyl}amino)-8-azabicyclo[3.2.1]oct-8-yl]-N-(2,2,2-trifluoroethyl)benzamide ACTIVITY = A | 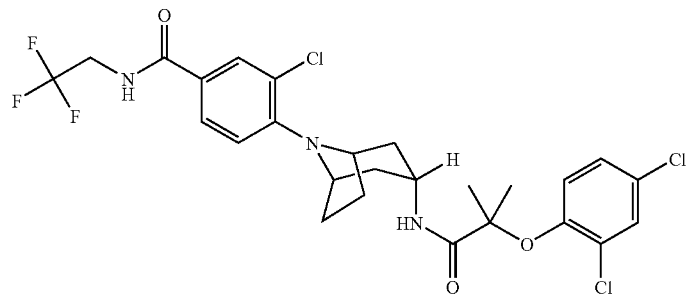 |
| 118 | 3-chloro-4-[3-endo-({[1-(4-chlorophenyl)cyclopropyl]carbonyl}amino)-8-azabicyclo[3.2.1]oct-8-yl]-N-cyclopropylbenzamide ACTIVITY = A | 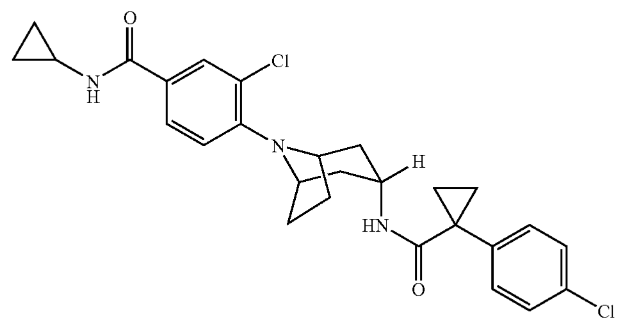 |
| 119 | 4-[3-endo-({[1-(4-chlorophenyl)cyclopropyl]carbonyl}amino)-8-azabicyclo[3.2.1]oct-8-yl]-N-cyclopropyl-2-fluorobenzamide ACTIVITY = A | 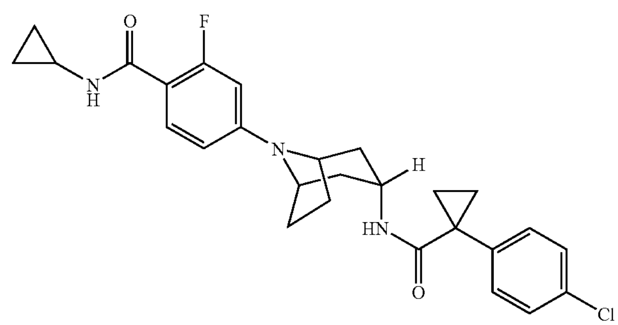 |
| 120 | 2-[(2,4-dichlorophenyl)oxy]-2-methyl-N-{8-[4-(methylsulfonyl)phenyl]-8-azabicyclo[3.2.1]oct-3-endo-yl}propanamide ACTIVITY = A | 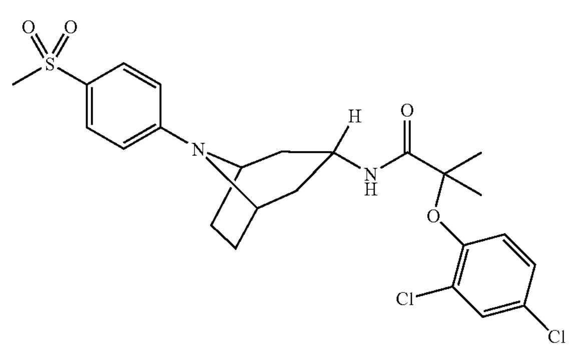 |

TABLE I-continued

| No. | Name/Activity | Structure |
|---|---|---|
| 121 | 6-[3-endo-({[1-(3,4-difluorophenyl)cyclopropyl]carbonyl}amino)-8-azabicyclo[3.2.1]oct-8-yl]-N-(2,2,2-trifluoroethyl)pyridine-3-carboxamide<br>ACTIVITY = A | 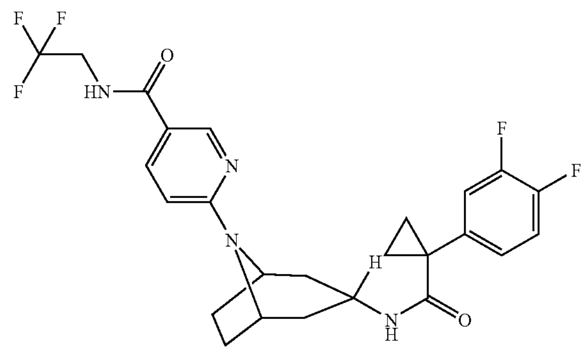 |
| 122 | 6-[3-endo-({[1-(3-chlorophenyl)cyclopropyl]carbonyl}amino)-8-azabicyclo[3.2.1]oct-8-yl]-N-(2,2,2-trifluoroethyl)pyridine-3-carboxamide<br>ACTIVITY = A | 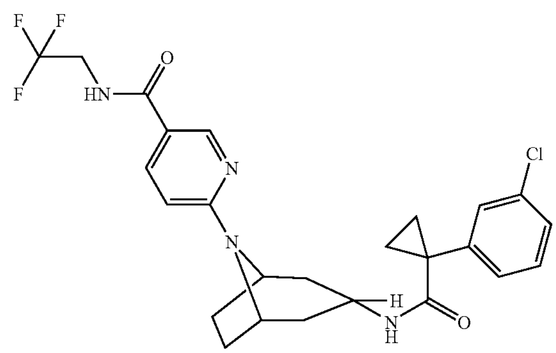 |
| 123 | 6-[3-endo-({[1-(3-fluorophenyl)cyclopropyl]carbonyl}amino)-8-azabicyclo[3.2.1]oct-8-yl]-N-(2,2,2-trifluoroethyl)pyridine-3-carboxamide<br>ACTIVITY = A | 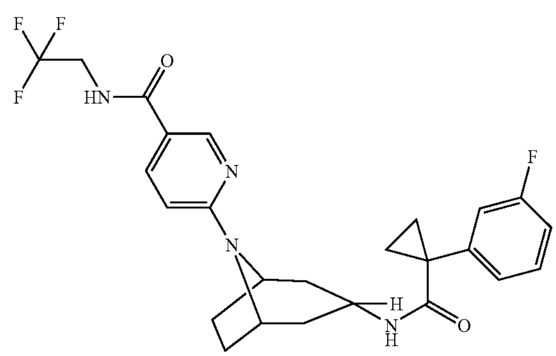 |
| 124 | 6-[3-endo-({2-[(3,5-dichloropyridin-2-yl)oxy]-2-methylpropanoyl}amino)-8-azabicyclo[3.2.1]oct-8-yl]pyridine-3-carboxamide<br>ACTIVITY = A | 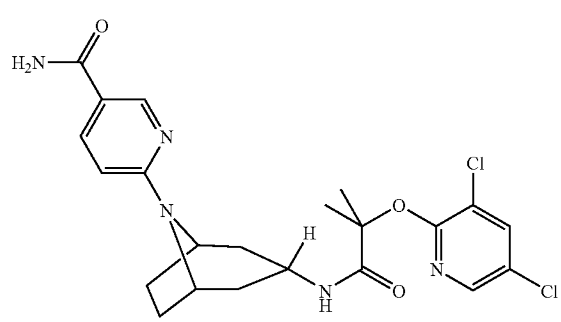 |

TABLE I-continued

| No. | Name/Activity | Structure |
|---|---|---|
| 125 | N-{8-[5-(aminosulfonyl)pyridin-2-yl]-8-azabicyclo[3.2.1]oct-3-endo-yl}-2-[(2,4-dichlorophenyl)oxy]-2-methylpropanamide<br>ACTIVITY = A | 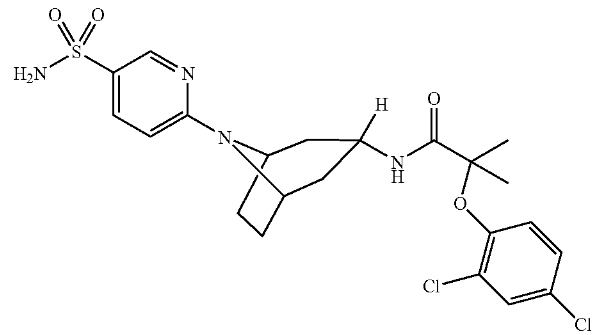 |
| 126 | 6-[3-endo-({2-[(2,4-dichlorophenyl)oxy]-2-methylpropanoyl}amino)-8-azabicyclo[3.2.1]oct-8-yl]-N-(2,2,3,3,3-pentafluoropropyl)pyridine-3-carboxamide<br>ACTIVITY = A | 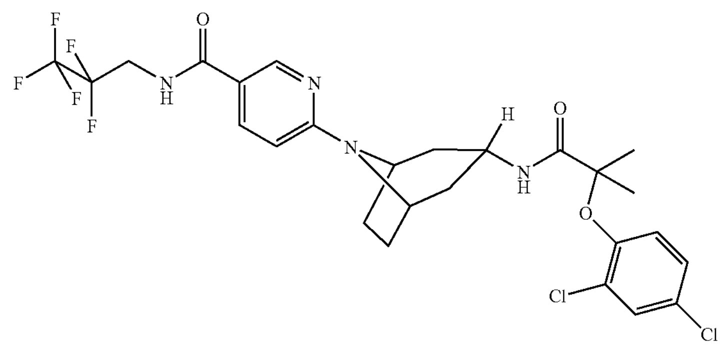 |
| 127 | 6-[3-endo-({2-[(5-chloro-3-fluoropyridin-2-yl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 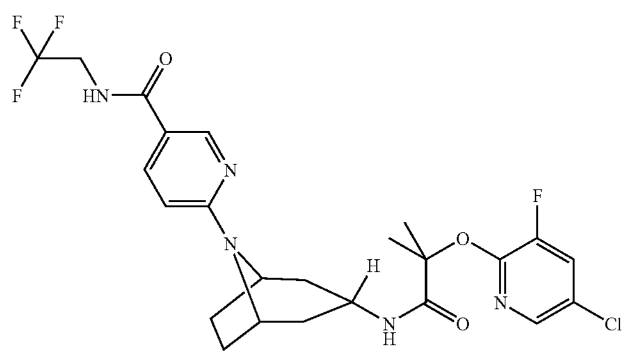 |
| 128 | 6-(3-endo-{[2-methyl-2-({4-[(trifluoromethyl)oxy]phenyl}oxy)propanoyl]amino}-8-azabicyclo[3.2.1]oct-8-yl)-N-(2,2,2-trifluoroethyl)pyridine-3-carboxamide<br>ACTIVITY = A | 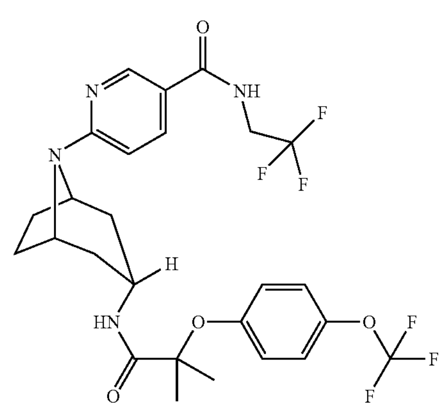 |

TABLE I-continued

| No. | Name/Activity | Structure |
|---|---|---|
| 129 | 4-[3-endo-({2-[(2,4-dichlorophenyl)oxy]-2-methylpropanoyl}amino)-8-azabicyclo[3.2.1]oct-8-yl]-3-fluoro-N-(2,2,2-trifluoroethyl)benzamide ACTIVITY = A | 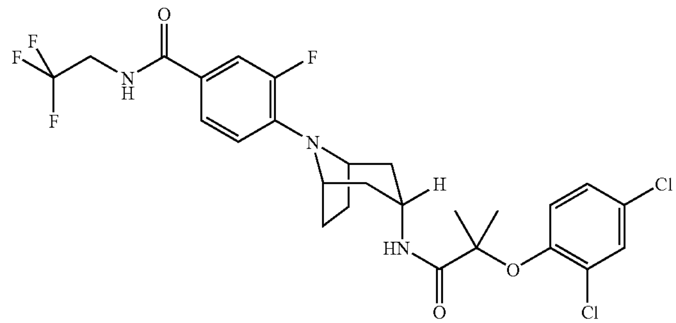 |
| 130 | N-cyclopropyl-4-[3-endo-({2-[(2,4-dichlorophenyl)oxy]-2-methylpropanoyl}amino)-8-azabicyclo[3.2.1]oct-8-yl]-2-fluorobenzamide ACTIVITY = A | 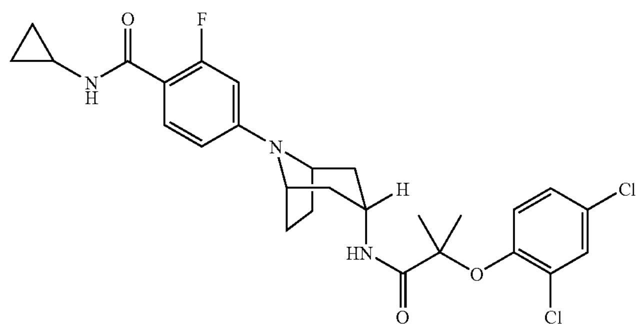 |
| 131 | 5-chloro-6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide ACTIVITY = A | 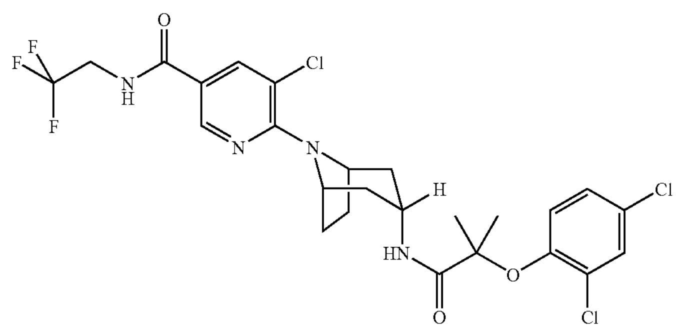 |
| 132 | N-cyclopropyl-4-[3-endo-({2-[(2,4-dichlorophenyl)oxy]-2-methylpropanoyl}amino)-8-azabicyclo[3.2.1]oct-8-yl]benzamide ACTIVITY = A | 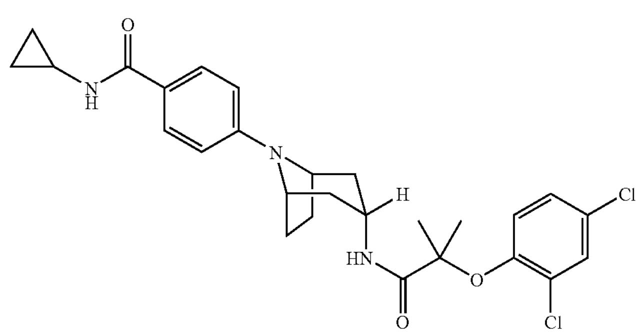 |

TABLE I-continued

| No. | Name/Activity | Structure |
|---|---|---|
| 133 | N-{4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide<br>ACTIVITY = A | 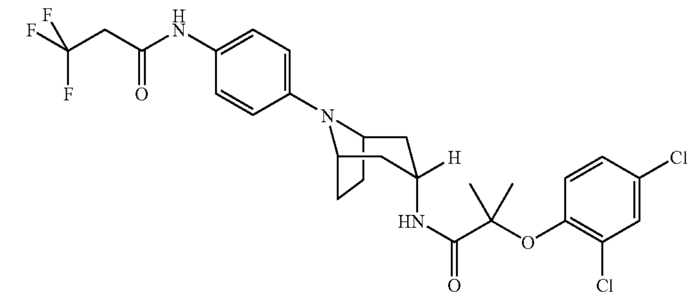 |
| 134 | 2-[(2,4-dichlorophenyl)oxy]-2-methyl-N-{8-[5-({[(2,2,2-trifluoroethyl)amino]carbonyl}amino)pyridin-2-yl]-8-azabicyclo[3.2.1]oct-3-endo-yl}propanamide<br>ACTIVITY = A | 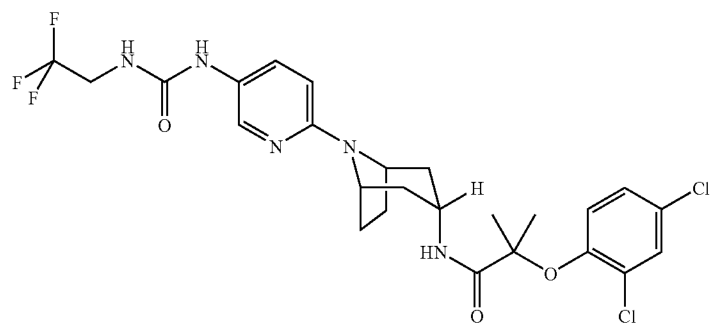 |
| 135 | 2-[(2,4-dichlorophenyl)oxy]-2-methyl-N-{8-[4-({[(2,2,2-trifluoroethyl)amino]carbonyl}amino)phenyl]-8-azabicyclo[3.2.1]oct-3-endo-yl}propanamide<br>ACTIVITY = A | 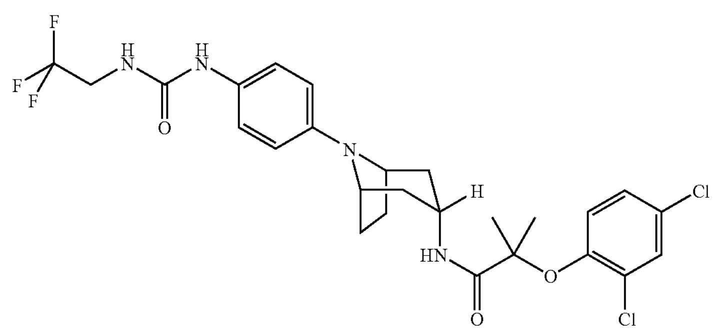 |
| 136 | N-{8-[2-chloro-4-({[(2,2,2-trifluoroethyl)amino]carbonyl}amino)phenyl]-8-azabicyclo[3.2.1]oct-3-endo-yl}-2-[(2,4-dichlorophenyl)oxy]-2-methylpropanamide<br>ACTIVITY = B | 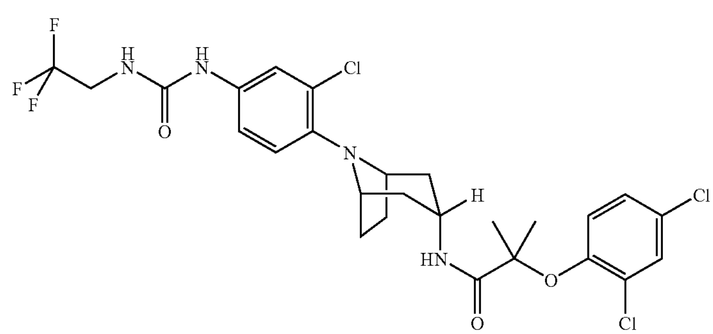 |

TABLE I-continued

| No. | Name/Activity | Structure |
|---|---|---|
| 137 | 2-[(2,4-dichlorophenyl)oxy]-N-{8-[2-fluoro-4-({[(2,2,2-trifluoroethyl)amino]carbonyl}amino)phenyl]-8-azabicyclo[3.2.1]oct-3-endo-yl}-2-methylpropanamide<br>ACTIVITY = A | 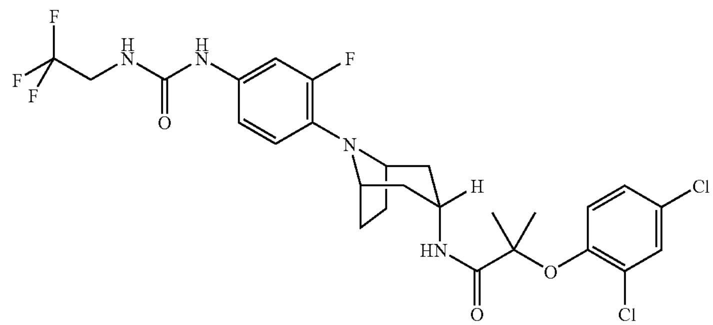 |
| 138 | N-{3-chloro-4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide<br>ACTIVITY = B | 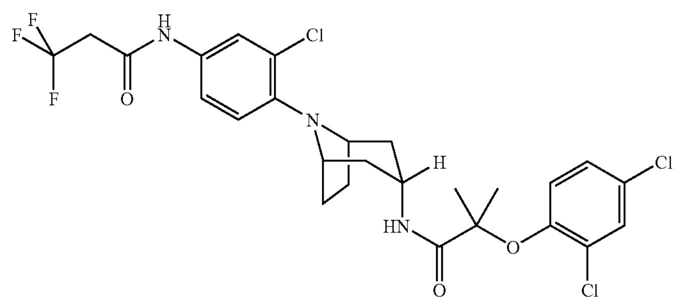 |
| 139 | N-{4-[3-endo-({2-[(2,4-dichlorophenyl)oxy]-2-methylpropanoyl}amino)-8-azabicyclo[3.2.1]oct-8-yl]-3-fluorophenyl}-3,3,3-trifluoropropanamide<br>ACTIVITY = A | 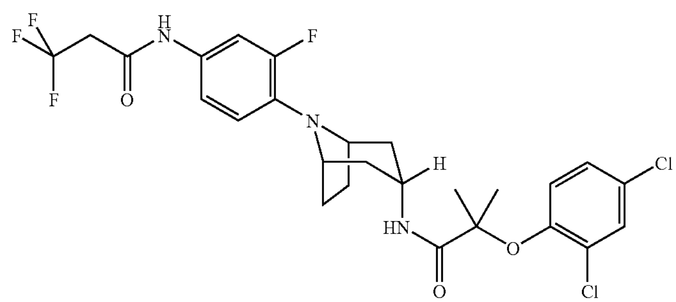 |
| 140 | 2-[(2,4-dichlorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 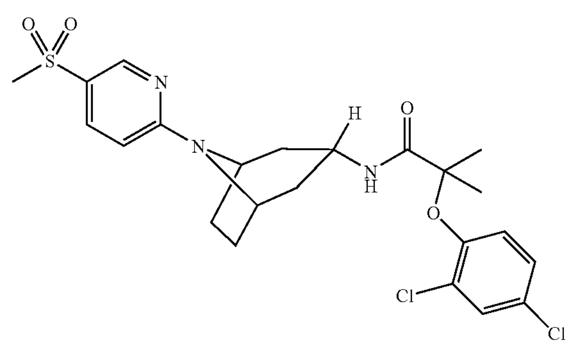 |
| 141 | 6-[3-endo-({[1-(3,4-difluorophenyl)cyclopropyl]carbonyl}amino)-8-azabicyclo[3.2.1]oct-8-yl]pyridine-3-carboxamide<br>ACTIVITY = A | 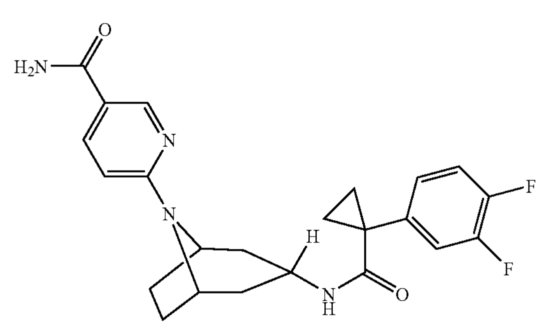 |

TABLE I-continued

| No. | Name/Activity | Structure |
|---|---|---|
| 142 | 6-[3-endo-({2-[(5-chloro-3-fluoropyridin-2-yl)oxy]-2-methylpropanoyl}amino)-8-azabicyclo[3.2.1]oct-8-yl]pyridine-3-carboxamide<br>ACTIVITY = A | 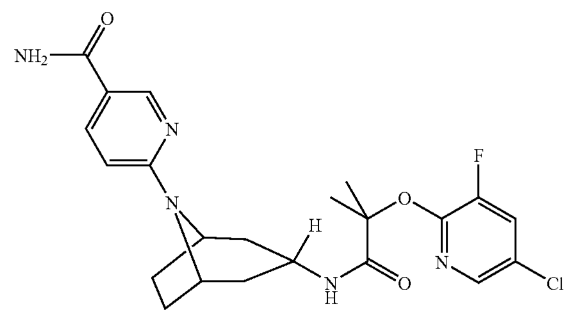 |
| 143 | N-cyclopropyl-2-[3-endo-({2-[(2,4-dichlorophenyl)oxy]-2-methylpropanoyl}amino)-8-azabicyclo[3.2.1]oct-8-yl]pyridine-4-carboxamide<br>ACTIVITY = B | 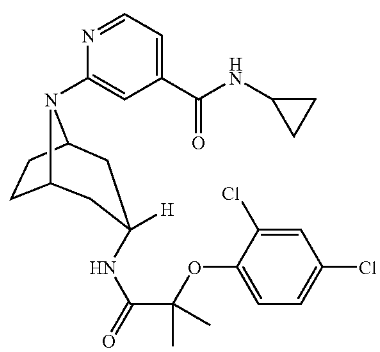 |
| 144 | 6-{3-endo-[(2-{[4-chloro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 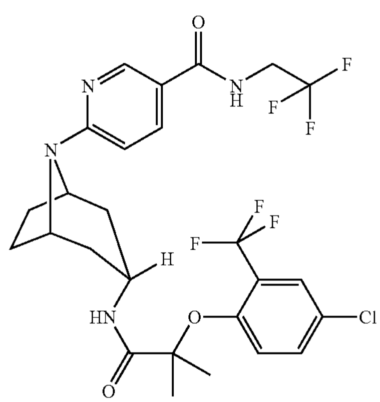 |
| 145 | 6-{3-endo-[(2-{[4-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 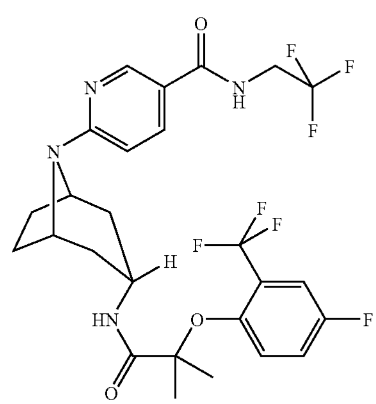 |

TABLE I-continued

| No. | Name/Activity | Structure |
|---|---|---|
| 146 | 2-[(2,4-dichlorophenyl)oxy]-2-methyl-N-(8-{5-[(trifluoroacetyl)amino]pyridin-2-yl}-8-azabicyclo[3.2.1]oct-3-endo-yl)propanamide<br>ACTIVITY = A | 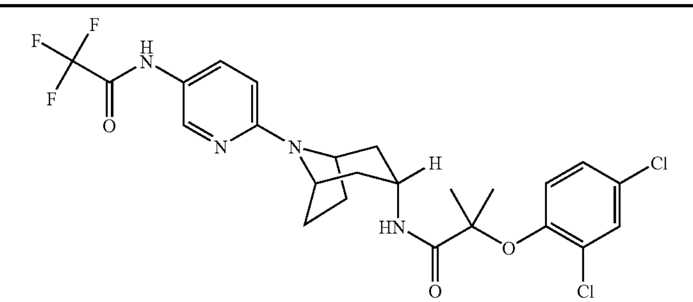 |
| 147 | N-{6-[3-endo-({2-[(2,4-dichlorophenyl)oxy]-2-methylpropanoyl}amino)-8-azabicyclo[3.2.1]oct-8-yl]pyridin-3-yl}-3,3,3-trifluoropropanamide<br>ACTIVITY = A | 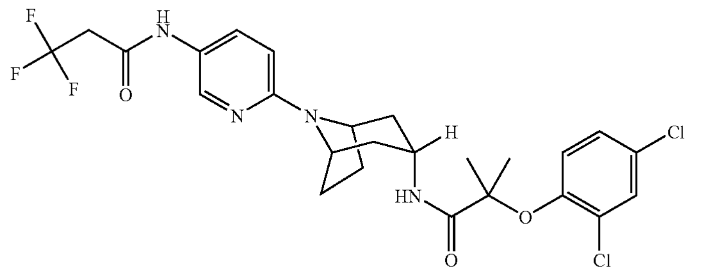 |
| 148 | 4-[3-endo-({[1-(4-chlorophenyl)cyclopropyl]carbonyl}amino)-8-azabicyclo[3.2.1]oct-8-yl]-N-cyclopropyl-3-fluorobenzamide<br>ACTIVITY = A | 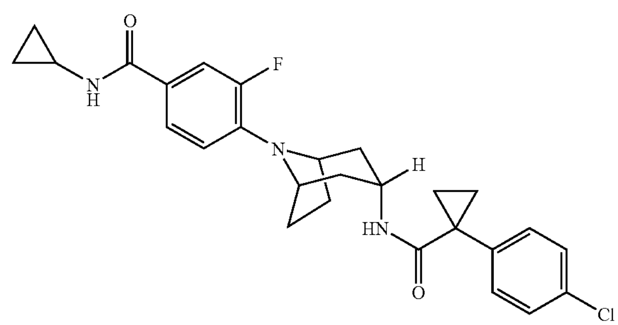 |
| 149 | 6-{3-endo-[(2-{[3-chloro-5-(trifluoromethyl)pyridin-2-yl]oxy}-2-methylpropanoyl)amino]-8-azabicyclo[3.2.1]oct-8-yl}pyridine-3-carboxamide<br>ACTIVITY = A | 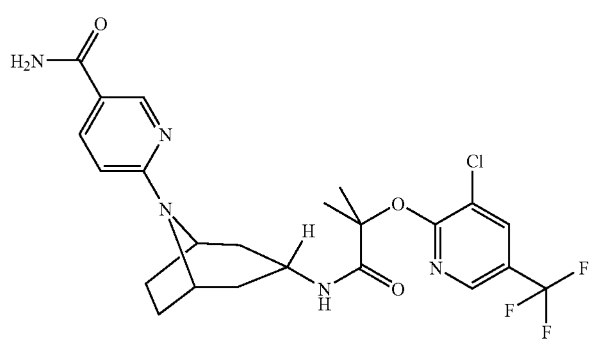 |
| 150 | 6-{3-endo-(2-methyl-2-{[5-(trifluoromethyl)pyridin-2-yl]oxy}propanoyl)amino]-8-azabicyclo[3.2.1]oct-8-yl}pyridine-3-carboxamide<br>ACTIVITY = A | 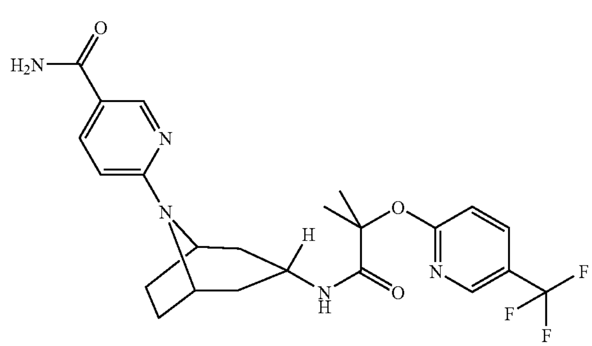 |

TABLE I-continued

| No. | Name/ Activity | Structure |
|---|---|---|
| 151 | 6-{3-endo-[(2-{[3-chloro-5-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 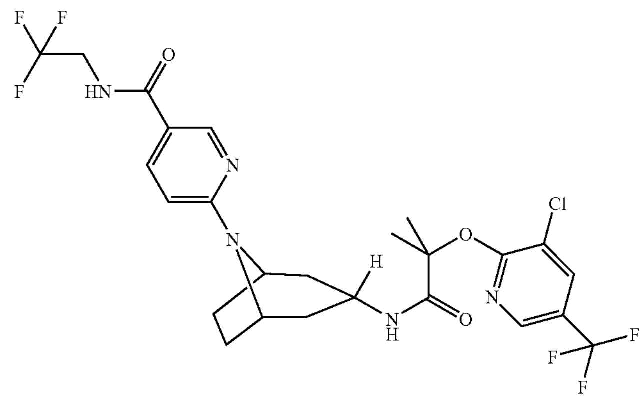 |
| 152 | 6-{3-endo-[(2-methyl-2-{[5-(trifluoromethyl)pyridin-2-yl]oxy}propanoyl)amino]-8-azabicyclo[3.2.1]oct-8-yl}-N-(2,2,2-trifluoroethyl)pyridine-3-carboxamide<br>ACTIVITY = B | 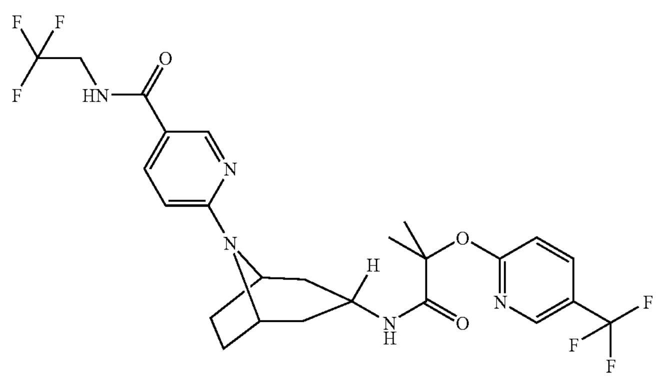 |
| 153 | 2-[(2,3-dichloro-4-fluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 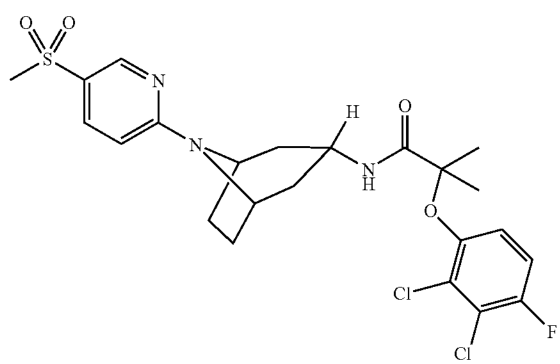 |
| 154 | 2-[(2,5-dichloro-4-fluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 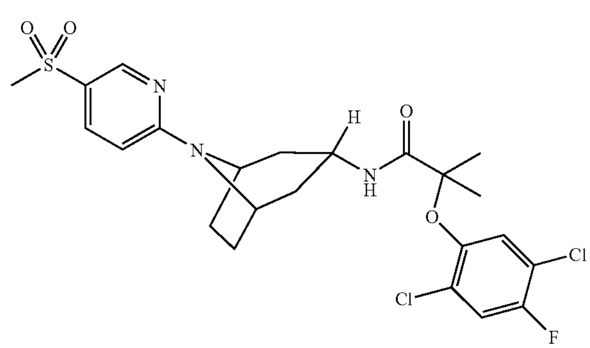 |

TABLE I-continued

| No. | Name/Activity | Structure |
|---|---|---|
| 155 | 2-[(2-chloro-4-fluorophenyl)oxy]-2-methyl-N-{8-[5-(methylsulfonyl)pyridin-2-yl]-8-azabicyclo[3.2.1]oct-3-endo-yl}propanamide ACTIVITY = A | 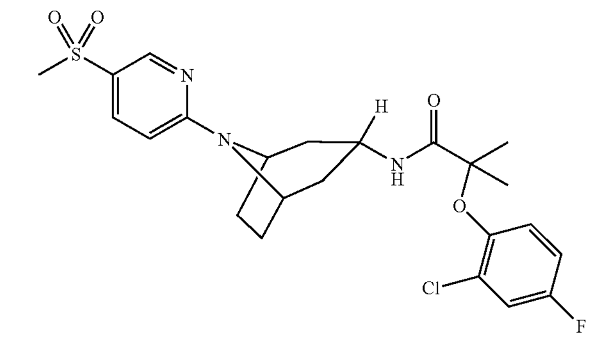 |
| 156 | 2-[(2,4-dichlorophenyl)oxy]-2-methyl-N-{8-[3-(methylsulfonyl)phenyl]-8-azabicyclo[3.2.1]oct-3-endo-yl}propanamide ACTIVITY = B | 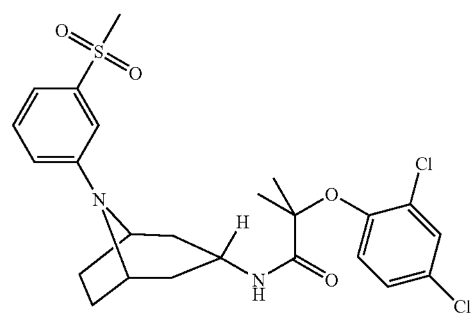 |
| 157 | N-{8-[5-(aminosulfonyl)pyridin-2-yl]-8-azabicyclo[3.2.1]oct-3-endo-yl}-2-[(2,5-dichloro-4-fluorophenyl)oxy]-2-methylpropanamide ACTIVITY = A | 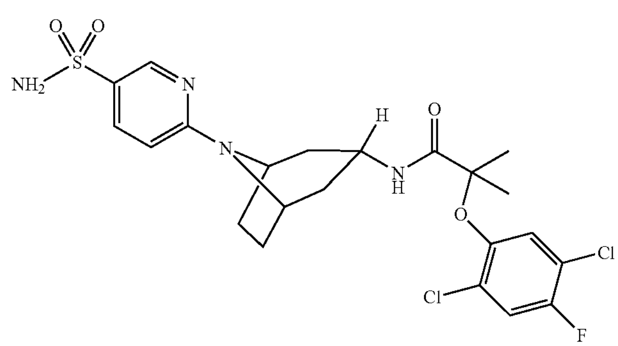 |
| 158 | N-{8-[5-(aminosulfonyl)pyridin-2-yl]-8-azabicyclo[3.2.1]oct-3-endo-yl}-2-[(2-chloro-4-fluorophenyl)oxy]-2-methylpropanamide ACTIVITY = A | 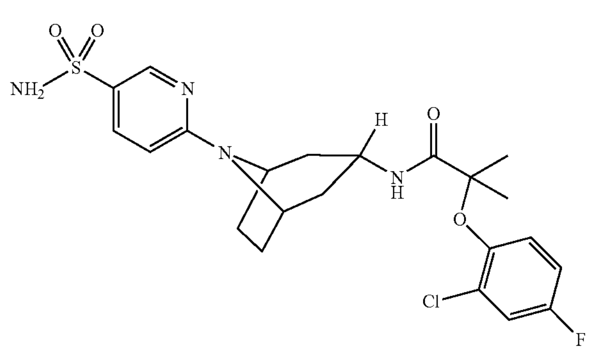 |

| No. | Name/Activity | Structure |
|---|---|---|
| 159 | 6-[3-endo-({2-[(2-chloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide<br>ACTIVITY = A | 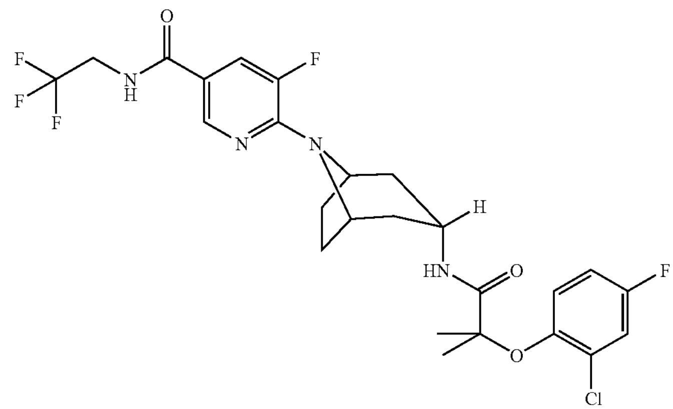 |
| 160 | 6-[3-endo-({2-[(2,4-dichlorophenyl)oxy]-2-methylpropanoyl}amino)-8-azabicyclo[3.2.1]oct-8-yl]-5-fluoro-N-(2,2,2-trifluoroethyl)pyridine-3-carboxamide<br>ACTIVITY = A | 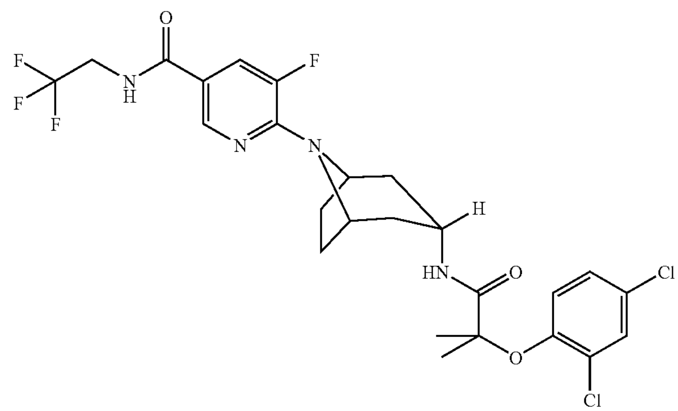 |
| 161 | 6-[3-endo-({2-[(3,5-dichloropyridin-2-yl)oxy]-2-methylpropanoyl}amino)-8-azabicyclo[3.2.1]oct-8-yl]-5-fluoro-N-(2,2,2-trifluoroethyl)pyridine-3-carboxamide<br>ACTIVITY = A | 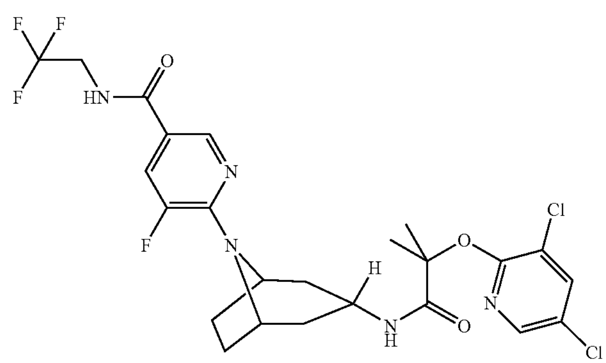 |
| 162 | 6-[3-endo-({2-[(2,5-dichloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide<br>ACTIVITY = A | 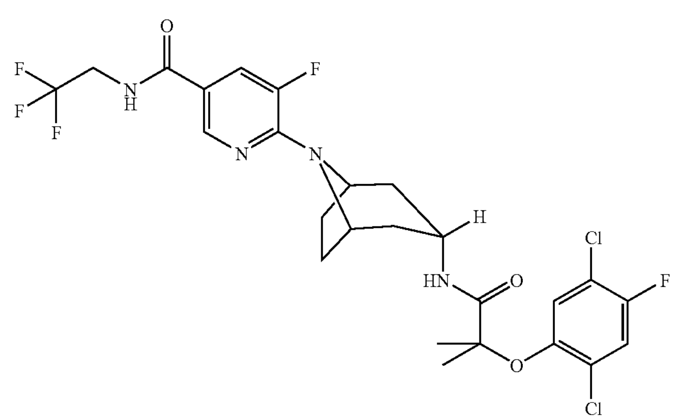 |

TABLE I-continued

| No. | Name/Activity | Structure |
|---|---|---|
| 163 | N-cyclopropyl-5-[3-endo-({2-[(2,4-dichlorophenyl)oxy]-2-methylpropanoyl}amino)-8-azabicyclo[3.2.1]oct-8-yl]pyridine-2-carboxamide<br>ACTIVITY = A | 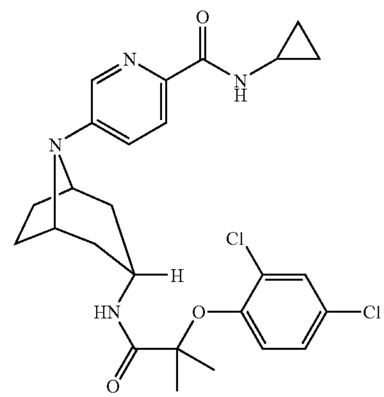 |
| 164 | 6-{3-endo-[(2-methyl-2-{[2-(trifluoromethyl)phenyl]oxy}propanoyl)amino]-8-azabicyclo[3.2.1]oct-8-yl}pyridine-3-carboxamide<br>ACTIVITY = A | 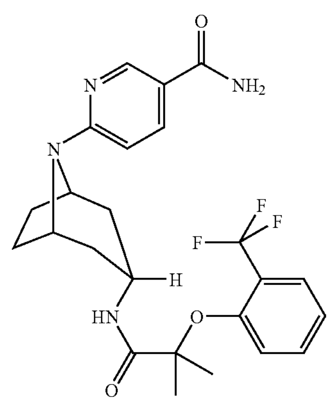 |
| 165 | 6-(3-endo-{[2-(3,4-difluorophenyl)-2-methylpropanoyl]amino}-8-azabicyclo[3.2.1]oct-8-yl)pyridine-3-carboxamide<br>ACTIVITY = A | 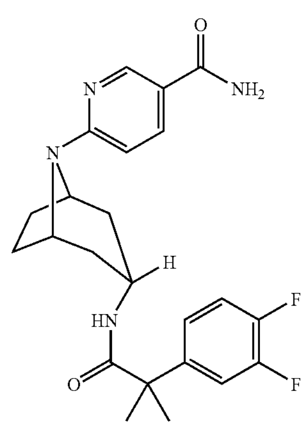 |

TABLE I-continued

| No. | Name/Activity | Structure |
|---|---|---|
| 166 | 4-[3-endo-({2-[(3,4-dichlorophenyl)oxy]-2-methylpropanoyl}amino)-8-azabicyclo[3.2.1]oct-8-yl]-N-(2,2,2-trifluoroethyl)benzamide<br>ACTIVITY = A | 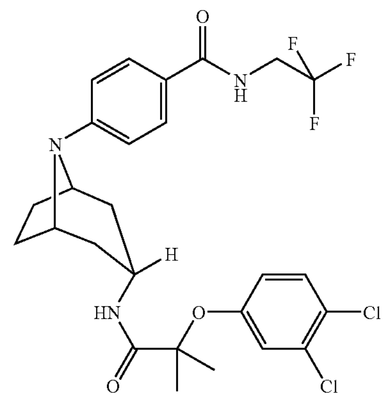 |
| 167 | 4-[3-endo-({2-[(4-chloro-3-fluorophenyl)oxy]-2-methylpropanoyl}amino)-8-azabicyclo[3.2.1]oct-8-yl]-N-(2,2,2-trifluoroethyl)benzamide<br>ACTIVITY = A | 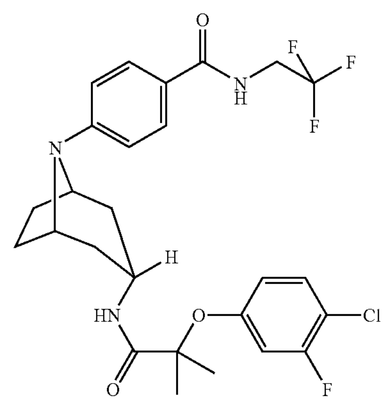 |
| 168 | 6-{3-endo-[(2-{[4-fluoro-2-(trifluoromethyl)phenyl]oxy}-2-methylpropanoyl)amino]-8-azabicyclo[3.2.1]oct-8-yl}pyridine-3-carboxamide<br>ACTIVITY = A | 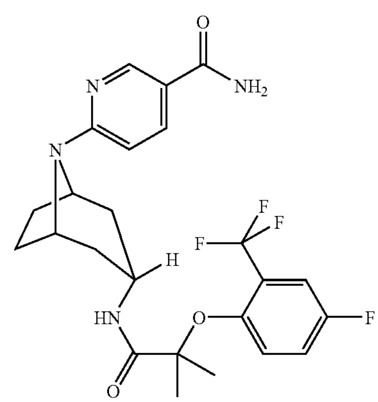 |
| 169 | 6-{3-endo-[(2-{[4-chloro-2-(trifluoromethyl)phenyl]oxy}-2-methylpropanoyl)amino]-8-azabicyclo[3.2.1]oct-8-yl}pyridine-3-carboxamide<br>ACTIVITY = A | 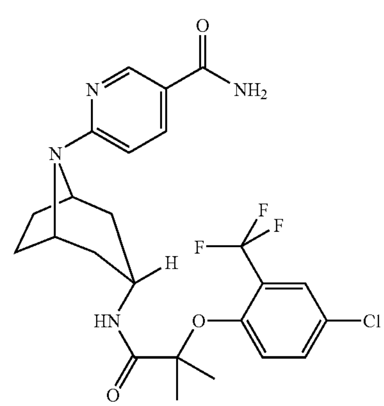 |

TABLE I-continued

| No. | Name/Activity | Structure |
|---|---|---|
| 170 | 5-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-2-carboxamide<br>ACTIVITY = A | 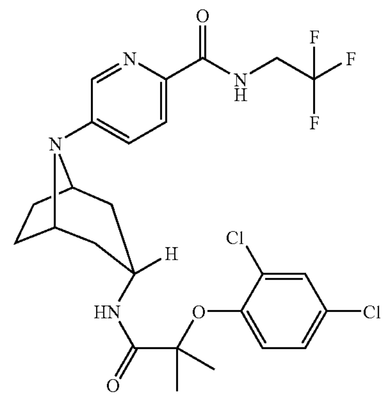 |
| 171 | 2-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-4-carboxamide<br>ACTIVITY = B | 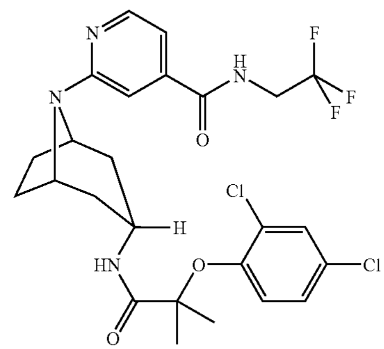 |
| 172 | 6-{3-endo-[(2-methyl-2-{[4-(trifluoromethyl)phenyl]oxy}propanoyl)amino]-8-azabicyclo[3.2.1]oct-8-yl}pyridine-3-carboxamide<br>ACTIVITY = A | 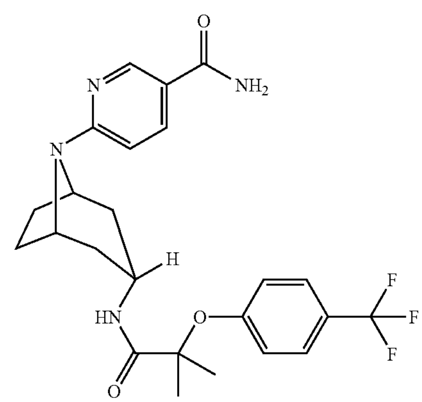 |
| 173 | 2-[(2-chloro-4-fluorophenyl)oxy]-2-methyl-N-{8-[4-(methylsulfonyl)phenyl]-8-azabicyclo[3.2.1]oct-3-endo-yl}propanamide<br>ACTIVITY = A | 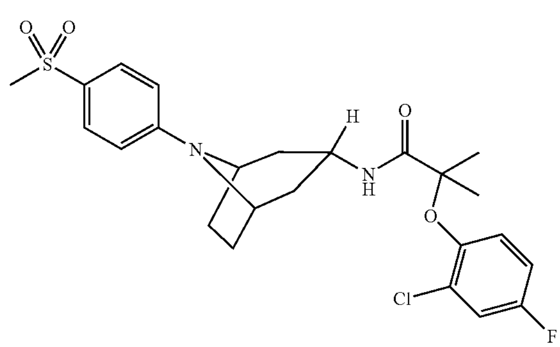 |

TABLE I-continued

| No. | Name/Activity | Structure |
|---|---|---|
| 174 | 2-[(2,5-dichloro-4-fluorophenyl)oxy]-2-methyl-N-{8-[4-(methylsulfonyl)phenyl]-8-azabicyclo[3.2.1]oct-3-endo-yl}propanamide ACTIVITY = B | 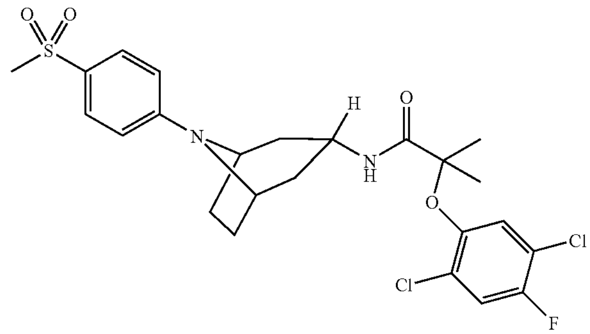 |
| 175 | 2-[(3,5-dichloropyridin-2-yl)oxy]-2-methyl-N-{8-[4-(methylsulfonyl)phenyl]-8-azabicyclo[3.2.1]oct-3-endo-yl}propanamide ACTIVITY = A | 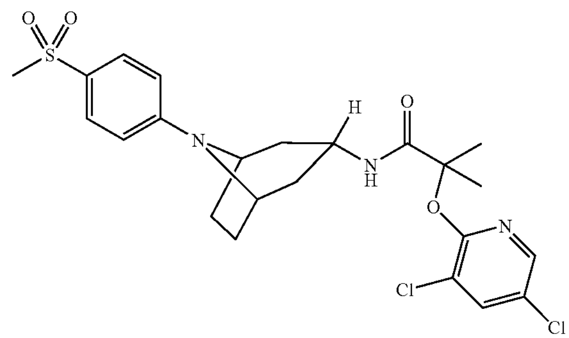 |
| 176 | 2-{[4-fluoro-2-(trifluoromethyl)phenyl]oxy}-2-methyl-N-{8-[5-(methylsulfonyl)pyridin-2-yl]-8-azabicyclo[3.2.1]oct-3-endo-yl}propanamide ACTIVITY = A | 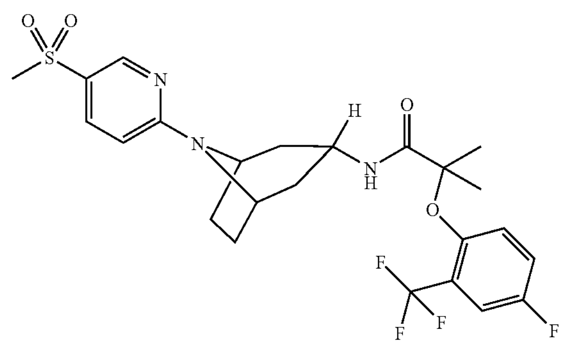 |
| 177 | N-{8-[5-(aminosulfonyl)pyridin-2-yl]-8-azabicyclo[3.2.1]oct-3-endo-yl}-2-{[4-fluoro-2-(trifluoromethyl)phenyl]oxy}-2-methylpropanamide ACTIVITY = A | 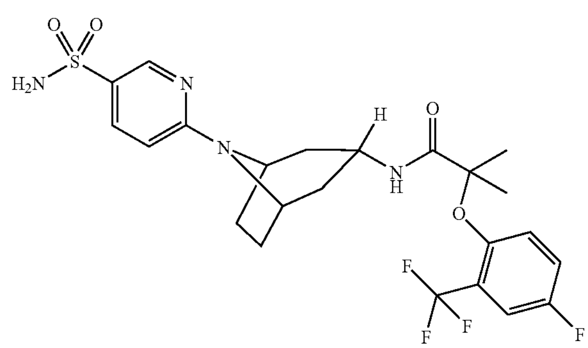 |

TABLE I-continued

| No. | Name/Activity | Structure |
|---|---|---|
| 178 | 2-[(2,6-dichloro-4-fluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 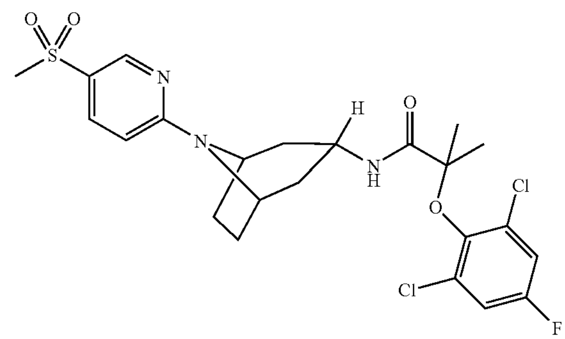 |
| 179 | 2-{[2-chloro-4-fluoro-6-(trifluoromethyl)phenyl]oxy}-2-methyl-N-{8-{5-(methylsulfonyl)pyridin-2-yl]-8-azabicyclo[3.2.1]oct-3-endo-yl}propanamide<br>ACTIVITY = A | 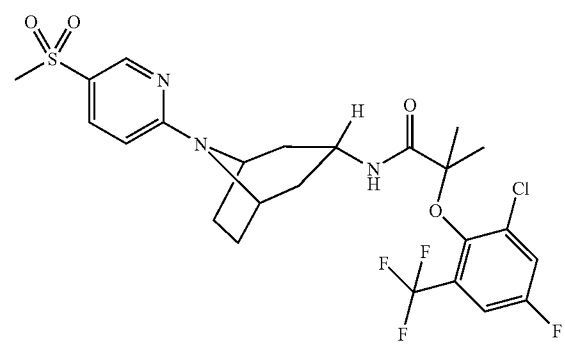 |
| 180 | 2-methyl-2-{[4-(methyloxy)phenyl]oxy}-N-{8-[5-(methylsulfonyl)pyridin-2-yl]-8-azabicyclo[3.2.1]oct-3-endo-yl}propanamide<br>ACTIVITY = A | 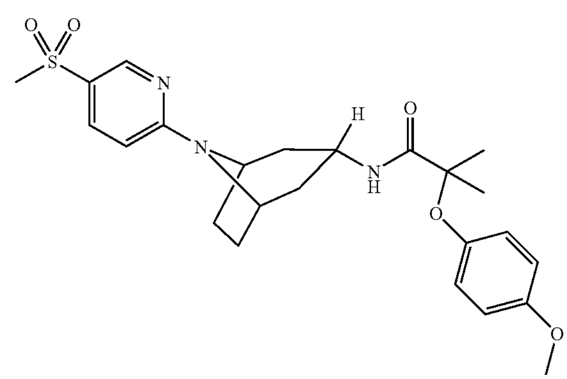 |
| 181 | N-{8-[5-(aminosulfonyl)pyridin-2-yl]-8-azabicyclo[3.2.1]oct-3-endo-yl}-2-methyl-2-{[4-(methyloxy)phenyl]oxy}propanamide<br>ACTIVITY = A | 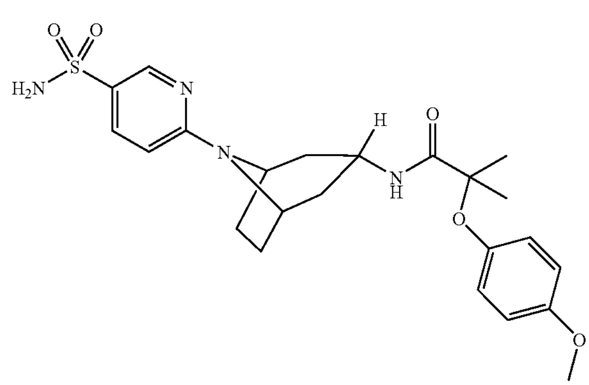 |

| No. | Name/Activity | Structure |
|-----|---------------|-----------|
| 182 | 2-methyl-2-{[4-(methyloxy)phenyl]oxy}-N-{8-[4-(methylsulfonyl)phenyl]-8-azabicyclo[3.2.1]oct-3-endo-yl}propanamide<br>ACTIVITY = B | 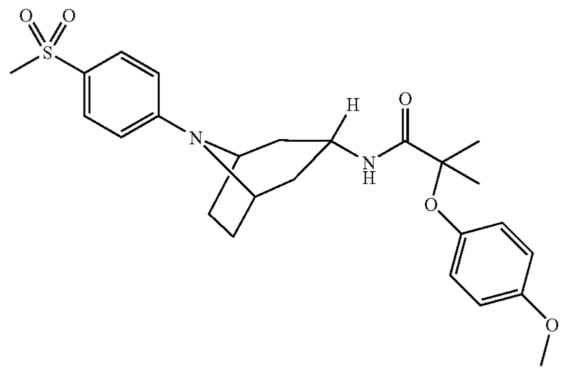 |
| 183 | 6-{3-endo-[(2-{[2-chloro-4-(trifluoromethyl)phenyl]oxy}-2-methylpropanoyl)amino]-8-azabicyclo[3.2.1]oct-8-yl}pyridine-3-carboxamide<br>ACTIVITY = A | 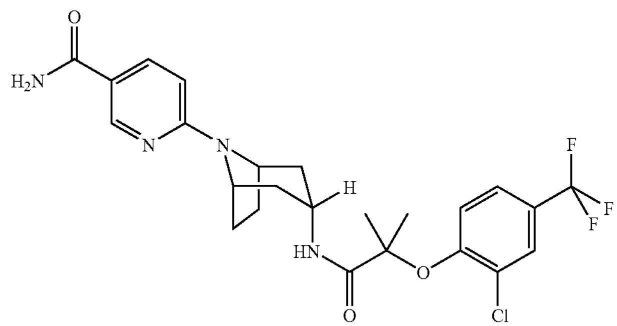 |
| 184 | 6-{3-endo-[(2-{[2-chloro-4-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 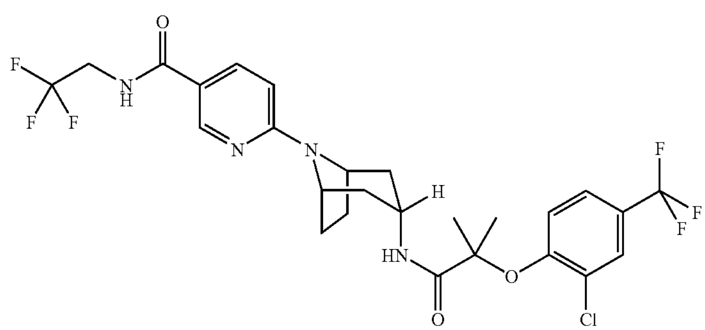 |
| 185 | 6-{3-endo-[(2-{4-chloro-3-(trifluoromethyl)phenyl]oxy}-2-methylpropanoyl)amino]-8-azabicyclo[3.2.1]oct-8-yl}pyridine-3-carboxamide<br>ACTIVITY = A | 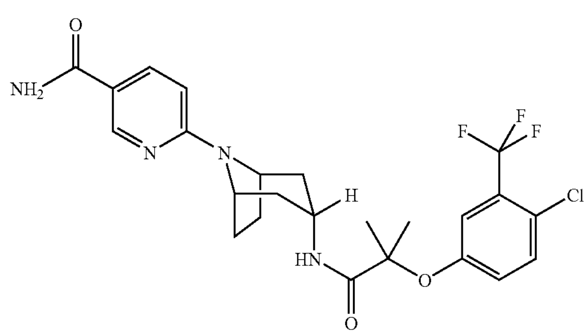 |

TABLE I-continued

| No. | Name/Activity | Structure |
|---|---|---|
| 186 | 6-{3-endo-[(2-{[4-chloro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 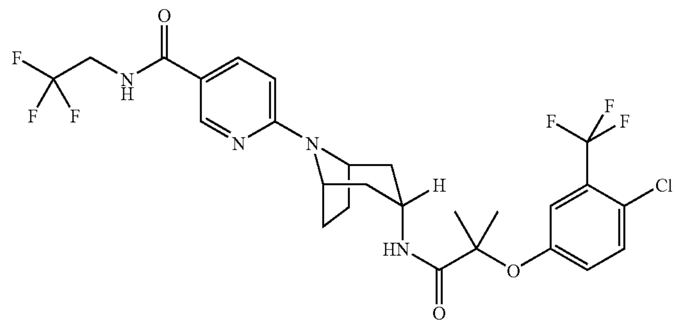 |
| 187 | 6-{3-endo-[(2-{[4-fluoro-3-(trifluoromethyl)phenyl]oxy}-2-methylpropanoyl)amino]-8-azabicyclo[3.2.1]oct-8-yl}pyridine-3-carboxamide<br>ACTIVITY = A | 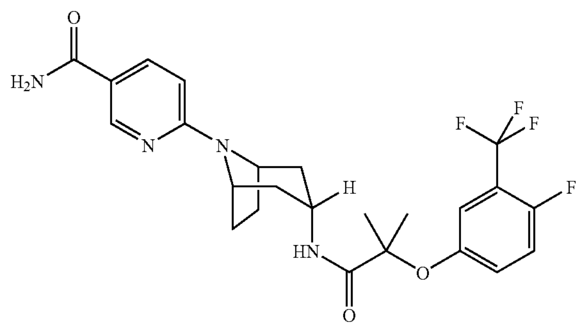 |
| 188 | 6-{3-endo-[(2-{[4-fluoro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 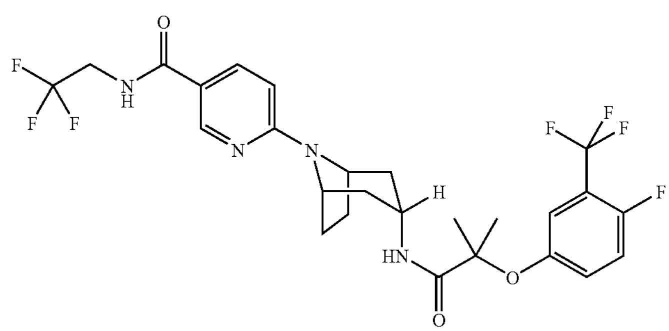 |
| 189 | 6-{3-endo-[(2-{[2-fluoro-5-(trifluoromethyl)phenyl]oxy}-2-methylpropanoyl)amino]-8-azabicyclo[3.2.1]oct-8-yl}pyridine-3-carboxamide<br>ACTIVITY = A | 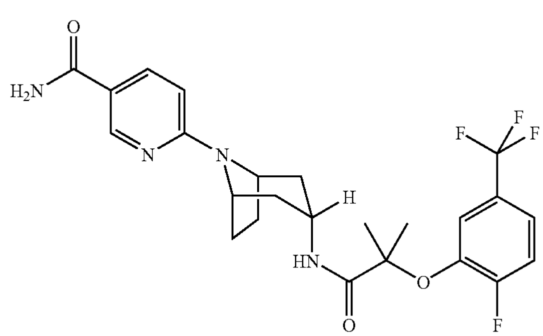 |

TABLE I-continued

| No. | Name/Activity | Structure |
|---|---|---|
| 190 | 6-{3-endo-[(2-{[2-fluoro-5-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide ACTIVITY = A | 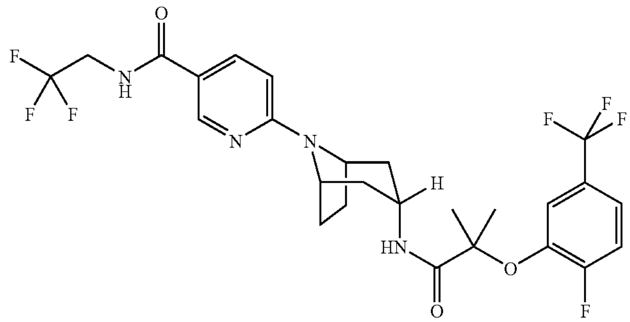 |
| 191 | N-{8-[5-(aminosulfonyl)pyridin-2-yl]-8-azabicyclo[3.2.1]oct-3-endo-yl}-2-[(3,5-dichloropyridin-2-yl)oxy]-2-methylpropanamide ACTIVITY = A | 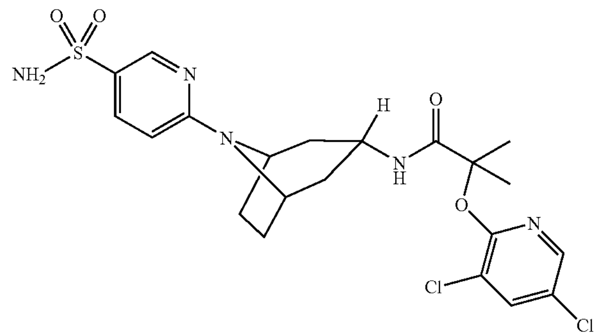 |
| 192 | N-{8-[4-(aminosulfonyl)phenyl]-8-azabicyclo[3.2.1]oct-3-endo-yl}-2-methyl-2-{[5-(trifluoromethyl)pyridin-2-yl]oxy}propanamide ACTIVITY = B | 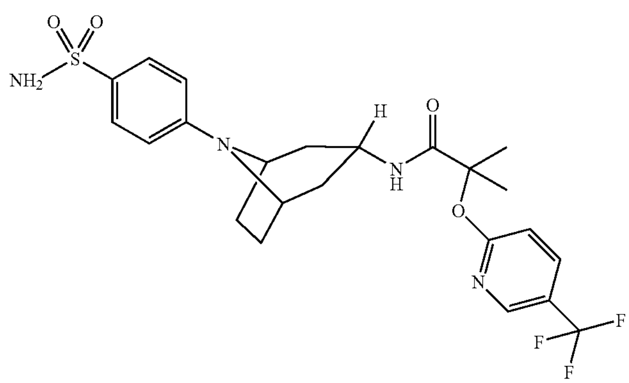 |
| 193 | 2-[(3,5-dichloropyridin-2-yl)oxy]-2-methyl-N-{8-[5-(methylsulfonyl)pyridin-2-yl]-8-azabicyclo[3.2.1]oct-3-endo-yl}propanamide ACTIVITY = A | 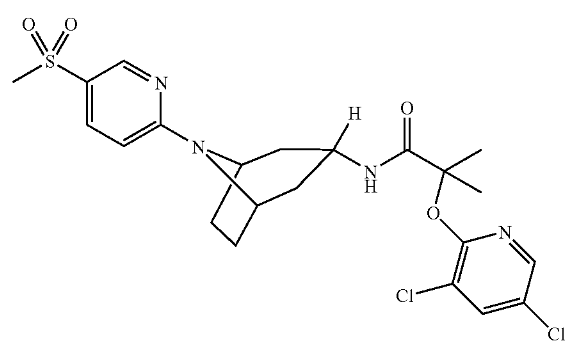 |

TABLE I-continued

| No. | Name/Activity | Structure |
|---|---|---|
| 194 | 2-[(5-chloro-3-fluoropyridin-2-yl)oxy]-2-methyl-N-{8-[5-(methylsulfonyl)pyridin-2-yl]-8-azabicyclo[3.2.1]oct-3-endo-yl}propanamide<br>ACTIVITY = B | 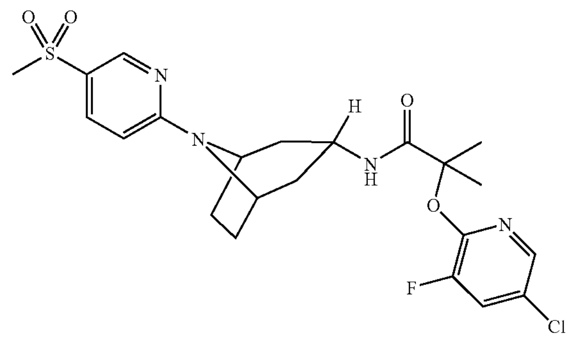 |
| 195 | 2-[(5-chloro-3-fluoropyridin-2-yl)oxy]-2-methyl-N-{8-[4-(methylsulfonyl)phenyl]-8-azabicyclo[3.2.1]oct-3-endo-yl}propanamide<br>ACTIVITY = B | 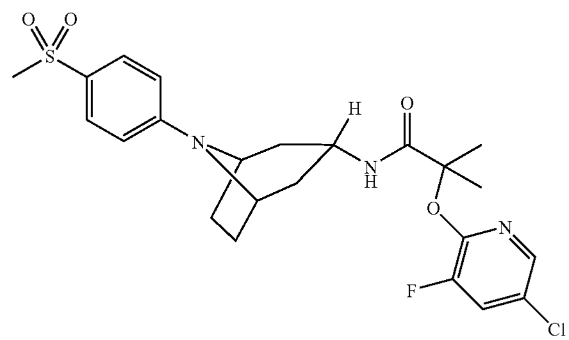 |
| 196 | 2-methyl-N-{8-[4-(methylsulfonyl)phenyl]-8-azabicyclo[3.2.1]oct-3-endo-yl}-2-{[5-(trifluoromethyl)pyridin-2-yl]oxy}propanamide<br>ACTIVITY = B | 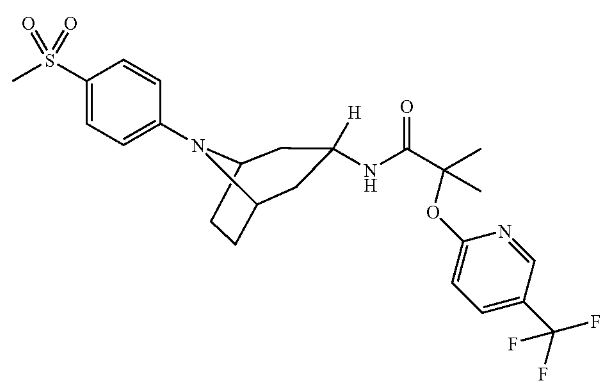 |
| 197 | 2-methyl-N-{8-[5-(methylsulfonyl)pyridin-2-yl]-8-azabicyclo[3.2.1]oct-3-endo-yl}-2-[(2,4,5-trichlorophenyl)oxy]propanamide<br>ACTIVITY = A | 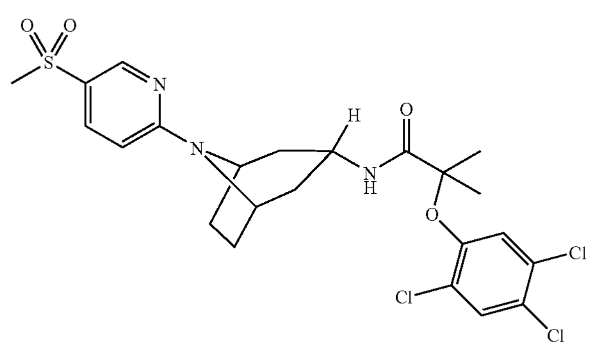 |

TABLE I-continued

| No. | Name/Activity | Structure |
|---|---|---|
| 198 | N-{8-[5-(aminosulfonyl)pyridin-2-yl]-8-azabicyclo[3.2.1]oct-3-endo-yl}-2-methyl-2-[(2,4,5-trichlorophenyl)oxy]propanamide<br>ACTIVITY = A | 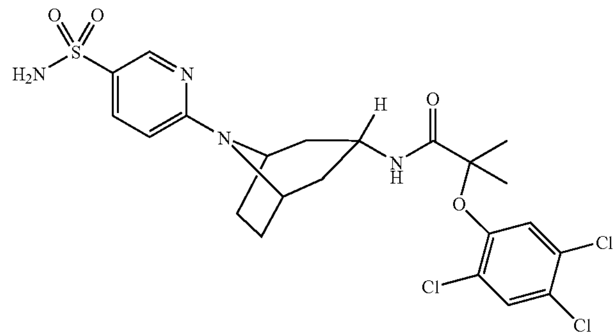 |
| 199 | 2-methyl-N-{8-[4-(methylsulfonyl)phenyl]-8-azabicyclo[3.2.1]oct-3-endo-yl}-2-[(2,4,5-trichlorophenyl)oxy]propanamide<br>ACTIVITY = A | 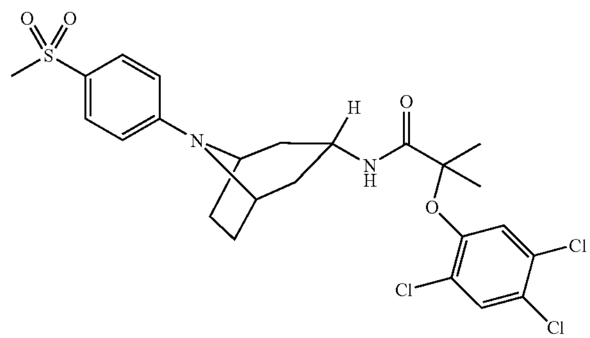 |
| 200 | 2-[(2,4-difluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 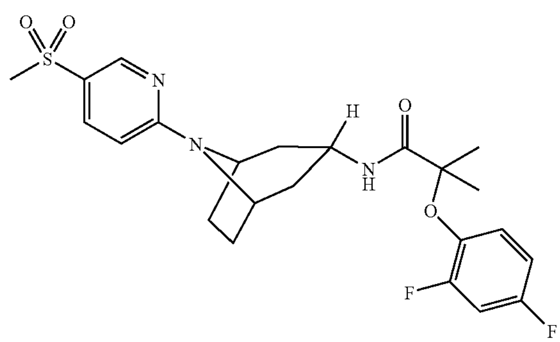 |
| 201 | 2-[(4-chlorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 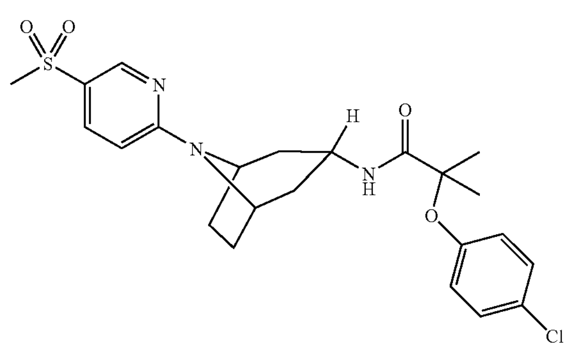 |

TABLE I-continued

| No. | Name/Activity | Structure |
|---|---|---|
| 202 | N-{8-[5-(aminosulfonyl)pyridin-2-yl]-8-azabicyclo[3.2.1]oct-3-endo-yl}-2-[(4-chlorophenyl)oxy]-2-methylpropanamide<br>ACTIVITY = A | 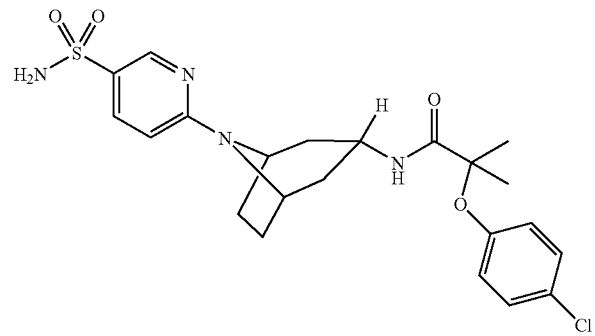 |
| 203 | 2-[(4-chlorophenyl)oxy]-2-methyl-N-{8-[4-(methylsulfonyl)phenyl]-8-azabicyclo[3.2.1]oct-3-endo-yl}propanamide<br>ACTIVITY = B | 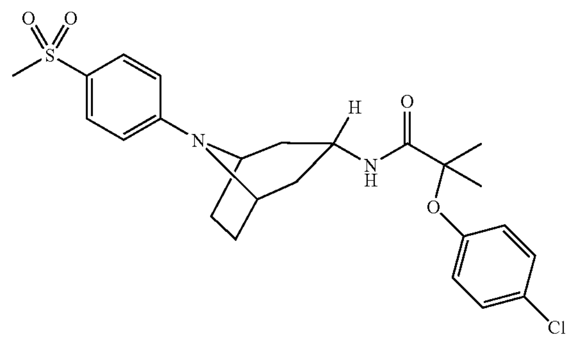 |
| 204 | 2-[(3,4-dichlorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 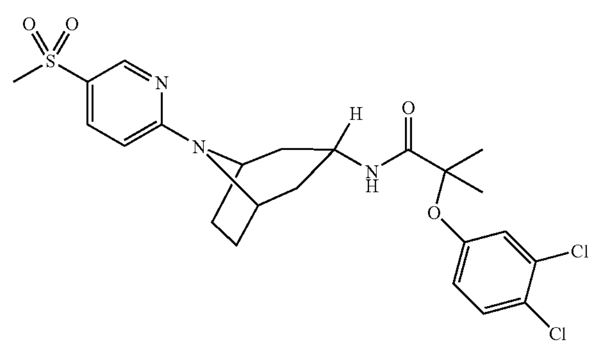 |
| 205 | N-{8-[5-(aminosulfonyl)pyridin-2-yl]-8-azabicyclo[3.2.1]oct-3-endo-yl}-2-[(3,4-dichlorophenyl)oxy]-2-methylpropanamide<br>ACTIVITY = A | 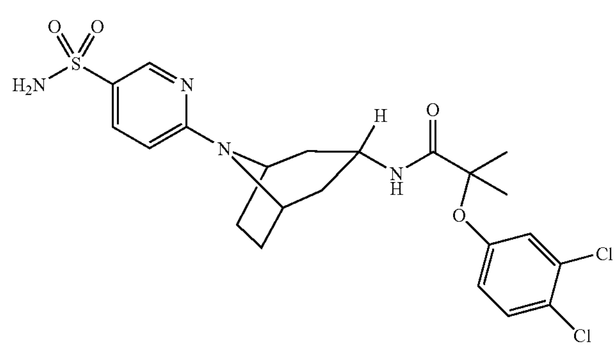 |

TABLE I-continued

| No. | Name/Activity | Structure |
|---|---|---|
| 206 | 2-[(3,4-dichlorophenyl)oxy]-2-methyl-N-{8-[4-(methylsulfonyl)phenyl]-8-azabicyclo[3.2.1]oct-3-endo-yl}propanamide<br>ACTIVITY = B | 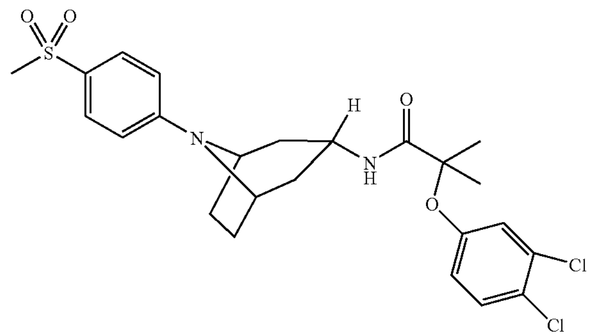 |
| 207 | 2-[(3,4-difluorophenyl)oxy]-2-methyl-N-{8-[5-(methylsulfonyl)pyridin-2-yl]-8-azabicyclo[3.2.1]oct-3-endo-yl}propanamide<br>ACTIVITY = B | 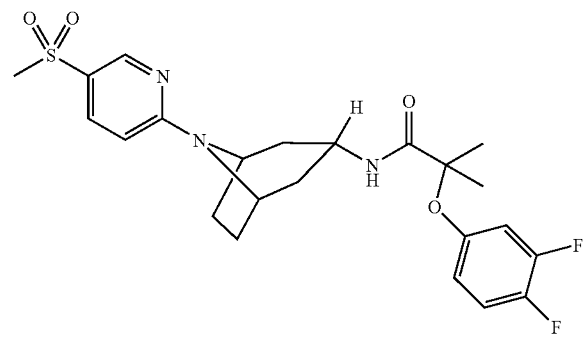 |
| 208 | N-{8-[5-(aminosulfonyl)pyridin-2-yl]-8-azabicyclo[3.2.1]oct-3-endo-yl}-2-[(3,4-difluorophenyl)oxy]-2-methylpropanamide<br>ACTIVITY = B | 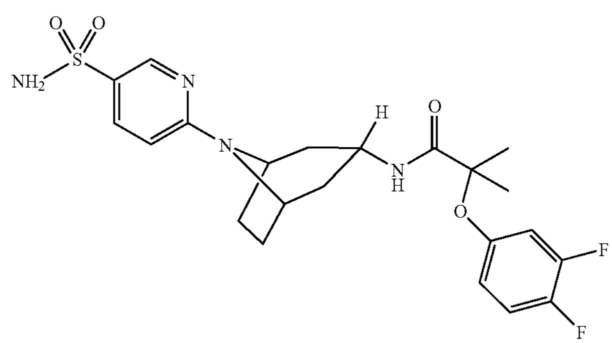 |
| 209 | 2-[(3,4-difluorophenyl)oxy]-2-methyl-N-{8-[4-(methylsulfonyl)phenyl]-8-azabicyclo[3.2.1]oct-3-endo-yl}propanamide<br>ACTIVITY = B | 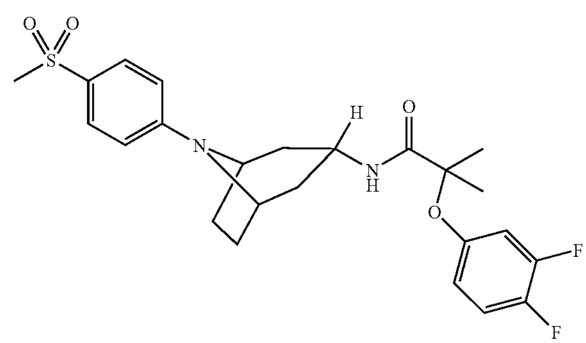 |

TABLE I-continued

| No. | Name/Activity | Structure |
|-----|---------------|-----------|
| 210 | 4-[3-endo-({2-[(3,4-difluorophenyl)oxy]-2-methylpropanoyl}amino)-8-azabicyclo[3.2.1]oct-8-yl]-N-(2,2,2-trifluoroethyl)benzamide<br>ACTIVITY = A | 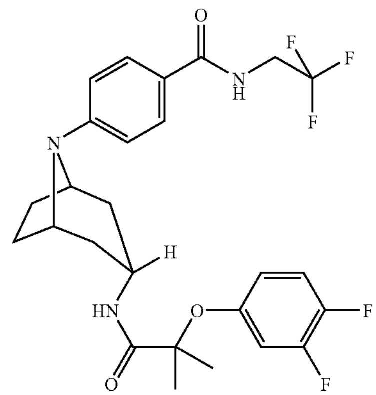 |
| 211 | N-{8-[5-(aminosulfonyl)pyridin-2-yl]-8-azabicyclo[3.2.1]oct-3-endo-yl}-2-{[4-chloro-2-(trifluoromethyl)phenyl]oxy}-2-methylpropanamide<br>ACTIVITY = A | 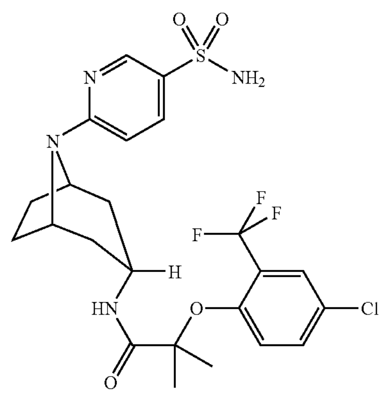 |
| 212 | 2-[(2-chloro-4-methylphenyl)oxy]-2-methyl-N-{8-[5-(methylsulfonyl)pyridin-2-yl]-8-azabicyclo[3.2.1]oct-3-endo-yl}propanamide<br>ACTIVITY = A | 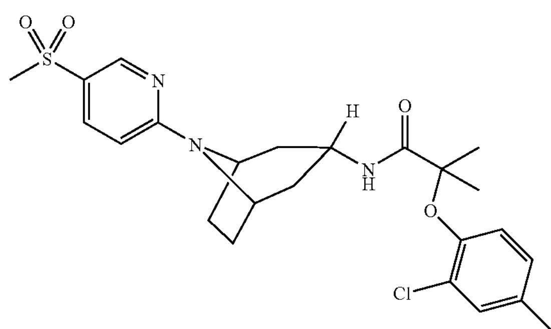 |
| 213 | N-{8-[5-(aminosulfonyl)pyridin-2-yl]-8-azabicyclo[3.2.1]oct-3-endo-yl}-2-[(2-chloro-4-methylphenyl)oxy]-2-methylpropanamide<br>ACTIVITY = A | 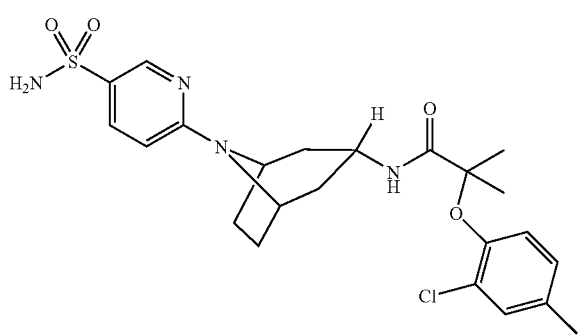 |

TABLE I-continued

| No. | Name/Activity | Structure |
|---|---|---|
| 214 | 2-[(2-chloro-4-methylphenyl)oxy]-2-methyl-N-{8-[4-(methylsulfonyl)phenyl]-8-azabicyclo[3.2.1]oct-3-endo-yl}propanamide ACTIVITY = A | 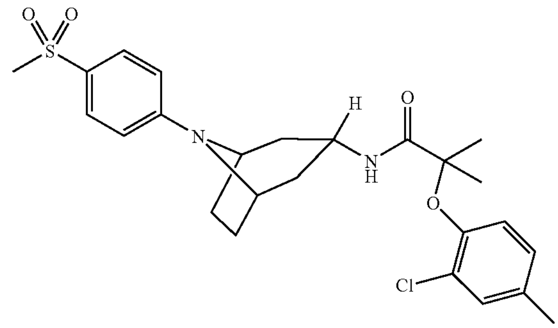 |
| 215 | N-{8-[5-(aminosulfonyl)pyridin-2-yl]-8-azabicyclo[3.2.1]oct-3-endo-yl}-2-[(2,3-dichloro-4-fluorophenyl)oxy]-2-methylpropanamide ACTIVITY = A | 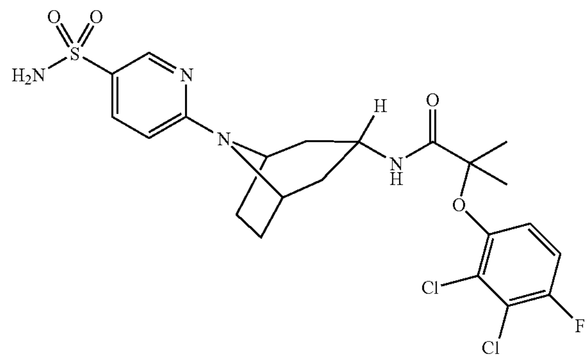 |
| 216 | N-{8-[5-(aminosulfonyl)pyridin-2-yl]-8-azabicyclo[3.2.1]oct-3-endo-yl}-2-methyl-2-[(2,4,5-trifluorophenyl)oxy]propanamide ACTIVITY = A | 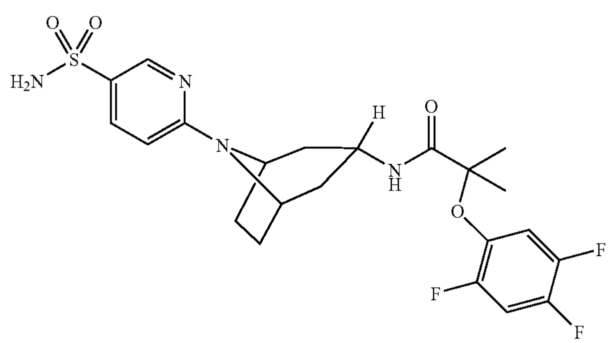 |
| 217 | 2-[(4-fluoro-2-methylphenyl)oxy]-2-methyl-N-{8-[5-(methylsulfonyl)pyridin-2-yl]-8-azabicyclo[3.2.1]oct-3-endo-yl}propanamide ACTIVITY = A | 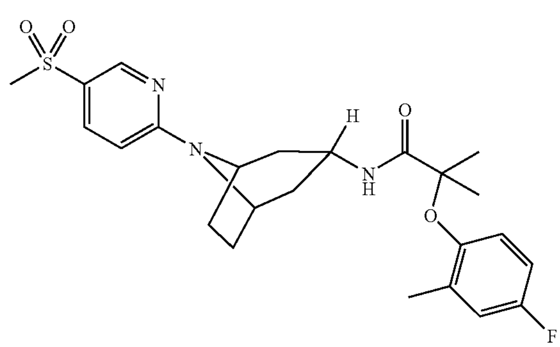 |

TABLE I-continued

| No. | Name/Activity | Structure |
|-----|---------------|-----------|
| 218 | N-{8-[5-(aminosulfonyl)pyridin-2-yl]-8-azabicyclo[3.2.1]oct-3-endo-yl}-2-[(4-fluoro-2-methylphenyl)oxy]-2-methylpropanamide<br>ACTIVITY = A | 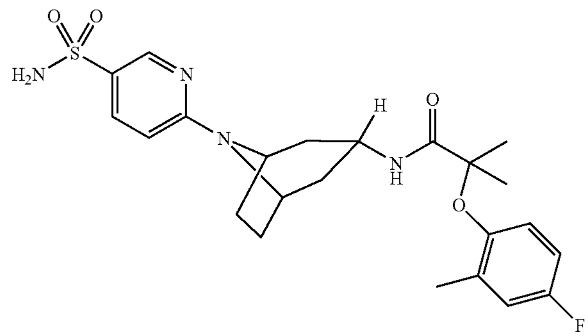 |
| 219 | 2-[(4-fluoro-2-methylphenyl)oxy]-2-methyl-N-{8-[4-(methylsulfonyl)phenyl]-8-azabicyclo[3.2.1]oct-3-endo-yl}propanamide<br>ACTIVITY = A | 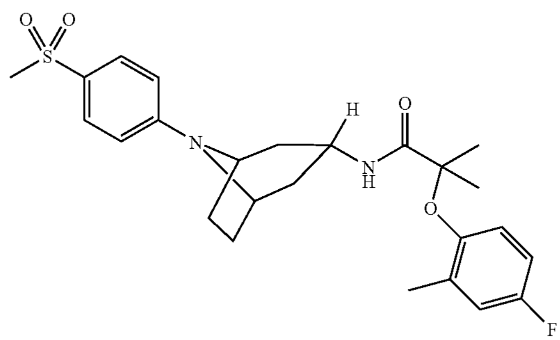 |
| 220 | 2-{[4-fluoro-2-(methyloxy)phenyl]oxy}-2-methyl-N-{8-[5-methylsulfonyl)pyridin-2-yl]-8-azabicyclo[3.2.1]oct-3-endo-yl}propanamide<br>ACTIVITY = A | 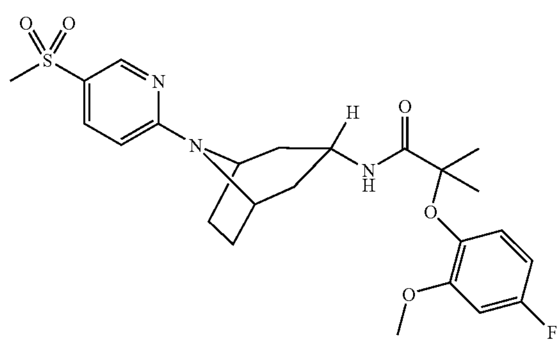 |
| 221 | N-{8-[5-(aminosulfonyl)pyridin-2-yl]-8-azabicyclo[3.2.1]oct-3-endo-yl}-2-{[4-fluoro-2-(methyloxy)phenyl]oxy}-2-methylpropanamide<br>ACTIVITY = A | 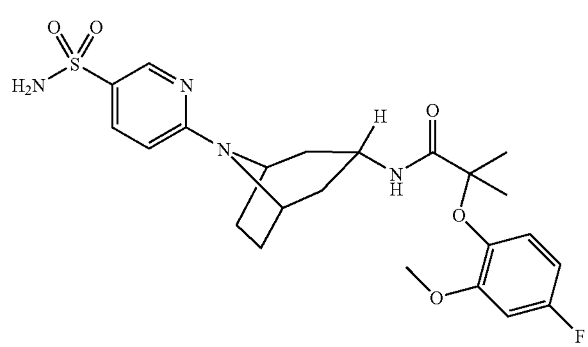 |

TABLE I-continued

| No. | Name/Activity | Structure |
|---|---|---|
| 222 | 2-{[4-fluoro-2-(methyloxy)phenyl]oxy}-2-methyl-N-{8-[4-(methylsulfonyl)phenyl]-8-azabicyclo[3.2.1]oct-3-endo-yl}propanamide<br>ACTIVITY = A | 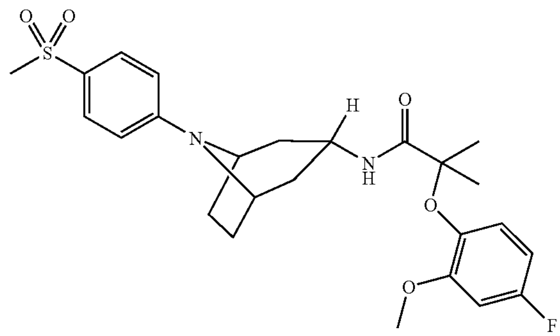 |
| 223 | 2-[(4-chloro-2-fluorophenyl)oxy]-2-methyl-N-{8-[4-(methylsulfonyl)phenyl]-8-azabicyclo[3.2.1]oct-3-endo-yl}propanamide<br>ACTIVITY = A | 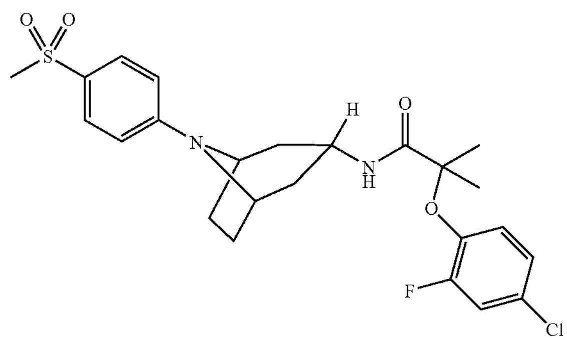 |
| 224 | 2-[(2,4-difluorophenyl)oxy]-2-methyl-N-{8-[4-(methylsulfonyl)phenyl]-8-azabicyclo[3.2.1]oct-3-endo-yl}propanamide<br>ACTIVITY = A | 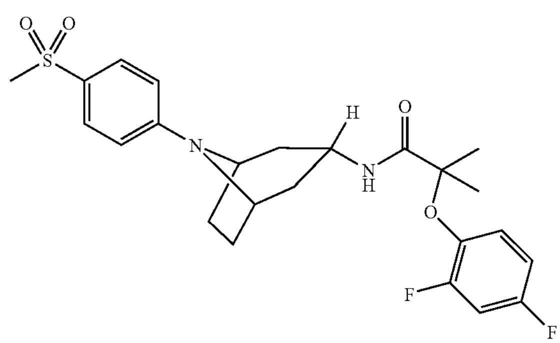 |
| 225 | 2-[(2-chloro-4,5-difluorophenyl)oxy]-2-methyl-N-{8-[4-(methylsulfonyl)phenyl]-8-azabicyclo[3.2.1]oct-3-endo-yl}propanamide<br>ACTIVITY = A | 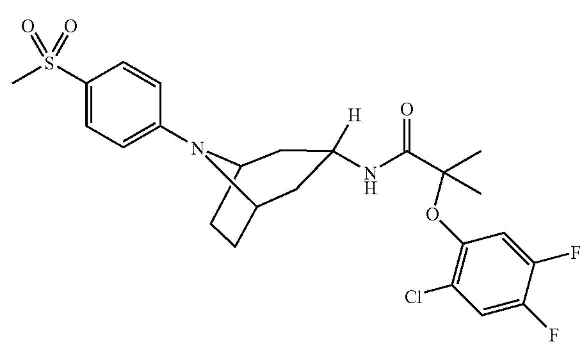 |

TABLE I-continued

| No. | Name/Activity | Structure |
|---|---|---|
| 226 | 2-[(3-chloro-4-fluorophenyl)oxy]-2-methyl-N-{8-[5-(methylsulfonyl)pyridin-2-yl]-8-azabicyclo[3.2.1]oct-3-endo-yl}propanamide ACTIVITY = A | 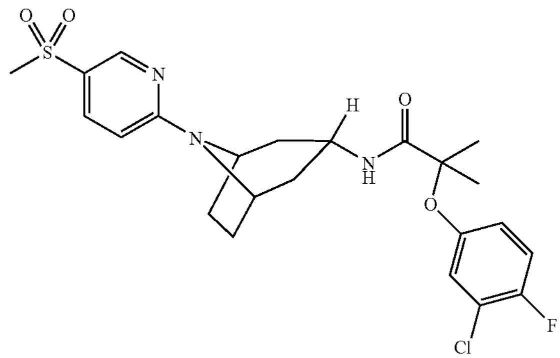 |
| 227 | N-{8-[5-(aminosulfonyl)pyridin-2-yl]-8-azabicyclo[3.2.1]oct-3-endo-yl}-2-[(3-chloro-4-fluorophenyl)oxy]-2-methylpropanamide ACTIVITY = A | 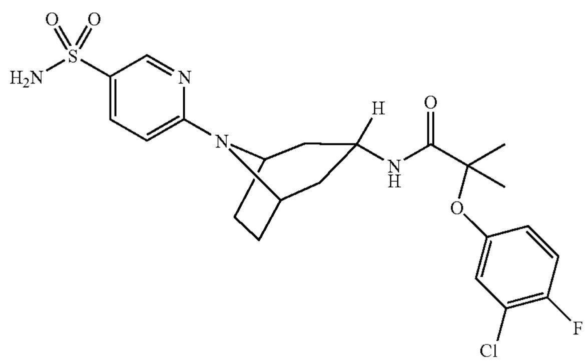 |
| 228 | 2-[(3-chloro-4-fluorophenyl)oxy]-2-methyl-N-{8-[4-(methylsulfonyl)phenyl]-8-azabicyclo[3.2.1]oct-3-endo-yl}propanamide ACTIVITY = B | 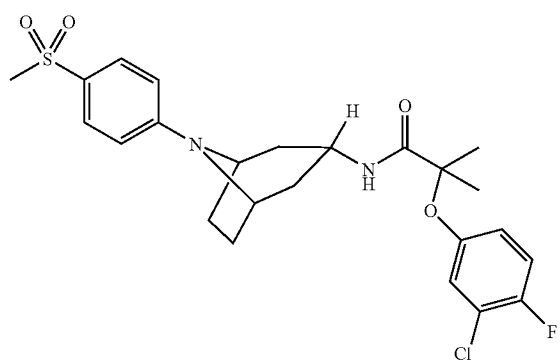 |
| 229 | 2-[(4-chloro-2-fluorophenyl)oxy]-2-methyl-N-{8-[5-(methylsulfonyl)pyridin-2-yl]-8-azabicyclo[3.2.1]oct-3-endo-yl}propanamide ACTIVITY = A | 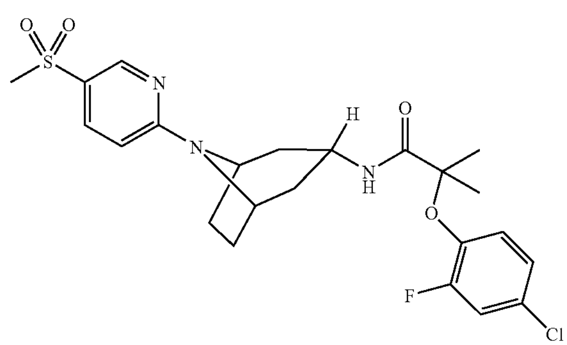 |

TABLE I-continued

| No. | Name/Activity | Structure |
|---|---|---|
| 230 | 2-[(4-fluorophenyl)oxy]-2-methyl-N-{8-[5-(methylsulfonyl)pyridin-2-yl]-8-azabicyclo[3.2.1]oct-3-endo-yl}propanamide<br>ACTIVITY = B | 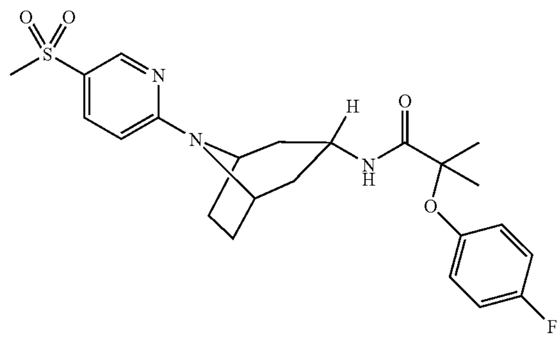 |
| 231 | 2-[(2-chloro-4,5-difluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 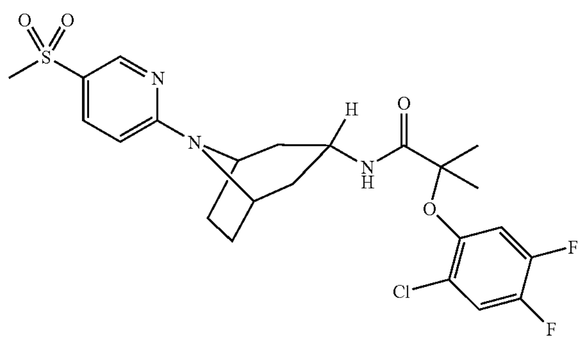 |
| 232 | 2-methyl-N-{8-[5-(methylsulfonyl)pyridin-2-yl]-8-azabicyclo[3.2.1]oct-3-endo-yl}-2-[(2,4,5-trifluorophenyl)oxy]propanamide<br>ACTIVITY = A | 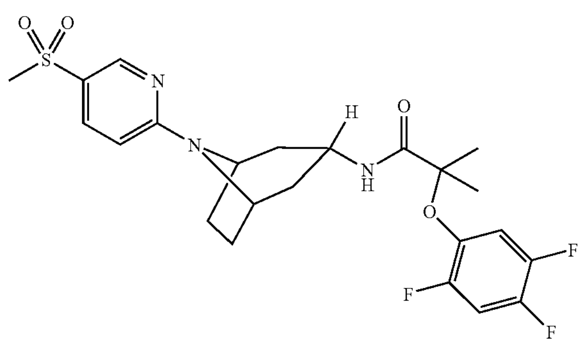 |
| 233 | 2-[(4-fluorophenyl)oxy]-2-methyl-N-{8-[4-(methylsulfonyl)phenyl]-8-azabicyclo[3.2.1]oct-3-endo-yl}propanamide<br>ACTIVITY = B | 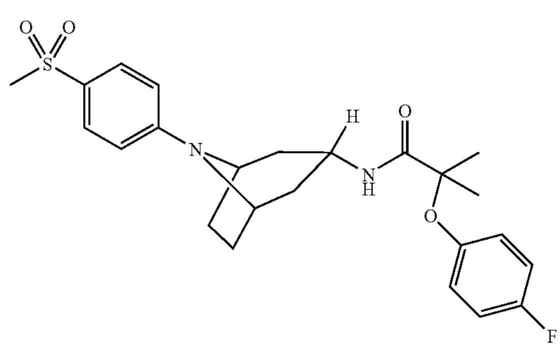 |

TABLE I-continued

| No. | Name/Activity | Structure |
|---|---|---|
| 234 | 2-methyl-N-{8-[4-(methylsulfonyl)phenyl]-8-azabicyclo[3.2.1]oct-3-endo-yl}-2-[(2,4,5-trifluorophenyl)oxy]propanamide<br>ACTIVITY = B | 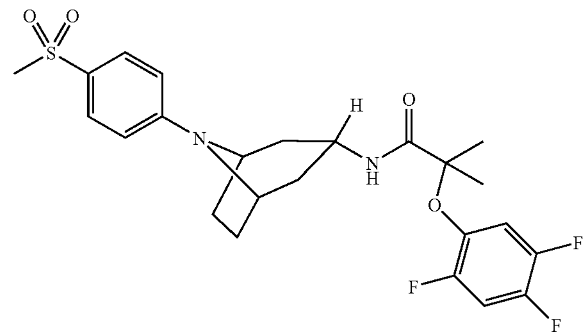 |
| 235 | 2-[(2,3-dichloro-4-fluorophenyl)oxy]-2-methyl-N-{8-[4-(methylsulfonyl)phenyl]-8-azabicyclo[3.2.1]oct-3-endo-yl}propanamide<br>ACTIVITY = A | 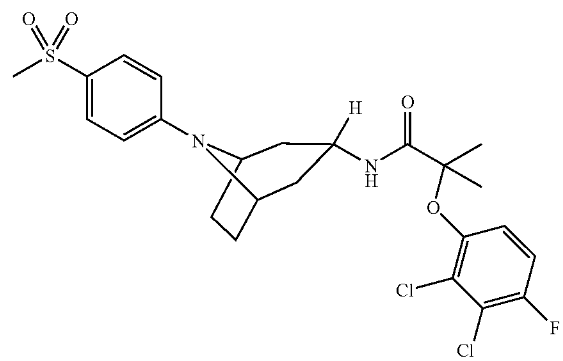 |
| 236 | 2-[(2,4-dichloro-5-fluorophenyl)oxy]-2-methyl-N-{8-[5-(methylsulfonyl)pyridin-2-yl]-8-azabicyclo[3.2.1]oct-3-endo-yl}propanamide<br>ACTIVITY = A | 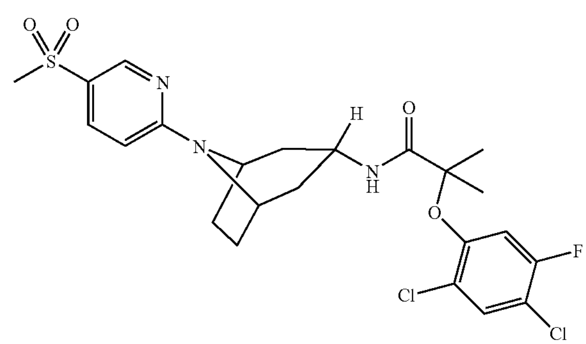 |
| 237 | 2-[(2,4-dichloro-5-fluorophenyl)oxy]-2-methyl-N-{8-[4-(methylsulfonyl)phenyl]-8-azabicyclo[3.2.1]oct-3-endo-yl}propanamide<br>ACTIVITY = A | 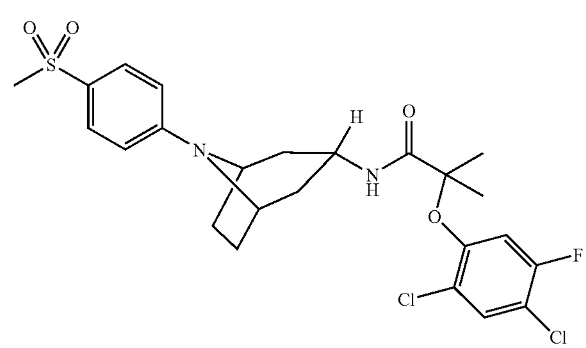 |

TABLE I-continued

| No. | Name/Activity | Structure |
|---|---|---|
| 238 | N-{8-[5-(aminosulfonyl)pyridin-2-yl]-8-azabicyclo[3.2.1]oct-3-endo-yl}-2-[(2,6-dichloro-4-fluorophenyl)oxy]-2-methylpropanamide ACTIVITY = A | 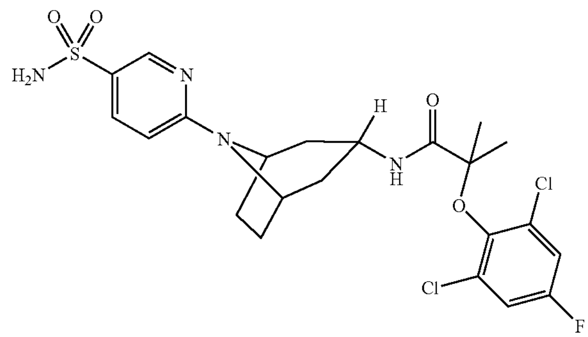 |
| 239 | 2-[(2,6-dichloro-4-fluorophenyl)oxy]-2-methyl-N-{8-[4-(methylsulfonyl)phenyl]-8-azabicyclo[3.2.1]oct-3-endo-yl}propanamide ACTIVITY = A | 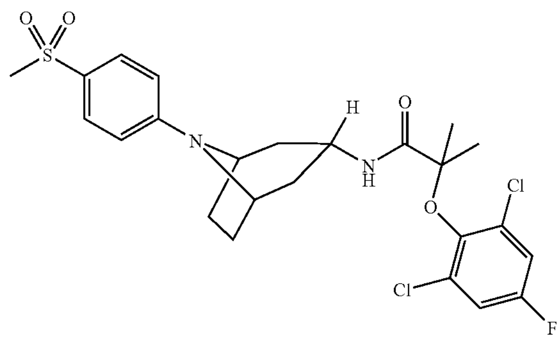 |
| 240 | 2-[(4-chloro-3-fluorophenyl)oxy]-2-methyl-N-{8-[5-(methylsulfonyl)pyridin-2-yl]-8-azabicyclo[3.2.1]oct-3-endo-yl}propanamide ACTIVITY = A | 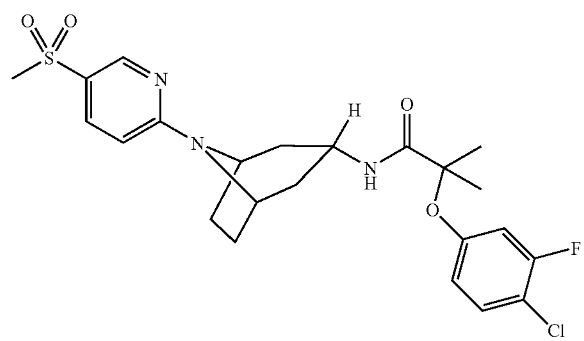 |
| 241 | 2-[(4-chloro-3-fluorophenyl)oxy]-2-methyl-N-{8-[4-(methylsulfonyl)phenyl]-8-azabicyclo[3.2.1]oct-3-endo-yl}propanamide ACTIVITY = B | 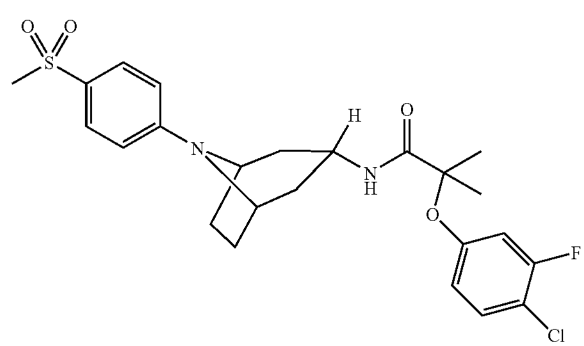 |

TABLE I-continued

| No. | Name/Activity | Structure |
|---|---|---|
| 242 | N-{8-[5-(aminosulfonyl)pyridin-2-yl]-8-azabicyclo[3.2.1]oct-3-endo-yl}-2-[(4-chloro-3-fluorophenyl)oxy]-2-methylpropanamide<br>ACTIVITY = A | 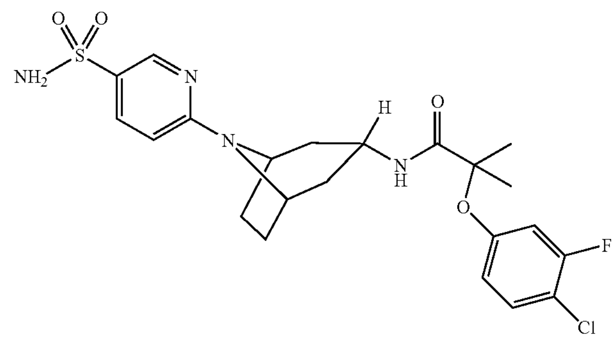 |
| 243 | 2-methyl-N-{8-[5-(methylsulfonyl)pyridin-2-yl]-8-azabicyclo[3.2.1]oct-3-endo-yl}-2-{[4-(trifluoromethyl)phenyl]oxy}propanamide<br>ACTIVITY = B | 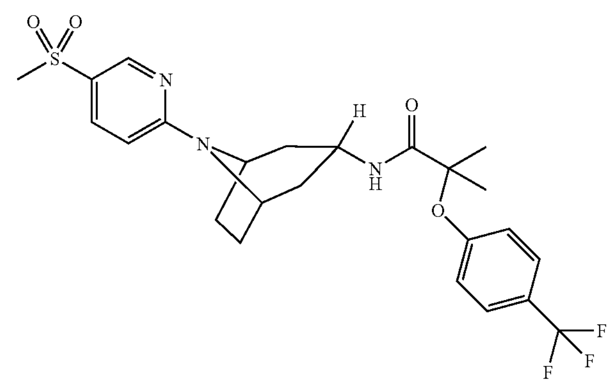 |
| 244 | N-{8-[5-(aminosulfonyl)pyridin-2-yl]-8-azabicyclo[3.2.1]oct-3-endo-yl}-2-methyl-2-{[4-(trifluoromethyl)phenyl]oxy}propanamide<br>ACTIVITY = B | 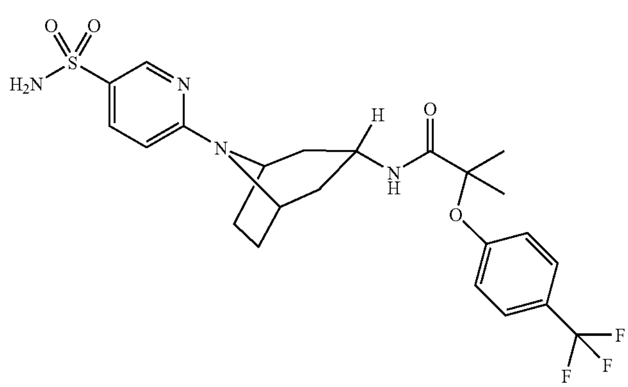 |
| 245 | 2-methyl-N-{8-[4-(methylsulfonyl)phenyl]-8-azabicyclo[3.2.1]oct-3-endo-yl}-2-{[4-(trifluoromethyl)phenyl]oxy}propanamide<br>ACTIVITY = B | 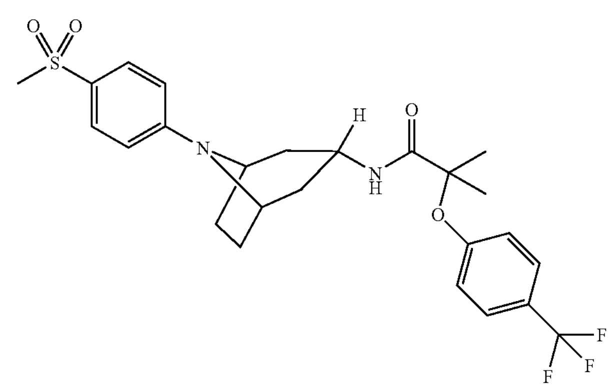 |

TABLE I-continued

| No. | Name/Activity | Structure |
|---|---|---|
| 246 | N-{8-[5-(aminosulfonyl)pyridin-2-yl]-8-azabicyclo[3.2.1]oct-3-endo-yl}-2-{[3-chloro-5-(trifluoromethyl)pyridin-2-yl]oxy}-2-methylpropanamide ACTIVITY = B | 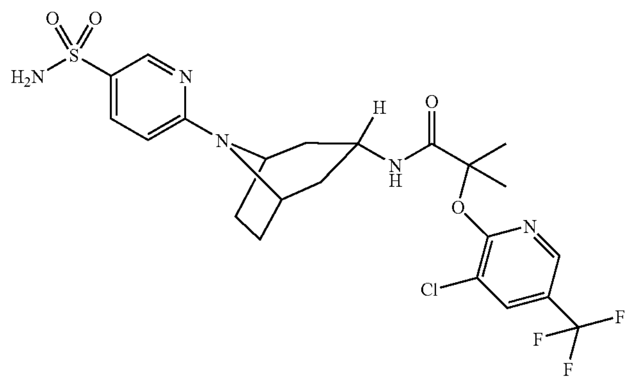 |
| 247 | N-{8-[5-(aminosulfonyl)pyridin-2-yl]-8-azabicyclo[3.2.1]oct-3-endo-yl}-2-[(5-chloro-3-fluoropyridin-2-yl)oxy]-2-methylpropanamide ACTIVITY = B | 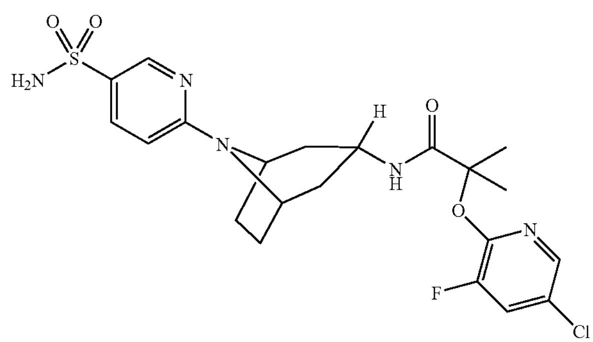 |
| 248 | 2-{[3-chloro-5-(trifluoromethyl)pyridin-2-yl]oxy}-2-methyl-N-{8-[5-(methylsulfonyl)pyridin-2-yl]-8-azabicyclo[3.2.1]oct-3-endo-yl}propanamide ACTIVITY = B | 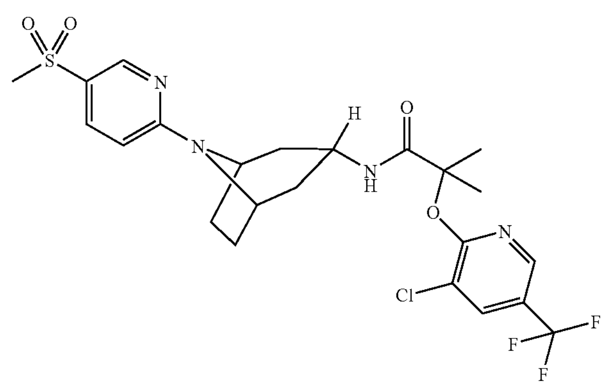 |
| 249 | 2-{[3-chloro-5-(trifluoromethyl)pyridin-2-yl]oxy}-2-methyl-N-{8-[4-(methylsulfonyl)phenyl]-8-azabicyclo[3.2.1]oct-3-endo-yl}propanamide ACTIVITY = B | 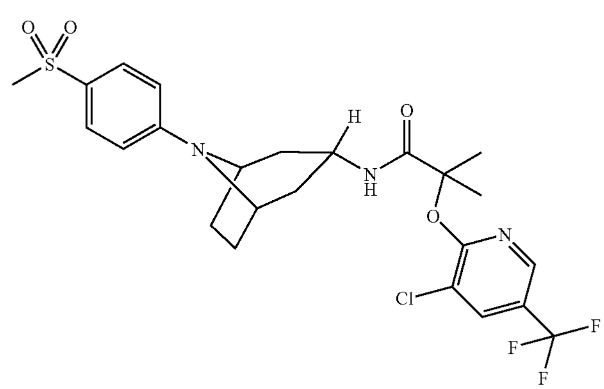 |

TABLE I-continued

| No. | Name/Activity | Structure |
|---|---|---|
| 250 | 2-{[4-fluoro-2-(trifluoromethyl)phenyl]oxy}-2-methyl-N-{8-[4-(methylsulfonyl)phenyl]-8-azabicyclo[3.2.1]oct-3-endo-yl}propanamide<br>ACTIVITY = A | 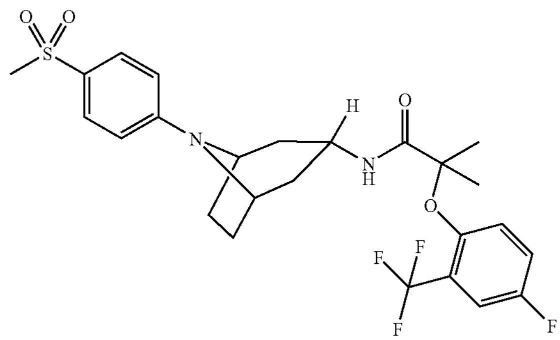 |
| 251 | N-{8-[5-(aminosulfonyl)pyridin-2-yl]-8-azabicyclo[3.2.1]oct-3-endo-yl}-2-{[2-chloro-4-fluoro-6-(trifluoromethyl)phenyl]oxy}-2-methylpropanamide<br>ACTIVITY = A | 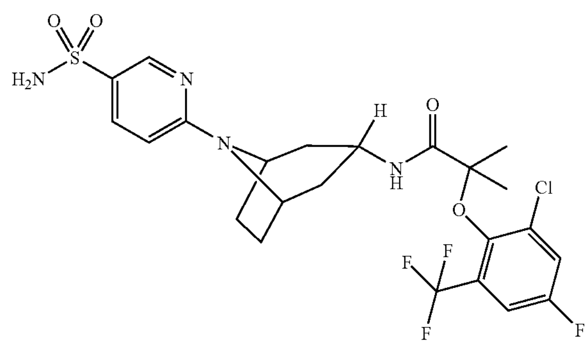 |
| 252 | 2-{[2-chloro-4-fluoro-6-(trifluoromethyl)phenyl]oxy}-2-methyl-N-{8-[4-(methylsulfonyl)phenyl]-8-azabicyclo[3.2.1]oct-3-endo-yl}propanamide<br>ACTIVITY = A | 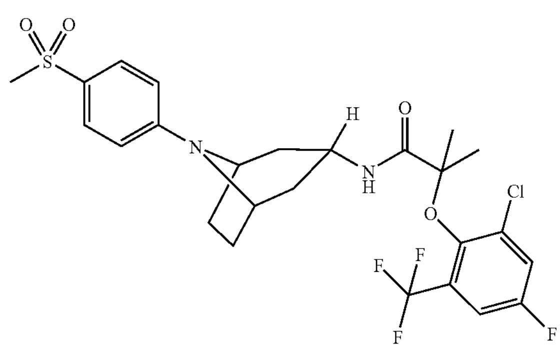 |
| 253 | 2-{[2-chloro-4-(methyloxy)phenyl]oxy}-2-methyl-N-{8-[5-(methylsulfonyl)pyridin-2-yl]-8-azabicyclo[3.2.1]oct-3-endo-yl}propanamide<br>ACTIVITY = A | 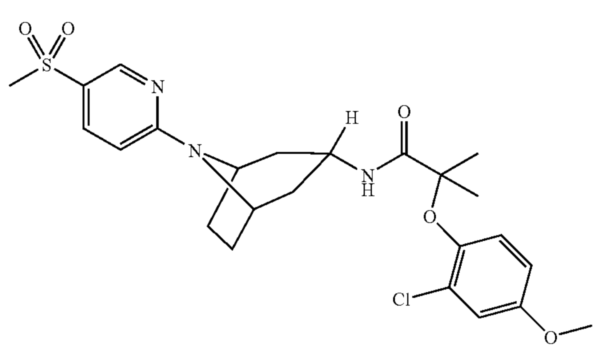 |

TABLE I-continued

| No. | Name/Activity | Structure |
|---|---|---|
| 254 | 2-{[2-chloro-4-(methyloxy)phenyl]oxy}-2-methyl-N-{8-[4-(methylsulfonyl)phenyl]-8-azabicyclo[3.2.1]oct-3-endo-yl}propanamide<br>ACTIVITY = A | 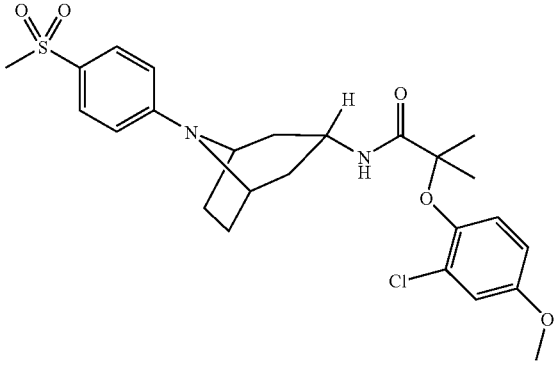 |
| 255 | 2-methyl-N-{8-[5-(methylsulfonyl)pyridin-2-yl]-8-azabicyclo[3.2.1]oct-3-endo-yl}-2-{[2-(trifluoromethyl)phenyl]oxy}propanamide<br>ACTIVITY = A | 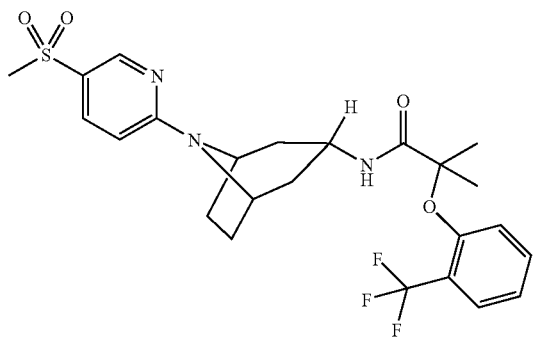 |
| 256 | N-{8-[5-(aminosulfonyl)pyridin-2-yl]-8-azabicyclo[3.2.1]oct-3-endo-yl}-2-methyl-2-{[2-(trifluoromethyl)phenyl]oxy}propanamide<br>ACTIVITY = A | 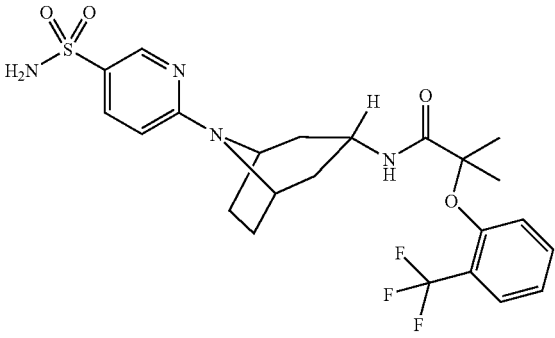 |
| 257 | 2-methyl-N-{8-[4-(methylsulfonyl)phenyl]-8-azabicyclo[3.2.1]oct-3-endo-yl}-2-{[2-(trifluoromethyl)phenyl]oxy}propanamide<br>ACTIVITY = A | 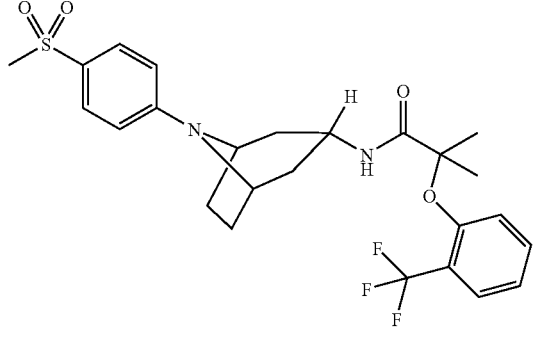 |

TABLE I-continued

| No. | Name/Activity | Structure |
|---|---|---|
| 258 | 2-methyl-N-{8-[5-(methylsulfonyl)pyridin-2-yl]-8-azabicyclo[3.2.1]oct-3-endo-yl}-2-[(2,4,6-trifluorophenyl)oxy]propanamide<br>ACTIVITY = A | 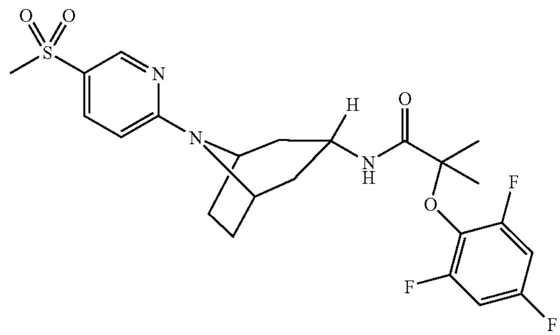 |
| 259 | N-{8-[5-(aminosulfonyl)pyridin-2-yl]-8-azabicyclo[3.2.1]oct-3-endo-yl}-2-methyl-2-[(2,4,6-trifluorophenyl)oxy]propanamide<br>ACTIVITY = A | 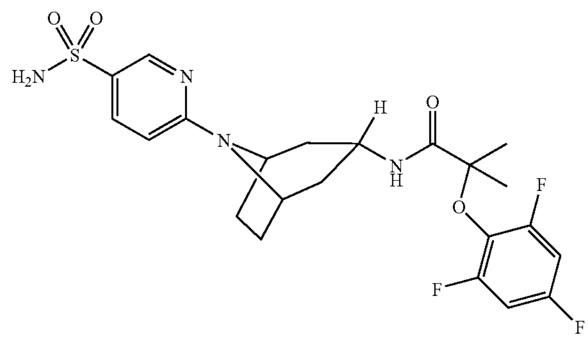 |
| 260 | 2-methyl-N-{8-[4-(methylsulfonyl)phenyl]-8-azabicyclo[3.2.1]oct-3-endo-yl}-2-[(2,4,6-trifluorophenyl)oxy]propanamide<br>ACTIVITY = A | 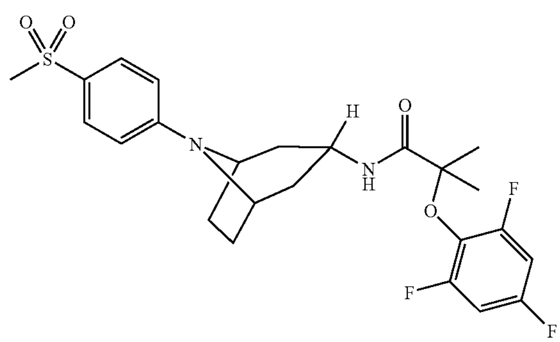 |
| 261 | N-{8-[5-(aminosulfonyl)pyridin-2-yl]-8-azabicyclo[3.2.1]oct-3-endo-yl}-2-[(2,4-dichloro-5-fluorophenyl)oxy]-2-methylpropanamide<br>ACTIVITY = A | 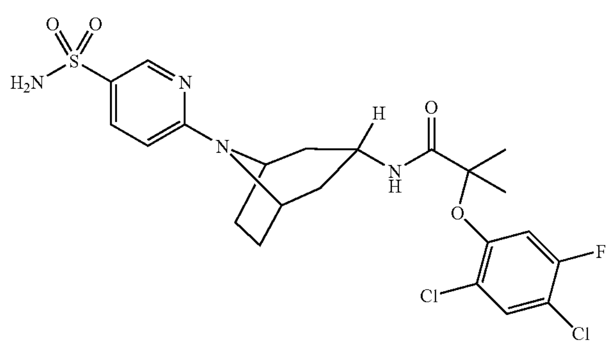 |

TABLE I-continued

| No. | Name/Activity | Structure |
|---|---|---|
| 262 | N-{8-[5-(aminosulfonyl)pyridin-2-yl]-8-azabicyclo[3.2.1]oct-3-endo-yl}-2-[(2-chloro-4,5-difluorophenyl)oxy]-2-methylpropanamide<br>ACTIVITY = A | 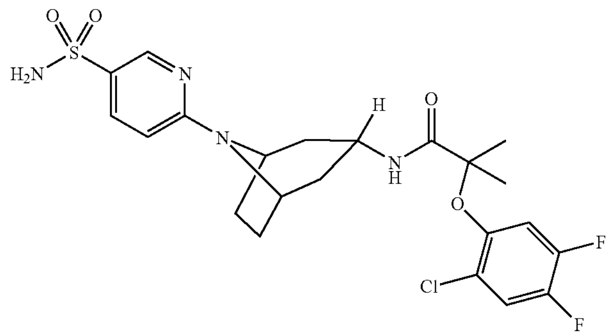 |
| 263 | 2-{[4-chloro-2-(trifluoromethyl)phenyl]oxy}-2-methyl-N-{8-[5-(methylsulfonyl)pyridin-2-yl]-8-azabicyclo[3.2.1]oct-3-endo-yl}propanamide<br>ACTIVITY = A | 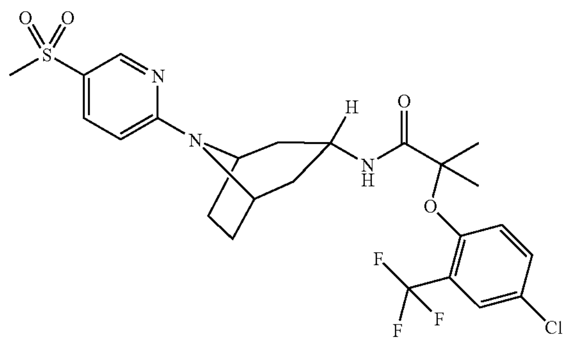 |
| 264 | N-{8-[5-(aminosulfonyl)pyridin-2-yl]-8-azabicyclo[3.2.1]oct-3-endo-yl}-2-[(4-fluorophenyl)oxy]-2-methylpropanamide<br>ACTIVITY = A | 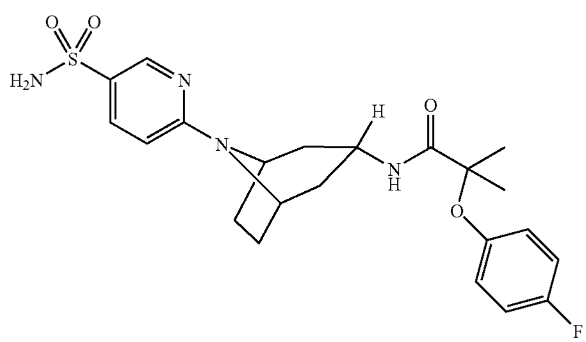 |
| 265 | 6-[3-endo-({2-[(2-chloro-4-fluorophenyl)oxy]-2-methylpropanoyl}amino)-8-azabicyclo[3.2.1]oct-8-yl]-N-cyclopropylpyridine-3-carboxamide<br>ACTIVITY = A | 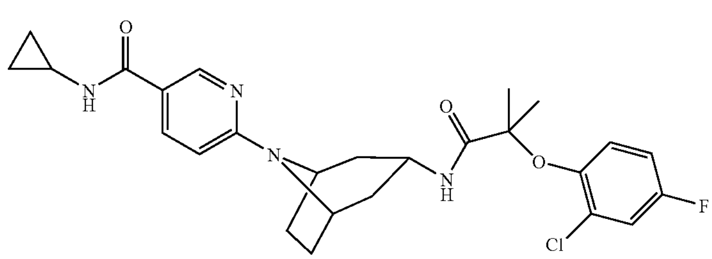 |

TABLE I-continued

| No. | Name/Activity | Structure |
|---|---|---|
| 266 | 6-[3-endo-({2-[(3-chlorobiphenyl-4-yl)oxy]-2-methylpropanoyl}amino)-8-azabicyclo[3.2.1]oct-8-yl]pyridine-3-carboxamide<br>ACTIVITY = A | 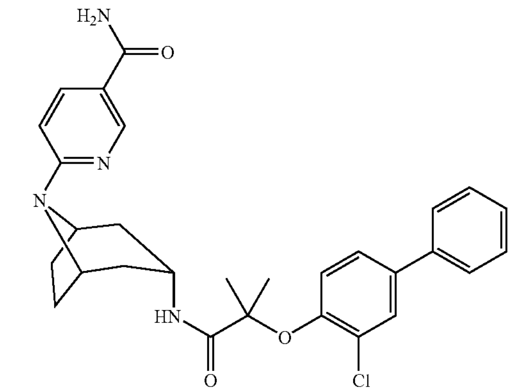 |
| 267 | 2-{[5-fluoro-2-(trifluoromethyl)phenyl]oxy}-2-methyl-N-{8-[5-(methylsulfonyl)pyridin-2-yl]-8-azabicyclo[3.2.1]oct-3-endo-yl}propanamide<br>ACTIVITY = A | 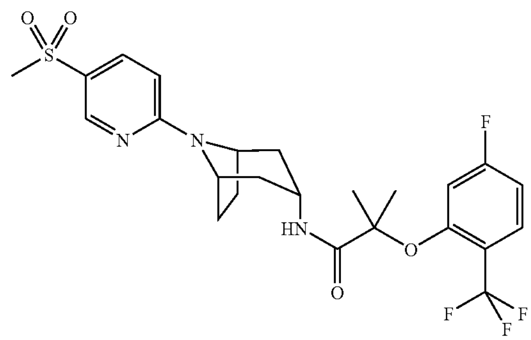 |
| 268 | 6-[3-endo-({2-[(2,4-dichlorophenyl)oxy]-2-methylpropanoyl}amino)-8-azabicyclo[3.2.1]oct-8-yl]-N-(2,2-difluorocyclopropyl)pyridine-3-carboxamide<br>ACTIVITY = A | 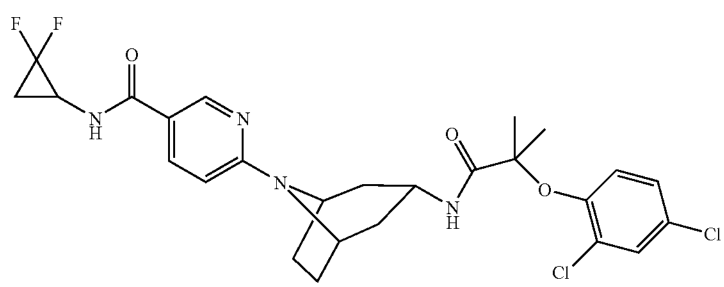 |
| 269 | 6-{3-endo-[(2-{[4-fluoro-2-(methylsulfonyl)phenyl]oxy}-2-methylpropanoyl)amino]-8-azabicyclo[3.2.1]oct-8-yl}pyridine-3-carboxamide<br>ACTIVITY = A | 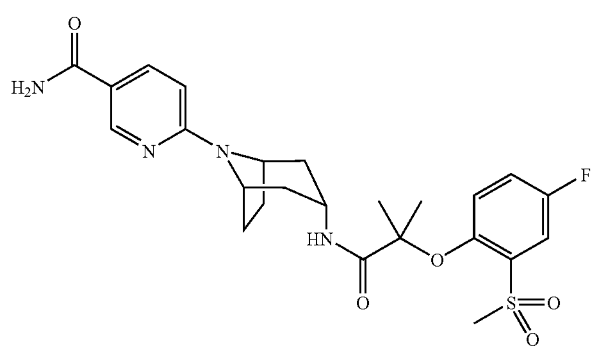 |

TABLE I-continued

| No. | Name/Activity | Structure |
|---|---|---|
| 270 | 2-[(2,5-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide<br>ACTIVITY = A | 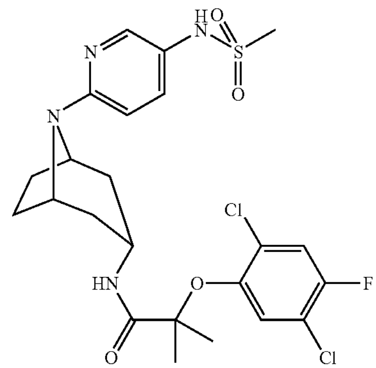 |
| 271 | 6-[3-endo-({2-[(1-chloronaphthalen-2-yl)oxy]-2-methylpropanoyl}amino)-8-azabicyclo[3.2.1]oct-8-yl]pyridine-3-carboxamide<br>ACTIVITY = A | 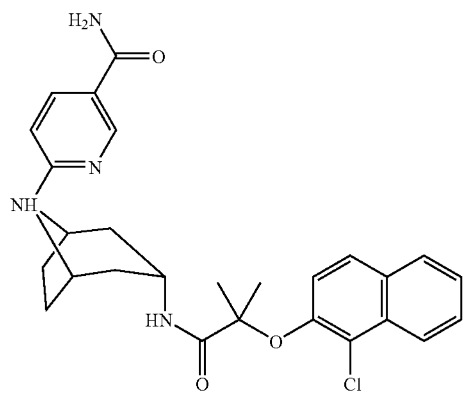 |
| 272 | 2-{[4-fluoro-3-(trifluoromethyl)phenyl]oxy}-2-methyl-N-{8-[5-(methylsulfonyl)pyridin-2-yl]-8-azabicyclo[3.2.1]oct-3-endo-yl}propanamide<br>ACTIVITY = B | 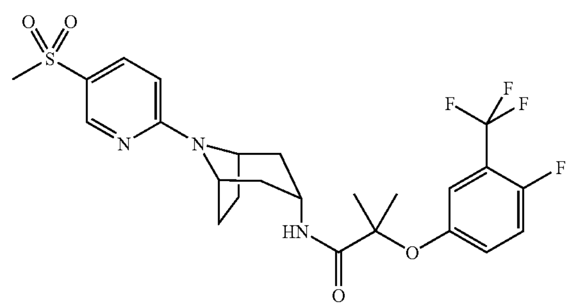 |
| 273 | 6-{3-endo-[(2-{[5-chloro-3-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 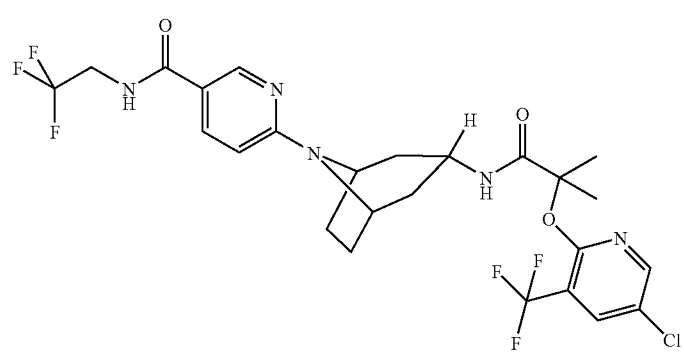 |

TABLE I-continued

| No. | Name/ Activity | Structure |
|---|---|---|
| 274 | 6-[3-endo-({2-[(2,4-dichlorophenyl)sulfonyl]-2-methylpropanoyl}amino)-8-azabicyclo[3.2.1]oct-8-yl]pyridine-3-carboxamide<br>ACTIVITY = A | 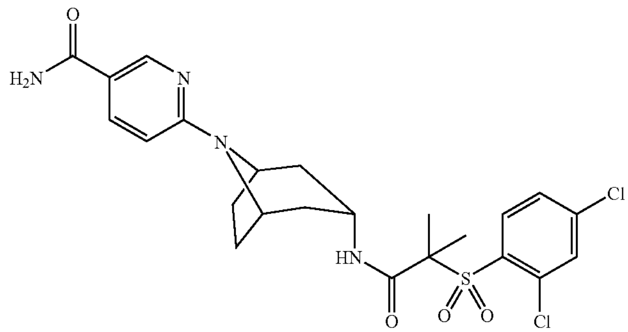 |
| 275 | 2-[(2-chloro-4-fluorophenyl)oxy]-2-methyl-N-{8-[6-(methylsulfonyl)pyridin-3-yl]-8-azabicyclo[3.2.1]oct-3-endo-yl}propanamide<br>ACTIVITY = A | 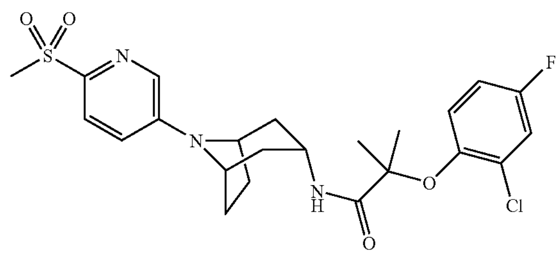 |
| 276 | 2-[(2-chloro-4-fluorophenyl)oxy]-2-methyl-N-(8-{5-[5-(trifluoromethyl)-1,2,4-oxadiazol-3-yl]pyridin-2-yl}-8-azabicyclo[3.2.1]oct-3-endo-yl)propanamide<br>ACTIVITY = B | 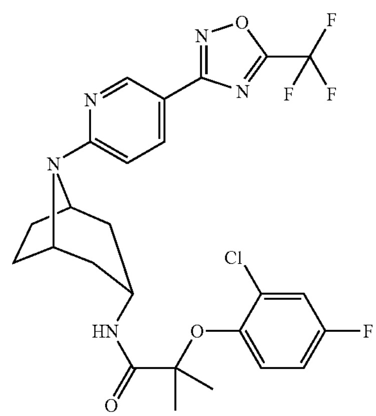 |
| 277 | 6-[3-endo-({2-[(5-chloro-4'-fluorobiphenyl-2-yl)oxy]-2-methylpropanoyl}amino)-8-azabicyclo[3.2.1]oct-8-yl]pyridine-3-carboxamide<br>ACTIVITY = A | 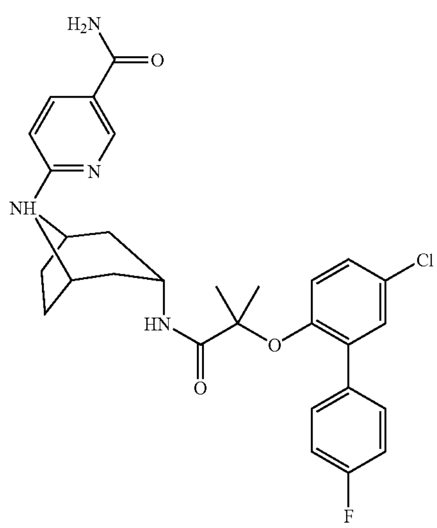 |

TABLE I-continued

| No. | Name/Activity | Structure |
|---|---|---|
| 278 | N-{5-chloro-6-[3-endo-({2-[(2,4-dichlorophenyl)oxy]-2-methylpropanoyl}amino)-8-azabicyclo[3.2.1]oct-8-yl]pyridin-3-yl}-3,3,3-trifluoropropanamide<br>ACTIVITY = B | 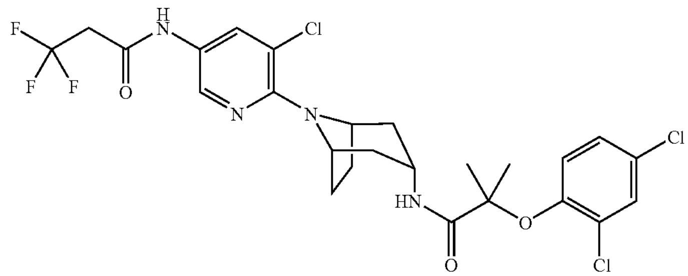 |
| 279 | 4-{[3-endo-({2-[(2,4-dichlorophenyl)oxy]-2-methylpropanoyl}amino)-8-azabicyclo[3.2.1]oct-8-yl]carbonyl}benzamide<br>ACTIVITY = B | 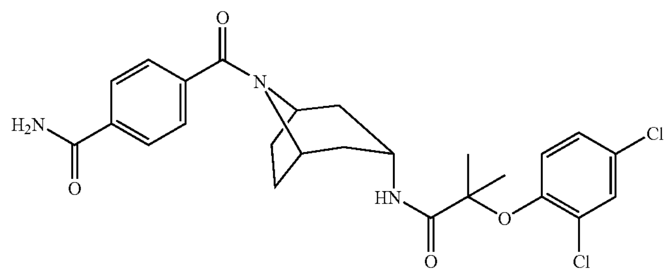 |
| 280 | 1-[4-fluoro-3-(trifluoromethyl)phenyl]-N-{8-[5-(methylsulfonyl)pyridin-2-yl]-8-azabicyclo[3.2.1]oct-3-endo-yl}cyclopropanecarboxamide<br>ACTIVITY = B | 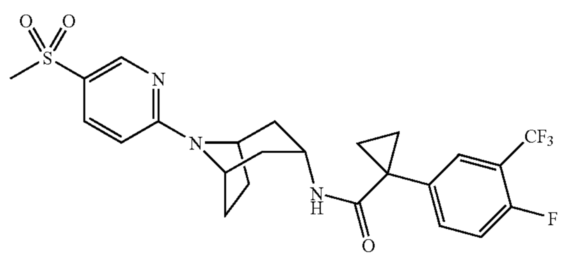 |
| 281 | 1-(3,4-difluorophenyl)-N-{8-[5-(methylsulfonyl)pyridin-2-yl]-8-azabicyclo[3.2.1]oct-3-endo-yl}cyclopropanecarboxamide<br>ACTIVITY = B | 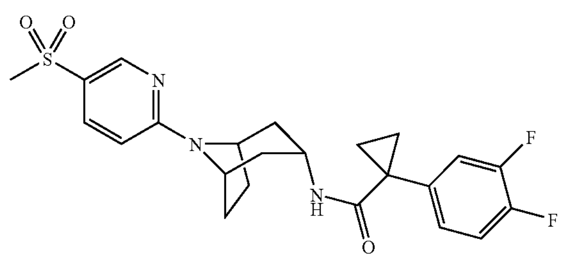 |
| 282 | 6-[3-endo-({2-[(3-chloro-4'-fluorobiphenyl-4-yl)oxy]-2-methylpropanoyl}amino)-8-azabicyclo[3.2.1]oct-8-yl]pyridine-3-carboxamide<br>ACTIVITY = A | 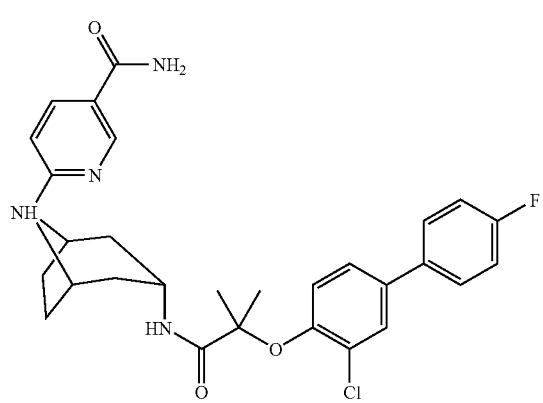 |

TABLE I-continued

| No. | Name/Activity | Structure |
|---|---|---|
| 283 | 2-{[4-fluoro-2-(trifluoromethyl)phenyl]oxy}-2-methyl-N-(8-{4-[(methylsulfonyl)amino]phenyl}-8-azabicyclo[3.2.1]oct-3-endo-yl)propanamide<br>ACTIVITY = A | 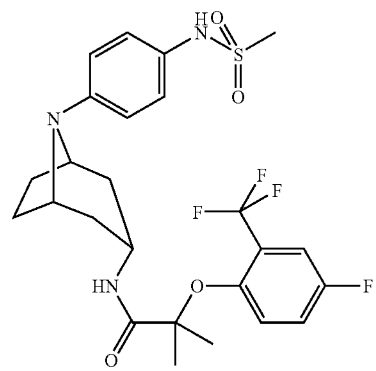 |
| 284 | 2-{[4-chloro-2-(trifluoromethyl)phenyl]oxy}-2-methyl-N-{8-[4-(methylsulfonyl)phenyl]-8-azabicyclo[3.2.1]oct-3-endo-yl}propanamide<br>ACTIVITY = A | 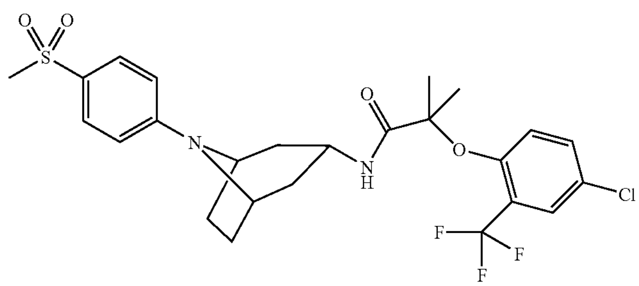 |
| 285 | 6-[3-endo-({2-[(4-chloro-2-cyclohexylphenyl)oxy]-2-methylpropanoyl}amino)-8-azabicyclo[3.2.1]oct-8-yl]pyridine-3-carboxamide<br>ACTIVITY = A | 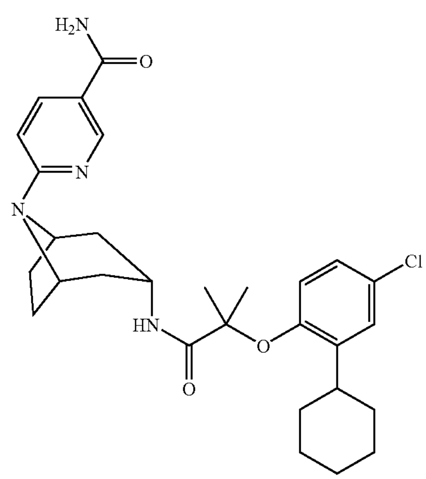 |
| 286 | 6-[3-endo-({2-[(2,4-dichlorophenyl)thio]-2-methylpropanoyl}amino)-8-azabicyclo[3.2.1]oct-8-yl]pyridine-3-carboxamide<br>ACTIVITY = A | 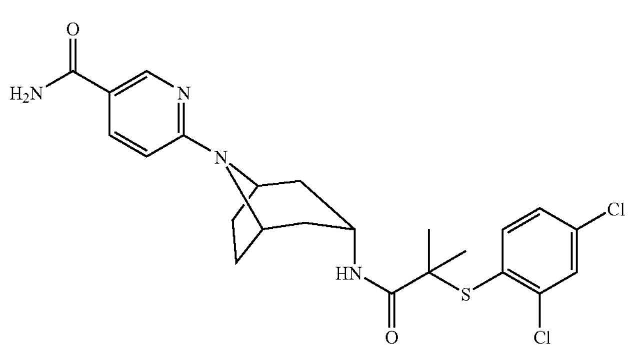 |

TABLE I-continued

| No. | Name/ Activity | Structure |
|---|---|---|
| 287 | 6-[3-endo-({2-[(2,4-dichlorophenyl)oxy]-2-methylpropanoyl}amino)-8-azabicyclo[3.2.1]oct-8-yl]pyridine-3-carboxylic acid<br>ACTIVITY = A | 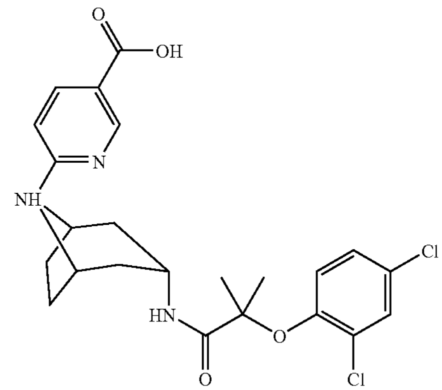 |
| 288 | 2-{[4-fluoro-2-(trifluoromethyl)phenyl]oxy}-2-methyl-N-{8-[6-(methylsulfonyl)pyridin-3-yl]-8-azabicyclo[3.2.1]oct-3-endo-yl}propanamide<br>ACTIVITY = B | 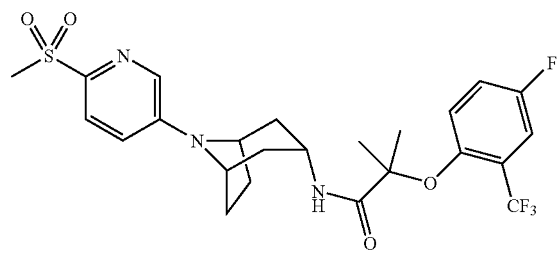 |
| 289 | 6-{3-endo-[({1-[3-(methylsulfonyl)phenyl]cyclopropyl}carbonyl)amino]-8-azabicyclo[3.2.1]oct-8-yl}-N-(2,2,2-trifluoroethyl)pyridine-3-carboxamide<br>ACTIVITY = B | 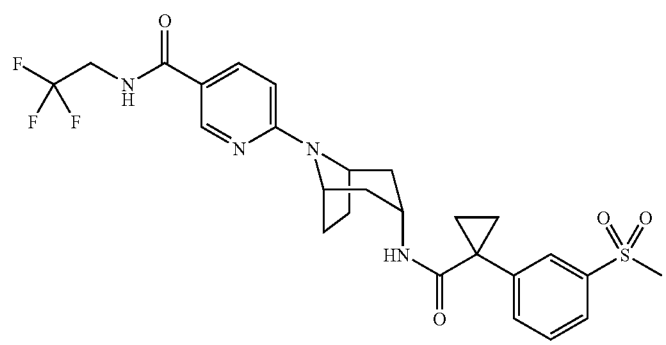 |
| 290 | 2-[(2,3-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide<br>ACTIVITY = A | 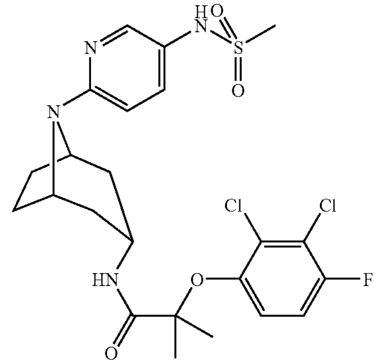 |

TABLE I-continued

| No. | Name/Activity | Structure |
|---|---|---|
| 291 | 3-{[3-endo-({2-[(2,4-dichlorophenyl)oxy]-2-methylpropanoyl}amino)-8-azabicyclo[3.2.1]oct-8-yl]methyl}benzamide ACTIVITY = B | 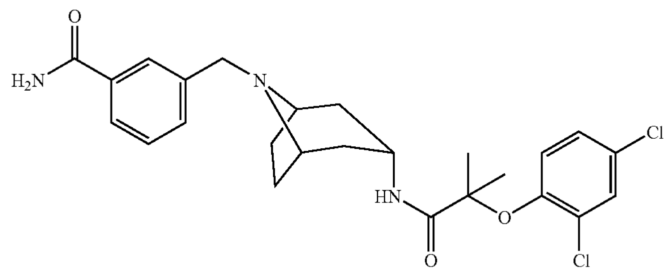 |
| 292 | 2-{[4-fluoro-2-(trifluoromethyl)phenyl]oxy}-2-methyl-N-{8-[6-(1H-tetrazol-5-yl)pyridin-3-yl]-8-azabicyclo[3.2.1]oct-3-endo-yl}propanamide ACTIVITY = A | 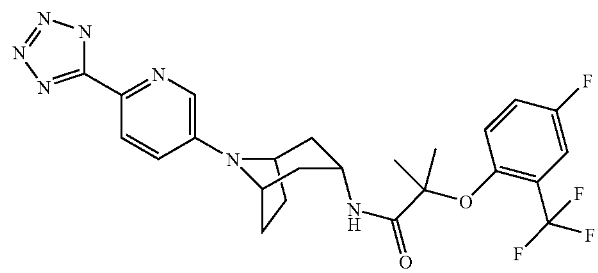 |
| 293 | N-{8-[5-(aminosulfonyl)pyridin-2-yl]-8-azabicyclo[3.2.1]oct-3-endo-yl}-2-{[4-chloro-2-(methylsulfonyl)phenyl]oxy}-2-methylpropanamide ACTIVITY = B | 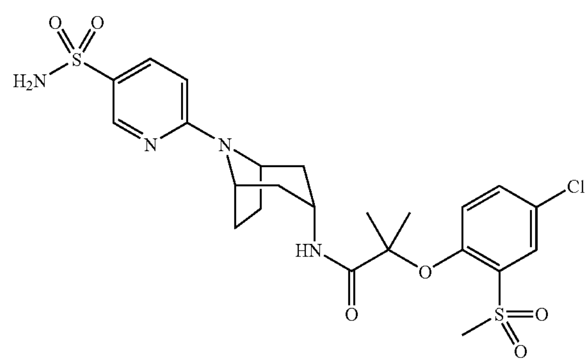 |
| 294 | N-{8-[5-(aminosulfonyl)pyridin-2-yl]-8-azabicyclo[3.2.1]oct-3-endo-yl}-2-[(2,4-difluorophenyl)oxy]-2-methylpropanamide ACTIVITY = A | 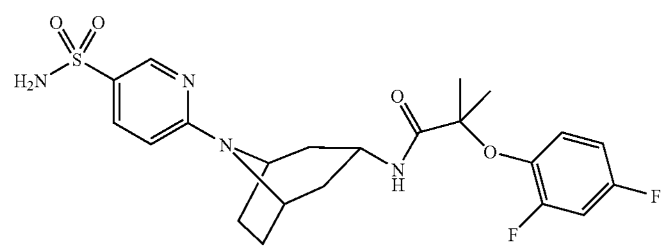 |
| 295 | 4-{[3-endo-({2-[(2,4-dichlorophenyl)oxy]-2-methylpropanoyl}amino)-8-azabicyclo[3.2.1]oct-8-yl]methyl}benzamide ACTIVITY = B | 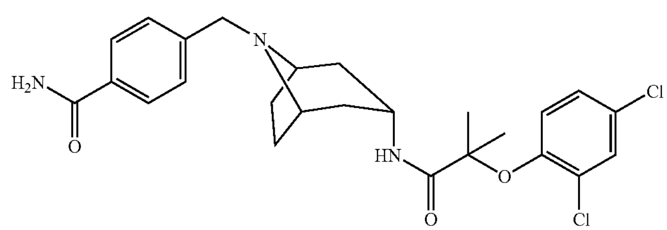 |

TABLE I-continued

| No. | Name/Activity | Structure |
|---|---|---|
| 296 | 6-{3-endo-[(2-{[4-fluoro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 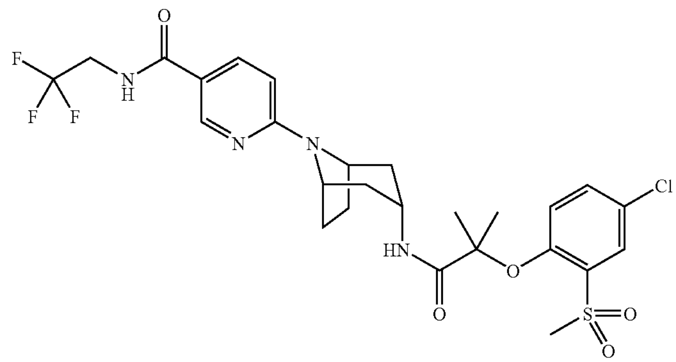 |
| 297 | 6-[3-endo-({2-[(4-chloronaphthalen-1-yl)oxy]-2-methylpropanoyl}amino)-8-azabicyclo[3.2.1]oct-8-yl]pyridine-3-carboxamide<br>ACTIVITY = A | 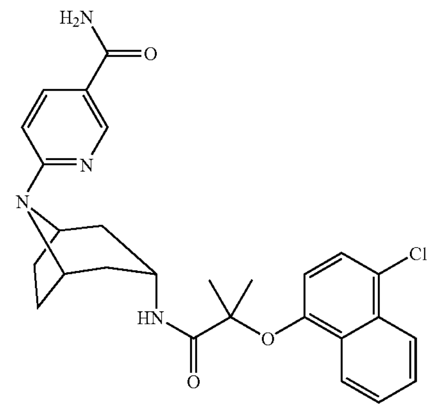 |
| 298 | N-{8-[5-(aminosulfonyl)pyridin-2-yl]-8-azabicyclo[3.2.1]oct-3-endo-yl}-2-{[4-fluoro-2-(methylsulfonyl)phenyl]oxy}-2-methylpropanamide<br>ACTIVITY = B | 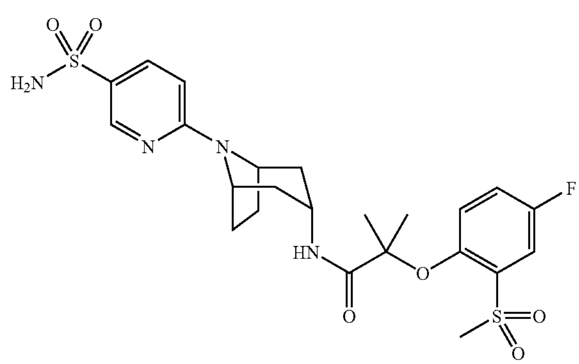 |
| 299 | 2-{[4-chloro-2-(trifluoromethyl)phenyl]oxy}-2-methyl-N-{8-[6-(methylsulfonyl)pyridin-3-yl]-8-azabicyclo[3.2.1]oct-3-endo-yl}propanamide<br>ACTIVITY = A | 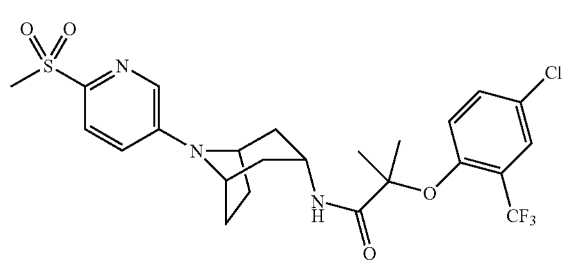 |

TABLE I-continued

| No. | Name/Activity | Structure |
|---|---|---|
| 300 | 6-{3-endo-[(2-methyl-2-{[2-(methylsulfonyl)phenyl]oxy}-propanoyl)amino]-8-azabicyclo[3.2.1]oct-8-yl}-N-(2,2,2-trifluoroethyl)pyridine-3-carboxamide<br>ACTIVITY = B | 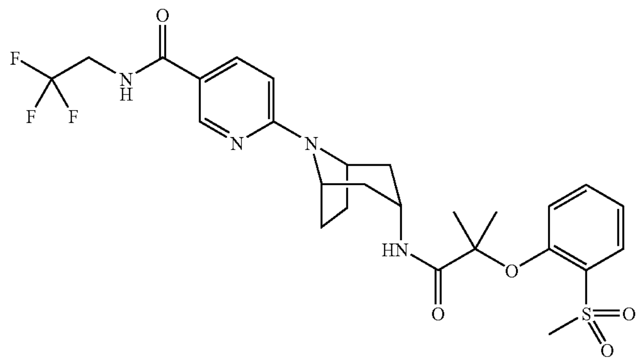 |
| 301 | 3-{[4-chloro-2-(trifluoromethyl)phenyl]oxy}-2,2-dimethyl-N-{8-[5-(methylsulfonyl)pyridin-2-yl]-8-azabicyclo[3.2.1]oct-3-endo-yl}propanamide<br>ACTIVITY = B | 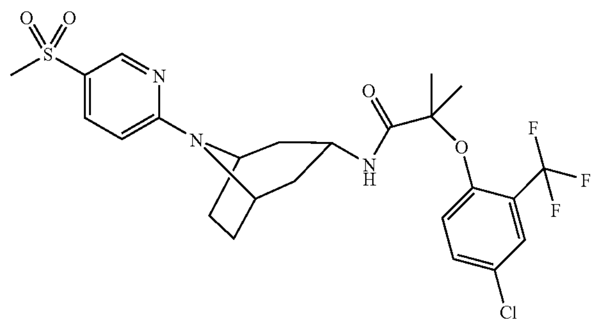 |
| 302 | 6-[(8-{2-[(2,4-dichlorophenyl)oxy]-2-methylpropanoyl}-8-azabicyclo[3.2.1]oct-3-endo-yl)amino]pyridine-3-carboxamide<br>ACTIVITY = A | 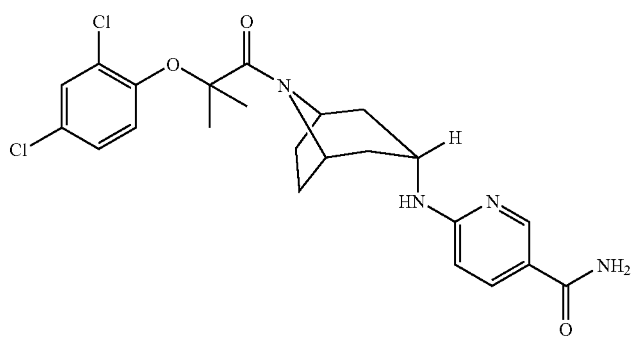 |
| 303 | 6-[3-endo-({2-[2,5-dichloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 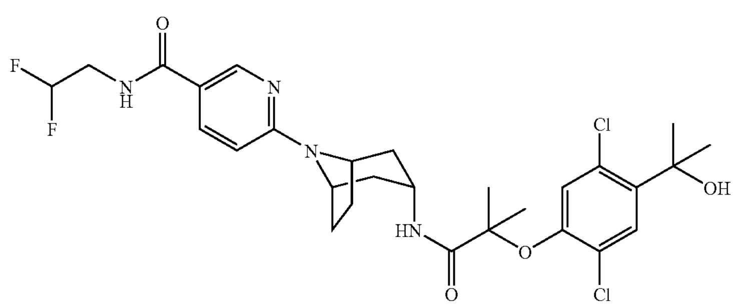 |

TABLE I-continued

| No. | Name/Activity | Structure |
|---|---|---|
| 304 | 6-[3-endo-({2-[2-chloro-5-fluoro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 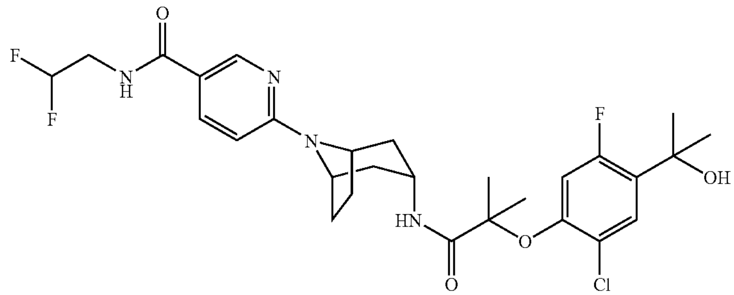 |
| 305 | N-(2,2-difluoroethyl)-6-[3-endo-({2-[2-fluoro-4-(2-hydroxypropan-2-yl)phenoxy]-2-methylpropanoyl}amino)-8-azabicyclo[3.2.1]oct-8-yl]pyridine-3-carboxamide<br>ACTIVITY = A | 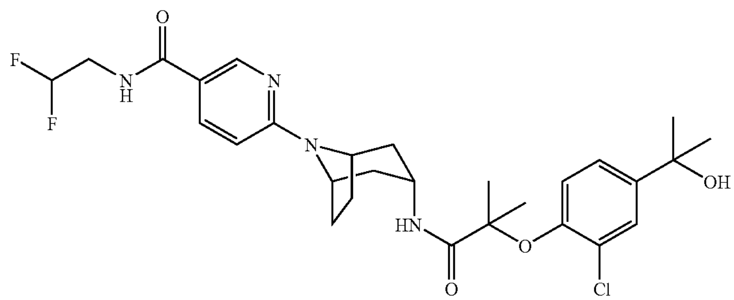 |
| 306 | 2-{[4-chloro-2-(trifluoromethyl)phenyl]oxy}-2-methyl-N-{8-[6-(1H-tetrazol-5-yl)pyridin-3-yl]-8-azabicyclo[3.2.1]oct-3-endo-yl}propanamide<br>ACTIVITY = A | 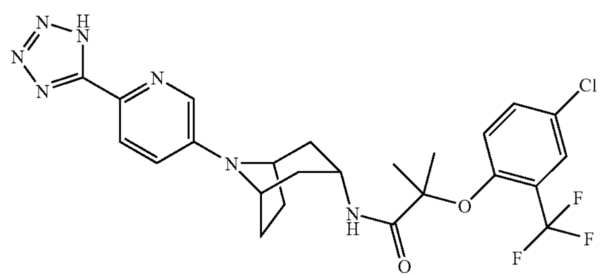 |
| 307 | 2-[(2,4-dichlorophenyl)oxy]-2-methyl-N-{8-[6-(methylsulfonyl)pyridin-3-yl]-8-azabicyclo[3.2.1]oct-3-endo-yl}propanamide<br>ACTIVITY = A | 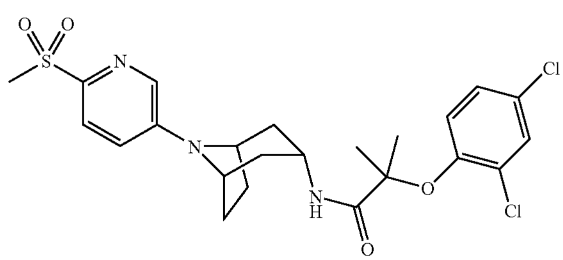 |
| 308 | 2-[(2,4-dichlorophenyl)sulfonyl]-2-methyl-N-{8-[5-(methylsulfonyl)pyridin-2-yl]-8-azabicyclo[3.2.1]oct-3-endo-yl}propanamide<br>ACTIVITY = B | 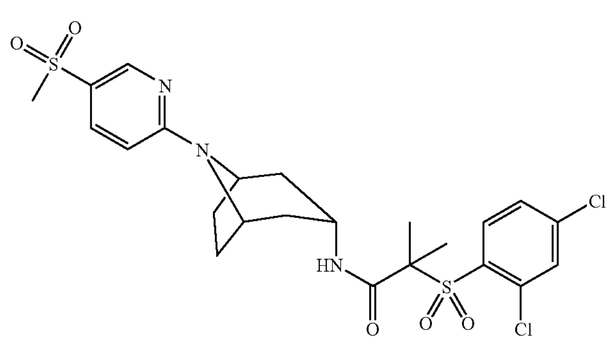 |

TABLE I-continued

| No. | Name/ Activity | Structure |
|---|---|---|
| 309 | 6-{3-endo-[(2-{[5-fluoro-2-(trifluoromethyl)phenyl]oxy}-2-methylpropanoyl)amino]-8-azabicyclo[3.2.1]oct-8-yl}pyridine-3-carboxamide ACTIVITY = A | 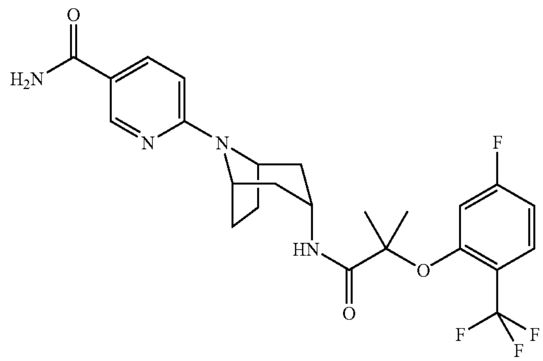 |
| 310 | 6-(3-endo-{[2-methyl-2-(quinolin-2-yloxy)propanoyl]amino}-8-azabicyclo[3.2.1]oct-8-yl)pyridine-3-carboxamide ACTIVITY = A | 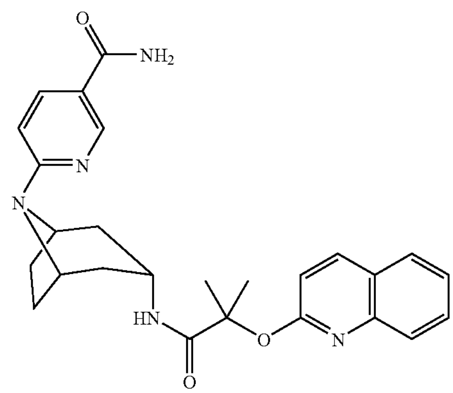 |
| 311 | 6-{3-endo-[({1-[3-(methylsulfonyl)phenyl]cyclopropyl}carbonyl)amino]-8-azabicyclo[3.2.1]oct-8-yl}pyridine-3-carboxamide ACTIVITY = A | 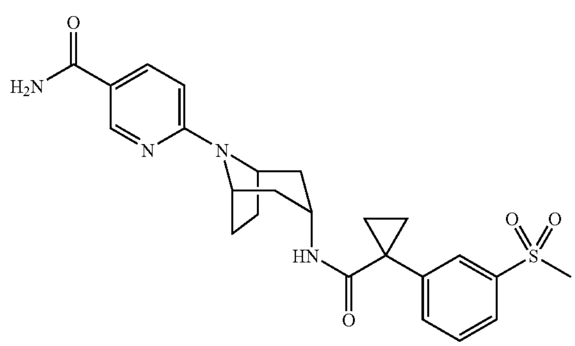 |
| 312 | 6-{3-endo-[(3-{[4-chloro-2-(trifluoromethyl)phenyl]oxy}-2,2-dimethylpropanoyl)amino]-8-azabicyclo[3.2.1]oct-8-yl}-N-(2,2,2-trifluoroethyl)pyridine-3-carboxamide ACTIVITY = A | 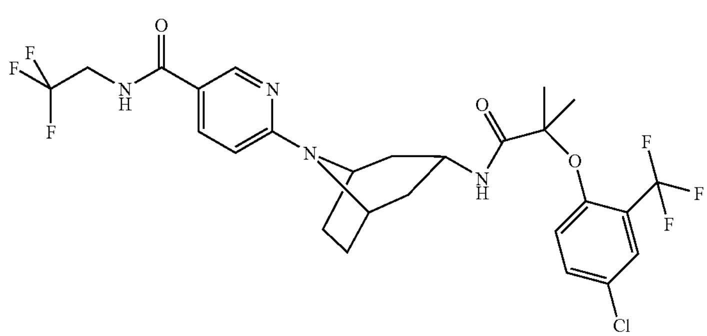 |

TABLE I-continued

| No. | Name/Activity | Structure |
|---|---|---|
| 313 | N-{8-[5-(aminosulfonyl)pyridin-2-yl]-8-azabicyclo[3.2.1]oct-3-endo-yl}-1-[3-(methylsulfonyl)phenyl]cyclopropanecarboxamide ACTIVITY = B | 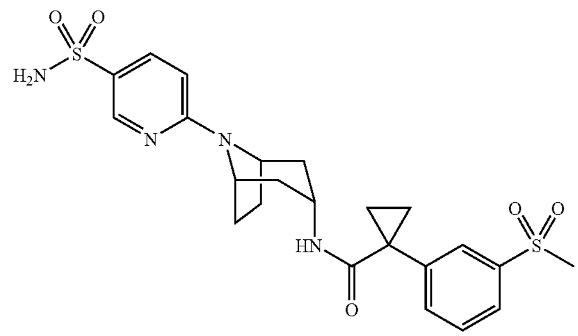 |
| 314 | 2-{[5-chloro-3-(trifluoromethyl)pyridin-2-yl]oxy}-2-methyl-N-{8-[5-(methylsulfonyl)pyridin-2-yl]-8-azabicyclo[3.2.1]oct-3-endo-yl}propanamide ACTIVITY = A | 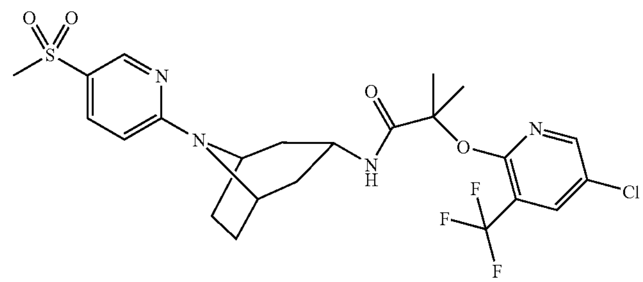 |
| 315 | 2-[(2-chloro-4-fluorophenyl)oxy]-2-methyl-N-(8-{4-[(methylsulfonyl)amino]phenyl}-8-azabicyclo[3.2.1]oct-3-endo-yl)propanamide ACTIVITY = A | 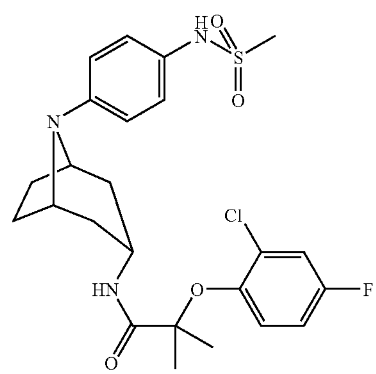 |
| 316 | 6-(3-endo-{[2-methyl-2-(naphthalen-2-yloxy)propanoyl]amino}-8-azabicyclo[3.2.1]oct-8-yl)pyridine-3-carboxamide ACTIVITY = A | 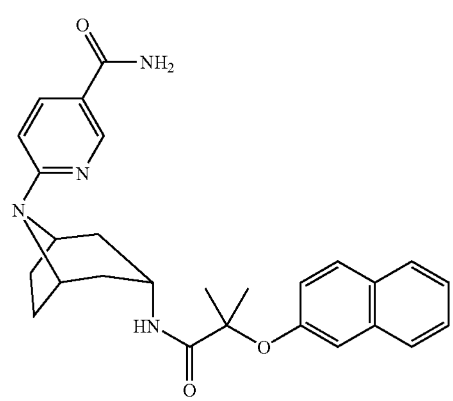 |

TABLE I-continued

| No. | Name/Activity | Structure |
|---|---|---|
| 317 | 6-[3-endo-({2-[(2,4-dichlorophenyl)oxy]-2-methylpropanoyl}amino)-8-azabicyclo[3.2.1]oct-8-yl]-N-oxetan-3-ylpyridine-3-carboxamide<br>ACTIVITY = A | 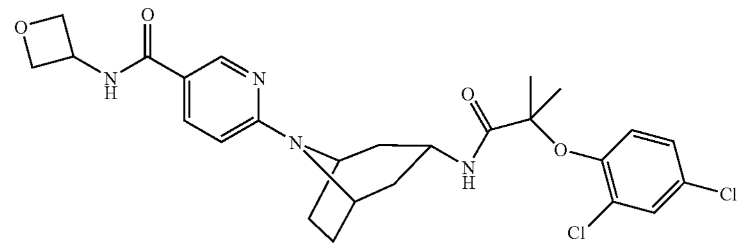 |
| 318 | 6-(3-endo-{[2-methyl-2-(quinolin-4-yloxy)propanoyl]amino}-8-azabicyclo[3.2.1]oct-8-yl)pyridine-3-carboxamide<br>ACTIVITY = A | 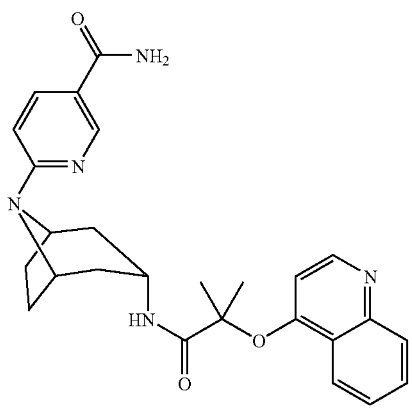 |
| 319 | 6-{3-endo-[(2-{[5-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 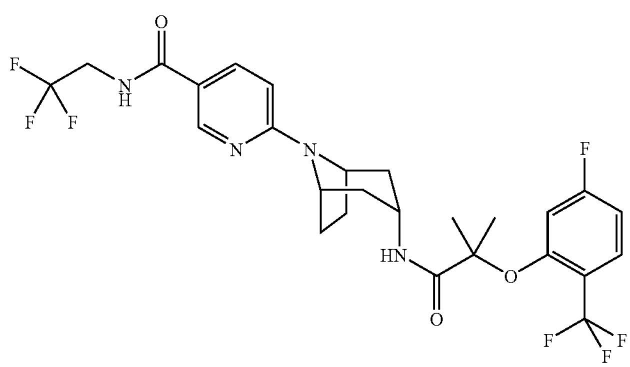 |
| 320 | 6-[3-endo-({2-[(4-chloro-2-cyclopentylphenyl)oxy]-2-methylpropanoyl}amino)-8-azabicyclo[3.2.1]oct-8-yl]pyridine-3-carboxamide<br>ACTIVITY = A | 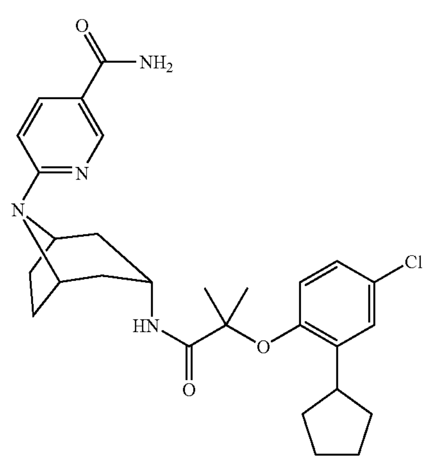 |

TABLE I-continued

| No. | Name/Activity | Structure |
|---|---|---|
| 321 | 6-{3-endo-[(2-{[4-chloro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide<br>ACTIVITY = A | 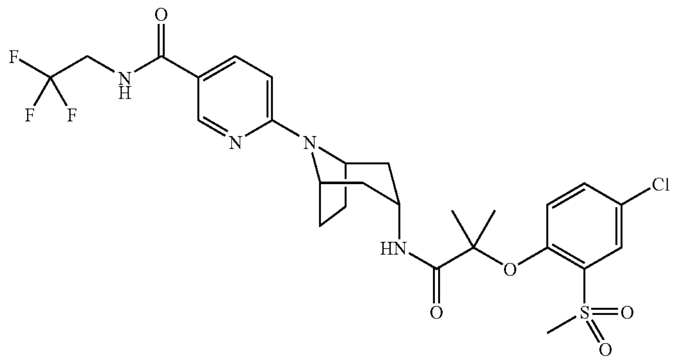 |
| 322 | 6-[3-endo-({2-[(5-chlorobiphenyl-2-yl)oxy]-2-methylpropanoyl}amino)-8-azabicyclo[3.2.1]oct-8-yl]pyridine-3-carboxamide<br>ACTIVITY = A | 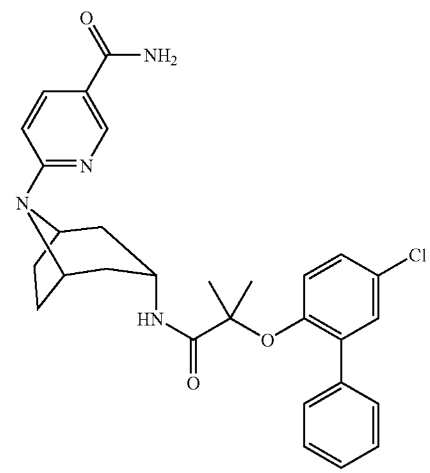 |
| 323 | 6-{[3-endo-({2-[(2,4-dichlorophenyl)oxy]-2-methylpropanoyl}amino)-8-azabicyclo[3.2.1]oct-8-yl]methyl}pyridine-3-carboxamide<br>ACTIVITY = B | 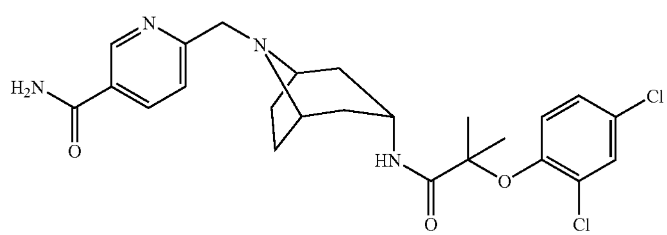 |
| 324 | 2-{[4-chloro-2-(methylsulfonyl)phenyl]oxy}-2-methyl-N-{8-[5-(methylsulfonyl)pyridin-2-yl]-8-azabicyclo[3.2.1]oct-3-endo-yl}propanamide<br>ACTIVITY = B | 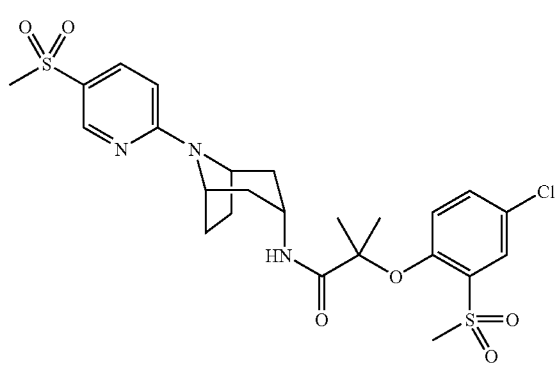 |

TABLE I-continued

| No. | Name/Activity | Structure |
|---|---|---|
| 325 | 2-{[5-chloro-3-(trifluoromethyl)pyridin-2-yl]oxy}-2-methyl-N-{8-[4-(methylsulfonyl)phenyl]-8-azabicyclo[3.2.1]oct-3-endo-yl}propanamide<br>ACTIVITY = A | 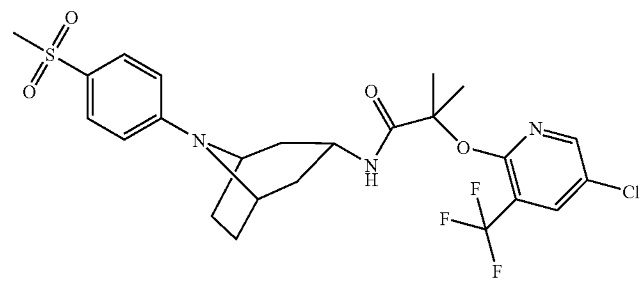 |
| 326 | 6-{3-endo-[(2-methyl-2-{[2-(methylsulfonyl)phenyl]oxy}propanoyl)amino]-8-azabicyclo[3.2.1]oct-8-yl}pyridine-3-carboxamide<br>ACTIVITY = A | 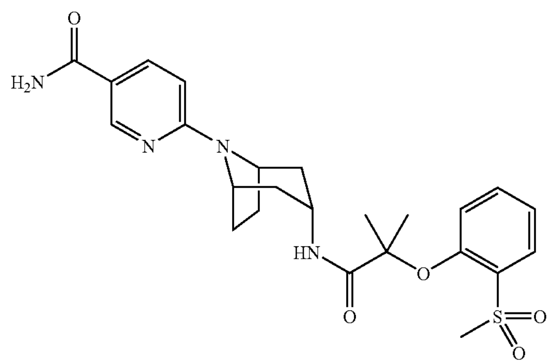 |
| 327 | 3-{[3-endo-({2-[(2,4-dichlorophenyl)oxy]-2-methylpropanoyl}amino)-8-azabicyclo[3.2.1]oct-8-yl]carbonyl}benzamide<br>ACTIVITY = B | 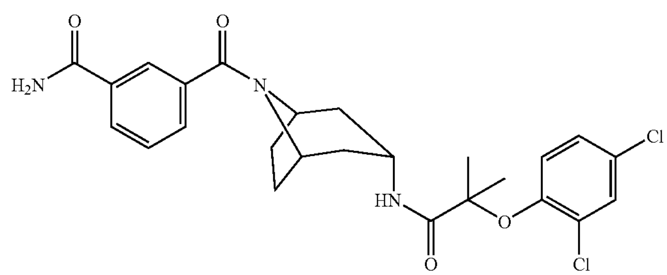 |
| 328 | 2-[(2,4-dichlorophenyl)thio]-2-methyl-N-{8-[5-(methylsulfonyl)pyridin-2-yl]-8-azabicyclo[3.2.1]oct-3-endo-yl}propanamide<br>ACTIVITY = A | 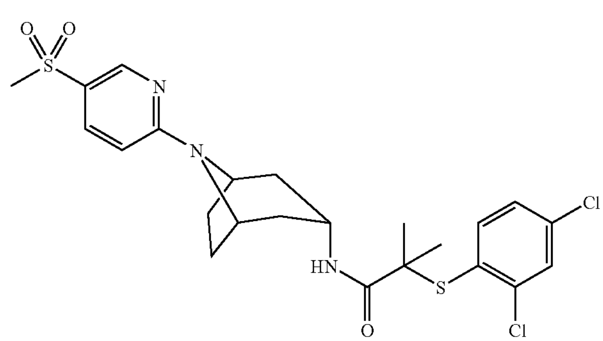 |

TABLE I-continued

| No. | Name/Activity | Structure |
|---|---|---|
| 329 | 2-[(3,4-dichlorophenyl)oxy]-2-methyl-N-(8-{4-[(methylsulfonyl)amino]phenyl}-8-azabicyclo[3.2.1]oct-3-endo-yl)propanamide<br>ACTIVITY = A | 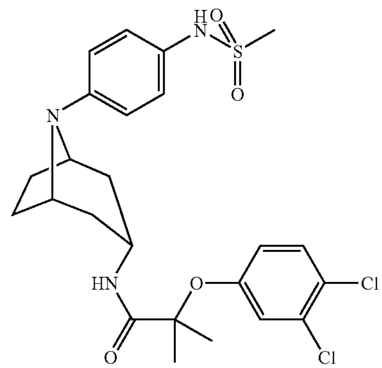 |
| 330 | 2-[(2-chloro-4-fluorophenyl)oxy]-2-methyl-N-(8-{5-[3-(trifluoromethyl)-1H-1,2,4-triazol-5-yl]pyridin-2-yl}-8-azabicyclo[3.2.1]oct-3-endo-yl)propanamide<br>ACTIVITY = B | 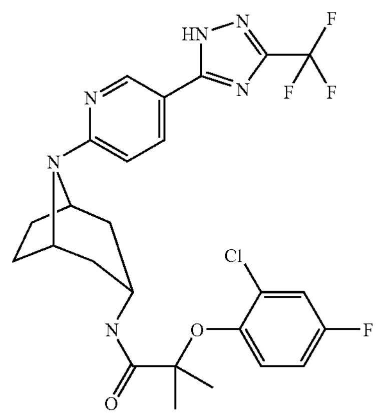 |
| 331 | 6-{3-endo-[(2-{[4-chloro-2-(1-methylethyl)phenyl]oxy}-2-methylpropanoyl)amino]-8-azabicyclo[3.2.1]oct-8-yl}pyridine-3-carboxamide<br>ACTIVITY = A | 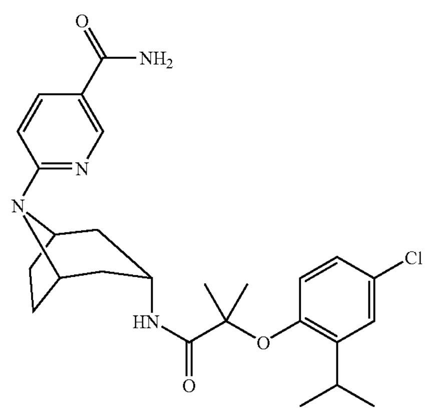 |
| 332 | 1-(3-chloro-4-fluorophenyl)-N-{8-[5-(methylsulfonyl)pyridin-2-yl]-8-azabicyclo[3.2.1]oct-3-endo-yl}cyclopropanecarboxamide<br>ACTIVITY = A | 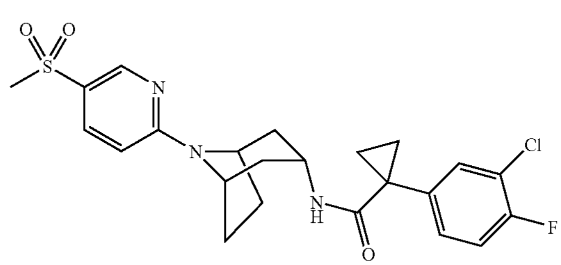 |

TABLE I-continued

| No. | Name/Activity | Structure |
|---|---|---|
| 333 | 2-{[4-chloro-2-(trifluoromethyl)phenyl]oxy}-2-methyl-N-(8-{5-[(methylsulfonyl)amino]pyridin-2-yl}-8-azabicyclo[3.2.1]oct-3-endo-yl)propanamide<br>ACTIVITY = A | 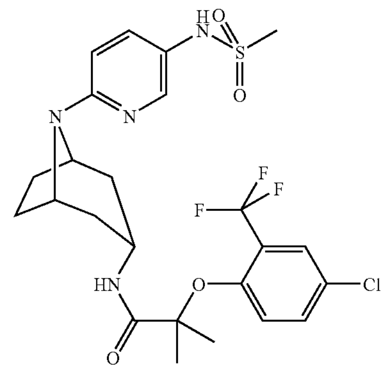 |
| 334 | 6-{3-endo-[(2-{[4-chloro-2-(methylsulfonyl)phenyl]oxy}-2-methylpropanoyl)amino]-8-azabicyclo[3.2.1]oct-8-yl}pyridine-3-carboxamide<br>ACTIVITY = A | 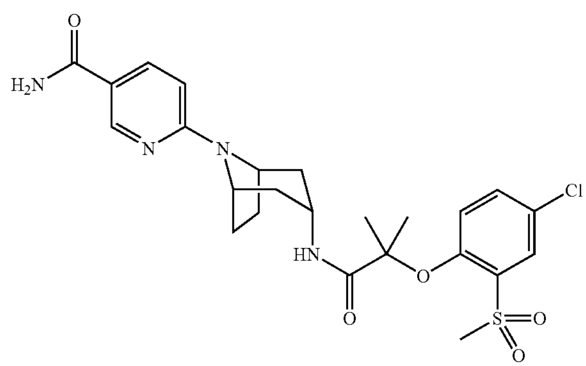 |
| 335 | 2-{[2-fluoro-5-(trifluoromethyl)phenyl]oxy}-2-methyl-N-{8-[5-(methylsulfonyl)pyridin-2-yl]-8-azabicyclo[3.2.1]oct-3-endo-yl}propanamide<br>ACTIVITY = B | 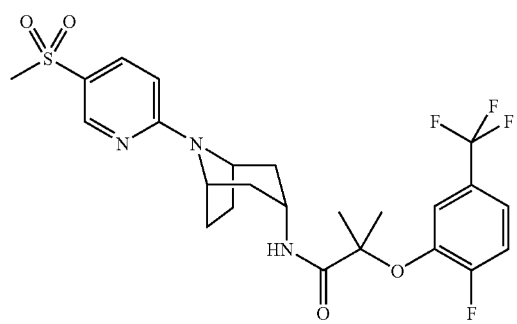 |
| 336 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(2-hydroxy-2-methylpropyl)pyridine-3-carboxamide<br>ACTIVITY = A | 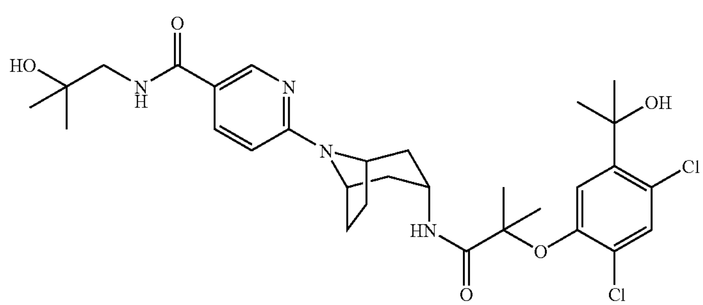 |

TABLE I-continued

| No. | Name/Activity | Structure |
|---|---|---|
| 337 | 6-(3-endo-{[2-(2-bromo-4-chlorophenoxy)-2-methylpropanoyl]amino}-8-azabicyclo[3.2.1]oct-8-yl)-N-(2,2,2-trifluoroethyl)pyridine-3-carboxamide<br>ACTIVITY = A | 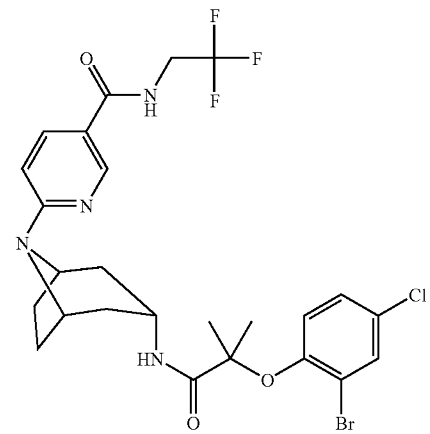 |
| 338 | 6-(3-endo-{[2-methyl-2-(naphthalen-2-yloxy)propanoyl]amino}-8-azabicyclo[3.2.1]oct-8-yl)-N-(2,2,2-trifluoroethyl)pyridine-3-carboxamide<br>ACTIVITY = A | 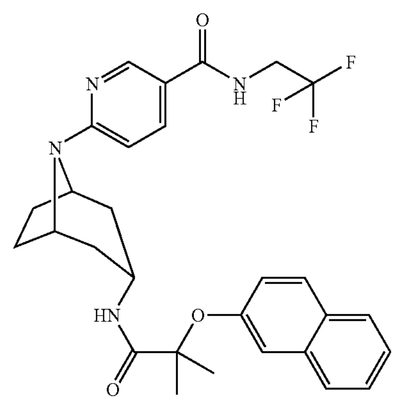 |
| 339 | 6-(3-endo-{[2-(isoquinolin-1-yloxy)-2-methylpropanoyl]amino}-8-azabicyclo[3.2.1]oct-8-yl)pyridine-3-carboxamide<br>ACTIVITY = A | 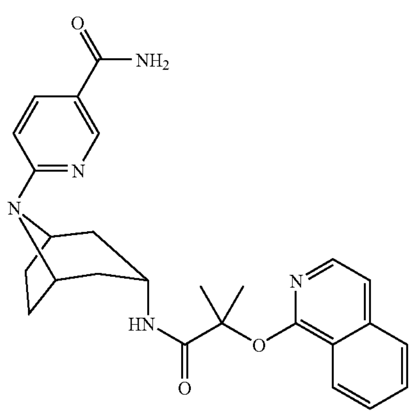 |
| 340 | 6-(3-endo-{[2-(2,4-dichlorophenoxy)-2-methylpropanoyl]amino}-8-azabicyclo[3.2.1]oct-8-yl)-N-[2-(pyrrolidin-1-yl)ethyl]pyridine-3-carboxamide<br>ACTIVITY = A | 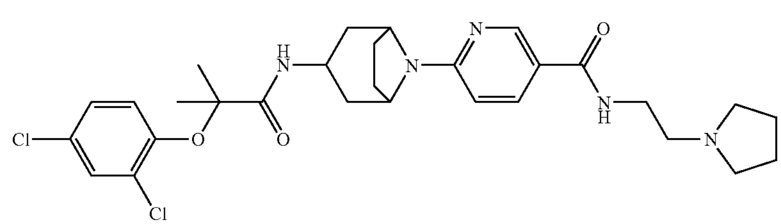 |

TABLE I-continued

| No. | Name/Activity | Structure |
|---|---|---|
| 341 | 6-(3-endo-{[2-(2,4-dichlorophenoxy)-2-methylpropanoyl]amino}-8-azabicyclo[3.2.1]oct-8-yl)-N-[3-(1h-imidazol-1-yl)propyl]pyridine-3-carboxamide<br>ACTIVITY = A | 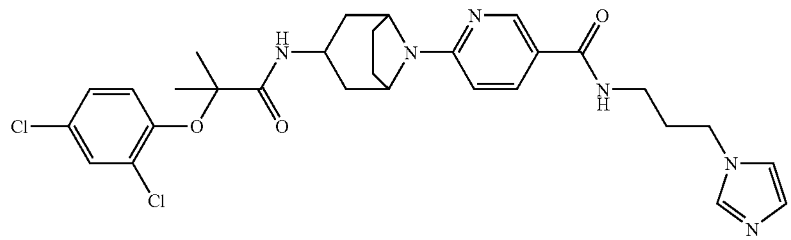 |
| 342 | 6-(3-endo-{[2-(2,4-dichlorophenoxy)-2-methylpropanoyl]amino}-8-azabicyclo[3.2.1]oct-8-yl)-N-(pyridin-4-ylmethyl)pyridine-3-carboxamide<br>ACTIVITY = A | 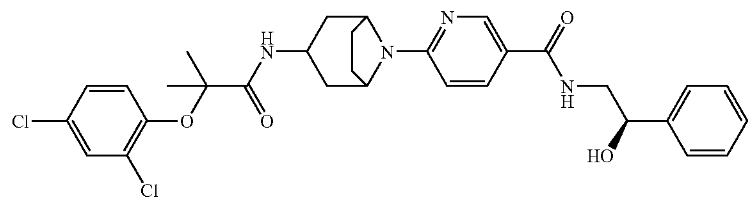 |
| 343 | 6-[3-endo-({2-[4-chloro-2-(trifluoromethyl)phenoxy]-2-methylpropanoyl}amino)-8-azabicyclo[3.2.1]oct-8-yl]-N-(2,2-difluoroethyl)pyridine-3-carboxamide<br>ACTIVITY = A | 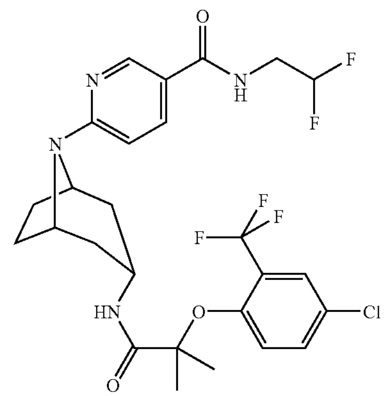 |
| 344 | 6-[3-endo-({2-[(4-chlorobiphenyl-3-yl)oxy]-2-methylpropanoyl}amino)-8-azabicyclo[3.2.1]oct-8-yl]pyridine-3-carboxamide<br>ACTIVITY = A | 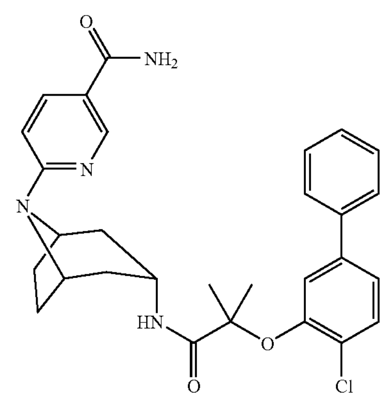 |
| 345 | 6-[3-endo-({2-[4-chloro-2-(trifluoromethyl)phenoxy]-2-methylpropanoyl}amino)-8-azabicyclo[3.2.1]oct-8-yl]-N-(2,2-difluorocyclopropyl)pyridine-3-carboxamide<br>ACTIVITY = A | 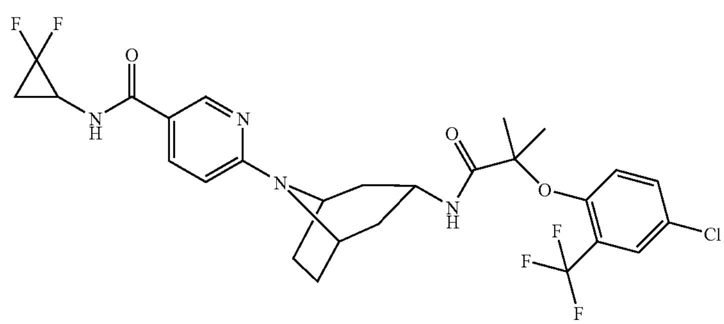 |

TABLE I-continued

| No. | Name/Activity | Structure |
|---|---|---|
| 346 | 6-[3-endo-({2-[(4-chloro-4'-fluorobiphenyl-3-yl)oxy]-2-methylpropanoyl}amino)-8-azabicyclo[3.2.1]oct-8-yl]pyridine-3-carboxamide<br>ACTIVITY = A | 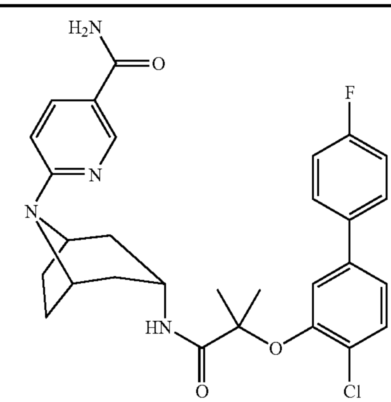 |
| 347 | 6-[3-endo-({2-methyl-2-[2-(trifluoromethoxy)phenoxy]propanoyl}amino)-8-azabicyclo[3.2.1]oct-8-yl]-N-(2,2,2-trifluoroethyl)pyridine-3-carboxamide<br>ACTIVITY = A | 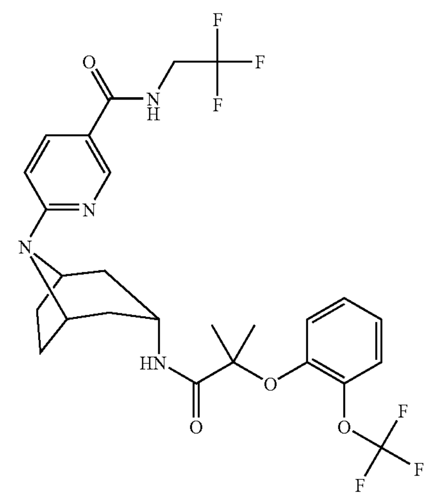 |
| 348 | 6-[3-endo-({2-[(1-chloronaphthalen-2-yl)oxy]-2-methylpropanoyl}amino)-8-azabicyclo[3.2.1]oct-8-yl]-N-(2,2,2-trifluoroethyl)pyridine-3-carboxamide<br>ACTIVITY = A | 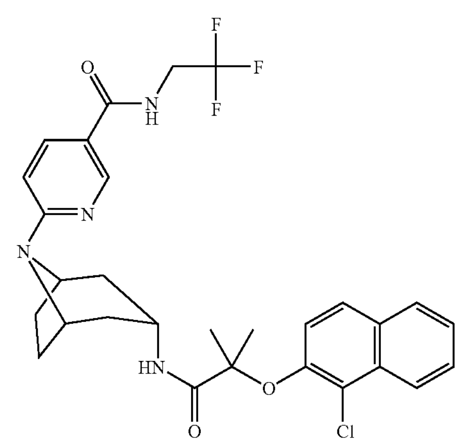 |
| 349 | 6-(3-endo-{[2-(2-chloro-4-fluorophenoxy)-2-methylpropanoyl]amino}-8-azabicyclo[3.2.1]oct-8-yl)-N-(2,2-difluorocyclopropyl)pyridine-3-carboxamide<br>ACTIVITY = A | 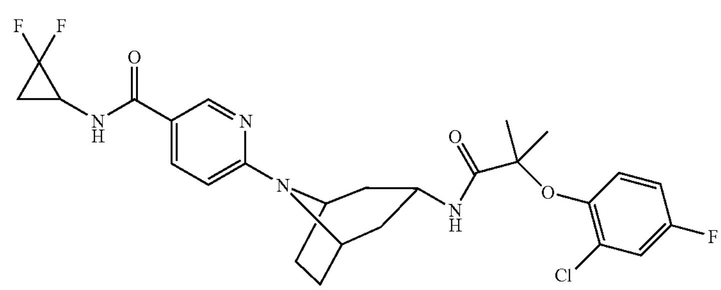 |

TABLE I-continued

| No. | Name/Activity | Structure |
|---|---|---|
| 350 | 6-(3-endo-{[2-(2,4-dichlorophenoxy)-2-methylpropanoyl]amino}-8-azabicyclo[3.2.1]oct-8-yl)-N-[2-methyl-1-(pyrrolidin-1-yl)propan-2-yl]pyridine-3-carboxamide<br>ACTIVITY = A | 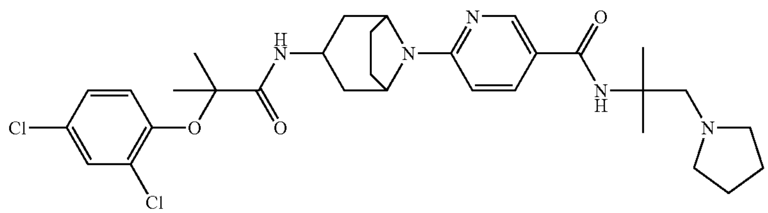 |
| 351 | 6-[3-endo-({2-[4-chloro-2-(dimethylsulfamoyl)phenoxy]-2-methylpropanoyl}amino)-8-azabicyclo[3.2.1]oct-8-yl]-n-(2,2,2-trifluoroethyl)pyridine-3-carboxamide<br>ACTIVITY = A | 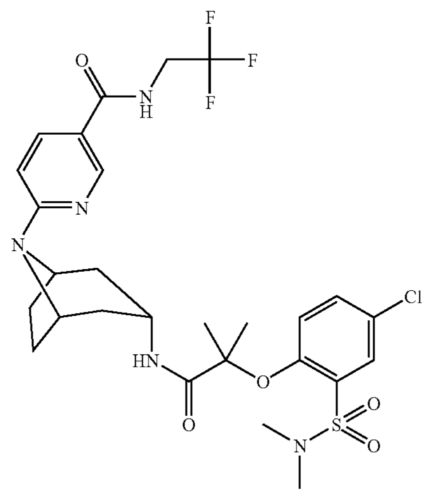 |
| 352 | 6-[3-endo-({2-[4-chloro-2-(2-methoxyethoxy)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 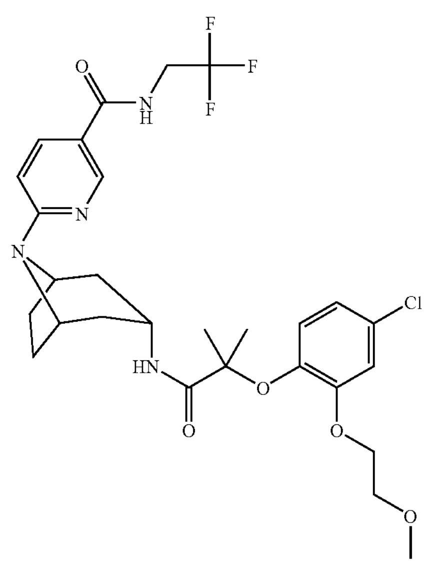 |

TABLE I-continued

| No. | Name/Activity | Structure |
|---|---|---|
| 353 | 6-[3-endo-({2-[4-chloro-2-(propan-2-yl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 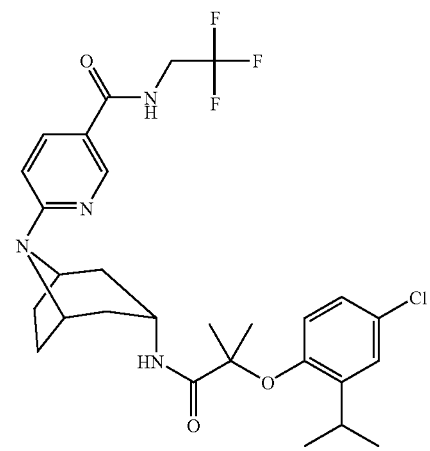 |
| 354 | 6-(3-endo-{[2-(isoquinolin-1-yloxy)-2-methylpropanoyl]amino}-8-azabicyclo[3.2.1]oct-8-yl)-N-(2,2,2-trifluoroethyl)pyridine-3-carboxamide<br>ACTIVITY = A | 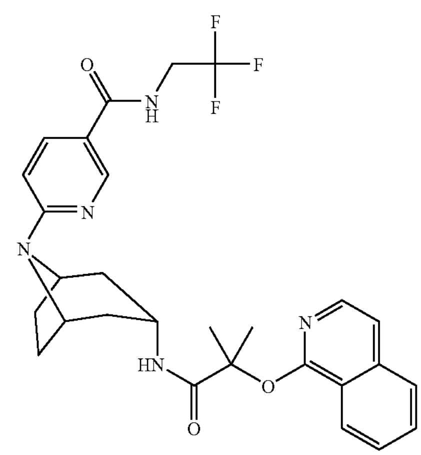 |
| 355 | 6-(3-endo-{[2-(2,4-dichlorophenoxy)-2-methylpropanoyl]amino}-8-azabicyclo[3.2.1]oct-8-yl)-N-(2,2-difluoroethyl)pyridine-3-carboxamide<br>ACTIVITY = A | 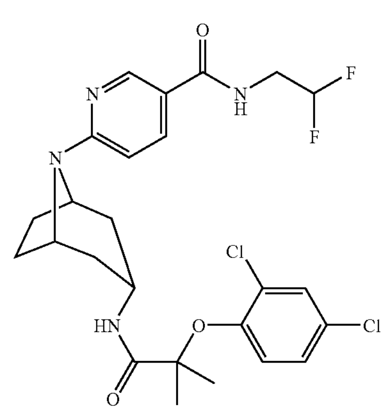 |

TABLE I-continued

| No. | Name/Activity | Structure |
|---|---|---|
| 356 | 6-[3-endo-({2-[2-chloro-4-(hydroxymethyl)phenoxy]-2-methylpropanoyl}amino)-8-azabicyclo[3.2.1]oct-8-yl]-N-(2,2,2-trifluoroethyl)pyridine-3-carboxamide ACTIVITY = | 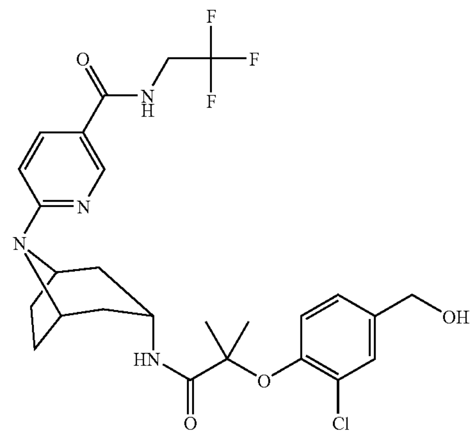 |
| 357 | 6-[3-endo-({2-[4-chloro-2-(methylsulfonyl)phenoxy]-2-methylpropanoyl}amino)-8-azabicyclo[3.2.1]oct-8-yl]-N-(2,2-difluorocyclopropyl)pyridine-3-carboxamide ACTIVITY = A | 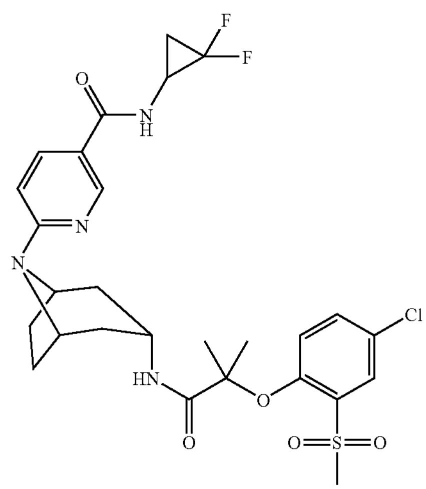 |
| 358 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(2-hydroxy-2-methylpropyl)pyridine-3-carboxamide ACTIVITY = A | 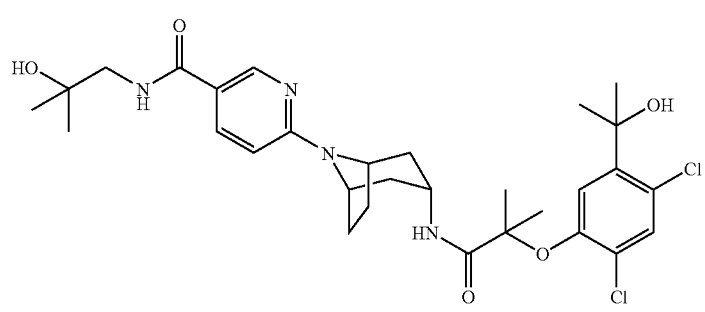 |

TABLE I-continued

| No. | Name/Activity | Structure |
|---|---|---|
| 359 | 6-[3-endo-({2-[4-chloro-2-(morpholin-4-yl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 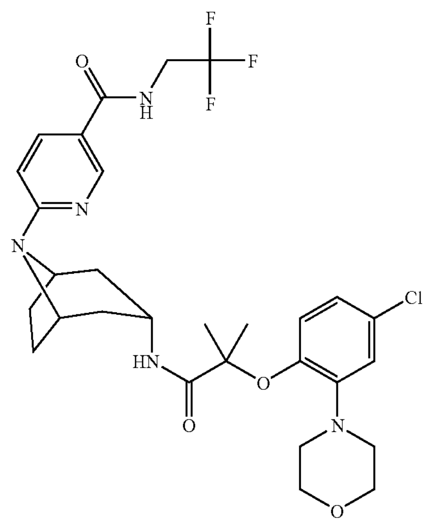 |
| 360 | 6-(3-endo-{[2-(2-carbamoyl-4-chlorophenoxy)-2-methylpropanoyl]amino}-8-azabicyclo[3.2.1]oct-8-yl)-N-(2,2,2-trifluoroethyl)pyridine-3-carboxamide<br>ACTIVITY = A | 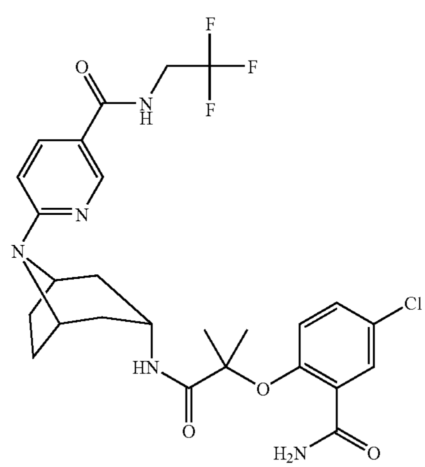 |
| 361 | 6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 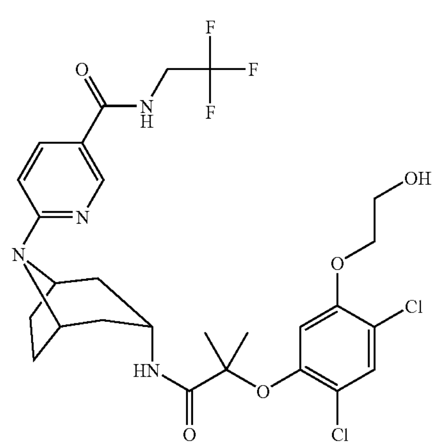 |

TABLE I-continued

| No. | Name/Activity | Structure |
|---|---|---|
| 362 | 6-(3-endo-{[2-(2,4-dichlorophenoxy)-2-methylpropanoyl]amino}-8-azabicyclo[3.2.1]oct-8-yl)-N-[2-(morpholin-4-yl)ethyl]pyridine-3-carboxamide ACTIVITY = A | 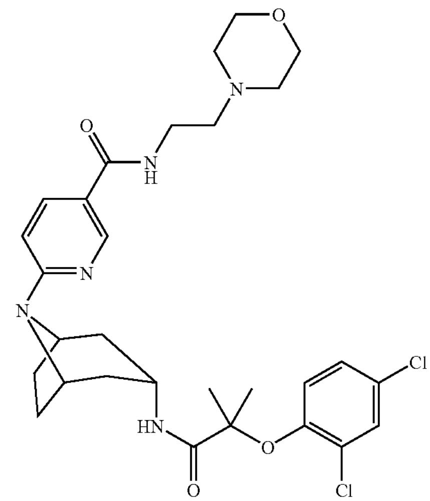 |
| 363 | 6-[3-endo-({2-[4-chloro-2-(trifluoromethoxy)phenoxy]-2-methylpropanoyl}amino)-8-azabicyclo[3.2.1]oct-8-yl]-N-(2,2,2-trifluoroethyl)pyridine-3-carboxamide ACTIVITY = A | 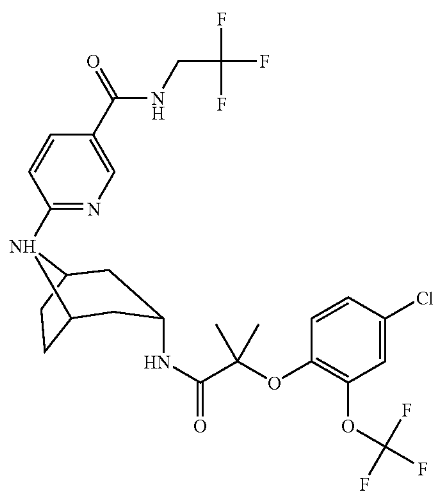 |
| 364 | 6-[3-endo-({2-[4-chloro-2-(difluoromethyl)phenoxy]-2-methylpropanoyl}amino)-8-azabicyclo[3.2.1]oct-8-yl]-N-(2,2,2-trifluoroethyl)pyridine-3-carboxamide ACTIVITY = A | 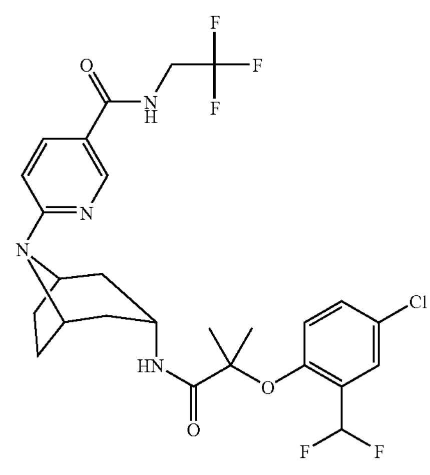 |

TABLE I-continued

| No. | Name/Activity | Structure |
|---|---|---|
| 365 | 2-[4-chloro-2-(difluoromethyl)phenoxy]-2-methyl-N-{8-[5-(methylsulfonyl)pyridin-2-yl]-8-azabicyclo[3.2.1]oct-3-endo-yl}propanamide<br>ACTIVITY = A | 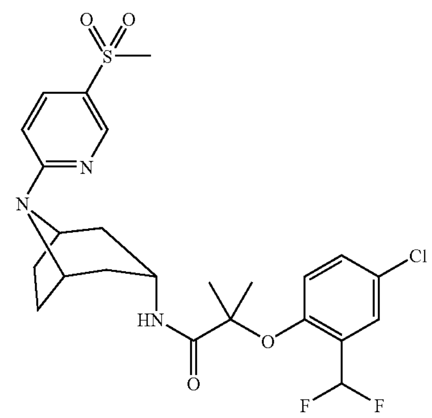 |
| 366 | 6-(3-endo-{[2-(1h-indol-4-yloxy)-2-methylpropanoyl]amino}-8-azabicyclo[3.2.1]oct-8-yl)-N-(2,2,2-trifluoroethyl)pyridine-3-carboxamide<br>ACTIVITY = A | 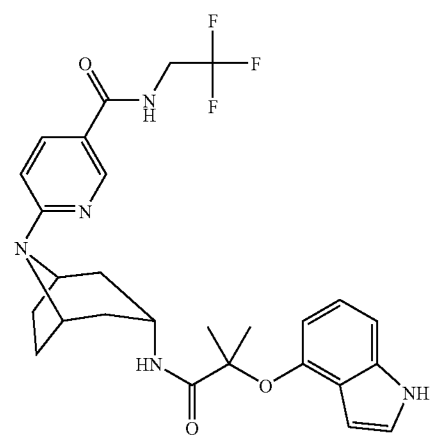 |
| 367 | 6-(3-endo-{[2-(2,4-dichlorophenoxy)-2-methylpropanoyl]amino}-8-azabicyclo[3.2.1]oct-8-yl)-N-(2-hydroxyethyl)pyridine-3-carboxamide<br>ACTIVITY = A | 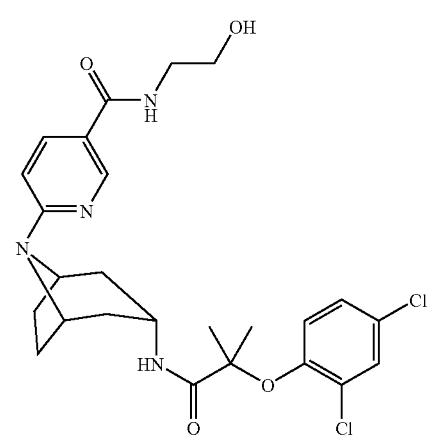 |

TABLE I-continued

| No. | Name/Activity | Structure |
|---|---|---|
| 368 | 6-[3-endo-({2-[4-chloro-2-(methylsulfonyl)phenoxy]-2-methylpropanoyl}amino)-8-azabicyclo[3.2.1]oct-8-yl]-N-(propan-2-yl)pyridine-3-carboxamide ACTIVITY = A | 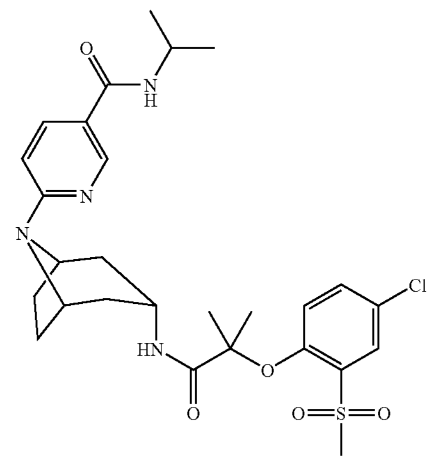 |
| 369 | N-(2,2-difluorocyclopropyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide ACTIVITY = A | 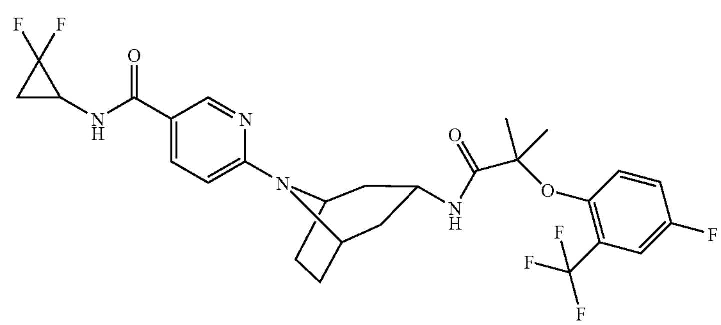 |
| 370 | 6-[3-endo-({2-[4-chloro-2-(trifluoromethyl)phenoxy]-2-methylpropanoyl}amino)-8-azabicyclo[3.2.1]oct-8-yl]-N-(propan-2-yl)pyridine-3-carboxamide ACTIVITY = A | 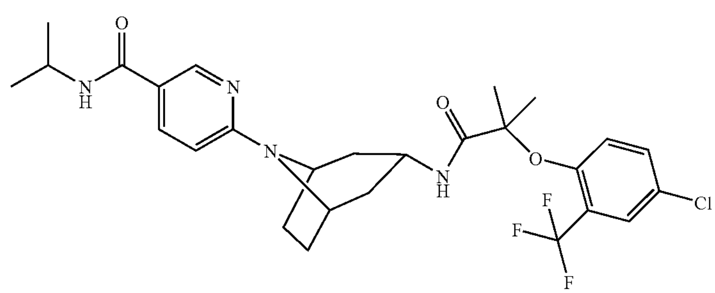 |
| 371 | 6-(3-endo-{[2-(2-chloro-4-fluorophenoxy)-2-methylpropanoyl]amino}-8-azabicyclo[3.2.1]oct-8-yl)-N-(2,2-difluoroethyl)pyridine-3-carboxamide ACTIVITY = A | 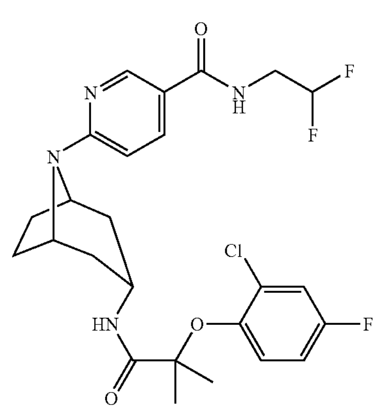 |

TABLE I-continued

| No. | Name/ Activity | Structure |
|---|---|---|
| 372 | N-(2,2-difluoroethyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide<br>ACTIVITY = A | 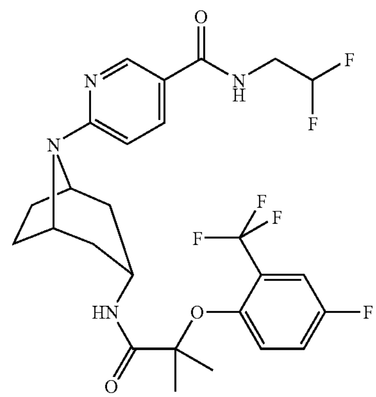 |
| 373 | 6-(3-endo-{[2-(2,4-dichlorophenoxy)-2-methylpropanoyl]amino}-8-azabicyclo[3.2.1]oct-8-yl)-N-[(2R)-1,1,1-trifluoropropan-2-yl]pyridine-3-carboxamide<br>ACTIVITY = A | 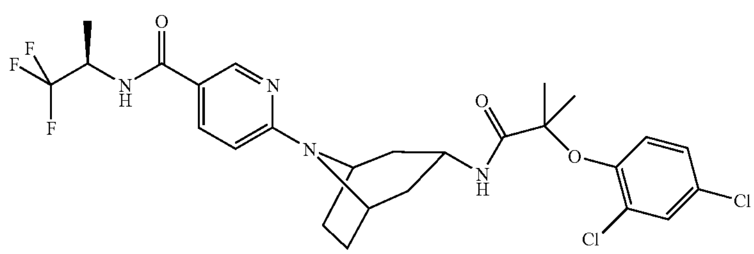 |
| 374 | 6-(3-endo-{[2-(2,4-dichlorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 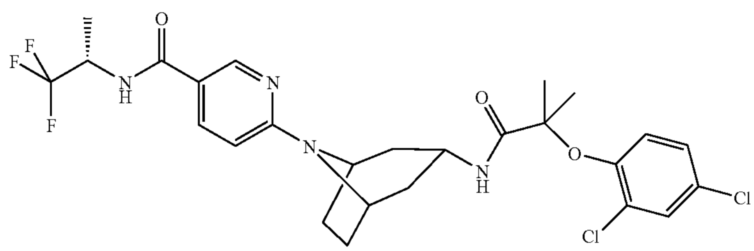 |
| 375 | 5-chloro-2-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)benzoic acid<br>ACTIVITY = A | 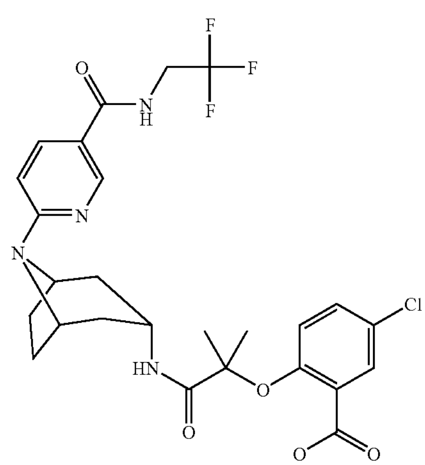 |

TABLE I-continued

| No. | Name/Activity | Structure |
|---|---|---|
| 376 | 6-[3-endo-({2-[4-chloro-2-(hydroxymethyl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 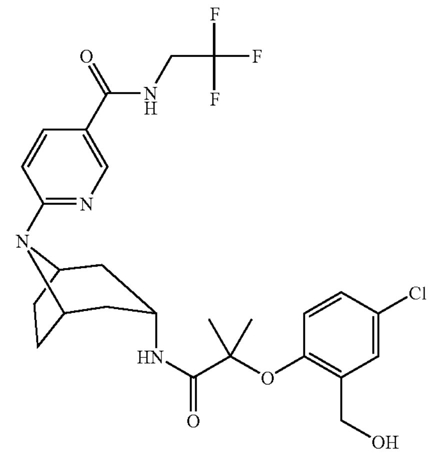 |
| 377 | 6-(3-endo-{[2-(2,4-dichlorophenoxy)-2-methylpropanoyl]amino}-8-azabicyclo[3.2.1]oct-8-yl)-N-[2-(diethylamino)ethyl]pyridine-3-carboxamide<br>ACTIVITY = A | 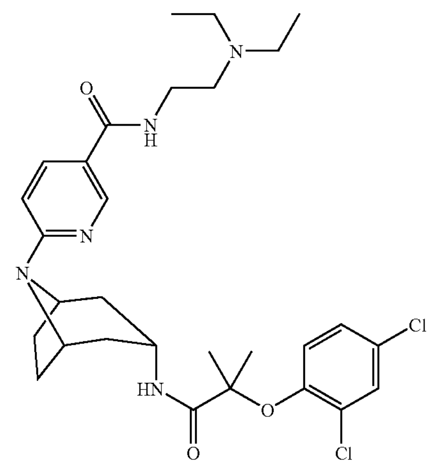 |
| 378 | 6-(3-endo-{[2-(2,4-dichlorophenoxy)-2-methylpropanoyl]amino}-8-azabicyclo[3.2.1]oct-8-yl)-N-(tetrahydro-2h-pyran-4-yl)pyridine-3-carboxamide<br>ACTIVITY = A | 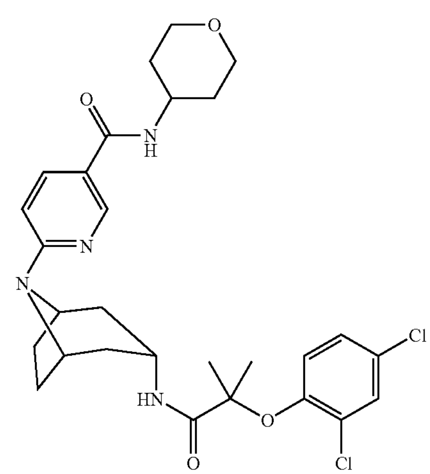 |

TABLE I-continued

| No. | Name/Activity | Structure |
|---|---|---|
| 379 | 6-(3-endo-{[2-(2,4-dichlorophenoxy)-2-methylpropanoyl]amino}-8-azabicyclo[3.2.1]oct-8-yl)-N-(1,1-dioxidotetrahydro-2h-thiopyran-4-yl)pyridine-3-carboxamide<br>ACTIVITY = A | 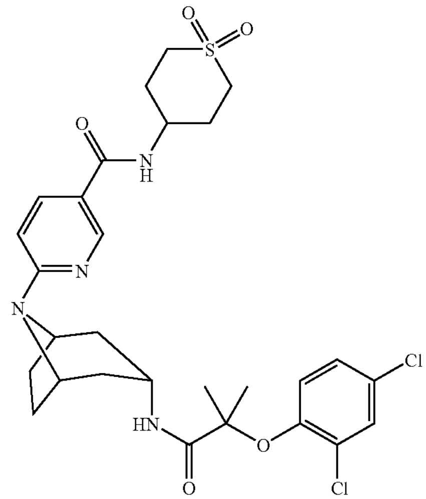 |
| 380 | 6-(3-endo-{[2-(2,4-dichlorophenoxy)-2-methylpropanoyl]amino}-8-azabicyclo[3.2.1]oct-8-yl)-N-(tetrahydro-2H-thiopyran-4-yl)pyridine-3-carboxamide<br>ACTIVITY = A | 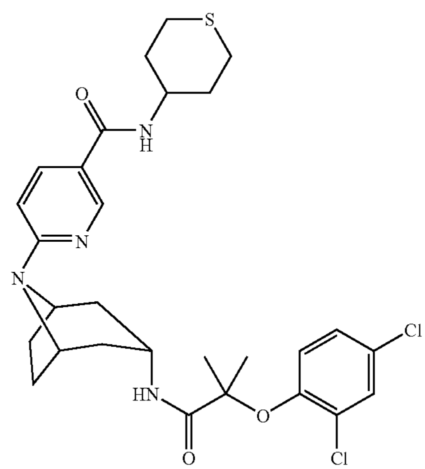 |
| 381 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(3,3,3-trifluoro-2-hydroxypropyl)pyridine-3-carboxamide<br>ACTIVITY = A | 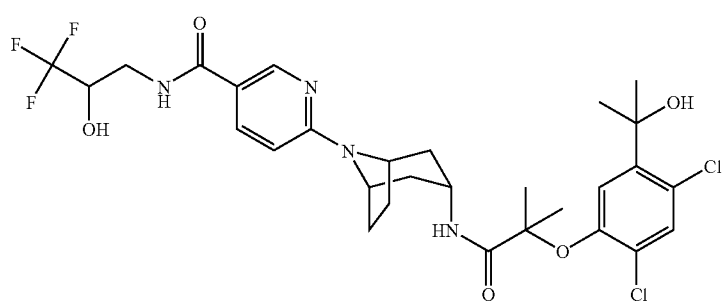 |

TABLE I-continued

| No. | Name/Activity | Structure |
|---|---|---|
| 382 | 6-[3-endo-({2-[2,4-dichloro-5-(2-methoxyethoxy)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 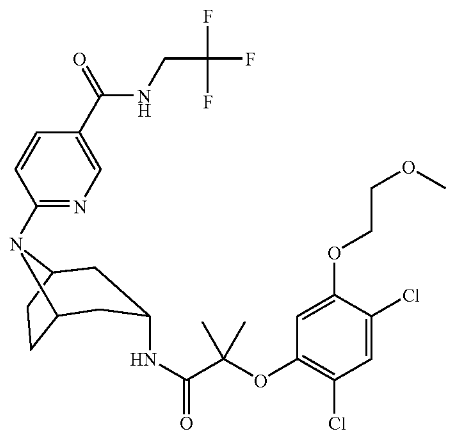 |
| 383 | 6-[3-endo-({2-[4-chloro-2-(2-hydroxyethyl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 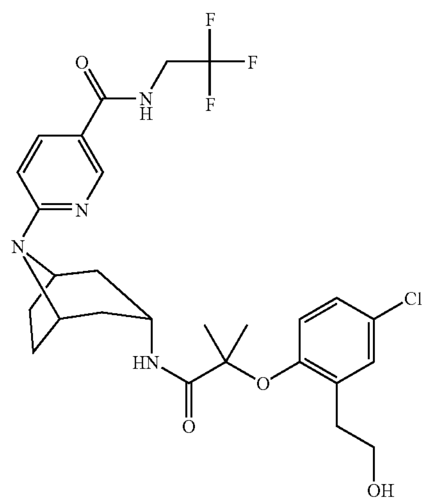 |
| 384 | 6-(3-endo-{[2-(2,4-dichlorophenoxy)-2-methylpropanoyl]amino}-8-azabicyclo[3.2.1]oct-8-yl)-N-[1-(hydroxymethyl)cyclopropyl]pyridine-3-carboxamide<br>ACTIVITY = A | 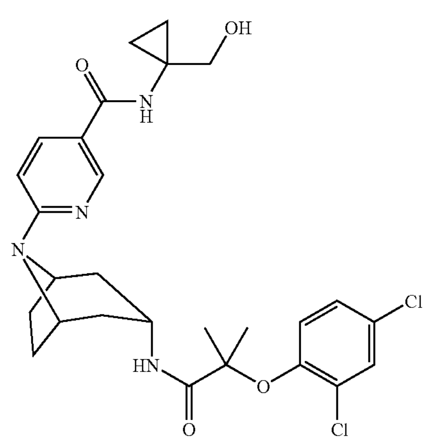 |

TABLE I-continued

| No. | Name/ Activity | Structure |
|---|---|---|
| 385 | 6-(3-endo-{[2-(1H-indazol-4-yloxy)-2-methylpropanoyl]amino}-8-azabicyclo[3.2.1]oct-8-yl)-N-(2,2,2-trifluoroethyl)pyridine-3-carboxamide<br>ACTIVITY = A | 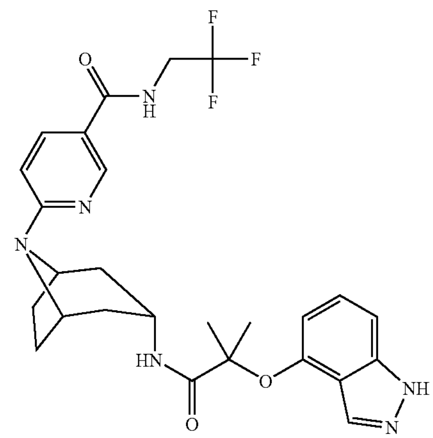 |
| 386 | 6-(3-endo-{[2-(2,4-dichlorophenoxy)-2-methylpropanoyl]amino}-8-azabicyclo[3.2.1]oct-8-yl)-N-(isoxazol-3-yl)pyridine-3-carboxamide<br>ACTIVITY = A | 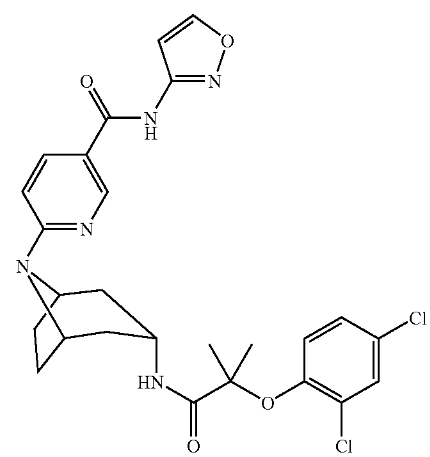 |
| 387 | 6-{3-endo-[(2-{4-chloro-2-[2-(1H-imidazol-1-yl)ethoxy]phenoxy}-2-methylpropanoyl)amino]-8-azabicyclo[3.2.1]oct-8-yl}-N-(2,2,2-trifluoroethyl)pyridine-3-carboxamide<br>ACTIVITY = B | 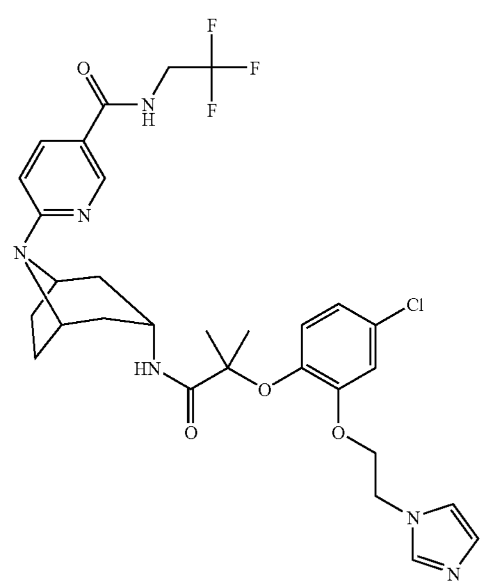 |

TABLE I-continued

| No. | Name/Activity | Structure |
|---|---|---|
| 388 | 6-(3-endo-{[2-(4-chloro-2-sulfamoylphenoxy)-2-methylpropanoyl]amino}-8-azabicyclo[3.2.1]oct-8-yl)-N-(2,2,2-trifluoroethyl)pyridine-3-carboxamide<br>ACTIVITY = B | 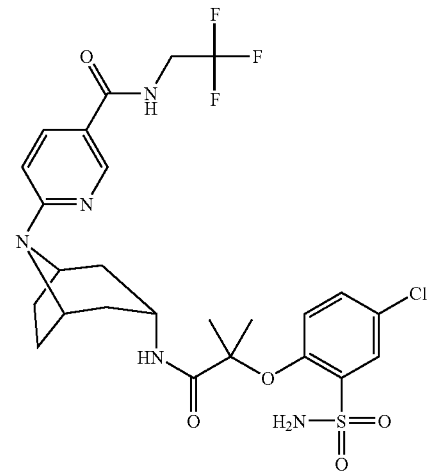 |
| 389 | 6-[3-endo-({2-[4-chloro-2-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 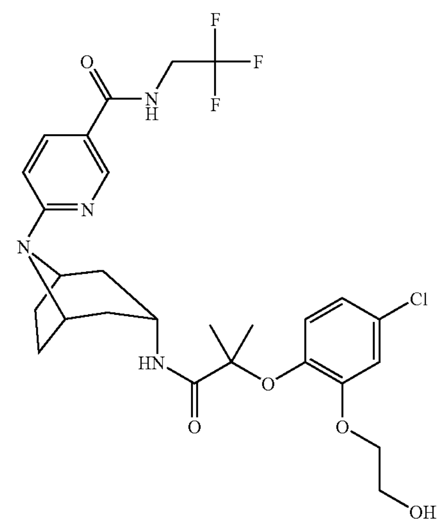 |
| 390 | 6-(3-endo-{[2-(1H-indol-7-yloxy)-2-methylpropanoyl]amino}-8-azabicyclo[3.2.1]oct-8-yl)-N-(2,2,2-trifluoroethyl)pyridine-3-carboxamide<br>ACTIVITY = A | 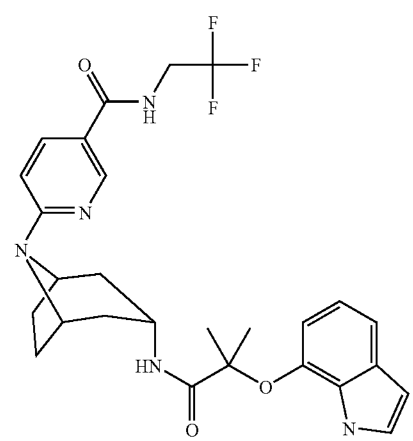 |

TABLE I-continued

| No. | Name/Activity | Structure |
|---|---|---|
| 391 | 6-[3-endo-({2-[2-chloro-4-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 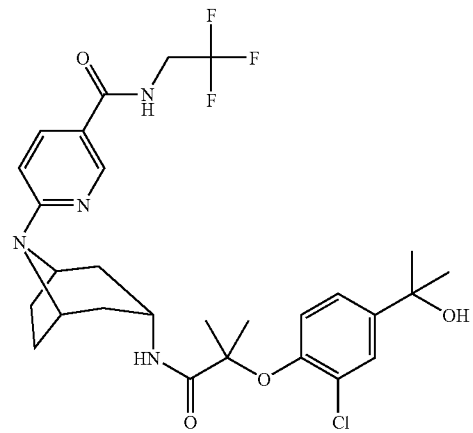 |
| 392 | 6-[3-endo-({2-[2,4-dichloro-5-(2-hydroxyethoxy)phenoxy]-2-methylpropanoyl}amino)-8-azabicyclo[3.2.1]oct-8-yl]-N-(2,2-difluorocyclopropyl)pyridine-3-carboxamide<br>ACTIVITY = A | 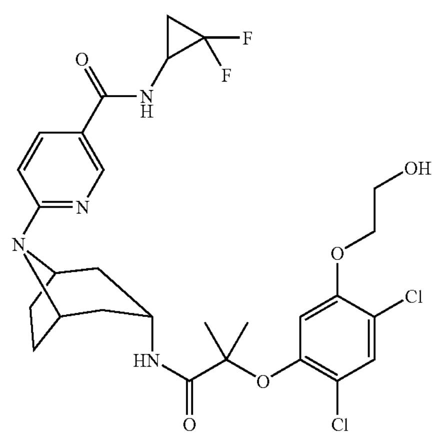 |
| 393 | 6-[3-endo-({2-[4-chloro-2-(difluoromethyl)phenoxy]-2-methylpropanoyl}amino)-8-azabicyclo[3.2.1]oct-8-yl]-N-(2,2-difluorocyclopropyl)pyridine-3-carboxamide<br>ACTIVITY = A | 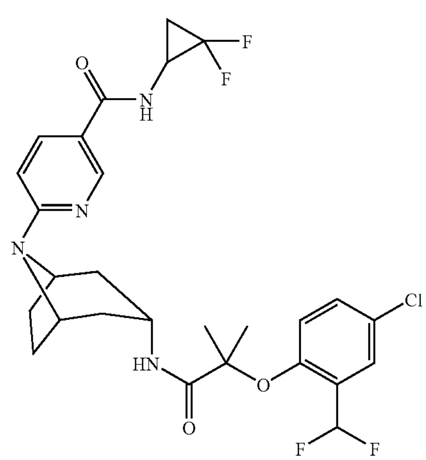 |

TABLE I-continued

| No. | Name/Activity | Structure |
|---|---|---|
| 394 | 6-[3-endo-({2-[4-chloro-2-(trifluoromethoxy)phenoxy]-2-methylpropanoyl}amino)-8-azabicyclo[3.2.1]oct-8-yl]-N-(2,2-difluorocyclopropyl)pyridine-3-carboxamide ACTIVITY = A | 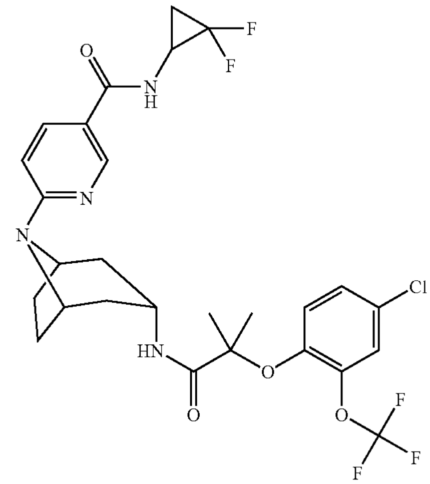 |
| 395 | 6-(3-endo-{[2-(2,4-dichlorophenoxy)-2-methylpropanoyl]amino}-8-azabicyclo[3.2.1]oct-8-yl)-N-(1-hydroxy-2-methylpropan-2-yl)pyridine-3-carboxamide ACTIVITY = A | 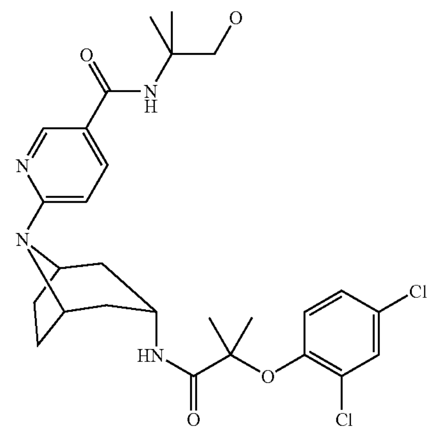 |
| 396 | 6-(3-endo-{[2-(2,4-dichlorophenoxy)-2-methylpropanoyl]amino}-8-azabicyclo[3.2.1]oct-8-yl)-n-(2-hydroxy-2-methylpropyl)pyridine-3-carboxamide ACTIVITY = A | 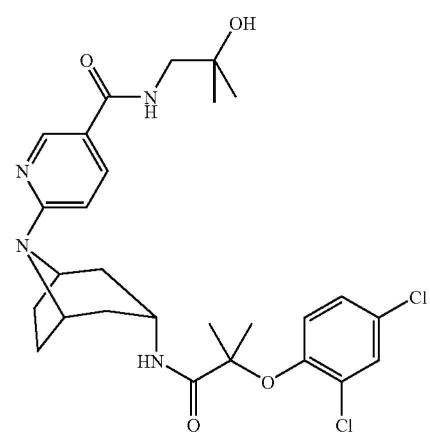 |
| 397 | 6-(3-endo-{[2-(2,4-dichlorophenoxy)-2-methylpropanoyl]amino}-8-azabicyclo[3.2.1]oct-8-yl)-N-[(2S)-1-hydroxypropan-2-yl]pyridine-3-carboxamide ACTIVITY = A | 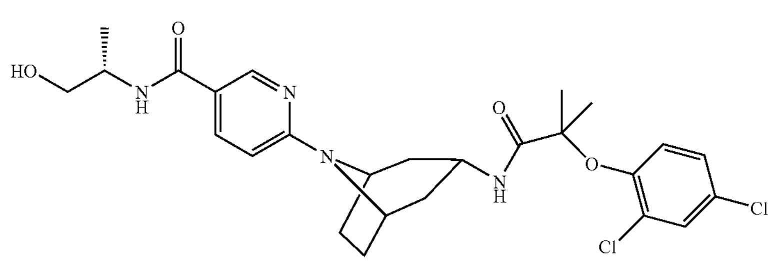 |

TABLE I-continued

| No. | Name/Activity | Structure |
|---|---|---|
| 398 | 6-(3-endo-{[2-(2,4-dichlorophenoxy)-2-methylpropanoyl]amino}-8-azabicyclo[3.2.1]oct-8-yl)-N-[(2R)-1-hydroxypropan-2-yl]pyridine-3-carboxamide<br>ACTIVITY = A | 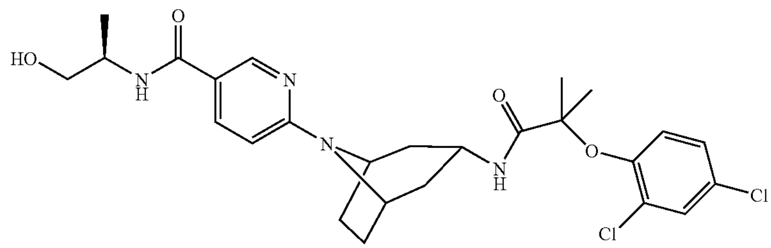 |
| 399 | 6-(3-endo-(2-(3,5-dichloropyridin-2-yloxy)-2-methylpropanamido)-8-azabicyclo[3.2.1]octan-8-yl)-N-(2,2-difluorocyclopropyl)nicotinamide<br>ACTIVITY = A | 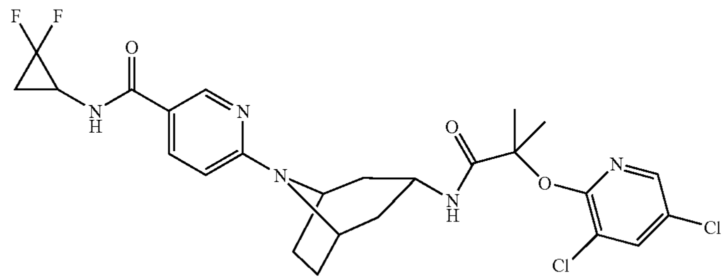 |
| 400 | 6-(3-endo-(2-(3,5-dichloropyridin-2-yloxy)-2-methylpropanamido)-8-azabicyclo[3.2.1]octan-8-yl)-N-isopropylnicotinamide<br>ACTIVITY = A | 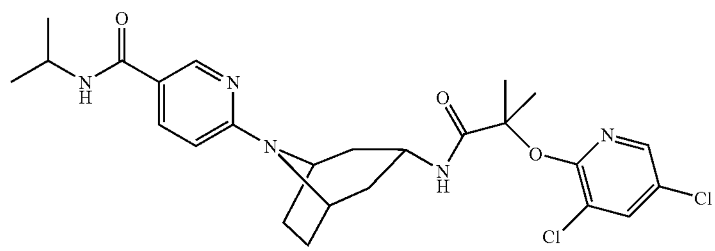 |
| 401 | 6-(3-endo-(2-(4-chloro-2-(trifluoromethoxy)phenoxy)-2-methylpropanamido)-8-azabicyclo[3.2.1]octan-8-yl)-N-(2,2-difluoroethyl)nicotinamide<br>ACTIVITY = A | 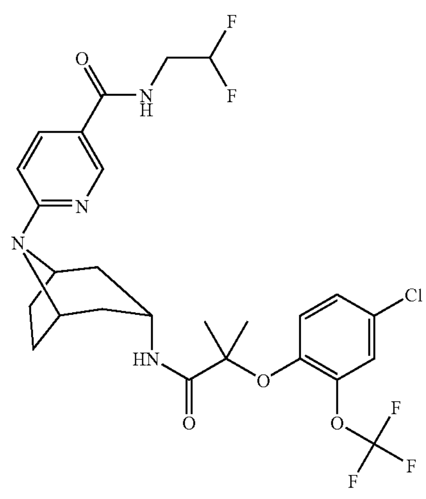 |

TABLE I-continued

| No. | Name/Activity | Structure |
|---|---|---|
| 402 | 6-(3-endo-(2-(2,4-dichloro-5-(2-hydroxyethoxy)phenoxy)-2-methylpropanamido)-8-azabicyclo[3.2.1]octan-8-yl)-N-(2,2-difluoroethyl)nicotinamide ACTIVITY = A | 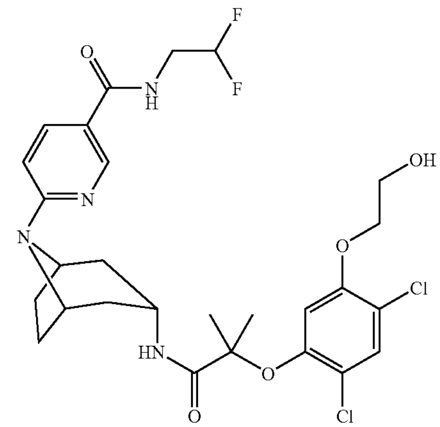 |
| 403 | 6-(3-endo-(2-(4-chloro-2-(difluoromethyl)phenoxy)-2-methylpropanamido)-8-azabicyclo[3.2.1]octan-8-yl)-N-(1-(hydroxymethyl)cyclopropyl)nicotinamide ACTIVITY = A | 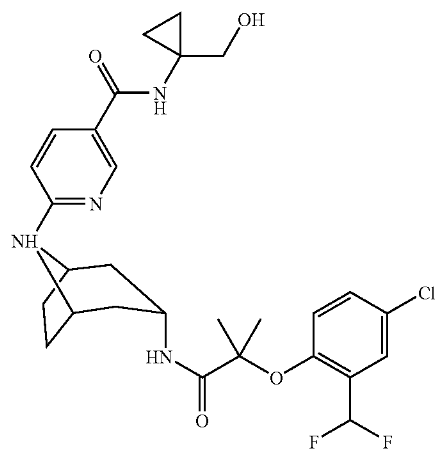 |
| 404 | 6-(3-endo-(2-(4-chloro-2-(difluoromethyl)phenoxy)-2-methylpropanamido)-8-azabicyclo[3.2.1]octan-8-yl)-N-(isoxazol-3-yl)nicotinamide ACTIVITY = A | 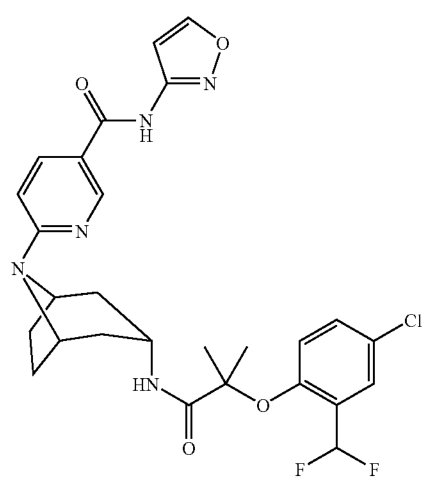 |

TABLE I-continued

| No. | Name/Activity | Structure |
|---|---|---|
| 405 | 6-(3-endo-(2-(2,4-dichloro-5-(2-(pyrrolidin-1-yl)ethoxy)phenoxy)-2-methylpropanamido)-8-azabicyclo[3.2.1]octan-8-yl)-N-(2,2,2-trifluoroethyl)nicotinamide<br>ACTIVITY = A | 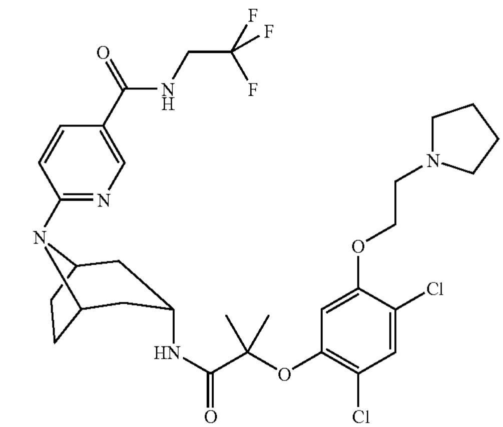 |
| 406 | 6-(3-endo-(2-(2,4-dichloro-5-(2-(4-methylpiperazin-1-yl)ethoxy)phenoxy)-2-methylpropanamido)-8-azabicyclo[3.2.1]octan-8-yl)-N-(2,2,2-trifluoroethyl)nicotinamide<br>ACTIVITY = A | 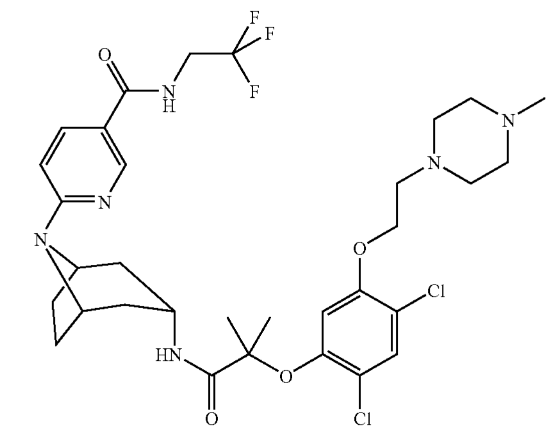 |
| 407 | 6-(3-endo-(2-(2,4-dichloro-5-(2-morpholinoethoxy)phenoxy)-2-methylpropanamido)-8-azabicyclo[3.2.1]octan-8-yl)-N-(2,2,2-trifluoroethyl)nicotinamide<br>ACTIVITY = A | 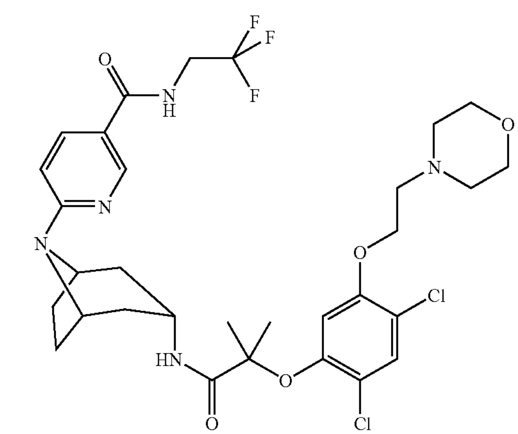 |
| 408 | 6-(3-endo-(2-(3,5-dichloropyridin-2-yloxy)-2-methylpropanamido)-8-azabicyclo[3.2.1]octan-8-yl)-N-(2,2-difluoroethyl)nicotinamide<br>ACTIVITY = A | 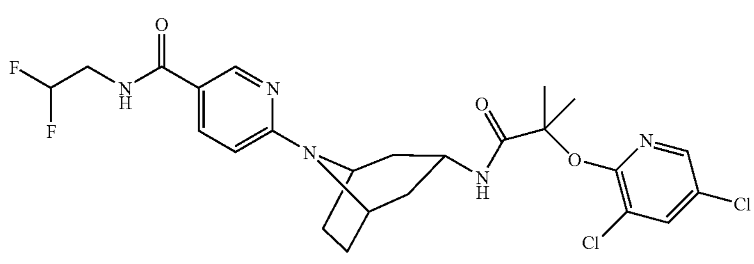 |

TABLE I-continued

| No. | Name/Activity | Structure |
|---|---|---|
| 409 | 6-(3-endo-(2-(5-chloro-3-fluoropyridin-2-yloxy)-2-methylpropanamido)-8-azabicyclo[3.2.1]octan-8-yl)-N-(2,2-difluoroethyl)nicotinamide ACTIVITY = A | 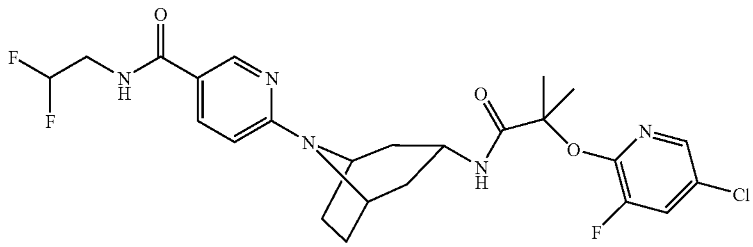 |
| 410 | 6-(3-endo-(2-(4-chloro-2-(trifluoromethoxy)phenoxy)-2-methylpropanamido)-8-azabicyclo[3.2.1]octan-8-yl)-N-((S)-1,1,1-trifluoropropan-2-yl)nicotinamide ACTIVITY = A | 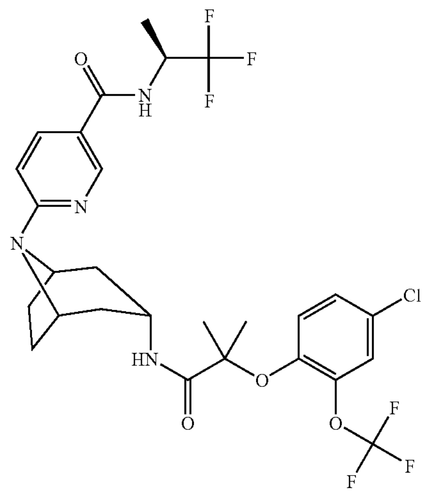 |
| 411 | 6-(3-endo-(2-(4-chloro-2-(difluoromethyl)phenoxy)-2-methylpropanamido)-8-azabicyclo[3.2.1]octan-8-yl)-N-((R)-1,1,1-trifluoropropan-2-yl)nicotinamide ACTIVITY = A | 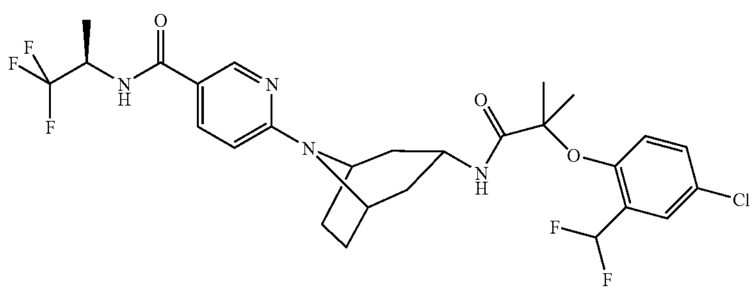 |
| 412 | 6-(3-endo-(2-(4-chloro-2-(trifluoromethyl)phenoxy)-2-methylpropanamido)-8-azabicyclo[3.2.1]octan-8-yl)-N-((R)-1,1,1-trifluoropropan-2-yl)nicotinamide ACTIVITY = A | 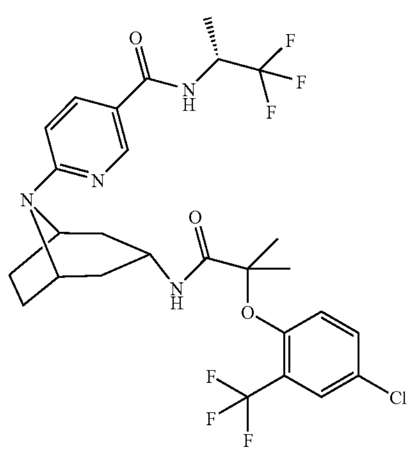 |

TABLE I-continued

| No. | Name/Activity | Structure |
|---|---|---|
| 413 | 2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)acetic acid<br>ACTIVITY = A | 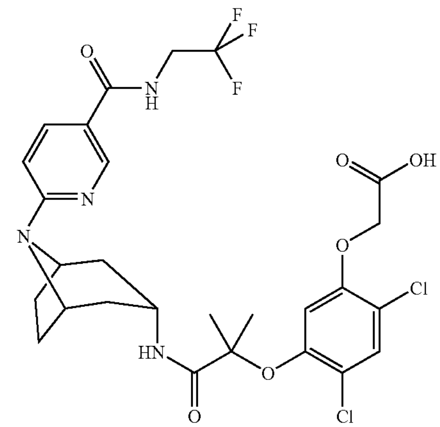 |
| 414 | 2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)-2-methylpropanoic acid<br>ACTIVITY = B | 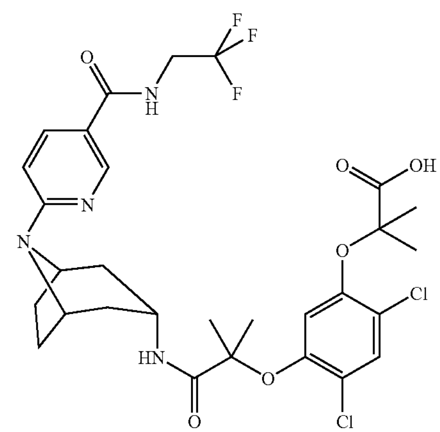 |
| 415 | 6-[3-endo-({2-[4-chloro-2-(trifluoromethoxy)phenoxy]-2-methylpropanoyl}amino)-8-azabicyclo[3.2.1]oct-8-yl]-N-[(2R)-1,1,1-trifluoropropan-2-yl]pyridine-3-carboxamide<br>ACTIVITY = A | 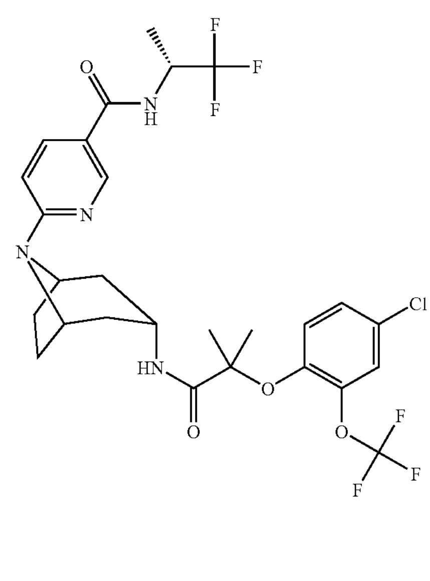 |

TABLE I-continued

| No. | Name/Activity | Structure |
|---|---|---|
| 416 | 6-[3-endo-({2-[4-chloro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = A | 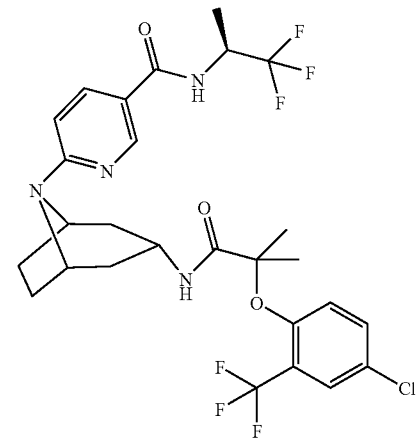 |
| 417 | 6-[3-endo-({2-[(3,5-dichloropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = A | 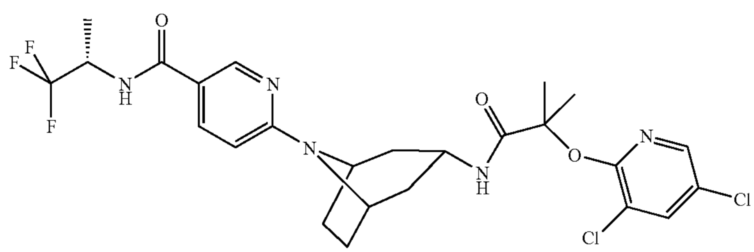 |
| 418 | 6-[3-endo-({2-[2-(difluoromethyl)-4-fluorophenoxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = A | 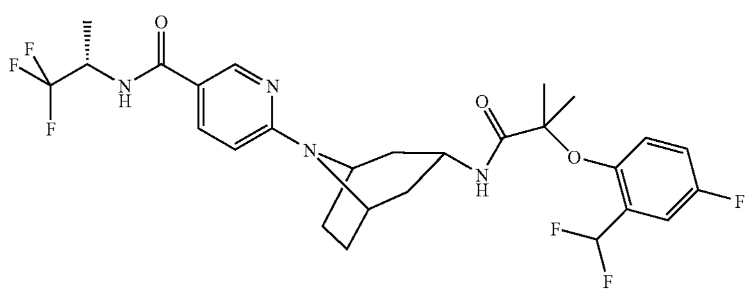 |
| 419 | 6-[3-endo-({2-[(5-chloro-3-fluoropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = B | 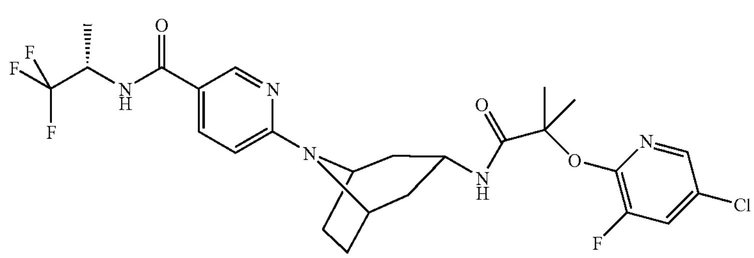 |
| 420 | 6-(3-endo-{[2-(4-chlorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = B | 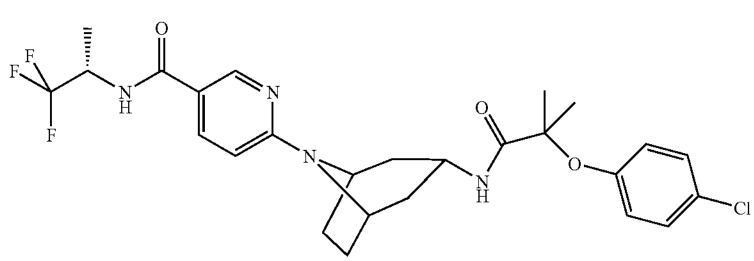 |

TABLE I-continued

| No. | Name/Activity | Structure |
|---|---|---|
| 421 | 6-(3-endo-{[2-(2,4-dichlorophenoxy)-2-methylpropanoyl]amino}-8-azabicyclo[3.2.1]oct-8-yl)-N-(3,3,3-trifluoro-2-hydroxypropyl)pyridine-3-carboxamide ACTIVITY = A | 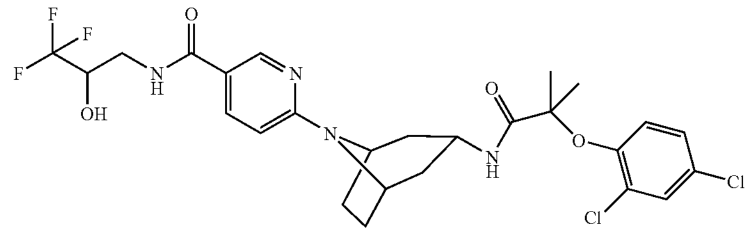 |
| 422 | 6-[3-endo-({2-[4-chloro-2-(methylsulfonyl)phenoxy]-2-methylpropanoyl}amino)-8-azabicyclo[3.2.1]oct-8-yl]-N-(2,2-difluoroethyl)pyridine-3-carboxamide ACTIVITY = A | 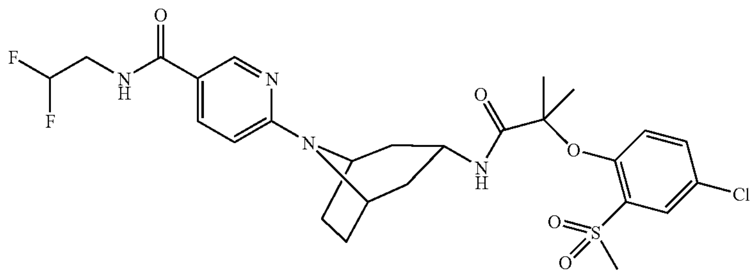 |
| 423 | 6-[3-endo-({2-[4-fluoro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide ACTIVITY = A | 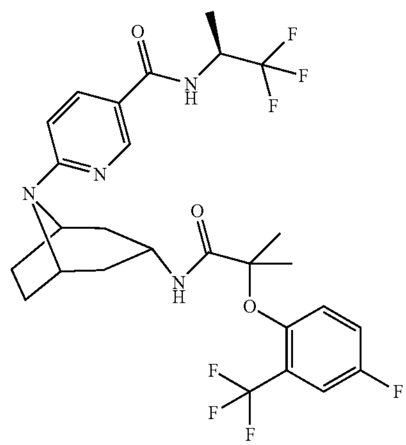 |
| 424 | 6-[3-endo-({2-[4-chloro-2-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide ACTIVITY = A | 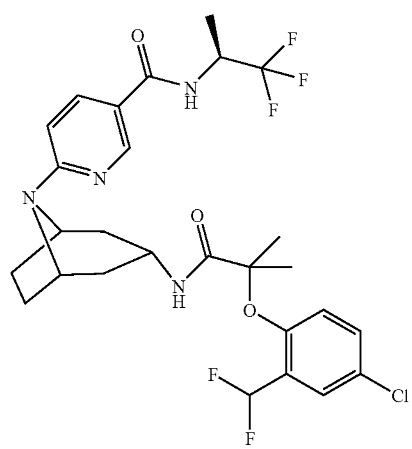 |

TABLE I-continued

| No. | Name/Activity | Structure |
|---|---|---|
| 425 | 6-(3-endo-{[2-(2,4-dichloro-5-fluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 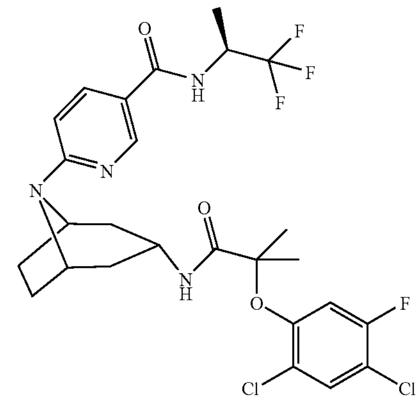 |
| 426 | 6-{3-endo-[(2-{5-[(1-amino-2-methyl-1-oxopropan-2-yl)oxy]-2,4-dichlorophenoxy}-2-methylpropanoyl)amino]-8-azabicyclo[3.2.1]oct-8-yl}-N-(2,2,2-trifluoroethyl)pyridine-3-carboxamide<br>ACTIVITY = A | 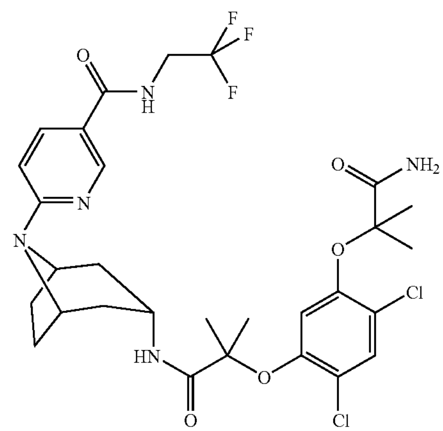 |
| 427 | 6-[3-endo-({2-[4-chloro-2-(trifluoromethoxy)phenoxy]-2-methylpropanoyl}amino)-8-azabicyclo[3.2.1]oct-8-yl]-N-[1-(hydroxymethyl)cyclopropyl]pyridine-3-carboxamide<br>ACTIVITY = A | 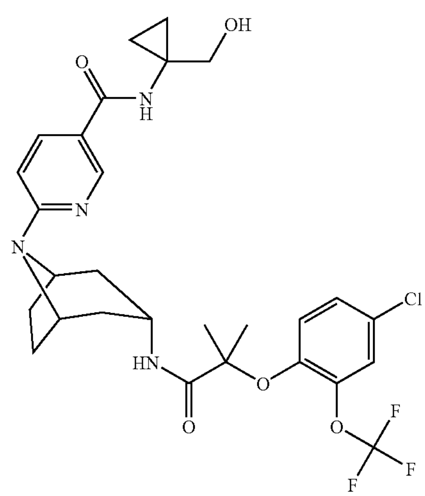 |

TABLE I-continued

| No. | Name/Activity | Structure |
|---|---|---|
| 428 | 6-[3-endo-({2-[2,4-dichloro-5-(hydroxymethyl)phenoxy]-2-methylpropanoyl}amino)-8-azabicyclo[3.2.1]oct-8-yl]-N-(2,2-difluoroethyl)pyridine-3-carboxamide<br>ACTIVITY = A | 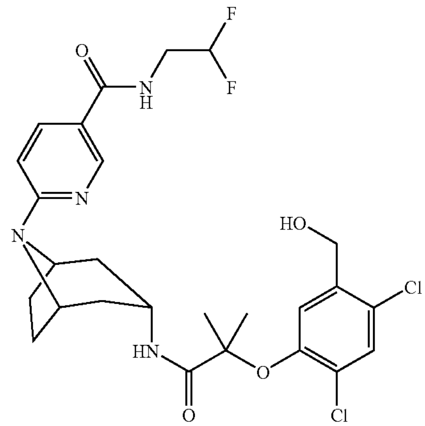 |
| 429 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 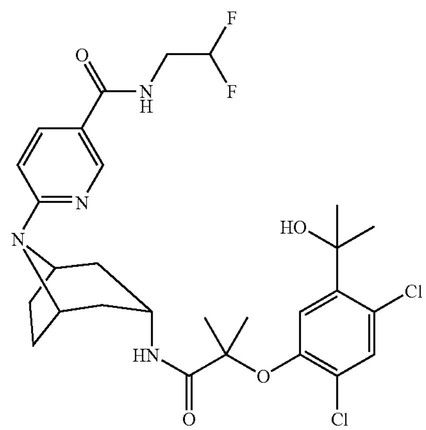 |
| 430 | 6-(3-endo-{[2-(2-chloro-4,5-difluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 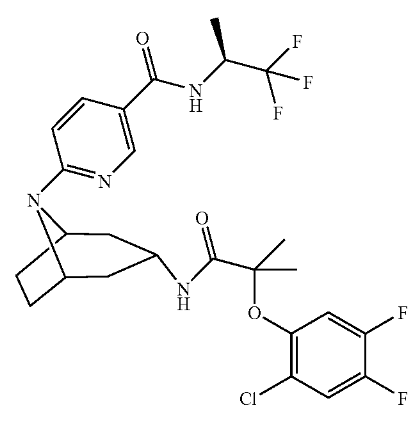 |

TABLE I-continued

| No. | Name/Activity | Structure |
|---|---|---|
| 431 | 6-(3-endo-{[2-(2,4-difluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 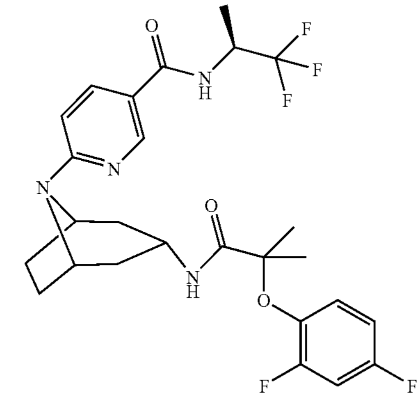 |
| 432 | 6-[3-endo-({2-[4-chloro-2-(methylsulfonyl)phenoxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = B | 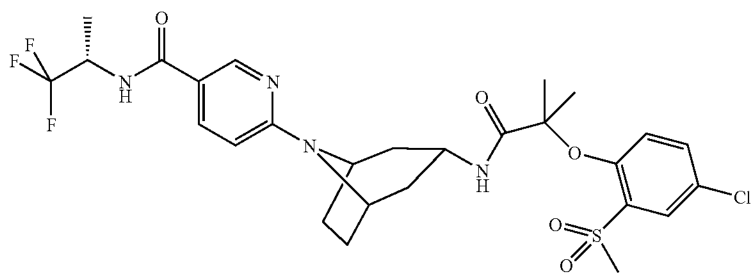 |
| 433 | 6-[3-endo-({2-[4-chloro-2-(difluoromethyl)phenoxy]-2-methylpropanoyl}amino)-8-azabicyclo[3.2.1]oct-8-yl]-N-(2,2-difluoroethyl)pyridine-3-carboxamide<br>ACTIVITY = A | 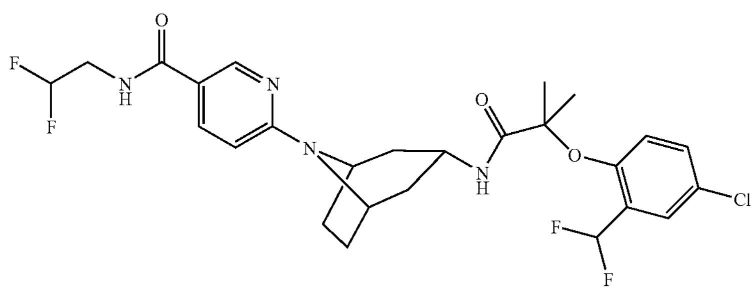 |
| 434 | 6-(3-endo-{[2-(2-chloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 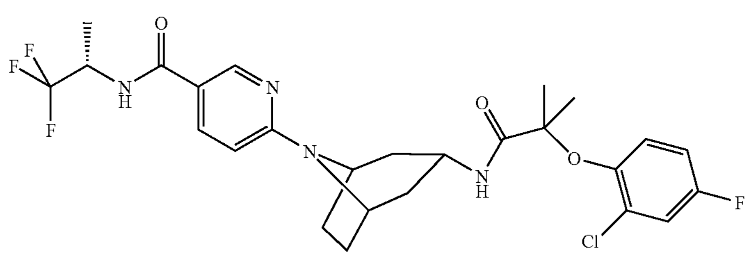 |
| 435 | 6-(3-endo-{[2-(4-chloro-2-fluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 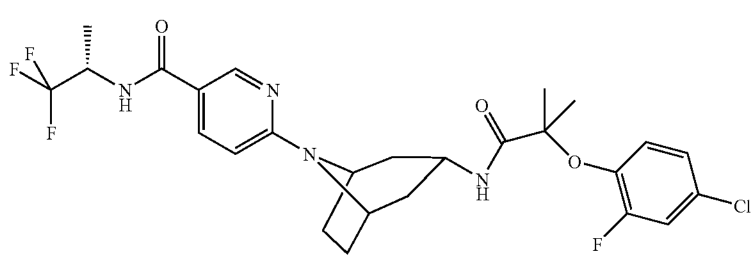 |

TABLE I-continued

| No. | Name/Activity | Structure |
|---|---|---|
| 436 | 6-(3-endo-{[2-(2,4-dichloro-5-fluorophenoxy)-2-methylpropanoyl]amino}-8-azabicyclo[3.2.1]oct-8-yl)-N-(2,2-difluoroethyl)pyridine-3-carboxamide<br>ACTIVITY = A | 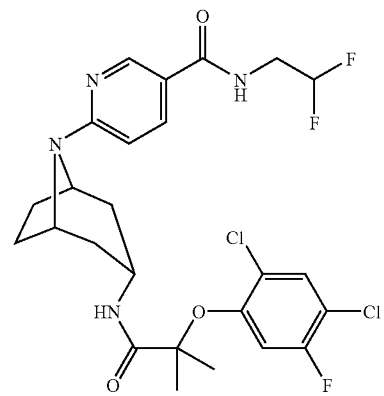 |
| 437 | 6-(3-endo-{[2-(2,3-dichloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide<br>ACTIVITY = A | 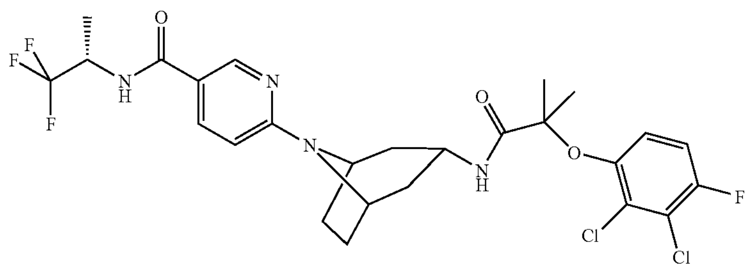 |
| 438 | 6-[3-endo-({2-[4-chloro-2-(trifluoromethoxy)phenoxy]-2-methylpropanoyl}amino)-8-azabicyclo[3.2.1]oct-8-yl]-N-(2-hydroxy-2-methylpropyl)pyridine-3-carboxamide<br>ACTIVITY = A | 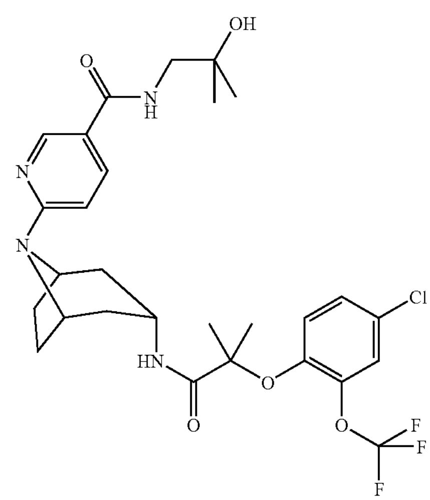 |
| 439 | 6-{3-endo-[(2-{[3-(difluoromethyl)-5-fluoropyridin-2-yl]oxy}-2-methylpropanoyl)amino]-8-azabicyclo[3.2.1]oct-8-yl}-N-[(2S)-1,1,1-trifluoropropan-2-yl]pyridine-3-carboxamide<br>ACTIVITY = B | 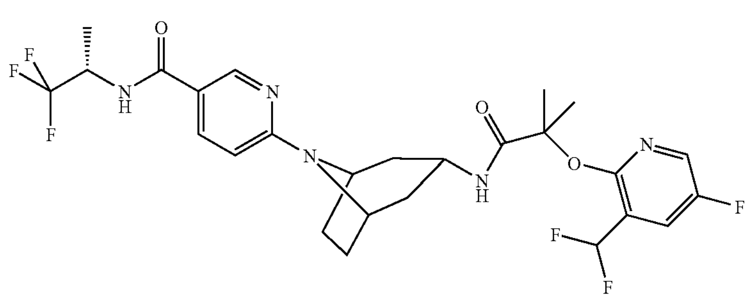 |

TABLE I-continued

| No. | Name/Activity | Structure |
|---|---|---|
| 440 | N-(2,2-difluoroethyl)-6-{3-endo-[(2-{[3-(difluoromethyl)-5-fluoropyridin-2-yl]oxy}-2-methylpropanoyl)amino]-8-azabicyclo[3.2.1]oct-8-yl}pyridine-3-carboxamide<br>ACTIVITY = A | 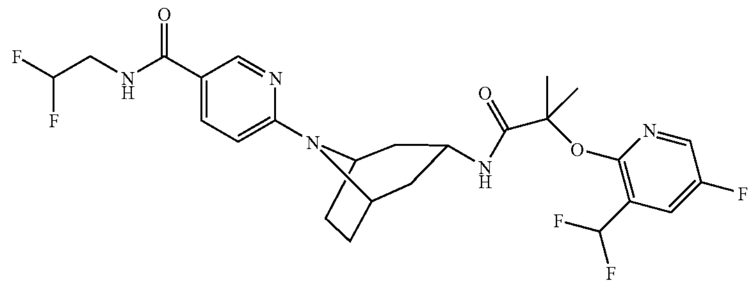 |
| 441 | 6-(3-endo-{[2-(2,3-dichloro-4-fluorophenoxy)-2-methylpropanoyl]amino}-8-azabicyclo[3.2.1]oct-8-yl)-N-(2,2-difluoroethyl)pyridine-3-carboxamide<br>ACTIVITY = A | 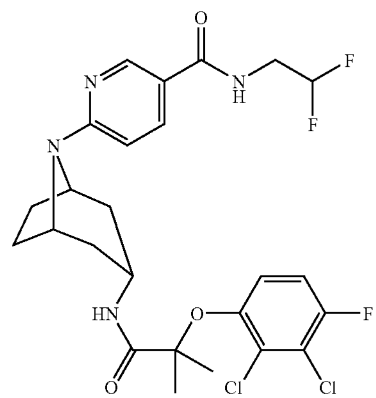 |
| 442 | 6-(3-endo-{[2-(2-chloro-4,5-difluorophenoxy)-2-methylpropanoyl]amino}-8-azabicyclo[3.2.1]oct-8-yl)-N-(2,2-difluoroethyl)pyridine-3-carboxamide<br>ACTIVITY = A | 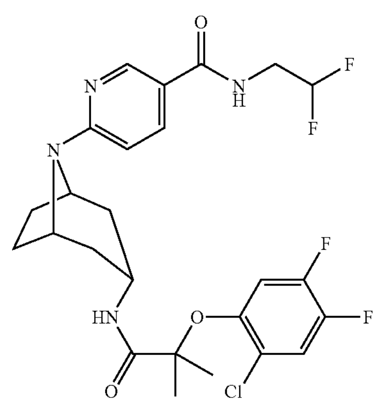 |
| 443 | N-(2,2-difluoroethyl)-6-(3-endo-{[2-(2,4-difluorophenoxy)-2-methylpropanoyl]amino}-8-azabicyclo[3.2.1]oct-8-yl)pyridine-3-carboxamide<br>ACTIVITY = A | 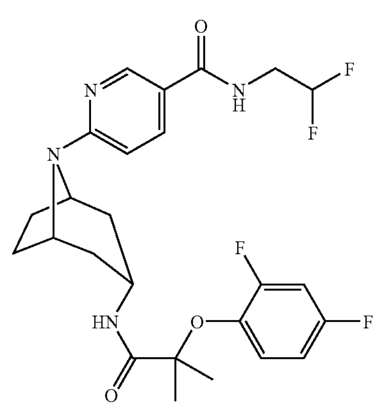 |

TABLE I-continued

| No. | Name/Activity | Structure |
|---|---|---|
| 444 | [2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]acetic acid<br>ACTIVITY = A | 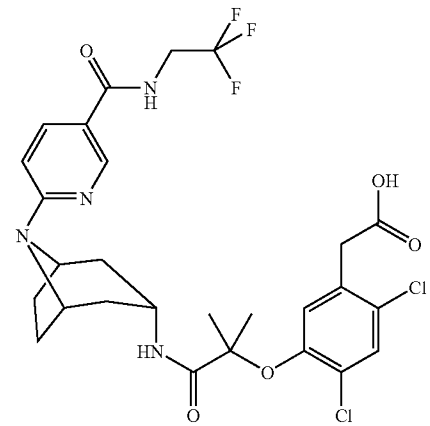 |
| 445 | 2-[2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]-2-methylpropanoic acid<br>ACTIVITY = A | 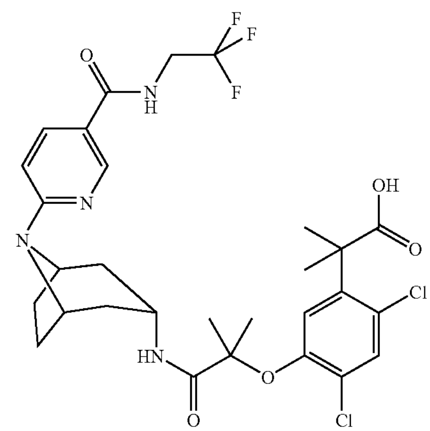 |
| 446 | 6-[3-endo-({2-[5-(1-amino-2-methyl-1-oxopropan-2-yl)-2,4-dichlorophenoxy]-2-methylpropanoyl}amino)-8-azabicyclo[3.2.1]oct-8-yl]-N-(2,2,2-trifluoroethyl)pyridine-3-carboxamide<br>ACTIVITY = A | 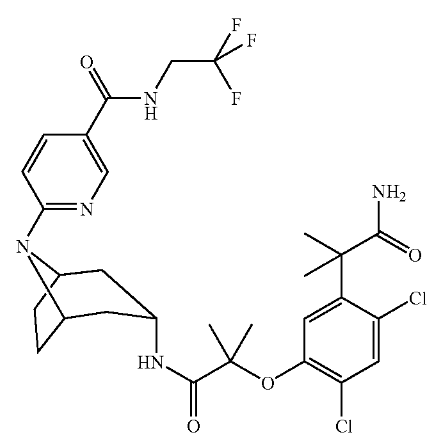 |

TABLE I-continued

| No. | Name/Activity | Structure |
|---|---|---|
| 447 | 6-(3-endo-{[2-(4-chloro-2-fluorophenoxy)-2-methylpropanoyl]amino}-8-azabicyclo[3.2.1]oct-8-yl)-N-(2,2-difluoroethyl)pyridine-3-carboxamide<br>ACTIVITY = A | 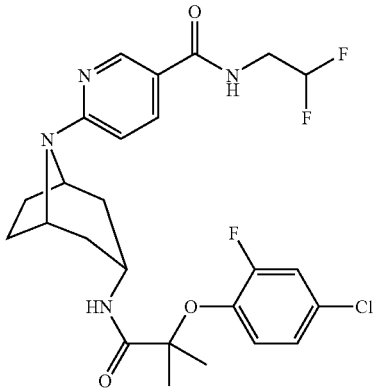 |
| 448 | 6-[3-endo-({2-[4-chloro-2-(trifluoromethoxy)phenoxy]-2-methylpropanoyl}amino)-8-azabicyclo[3.2.1]oct-8-yl]-N-(3,3,3-trifluoro-2-hydroxypropyl)pyridine-3-carboxamide<br>ACTIVITY = A | 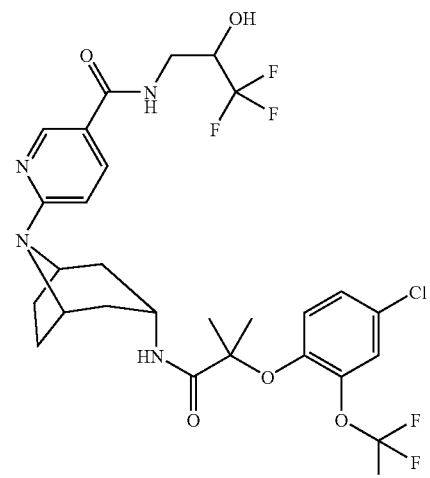 |
| 449 | 6-[3-endo-({2-[4-chloro-2-(difluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide<br>ACTIVITY = A | 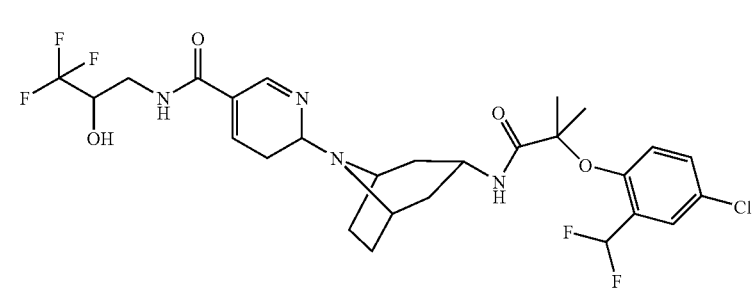 |
| 450 | 6-(3-endo-{[2-(2,4-dichloro-5-fluorophenoxy)-2-methylpropanoyl]amino}-8-azabicyclo[3.2.1]oct-8-yl)-N-[(2R)-1,1,1-trifluoropropan-2-yl]pyridine-3-carboxamide<br>ACTIVITY = A | 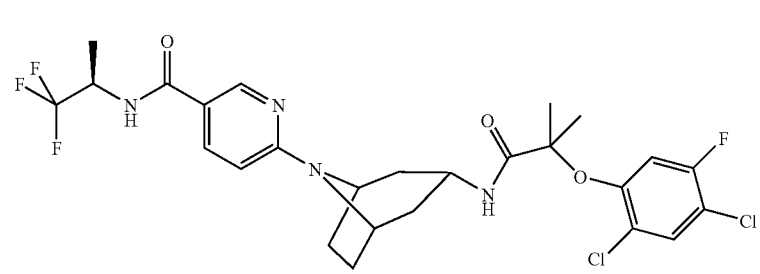 |

TABLE I-continued

| No. | Name/Activity | Structure |
|---|---|---|
| 451 | 6-(3-endo-{[2-(2-chloro-4,5-difluorophenoxy)-2-methylpropanoyl]amino}-8-azabicyclo[3.2.1]oct-8-yl)-N-[(2R)-1,1,1-trifluoropropan-2-yl]pyridine-3-carboxamide<br>ACTIVITY = A | 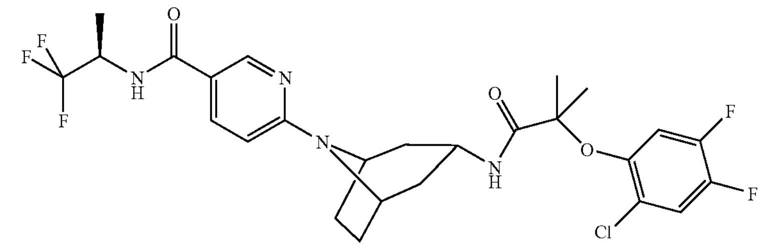 |
| 452 | 6-(3-endo-{[2-(2-chloro-4-fluorophenoxy)-2-methylpropanoyl]amino}-8-azabicyclo[3.2.1]oct-8-yl)-N-[(2R)-1,1,1-trifluoropropan-2-yl]pyridine-3-carboxamide<br>ACTIVITY = A | 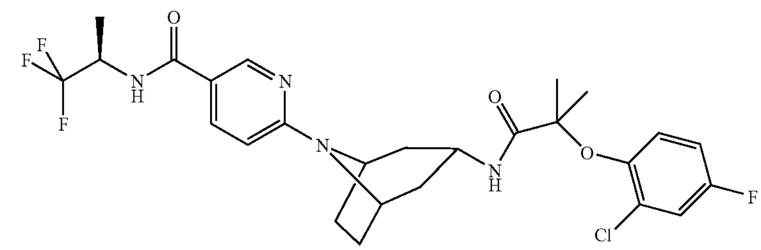 |
| 453 | 6-[3-endo-({2-[2-chloro-4-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide<br>ACTIVITY = A | 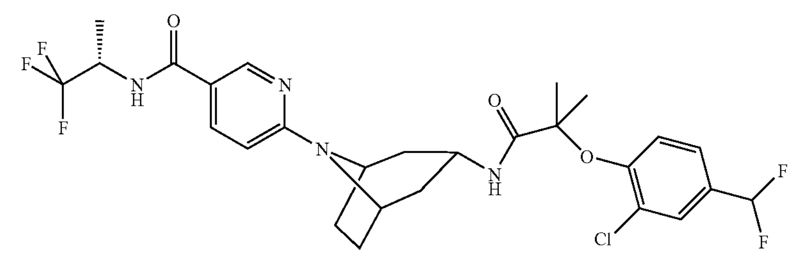 |
| 454 | 2-[4-chloro-2-(trifluoromethoxy)phenoxy]-n-(8-{5-[(3-hydroxypyrrolidin-1-yl)carbonyl]pyridin-2-yl}-8-azabicyclo[3.2.1]oct-3-endo-yl)-2-methylpropanamide<br>ACTIVITY = A | 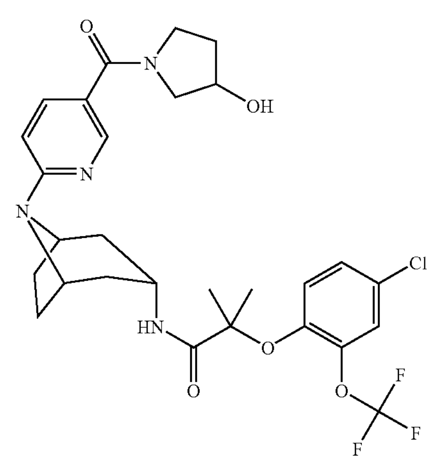 |

TABLE I-continued

| No. | Name/Activity | Structure |
|---|---|---|
| 455 | 2-[4-chloro-2-(trifluoromethoxy)phenoxy]-n-[8-(5-{[(2s)-2-(hydroxymethyl)pyrrolidin-1-yl]carbonyl}pyridin-2-yl)-8-azabicyclo[3.2.1]oct-3-endo-yl]-2-methylpropanamide<br>ACTIVITY = A | 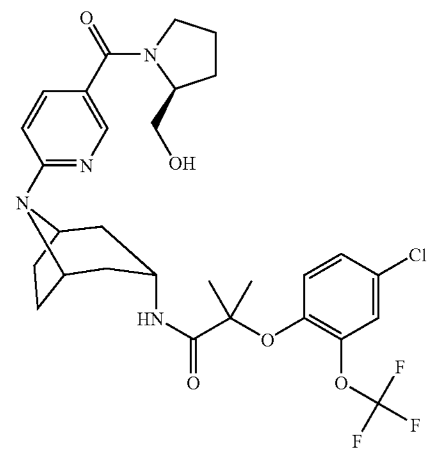 |
| 456 | 6-(3-endo-{[2-(2,4-dichlorophenoxy)-2-methylpropanoyl]amino}-8-azabicyclo[3.2.1]oct-8-yl)-N-[(2S)-3,3,3-trifluoro-2-hydroxypropyl]pyridine-3-carboxamide<br>ACTIVITY = A | 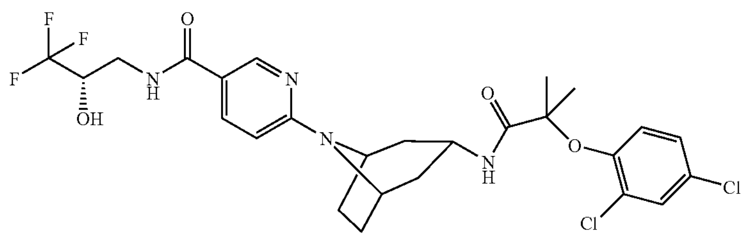 |
| 457 | 6-(3-endo-{[2-(2-chloro-4-fluorophenoxy)-2-methylpropanoyl]amino}-8-azabicyclo[3.2.1]oct-8-yl)-N-(3,3,3-trifluoro-2-hydroxypropyl)pyridine-3-carboxamide<br>ACTIVITY = A | 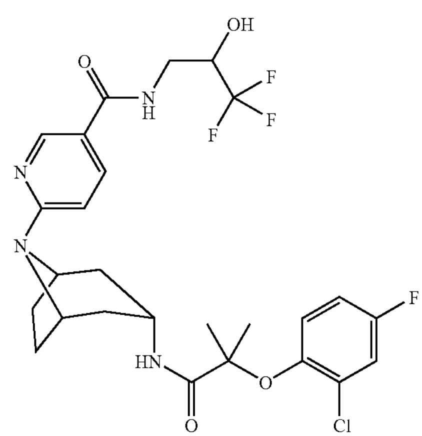 |
| 458 | 6-[3-endo-({2-[4-chloro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide<br>ACTIVITY = A | 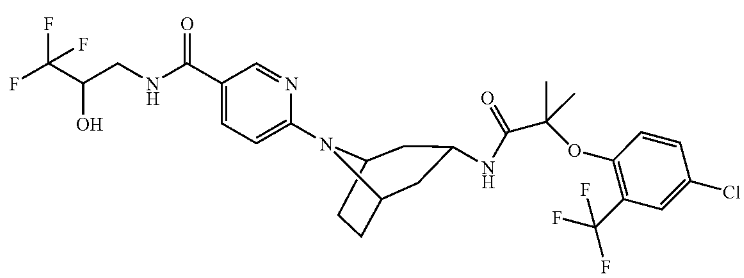 |

TABLE I-continued

| No. | Name/Activity | Structure |
|---|---|---|
| 459 | 6-[3-endo-({2-[4-fluoro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide<br>ACTIVITY = A | 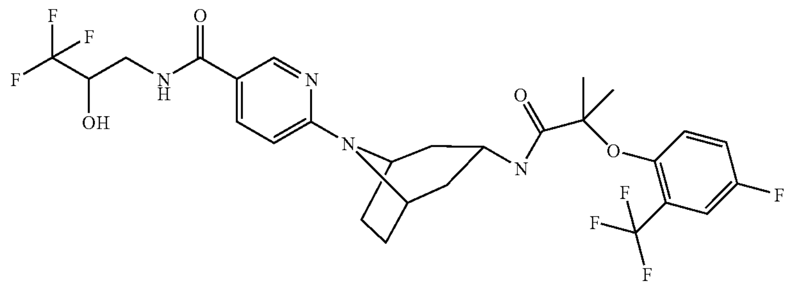 |
| 460 | [2,4-dichloro-5-({1-[(8-{5-[(2,2-difluoroethyl)carbamoyl]pyridin-2-yl}-8-azabicyclo[3.2.1]oct-3-endo-yl)amino]-2-methyl-1-oxopropan-2-yl}oxy)phenyl]acetic acid<br>ACTIVITY = A | 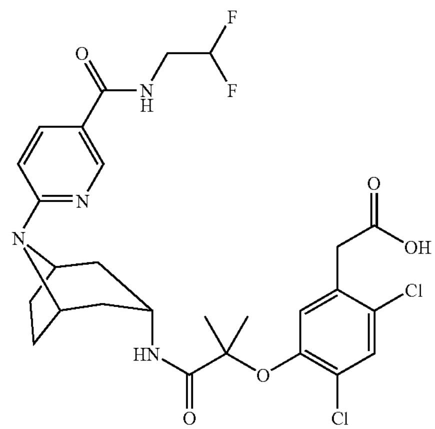 |
| 461 | 2-(2,4-dichlorophenoxy)-n-[8-(5-{[(3r)-3-hydroxypyrrolidin-1-yl]carbonyl}pyridin-2-yl)-8-azabicyclo[3.2.1]oct-3-endo-yl]-2-methylpropanamide<br>ACTIVITY = A | 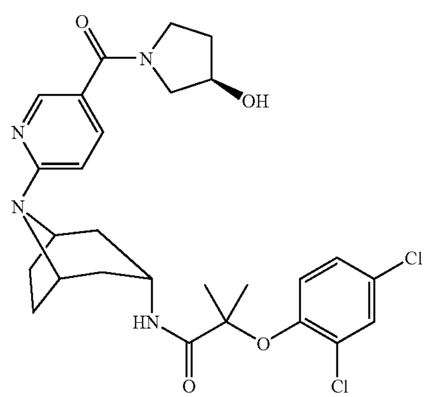 |
| 462 | 2-(2,4-dichlorophenoxy)-N-[8-(5-{[(3s)-3-hydroxypyrrolidin-1-yl]carbonyl}pyridin-2-yl)-8-azabicyclo[3.2.1]oct-3-endo-yl]-2-methylpropanamide<br>ACTIVITY = A | 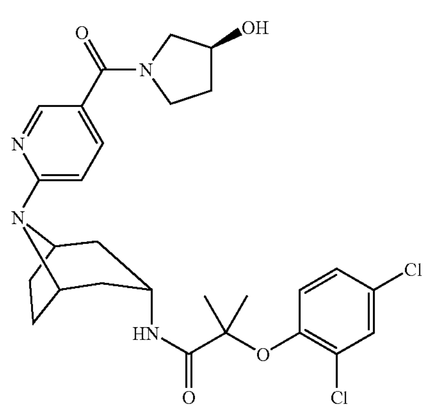 |

TABLE I-continued

| No. | Name/Activity | Structure |
|---|---|---|
| 463 | 6-(3-endo-{[2-(2,4-dichlorophenoxy)-2-methylpropanoyl]amino}-8-azabicyclo[3.2.1]oct-8-yl)-N-(1,1,1-trifluoro-3-hydroxypropan-2-yl)pyridine-3-carboxamide ACTIVITY = A | 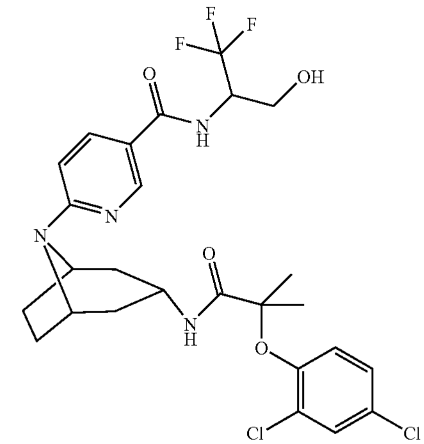 |
| 464 | 6-[3-endo-({2-[2,5-dichloro-4-(hydroxymethyl)phenoxy]-2-methylpropanoyl}amino)-8-azabicyclo[3.2.1]oct-8-yl]-N-(2,2-difluoroethyl)pyridine-3-carboxamide ACTIVITY = A | 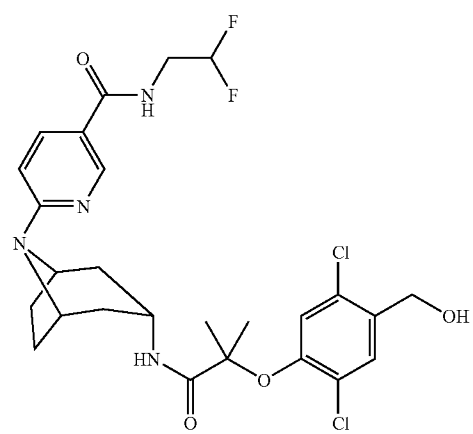 |
| 465 | 6-[3-endo-({2-[4-chloro-2-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide ACTIVITY = A | 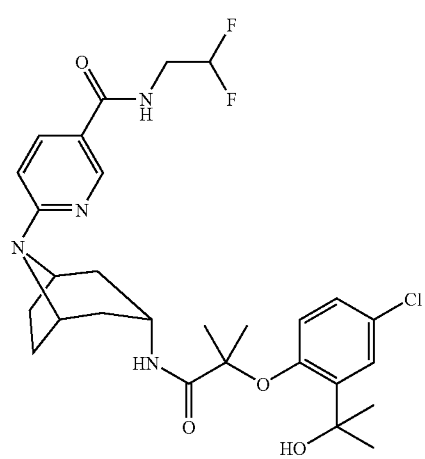 |

TABLE I-continued

| No. | Name/Activity | Structure |
|---|---|---|
| 466 | 6-(3-endo-(2-(4-chloro-2-fluoro-5-(2-hydroxypropan-2-yl)phenoxy)-2-methylpropanamido)-8-azabicyclo[3.2.1]octan-8-yl)-N-(2,2-difluoroethyl)nicotinamide ACTIVITY = A | 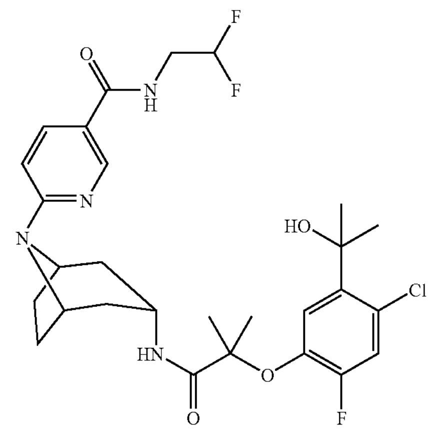 |
| 467 | N-(2,2-difluoroethyl)-6-(3-endo-(2-(4-fluoro-2-(2-hydroxypropan-2-yl)phenoxy)-2-methylpropanamido)-8-azabicyclo[3.2.1]octan-8-yl)nicotinamide ACTIVITY = A | 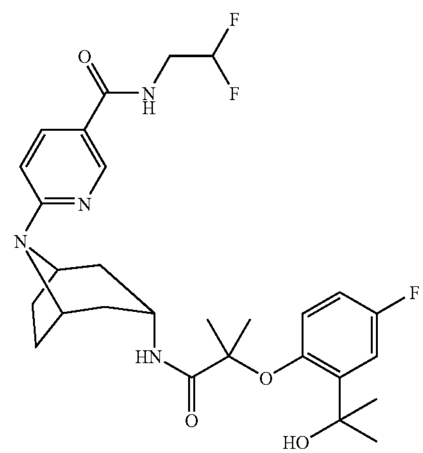 |
| 468 | N-(2,2-difluoroethyl)-6-[3-endo-({2-[2,4-difluoro-5-(2-hydroxypropan-2-yl)phenoxy]-2-methylpropanoyl}amino)-8-azabicyclo[3.2.1]oct-8-yl]pyridine-3-carboxamide ACTIVITY = A | 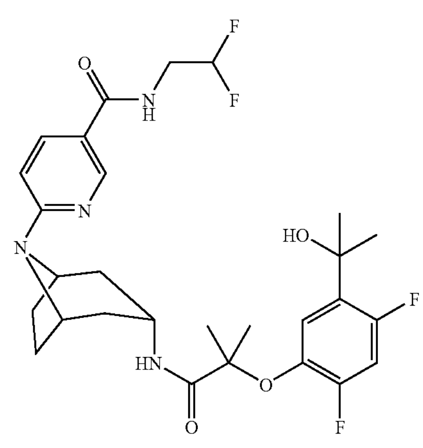 |

TABLE I-continued

| No. | Name/ Activity | Structure |
|---|---|---|
| 469 | 6-[3-endo-({2-[4-chloro-2-(difluoromethoxy)phenoxy]-2-methylpropanoyl}amino)-8-azabicyclo[3.2.1]oct-8-yl]-N-(2,2-difluoroethyl)pyridine-3-carboxamide<br>ACTIVITY = A | 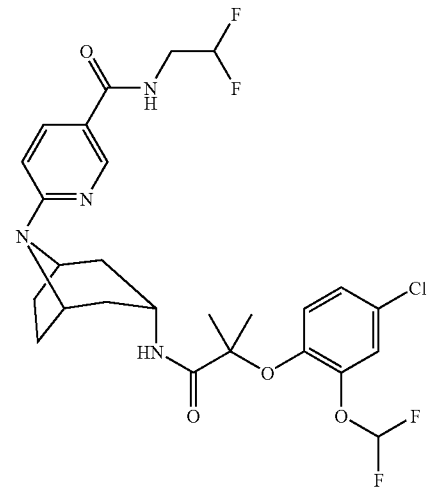 |
| 470 | 6-(3-endo-{[2-(2,4-dichlorophenoxy)-2-methylpropanoyl]amino}-8-azabicyclo[3.2.1]oct-8-yl)-N-[3,3,3-trifluoro-2-(morpholin-4-yl)propyl]pyridine-3-carboxamide<br>ACTIVITY = A | 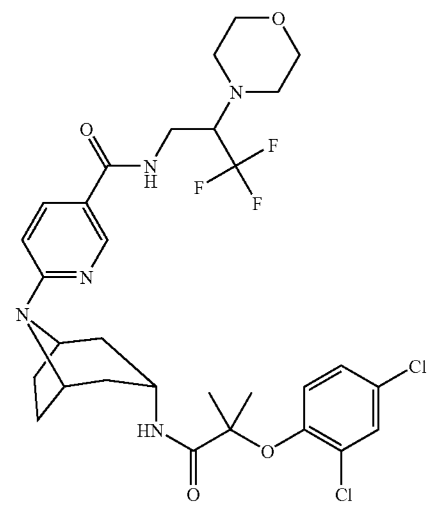 |
| 471 | 6-[3-endo-({2-[2-chloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 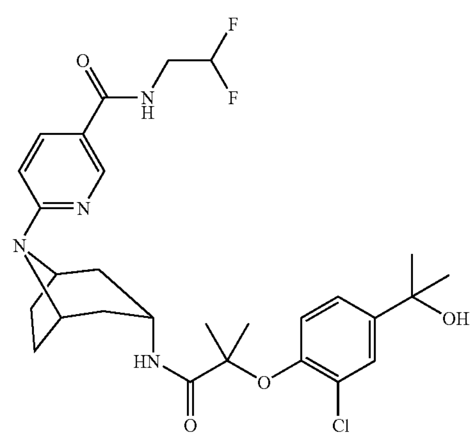 |

TABLE I-continued

| No. | Name/Activity | Structure |
|---|---|---|
| 472 | 6-[3-endo-({2-[2-chloro-4-fluoro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 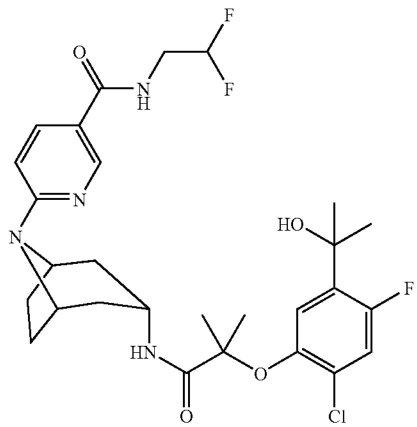 |
| 473 | 6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxamide<br>ACTIVITY = A | 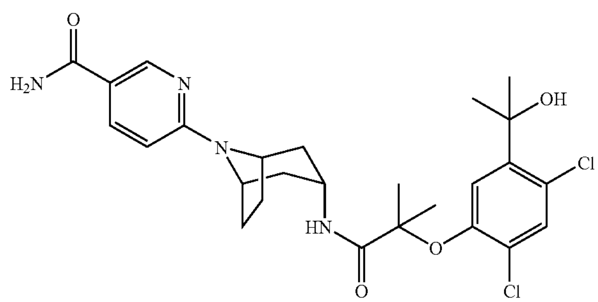 |
| 474 | 6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxylic acid<br>ACTIVITY = B | 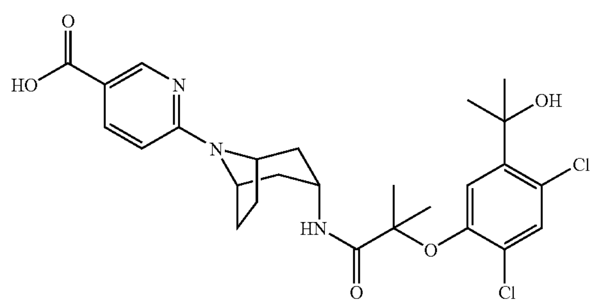 |
| 475 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide<br>ACTIVITY = A | 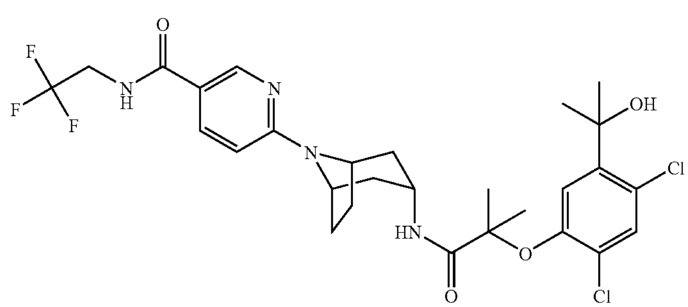 |

TABLE I-continued

| No. | Name/Activity | Structure |
|---|---|---|
| 476 | 6-(3-endo-{[2-(2,4-dichlorophenoxy)-2-methylpropanoyl]amino}-8-azabicyclo[3.2.1]oct-8-yl)-N-(3,3,3-trifluoro-2-oxopropyl)pyridine-3-carboxamide<br>ACTIVITY = A | 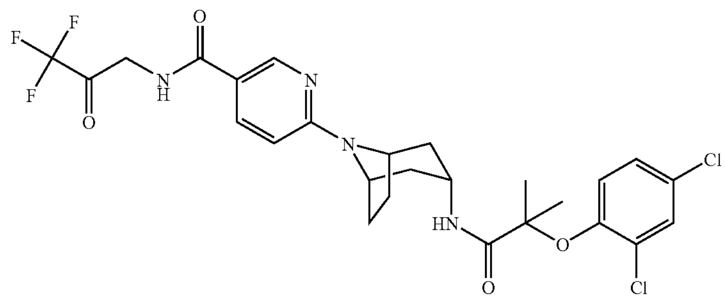 |
| 477 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(propan-2-yl)pyridine-3-carboxamide<br>ACTIVITY = A | 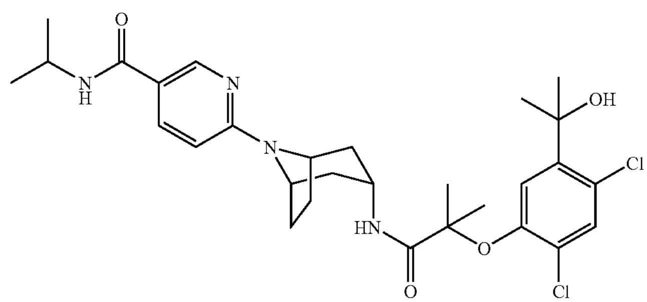 |
| 478 | 6-[3-endo-({2-[2,4-dichloro-5-(prop-1-en-2-yl)phenoxy]-2-methylpropanoyl}amino)-8-azabicyclo[3.2.1]oct-8-yl]-N-(2,2-difluoroethyl)pyridine-3-carboxamide<br>ACTIVITY = A | 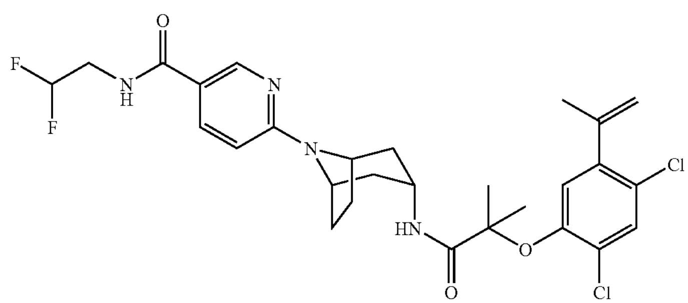 |
| 479 | 6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide 1-oxide<br>ACTIVITY = B | 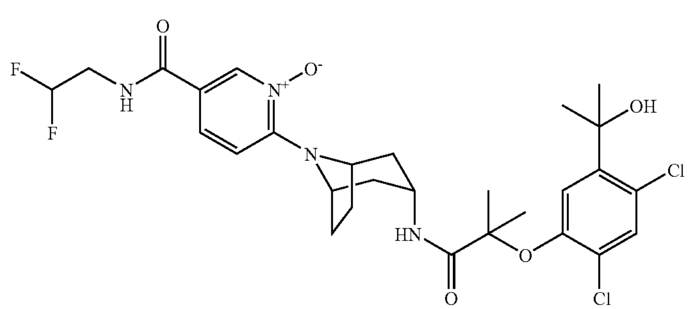 |

All compounds in Table I are endo-isomers (endo-isomers means exactly the same thing as endo-isomers for all compounds in Table I) in respect to the 8-azabicyclo[3.2.1]oct-8-yl moiety. The endo-isomer is represented by the following orientation in fig (a):

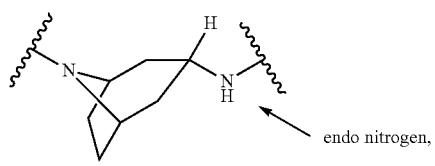

FIG. (a)

endo nitrogen, which for purposes of this application represents exactly the same moiety as shown in fig (b):

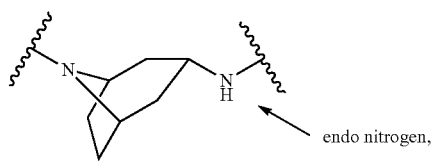

FIG. (b)

endo nitrogen, wherein the exo-hydrogen is assumed to be present whether it is drawn as shown in fig (a) or not shown in fig (b).

Compounds with ACTIVITY=A in Table 1 have been measured by assays described herein to have human 11 β-HSD1 $IC_{50}$ values of less than 200 nM. Another embodiment of this disclosure relates to the group of compounds in Table 1 that have ACTIVITY=A.

Compounds with ACTIVITY=B in Table 1 have been measured by assays described herein to have human 11 β-HSD1 $IC_{50}$ values of less than 2000 nM. Another embodiment of this disclosure relates to the group of compounds in Table 1 that have ACTIVITY=B.

Compounds with ACTIVITY=C in Table 1 have been measured by assays described herein to have human 11 β-HSD $IC_{50}$ values of less than 10,000 nM. Another embodiment of this disclosure relates to the group of compounds in Table 1 that have ACTIVITY=C.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be in the form of a pharmaceutical composition comprising the compound according to claim 1 and a pharmaceutically acceptable carrier, excipient, or diluent.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for treating insulin-dependent diabetes mellitus, wherein the methods comprise administering to a mammal in need of the treatment a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for treating non-insulin-dependent diabetes mellitus (type 2 diabetes), wherein the methods comprise administering to a mammal in need of the treatment a therapeutically effective amount of a compound according to I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for treating insulin, wherein the methods comprise administering to a mammal in need the treatment a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for treating obesity, wherein the methods comprise administering to a mammal in need of the treatment a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for modulating cortisol production, wherein the methods comprise administering to a mammal in need of the treatment a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in methods for modulating hepatic glucose production, wherein the methods comprise administering to a mammal in need of thereof a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or a pharmaceutically acceptable salt thereof, can each be used in methods for treating an 11 β-HSD 1-mediated condition or disorder, wherein the methods comprise administering to a mammal in need of the treatment a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in method for modulating the function of 11 β-HSD1 in a cell, wherein the methods comprise administering to a mammal in need thereof a therapeutically effective amount of a compound according to Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in a method for treating a mammal in need of the treatment one or more conditions selected from (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12)

atherosclerosis and its sequelae, (13) vascular restenosis, (14) pancreatitis, (15) abdominal obesity, (16) neurodegenerative disease, (17) retinopathy, (18) nephropathy, (19) neuropathy, and (20) Syndrome X, wherein the method comprises administering to the mammal a therapeutically effective amount of a compound according to any one of Formula I, I(A), I(B), I(C), I(D), I(E), I(F), I(G), I(H), I(I), I(J), I(K) I((L), I(M) or (I(N), or a pharmaceutically acceptable salt thereof.

In another embodiment, the compounds of Formula I, I(A), I(B), I(C), I(D), I(E), I(F), I(G), I(H), I(I), I(J), I(K) I((L), I(M) or (I(N), or pharmaceutically acceptable salts thereof, can each be used in a method for treating in a mammal in need of the treatment one or more conditions selected from (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, and (20) Syndrome X, wherein the method comprises administering to the mammal a therapeutically effective amount of a first compound according to any one of Formula I, I(A), I(B), I(C), I(D), I(E), I(F), I(G), I(H), I(I), I(J), I(K) I((L), I(M) or (I(N), I, I(A), I(B), I(C), I(D), I(E), I(F), I(G), I(H), I(I), I(J), I(K) I((L), I(M) or (I(N), or a pharmaceutically acceptable salt thereof, and one or more other compounds selected from: (a) DPP-IV inhibitors; (b) insulin sensitizers selected from PPAR agonists and biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, or PACAP receptor 3 agonists; (j) cholesterol lowering agents selected from RMG-CoA reductase inhibitors, sequestrants, nicotinyl alcohol, nicotinic acid and salts thereof, PPAR α-agonists, PPAR α/γ dual agonists, inhibitors of cholesterol absorption, acyl CoA: cholesterol acyltransferase inhibitors, and anti-oxidants; (k) PPAR δ agonists; (l) antiobesity compounds; (m) ileal bile acid transporter inhibitors; (n) anti-inflammatory agents, excluding glucocorticoids; and (o) protein tyrosine phosphatase-1B (PTP-1B) inhibitors.

The following abbreviations and terms have the indicated meanings throughout:

| Abbreviation | Meaning |
| --- | --- |
| Ac | Acetyl |
| Br | Broad |
| ° C. | degrees Celsius |
| c- | Cyclo |
| CBZ | CarboBenZoxy = benzyloxycarbonyl |
| D | Doublet |
| Dd | doublet of doublet |
| Dt | doublet of triplet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| L | liter(s) |

-continued

| Abbreviation | Meaning |
| --- | --- |
| M | molar or molarity |
| M | Multiplet |
| Me | Methyl |
| Mesyl | Methanesulfonyl |
| Mg | milligram(s) |
| MHz | megahertz (frequency) |
| Min | minute(s) |
| mL | milliliter(s) |
| mM | Millimolar |
| Mmol | millimole(s) |
| Mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | Phenyl |
| PhOH | Phenol |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| Q | Quartet |
| RT | Room temperature |
| Sat'd | Saturated |
| S | Singlet |
| s- | Secondary |
| t- | Tertiary |
| t or tr | Triplet |
| TBDMS | t-butyldimethylsilyl |
| TES | Triethylsilyl |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| Trt | triphenylmethyl |
| uL | microliter(s) |
| uM | Micromole(s) or micromolar |

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond, "─────" means a single or double bond. When a group is depicted removed from its parent formula, the "⌇⌇⌇" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

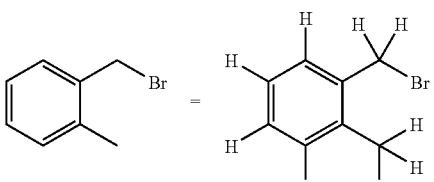

If a group "R" is depicted as "floating" on a ring system, as for example in the formula:

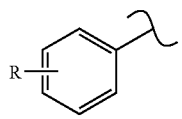

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

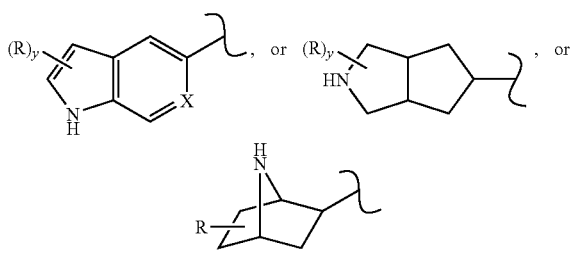

then, unless otherwise defined, a substituent "R" can reside on any atom of the fused ring system, assuming replacement of a depicted hydrogen (for example the —N(H)— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

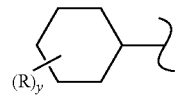

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a geminal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

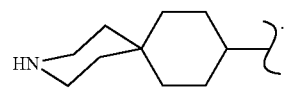

"Administration" and variants thereof (e.g., "administering" a compound) in reference to a compound of this disclosure (i.e., a compound of Formula I as described herein) means introducing the compound or a prodrug of the compound into the system of the animal in need of treatment. When a compound of this disclosure or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkyl" is intended to include molecules having 1-12 carbons in size ($C_1$-$C_{12}$)alkyl, which can be straight chained or branched. For example, "$C_6$ alkyl" can refer to an n-hexyl, iso-hexyl, cyclobutylethyl, and the like. Alkyl is intended to include lower alkyl groups of from 1-6 carbons in size, such as methyl, ethyl, propyl, isopropyl, butyl, s-butyl, t-butyl, isobutyl, pentyl, hexyl and the like. Higher alkyl refers to alkyl groups containing more that six carbon atoms. An alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl; and for example, "propyl" or "$C_3$ alkyl" each include n-propyl and isopropyl.

The terms "NH" or "—N(H)—" when meant to be a bivalent group are the same thing and is to be read as the nitrogen being attached to each of the two groups.

—($C_1$-$C_6$)alkyl is a subset of alkyl groups that are from one to six carbon atoms in length, and can be straight chained or branched.

—($C_1$-$C_3$)alkyl is a subset of alkyl groups that are from one to three carbon atoms in length, and can be straight chained or branched.

"alkenyl" is intended to be an alkyl that contains at least one double bond between two carbons. Non-limiting examples of alkenyl include vinyl, allyl, isoprenyl, and the like.

"alkynyl" is intended to be an alkyl that contains at least one triple bond between two carbons.

"Cycloalkyl" means a non-aromatic mono- or multicyclic ring system comprising about 3 to about 14 carbon atoms. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"—($C_3$-$C_6$)cycloalkyl" is a subset of cycloalkyl and means a non-aromatic monocyclic ring system comprising from 3 to 6 carbon atoms.

"Alkyl substituted with one or more halo and hydroxy" means an alkyl group substituted with 1, 2, or 3 hydroxy or 1, 2 or 3 halo.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$)).

"Alkoxy" or "alkoxyl" both refer to the group —O-alkyl, wherein the term "alkyl" is as defined hereinabove. Non-limiting examples of alkoxy include methoxy, ethoxy, propoxy, isopropoxy, and the like.

"—$(C_1$-$C_6)$alkoxy" is a subset of alkoxy and refers to the group —O—$(C_1$-$C_6)$alkyl, wherein the term "$(C_1$-$C_6)$alkyl" is as defined hereinabove.

"—$(C_1$-$C_3)$alkoxy" is a subset of alkoxy and refers to the group —O—$(C_1$-$C_3)$alkyl, wherein the term "$(C_1$-$C_3)$alkyl" is as defined hereinabove.

"Aryl" means a monovalent six- to fourteen-membered mono- or multicyclic ring, wherein the monocyclic ring is aromatic and at least one of the rings in the multicyclic ring is aromatic. A multicyclic ring that contains only one aryl ring is intended to be included within the definition of aryl. Representative non-limiting examples of aryl include phenyl, naphthyl, and the like.

"Arylalkyl" means a residue in which an aryl moiety, as defined above, is attached to a parent structure via one of an alkyl (i.e, alkylene, alkenylene, or alkynylene). Examples include benzyl, phenethyl, phenylvinyl, phenylallyl and the like. The "alkyl" portion of the group can be one to ten carbons.

"—$(C_1$-$C_6)$alkylaryl" is a subset of arylalkyl wherein the moiety is attached to a parent structure via a "—$(C_1$-$C_6)$ alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the compounds disclosed herein can themselves have spiro rings attached thereto via a single ring atom of the fused-polycyclic.

"Halogen" or "halo" both refer to fluorine, chlorine, bromine or iodine.

"Haloalkyl" (which includes alkyl optionally substituted with up to 8 halogens) and "haloaryl" refer generically to alkyl and aryl groups that are substituted with one or more halogens, respectively. Non-limiting examples of "haloalkyl" include 3,3,3-trifluoro-1-methylpropyl, 2-methyl-1-(trifluoromethyl)propyl, —$CH_2F$, —$CHCl_2$ and —$CF_3$.

"Heteroatom" refers to O, S, N, or P.

"Heterocycloalkyl" refers to a stable 4-12 membered monocyclic or multicyclic ring, wherein at least one of the rings contains at least one heteroatom and wherein there are no aromatic rings. Heterocycloalkyl is meant to include multicyclic rings, wherein one ring contains a heteroatom and another ring does not contain a heteroatom. Non-limiting examples of heterocycloalkyl include piperadinyl, piperazinyl, furanyl, pyrrolidinyl, morpholinyl.

"(4-6 membered) heterocycloalkyl" is a subset of heterocycloalkyl and refers to a stable 4-6 membered monocyclic ring containing at least one heteroatom and wherein there are no aromatic rings.

"Heterocycloalkylalkyl" refers to a heterocycloalkyl, as defined herein, attached to the parent moiety through an "alkyl," as defined herein.

"Amino" refers to —$NH_2$.

"Alkylamino" refers to —NH(alkyl), wherein "alkyl" is as defined above, and wherein the parent moiety is attached to the nitrogen atom.

"Dialkylamino" refers to —$N(alkyl)_2$, wherein "alkyl" is as defined above, and wherein the parent moiety is attached to the nitrogen atom.

"Dialkylaminoalkyl" refers to -(alkyl)$N(alkyl)_2$, wherein "alkyl" is as defined above.

"Aminoalkyl" refers to -(alkyl)$NH_2$, wherein "alkyl" is as defined above, and wherein the parent moiety is attached to the alkyl group. The amino group can be attached at any point along the alkyl group.

"Heteroaryl" means a 5- to 12-membered, monocyclic aromatic heterocyclyl (where heterocyclyl is defined herein) or bicyclic heterocyclyl ring system (where at least one of the rings in the bicyclic system is aromatic) where the monocyclic ring and at least one of the rings in the bicyclic ring system contains one, two, three, four, or five heteroatom(s) selected from nitrogen, oxygen, phosphorous, and sulfur. The ring containing the heteroatom can be aromatic or non-aromatic. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzodioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

"(5-6 membered) Heteroaryl" is a subset of heteroaryl and means a 5 to 6-membered aromatic heterocyclyl ring system where the monocyclic ring and at least one of the contains one, two, three or four heteroatom(s) selected from nitrogen, oxygen, phosphorous, and sulfur. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl and pyrrolyl.

"Carbonyl" refers to the group "—C(O)—", which is bivalent.

"Aminocarbonyl" refers to the group "—C(O)—$NH_2$," wherein the parent moiety is attached to the carbonyl group.

"Alkoxycarbonyl" refers to the group "—C(O)alkoxy," wherein alkoxy is as defined above, and the parent moiety is attached to the carbonyl. A non-limiting example includes —C(O)—$OC(CH_3)_3$.

"Hydroxyalkynyl" refers to a group wherein the parent moiety is attached to the alkynyl group, and a hydroxyl group is attached to the alkynyl. A non-limiting example includes 4-hydroxybut-1-yn-1-yl.

"Hydroxyalkyl" refers to a group wherein the parent moiety is attached to the alkyl group, and a hydroxyl group is attached to the alkyl.

"Amino(imino)alkyl" refers to a group represented by -alkyl-C(=NH)—NH$_2$, wherein alkyl is as defined above. A non-limiting example includes amino(imino)methyl.

"Dihydroxyalkyl" refers to a group wherein the parent moiety is attached to the alkyl group, and a two hydroxyl groups are attached to the alkyl, wherein the "alkyl" portion is as defined above.

"Alkylaminoalkylamino" refers to —N(H)(alkyl)N(H)(alkyl), as shown below, wherein the "alkyl" portion is as defined above.

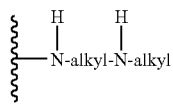

"Aminoalkylamino" refers to —N(H)(alkyl)NH$_2$, as shown below, wherein the "alkyl" portion is as defined above.

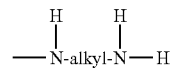

"Dialkylaminoalkoxy" refers to -(alkoxy)N(alkyl)$_2$, wherein the "alkoxy" and "alkyl" portions are both as defined above. One such non-limiting example of "dialkylaminoalkoxy" includes dimethylaminoethyloxy represented by —O—(CH$_2$)$_2$N(CH$_3$)$_2$.

"Alkylsulfonylalkylamino" refers to —NH$_2$—S(O)$_2$-alkyl, wherein the amino portion of this group is attached to the parent moiety, and wherein the "alkyl" portions is as defined above. A non-limiting example includes methyl sulfonyl ethyl amino.

The phrases "the compounds in this disclosure," the compounds in the disclosure, the compounds disclosed herein, compounds of this disclosure, and similar phrases that contain both of the words "compounds" and "disclosure" are meant to mean compounds of Formula I, and all of the embodiments thereof described herein.

In the case where there is a point of attachment for a monovalent substituent, such as —CH$_3$, —NH$_2$, or —OH, the indication of where the point of attachment is not necessary. That is, —CH$_3$ has the same meaning as CH$_3$, —NH$_2$ has the same meaning as NH$_2$, and —OH has the same meaning as OH.

In Table 1, where there appears to be an empty valence for oxygen or nitrogen for any of the compounds listed in this table, where the name of the structure requires that the empty valence is filled with hydrogen, it is assumed that the missing valence is filled with hydrogen for each of these cases.

When a group is referred to as "—(C$_1$-C$_6$)alkyl heterocyclyl" the heterocyclyl is attached to a parent structure via an alkyl group.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" means substituted or unsubstituted and refers to all subsequent modifiers in a term unless otherwise specified. So, for example, in the term "optionally substituted arylalkyl," both the "alkyl" portion and the "aryl" portion of the molecule can be substituted or unsubstituted.

Unless otherwise specified, the term "optionally substituted" applies to the chemical moiety immediately preceding it. For instance, if a variable group (such as R) is defined as aryl, optionally substituted alkyl, or cycloalkyl, then only the alkyl group is optionally substituted.

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo[3,2-b]furan, 2,3,3a,4,7,7a-hexahydro-1H-indene, 7-aza-bicyclo[2.2.1]-heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

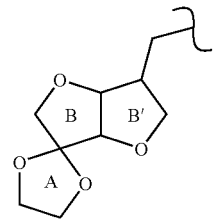

Some of the compounds of the disclosure can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

"Mammal" for the purposes of this disclosure includes humans (including patients receiving treatment) and other animals. Thus, the methods are applicable to both human therapy and veterinary applications. In a preferred embodiment, the mammal is a patient, and more preferably, the mammal is human.

"Therapeutically effective amount" is an amount of a compound of this disclosure, that when administered to a patient, ameliorates a symptom of the disease. The amount of a compound of this disclosure which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this disclosure include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this disclosure include, but are not limited to, primary amides, and secondary and tertiary alkyl amides (for example with between about one and about six carbons). Amides and esters of the compounds of this disclosure can be prepared according to conventional methods. A thorough discussion of prodrugs is provided in T. Higuchi and V. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of this disclosure or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of this disclosure is known to one of skill in the art in light of the present disclosure.

The compounds of this disclosure also include N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that can be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular 11 β-HSD1-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of this disclosure as their ligand component, are an aspect of this disclosure.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds disclosed herein can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In certain other preferred embodiments, administration can preferably be by the oral route. Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of this disclosure as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compounds in this disclosure can also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms, as described above, can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of this disclosure, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of this disclosure with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this disclosure include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated for the compounds in this disclosure.

Compressed gases can be used to disperse a compound of this disclosure in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of this disclosure, or a pharmaceutically acceptable salt thereof, and 99% to 1% by weight of a suitable pharmaceutical excipient. In one example, the composition will be between about 5% and about 75% by weight of a compound(s) of this disclosure, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of this disclosure, or a pharmaceutically acceptable salt thereof, for treatment of a disease-state in accordance with the teachings of this disclosure.

The compounds of this disclosure, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of this disclosure can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of this disclosure as the/an active agent, and, in addition, can include other medicinal agents and pharmaceutical agents. Compositions of the compounds in this disclosure can be used in combination with anticancer and/or other agents that are generally administered to a patient being treated for cancer, e.g. surgery, radiation and/or chemotherapeutic agent(s). Chemotherapeutic agents that can be useful for administration in combination with compounds of Formula I in treating cancer include alkylating agents, platinum containing agents.

If formulated as a fixed dose, such combination products employ the compounds of this disclosure within the dosage range described above and the other pharmaceutically active agent(s) within its approved dosage range. Compounds of this disclosure can alternatively be used sequentially with known pharmaceutically acceptable agent(s) when a combination formulation is inappropriate.

The examples and scheme below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

Synthetic Procedures

The compounds disclosed herein, or their pharmaceutically acceptable salts, can have asymmetric carbon atoms, oxidized sulfur atoms or quaternized nitrogen atoms in their structure.

As stated above, all of the compounds disclosed herein include either their free base form or their pharmaceutically acceptable salts whether it is stated in the specification that these compounds can exist as their pharmaceutically acceptable salt or not. So, for instance, for any given embodiment of the compound of Formula I (including embodiments relating to the compounds themselves or method of use thereof), this embodiment includes either its free base form or any of its pharmaceutically acceptable salts, whether this is stated within this embodiment or not.

In addition, all of the compounds disclosed herein, including any of their pharmaceutically acceptable salts, can exist as single stereoisomers (including single enantiomers and single diastereomers), racemates, mixtures of enantiomers and diastereomers and polymorphs. Sterioisomers of the compounds in this disclosure include geometric isomers and optical isomers, such as atropisomers. The compounds disclosed herein can also exist as geometric isomers. All such single stereoisomers, racemates and mixtures thereof, and geometric isomers are intended to be within the scope of the compounds disclosed herein.

It is assumed that when considering generic descriptions of compounds of the disclosed herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

In addition, the compounds of this disclosure can exist in unsolvated as well as solvated forms with pharmaceutically acceptable solvents such as water, ethanol, and the like. In general, the solvated forms are considered equivalent to the unsolvated forms for the purposes of the compounds of this disclosure.

In addition, it is intended that the present disclosure cover compounds made either using standard organic synthetic techniques, including combinatorial chemistry or by biological methods, such as bacterial digestion, metabolism, enzymatic conversion, and the like.

The examples and scheme below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

The terms "modulate", "modulation" and the like refer to the ability of a compound to increase or decrease the function, or activity of, for example, 11 β-HSD1. "Modulation", as used herein in its various forms, is intended to encompass inhibition, antagonism, partial antagonism, activation, agonism and/or partial agonism of the activity associated with 11 β-HSD1. 11 β-HSD1 inhibitors are compounds that, e.g., bind to, partially or totally block stimulation, decrease, prevent, delay activation, inactivate, desensitize, or down regulate signal transduction. 11 β-HSD1 activators are compounds that, e.g., bind to, stimulate, increase, open, activate, facilitate, enhance activation, sensitize or up regulate signal transduction. The ability of a compound to modulate 11 β-HSD1 can be demonstrated in an enzymatic assay or a cell-based assay. For example, the inhibition of 11 β-HSD1 may decrease cortisol levels in a patient and/or increase cortisone levels in a patient by blocking the conversion of cortisone to cortisol.

The term "HSD" as used herein, refers to hydroxysteroid dehydrogenase enzymes in general, including, but not limited to, 11-beta-hydroxysteroid dehydrogenases (11 β-HSDs including 11 β-HSD1), 17 β-hydroxysteroid dehydrogenases (17 β-HSDs), 20α-hydroxysteroid dehydrogenases (20α-HSDs), 3-alpha-hydroxysteroid dehydrogenases (3α-HSDs), and all isoforms thereof.

The term "11 β-HSD1" as used herein, refers to the 11 β-hydroxysteroid dehydrogenase type 1 enzyme, variant, or isoform thereof. 11 β-HSD1 variants include proteins substantially homologous to native 11 β-HSD1, i.e., proteins having one or more naturally or non-naturally occurring amino acid deletions, insertions or substitutions (e.g., 11 β-HSD1 derivatives, homologs and fragments). The amino acid sequence of a 11 β-HSD1 variant can be at least about 80% identical to a native 11 β-HSD1, or at least about 90% identical, or at least about 95% identical.

As used herein, the phrase "HSD-responsive condition or disorder" and related terms and phrases refer to a condition or disorder that responds favorably to modulation of a hydroxysteroid dehydrogenase enzyme (HSD), such as 11 β-HSD1. Favorable responses to HSD modulation include alleviation or abrogation of the disease and/or its attendant symptoms, inhibition of the disease, i.e., arrest or reduction of the development of the disease, or its clinical symptoms, and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and at least partially responsive to or affected by HSD modulation (e.g., an HSD inhibitor results in some improvement in a mammal well-being in at least some mammals). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11 β-HSD1-responsive condition or disorder" and related terms and phrases refer to a condition or disorder that responds favorably to modulation of 11 β-HSD1 activity. Favorable responses to 11 β-HSD1 modulation include alleviation or abrogation of the disease and/or its attendant symptoms, inhibition of the disease, i.e., arrest or reduction of the development of the disease, or its clinical symptoms, and regression of the disease or its clinical symptoms. An 11 β-HSD1 responsive condition or disease may be completely or partially responsive to 11 β-HSD1 modulation. An 11 β-HSD 1-responsive condition or disorder may be associated with inappropriate, e.g., less than or greater than normal, 11 β-HSD1 activity and at least partially responsive to or affected by 11 β-HSD1 modulation (e.g., an 11 β-HSD1 inhibitor results in some improvement in patient well-being in at least some patients). Inappropriate 11 β-HSD1 functional activity might arise as the result of 11 β-HSD1 expression in cells which normally do not express 11 β-HSD1, decreased 11 β-HSD1 expression or increased 11 β-HSD1 expression.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11 β-HSD1-mediated condition or disorder" and related terms and phrases refer to a condition or disorder characterized by inappropriate, e.g., less than or greater than normal, 11 β-HSD1 activity. An 11 β-HSD1-mediated condition or disorder may be completely or partially characterized by inappropriate 11 β-HSD1 activity. However, an 11 β-HSD1-mediated condition or disorder is one in which modulation of 11 β-HSD1 results in some effect on the underlying condition or disease (e.g., a 11 β-HSD1 inhibitor results in some improvement in patient well-being in at least some patients).

The examples and schemes below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

Synthesis of Compounds:

Schemes for the preparation of compounds of the invention and a description of the synthetic protocols are provided below.

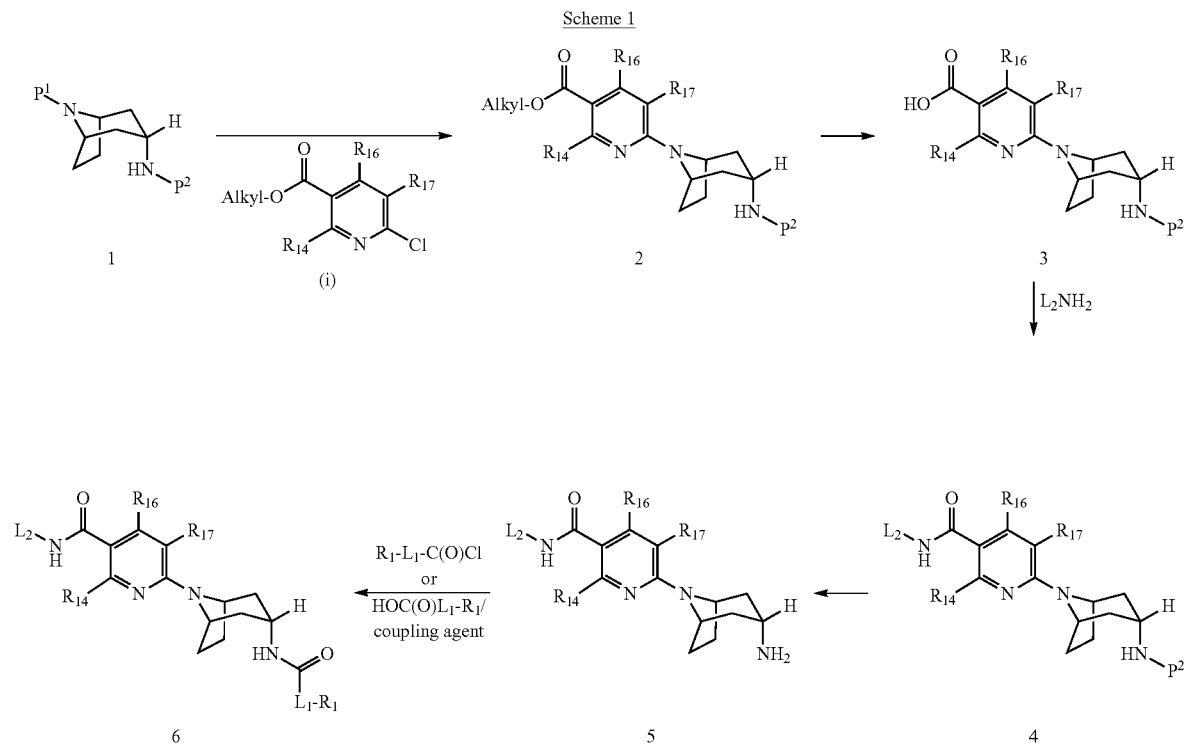

Various compounds of Formula (I), as depicted by formula (6), can be prepared according to Scheme 1, wherein $L_1$, $L_2$, $R_1$, $R_{14}$, $R_{16}$ and $R_{17}$ are as defined within the specification above, and $P^1$ and $P^2$ are as defined below.

Various compounds of Formula (I), as depicted by formula (6), can be prepared starting from a suitably protected 3-endo-aminotropane (1). For example, in the case where $P^1$ is H and $P^2$ is BOC or another suitable amine protecting group, amine 1 can be converted to the corresponding 6-(tropan-8-yl)nicotinate ester (2) upon reaction with a 6-chloronicotinate ester of formula (I) (such as commercially available 6-chloronicotinate ester) by heating in an appropriate aprotic solvent in the presence of a base such as triethylamine. Hydrolysis of ester 2 to afford the nicotinic acid intermediate (3) can be carried out under typical saponification conditions. The formation of carboxamide (4) to introduce group $L_2$ is straightforward and can be achieved using standard peptide coupling methodologies involving acid 3 and, for example, an amine such as $L_2NH_2$. Acylation of $ClC(O)L_1$-$R_1$, or coupling with $HOC(O)L_1$-$R_1$, and a coupling agent, such as EDC, can then be carried out by removal of the protecting group $P^2$ to yield the corresponding amine (5) and subsequent acylation of $ClC(O)L_1$-$R_1$, or coupling with $HOC(O)L_1$-$R_1$, under standard conditions to afford the final product 6.

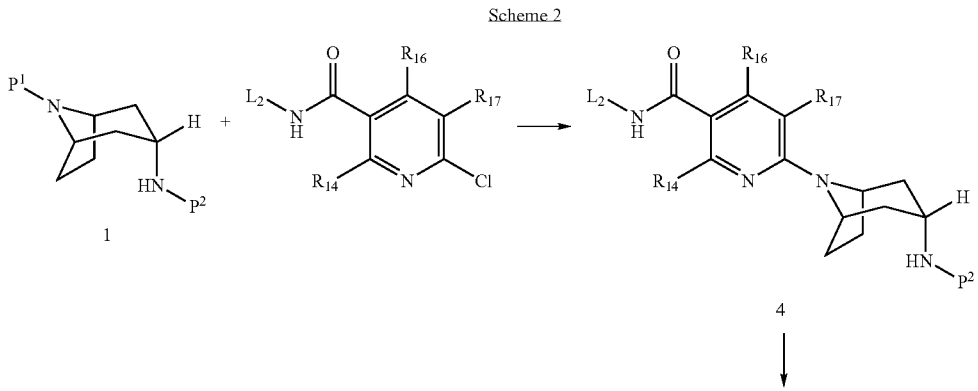

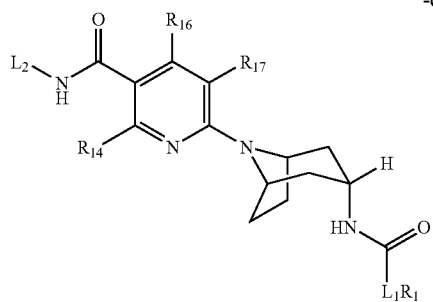

6

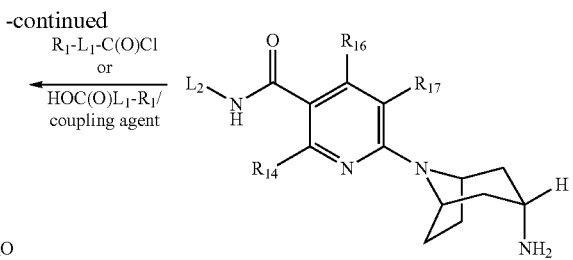

-continued

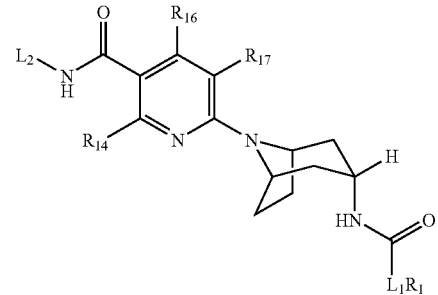

5

Alternatively, various compounds of Formula (I), as depicted by formula (6), can be prepared according to Scheme 2, wherein $L_1, L_2, R_1, R_{14}, R_{16}$ and $R_{17}$ are as defined within the specification above, and $P^1$ and $P^2$ are as defined below.

Various compounds of Formula (I), as depicted by formula (6) in Scheme 2, can be prepared starting from the reaction of amine 1, for example, where $P^1$ is H and $P^2$ is BOC, and a suitable 6-chloronicotinamide by heating in an appropriate solvent and in the presence of a base. The resulting carboxamide 4 then can be converted to products 6 as described previously in Scheme 1.

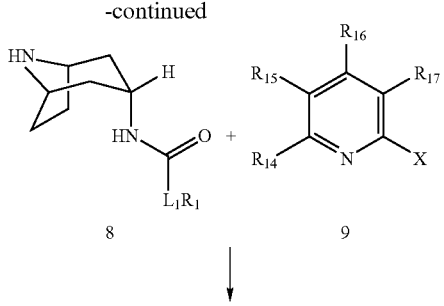

8    9

Scheme 3

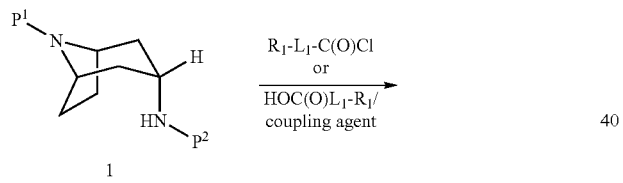

1

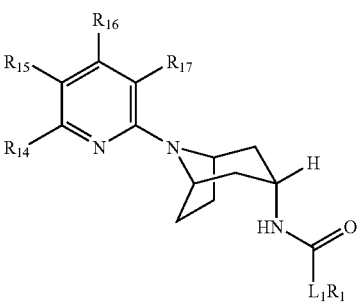

10

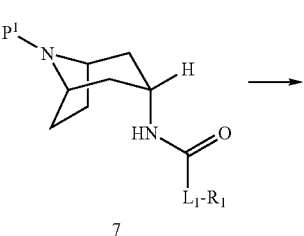

7

Various compounds of Formula (I), as depicted by formula (10), can be prepared according to Scheme 3, wherein $L_1$, $R_1$, $R_{14}$, $R_{15}$, $R_{16}$ and $R_{17}$ are as defined within the specification above, X is halo, and $P^1$ and $P^2$ are as defined below.

Various compounds of Formula (I), as depicted by formula (10), can be prepared according to Scheme 3 starting from a suitably protected 3-endo-aminotropane 1. For example, in the case where $P^1$ is Troc or another suitable amine protecting group and $P^2$ is H, amine 1 can then undergo acylation with an acid halide (ClC(O)$L_1$-$R_1$), or coupling with HOC(O)$L_1$-$R_1$, and a coupling agent, such as EDC, under standard conditions to afford the compound of formula (7). The resulting carboxamide (7) can be deprotected to give an intermediate amine (8) which can react with an appropriately substituted 2-halopyridine (9) to afford the final product 10.

Scheme 4

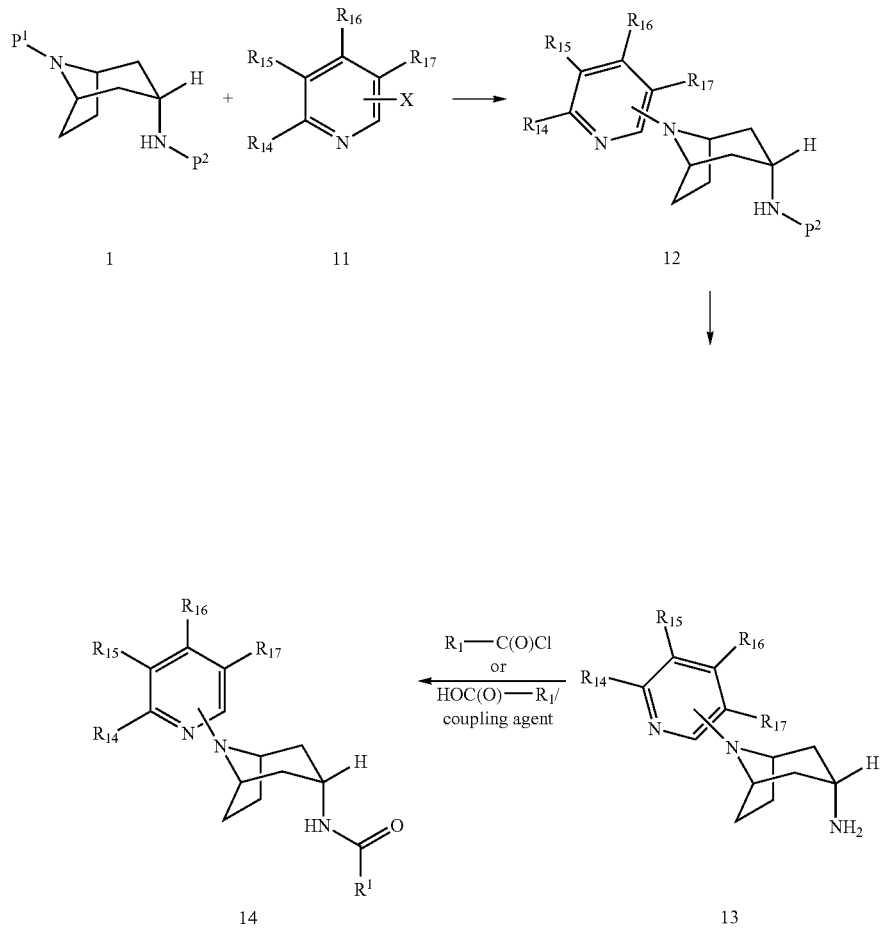

Various compounds of formula (I), as depicted by formula (14), can be prepared according to Scheme 4, wherein $L_1$, $R_1$, $R_{14}$, $R_{15}$, $R_{16}$ and $R_{17}$ are as defined within the specification above, X is halo, and $P^1$ and $P^2$ are as defined below.

Compounds of the invention (14) can be prepared starting from a suitably protected 3-endo-aminotropane (1). For example, in the case where $P^1$ is H and $P^2$ is BOC, amine 1 can be converted to the corresponding aminopyridine (12) upon reaction with a halopyridine (11), such as an optionally substituted 3-bromopyridine, under standard Buchwald amination conditions. Intermediate 12 then can be deprotected to yield an amine (13) which can undergo acylation with ClC(O)$L_1$-$R_1$, or coupling with HOC(O)$L_1$-$R_1$, and a coupling agent, such as EDC, under standard conditions to afford the final product 14.

Scheme 5

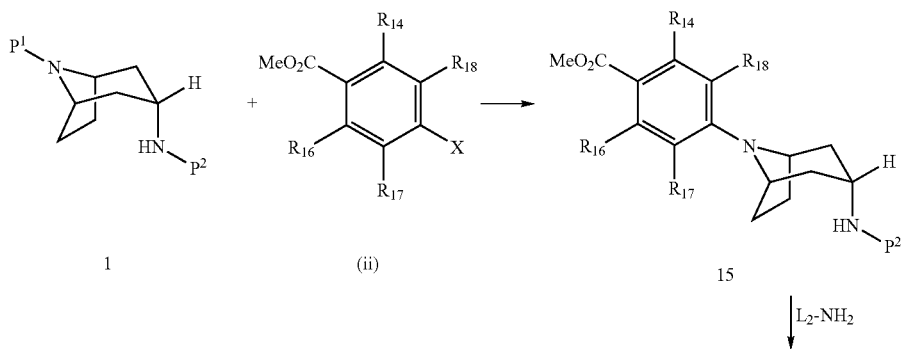

323    324

-continued

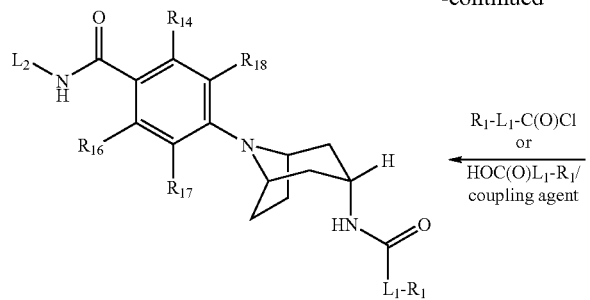 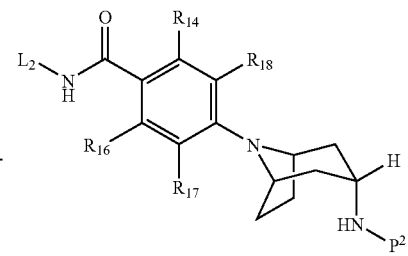

17    16

Various compounds of formula (I), as depicted by formula (17), can be prepared according to Scheme 5, wherein $L_1$, $L_2$, $R_1$, $R_{14}$, $R_{15}$, $R_{16}$ and $R_{17}$ are as defined within the specification above, X is halo, and $P^1$ and $P^2$ are as defined below.

protecting group $P^2$ and acylation of the resulting amine with ClC(O)$L_1$-$R_1$, or coupling with HOC(O)$L_1$-$R_1$, and a coupling agent, such as EDC, under standard conditions to afford the final product 17.

Scheme 6

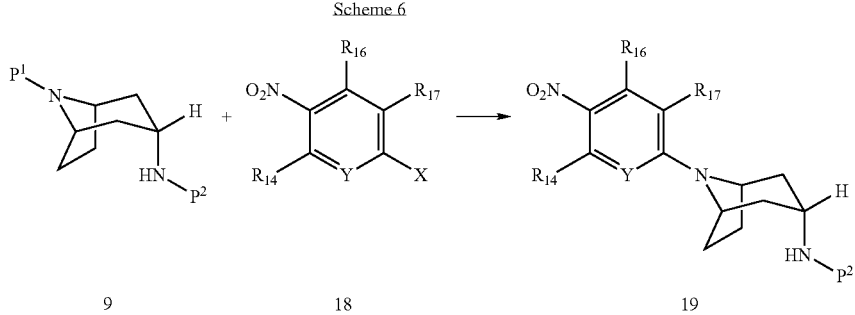

9    18    19

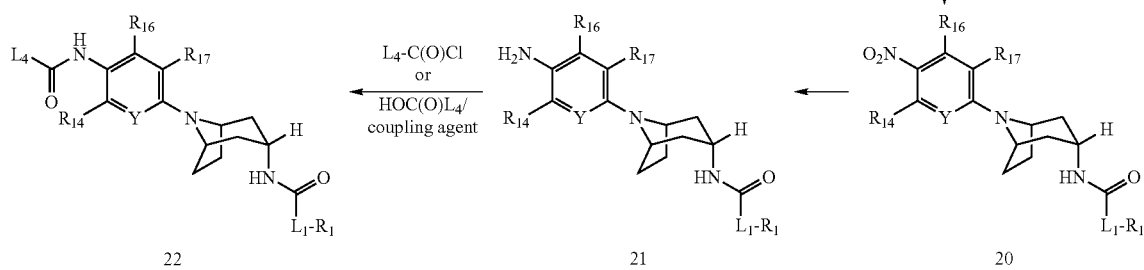

22    21    20

Various compounds of formula (I), as depicted by formula (17), can be prepared starting from a suitably protected 3-endo-aminotropane (1). For example, in the case where $P^1$ is H and $P^2$ is BOC, amine 1 can be converted to the corresponding aminobenzoate ester (15) upon reaction with a 4-halobenzoate ester, such as an optionally substituted 4-bromobenzoate ester, under standard Buchwald amination conditions. Hydrolysis of ester 15 can be carried out under typical saponification conditions. The formation of carboxamide (16) can be achieved using standard peptide coupling methodologies involving the resulting acid and an amine, such as $L_2$-$NH_2$. Introduction of an appropriate $R_1$ functional group can then be carried out over two steps by removal of the Various compounds of Formula (I), as depicted by formula (22), can be prepared according to Scheme 6, wherein $L_1$, $L_4$, $R_1$, $R_{16}$ and $R_{17}$ are as defined within the specification above, X is halo, Y is N or CH, and $P^1$ and $P^2$ are as defined below.

Various compounds of Formula (I), as depicted by formula (22), can be prepared starting from a suitably protected 3-endo-aminotropane (9). For example, in the case where $P^1$ is H and $P^2$ is BOC, amine 9 can be converted to the corresponding 2-amino-5-nitropyridine, Y=N (19) upon reaction with an optionally substituted 2-chloro-5-nitropyridine (18, X=Cl) by heating in a suitable aprotic solvent and in the presence of a base, such as potassium carbonate. Alternatively, amine 9 can be converted to the corresponding 2-amino-5-nitrobenzene, Y=CH (19) upon reaction with an optionally substituted 2-chloro-5-nitrobenzene (18, X═Cl) by heating in a suitable aprotic solvent and in the presence of a base, such as potassium carbonate. Introduction of an appropriate $R_1$ functional group can then be carried out over two steps by removal of the protecting group $P^2$ and acylation of the resulting amine with $ClC(O)L_1$-$R_1$ or coupling with $HOC(O)L_1$-$R_1$ and a coupling agent, such as EDC, under standard conditions to afford the carboxamide (20). Reduction of the nitro moiety of intermediate 20 can be achieved under literature conditions, such as with iron powder and saturated ammonium chloride in methanol at reflux. The resulting amine (21) then can undergo acylation with $L_4C(O)Cl$ or coupling with $HOC(O)L_4$ and a coupling agent, such as EDC, using standard methodologies to afford the final product 22.

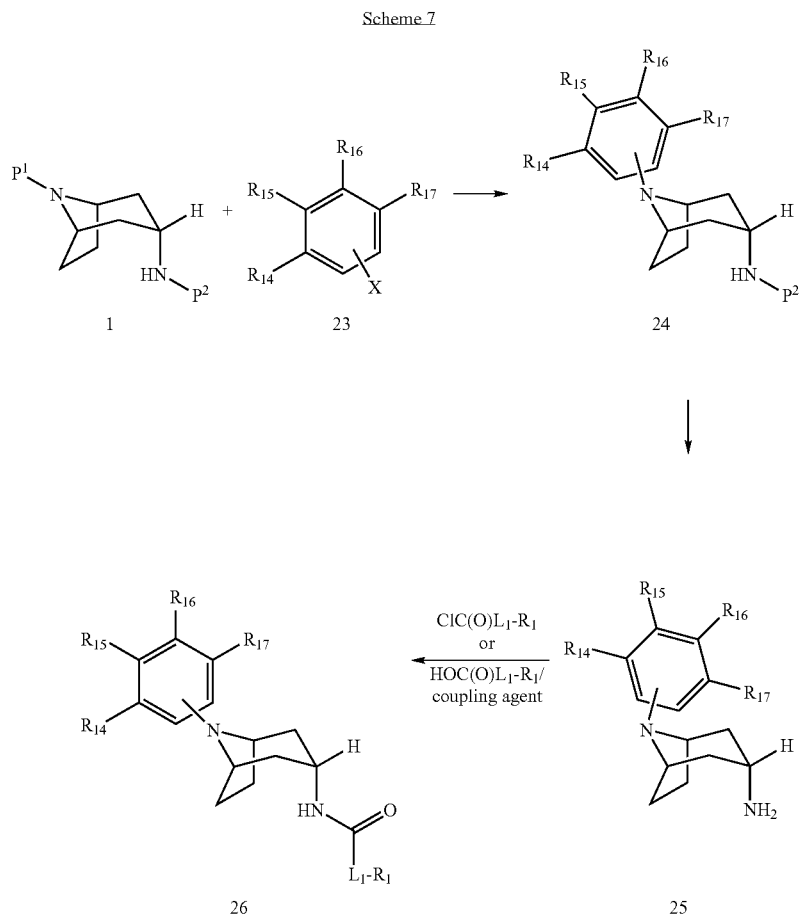

Scheme 7

Various compounds of Formula (I), as depicted by formula (26), can be prepared according to Scheme 7, wherein $L_1$, $R_1$, $R_{14}$, $R_{15}$, $R_{16}$ and $R_{17}$ are as defined within the specification above, X is halo, and $P^1$ and $P^2$ are as defined below.

Compounds of formula (26) can be prepared starting from a suitably protected 3-endo-aminotropane (1). For example, in the case where $P^1$ is H and $P^2$ is BOC, amine 1 can be converted to the corresponding aminobenzene (24) upon reaction with a halobenzene (23), such as an optionally substituted 3-bromobenzene, under standard Buchwald amination conditions. Intermediate 24 then can be deprotected to yield an amine (25) which can undergo acylation with $ClC(O)L_1$-$R_1$, or coupling with $HOC(O)L_1$-$R_1$ and a coupling agent, such as EDC, under standard conditions to afford the final product 26.

Scheme 8

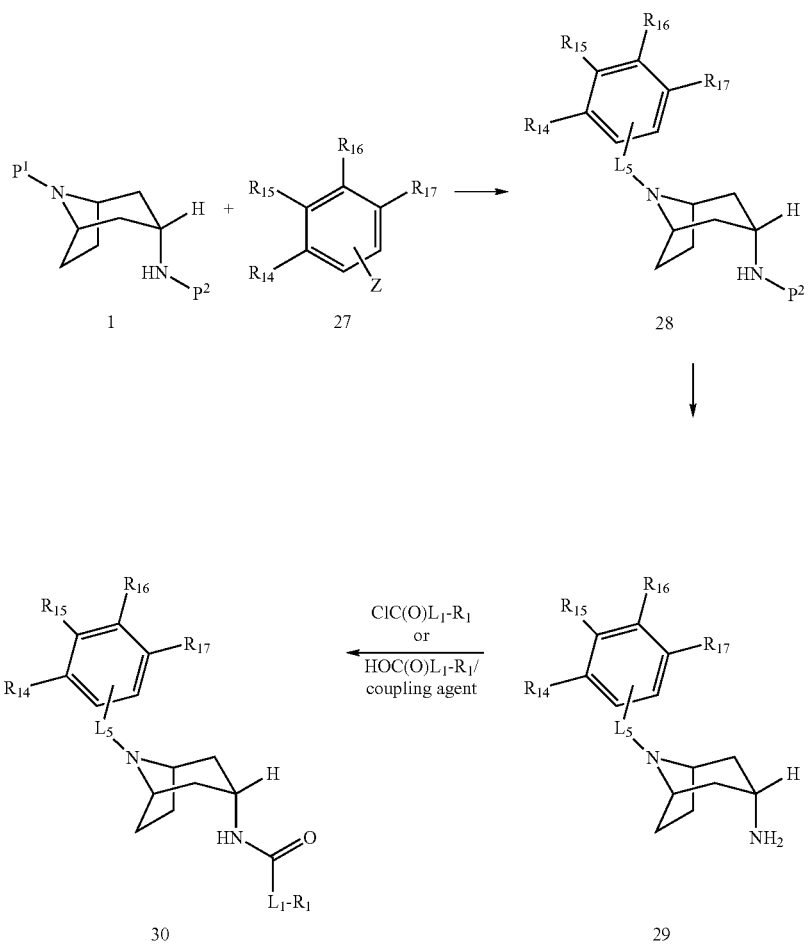

Various compounds of Formula (I), as depicted by formula (30), can be prepared according to Scheme 7, wherein $L_1$, $L_5$, $R_1$, $R_{14}$, $R_{15}$, $R_{16}$ and $R_{17}$ are as defined within the specification above, Z is CHO or $CO_2H$, and $P^1$ and $P^2$ are as defined below.

Compounds of formula (30) can be prepared starting from a suitably protected 3-endo-aminotropane (1). For example, in the case where $P^1$ is H and $P^2$ is BOC, amine 1 can be converted to the corresponding benzylamine, $L_5$=methylene (28) upon reaction with a benzaldehyde, Z=CHO (27), such as an optionally substituted 3-benzaldehyde, under standard reductive amination conditions. Alternatively, amine 1 can be converted to the corresponding benzamide, $L_5$=carbonyl (28) upon reaction with a benzoic acid, Z=C(O)OH (27) under standard coupling conditions. Intermediate 28 then can be deprotected to yield an amine (29) which can undergo acylation with $ClC(O)L_1$-$R_1$, or coupling with $HOC(O)L_1$-$R_1$, and a coupling agent, such as EDC, under standard conditions to afford the final product 30.

Experimental Section

EXAMPLE 1(A)

Methyl 6-[3-endo-({[1-(4-chlorophenyl)cyclopropyl]carbonyl}amino)-8-azabicyclo[3.2.1]oct-8-yl]pyridine-3-carboxylate,

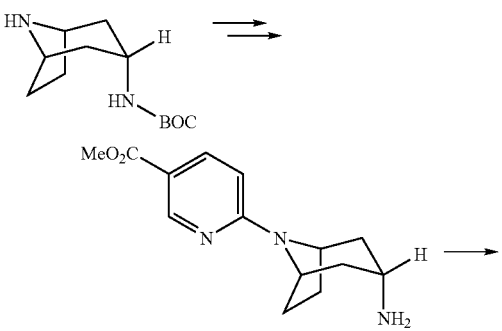

-continued

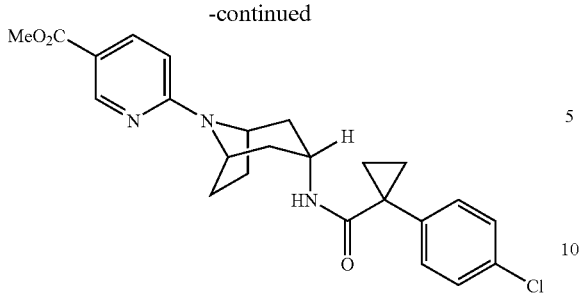

A mixture of tert-butyl 8-azabicyclo[3.2.1]octan-3-endo-ylcarbamate (0.79 g, 3.5 mmol), prepared as shown in EXAMPLE 1(B) below, commercially available methyl 6-chloronicotinate (0.60 g, 3.5 mmol), triethylamine (1.5 mL, 11 mmol) and DME (3.5 mL) was heated at 125° C. in a sealed pressure tube. After 18 h, the reaction mixture was allowed to cool to room temperature and diluted with DCM (30 mL). The resulting mixture was washed in succession with satd $K_2CO_3$, water and brine, and then dried (anhyd $Na_2SO_4$) and filtered. The filtrate was concentrated under reduced pressure to give a residue, that was purified by flash chromatography (silica gel, EtOAc/Hex, 20:80 to 60:40) to afford methyl 6-(3-endo-(tert-butoxycarbonylamino)-8-azabicyclo[3.2.1]octan-8-yl)nicotinate (0.56 g mg, 44%) as a white solid. $^1$H NMR (400 MHz, CDCl$_3$): δ 8.77 (d, J=2.3 Hz, 1H), 7.98 (dd, J=9.4, 2.3 Hz, 1H), 7.44-7.38 (m, 4H), 6.42 (d, J=8.8 Hz, 1H), 5.83 (d, 7.6 Hz, 1H), 4.48 (br s, 2H), 4.03-3.96 (m, 1H), 3.85 (s, 3H), 2.18-2.10 (m, 2H), 2.01-1.95 (m, 2H), 1.62-1.60 (m, 2H), 1.57-1.50 (m, 2H), 1.38-1.30 (m, 2H), 1.06-1.02 (m, 2H). MS (EI): 440 (MH$^+$).

A suspension of methyl 6-(3-endo-(tert-butoxycarbonylamino)-8-azabicyclo[3.2.1]octan-8-yl)nicotinate (0.56 g, 1.6 mmol) in DCM (3 mL) was charged with trifluoroacetic acid (3 mL) and stirred 1 h at ambient temperature. The reaction mixture was cautiously neutralized with satd NaHCO$_3$ and extracted with DCM (3×20 mL). The combined extracts were washed with brine, dried (anhyd Na$_2$SO$_4$) and concentrated under reduced pressure to yield methyl 6-(3-endo-amino-8-azabicyclo[3.2.1]octan-8-yl)nicotinate (0.40 g, 96%) as a white solid. GC-MS (EI, 70 eV) m/z 261 (M$^+$).

A suspension of commercially available 1-(4-chlorophenyl)cyclopropanecarboxylic acid (0.41 g, 2.1 mmol) in DCM (3 mL) was charged with oxalyl chloride (0.35 mL, 4.0 mmol) and N,N-dimethylformamide (5 μL) and stirred 2 h at ambient temperature. The reaction mixture was concentrated under reduced pressure. The resulting acid chloride was diluted with 1,2-dichloroethane (4 mL) and then added to a solution of methyl 6-(3-endo-amino-8-azabicyclo[3.2.1]octan-8-yl)nicotinate (0.18 g, 0.70 mmol), DIEA (0.24 mL, 1.4 mmol) and DMAP (10 mg) in 1,2-dichloroethane (2 mL). After stirring 2 h, the reaction mixture was diluted with EtOAc, washed with satd NaHCO$_3$ and brine, dried (anhyd Na$_2$SO$_4$) and concentrated under reduced pressure. The residue was purified by chromatography (silica, EtOAc/Hex, 20:80 to 75:25) to afford the title compound (0.31 g, quant) as a white solid. $^1$H NMR (400 MHz, DCM-d$_2$): δ 8.63 (s, 1H); MS (EI): 440 (MH$^+$).

EXAMPLE 1(B)

tert-butyl 8-azabicyclo[3.2.1]octan-3-endo-ylcarbamate

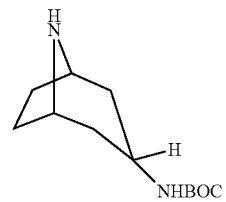

STEP 1: To a 5 L round-bottom flask was added 8-methyl-8-azabicyclo[3.2.1]octan-3-endo-amine (432 g, 3.1 mol), 2 L of dry 1,4-dioxane, 675 mL of deionized water and 468 g of dry triethylamine. Di-tert-butyl dicarbonate (solution in 1.2 L of dioxane) was added dropwise to the stirring solution at room temperature over 16 h. The reaction mixture was concentrated and the resulting residue suspended in 2.5 L of methylene chloride. then washed twice with 1 L of water, dried with anhydrous magnesium sulfate, filtered, and volatile organics removed by rotary evaporation to yield 617 g (83%) of tert-butyl 8-methyl-8-azabicyclo[3.2.1]octan-3-yl-carbamate (mp 79-81° C.).

STEP 2: To a 5 L round-bottom flask was added 480 g (2.0 mol) of tert-butyl 8-methyl-8-azabicyclo[3.2.1]octan-3-endo-ylcarbamate, 2 L of toluene, and 69 g (0.5 mol) of potassium carbonate. 2,2,2-Trichloroethyl chloroformate (347 mL, 2.4 mol) was added dropwise at room temperature over 6 h and the reaction heated at reflux temperature for 8 h. After the solution was cooled to room temperature, 1.2 L of water was added to the reaction solution and stirred 0.5 h. The organic layer was separated and washed with 1 L of brine, dried with anhydrous magnesium sulfate, filtered, and concentrated to yield a cloudy oil. The oil was triturated with 700 mL of a 3:2 ethyl ether/hexanes solution to yield 280 g (mp 131-135° C.) of 2,2,2-trichloroethyl 3-endo-(tert-butoxycarbonylamino)-8-azabicyclo[3.2.1]octane-8-carboxylate as a solid that was collected by filtration. The mother liquour was concentrated and titruated further to yield a less pure sample of the Troc protected diamine (129 g, mp 116-118° C.).

STEP 3: To a 5 L round-bottom flask was added 360 g (0.9 mol) of 2,2,2-trichloroethyl 3-endo-(tert-butoxycarbonylamino)-8-azabicyclo[3.2.1]octane-8-carboxylate, 2.8 L of methanol and 675 g (12.6 mol) of ammonium chloride. The solution was heated to reflux and 387 g (7.5 mol) of zinc dust was carefully added in small portions over 0.5 h. Upon complete addition of the zinc dust, the reaction was heated at reflux temperature for 2 h then cooled to room temperature. The reaction filtered through a thin pad a Celite 545, and the methanol removed by rotary evaporation. The resulting solid was dissolved in 800 mL of methylene chloride and stirred with 600 mL of concentrated ammonium hydroxide for 0.5 h. The organic layer was separated, washed with 600 mL of water, dried with anhydrous magnesium sulfate, filtered, and concentrated to yield an oil. The residue was dissolved in 200 mL of methylene chloride and 1 L of ethyl ether then filtered. The resulting solution was chilled to 0° C. and 215 mL of 4N hydrogen chloride in dioxane were added slowly, dropwise over 0.5 h, being sure to maintain the reaction solution temperature close to 0° C. After the addition was complete, 200 mL of methylene chloride and 1.4 L of ethyl ether were added to the cooled solution and a pale white precipitate formed. The resulting solid was collected by filtration to yield 173 g (85%) of tert-butyl 8-azabicyclo[3.2.1]octan-3-endo-ylcarbamate hydrochloride salt.

EXAMPLE 2

6-[3-endo-({[1-(4-chlorophenyl)cyclopropyl]carbonyl}amino)-8-azabicyclo[3.2.1]oct-8-yl]pyridine-3-carboxylic acid

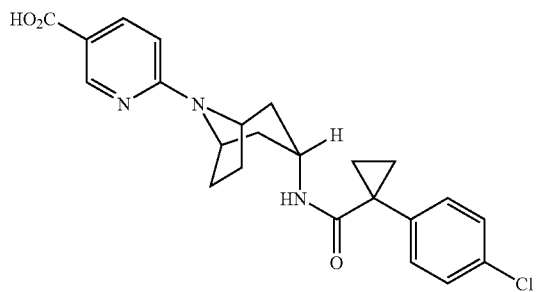

A suspension of methyl 6-(3-endo-(1-(4-chlorophenyl)-cyclopropanecarboxamido)-8-azabicyclo[3.2.1]octan-8-yl) nicotinate (0.30 g, 0.69 mmol) from Example 1 in methanol (5 mL) was charged with 3N NaOH (1.0 mL, 3.0 mmol) and then heated 2 h at 50° C. After cooling to ambient temperature, the reaction mixture was neutralized to pH 5 using 1N HCl and then extracted with DCM (3×25 mL). The combined extracts were dried (anhyd $Na_2SO_4$) and concentrated under reduced pressure to afford the title compound (0.29 g, quant) as a white solid. $^1$H NMR (400 MHz, $CDCl_3$): δ 8.83 (d, J=2.4 Hz, 1H), 8.01 (dd, J=9.1, 2.4 Hz, 1H), 7.44-7.38 (m, 4H), 6.43 (d, J=9.1 Hz, 1H), 5.83 (d, J=7.9 Hz, 1H), 4.51 (br s, 2H), 4.04-3.98 (m, 1H), 2.19-2.10 (m, 2H), 2.02-1.96 (m, 2H), 1.63-1.52 (m, 4H), 1.39-1.31 (2H), 1.07-1.02 (2H); MS (EI): 426 (MH$^+$).

EXAMPLE 3

6-[3-endo-({[1-(4-chlorophenyl)cyclopropyl]carbonyl}amino)-8-azabicyclo[3.2.1]oct-8-yl]-N-cyclopropylpyridine-3-carboxamide

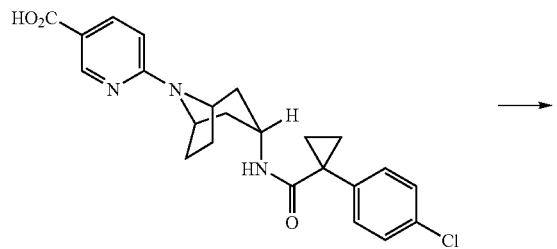

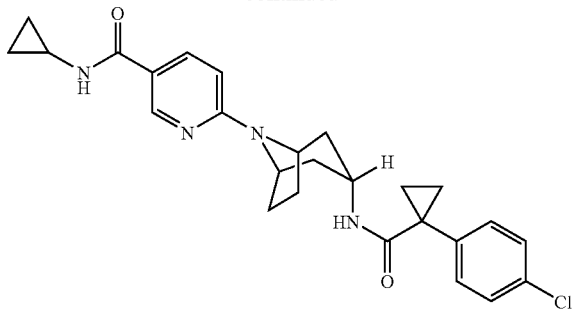

To a suspension of 6-[3-endo-({[1-(4-chlorophenyl)cyclopropyl]carbonyl}amino)-8-azabicyclo[3.2.1]oct-8-yl]pyridine-3-carboxylic acid (0.29 g, 0.68 mmol) from Example 2 in DCM (6 mL) was added 1,1'-carbonyldiimidazole (0.12 g. 0.75 mmol) with stirring. After 20 minutes, the reaction mixture was charged with DMAP (10 mg) and cyclopropylamine (46 μL, 0.80 mmol). After stirring 12 h, the reaction mixture was concentrated under reduced pressure. The residue was purified by chromatography (silica, EtOAc/Hex, 50:50 to 100:0) to give the title compound (99 mg, 31%) as a white solid. $^1$H NMR (400 MHz, $CDCl_2$): δ 8.47 (d, J=2.4 Hz, 1H), 7.84 (dd, J=8.7, 2.4 Hz, 1H), 7.43-7.37 (m, 4H), 6.43 (d, J=9.2 Hz, 1H), 6.04 (br s, 1H), 5.83 (d, J=6.8 Hz, 1H), 4.43 (br s, 2H), 4.00-3.94 (m, 1H), 2.89-2.82 (m, 1H), 2.16-2.08 (m, 2H), 2.01-1.95 (m, 2H), 1.62-1.58 (m, 4H), 1.54-1.47 (2H), 1.36-1.29 (2H), 1.06-1.02 (m, 2H), 0.87-0.82 (m, 2H), 0.61-0.56 (m, 2H). MS (EI): 465 (MH$^+$).

Using the same or analogous synthetic techniques described in any of the Examples and/or substituting with alternative commercial or literature reagents, the following compounds of the invention were prepared:

6-[3-endo-({[1-(4-chlorophenyl)cyclobutyl]carbonyl}amino)-8-azabicyclo[3.2.1]oct-8-yl]-N-cyclopropylpyridine-3-carboxamide, MS (EI): 479 (MH$^+$).

6-[3-endo-({[1-(4-chlorophenyl)cyclopentyl]carbonyl}amino)-8-azabicyclo[3.2.1]oct-8-yl]-N-cyclopropylpyridine-3-carboxamide, MS (EI): 493 (MH$^+$).

N-cyclopropyl-6-[3-endo-({[1-(2,4-dichlorophenyl)cyclopropyl]carbonyl}amino)-8-azabicyclo[3.2.1]oct-8-yl]pyridine-3-carboxamide, MS (EI): 499 (MH$^+$).

N-cyclopropyl-6-(3-endo-{[(1-phenylcyclopropyl)carbonyl]amino}-8-azabicyclo[3.2.1]oct-8-yl)pyridine-3-carboxamide, MS (EI): 431 (MH$^+$).

N-cyclopropyl-6-[3-endo-({[1-(3,4-dichlorophenyl)cyclopropyl]carbonyl}amino)-8-azabicyclo[3.2.1]oct-8-yl]pyridine-3-carboxamide, MS (EI): 499 (MH$^+$).

N-cyclopropyl-6-[3-endo-({[1-(4-fluorophenyl)cyclopropyl]carbonyl}amino)-8-azabicyclo[3.2.1]oct-8-yl]pyridine-3-carboxamide, MS (EI): 449 (MH$^+$).

6-[3-endo-({[1-(3-chlorophenyl)cyclopropyl]carbonyl}amino)-8-azabicyclo[3.2.1]oct-8-yl]-N-cyclopropylpyridine-3-carboxamide, MS (EI): 465 (MH$^+$).

6-[3-endo-({[1-(2-chlorophenyl)cyclopropyl]carbonyl}amino)-8-azabicyclo[3.2.1]oct-8-yl]-N-cyclopropylpyridine-3-carboxamide, MS (EI): 465 (MH$^+$).

6-(3-endo-{[2-(4-chlorophenyl)-2-methylpropanoyl]amino}-8-azabicyclo[3.2.1]oct-8-yl)-N-cyclopropylpyridine-3-carboxamide, MS (EI): 467 (MH$^+$).

N-cyclopropyl-6-{3-endo-[(2-methyl-2-phenylpropanoyl)amino]-8-azabicyclo[3.2.1]oct-8-yl}pyridine-3-carboxamide, MS (EI): 433 (MH$^+$). $^1$H NMR (400 MHz, $CDCl_3$): δ 8.46 (d, J=2.9 Hz, 1H), 7.84 (dd, J=8.3, 2.0 Hz, 1H), 7.45-7.41 (m, 4H), 7.34-7.30 (m, 1H), 6.43 (d, J=9.3 Hz, 1H), 6.03 (br s, 1H), 5.61 (d, J=8.3 Hz, 1H), 4.41 (br s, 2H), 3.99-3.93 (m, 1H), 2.89-2.82 (m, 1H), 2.16-2.08 (m, 2H), 1.93-1.87 (m, 2H), 1.50-1.43 (m, 2H), 1.28-1.21 (m, 2H), 0.87-0.81 (m, 2H), 0.61-0.56 (m, 2H). MS (EI): 433 (MH$^+$).

N-cyclopropyl-6-[3-endo-({[1-(4-methylphenyl)cyclopropyl]carbonyl}amino)-8-azabicyclo[3.2.1]oct-8-yl]pyridine-3-carboxamide, MS (EI): 445 (MH$^+$).

6-[3-endo-({2-[(2-chlorophenyl)oxy]-2-methylpropanoyl}amino)-8-azabicyclo[3.2.1]oct-8-yl]-N-cyclopropylpyridine-3-carboxamide, MS (EI): 483 (MH$^+$).

6-(3-endo-{[2-(3-chlorophenyl)-2-methylpropanoyl]amino}-8-azabicyclo[3.2.1]oct-8-yl)-N-cyclopropylpyridine-3-carboxamide, MS (EI): 467 (MH$^+$).

6-(3-endo-{[2-(4-chlorophenyl)-2-methylpropanoyl]amino}-8-azabicyclo[3.2.1]oct-8-yl)-N-(2,2,2-trifluoroethyl)pyridine-3-carboxamide, MS (EI): 509 (MH$^+$).

EXAMPLE 4

6-[3-endo-({2-[(4-chlorophenyl)oxy]-2-methylpropanoyl}amino)-8-azabicyclo[3.2.1]oct-8-yl]-N-cyclopropylpyridine-3-carboxamide

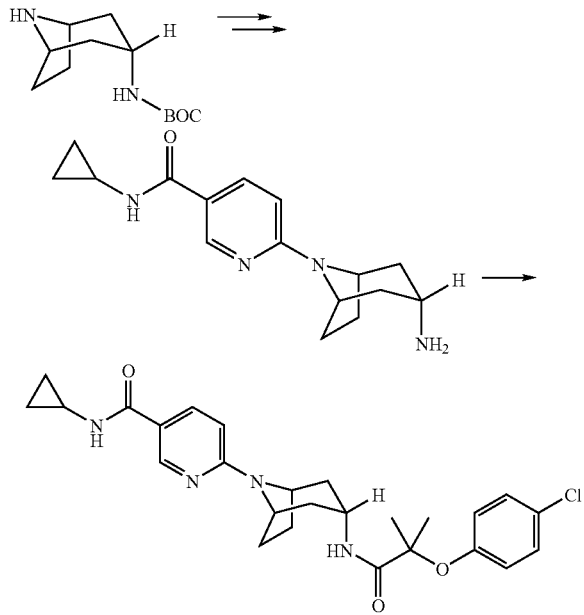

A mixture of tert-butyl 8-azabicyclo[3.2.1]octan-3-endo-ylcarbamate hydrochloride (5.3 g, 20 mmol) made according to EXAMPLE 1 (A), 6-chloro-N-cyclopropylnicotinamide (3.9 g, 20 mmol) (prepared from combining methyl 6-chloronicotinate and cyclopropylamine, both of which are commercially available) K$_2$CO$_3$ (11 g, 80 mmol) and MeCN (40 mL) was heated 16 h at 125° C. in a sealed pressure flask. The reaction mixture was allowed to cool to room temperature, diluted with EtOAc (50 mL) and filtered. The filtrate was concentrated under reduced pressure to give a residue, that was purified by flash chromatography (silica gel, EtOAc/Hex, 50:50 to 100:0) to afford tert-butyl 8-(5-(cyclopropylcarbamoyl)pyridin-2-yl)-8-azabicyclo[3.2.1]octan-3-endo-ylcarbamate (1.7 g, 22%) as a white solid. $^1$H NMR (400 MHz, DCM-d$_2$): δ 8.48 (d, J=2.8 Hz, 1H), 7.81 (dd, J=8.8, 2.8 Hz, 1H), 7.30-7.25 (m, 4H), 7.21 (d, J=8.3 Hz, 1H), 6.93-6.88 (m, 2H), 6.51 (d, J=8.8 Hz, 1H), 6.13 (br s, 1H), 4.54 (br s, 2H) 4.05-3.98 (m, 1H), 2.89-2.79 (m, 1H), 2.28-2.19 (m, 2H), 2.14-2.08 (m, 2H), 1.89-1.82 (m, 2H), 1.68-1.59 (m, 2H), 1.48 (s, 6H), 0.83-0.77 (2H), 0.59-0.54 (2H).

To a solution of tert-butyl 8-(5-(cyclopropylcarbamoyl)pyridin-2-yl)-8-azabicyclo[3.2.1]-octan-3-endo-ylcarbamate (1.7 g, 4.3 mmol) in DCM (30 mL, anhyd) was added slowly a 2N solution of HCl in diethyl ether (22 mL, 44 mmol) with stirring. After 2 h at ambient temperature, the reaction mixture was concentrated. The resulting solids were triturated with diethyl ether and dried under high vacuum to afford 6-(3-endo-amino-8-azabicyclo[3.2.1]octan-8-yl)-N-cyclopropylnicotinamide dihydrochloride (1.5 g, quant). $^1$H NMR (400 MHz, MeOH-d$_4$): δ 8.63 (s, 1H).

To a solution of 6-(3-endo-amino-8-azabicyclo[3.2.1]octan-8-yl)-N-cyclopropyl-nicotinamide dihydrochloride (0.12 g, 0.32 mmol), DIEA (0.33 mL, 1.9 mmol) and DMAP (10 mg) in DCM (4 mL) was added commercially available 2-(4-chlorophenoxy)-2-methylpropanoyl chloride (0.13 g, 0.56 mmol) with stirring. After 2 h, the reaction mixture was diluted with DCM, washed with satd NaHCO$_3$ and concentrated under reduced pressure. The resulting residue was purified by chromatography (silica, EtOAc/Hex, 80:20 to 100:0) to yield the title compound (37 mg, 24%) as a white solid. $^1$H NMR (400 MHz, DCM-d$_2$): δ 8.63 (s, 1H); MS (EI): 483 (MH$^+$).

Using the same or analogous synthetic techniques described in any of the Examples and/or substituting with alternative commercial or literature reagents, the following compounds of the invention were prepared:

6-[3-endo-({2-[(3-chlorophenyl)oxy]-2-methylpropanoyl}amino)-8-azabicyclo[3.2.1]oct-8-yl]-N-cyclopropylpyridine-3-carboxamide, MS (EI): 483 (MH$^+$).

N-cyclopropyl-6-(3-endo-{[2-methyl-2-(phenyloxy)propanoyl]amino}-8-azabicyclo[3.2.1]oct-8-yl)pyridine-3-carboxamide, MS (EI): 449 (MH$^+$).

N-cyclopropyl-6-[3-endo-({[1-(3,4-difluorophenyl)cyclopropyl]carbonyl}amino)-8-azabicyclo[3.2.1]oct-8-yl]pyridine-3-carboxamide, MS (EI): 467 (MH$^+$).

N-cyclopropyl-6-[3-endo-({2-[(3,4-difluorophenyl)oxy]-2-methylpropanoyl}amino)-8-azabicyclo[3.2.1]oct-8-yl]pyridine-3-carboxamide, MS (EI): 485 (MH$^+$).

6-(3-endo-{[2-(2-chlorophenyl)-2-methylpropanoyl]amino}-8-azabicyclo[3.2.1]oct-8-yl)-N-cyclopropylpyridine-3-carboxamide, MS (EI): 467 (MH$^+$).

6-[3-endo-({2-[(2-chloro-4-fluorophenyl)oxy]-2-methylpropanoyl}amino)-8-azabicyclo[3.2.1]oct-8-yl]-N-cyclopropylpyridine-3-carboxamide, MS (EI): 501 (MH$^+$).

N-cyclopropyl-6-[3-endo-({2-[(2,4-difluorophenyl)oxy]-2-methylpropanoyl}amino)-8-azabicyclo[3.2.1]oct-8-yl]pyridine-3-carboxamide, MS (EI): 485 (MH$^+$). $^1$H NMR (400 MHz, CD$_2$Cl$_2$): δ 8.41 (d, J=2.5 Hz, 1H), 7.79 (dd, J=8.9, 2.5 Hz, 1H), 7.56 (d, J=7.4 Hz, 1H), 7.06 (m, 1H), 6.91 (m, 1H), 6.82 (m, 1H), 6.45 (d, J=8.9 Hz, 1H), 6.13 (s, 1H), 4.55 (br s, 2H), 3.98 (m, 1H), 2.79 (m, 1H), 2.26-1.98 (m, 6H), 1.69 (d, J=14.9 Hz, 2H), 1.59 (s, 2H), 1.42 (s, 6H), 0.77 (m, 2H), 0.54 (m, 2H); MS (EI): 485 (MH$^+$)

N-cyclopropyl-6-{3-endo-[(2-methyl-2-{[4-(trifluoromethyl)phenyl]oxy}propanoyl)-amino]-8-azabicyclo[3.2.1]oct-8-yl}pyridine-3-carboxamide, MS (EI): 517 (MH$^+$).

6-[3-endo-({2-[(4-cyanophenyl)oxy]-2-methylpropanoyl}amino)-8-azabicyclo[3.2.1]oct-8-yl]-N-cyclopropylpyridine-3-carboxamide, MS (EI): 474 (MH+).

N-cyclopropyl-6-[3-endo-({[1-(3-fluorophenyl)cyclopropyl]carbonyl}amino)-8-azabicyclo[3.2.1]oct-8-yl]pyridine-3-carboxamide, MS (EI): 449 (MH+).

6-[3-endo-({2-[(4-chloro-2-fluorophenyl)oxy]-2-methylpropanoyl}amino)-8-azabicyclo[3.2.1]oct-8-yl]-N-cyclopropylpyridine-3-carboxamide, MS (EI): 501 (MH+).

N-cyclopropyl-6-[3-endo-({2-[(3,4-dichlorophenyl)oxy]-2-methylpropanoyl}amino)-8-azabicyclo[3.2.1]oct-8-yl]pyridine-3-carboxamide, MS (EI): 517 (MH+).

6-[3-endo-({2-[(4-chloro-3-fluorophenyl)oxy]-2-methylpropanoyl}amino)-8-azabicyclo[3.2.1]oct-8-yl]-N-cyclopropylpyridine-3-carboxamide, MS (EI): 501 (MH+).

N-cyclopropyl-6-{3-endo-[(2-methyl-2-{[4-(methyloxy)phenyl]oxy}propanoyl)amino]-8-azabicyclo[3.2.1]oct-8-yl}pyridine-3-carboxamide, MS (EI): 479 (MH+).

N-cyclopropyl-6-[3-endo-({[1-(phenyloxy)cyclopropyl]carbonyl}amino)-8-azabicyclo[3.2.1]oct-8-yl]pyridine-3-carboxamide, MS (EI): 447 (MH+).

N-cyclopropyl-6-[3-endo-({[1-(phenyloxy)cyclobutyl]carbonyl}amino)-8-azabicyclo[3.2.1]oct-8-yl]pyridine-3-carboxamide, MS (EI): 461 (MH+).

6-{3-endo-[({1-[(4-chlorophenyl)oxy]cyclobutyl}carbonyl)amino]-8-azabicyclo[3.2.1]oct-8-yl}-N-cyclopropylpyridine-3-carboxamide, MS (EI): 495 (MH+).

N-cyclopropyl-6-(3-endo-{[2-(phenyloxy)propanoyl]amino}-8-azabicyclo[3.2.1]oct-8-yl)pyridine-3-carboxamide, MS (EI): 435 (MH+).

6-[3-endo-({2-[(4-chlorophenyl)oxy]propanoyl}amino)-8-azabicyclo[3.2.1]oct-8-yl]-N-cyclopropylpyridine-3-carboxamide, MS (EI): 469 (MH+).

6-{3-endo-[({1-[(4-chlorophenyl)oxy]cyclopropyl}carbonyl)amino]-8-azabicyclo[3.2.1]oct-8-yl}-N-cyclopropylpyridine-3-carboxamide, MS (EI): 481 (MH+).

2-[(4-chlorophenyl)oxy]-2-methyl-N-(8-pyrazin-2-yl-8-azabicyclo[3.2.1]oct-3-endo-yl)propanamide, MS (EI): 401 (MH+).

N-cyclopropyl-6-[3-endo-({2-[(2,5-dichlorophenyl)oxy]-2-methylpropanoyl}amino)-8-azabicyclo[3.2.1]oct-8-yl]pyridine-3-carboxamide, MS (EI): 517 (MH+).

N-cyclopropyl-6-[3-endo-({2-[(2,4-dichlorophenyl)oxy]propanoyl}amino)-8-azabicyclo[3.2.1]oct-8-yl]pyridine-3-carboxamide, MS (EI): 503 (MH+).

5-chloro-N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide, MS (EI): 551 (MH+).

N-[8-(5-acetylpyridin-2-yl)-8-azabicyclo[3.2.1]oct-3-endo-yl]-2-[(2,4-dichlorophenyl)oxy]-2-methylpropanamide, MS (EI): 476 (MH+).

6-[3-endo-({2-[(4-chlorophenyl)oxy]-2-methylpropanoyl}amino)-8-azabicyclo[3.2.1]oct-8-yl]-N-[2-(methyloxy)ethyl]pyridine-3-carboxamide, MS (EI): 501 (MH+).

6-[3-endo-({2-[(2,4-dichloro-5-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 577 (MH+).

N-cyclopropyl-6-[3-endo-({2-[(2,4-dichloro-5-fluorophenyl)oxy]-2-methylpropanoyl}amino)-8-azabicyclo[3.2.1]oct-8-yl]pyridine-3-carboxamide, MS (EI): 535 (MH+).

6-[3-endo-({2-[(3-chloro-4-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 543 (MH+).

6-[3-endo-({2-[(3-chloro-4-fluorophenyl)oxy]-2-methylpropanoyl}amino)-8-azabicyclo[3.2.1]oct-8-yl]-N-(1-methylethyl)pyridine-3-carboxamide, MS (EI): 503 (MH+).

6-[3-endo-({2-[(2-chloro-4,5-difluorophenyl)oxy]-2-methylpropanoyl}amino)-8-azabicyclo[3.2.1]oct-8-yl]pyridine-3-carboxamide, MS (EI): 479 (MH+).

6-[3-endo-({2-[(2,3-dichloro-4-fluorophenyl)oxy]-2-methylpropanoyl}amino)-8-azabicyclo[3.2.1]oct-8-yl]pyridine-3-carboxamide, $^1$H NMR (400 MHz, DMSO-$d_6$): δ 8.62 (d, J=2.6 Hz, 1H), 7.95 (dd, J=8.6, 2.2 Hz, 1H), 7.73 (d, J=6.0 Hz, 1H), 7.94 (t, J=9.0 Hz, 1H), 7.16-7.10 (m, 2H), 6.74 (d, J=9.0 Hz, 1H), 4.55 (br s, 2H), 3.83-3.75 (m, 1H), 2.15-2.06 (m, 2H), 1.99-1.91 (m, 4H), 1.80-1.73 (m, 2H), 1.49 (s, 6H). MS (EI): 495 (MH+).

6-[3-endo-({2-[(2,5-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 577 (MH+).

6-[3-endo-({2-[(2,5-dichloro-4-fluorophenyl)oxy]-2-methylpropanoyl}amino)-8-azabicyclo[3.2.1]oct-8-yl]pyridine-3-carboxamide, MS (EI): 495 (MH+).

6-[3-endo-({2-[(2,3-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 577 (MH+).

6-[3-endo-({[1-(3-chlorophenyl)cyclopropyl]carbonyl}amino)-8-azabicyclo[3.2.1]oct-8-yl]pyridine-3-carboxamide, MS (EI): 425 (MH+).

6-[3-endo-({[1-(3,4-dichlorophenyl)cyclopropyl]carbonyl}amino)-8-azabicyclo[3.2.1]oct-8-yl]pyridine-3-carboxamide, MS (EI): 459 (MH+).

6-[3-endo-({[1-(3-fluorophenyl)cyclopropyl]carbonyl}amino)-8-azabicyclo[3.2.1]oct-8-yl]pyridine-3-carboxamide, MS (EI): 409 (MH+).

6-[3-endo-({2-[(4-chloro-2-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 543 (MH+).

2-[(2,4-dichlorophenyl)oxy]-2-methyl-N-(8-pyridin-3-yl-8-azabicyclo[3.2.1]oct-3-endo-yl)propanamide, MS (EI): 543 (MH+).

6-{3-endo-[2-(3,5-dichloro-pyridin-2-yloxy)-2-methyl-propionylamino]-8-azabicyclo[3.2.1]oct-8-yl}-N-(2,2,2-trifluoro-ethyl)-nicotinamide, MS (EI): 434 (MH+).

6-{3-endo-[2-(5-chloro-pyridin-2-yloxy)-2-methyl-propionylamino]-8-azabicyclo[3.2.1]oct-8-yl}-N-(2,2,2-trifluoro-ethyl)-nicotinamide, MS (EI): 526 (MH+).

6-{3-endo-[2-(5-fluoro-pyridin-2-yloxy)-2-methyl-propionylamino]-8-azabicyclo[3.2.1]oct-8-yl}-N-(2,2,2-trifluoro-ethyl)-nicotinamide, MS (EI): 510 (MH+).

Methyl 6-[3-endo-({2-[(2,4-dichlorophenyl)oxy]-2-methylpropanoyl}-amino)-8-azabicyclo[3.2.1]oct-8-yl]pyridine-3-carboxylate, MS (EI): 492 (MH+).

1-(4-Chloro-phenyl)-cyclopropanecarboxylic acid [8-(5-nitro-pyridin-2-yl)-8-azabicyclo[3.2.1]oct-3-endo-yl]-amide, MS (EI): 427 (MH+).

2-(2,4-Dichloro-phenoxy)-2-methyl-N-[8-(5-nitro-pyridin-2-yl)-8-azabicyclo[3.2.1]oct-3-endo-yl]-propionamide, MS (EI): 479 (MH+).

N-cyclopropyl-5-[3-endo-({2-[(2,4-dichlorophenyl)oxy]-2-methylpropanoyl}amino)-8-azabicyclo[3.2.1]oct-8-yl]pyridine-2-carboxamide, MS (EI): 517 (MH+).

5-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-2-carboxamide, MS (EI): 559 (MH⁺).

2-{[4-chloro-2-(trifluoromethyl)phenyl]oxy}-2-methyl-N-{8-[6-(1H-tetrazol-5-yl)pyridin-3-yl]-8-azabicyclo[3.2.1]oct-3-endo-yl}propanamide, MS (EI): 536 (MH⁺).

2-{[4-fluoro-2-(trifluoromethyl)phenyl]oxy}-2-methyl-N-{8-[6-(methylsulfonyl)pyridin-3-yl]-8-azabicyclo[3.2.1]oct-3-endo-yl}propanamide, MS (EI): 530 (MH⁺).

2-[(2,4-dichlorophenyl)oxy]-2-methyl-N-{8-[6-(methylsulfonyl)pyridin-3-yl]-8-azabicyclo[3.2.1]oct-3-endo-yl}propanamide, MS (EI): 512 (MH⁺).

2-{[4-chloro-2-(trifluoromethyl)phenyl]oxy}-2-methyl-N-{8-[6-(methylsulfonyl)pyridin-3-yl]-8-azabicyclo[3.2.1]oct-3-endo-yl}propanamide, MS (EI): 546 (MH⁺).

2-[(2-chloro-4-fluorophenyl)oxy]-2-methyl-N-{8-[6-(methylsulfonyl)pyridin-3-endo-yl]-8-azabicyclo[3.2.1]oct-3-yl}propanamide, MS (EI): 496 (MH⁺).

6-{3-endo-[(2-methyl-2-{[4-(trifluoromethyl)phenyl]oxy}propanoyl)amino]-8-azabicyclo[3.2.1]oct-8-yl]-N-(2,2,2-trifluoroethyl)pyridine-3-carboxamide, MS (EI): 559 (MH⁺).

6-{3-endo-[(2-methyl-2-{[2-(trifluoromethyl)phenyl]oxy}propanoyl)amino]-8-azabicyclo[3.2.1]oct-8-yl}-N-(2,2,2-trifluoroethyl)pyridine-3-carboxamide, MS (EI): 559 (MH⁺).

N-cyclopropyl-6-{3-endo-[(2-methyl-2-{[2-(trifluoromethyl)phenyl]oxy}propanoyl)amino]-8-azabicyclo[3.2.1]oct-8-yl}pyridine-3-carboxamide, MS (EI): 517 (MH⁺).

2-[(2,4-dichlorophenyl)oxy]-2-methyl-N-{8-[5-(1H-tetrazol-5-yl)pyridin-2-yl]-8-azabicyclo[3.2.1]oct-3-endo-yl}propanamide, MS (EI): 502 (MH⁺).

6-[3-endo-({2-[(3,5-dichloropyridin-2-yl)oxy]-2-methylpropanoyl}amino)-8-azabicyclo[3.2.1]oct-8-yl]-N-(2,2,2-trifluoroethyl)pyridine-3-carboxamide, MS (EI): 560 (MH⁺).

6-[3-endo-({[1-(3,4-difluorophenyl)cyclopropyl]carbonyl}amino)-8-azabicyclo[3.2.1]oct-8-yl]-N-(2,2,2-trifluoroethyl)pyridine-3-carboxamide, MS (EI): 509 (MH⁺).

6-[3-endo-({[1-(3-chlorophenyl)cyclopropyl]carbonyl}amino)-8-azabicyclo[3.2.1]oct-8-yl]-N-(2,2,2-trifluoroethyl)pyridine-3-carboxamide, MS (EI): 507 (MH⁺).

6-[3-endo-({[1-(3-fluorophenyl)cyclopropyl]carbonyl}amino)-8-azabicyclo[3.2.1]oct-8-yl]-N-(2,2,2-trifluoroethyl)pyridine-3-carboxamide, MS (EI): 491 (MH⁺).

6-[3-endo-({2-[(3,5-dichloropyridin-2-yl)oxy]-2-methylpropanoyl}amino)-8-azabicyclo[3.2.1]oct-8-yl]pyridine-3-carboxamide, MS (EI): 478 (MH⁺).

N-{8-[5-(aminosulfonyl)pyridin-2-yl]-8-azabicyclo[3.2.1]oct-3-endo-yl}-2-[(2,4-dichlorophenyl)oxy]-2-methylpropanamide, MS (EI): 513 (MH⁺).

6-[3-endo-({2-[(2,4-dichlorophenyl)oxy]-2-methylpropanoyl}amino)-8-azabicyclo[3.2.1]oct-8-yl]-N-(2,2,3,3,3-pentafluoropropyl)pyridine-3-carboxamide, MS (EI): 609 (MH⁺).

6-[3-endo-({2-[(5-chloro-3-fluoropyridin-2-yl)oxy]-2-methylpropanoyl}amino)-8-azabicyclo[3.2.1]oct-8-yl]-N-(2,2,2-trifluoroethyl)pyridine-3-carboxamide, MS (EI): 544 (MH⁺).

6-(3-endo-{[2-methyl-2-({4-[(trifluoromethyl)oxy]phenyl}oxy)propanoyl]amino}-8-azabicyclo[3.2.1]oct-8-yl)-N-(2,2,2-trifluoroethyl)pyridine-3-carboxamide, MS (EI): 575 (MH⁺).

5-chloro-6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide, MS (EI): 594 (MH⁺).

2-[(2,4-dichlorophenyl)oxy]-2-methyl-N-{8-[5-(methylsulfonyl)pyridin-2-yl]-8-azabicyclo[3.2.1]oct-3-endo-yl}propanamide, MS (EI): 512 (MH⁺).

6-[3-endo-({[1-(3,4-difluorophenyl)cyclopropyl]carbonyl}amino)-8-azabicyclo[3.2.1]oct-8-yl]pyridine-3-carboxamide, MS (EI): 426 (MH⁺) 1H NMR (CDCl3, 400 MHz): δ 8.55 (s, 1H), 7.90 (d, J=5.6 Hz, 1H), 7.13 (m, 3H), 6.49 (d, J=5.6 Hz, 1H), 4.88 (d, J=5.2 Hz, 1H), 4.56 (s, 2H), 4.42 (m, 1H), 2.08 (m, 2H), 1.93 (m, 2H), 1.84 (d, J=5.2 Hz, 2H), 1.56 (m, 2H), 1.28 (t, J=7.6 Hz, 2H), 0.98 (m, 2H). MS (EI): 426 (MH⁺).

6-[3-endo-({2-[(5-chloro-3-fluoropyridin-2-yl)oxy]-2-methylpropanoyl}amino)-8-azabicyclo[3.2.1]oct-8-yl]pyridine-3-carboxamide, MS (EI): 462 (MH⁺).

N-cyclopropyl-2-[3-endo-({2-[(2,4-dichlorophenyl)oxy]-2-methylpropanoyl}amino)-8-azabicyclo[3.2.1]oct-8-yl]pyridine-4-carboxamide, MS (EI): 517 (MH⁺).

6-{3-[(2-{[4-chloro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 593 (MH⁺).

6-{3-endo-[(2-{[4-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 577 (MH⁺).

6-{3-endo-[(2-{[3-chloro-5-(trifluoromethyl)pyridin-2-yl]oxy}-2-methylpropanoyl)amino]-8-azabicyclo[3.2.1]oct-8-yl}pyridine-3-carboxamide, MS (EI): 512 (MH⁺).

6-{3-endo-[(2-methyl-2-{[5-(trifluoromethyl)pyridin-2-yl]oxy}propanoyl)amino]-8-azabicyclo[3.2.1]oct-8-yl}pyridine-3-carboxamide, MS (EI): 477 (MH⁺).

6-{3-endo-[(2-{[3-chloro-5-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide, MS (EI): 594 (MH⁺).

6-{3-endo-[(2-methyl-2-{[5-(trifluoromethyl)pyridin-2-yl]oxy}propanoyl)amino]-8-azabicyclo[3.2.1]oct-8-yl}-N-(2,2,2-trifluoroethyl)pyridine-3-carboxamide, MS (EI): 560 (MH⁺).

2-[(2,3-dichloro-4-fluorophenyl)oxy]-2-methyl-N-{8-[5-(methylsulfonyl)pyridin-2-yl]-8-azabicyclo[3.2.1]oct-3-endo-yl}propanamide, MS (EI): 530 (MH⁺). The phenol can be prepared according to the procedure reported in Tetrahedron Letters, 1995, 36, 3893-3896.

2-[(2,5-dichloro-4-fluorophenyl)oxy]-2-methyl-N-{8-[5-(methylsulfonyl)pyridin-2-yl]-8-azabicyclo[3.2.1]oct-3-endo-yl}propanamide, MS (EI): 530 (MH⁺).

2-[(2-chloro-4-fluorophenyl)oxy]-2-methyl-N-{8-[5-(methylsulfonyl)pyridin-2-yl]-8-azabicyclo[3.2.1]oct-3-endo-yl}propanamide, MS (EI): 496 (MH⁺).

N-{8-[5-(aminosulfonyl)pyridin-2-yl]-8-azabicyclo[3.2.1]oct-3-endo-yl}-2-[(2,5-dichloro-4-fluorophenyl)oxy]-2-methylpropanamide, MS (EI): 531 (MH⁺).

N-{8-[5-(aminosulfonyl)pyridin-2-yl]-8-azabicyclo[3.2.1]oct-3-endo-yl}-2-[(2-chloro-4-fluorophenyl)oxy]-2-methylpropanamide, MS (EI): 497 (MH⁺).

6-[3-endo-({2-[(2-chloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide, MS (EI): 561 (MH⁺). The requisite fluoropyridine starting material can be prepared according to a procedure outlined in J. Org. Chem. 2005, 70, 3039-3045.

6-[3-endo-({2-[(2,4-dichlorophenyl)oxy]-2-methylpropanoyl}amino)-8-azabicyclo[3.2.1]oct-8-yl]-5-fluoro-N-(2,2,2-trifluoroethyl)pyridine-3-carboxamide, MS (EI): 577 (MH$^+$).

6-[3-endo-({2-[(3,5-dichloropyridin-2-yl)oxy]-2-methylpropanoyl}amino)-8-azabicyclo[3.2.1]oct-8-yl]-5-fluoro-N-(2,2,2-trifluoroethyl)pyridine-3-carboxamide, MS (EI): 578 (MH$^+$).

6-[3-endo-({2-[(2,5-dichloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide, MS (EI): 595 (MH$^+$).

6-{3-endo-[(2-methyl-2-{[2-(trifluoromethyl)phenyl]oxy}propanoyl)amino]-8-azabicyclo[3.2.1]oct-8-yl}pyridine-3-carboxamide, MS (EI): 476 (MH$^+$).

6-(3-endo-{[2-(3,4-difluorophenyl)-2-methylpropanoyl]amino}-8-azabicyclo[3.2.1]oct-8-yl)pyridine-3-carboxamide, MS (EI): 428 (MH$^+$).

6-{3-endo-[(2-{[4-fluoro-2-(trifluoromethyl)phenyl]oxy}-2-methylpropanoyl)amino]-8-azabicyclo[3.2.1]oct-8-yl}pyridine-3-carboxamide, MS (EI): 494 (MH$^+$).

6-{3-endo-[(2-{[4-chloro-2-(trifluoromethyl)phenyl]oxy}-2-methylpropanoyl)amino]-8-azabicyclo[3.2.1]oct-8-yl}pyridine-3-carboxamide, MS (EI): 511 (MH$^+$).

2-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-4-carboxamide, MS (EI): 559 (MH$^+$).

6-{3-endo-[(2-methyl-2-{[4-(trifluoromethyl)phenyl]oxy}propanoyl)amino]-8-azabicyclo[3.2.1]oct-8-yl}pyridine-3-carboxamide, MS (EI): 476 (MH$^+$).

2-{[4-fluoro-2-(trifluoromethyl)phenyl]oxy}-2-methyl-N-{8-[5-(methylsulfonyl)pyridin-2-yl]-8-azabicyclo[3.2.1]oct-3-endo-yl}propanamide, MS (EI): 530 (MH$^+$).

N-{8-[5-(aminosulfonyl)pyridin-2-yl]-8-azabicyclo[3.2.1]oct-3-endo-yl}-2-{[4-fluoro-2-(trifluoromethyl)phenyl]oxy}-2-methylpropanamide, MS (EI): 531 (MH$^+$).

2-[(2,6-dichloro-4-fluorophenyl)oxy]-2-methyl-N-{8-[5-(methylsulfonyl)pyridin-2-yl]-8-azabicyclo[3.2.1]oct-3-endo-yl}propanamide, MS (EI): 530 (MH$^+$).

2-{[2-chloro-4-fluoro-6-(trifluoromethyl)phenyl]oxy}-2-methyl-N-{8-[5-(methylsulfonyl)pyridin-2-yl]-8-azabicyclo[3.2.1]oct-3-endo-yl}propanamide, MS (EI): 564 (MH$^+$).

2-methyl-2-{[4-(methyloxy)phenyl]oxy}-N-{8-[5-(methylsulfonyl)pyridin-2-yl]-8-azabicyclo[3.2.1]oct-3-endo-yl}propanamide, MS (EI): 474 (MH$^+$).

N-{8-[5-(aminosulfonyl)pyridin-2-yl]-8-azabicyclo[3.2.1]oct-3-endo-yl}-2-methyl-2-{[4-(methyloxy)phenyl]oxy}propanamide, MS (EI): 475 (MH$^+$).

6-{3-endo-[(2-{[2-chloro-4-(trifluoromethyl)phenyl]oxy}-2-methylpropanoyl)amino]-8-azabicyclo[3.2.1]oct-8-yl}pyridine-3-carboxamide, MS (EI): 511 (MH$^+$).

6-{3-endo-[(2-{[2-chloro-4-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 593 (MH$^+$).

6-{3-endo-[(2-{[4-chloro-3-(trifluoromethyl)phenyl]oxy}-2-methylpropanoyl)amino]-8-azabicyclo[3.2.1]oct-8-yl}pyridine-3-carboxamide, MS (EI): 511 (MH$^+$).

6-{3-endo-[(2-{[4-chloro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 593 (MH$^+$).

6-{3-endo-[(2-{[4-fluoro-3-(trifluoromethyl)phenyl]oxy}-2-methylpropanoyl)amino]-8-azabicyclo[3.2.1]oct-8-yl}pyridine-3-carboxamide, MS (EI): 494 (MH$^+$).

6-{3-endo-[(2-{[4-fluoro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 577 (MH$^+$).

6-{3-endo-[(2-{[2-fluoro-5-(trifluoromethyl)phenyl]oxy}-2-methylpropanoyl)amino]-8-azabicyclo[3.2.1]oct-8-yl}pyridine-3-carboxamide, MS (EI): 495 (MH$^+$).

6-{3-endo-[(2-{[2-fluoro-5-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 577 (MH$^+$).

N-{8-[5-(aminosulfonyl)pyridin-2-yl]-8-azabicyclo[3.2.1]oct-3-endo-yl}-2-[(3,5-dichloropyridin-2-yl)oxy]-2-methylpropanamide, MS (EI): 514 (MH$^+$).

2-[(3,5-dichloropyridin-2-yl)oxy]-2-methyl-N-{8-[5-(methylsulfonyl)pyridin-2-yl]-8-azabicyclo[3.2.1]oct-3-endo-yl}propanamide, MS (EI): 513 (MH$^+$).

2-[(5-chloro-3-fluoropyridin-2-yl)oxy]-2-methyl-N-{8-[5-(methylsulfonyl)pyridin-2-yl]-8-azabicyclo[3.2.1]oct-3-endo-yl}propanamide, MS (EI): 497 (MH$^+$).

2-methyl-N-{8-[5-(methylsulfonyl)pyridin-2-yl]-8-azabicyclo[3.2.1]oct-3-yl}-2-{[5-(trifluoromethyl)pyridin-2-yl]oxy}propanamide, MS (EI): 513 (MH$^+$).

2-methyl-N-{8-[5-(methylsulfonyl)pyridin-2-yl]-8-azabicyclo[3.2.1]oct-3-endo-yl}-2-[(2,4,5-trichlorophenyl)oxy]propanamide, MS (EI): 547 (MH$^+$).

N-{8-[5-(aminosulfonyl)pyridin-2-yl]-8-azabicyclo[3.2.1]oct-3-endo-yl}-2-methyl-2-[(2,4,5-trichlorophenyl)oxy]propanamide, MS (EI): 548 (MH$^+$).

2-[(2,4-difluorophenyl)oxy]-2-methyl-N-{8-[5-(methylsulfonyl)pyridin-2-yl]-8-azabicyclo[3.2.1]oct-3-endo-yl}propanamide, MS (EI): 480 (MH$^+$).

2-[(4-chlorophenyl)oxy]-2-methyl-N-{8-[5-(methylsulfonyl)pyridin-2-yl]-8-azabicyclo[3.2.1]oct-3-endo-yl}propanamide, MS (EI): 478 (MH$^+$).

N-{8-[5-(aminosulfonyl)pyridin-2-yl]-8-azabicyclo[3.2.1]oct-3-endo-yl}-2-[(4-chlorophenyl)oxy]-2-methylpropanamide, MS (EI): 479 (MH$^+$).

2-[(3,4-dichlorophenyl)oxy]-2-methyl-N-{8-[5-(methylsulfonyl)pyridin-2-yl]-8-azabicyclo[3.2.1]oct-3-endo-yl}propanamide, MS (EI): 512 (MH$^+$).

N-{8-[5-(aminosulfonyl)pyridin-2-yl]-8-azabicyclo[3.2.1]oct-3-endo-yl}-2-[(3,4-dichlorophenyl)oxy]-2-methylpropanamide, MS (EI): 513 (MH$^+$).

2-[(3,4-difluorophenyl)oxy]-2-methyl-N-{8-[5-(methylsulfonyl)pyridin-2-yl]-8-azabicyclo[3.2.1]oct-3-endo-yl}propanamide, MS (EI): 480 (MH$^+$).

N-{8-[5-(aminosulfonyl)pyridin-2-yl]-8-azabicyclo[3.2.1]oct-3-endo-yl}-2-[(3,4-difluorophenyl)oxy]-2-methylpropanamide, MS (EI): 481 (MH$^+$).

N-{8-[5-(aminosulfonyl)pyridin-2-yl]-8-azabicyclo[3.2.1]oct-3-endo-yl}-2-{[4-chloro-2-(trifluoromethyl)phenyl]oxy}-2-methylpropanamide, MS (EI): 547 (MH$^+$).

2-[(2-chloro-4-methylphenyl)oxy]-2-methyl-N-{8-[5-(methylsulfonyl)pyridin-2-yl]-8-azabicyclo[3.2.1]oct-3-endo-yl}propanamide, MS (EI): 492 (MH$^+$).

N-{8-[5-(aminosulfonyl)pyridin-2-yl]-8-azabicyclo[3.2.1]oct-3-endo-yl}-2-[(2-chloro-4-methylphenyl)oxy]-2-methylpropanamide, MS (EI): 493 (MH$^+$).

N-{8-[5-(aminosulfonyl)pyridin-2-yl]-8-azabicyclo[3.2.1]oct-3-endo-yl}-2-[(2,3-dichloro-4-fluorophenyl)oxy]-2-methylpropanamide, MS (EI): 531 (MH$^+$).

N-{8-[5-(aminosulfonyl)pyridin-2-yl]-8-azabicyclo[3.2.1]oct-3-endo-yl}-2-methyl-2-[(2,4,5-trifluorophenyl)oxy]propanamide, MS (EI): 499 (MH$^+$).

2-[(4-fluoro-2-methylphenyl)oxy]-2-methyl-N-{8-[5-(methylsulfonyl)pyridin-2-yl]-8-azabicyclo[3.2.1]oct-3-endo-yl}propanamide, MS (EI): 476 (MH$^+$).

N-{8-[5-(aminosulfonyl)pyridin-2-yl]-8-azabicyclo[3.2.1]oct-3-endo-yl}-2-[(4-fluoro-2-methylphenyl)oxy]-2-methylpropanamide, MS (EI): 477 (MH$^+$).

2-{[4-fluoro-2-(methyloxy)phenyl]oxy}-2-methyl-N-{8-[5-(methylsulfonyl)pyridin-2-yl]-8-azabicyclo[3.2.1]oct-3-endo-yl}propanamide, MS (EI): 492 (MH$^+$).

N-{8-[5-(aminosulfonyl)pyridin-2-yl]-8-azabicyclo[3.2.1]oct-3-endo-yl}-2-{[4-fluoro-2-(methyloxy)phenyl]oxy}-2-methylpropanamide, MS (EI): 493 (MH$^+$).

2-[(3-chloro-4-fluorophenyl)oxy]-2-methyl-N-{8-[5-(methylsulfonyl)pyridin-2-yl]-8-azabicyclo[3.2.1]oct-3-endo-yl}propanamide, MS (EI): 496 (MH$^+$).

N-{8-[5-(aminosulfonyl)pyridin-2-yl]-8-azabicyclo[3.2.1]oct-3-endo-yl}-2-[(3-chloro-4-fluorophenyl)oxy]-2-methylpropanamide, MS (EI): 497 (MH$^+$).

2-[(4-chloro-2-fluorophenyl)oxy]-2-methyl-N-{8-[5-(methylsulfonyl)pyridin-2-yl]-8-azabicyclo[3.2.1]oct-3-endo-yl}propanamide, MS (EI): 496 (MH$^+$).

2-[(4-fluorophenyl)oxy]-2-methyl-N-{8-[5-(methylsulfonyl)pyridin-2-yl]-8-azabicyclo[3.2.1]oct-3-endo-yl}propanamide, MS (EI): 462 (MH$^+$).

2-[(2-chloro-4,5-difluorophenyl)oxy]-2-methyl-N-{8-[5-(methylsulfonyl)pyridin-2-yl]-8-azabicyclo[3.2.1]oct-3-endo-yl}propanamide, MS (EI): 514 (MH$^+$).

2-methyl-N-{8-[5-(methylsulfonyl)pyridin-2-yl]-8-azabicyclo[3.2.1]oct-3-endo-yl}-2-[(2,4,5-trifluorophenyl)oxy]propanamide, MS (EI): 498 (MH$^+$).

2-[(2,4-dichloro-5-fluorophenyl)oxy]-2-methyl-N-{8-[5-(methylsulfonyl)pyridin-2-yl]-8-azabicyclo[3.2.1]oct-3-endo-yl}propanamide, MS (EI): 530 (MH$^+$).

N-{8-[5-(aminosulfonyl)pyridin-2-yl]-8-azabicyclo[3.2.1]oct-3-endo-yl}-2-[(2,6-dichloro-4-fluorophenyl)oxy]-2-methylpropanamide, MS (EI): 531 (MH$^+$).

N-{8-[5-(aminosulfonyl)pyridin-2-yl]-8-azabicyclo[3.2.1]oct-3-endo-yl}-2-[(4-cyanophenyl)oxy]-2-methylpropanamide, MS (EI): 470 (MH$^+$).

2-[(4-chloro-3-fluorophenyl)oxy]-2-methyl-N-{8-[5-(methylsulfonyl)pyridin-2-yl]-8-azabicyclo[3.2.1]oct-3-endo-yl}propanamide, MS (EI): 496 (MH$^+$).

N-{8-[5-(aminosulfonyl)pyridin-2-yl]-8-azabicyclo[3.2.1]oct-3-endo-yl}-2-[(4-chloro-3-fluorophenyl)oxy]-2-methylpropanamide, MS (EI): 497 (MH$^+$).

2-methyl-N-{8-[5-(methylsulfonyl)pyridin-2-yl]-8-azabicyclo[3.2.1]oct-3-endo-yl}-2-{[4-(trifluoromethyl)phenyl]oxy}propanamide, MS (EI): 512 (MH$^+$).

N-{8-[5-(aminosulfonyl)pyridin-2-yl]-8-azabicyclo[3.2.1]oct-3-endo-yl}-2-methyl-2-{[4-(trifluoromethyl)phenyl]oxy}propanamide, MS (EI): 513 (MH$^+$).

N-{8-[5-(aminosulfonyl)pyridin-2-yl]-8-azabicyclo[3.2.1]oct-3-endo-yl}-2-{[3-chloro-5-(trifluoromethyl)pyridin-2-yl]oxy}-2-methylpropanamide, MS (EI): 548 (MH$^+$).

N-{8-[S-(aminosulfonyl)pyridin-2-yl]-8-azabicyclo[3.2.1]oct-3-endo-yl}-2-[(5-chloro-3-fluoropyridin-2-yl)oxy]-2-methylpropanamide, MS (EI): 498 (MH$^+$).

2-{[3-chloro-5-(trifluoromethyl)pyridin-2-yl]oxy}-2-methyl-N-{8-[5-(methylsulfonyl)pyridin-2-yl]-8-azabicyclo[3.2.1]oct-3-endo-yl}propanamide, MS (EI): 547 (MH$^+$).

2-{[3-chloro-5-(trifluoromethyl)pyridin-2-yl]oxy}-2-methyl-N-{8-[4-(methylsulfonyl)phenyl]-8-azabicyclo[3.2.1]oct-3-endo-yl}propanamide, MS (EI): 546 (MH$^+$).

N-{8-[5-(aminosulfonyl)pyridin-2-yl]-8-azabicyclo[3.2.1]oct-3-endo-yl}-2-{[2-chloro-4-fluoro-6-(trifluoromethyl)phenyl]oxy}-2-methylpropanamide, MS (EI): 565 (MH$^+$).

2-{[2-chloro-4-(methyloxy)phenyl]oxy}-2-methyl-N-{8-[5-(methylsulfonyl)pyridin-2-yl]-8-azabicyclo[3.2.1]oct-3-endo-yl}propanamide, MS (EI): 508 (MH$^+$).

2-methyl-N-{8-[5-(methylsulfonyl)pyridin-2-yl]-8-azabicyclo[3.2.1]oct-3-endo-yl}-2-{[2-(trifluoromethyl)phenyl]oxy}propanamide, MS (EI): 512 (MH$^+$).

N-{8-[5-(aminosulfonyl)pyridin-2-yl]-8-azabicyclo[3.2.1]oct-3-endo-yl}-2-methyl-2-{[2-(trifluoromethyl)phenyl]oxy}propanamide, MS (EI): 513 (MH$^+$).

2-methyl-N-{8-[5-(methylsulfonyl)pyridin-2-yl]-8-azabicyclo[3.2.1]oct-3-endo-yl}-2-[(2,4,6-trifluorophenyl)oxy]propanamide, MS (EI): 498 (MH$^+$).

N-{8-[5-(aminosulfonyl)pyridin-2-yl]-8-azabicyclo[3.2.1]oct-3-endo-yl}-2-methyl-2-[(2,4,6-trifluorophenyl)oxy]propanamide, MS (EI): 499 (MH$^+$).

N-{8-[5-(aminosulfonyl)pyridin-2-yl]-8-azabicyclo[3.2.1]oct-3-endo-yl}-2-[(2,4-dichloro-5-fluorophenyl)oxy]-2-methylpropanamide, MS (EI): 531 (MH$^+$).

N-{8-[5-(aminosulfonyl)pyridin-2-yl]-8-azabicyclo[3.2.1]oct-3-endo-yl}-2-[(2-chloro-4,5-difluorophenyl)oxy]-2-methylpropanamide, MS (EI): 515 (MH$^+$).

N-{8-[5-(aminosulfonyl)pyridin-2-yl]-8-azabicyclo[3.2.1]oct-3-endo-yl}-2-[(4-fluorophenyl)oxy]-2-methylpropanamide, MS (EI): 463 (MH$^+$).

N-{8-[5-(aminosulfonyl)pyridin-2-yl]-8-azabicyclo[3.2.1]oct-3-endo-yl}-2-[(2,4-difluorophenyl)oxy]-2-methylpropanamide, MS (EI): 481 (MH$^+$).

N-{5-chloro-6-[3-({2-[(2,4-dichlorophenyl)oxy]-2-methylpropanoyl}amino)-8-azabicyclo[3.2.1]oct-8-yl]pyridin-3-endo-yl}-3,3,3-trifluoropropanamide, MS (EI): 594 (MH$^+$) 1H NMR (CDCl3, 400 MHz): d 8.09 (d, J=1.6 Hz, 1H), 7.97 (d, J=2.4 Hz, 1H), 7.93 (s, 1H), 7.63 (d, J=7.6 Hz, 1H), 7.44 (d, J=2.8 Hz, 1H), 7.21 (dd, J=9.2 Hz, 1H), 7.04 (d, J=8.8 Hz, 1H), 4.55 (s, 2H), 4.18 (q, J=7.2 Hz, 1H), 3.24 (q, J=10.4 Hz, 2H), 2.46-2.44 (m, 2H), 2.09-2.07 (m, 2H), 1.95-1.92 (m, (2H), 1.76 (d, J=15.2 Hz, 2H), 1.55 (s, 6H). MS (EI): 594 (MH$^+$).

2-{[4-fluoro-3-(trifluoromethyl)phenyl]oxy}-2-methyl-N-{8-[5-(methylsulfonyl)pyridin-2-yl]-8-azabicyclo[3.2.1]oct-3-endo-yl}propanamide, MS (EI): 530 (MH$^+$).

2-{[2-fluoro-5-(trifluoromethyl)phenyl]oxy}-2-methyl-N-{8-[5-(methylsulfonyl)pyridin-2-yl]-8-azabicyclo[3.2.1]oct-3-endo-yl}propanamide, MS (EI): 530 (MH$^+$).

2-{[5-chloro-3-(trifluoromethyl)pyridin-2-yl]oxy}-2-methyl-N-{8-[5-(methylsulfonyl)pyridin-2-yl]-8-azabicyclo[3.2.1]oct-3-endo-yl}propanamide, MS (EI): 547 (MH$^+$).

6-{3-[(2-{[5-chloro-3-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide, MS (EI): 594 (MH$^+$). The synthesis of the requisite hydroxypyridine is reported in Heterocycles, 1984, 22, 117-124.

2-[(2-chloro-4-fluorophenyl)oxy]-2-methyl-N-(8-{5-[5-(trifluoromethyl)-1,2,4-oxadiazol-3-yl]pyridin-2-yl}-8-azabicyclo[3.2.1]oct-3-endo-yl)propanamide, MS (EI): 554 (MH$^+$). This compound can be prepared by treating 2-(2-chloro-4-fluorophenoxy)-N-(8-(5-cyanopyridin-2-yl)-8-azabicyclo[3.2.1]octan-3-endo-yl)-2-methylpropanamide with hydroxylamine and trifluoroacetic acid according to a procedure described in Bioorg. Med. Chem. Lett. 2006, 16, 3679-3683.

2-[(2-chloro-4-fluorophenyl)oxy]-2-methyl-N-(8-{5-[3-(trifluoromethyl)-1H-1,2,4-triazol-5-yl]pyridin-2-yl}-8-azabicyclo[3.2.1]oct-3-endo-yl)propanamide, MS (EI): 553 (MH$^+$). This compound can be prepared by treating 2-[(2-chloro-4-fluorophenyl)oxy]-2-methyl-N-(8-{5-[5-(trifluoromethyl)-1,2,4-oxadiazol-3-endo-yl]pyridin-2- yl}-8-azabicyclo[3.2.1]oct-3-yl)propanamide with hydrazine according to a procedure described in J. Org. Chem. 2003, 68, 605-608.

3-{[4-chloro-2-(trifluoromethyl)phenyl]oxy}-2,2-dimethyl-N-{8-[5-(methylsulfonyl)pyridin-2-yl]-8-azabicyclo[3.2.1]oct-3-endo-yl}propanamide, MS (EI): 560 (MH$^+$). The phenol can be prepared according to the procedure in J. Org. Chem. 2003, 68, 8261-8263.

6-{3-[(3-endo-{[4-chloro-2-(trifluoromethyl)phenyl]oxy}-2,2-dimethylpropanoyl)amino]-8-azabicyclo[3.2.1]oct-8-yl}-N-(2,2,2-trifluoroethyl)pyridine-3-carboxamide, MS (EI): 607 (MH$^+$).

6-{3-endo-[(2-{[4-fluoro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 687 (MH$^+$). The requisite phenol can be obtained by treating 2-bromo-4-chloro-1-methoxybenzene with n-butyllithium and dimethyldisulfide according to a procedure reported in J. Med. Chem. 1984, 27, 881-888. Deprotection of the resulting methylether with boron tribromide under literature conditions provides 4-chloro-2-(methylthio)phenol.

6-{3-endo-[(2-{[4-fluoro-2-(methylsulfonyl)phenyl]oxy}-2-methylpropanoyl)amino]-8-azabicyclo[3.2.1]oct-8-yl}pyridine-3-carboxamide, MS (EI): 505 (MH$^+$).

6-{3-endo-[(2-methyl-2-{[2-(methylsulfonyl)phenyl]oxy}propanoyl)amino]-8-azabicyclo[3.2.1]oct-8-yl}-N-(2,2,2-trifluoroethyl)pyridine-3-carboxamide, MS (EI): 569 (MH$^+$).

6-{3-endo-[(2-methyl-2-{[2-(methylsulfonyl)phenyl]oxy}propanoyl)amino]-8-azabicyclo[3.2.1]oct-8-yl}pyridine-3-carboxamide, MS (EI): 487 (MH$^+$).

6-{3-endo-[(2-{[5-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 577 (MH$^+$).

6-{3-endo-[(2-{[5-fluoro-2-(trifluoromethyl)phenyl]oxy}-2-methylpropanoyl)amino]-8-azabicyclo[3.2.1]oct-8-yl}pyridine-3-carboxamide, MS (EI): 494 (MH$^+$).

2-{[5-fluoro-2-(trifluoromethyl)phenyl]oxy}-2-methyl-N-{8-[5-(methylsulfonyl)pyridin-2-yl]-8-azabicyclo[3.2.1]oct-3-endo-yl}propanamide, 1H NMR (CDCl$_3$, 400 MHz): d 8.63 (d, J=2.0 Hz, 1H), 7.85 (dd, J=8.4 Hz, 1H), 7.64-7.62 (m, 1H), 7.04 (d, J=7.2 Hz, 1H), 6.85-6.83 (m, 2H), 6.51 (d, J=8.8 Hz, 1H), 4.59 (s, 2H), 4.12 (q, J=6.8 Hz, 1H), 3.04 (s, 3H), 2.29-2.26 (m, 2H), 2.14-2.10 (m, 2H), 1.83-1.80 (m, 2H), 1.75-1.71 (m, 8H). MS (EI): 530 (MH$^+$).

2-{[4-fluoro-2-(trifluoromethyl)phenyl]oxy}-2-methyl-N-{8-[6-(1H-tetrazol-5-yl)pyridin-3-yl]-8-azabicyclo[3.2.1]oct-3-endo-yl}propanamide, MS (EI): 520 (MH$^+$). This compound can be prepared by treatment of N-(8-(6-cyanopyridin-3-yl)-8-azabicyclo[3.2.1]octan-3-endo-yl)-2-(4-fluoro-2-(trifluoromethyl)phenoxy)-2-methylpropanamide with sodium azide according to the procedure in Synth. Commun, 2006, 36, 1809-1814.

2-{[4-chloro-2-(methylsulfonyl)phenyl]oxy}-2-methyl-N-{8-[5-(methylsulfonyl)pyridin-2-yl]-8-azabicyclo[3.2.1]oct-3-endo-yl}propanamide, $^1$H NMR (CDCl$_3$, 400 MHz): d 8.59 (d, J=2.4 Hz, 1H), 7.97 (d, J=2.8 Hz, 1H), 7.82 (dd, J=9.2 Hz, 1H), 7.51 (dd, J=9.2 Hz, 1H), 7.24 (d, J=6.4 Hz, 1H), 7.08 (d, J=8.8 Hz, 1H), 6.47 (d, J=8.8 Hz, 1H), 4.52 (s, 2H), 3.86 (q, J=6.0 Hz, 1H), 3.27 (s, 3H), 3.05 (s, 3H), 2.21-2.18 (m, 2H), 1.98-1.95 (m, 2H), 1.89-1.84 (m, 8H), 1.65 (d, J=20.8 Hz, 2H). MS (EI): 556 (MH$^+$).

N-{8-[5-(aminosulfonyl)pyridin-2-yl]-8-azabicyclo[3.2.1]oct-3-endo-yl}-2-{[4-chloro-2-(methylsulfonyl)phenyl]oxy}-2-methylpropanamide, MS (EI): 557 (MH$^+$).

6-{3-endo-[(2-{[4-chloro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide, MS (EI): 603 (MH$^+$).

6-{3-endo-[(2-{[4-chloro-2-(methylsulfonyl)phenyl]oxy}-2-methylpropanoyl)amino]-8-azabicyclo[3.2.1]oct-8-yl}pyridine-3-carboxamide, MS (EI): 521 (MH$^+$).

N-{8-[5-(aminosulfonyl)pyridin-2-yl]-8-azabicyclo[3.2.1]oct-3-endo-yl}-2-{[4-fluoro-2-(methylsulfonyl)phenyl]oxy}-2-methylpropanamide, MS (EI): 541 (MH$^+$).

N-{8-[5-(aminosulfonyl)pyridin-2-yl]-8-azabicyclo[3.2.1]oct-3-endo-yl}-1-[3-(methylsulfonyl)phenyl]cyclopropanecarboxamide, MS (EI): 505 (MH$^+$).

6-{3-endo-[({1-[3-(methylsulfonyl)phenyl]cyclopropyl}carbonyl)amino]-8-azabicyclo[3.2.1]oct-8-yl}-N-(2,2,2-trifluoroethyl)pyridine-3-carboxamide, MS (EI): 551 (MH$^+$).

6-{3-endo-[({1-[3-(methylsulfonyl)phenyl]cyclopropyl}carbonyl)amino]-8-azabicyclo[3.2.1]oct-8-yl}pyridine-3-carboxamide, MS (EI): 469 (MH$^+$).

2-[(2,4-dichlorophenyl)thio]-2-methyl-N-{8-[5-(methylsulfonyl)pyridin-2-yl]-8-azabicyclo[3.2.1]oct-3-endo-yl}propanamide, $^1$H NMR (CDCl$_3$, 400 MHz): δ 8.63 (s, 1H), 7.85 (d, J=5.2 Hz, 1H), 7.46 (m, 2H), 7.22 (m, 2H), 6.52 (d, J=4.8 Hz, 1H), 4.59 (s, 2H), 4.08 (m, 1H), 3.04 (s, 3H), 2.21 (m, 4H), 1.89 (d, J=8.0 Hz, 2H), 1.69 (d, J=14.8 Hz, 2H), 1.64 (s, 6H). MS (EI): 529 (MH$^+$).

6-[3-endo-({2-[(2,4-dichlorophenyl)thio]-2-methylpropanoyl}amino)-8-azabicyclo[3.2.1]oct-8-yl]pyridine-3-carboxamide, $^1$H NMR (CDCl$_3$, 400 MHz): δ 8.58 (d, J=2.4 Hz, 1H), 7.92 (dd, J=8.8 Hz, 1H), 7.45 (d, J=2.0 Hz, 2H), 7.19 (m, 2H), 6.50 (d, J=8.8 Hz, 1H), 4.56 (br s, 2H), 4.05 (q, J=8.0 Hz, 1H), 2.22 (m, 2H), 2.16 (m, 2H), 1.85 (d, J=8.4 Hz, 2H), 1.61 (s, 6H). MS (EI): 493 (MH$^+$).

6-[3-endo-({2-[(2,4-dichlorophenyl)oxy]-2-methylpropanoyl}amino)-8-azabicyclo[3.2.1]oct-8-yl]-N-oxetan-3-ylpyridine-3-carboxamide, MS (EI): 533 (MH$^+$).

2-[(2,4-dichlorophenyl)sulfonyl]-2-methyl-N-{8-[5-(methylsulfonyl)pyridin-2-yl]-8-azabicyclo[3.2.1]oct-3-endo-yl}propanamide, $^1$H NMR (CDCl$_3$, 400 MHz): δ 8.63 (s, 1H), 7.98 (d, J=8.4 Hz, 1H), 7.84 (d, J=8.8 Hz, 1H), 7.48 (m, 2H), 6.56 (d, J=8.8 Hz, 1H), 4.65 (s, 2H), 4.13 (m, 1H), 3.05 (s, 3H), 2.21 (m, 4H), 2.23 (m, 6H), 1.82 (d, J=14.4 Hz, 2H), 1.57 (s, 6H). MS (EI): 561 (MH$^+$). The requisite acid can be prepared by oxidation of 2-(2,4-dichlorophenylthio)-2-methylpropanoic acid to 2-(2,4-dichlorophenylsulfonyl)-2-methylpropanoic acid with chromium trioxide according to literature procedures. 1-(3,4-difluorophenyl)-N-{8-[5-(methylsulfonyl)pyridin-2-yl]-8-azabicyclo[3.2.1]oct-3-endo-yl}cyclopropanecarboxamide, MS (EI): 462 (MH$^+$).

1-(3-chloro-4-fluorophenyl)-N-{8-[5-(methylsulfonyl)pyridin-2-yl]-8-azabicyclo[3.2.1]oct-3-endo-yl}cyclopropanecarboxamide, MS (EI): 478 (MH$^+$).

1-[4-fluoro-3-(trifluoromethyl)phenyl]-N-{8-[5-(methylsulfonyl)pyridin-2-yl]-8-azabicyclo[3.2.1]oct-3-endo-yl}cyclopropanecarboxamide, MS (EI): 512 (MH$^+$).

6-[3-endo-({2-[(2,4-dichlorophenyl)sulfonyl]-2-methylpropanoyl}amino)-8-azabicyclo[3.2.1]oct-8-yl]pyridine-3-carboxamide, $^1$H NMR (CDCl$_3$, 400 MHz): δ 8.56 (d, J=2.4 Hz, 1H), 7.86 (m, 3H), 7.67 (d, J=8.8 Hz, 2H), 7.33 (d, J=5.2 Hz, 1H), 7.06 (br s, 1H), 6.74 (d, J=9.2 Hz, 1H), 4.51 (br s, 2H), 3.64 (s, 1H), 1.95 (m, 6H), 1.73 (d, J=14.4 Hz, 2H), 1.50 (s, 6H). MS (EI): 525 (MH$^+$).

6-[3-endo-({2-[(2,4-dichlorophenyl)oxy]-2-methylpropanoyl}amino)-8-azabicyclo[3.2.1]oct-8-yl]pyridine-3-carboxylic acid, MS (EI): 528 (MH$^+$).

6-[3-endo-({2-[(2,4-dichlorophenyl)oxy]-2-methylpropanoyl}amino)-8-azabicyclo[3.2.1]oct-8-yl]-N-(2,2-difluorocyclopropyl)pyridine-3-carboxamide, MS (EI): 553 (MH$^+$).

6-[3-endo-({2-[(4-chloro-2-cyclohexylphenyl)oxy]-2-methylpropanoyl}amino)-8-azabicyclo[3.2.1]oct-8-yl]pyridine-3-carboxamide, MS (EI): 525 (MH$^+$).

6-[3-endo-({2-[(1-chloronaphthalen-2-yl)oxy]-2-methylpropanoyl}amino)-8-azabicyclo[3.2.1]oct-8-yl]pyridine-3-carboxamide, MS (EI): 493 (MH$^+$).

6-[3-endo-({2-[(4-chloronaphthalen-1-yl)oxy]-2-methylpropanoyl}amino)-8-azabicyclo[3.2.1]oct-8-yl]pyridine-3-carboxamide, MS (EI): 493 (MH$^+$).

6-[3-endo-({2-[(3-chlorobiphenyl-4-yl)oxy]-2-methylpropanoyl}amino)-8-azabicyclo[3.2.1]oct-8-yl]pyridine-3-carboxamide, MS (EI): 519 (MH$^+$).

6-(3-endo-{[2-methyl-2-(naphthalen-2-yloxy)propanoyl]amino}-8-azabicyclo[3.2.1]oct-8-yl)pyridine-3-carboxamide, MS (EI): 459 (MH$^+$).

6-[3-endo-({2-[(4-chloro-2-cyclopentylphenyl)oxy]-2-methylpropanoyl}amino)-8-azabicyclo[3.2.1]oct-8-yl]pyridine-3-carboxamide, MS (EI): 511 (MH$^+$).

6-[3-endo-({2-[(5-chlorobiphenyl-2-yl)oxy]-2-methylpropanoyl}amino)-8-azabicyclo[3.2.1]oct-8-yl]pyridine-3-carboxamide, MS (EI): 519 (MH$^+$).

6-[3-endo-({2-[(3-chloro-4'-fluorobiphenyl-4-yl)oxy]-2-methylpropanoyl}amino)-8-azabicyclo[3.2.1]oct-8-yl]pyridine-3-carboxamide, MS (EI): 537 (MH$^+$). The fibric acid can be prepared according to a procedure outlined in J. Med. Chem. 2006, 49, 6638-6641.

6-[3-endo-({2-[(5-chloro-4'-fluorobiphenyl-2-yl)oxy]-2-methylpropanoyl}amino)-8-azabicyclo[3.2.1]oct-8-yl]pyridine-3-carboxamide, MS (EI): 537 (MH$^+$).

6-{3-endo-[(2-{[4-chloro-2-(1-methylethyl)phenyl]oxy}-2-methylpropanoyl)amino]-8-azabicyclo[3.2.1]oct-8-yl}pyridine-3-carboxamide, MS (EI): 485 (MH$^+$). The requisite phenol can be prepared according to a procedure in J. Org. Chem. 1985, 50, 2145-2148.

6-(3-endo-{[2-methyl-2-(quinolin-4-yloxy)propanoyl]amino}-8-azabicyclo[3.2.1]oct-8-yl)pyridine-3-carboxamide, MS (EI): 460 (MH$^+$).

6-(3-endo-{[2-methyl-2-(quinolin-2-yloxy)propanoyl]amino}-8-azabicyclo[3.2.1]oct-8-yl)pyridine-3-carboxamide, MS (EI): 460 (MH$^+$).

6-[3-endo-({2-[(2-bromo-4-chlorophenyl)oxy]-2-methylpropanoyl}amino)-8-azabicyclo[3.2.1]oct-8-yl]-N-(2,2,2-trifluoroethyl)pyridine-3-carboxamide, MS (EI): 604 (MH$^+$).

EXAMPLE 5

6-[3-endo-({[1-(4-chlorophenyl)cyclopropyl]carbonyl}amino)-8-azabicyclo[3.2.1]oct-8-yl]pyridine-3-carboxamide

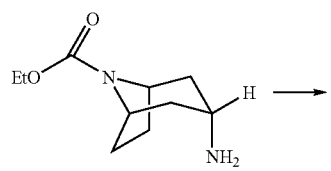

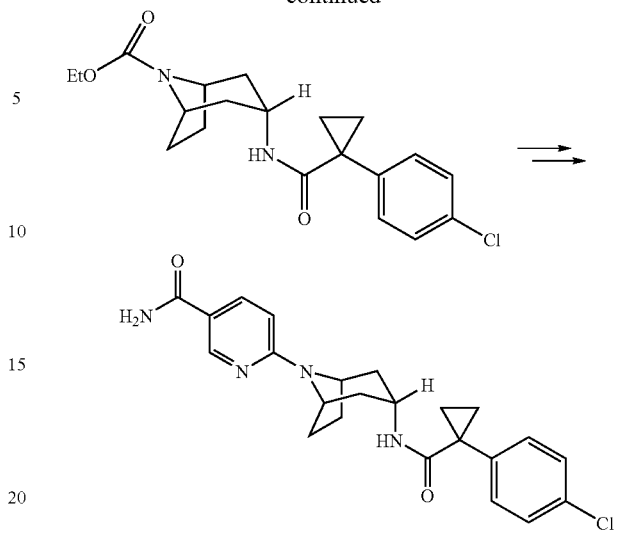

A solution of commercially available 1-(4-chlorophenyl)-1-cyclopropanecarboxylic acid (7.4 g, 38 mmol) in DCM (75 mL) was chilled to 0° C. and treated with oxalyl chloride (6.6 mL, 76 mmol) and DMF (0.1 mL). The ice-water bath was removed and the reaction mixture was allowed to stir 3 hours at room temperature. The volatiles were removed under reduced pressure and co-evaporated with toluene (2×2 mL). The resulting acid chloride was diluted with DCE (40 mL) and added to a cooled (0° C.) solution of ethyl 3-endo-amino-8-azabicyclo[3.2.1]octane-8-carboxylate (5.0 g, 25 mmol) (made by adding ethyl carbonochloridate to the compound from Example 1 (B)), DIEA (8.8 mL, 50 mmol) and DMAP (154 mg, 1.3 mmol) in DCE (85 mL). The ice-water bath was removed and the reaction mixture was allowed to warm to room temperature. After 16 hours, the mixture was diluted with DCM (400 mL), washed with water (100 mL), then dried (anhyd Na$_2$SO$_4$) and filtered. The filtrate was concentrated under reduced pressure to give a residue that was purified by flash chromatography (silica gel, EtOAc/Hex, 50:50 to 80:20) to afford ethyl 3-endo-(1-(4-chlorophenyl)cyclopropane-carboxamido)-8-azabicyclo[3.2.1]octane-8-carboxylate (4.4 g, 42%) as a yellow crystalline solid. $^1$H NMR (400 MHz, CDCl$_3$): δ 7.41-7.34 (m, 4H), 5.73 (d, J=7.5 Hz, 1H), 4.23-4.02 (m, 5H), 2.21-1.96 (m, 2H), 1.90-1.81 (m, 2H), 1.62-1.57 (m, 2H), 1.56-1.44 (m, 2H), 1.25-1.09 (m, 5H), 1.05-1.00 (m, 2H).

Ethyl 3-endo-(1-(4-chlorophenyl)cyclopropanecarboxamido)-8-azabicyclo[3.2.1]octane-8-carboxylate was heated in 30% HBr/AcOH (20 mL) at 100° C. After 2 hours, the reaction mixture was cooled and a precipitate was formed upon cooling. The mixture was diluted with EtOAc (20 mL) and the solids were collected by filtration to afford N-(8-azabicyclo-[3.2.1]octan-3-endo-yl)-1-(4-chlorophenyl)cyclopropanecarboxamide hydrobromide (4.0 g, quant) as a yellow solid. $^1$H NMR (400 MHz, CD$_3$OD): δ 7.55-7.47 (m, 4H), 6.22 (d, J=5.7 Hz, 1H), 4.02-3.95 (m, 3H), 2.27-2.19 (m, 4H), 1.70-1.62 (m, 2H), 1.57-1.53 (m, 2H), 1.19-1.15 (m, 2H).

A mixture of N-(8-azabicyclo[3.2.1]octan-3-endo-yl)-1-(4-chlorophenyl)cyclopropane-carboxamide hydrobromide (0.40 g, 1.0 mmol), 6-chloronicotinamide (163 mg, 1.0 mmol), K$_2$CO$_3$ (500 mg, 3.6 mmol) and acetonitrile (2 mL) was heated at 120° C. in a sealed pressure tube. After 30 hours, the reaction mixture was cooled to room temperature and was partitioned between water and EtOAc (10 mL). The layers were separated and the aqueous portion was extracted with EtOAc (2×10 mL). The combined organic extracts were washed with brine, then dried (anhyd Na$_2$SO$_4$) and filtered. The filtrate was concentrated under reduced pressure to give an off-white solid, which was triturated with hot EtOAc and filtered to afford 6-[3-endo-({[1-(4-chlorophenyl)cyclopropyl]carbonyl}amino)-8-azabicyclo[3.2.1]oct-8-yl]pyridine-3-carboxamide (175 mg, 40%) as a white solid. $^1$H NMR (400 MHz, CDCl$_3$): δ 8.55 (d, J=2.2 Hz, 1H), 7.90 (d, J=8.9, 2.2 Hz, 1H), 7.43-7.38 (m, 4H), 6.46 (d, J=9.2 Hz, 1H), 5.83 (d, J=6.9 Hz, 1H), 5.61 (br s, 2H), 4.46 (br s, 2H), 4.03-3.95 (m, 1H), 2.18-2.10 (m, 2H), 2.02-1.96 (m, 2H), 1.63-1.50 (m, 6H), 1.37-1.31 (m, 2H), 1.06-1.02 (m, 2H); MS (EI): 425 (MH$^+$).

Using the same or analogous synthetic techniques described in any of the Examples and/or substituting with alternative commercial or literature reagents, the following compounds of the invention were prepared:

2-[3-endo-({[1-(4-chlorophenyl)cyclopropyl]carbonyl}amino)-8-azabicyclo[3.2.1]oct-8-yl]pyridine-3-carboxamide, MS (EI): 425 (MH$^+$).

1-(4-chlorophenyl)-N-{8-[3-(trifluoromethyl)pyridin-2-yl]-8-azabicyclo[3.2.1]oct-3-endo-yl}cyclopropanecarboxamide, MS (EI): 450 (MH$^+$).

1-(4-chlorophenyl)-N-[8-(5-cyanopyridin-2-yl)-8-azabicyclo[3.2.1]oct-3-endo-yl]cyclopropanecarboxamide, MS (EI): 407 (MH$^+$).

6-[3-endo-({[1-(4-chlorophenyl)cyclopropyl]carbonyl}amino)-8-azabicyclo[3.2.1]oct-8-yl]-N-(1-methylethyl)pyridine-3-carboxamide, MS (EI): 467 (MH$^+$).

1-(4-chlorophenyl)-N-[8-(4-cyanopyridin-2-yl)-8-azabicyclo[3.2.1]oct-3-endo-yl]cyclopropanecarboxamide, $^1$H NMR (400 MHz, CDCl$_3$): δ 8.23 (d, J=5.5 Hz, 1H), 7.44-7.38 (m, 4H), 6.69 (d, J=4.8 Hz, 1H), 6.63 (s, 1H), 5.82 (d, J=6.9 Hz, 1H), 4.38 (br s, 2H), 4.03-3.96 (m, 1H), 2.15-2.07 (m, 2H), 2.00-1.94 (m, 2H), 1.63-1.59 (m, 2H), 1.56-1.49 (m, 2H), 1.38-1.30 (m, 2H), 1.06-1.02 (m, 2H). MS (EI): 407 (MH$^+$).

6-[3-endo-({[1-(4-chlorophenyl)cyclopropyl]carbonyl}amino)-8-azabicyclo[3.2.1]oct-8-yl]-N-(2,2,2-trifluoroethyl)pyridine-3-carboxamide, $^1$H NMR (400 MHz, CDCl$_3$): δ 8.57 (d, J=2.5 Hz, 1H), 7.88 (dd, J=8.6, 2.5 Hz, 1H), 7.44-7.38 (m, 4H), 6.45 (d, J=8.6 Hz, 1H), 6.23 (br s, 1H), 5.83 (d, J=7.6 Hz, 1H), 4.46 (br s, 2H), 4.14-4.05 (m, 2H), 4.01-3.95 (m, 1H), 2.16-2.07 (m, 2H), 2.02-1.96 (m, 2H), 1.62-1.58 (m, 2H), 1.56-1.50 (m, 2H), 1.37-1.30 (m, 2H), 1.06-1.03 (m, 2H). MS (EI): 507 (MH$^+$).

6-[3-endo-({2-[(4-chlorophenyl)oxy]-2-methylpropanoyl}amino)-8-azabicyclo[3.2.1]oct-8-yl]-N-(1-methylethyl)pyridine-3-carboxamide, $^1$H NMR (400 MHz, CDCl$_3$): δ 8.54 (d, J=2.7 Hz, 1H), 7.88 (d, J=8.7 Hz, 1H), 7.34-7.29 (m, 2H), 7.24 (d, J=8.2 Hz, 1H), 6.97-6.92 (m, 2H), 6.58 (d, J=9.3 Hz, 1H), 5.82 (d, J=8.7 Hz, 1H), 4.60 (br s, 2H), 4.28-4.18 (m, 2H), 4.10-4.03 (m, 1H), 2.33-2.24 (m, 2H), 2.18-2.12 (m, 2H), 1.94-1.87 (m, 2H), 1.73-1.66 (m, 2H), 1.53 (s, 6H), 1.26 (d, J=6.8 Hz, 6H). MS (EI): 485 (MH$^+$).

2-[(4-chlorophenyl)oxy]-N-[8-(5-cyanopyridin-2-yl)-8-azabicyclo[3.2.1]oct-3-endo-yl]-2-methylpropanamide, MS (EI): 425 (MH$^+$).

2-[3-endo-({2-[(4-chlorophenyl)oxy]-2-methylpropanoyl}amino)-8-azabicyclo[3.2.1]oct-8-yl]-N-cyclopropylpyrimidine-5-carboxamide, MS (EI): 484 (MH$^+$).

6-[3-endo-({2-[(4-chlorophenyl)oxy]-2-methylpropanoyl}amino)-8-azabicyclo[3.2.1]oct-8-yl]-N-cyclopropyl-5-methylpyridine-3-carboxamide, MS (EI): 497 (MH$^+$).

6-[3-endo-({2-[(4-chlorophenyl)oxy]-2-methylpropanoyl}amino)-8-azabicyclo[3.2.1]oct-8-yl]-N-cyclopropyl-2-methylpyridine-3-carboxamide, MS (EI): 497 (MH$^+$).

6-[3-endo-({2-[(2-chloro-4-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 543 (MH$^+$).

6-[3-endo-({2-[(2,4-dichlorophenyl)oxy]-2-methylpropanoyl}amino)-8-azabicyclo[3.2.1]oct-8-yl]-N-(1-methylethyl)pyridine-3-carboxamide, MS (EI): 519 (MH$^+$).

N-[8-(5-cyanopyridin-2-yl)-8-azabicyclo[3.2.1]oct-3-endo-yl]-2-[(2,4-dichlorophenyl)oxy]-2-methylpropanamide, MS (EI): 459 (MH$^+$).

6-[3-endo-({2-[(2,4-dichlorophenyl)oxy]-2-methylpropanoyl}amino)-8-azabicyclo[3.2.1]oct-8-yl]pyridine-3-carboxamide, MS (EI): 477 (MH$^+$). $^1$H NMR (DMSO, 400 MHz): δ 8.60 (s, 1H), 8.02 (d, J=8.8 Hz, 1H), 7.93 (d, J=8.8 Hz, 1H), 7.71 (s, 1H), 7.57 (s, 1H), 7.33 (d, J=5.2 Hz, 1H), 7.08 (s, 1H), 6.83 (d, J=8.8 Hz, 1H), 6.72 (d, J=9.2 Hz, 1H), 4.57 (s, 2H), 4.37 (m, 1H), 2.01 (m, 2H), 1.82 (m, 2H), 1.64 (m, 6H), 1.43 (s, 6H). MS (EI): 477 (MH$^+$).

EXAMPLE 6

2-[(2,4-dichlorophenyl)oxy]-N-{8-[5-(1-hydroxy-1-methylethyl)pyridin-2-yl]-8-azabicyclo[3.2.1]oct-3-endo-yl}-2-methylpropanamide

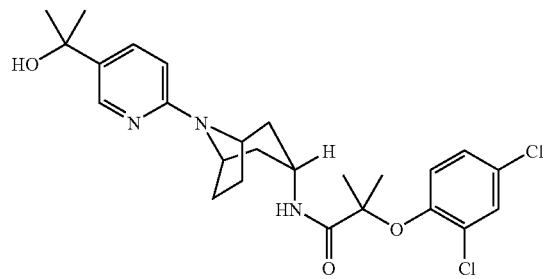

To a solution of methyl 6-[3-endo-({2-[(2,4-dichlorophenyl)oxy]-2-methylpropanoyl}-amino)-8-azabicyclo[3.2.1]oct-8-yl]pyridine-3-carboxylate (0.22 g, 0.45 mmol) in DCM (2 mL, anhyd) chilled to 0° C. was added 3.0M methylmagnesium bromide in diethyl ether (0.90 mL, 2.7 mmol). After complete addition, the flask was allowed to stir 1 h at ambient temperature. The reaction mixture was quenched by addition of satd NH$_4$Cl and extracted with DCM (2×20 mL). The combined extracts were dried (anhyd Na$_2$SO$_4$), concentrated under reduced pressure and purified by chromatography (silica, EtOAc/Hex, 50:50 to 100:0) to afford 2-[(2,4-dichlorophenyl)oxy]-N-{8-[5-(1-hydroxy-1-methylethyl)pyridin-2-yl]-8-azabicyclo[3.2.1]oct-3-endo-yl}-2-methylpropanamide (0.12 g, 55%) as a white solid.

$^1$H NMR (400 MHz, DCM-d$_2$): δ 8.24 (d, J=2.6 Hz, 1H), 7.60 (dd, J=9.0, 2.9 Hz, 1H), 7.54 (d, J=7.4 Hz, 1H), 7.46 (d, J=2.6 Hz, 1H), 7.23 (dd, J=8.7, 2.6 Hz, 1H), 7.07 (d, J=8.7 Hz, 1H), 6.54 (d, J=9.0 Hz, 1H), 4.48 (br s, 2H), 4.04-3.97 (m,

6-[3-endo-({2-[(3,4-dichlorophenyl)oxy]-2-methylpropanoyl}amino)-8-azabicyclo[3.2.1]oct-8-yl]-N-(2,2,2-trifluoroethyl)pyridine-3-carboxamide, MS (EI): 559 (MH+).

6-[3-endo-({2-[(4-chloro-3-fluorophenyl)oxy]-2-methylpropanoyl}amino)-8-azabicyclo[3.2.1]oct-8-yl]-N-(1-methylethyl)pyridine-3-carboxamide, MS (EI): 503 (MH+).

6-[3-endo-({2-[(3,4-difluorophenyl)oxy]-2-methylpropanoyl}amino)-8-azabicyclo[3.2.1]oct-8-yl]-N-(1-methylethyl)pyridine-3-carboxamide, MS (EI): 487 (MH+).

6-[3-endo-({2-[(2,5-dichlorophenyl)oxy]-2-methylpropanoyl}amino)-8-azabicyclo[3.2.1]oct-8-yl]-N-(2,2,2-trifluoroethyl)pyridine-3-carboxamide, MS (EI): 559 (MH+).

6-[3-endo-({2-[(2-chloro-5-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 543 (MH+).

6-[3-endo-({2-[(2-chloro-4-fluorophenyl)oxy]-2-methylpropanoyl}amino)-8-azabicyclo[3.2.1]oct-8-yl]pyridine-3-carboxamide, MS (EI): 461 (MH+).

6-[3-endo-({2-[(2-chloro-4,5-difluorophenyl)oxy]-2-methylpropanoyl}amino)-8-azabicyclo[3.2.1]oct-8-yl]-N-(2,2,2-trifluoroethyl)pyridine-3-carboxamide, MS (EI): 561 (MH+).

6-[3-endo-({2-[(2,4-dichloro-5-fluorophenyl)oxy]-2-methylpropanoyl}amino)-8-azabicyclo[3.2.1]oct-8-yl]pyridine-3-carboxamide, MS (EI): 495 (MH+).

6-[3-endo-({2-[(4-chloro-3-fluorophenyl)oxy]-2-methylpropanoyl}amino)-8-azabicyclo[3.2.1]oct-8-yl]-N-(2,2,2-trifluoroethyl)pyridine-3-carboxamide, MS (EI): 543 (MH+).

6-[3-endo-({2-[(3,4-difluorophenyl)oxy]-2-methylpropanoyl}amino)-8-azabicyclo[3.2.1]oct-8-yl]-N-(2,2,2-trifluoroethyl)pyridine-3-carboxamide, MS (EI): 527 (MH+).

6-[3-endo-({2-[(3,4-dichlorophenyl)oxy]-2-methylpropanoyl}amino)-8-azabicyclo[3.2.1]oct-8-yl]-N-(1-methylethyl)pyridine-3-carboxamide, MS (EI): 519 (MH+).

6-[3-endo-({2-[(2,4-dichlorophenyl)oxy]-2-methylpropanoyl}amino)-8-azabicyclo[3.2.1]oct-8-yl]-N-[2-(methyloxy)ethyl]pyridine-3-carboxamide, MS (EI): 535 (MH+).

6-[3-endo-({2-[(4-chlorophenyl)oxy]butanoyl}amino)-8-azabicyclo[3.2.1]oct-8-yl]-N-[2-(methyloxy)ethyl]pyridine-3-carboxamide, MS (EI): 501 (MH+).

6-[3-endo-({2-[(2-chloro-5-fluorophenyl)oxy]-2-methylpropanoyl}amino)-8-azabicyclo[3.2.1]oct-8-yl]-N-cyclopropylpyridine-3-carboxamide, MS (EI): 501 (MH+).

6-[3-endo-({2-[(2-chloro-4-fluorophenyl)oxy]-2-methylpropanoyl}amino)-8-azabicyclo[3.2.1]oct-8-yl]-N-(1-methylethyl)pyridine-3-carboxamide, MS (EI): 503 (MH+).

6-[3-endo-({2-[(4-chlorophenyl)oxy]propanoyl}amino)-8-azabicyclo[3.2.1]oct-8-yl]-N-[2-(methyloxy)ethyl]pyridine-3-carboxamide, MS (EI): 487 (MH+).

6-[3-endo-({2-[(2,4-dichlorophenyl)oxy]propanoyl}amino)-8-azabicyclo[3.2.1]oct-8-yl]-N-[2-(methyloxy)ethyl]pyridine-3-carboxamide, MS (EI): 521 (MH+).

6-[3-endo-({2-[(4-chlorophenyl)oxy]-2-methylpropanoyl}amino)-8-azabicyclo[3.2.1]oct-8-yl]-N-(2,2,2-trifluoroethyl)pyridine-3-carboxamide, MS (EI): 525 (MH+).

6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide, $^1$H NMR (CDCl3, 400 MHz): δ 8.61 (s, 1H), 7.91 (d, J=8.8 Hz, 1H), 7.36 (s, 2H), 7.12 (d, J=8.8 Hz, 1H), 6.90 (d, J=8.8 Hz, 1H), 6.80 (d, J=8.4 Hz, 1H), 6.54 (d, J=8.4 Hz, 2H), 4.63 (s, 2H), 4.51 (m, 1H), 4.09 (m, H), 2.12 (m, 2H), 2.04 (m, 4H), 1.60 (t, J=11.6 Hz, 2H), 1.55 (s, 6H). MS (EI): 559 (MH+).

6-[3-endo-({2-[(2-chlorophenyl)oxy]-2-methylpropanoyl}amino)-8-azabicyclo[3.2.1]oct-8-yl]-N-(2,2,2-trifluoroethyl)pyridine-3-carboxamide, MS (EI): 525 (MH+).

N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide, MS (EI): 517 (MH+).

EXAMPLE 7(A)

2-{[4-chloro-2-(trifluoromethyl)phenyl]oxy}-2-methyl-N-{8-[5-(methylsulfonyl)pyridin-2-yl]-8-azabicyclo[3.2.1]oct-3-endo-yl}propanamide

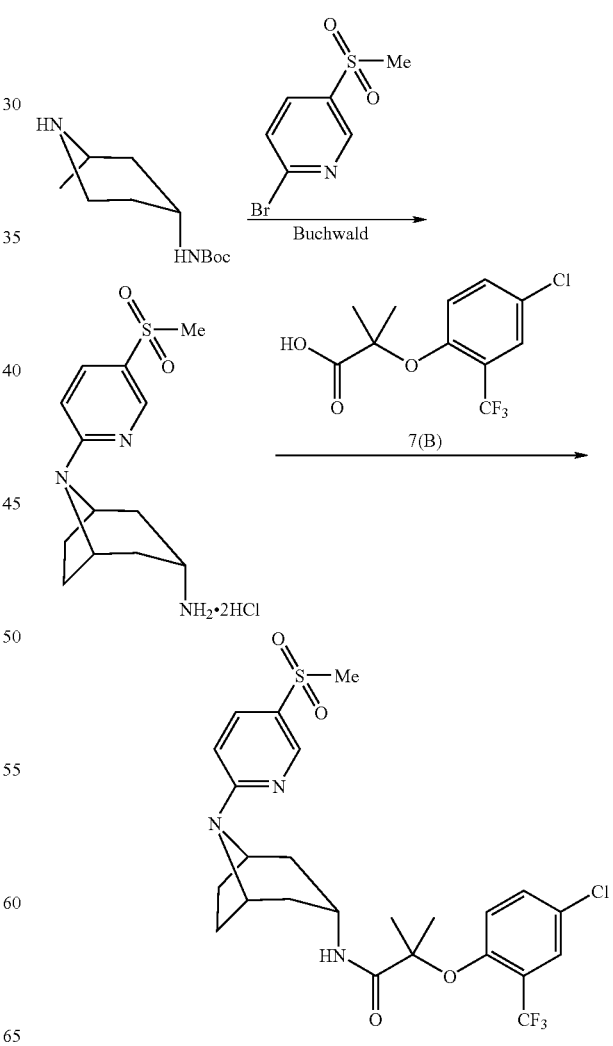

A mixture of tert-butyl 8-azabicyclo[3.2.1]octan-3-ylcarbamate (800 mg, 3.0 mmol) (from Example 1 (B), commercially available 2-bromo-5-methylsulfonylpyridine (600 mg, 2.54 mmol), Pd$_2$(dba)$_3$ (116 mg, 0.13 mmol), BINAP (119 mg, 0.19 mmol) and cesium carbonate (2.0 g, 6.1 mmol) in toluene (10 mL) was heated at 100° C. for 16 h. After cooling, the reaction mixture was passed through Celite, eluting with ethyl acetate. The organic layer was washed with water and brine, dried over MgSO$_4$, filtered and concentrated to give 442 mg (46%) of tert-butyl 8-(5-(methylsulfonyl)pyridin-2-yl)-8-aza-bicyclo[3.2.1]octan-3-endo-ylcarbamate. $^1$H NMR (400 MHz, CDCl$_3$): δ 8.62 (d, 1H), 7.83 (dd, 1H), 6.51 (d, 1H), 4.94 (br s, 1H), 4.61 (br s, 2H), 3.79 (m, 1H), 3.05 (s, 3H), 2.20 (m, 4H), 2.02 (m, 2H), 1.78 (d, 2H), 1.45 (s, 9H).

To a mixture of tert-butyl 8-(5-(methylsulfonyl)pyridin-2-yl)-8-azabicyclo[3.2.1]octan-3-endo-ylcarbamate (448 mg, 1.17 mmol, 1.0 eq) in MeOH (0.5 mL) was added 4M HCl in dioxane (1.2 mL, 4.70 mmol, 4 eq). The mixture became homogeneous after 1 min and a precipitate formed after 30 min. After a total of 2 h of stirring, the reaction mixture was sparged with a stream of nitrogen, then concentrated in vacuo to afford 215 mg of 8-(5-(methylsulfonyl)pyridin-2-yl)-8-azabicyclo[3.2.1]octan-3-endo-amine bis-hydrochloride as a white solid. $^1$H NMR (400 MHz, CD$_3$OD): δ 8.43 (d, J=2.3 Hz, 1H), 8.25 (dd, J=9.6, 2.3 Hz, 1H), 7.41 (d, J=9.6 Hz, 1H), 4.90 (br s, 2H), 3.52-3.45 (m, 1H), 3.22 (s, 3H), 2.68-2.58 (m, 2H), 2.39-2.33 (m, 2H), 2.16-2.09 (m, 2H), 2.01-1.94 (m, 2H). LCMS (0-99% MeCN/water, 5 min), T$_{ret}$=1.01 min, [M+H]$^+$=282.1 observed.

To a solution of 2-(4-chloro-2-(trifluoromethyl)phenoxy)-2-methylpropanoic acid (480 mg, 1.7 mmol, 1.75 eq) in 1,2-dichloroethane (10 mL) was added oxalyl chloride (0.33 mL, 3.74 mmol, 3.85 eq) followed by cat. DMF (few drops). The solution was stirred at room temperature for 1 h then concentrated under reduced pressure. The resulting acid chloride was dissolved in CH$_2$Cl$_2$ (3 mL) and added to a stirred solution of 8-(5-(methylsulfonyl)pyridin-2-yl)-8-azabicyclo[3.2.1]octan-3-endo-amine bis-hydrochloride (344 mg, 0.97 mmol, 1.0 eq) and N,N-diisopropylethylamine (1.2 mL, 6.79 mmol, 7.0 eq) in CH$_2$Cl$_2$ (3 mL). The resulting solution was stirred at room temperature for 1 h, after which it was diluted with CH$_2$Cl$_2$ and washed with satd. aq. NaHCO$_3$, brine, dried (Na$_2$SO$_4$) and concentrated in vacuo. The crude product was adhered to silica gel and purified by column chromatography (40-85% EtOAc/hexanes). Isolated a pale yellow solid which was stirred with diethyl ether and filtered to afford 370 mg (70%) of 2-(4-chloro-2-(trifluoromethyl)phenoxy)-2-methyl-N-(8-(5-(methylsulfonyl)pyridin-2-yl)-8-azabicyclo[3.2.1]octan-3-endo-yl)propanamide as a slightly off-white powder.

$^1$H NMR (400 MHz, CDCl$_3$): δ 8.56 (d, J=2.5 Hz, 1H), 7.81 (dd, J=9.0, 2.7 Hz, 1H), 7.62 (d, J=2.7 Hz, 1H), 7.46 (dd, J=8.9, 2.9 Hz, 1H), 6.98 (d, J=9.0 Hz, 1H), 6.94 (d, J=7.1 Hz, 1H), 6.53 (d, J=9.2 Hz, 1H), 4.57 (br s, 2H), 4.08-4.00 (m, 1H), 3.00 (s, 3H), 2.27-2.19 (m, 2H), 2.10-2.04 (m, 2H), 1.80-1.73 (m, 2H), 1.69-1.62 (m, 2H), 1.60 (s, 6H). LCMS (0-99% MeCN/water, 10 min), T$_{ret}$=6.21 min, [M+H]$^+$=546.3.

EXAMPLE 7(B)

2-(4-chloro-2-(trifluoromethyl)phenoxy)-2-methylpropanoic acid

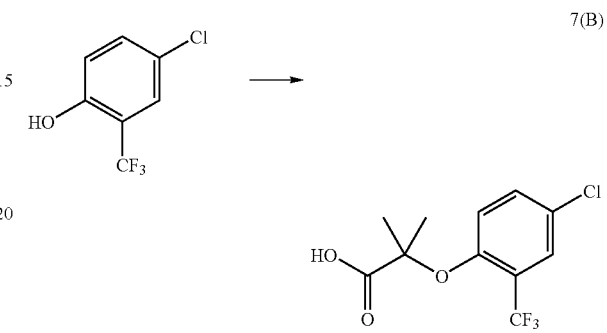

7(B)

A three-neck round bottom flask affixed with an overhead stirrer was charged with 4-chloro-2-(trifluoromethyl)phenol (prepared according methods described in U.S. Pat. No. 4,262,152), (5.0 g, 127 mmol, 1.0 eq) and dissolved in chloroform (3.3 mL) and acetone (8.4 mL). NaOH pellets (4.2 g, 104 mmol, 3.75 eq) were added in 2 portions and the mixture was stirred vigorously for 40 min. The resulting slurry was acidified to pH 2 with 3N HCl and extracted with EtOAc. The organic extracts were treated with satd. aq. sodium bicarbonate, and the basic layer was acidified to pH 4 with conc. HCl and extracted with EtOAc. The organic layer was washed with brine, dried over sodium sulfate and concentrated to afford 2.7 g (37%) of 2-(4-chloro-2-(trifluoromethyl)phenoxy)-2-methylpropanoic acid as a light brown crystalline solid. $^1$H NMR (400 MHz, CDCl$_3$): δ 7.57 (d, J=2.6 Hz, 1H), 7.40 (dd, J=8.9, 2.6 Hz, 1H), 6.91 (d, J=8.9 Hz, 1H), 1.67 (s, 6H). LCMS (0-99% MeCN/water, 5 min, negative ion), T$_{ret}$=2.99 min, [M–H]$^-$=281.3 observed.

Using the same or analogous synthetic techniques described in any of the Examples and/or substituting with alternative commercial or literature reagents, the following compounds of the invention were prepared:

4-[3-endo-({[1-(4-chlorophenyl)cyclopropyl]carbonyl}amino)-8-azabicyclo[3.2.1]oct-8-yl]-N-cyclopropylbenzamide, MS (EI): 464 (MH$^+$).

2-chloro-4-[3-endo-({[1-(4-chlorophenyl)cyclopropyl]carbonyl}amino)-8-azabicyclo[3.2.1]oct-8-yl]-N-cyclopropylbenzamide, MS (EI): 498 (MH$^+$).

4-{3-endo-[2-(2,4-dichloro-phenoxy)-2-methyl-propionylamino]-8-azabicyclo[3.2.1]oct-8-yl}-N-(2,2,2-trifluoroethyl)-benzamide, MS (EI): 558 (MH$^+$).

3-chloro-4-[3-endo-({2-[(2,4-dichlorophenyl)oxy]-2-methylpropanoyl}amino)-8-azabicyclo[3.2.1]oct-8-yl]-N-(2,2,2-trifluoroethyl)benzamide, MS (EI): 593 (MH$^+$).

3-chloro-4-[3-endo-({[1-(4-chlorophenyl)cyclopropyl]carbonyl}amino)-8-azabicyclo[3.2.1]oct-8-yl]-N-cyclopropylbenzamide, MS (EI): 499 (MH$^+$).

4-[3-endo-({[1-(4-chlorophenyl)cyclopropyl]carbonyl}amino)-8-azabicyclo[3.2.1]oct-8-yl]-N-cyclopropyl-2-fluorobenzamide, MS (EI): 482 (MH$^+$).

4-[3-endo-({2-[(2,4-dichlorophenyl)oxy]-2-methylpropanoyl}amino)-8-azabicyclo[3.2.1]oct-8-yl]-3-fluoro-N-(2,2,2-trifluoroethyl)benzamide, MS (EI): 576 (MH$^+$).

N-cyclopropyl-4-[3-endo-({2-[(2,4-dichlorophenyl)oxy]-2-methylpropanoyl}amino)-8-azabicyclo[3.2.1]oct-8-yl]-2-fluorobenzamide, MS (EI): 534 (MH$^+$).

N-cyclopropyl-4-[3-endo-({2-[(2,4-dichlorophenyl)oxy]-2-methylpropanoyl}amino)-8-azabicyclo[3.2.1]oct-8-yl]benzamide, MS (EI): 516 (MH$^+$).

4-[3-endo-({[1-(4-chlorophenyl)cyclopropyl]carbonyl}amino)-8-azabicyclo[3.2.1]oct-8-yl]-N-cyclopropyl-3-fluorobenzamide, MS (EI): 482 (MH$^+$).

4-[3-endo-({2-[(3,4-dichlorophenyl)oxy]-2-methylpropanoyl}amino)-8-azabicyclo[3.2.1]oct-8-yl]-N-(2,2,2-trifluoroethyl)benzamide, MS (EI): 558 (MH$^+$).

4-[3-endo-({2-[(4-chloro-3-fluorophenyl)oxy]-2-methylpropanoyl}amino)-8-azabicyclo[3.2.1]oct-8-yl]-N-(2,2,2-trifluoroethyl)benzamide, MS (EI): 542 (MH$^+$).

4-[3-endo-({2-[(3,4-difluorophenyl)oxy]-2-methylpropanoyl}amino)-8-azabicyclo[3.2.1]oct-8-yl]-N-(2,2,2-trifluoroethyl)benzamide, MS (EI): 526 (MH$^+$).

2-[(2,4-dichlorophenyl)oxy]-2-methyl-N-{8-[4-(methylsulfonyl)phenyl]-8-azabicyclo[3.2.1]oct-3-endo-yl}propanamide, MS (EI): 511 (MH$^+$).

2-[(2,4-dichlorophenyl)oxy]-2-methyl-N-{8-[3-(methylsulfonyl)phenyl]-8-azabicyclo[3.2.1]oct-3-endo-yl}propanamide, MS (EI): 511 (MH$^+$).

2-[(2-chloro-4-fluorophenyl)oxy]-2-methyl-N-{8-[4-(methylsulfonyl)phenyl]-8-azabicyclo[3.2.1]oct-3-endo-yl}propanamide, MS (EI): 495 (MH$^+$).

2-[(2,5-dichloro-4-fluorophenyl)oxy]-2-methyl-N-{8-[4-(methylsulfonyl)phenyl]-8-azabicyclo[3.2.1]oct-3-endo-yl}propanamide, MS (EI): 529 (MH$^+$).

2-[(3,5-dichloropyridin-2-yl)oxy]-2-methyl-N-{8-[4-(methylsulfonyl)phenyl]-8-azabicyclo[3.2.1]oct-3-endo-yl}propanamide, MS (EI): 512 (MH$^+$).

2-methyl-2-{[4-(methyloxy)phenyl]oxy}-N-{8-[4-(methylsulfonyl)phenyl]-8-azabicyclo[3.2.1]oct-3-endo-yl}propanamide, MS (EI): 473 (MH$^+$).

N-{8-[4-(aminosulfonyl)phenyl]-8-azabicyclo[3.2.1]oct-3-endo-yl}-2-methyl-2-{[5-(trifluoromethyl)pyridin-2-yl]oxy}propanamide, MS (EI): 513 (MH$^+$).

2-[(5-chloro-3-fluoropyridin-2-yl)oxy]-2-methyl-N-{8-[4-(methylsulfonyl)phenyl]-8-azabicyclo[3.2.1]oct-3-endo-yl}propanamide, MS (EI): 496 (MH$^+$).

2-methyl-N-{8-[4-(methylsulfonyl)phenyl]-8-azabicyclo[3.2.1]oct-3-endo-yl}-2-{[5-(trifluoromethyl)pyridin-2-yl]oxy}propanamide, MS (EI): 512 (MH$^+$).

2-methyl-N-{8-[4-(methylsulfonyl)phenyl]-8-azabicyclo[3.2.1]oct-3-endo-yl}-2-[(2,4,5-trichlorophenyl)oxy]propanamide, MS (EI): 546 (MH$^+$).

2-[(4-chlorophenyl)oxy]-2-methyl-N-{8-[4-(methylsulfonyl)phenyl]-8-azabicyclo[3.2.1]oct-3-endo-yl}propanamide, MS (EI): 477 (MH$^+$).

2-[(3,4-dichlorophenyl)oxy]-2-methyl-N-{8-[4-(methylsulfonyl)phenyl]-8-azabicyclo[3.2.1]oct-3-endo-yl}propanamide, MS (EI): 511 (MH$^+$).

2-[(3,4-difluorophenyl)oxy]-2-methyl-N-{8-[4-(methylsulfonyl)phenyl]-8-azabicyclo[3.2.1]oct-3-endo-yl}propanamide, MS (EI): 479 (MH$^+$).

2-[(2-chloro-4-methylphenyl)oxy]-2-methyl-N-{8-[4-(methylsulfonyl)phenyl]-8-azabicyclo[3.2.1]oct-3-endo-yl}propanamide, MS (EI): 491 (MH$^+$).

2-[(4-fluoro-2-methylphenyl)oxy]-2-methyl-N-{8-[4-(methylsulfonyl)phenyl]-8-azabicyclo[3.2.1]oct-3-endo-yl}propanamide, MS (EI): 475 (MH$^+$).

2-{[4-fluoro-2-(methyloxy)phenyl]oxy}-2-methyl-N-{8-[4-(methylsulfonyl)phenyl]-8-azabicyclo[3.2.1]oct-3-endo-yl}propanamide, MS (EI): 491 (MH$^+$).

2-[(4-chloro-2-fluorophenyl)oxy]-2-methyl-N-{8-[4-(methylsulfonyl)phenyl]-8-azabicyclo[3.2.1]oct-3-endo-yl}propanamide, MS (EI): 495 (MH$^+$).

2-[(2,4-difluorophenyl)oxy]-2-methyl-N-{8-[4-(methylsulfonyl)phenyl]-8-azabicyclo[3.2.1]oct-3-endo-yl}propanamide, MS (EI): 479 (MH$^+$).

2-[(2-chloro-4,5-difluorophenyl)oxy]-2-methyl-N-{8-[4-(methylsulfonyl)phenyl]-8-azabicyclo[3.2.1]oct-3-endo-yl}propanamide, MS (EI): 513 (MH$^+$).

2-[(3-chloro-4-fluorophenyl)oxy]-2-methyl-N-{8-[4-(methylsulfonyl)phenyl]-8-azabicyclo[3.2.1]oct-3-endo-yl}propanamide, MS (EI): 495 (MH$^+$).

2-[(4-fluorophenyl)oxy]-2-methyl-N-{8-[4-(methylsulfonyl)phenyl]-8-azabicyclo[3.2.1]oct-3-endo-yl}propanamide, MS (EI): 461 (MH$^+$).

2-methyl-N-{8-[4-(methylsulfonyl)phenyl]-8-azabicyclo[3.2.1]oct-3-endo-yl}-2-[(2,4,5-trifluorophenyl)oxy]propanamide, MS (EI): 497 (MH$^+$).

2-[(2,3-dichloro-4-fluorophenyl)oxy]-2-methyl-N-{8-[4-(methylsulfonyl)phenyl]-8-azabicyclo[3.2.1]oct-3-endo-yl}propanamide, MS (EI): 529 (MH$^+$).

2-[(2,4-dichloro-5-fluorophenyl)oxy]-2-methyl-N-{8-[4-(methylsulfonyl)phenyl]-8-azabicyclo[3.2.1]oct-3-endo-yl}propanamide, MS (EI): 529 (MH$^+$).

2-[(2,6-dichloro-4-fluorophenyl)oxy]-2-methyl-N-{8-[4-(methylsulfonyl)phenyl]-8-azabicyclo[3.2.1]oct-3-endo-yl}propanamide, MS (EI): 529 (MH$^+$).

2-[(4-chloro-3-fluorophenyl)oxy]-2-methyl-N-{8-[4-(methylsulfonyl)phenyl]-8-azabicyclo[3.2.1]oct-3-endo-yl}propanamide, MS (EI): 495 (MH$^+$).

2-methyl-N-{8-[4-(methylsulfonyl)phenyl]-8-azabicyclo[3.2.1]oct-3-endo-yl}-2-{[4-(trifluoromethyl)phenyl]oxy}propanamide, MS (EI): 511 (MH$^+$).

2-{[4-fluoro-2-(trifluoromethyl)phenyl]oxy}-2-methyl-N-{8-[4-(methylsulfonyl)phenyl]-8-azabicyclo[3.2.1]oct-3-yl}propanamide, MS (EI): 529 (MH$^+$).

2-{[2-chloro-4-fluoro-6-(trifluoromethyl)phenyl]oxy}-2-methyl-N-{8-[4-(methylsulfonyl)phenyl]-8-azabicyclo[3.2.1]oct-3-endo-yl}propanamide, MS (EI): 563 (MH$^+$).

2-{[2-chloro-4-(methyloxy)phenyl]oxy}-2-methyl-N-{8-[4-(methylsulfonyl)phenyl]-8-azabicyclo[3.2.1]oct-3-endo-yl}propanamide, MS (EI): 507 (MH$^+$).

2-methyl-N-{8-[4-(methylsulfonyl)phenyl]-8-azabicyclo[3.2.1]oct-3-endo-yl}-2-{[2-(trifluoromethyl)phenyl]oxy}propanamide, MS (EI): 511 (MH$^+$).

2-methyl-N-{8-[4-(methylsulfonyl)phenyl]-8-azabicyclo[3.2.1]oct-3-endo-yl}-2-[(2,4,6-trifluorophenyl)oxy]propanamide, MS (EI): 497 (MH$^+$).

2-{[4-chloro-2-(trifluoromethyl)phenyl]oxy}-2-methyl-N-{8-[4-(methylsulfonyl)phenyl]-8-azabicyclo[3.2.1]oct-3-endo-yl}propanamide, MS (EI): 545 (MH$^+$). tion with ClC(O)L$_1$-R$_1$, or coupling with HOC(O)L$_1$-R$_1$, and a coupling agent, such as EDC, under standard conditions to afford the final product 30.

2-{[5-chloro-3-(trifluoromethyl)pyridin-2-yl]oxy}-2-methyl-N-{8-[4-(methylsulfonyl)phenyl]-8-azabicyclo[3.2.1]oct-3-endo-yl}propanamide, MS (EI): 546 (MH+).

EXAMPLE 8

N-[8-(5-aminopyridin-2-yl)-8-azabicyclo[3.2.1]oct-3-endo-yl]-1-(4-chlorophenyl)cyclopropanecarboxamide

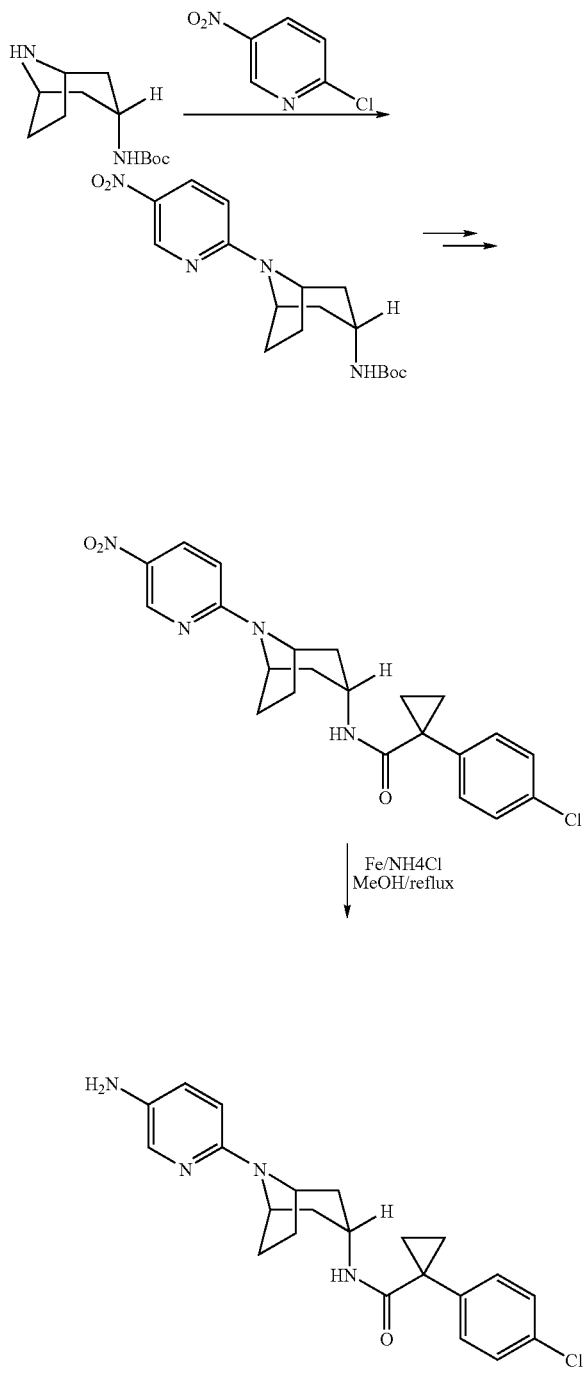

A mixture of tert-butyl 8-azabicyclo[3.2.1]octan-3-endo-ylcarbamate (0.80 g, 3.5 mmol) (from Example 1(B)), commercially available 2-chloro-5-nitropyridine (0.67 g, 4.2 mmol) and potassium carbonate (2.44 g, 17.7 mmol) in N-methylpyrrolidinone (6 mL) in a sealed tube was heated 4 h at 100° C. After cooling, the reaction mixture was diluted with EtOAc (20 mL), washed successively with water, 1N HCl and brine, dried (MgSO₄), filtered and evaporated to give tert-butyl 8-(5-nitropyridin-2-yl)-8-azabicyclo[3.2.1]octan-3-endo-ylcarbamate (1.2 g, 96%) as a yellow solid, which was used in the next step without purification. ¹H NMR (400 MHz, CDCl₃): δ 9.05 (d, 1H), 8.21 (dd, 1H), 6.45 (d, 1H), 3.82 (br s, 1H), 2.11 (m, 8H), 1.85 (d, 2H), 1.45 (s, 9H).

To a solution of tert-butyl 8-(5-nitropyridin-2-yl)-8-azabicyclo[3.2.1]octan-3-endo-ylcarbamate (1.14 g) in MeOH (50 mL) and DCM (10 mL) was added dropwise 2N HCl solution in ether (20 mL). After stirring 5 h, the resulting solution was evaporated to give 8-(5-nitropyridin-2-yl)-8-azabicyclo[3.2.1]octan-3-endo-amine hydrochloride (0.98 g, quant). ¹H NMR (400 MHz, CDCl₃): δ 8.97 (d, 1H), 8.35 (dd, 1H), 8.18 (br s, 3H), 6.90 (d, 1H), 2.24 (m, 4H), 2.02 (m, 4H), 1.83 (d, 2H).

A mixture of 8-(5-nitropyridin-2-yl)-8-azabicyclo[3.2.1]octan-3-endo-amine hydrochloride (0.98 g, 3.4 mmol), commercially available 1-(4-chlorophenyl)-1-cyclopropanecarboxylic acid (0.68 g, 3.5 mmol), EDCI (1.0 g, 5.3 mmol), HOBT (0.72 g, 5.3 mmol) and Et₃N (2.5 mL, 18 mmol) in DCM (20 mL) was stirred 18 h. The resulting mixture was washed with satd NaHCO₃ and brine successively, dried (MgSO₄), filtered and evaporated to give 1-(4-chlorophenyl)-N-(8-(5-nitropyridin-2-yl)-8-azabicyclo[3.2.1]octan-3-endo-yl)cyclopropanecarboxamide (1.37 g, 95%) as a yellow solid. ¹H NMR (400 MHz, DMSO-d₆): δ 9.03 (d, 1H), 8.18 (dd, 1H), 7.43 (AB q, 4H), 6.40 (d, 1H), 5.81 (d, 1H), 4.03 (m, 1H), 2.11 (m, 2H), 2.01 (m, 2H), 1.61 (m, 6H), 1.42 (m, 2H), 1.05 (m, 2H).

To a suspension of iron (0.90 g, 16.0 mmol) and 1-(4-chlorophenyl)-N-(8-(5-nitropyridin-2-yl)-8-azabicyclo[3.2.1]octan-3-endo-yl)cyclopropanecarboxamide (1.37 g, 3.2 mmol) in MeOH (100 mL) was added satd NH₄Cl (5 mL) over 5 min and the resulting reaction mixture was refluxed 18 h. After cooling, the reaction mixture was filtered through a Celite pad and washed with MeOH (20 mL). The filtrate was evaporated and partitioned between DCM (30 mL) and water (10 mL). The organic layer was separated, washed with brine, dried (MgSO₄), filtered and evaporated to give a residue. Purification of the residue by chromatography (silica, MeOH/DCM, 1:10) afforded N-[8-(5-aminopyridin-2-yl)-8-azabicyclo[3.2.1]oct-3-endo-yl]-1-(4-chlorophenyl)cyclopropanecarboxamide (0.91 g, 70%) as a light purple solid. ¹H NMR (400 MHz, CDCl₃): δ 7.74 (d, 1H), 7.40 (AB q, 4H), 6.96 (dd, 1H), 6.42 (d, 1H), 5.85 (d, 1H), 4.25 (br s, 2H), 3.96 (m, 1H), 2.19 (m, 2H), 1.94 (m, 2H), 1.59 (m, 2H), 1.41 (d, 2H), 1.26 (m, 2H), 1.02 (m, 2H). MS (EI): 397 (MH+).

Using the same or analogous synthetic techniques described in any of the Examples and/or substituting with alternative commercial or literature reagents, the following compounds of the invention were prepared:

N-[8-(5-aminopyridin-2-yl)-8-azabicyclo[3.2.1]oct-3-endo-yl]-2-[(2,4-dichlorophenyl)oxy]-2-methylpropanamide, MS (EI): 449 (MH+).

EXAMPLE 9

N-{8-[5-(acetylamino)pyridin-2-yl]-8-azabicyclo[3.2.1]oct-3-endo-yl}-1-(4-chlorophenyl)cyclopropanecarboxamide

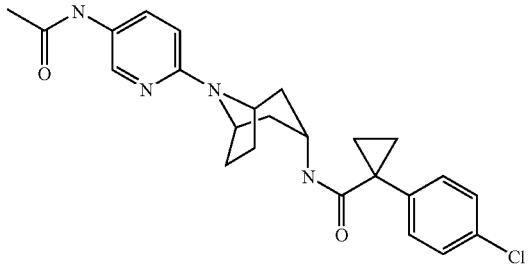

To a solution of N-[8-(5-aminopyridin-2-yl)-8-azabicyclo[3.2.1]oct-3-endo-yl]-1-(4-chlorophenyl)cyclopropanecarboxamide from Example 8 (0.16 g, 0.403 mmol) in pyridine (1 mL) and DCM (5 mL) was added acetyl chloride (0.2 mL, 2.81 mmol). After stirring 3 h, the reaction mixture was diluted with DCM (10 mL), washed with water and satd NH$_4$Cl, dried (MgSO$_4$), filtered and evaporated to give a residue. Purification of the residue by chromatography (silica, MeOH/DCM, 1:10) afforded N-{8-[5-(acetylamino)pyridin-2-yl]-8-azabicyclo[3.2.1]oct-3-endo-yl}-1-(4-chlorophenyl)cyclopropanecarboxamide (61 mg, 34%) as a light yellow solid. $^1$H NMR (400 MHz, CDCl$_3$): δ 8.06 (d, 1H), 7.80 (dd, 1H), 7.43 (AB q, 4H), 7.15 (br s, 1H), 6.48 (d, 1H), 5.85 (d, 1H), 4.33 (br s, 2H), 3.96 (m, 1H), 2.17 (m, 2H), 2.16 (s, 3H), 1.97 (m, 2H), 1.61 (m, 2H), 1.42 (d, 2H), 1.27 (m, 2H), 1.03 (m, 2H). MS (EI): 439 (MH+).

Using the same or analogous synthetic techniques described in any of the Examples and/or substituting with alternative commercial or literature reagents, the following compounds of the invention were prepared:

N-[8-(5-acetylpyridin-2-yl)-8-azabicyclo[3.2.1]oct-3-endo-yl]-1-(4-chlorophenyl)cyclopropanecarboxamide, MS (EI): 424 (MH+).

1-(4-chlorophenyl)-N-(8-{5-[(cyclopropylcarbonyl)amino]pyridin-2-yl}-8-azabicyclo[3.2.1]oct-3-endo-yl)cyclopropanecarboxamide, MS (EI): 465 (MH+).

1-(4-chlorophenyl)-N-(8-{5-[(methylsulfonyl)amino]pyridin-2-yl}-8-azabicyclo[3.2.1]oct-3-endo-yl)cyclopropanecarboxamide, MS (EI): 475 (MH+).

N-{6-[3-endo-({2-[(2,4-dichlorophenyl)oxy]-2-methylpropanoyl}amino)-8-azabicyclo[3.2.1]oct-8-yl]pyridin-3-yl}cyclopropanecarboxamide, MS (EI): 517 (MH+).

N-{8-[5-(acetylamino)pyridin-2-yl]-8-azabicyclo[3.2.1]oct-3-endo-yl}-2-[(2,4-dichlorophenyl)oxy]-2-methylpropanamide, MS (EI): 491 (MH+).

2-[(2,4-dichlorophenyl)oxy]-2-methyl-N-(8-{5-[(methylsulfonyl)amino]pyridin-2-yl}-8-azabicyclo[3.2.1]oct-3-endo-yl)propanamide, MS (EI): 527 (MH+). $^1$H NMR (CDCl3, 600 MHz): d 8.10 (d, J=2.4 Hz, 1H), 7.83 (dd, J=9.0 Hz, 1H), 7.65 (d, J=7.2 Hz, 1H), 7.45 (d, J=2.4 Hz, 1H), 7.39 (s, 1H), 7.21 (dd, J=8.4 Hz, 1H), 7.04 (d, J=9.0 Hz, 1H), 6.55 (d, J=9.0 Hz, 1H), 4.47 (s, 2H), 4.07 (q, J=7.2 Hz, 1H), 2.37-2.32 (m, 2H), 2.16 (s, 3H), 2.05-2.01 (m, 2H), 1.81 (br s, 2H), 1.68 (d, J=15.0 Hz, 2H), 1.55 (s, 6H). MS (EI): 491 (MH+).

N-{8-[4-(acetylamino)phenyl]-8-azabicyclo[3.2.1]oct-3-endo-yl}-2-[(2,4-dichlorophenyl)oxy]-2-methylpropanamide, MS (EI): 490 (MH+).

2-[(2,4-dichlorophenyl)oxy]-2-methyl-N-(8-{4-[(trifluoroacetyl)amino]phenyl}-8-azabicyclo[3.2.1]oct-3-endo-yl)propanamide, MS (EI): 544 (MH+).

N-{4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide, MS (EI): 588 (MH+).

2-[(2,4-dichlorophenyl)oxy]-2-methyl-N-{8-[5-({[(2,2,2-trifluoroethyl)amino]carbonyl}amino)pyridin-2-yl]-8-azabicyclo[3.2.1]oct-3-endo-yl}propanamide, MS (EI): 574 (MH+).

2-[(2,4-dichlorophenyl)oxy]-2-methyl-N-{8-[4-({[(2,2,2-trifluoroethyl)amino]carbonyl}amino)phenyl]-8-azabicyclo[3.2.1]oct-3-endo-yl}propanamide, MS (EI): 573 (MH+).

N-{8-[2-chloro-4-({[(2,2,2-trifluoroethyl)amino]carbonyl}amino)phenyl]-8-azabicyclo[3.2.1]oct-3-endo-yl}-2-[(2,4-dichlorophenyl)oxy]-2-methylpropanamide, MS (EI): 608 (MH+).

2-[(2,4-dichlorophenyl)oxy]-N-{8-[2-fluoro-4-({[(2,2,2-trifluoroethyl)amino]carbonyl}amino)phenyl]-8-azabicyclo[3.2.1]oct-3-endo-yl}-2-methylpropanamide, MS (EI): 591 (MH+).

N-{3-chloro-4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide, MS (EI): 593 (MH+).

N-{4-[3-endo-({2-[(2,4-dichlorophenyl)oxy]-2-methylpropanoyl}amino)-8-azabicyclo[3.2.1]oct-8-yl]-3-fluorophenyl}-3,3,3-trifluoropropanamide, MS (EI): 576 (MH+).

2-[(2,4-dichlorophenyl)oxy]-2-methyl-N-(8-{5-[(trifluoroacetyl)amino]pyridin-2-yl}-8-azabicyclo[3.2.1]oct-3-endo-yl)propanamide, MS (EI): 545 (MH+).

N-{6-[3-endo-({2-[(2,4-dichlorophenyl)oxy]-2-methylpropanoyl}amino)-8-azabicyclo[3.2.1]oct-8-yl]pyridin-3-yl}-3,3,3-trifluoropropanamide, MS (EI): 559 (MH+).

N-{5-chloro-6-[3-({2-[(2,4-dichlorophenyl)oxy]-2-methylpropanoyl}amino)-8-azabicyclo[3.2.1]oct-8-yl]pyridin-3-endo-yl}-3,3,3-trifluoropropanamide, MS (EI): 594 (MH+).

2-{[4-fluoro-2-(trifluoromethyl)phenyl]oxy}-2-methyl-N-(8-{4-[(methylsulfonyl)amino]phenyl}-8-azabicyclo[3.2.1]oct-3-endo-yl)propanamide, MS (EI): 544 (MH+).

2-[(2-chloro-4-fluorophenyl)oxy]-2-methyl-N-(8-{4-[(methylsulfonyl)amino]phenyl}-8-azabicyclo[3.2.1]oct-3-endo-yl)propanamide, MS (EI): 510 (MH+).

2-[(3,4-dichlorophenyl)oxy]-2-methyl-N-(8-{4-[(methylsulfonyl)amino]phenyl}-8-azabicyclo[3.2.1]oct-3-endo-yl)propanamide, MS (EI): 526 (MH+).

2-[(2,5-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide, MS (EI): 545 (MH+).

2-[(2,3-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide, MS (EI): 545 (MH+).

N-{8-[3-chloro-5-({[(2,2,2-trifluoroethyl)amino]carbonyl}amino)pyridin-2-yl]-8-azabicyclo[3.2.1]oct-3-endo-yl}-2-[(2,4-dichlorophenyl)oxy]-2-methylpropanamide, 1H NMR (DMSO-d6, 400 MHz): d 8.80 (s, 1H), 8.06 (d, J=2.4 Hz, 1H), 7.95 (d, J=2.0 Hz, 1H), 7.66 (d, J=2.8 Hz, 1H), 7.62 (d, J=6.4 Hz, 1H), 7.38 (dd, J=8.8 Hz, 1H), 7.08 (d, J=8.8 Hz, 1H), 6.89 (t, J=6.4 Hz, 1H), 4.28 (s, 2H), 3.91-3.87 (m, 3H), 2.27-2.24 (m, 2H), 1.80-1.86 (m, 6H), 1.43 (s, 6H). MS (EI): 609 (MH$^+$).

2-{[4-chloro-2-(trifluoromethyl)phenyl]oxy}-2-methyl-N-(8-{5-[(methylsulfonyl)amino]pyridin-2-yl}-8-azabicyclo[3.2.1]oct-3-endo-yl)propanamide, MS (EI): 561 (MH$^+$).

EXAMPLE 10

3-{[3-endo-({2-[(2,4-dichlorophenyl)oxy]-2-methylpropanoyl}amino)-8-azabicyclo[3.2.1]oct-8-yl]carbonyl}benzamide

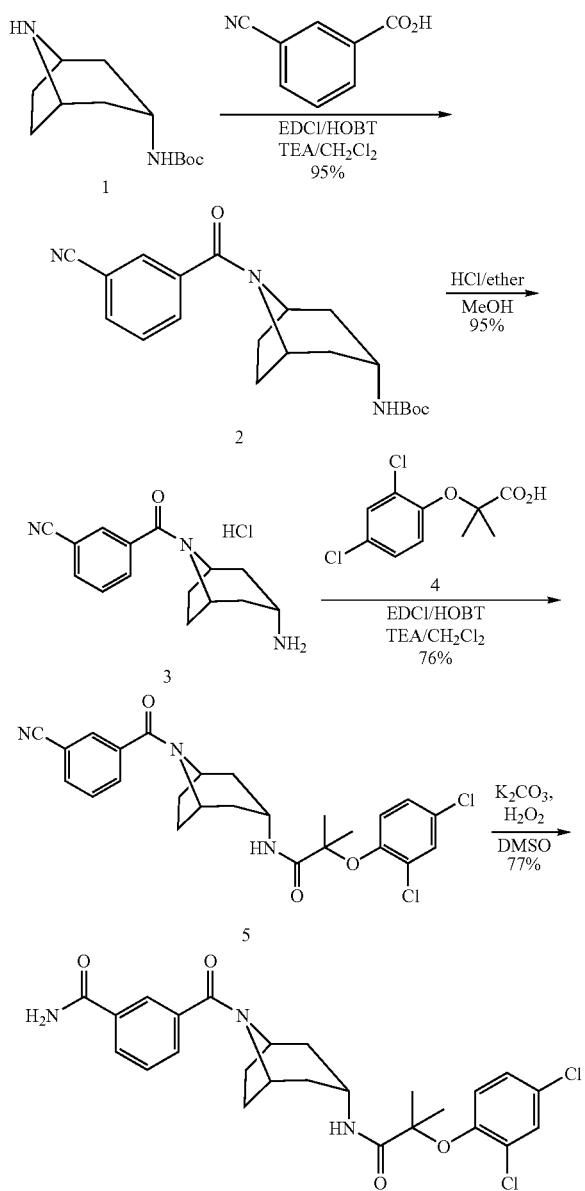

A mixture of tert-butyl 8-azabicyclo[3.2.1]octan-3-endo-ylcarbamate from Example 1(B) (2.3 g, 10.1 mmol), commercially available 4-cyanobenzoic acid (1.5 g, 10.2 mmol), EDCI (2.9 g, 15.1 mmol), HOBT (2.05 g, 15.1 mmol) and triethylamine (3.5 mL, 25.1 mmol) in CH$_2$Cl$_2$ (15 mL) was stirred 18 h at room temperature. The mixture was washed with 10% citric acid (10 mL), satd. aq. NaHCO$_3$ (10 mL) and brine (10 mL) successively. The organic solution was dried over MgSO$_4$, filtered and evaporated to give the product 2 (3.4 g, 9.56 mmol, 95% yield) which was used for the next step without further purification. Column chromatography (ethyl acetate to 1% methanol in ethyl acetate) of the residue gave tert-butyl 8-(3-cyanobenzoyl)-8-azabicyclo[3.2.1]octan-3-endo-ylcarbamate as a white solid (628 mg, 1.84 mmol, 91% yield). 1H NMR (CDCl$_3$, 400 MHz): δ 1.44 (s, 9H), 1.82 (m, 2H), 2.03 (m, 5H), 2.39 (m, 1H), 3.97 (m, 2H), 4.84 (br s, 1H), 7.55 (m, 1H), 7.74 (m, 3H).

To a solution of tert-butyl 8-(3-cyanobenzoyl)-8-azabicyclo[3.2.1]octan-3-endo-ylcarbamate (700 mg, 1.97 mmol) in methanol (30 mL) was added dropwise a solution 2N HCl solution in ether (10 mL). After stirring 16 h, the resulting mixture was evaporated to give 3-endo-(3-amino-8-azabicyclo[3.2.1]octane-8-carbonyl)benzonitrile as a HCl salt (547 mg, 1.87 mmol, 95% yield). 1H NMR (DMSO-d$_6$, 400 MHz): δ 1.83 (m, 6H), 2.25 (m, 2H), 3.39 (br s, 1H), 3.90 (br s, 1H), 4.31 (br s, 2H), 4.62 (br s, 1H), 7.50 (t, 1H), 7.56 (d, 1H), 7.98 (s, 1H), 8.14 (d, 1H), 8.27 (br s, 3H).

The reaction mixture of 3-(3-endo-amino-8-azabicyclo[3.2.1]octane-8-carbonyl)benzonitrile hydrochloride (300 mg, 1.03 mmol), commercially available 2-(2,4-dichlorophenoxy)-2-methylpropanoic acid (310 mg, 1.24 mmol), EDCI (300 mg, 1.54 mmol), HOBT (210 mg, 1.54 mmol) and triethylamine (0.75 mL, 5.38 mmol) in CH$_2$Cl$_2$ (10 mL) was stirred 18 h. The resulting mixture was washed with satd. aq. NaHCO$_3$ (5 mL) and brine (5 mL) successively, then dried over MgSO$_4$, filtered and evaporated to give a residue which was purified by column chromatography (ethyl acetate:CH$_2$Cl$_2$=1:1) to give N-(8-(3-cyanobenzoyl)-8-azabicyclo[3.2.1]octan-3-endo-yl)-2-(2,4-dichlorophenoxy)-2-methylpropanamide (378 mg, 0.78 mmol, 76% yield) as a white foam. 1H NMR (CDCl$_3$, 400 MHz): δ 1.55 (s, 6H), 1.85 (m, 2H), 2.00 (m, 3H), 2.20 (m, 3H), 2.50 (m, 1H), 4.04 (br s, 1H), 4.28 (q, 1H), 4.86 (br s, 1H), 7.05 (d, 1H), 7.22 (dd, 1H), 7.44 (d, 2H), 7.58 (m, 2H), 7.77 (m, 3H).

To a solution of N-(8-(3-cyanobenzoyl)-8-azabicyclo[3.2.1]octan-3-endo-yl)-2-(2,4-dichlorophenoxy)-2-methylpropanamide (310 mg, 0.637 mmol) in DMSO (2 mL) were added potassium carbonate (440 mg, 0.32 mmol) and hydrogen peroxide solution (ca. 30%, 0.4 mL) at 0° C. The resulting reaction mixture slow warmed to room temperature over 5 h. Excess of water (~100 mL) was added to the mixture and the resulting precipitate was collected and washed with water. The solid was dried in a vacuum to give 3-{[3-endo-({2-[(2,4-dichlorophenyl)oxy]-2-methylpropanoyl}amino)-8-azabicyclo[3.2.1]oct-8-yl]carbonyl}benzamide as a white solid (250 mg, 0.50 mmol, 77% yield). 1H NMR (CDCl$_3$, 400 MHz): δ 1.54 (s, 3H), 1.55 (s, 3H), 1.77 (d, 1H), 1.88 (d, 1H), 2.00 (m, 2H), 2.15 (m, 3H), 2.50 (m, 1H), 4.09 (br s, 1H), 4.14 (q, 1H), 4.88 (br s, 1H), 5.78 (br s, 1H), 6.35 (br s, 1H), 7.04 (d, 1H), 7.20 (dd, 1H), 7.44 (d, 1H), 7.52 (t, 1H), 7.58 (d, 1H), 7.63 (d, 1H), 7.93 (d, 1H), 7.94 (s, 1H). MS (EI): 504 (MH$^+$).

Using the same or analogous synthetic techniques described in any of the Examples and/or substituting with alternative commercial or literature reagents, the following compounds of the invention were prepared:

4-{[3-endo-({2-[(3,5-dichloropyridin-2-yl)oxy]-2-methylpropanoyl}amino)-8-azabicyclo[3.2.1]oct-8-yl]carbonyl}-N-(2,2,2-trifluoroethyl)benzamide, 1H NMR (CDCl$_3$, 400 MHz): δ 8.00 (s, 1H), 7.79 (d, J=5.6 Hz, 2H), 7.71 (s, 1H), 7.52 (t, J=4.0 Hz, 1H), 7.39 (d, J=5.6 Hz, 2H), 7.11 (d, J=4.8 Hz, 1H), 4.82 (s, 1H), 4.22 (q, J=4.4 Hz, 1H), 4.12 (m, 2H), 3.95 (s, 1H), 2.43 (m, 1H), 2.09 (m, 2H), 2.07 (m, 1H), 1.80 (m, 2H), 1.77 (m, 2H), 1.74 (d, J=3.2 Hz, 6H). MS (EI): 587 (MH+).

4-{[3-endo-({2-[(2,4-dichlorophenyl)oxy]-2-methylpropanoyl}amino)-8-azabicyclo[3.2.1]oct-8-yl]carbonyl}benzamide, MS (EI): 504 (MH+).

EXAMPLE 11

3-{[3-endo-({2-[(2,4-dichlorophenyl)oxy]-2-methylpropanoyl}amino)-8-azabicyclo[3.2.1]oct-8-yl]methyl}benzamide

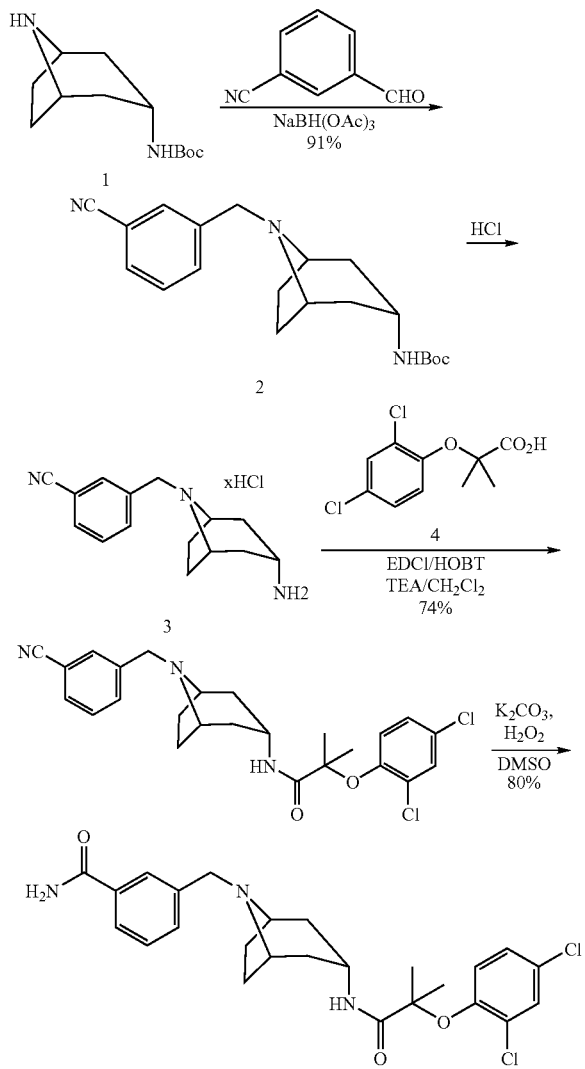

To a solution of commercially available 3-cyanobenzaldehyde (270 mg, 2.06 mmol) and of tert-butyl 8-azabicyclo[3.2.1]octan-3-endo-ylcarbamate (460 mg, 2.03 mmol) from Example 1(B) in dry CH$_2$Cl$_2$ (5 mL) were added AcOH (0.14 mL, 2.45 mmol) and NaBH(OAc)$_3$ (525 mg, 2.48 mmol) at room temperature. The resulting mixture was heated to ~50° C. over 1 h. After cooling, the reaction mixture was diluted with CH$_2$Cl$_2$ (15 mL), washed with satd. aq. NaHCO$_3$ solution (10 mL), dried over MgSO$_4$, filtered and evaporated to give a residue. Column chromatography (ethyl acetate to 1% methanol in ethyl acetate) of the residue gave tert-butyl 8-(3-cyanobenzyl)-8-azabicyclo[3.2.1]octan-3-endo-ylcarbamate as a white solid (628 mg, 1.84 mmol, 91% yield). 1H NMR (CDCl$_3$, 400 MHz): δ 1.44 (s, 9H), 1.64 (d, 2H), 1.86 (m, 2H), 2.14 (m, 4H), 3.12 (br s, 2H), 3.53 (ABq, 2H), 3.82 (m, 1H), 4.84 (br s, 1H), 7.42 (t, 1H), 7.52 (m, 1H), 7.62 (d, 4H), 7.69 (br s, 1H).

To a solution of tert-butyl 8-(3-cyanobenzyl)-8-azabicyclo[3.2.1]octan-3-endo-ylcarbamate (620 mg, 1.81 mmol) in CH$_2$Cl$_2$ (10 mL) was added dropwise a solution 2N HCl solution in ether (10 mL). After stirring 10 h, the resulting mixture was evaporated to give 3-((3-endo-amino-8-azabicyclo[3.2.1]octan-8-yl)methyl)benzonitrile dihydrochloride (570 mg, quantitative yield). 1H NMR (DMSO-d$_6$, 400 MHz): δ 2.06 (d, 2H), 2.26 (m, 2H), 2.44 (m, 2H), 2.82 (m, 2H), 3.87 (br s, 2H), 4.30 (ABq, 2H), 8.04 (d, 1H), 8.20 (d, 1H), 8.34 (s, 1H), 8.43 (br s, 3H).

A mixture of 3-((3-endo-amino-8-azabicyclo[3.2.1]octan-8-yl)methyl)benzonitrile dihydrochloride (470 mg, 1.49 mmol), commercially available 2-(2,4-dichlorophenoxy)-2-methylpropanoic acid (4) (447 mg, 1.79 mmol), EDCI (430 mg, 2.24 mmol), HOBT (304 mg, 2.24 mmol) and triethylamine (1.3 mL, 9.32 mmol) in CH$_2$Cl$_2$ (5 mL) was stirred 18 h. The resulting mixture was washed with satd. aq. NaHCO$_3$ solution (5 mL), brine (5 mL) successively, dried over MgSO$_4$, filtered and evaporated to give a residue which was purified by column chromatography (ethyl acetate: CH$_2$Cl$_2$=1:1) to give N-(8-(3-cyanobenzyl)-8-azabicyclo[3.2.1]octan-3-endo-yl)-2-(2,4-dichlorophenoxy)-2-methylpropanamide (526 mg, 1.11 mmol, 74% yield) as a solid. 1H NMR (CDCl$_3$, 400 MHz): δ 1.55 (s, 6H), 1.65 (d, 2H), 1.85 (m, 2H), 2.08 (m, 2H), 2.25 (m, 2H), 3.15 (br s, 2H), 3.55 (ABq, 2H), 4.17 (m, 1H), 7.04 (d, 1H), 7.20 (dd, 1H), 7.44 (m, 2H), 7.48 (m, 1H), 7.54 (m, 1H), 7.62 (d, 1H), 7.70 (br s, 1H).

To a solution of N-(8-(3-cyanobenzyl)-8-azabicyclo[3.2.1]octan-3-endo-yl)-2-(2,4-dichlorophenoxy)-2-methylpropanamide (470 mg, 0.99 mmol) in DMSO (4 mL) were added potassium carbonate (440 mg, 0.32 mmol) and hydrogen peroxide solution (ca. 30%, 0.5 mL) at 0° C. The resulting reaction mixture slow warmed to room temperature over 2 h. Excess of water (~100 mL) was added to the mixture and the resulting precipitate was collected. The solid was dissolved in ethyl acetate and the organic solution was dried over MgSO$_4$, filtered and evaporated to give a residue. Column chromatography (CH$_2$Cl$_2$: MeOH=10:1) of the residue gave 3-{[3-endo-({2-[(2,4-dichlorophenyl)oxy]-2-methylpropanoyl}amino)-8-azabicyclo[3.2.1]oct-8-yl]methyl}benzamide as a white foam (390 mg, 0.80 mmol, 80% yield). 1H NMR (CDCl$_3$, 400 MHz): δ 1.54 (s, 6H), 1.63 (d, 2H), 1.82 (m, 2H), 2.10 (m, 2H), 2.25 (m, 2H), 3.17 (br s, 2H), 3.55 (ABq, 2H), 4.14 (m, 1H), 6.51 (br s, 1H), 6.61 (br s, 1H), 7.03 (d, 1H), 7.20 (m, 1H), 7.38 (t, 2H), 7.42 (m, 1H), 7.49 (d, 1H), 7.56 (d, 1H), 7.72 (d, 1H), 7.85 (br s, 1H). MS (EI): 490 (MH+).

Using the same or analogous synthetic techniques described in any of the Examples and/or substituting with alternative commercial or literature reagents, the following compounds of the invention were prepared:

4-{[3-endo-({2-[(2,4-dichlorophenyl)oxy]-2-methylpropanoyl}amino)-8-azabicyclo[3.2.1]oct-8-yl]methyl}benzamide, 1H NMR (CDCl$_3$, 400 MHz): δ 7.91 (s, 1H), 7.80 (d, J=8.4 Hz, 1H), 7.67 (d, J=2.4 Hz, 1H), 7.46 (d, J=5.6 Hz, 1H), 7.39 (d, J=8.4 Hz, 2H), 7.36 (d, J=2.4 Hz, 1H), 3.93 (q, J=5.6 Hz, 1H), 3.52 (s, 2H), 3.06 (br s, 2H), 2.02 (m, 2H), 1.95 (m, 2H), 1.59 (m, 4H), 1.47 (s, 6H). MS (EI): 490 (MH+).

6-{[3-endo-({2-[(2,4-dichlorophenyl)oxy]-2-methylpropanoyl}amino)-8-azabicyclo[3.2.1]oct-8-yl]methyl}pyridine-3-carboxamide, MS (EI): 491 (MH+).

Using the same or analogous synthetic techniques described in any of the Examples (including any of Examples 1-11) and/or substituting with alternative commercial or literature reagents, the following compounds of the invention were prepared:

6-(3-endo-{[2-methyl-2-(naphthalen-2-yloxy)propanoyl]amino}-8-azabicyclo[3.2.1]oct-8-yl)-N-(2,2,2-trifluoroethyl)pyridine-3-carboxamide, MS (EI): 541 (MH+).

6-(3-endo-{[2-(isoquinolin-1-yloxy)-2-methylpropanoyl]amino}-8-azabicyclo[3.2.1]oct-8-yl)pyridine-3-carboxamide, MS (EI): 460 (MH+).

6-(3-endo-{[2-(2,4-dichlorophenoxy)-2-methylpropanoyl]amino}-8-azabicyclo[3.2.1]oct-8-yl)-N-[2-(pyrrolidin-1-yl)ethyl]pyridine-3-carboxamide, MS (EI): 575 (MH+).

6-(3-endo-{[2-(2,4-dichlorophenoxy)-2-methylpropanoyl]amino}-8-azabicyclo[3.2.1]oct-8-yl)-N-[3-(1 h-imidazol-1-yl)propyl]pyridine-3-carboxamide, MS (EI): 586 (MH+).

6-(3-endo-{[2-(2,4-dichlorophenoxy)-2-methylpropanoyl]amino}-8-azabicyclo[3.2.1]oct-8-yl)-N-(pyridin-4-ylmethyl)pyridine-3-carboxamide, MS (EI): 569 (MH+).

6-[3-endo-({2-[4-chloro-2-(trifluoromethyl)phenoxy]-2-methylpropanoyl}amino)-8-azabicyclo[3.2.1]oct-8-yl]-N-(2,2-difluoroethyl)pyridine-3-carboxamide, MS (EI): 575 (MH+).

6-[3-endo-({2-[4-chloro-2-(trifluoromethyl)phenoxy]-2-methylpropanoyl}amino)-8-azabicyclo[3.2.1]oct-8-yl]-N-(2,2-difluorocyclopropyl)pyridine-3-carboxamide, MS (EI): 587 (MH+).

6-[3-endo-({2-[(4-chlorobiphenyl-3-yl)oxy]-2-methylpropanoyl}amino)-8-azabicyclo[3.2.1]oct-8-yl]pyridine-3-carboxamide, MS (EI): 519 (MH+).

6-[3-endo-({2-[(4-chloro-4'-fluorobiphenyl-3-yl)oxy]-2-methylpropanoyl}amino)-8-azabicyclo[3.2.1]oct-8-yl]pyridine-3-carboxamide, MS (EI): 537 (MH+).

6-[3-endo-({2-methyl-2-[2-(trifluoromethoxy)phenoxy]propanoyl}amino)-8-azabicyclo[3.2.1]oct-8-yl]-N-(2,2,2-trifluoroethyl)pyridine-3-carboxamide, MS (EI): 575 (MH+).

6-[3-endo-({2-[(1-chloronaphthalen-2-yl)oxy]-2-methylpropanoyl}amino)-8-azabicyclo[3.2.1]oct-8-yl]-N-(2,2,2-trifluoroethyl)pyridine-3-carboxamide, MS (EI): 575 (MH+).

6-(3-endo-{[2-(2-chloro-4-fluorophenoxy)-2-methylpropanoyl]amino}-8-azabicyclo[3.2.1]oct-8-yl)-N-(2,2-difluorocyclopropyl)pyridine-3-carboxamide, MS (EI): 537 (MH+).

6-(3-endo-{[2-(2,4-dichlorophenoxy)-2-methylpropanoyl]amino}-8-azabicyclo[3.2.1]oct-8-yl)-N-[2-methyl-1-(pyrrolidin-1-yl)propan-2-yl]pyridine-3-carboxamide, MS (EI): 603 (MH+).

6-[3-endo-({2-[4-chloro-2-(dimethylsulfamoyl)phenoxy]-2-methylpropanoyl}amino)-8-azabicyclo[3.2.1]oct-8-yl]-n-(2,2,2-trifluoroethyl)pyridine-3-carboxamide, MS (EI): 632 (MH+). The requisite phenol is obtained by reacting 4-chlorophenol with N,N-dimethylsulfamoyl chloride and triethylamine in dichloromethane, followed by treatment with aluminum trichloride.

6-[3-endo-({2-[4-chloro-2-(2-methoxyethoxy)phenoxy]-2-methylpropanoyl}amino)-8-azabicyclo[3.2.1]oct-8-yl]-N-(2,2,2-trifluoroethyl)pyridine-3-carboxamide, MS (EI): 599 (MH+). The necessary phenol is synthesized by alkylation of catechol with 1-bromo-2-methoxyethane followed by chlorination according to a procedure in J. Org. Chem. 1985, 50, 2145-2148.

6-[3-endo-({2-[4-chloro-2-(propan-2-yl)phenoxy]-2-methylpropanoyl}amino)-8-azabicyclo[3.2.1]oct-8-yl]-N-(2,2,2-trifluoroethyl)pyridine-3-carboxamide, MS (EI): 567 (MH+). The necessary phenol is synthesized by chlorination of 2-isopropylphenol according to a procedure in J. Org. Chem. 1985, 50, 2145-2148.

6-(3-endo-{[2-(isoquinolin-1-yloxy)-2-methylpropanoyl]amino}-8-azabicyclo[3.2.1]oct-8-yl)-N-(2,2,2-trifluoroethyl)pyridine-3-carboxamide, MS (EI): 542 (MH+).

6-(3-endo-{[2-(2,4-dichlorophenoxy)-2-methylpropanoyl]amino}-8-azabicyclo[3.2.1]oct-8-yl)-N-(2,2-difluoroethyl)pyridine-3-carboxamide, MS (EI): 541 (MH+).

6-[3-endo-({2-[2-chloro-4-(hydroxymethyl)phenoxy]-2-methylpropanoyl}amino)-8-azabicyclo[3.2.1]oct-8-yl]-N-(2,2,2-trifluoroethyl)pyridine-3-carboxamide, MS (EI): 555 (MH+). The requisite fibrate was prepared in two steps by alkylation of 3-chloro-4-hydroxybenzaldehyde with ethyl 2-bromoisobutyrate followed by sodium borohydride reduction of the aldehyde.

6-[3-endo-({2-[4-chloro-2-(methylsulfonyl)phenoxy]-2-methylpropanoyl}amino)-8-azabicyclo[3.2.1]oct-8-yl]-N-(2,2-difluorocyclopropyl)pyridine-3-carboxamide, MS (EI): 597 (MH+).

6-(3-endo-{[2-(4-chloro-2-cyclopentylphenoxy)-2-methylpropanoyl]amino}-8-azabicyclo[3.2.1]oct-8-yl)-N-(2,2,2-trifluoroethyl)pyridine-3-carboxamide, MS (EI): 593 (MH+). The requisite phenol can be prepared by reaction of 4-chlorophenol and cyclopentanol in the presence of Montmorillonite K10 at 120° C.

6-[3-endo-({2-[4-chloro-2-(morpholin-4-yl)phenoxy]-2-methylpropanoyl}amino)-8-azabicyclo[3.2.1]oct-8-yl]-N-(2,2,2-trifluoroethyl)pyridine-3-carboxamide, MS (EI): 610 (MH+). The fibrate is prepared by reaction of ethyl 2-(2-bromo-4-chlorophenoxy)-2-methylpropanoate with morpholine under typical Buchwald amination conditions.

6-(3-endo-{[2-(2-carbamoyl-4-chlorophenoxy)-2-methylpropanoyl]amino}-8-azabicyclo[3.2.1]oct-8-yl)-N-(2,2,2-trifluoroethyl)pyridine-3-carboxamide, MS (EI): 568 (MH+). The carbamoyl group was installed in the final step by oxidation of the corresponding nitrile with hydrogen peroxide and potassium carbonate in dimethylsulfoxide.

6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide, MS (EI): 620 (MH+). Alkylation of 4,6-dichlorobenzene-1,3-diol with 2-bromoethanol provided the necessary phenol.

6-(3-endo-{[2-(2,4-dichlorophenoxy)-2-methylpropanoyl]amino}-8-azabicyclo[3.2.1]oct-8-yl)-N-[2-(morpholin-4-yl)ethyl]pyridine-3-carboxamide, MS (EI): 591 (MH+).

6-[3-endo-({2-[4-chloro-2-(trifluoromethoxy)phenoxy]-2-methylpropanoyl}amino)-8-azabicyclo[3.2.1]oct-8-yl]-N-(2,2,2-trifluoroethyl)pyridine-3-carboxamide, MS (EI): 609 (MH+). The requisite phenol is prepared by chlorination of 2-(trifluoromethoxy)phenol according to a procedure in J. Org. Chem. 1985, 50, 2145-2148.

6-[3-endo-({2-[4-chloro-2-(difluoromethyl)phenoxy]-2-methylpropanoyl}amino)-8-azabicyclo[3.2.1]oct-8-yl]-N-(2,2,2-trifluoroethyl)pyridine-3-carboxamide, MS (EI): 575 (MH+). The necessary fibrate is obtained by treatment of ethyl 2-(4-chloro-2-formylphenoxy)-2-methylpropanoate with (diethylamino)sulfur trifluoride.

2-[4-chloro-2-(difluoromethyl)phenoxy]-2-methyl-N-{8-[5-(methylsulfonyl)pyridin-2-yl]-8-azabicyclo[3.2.1]oct-3-endo-yl}propanamide, MS (EI): 528 (MH+).

6-(3-endo-{[2-(1 h-indol-4-yloxy)-2-methylpropanoyl]amino}-8-azabicyclo[3.2.1]oct-8-yl)-N-(2,2,2-trifluoroethyl)pyridine-3-carboxamide, MS (EI): 530 (MH+).

6-(3-endo-{[2-(2,4-dichlorophenoxy)-2-methylpropanoyl]amino}-8-azabicyclo[3.2.1]oct-8-yl)-N-(2-hydroxyethyl)pyridine-3-carboxamide, MS (EI): 521 (MH+).

6-[3-endo-({2-[4-chloro-2-(methylsulfonyl)phenoxy]-2-methylpropanoyl}amino)-8-azabicyclo[3.2.1]oct-8-yl]-N-(propan-2-yl)pyridine-3-carboxamide, MS (EI): 563 (MH+).

N-(2,2-difluorocyclopropyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide, MS (EI): 571 (MH+).

6-[3-endo-({2-[4-chloro-2-(trifluoromethyl)phenoxy]-2-methylpropanoyl}amino)-8-azabicyclo[3.2.1]oct-8-yl]-N-(propan-2-yl)pyridine-3-carboxamide, MS (EI): 553 (MH+).

6-(3-endo-{[2-(2-chloro-4-fluorophenoxy)-2-methylpropanoyl]amino}-8-azabicyclo[3.2.1]oct-8-yl)-N-(2,2-difluoroethyl)pyridine-3-carboxamide, MS (EI): 525 (MH+).

N-(2,2-difluoroethyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide, MS (EI): 559 (MH+).

6-(3-endo-{[2-(2,4-dichlorophenoxy)-2-methylpropanoyl]amino}-8-azabicyclo[3.2.1]oct-8-yl)-N-[(2R)-1,1,1-trifluoropropan-2-yl]pyridine-3-carboxamide, MS (EI): 573 (MH+).

6-(3-endo-{[2-(2,4-dichlorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 573 (MH+).

5-chloro-2-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)benzoic acid, MS (EI): 569 (MH+).

6-[3-endo-({2-[4-chloro-2-(hydroxymethyl)phenoxy]-2-methylpropanoyl}amino)-8-azabicyclo[3.2.1]oct-8-yl]-N-(2,2,2-trifluoroethyl)pyridine-3-carboxamide, MS (EI): 555 (MH+). The hydroxymethyl group was installed in the final step by treatment of 6-(3-endo-(2-(4-chloro-2-formylphenoxy)-2-methylpropanamido)-8-azabicyclo[3.2.1]octan-8-yl)-N-(2,2,2-trifluoroethyl)nicotinamide with sodium borohydride.

6-(3-endo-{[2-(2,4-dichlorophenoxy)-2-methylpropanoyl]amino}-8-azabicyclo[3.2.1]oct-8-yl)-N-[2-(diethylamino)ethyl]pyridine-3-carboxamide, MS (EI): 577 (MH+).

6-(3-endo-{[2-(2,4-dichlorophenoxy)-2-methylpropanoyl]amino}-8-azabicyclo[3.2.1]oct-8-yl)-N-(tetrahydro-2 h-pyran-4-yl)pyridine-3-carboxamide, $^1$H NMR (CDCl$_3$, 400 MHz): d 8.57 (d, J=2.0 Hz, 1H), 7.89 (dd, J=8.8 Hz, 1H), 7.66 (d, J=7.2 Hz, 1H), 7.45 (d, J=2.4 Hz, 1H), 7.22 (dd, J=8.4 Hz, 1H), 7.05 (d, J=8.8 Hz, 1H), 6.51 (d, J=8.8 Hz, 1H), 6.00 (d, J=7.6 Hz, 1H), 4.58 (br s, 2H), 4.24-3.97 (m, 4H), 3.52 (t, J=11.6 Hz, 2H), 2.31-2.17 (m, 4H), 2.07-1.97 (m, 4H), 1.73 (d, J=15.2 Hz, 2H), 1.55 (s, 6H). MS (EI): 562 (MH+).

6-(3-endo-{[2-(2,4-dichlorophenoxy)-2-methylpropanoyl]amino}-8-azabicyclo[3.2.1]oct-8-yl)-N-(1,1-dioxidotetrahydro-2 h-thiopyran-4-yl)pyridine-3-carboxamide, MS (EI): 610 (MH+).

6-(3-endo-{[2-(2,4-dichlorophenoxy)-2-methylpropanoyl]amino}-8-azabicyclo[3.2.1]oct-8-yl)-N-(tetrahydro-2H-thiopyran-4-yl)pyridine-3-carboxamide, 1H NMR (CDCl$_3$, 400 MHz): d 8.56 (d, J=2.0 Hz, 1H), 7.93 (dd, J=8.8 Hz, 1H), 7.77 (d, J=7.2 Hz, 1H), 7.50-7.46 (m, 2H), 7.23 (dd, J=8.8 Hz, 1H), 7.07 (d, J=8.8 Hz, 1H), 6.56 (d, J=9.2 Hz, 1H), 4.58 (br s, 2H), 4.28-4.21 (m, 1H), 4.07 (q, J=6.8 Hz, 1H), 3.24-3.11 (m, 4H), 2.36-2.04 (m, 10H), 1.76 (d, J=14.8 Hz, 2H), 1.55 (s, 6H). MS (EI): 578 (MH+).

6-[3-endo-({2-[2,4-dichloro-5-(2-methoxyethoxy)phenoxy]-2-methylpropanoyl}amino)-8-azabicyclo[3.2.1]oct-8-yl]-N-(2,2,2-trifluoroethyl)pyridine-3-carboxamide, MS (EI): 634 (MH+). The requisite phenol can be prepared by alkylation of 4,6-dichlorobenzene-1,3-diol with 1-bromo-2-methoxyethane using sodium hydride as a base.

6-[3-endo-({2-[4-chloro-2-(2-hydroxyethyl)phenoxy]-2-methylpropanoyl}amino)-8-azabicyclo[3.2.1]oct-8-yl]-N-(2,2,2-trifluoroethyl)pyridine-3-carboxamide, MS (EI): 569 (MH+). The requisite phenol is prepared by reduction of benzofuran-2(3H)-one with lithium aluminum hydride followed by chlorination according to a procedure in J. Org. Chem. 1985, 50, 2145-2148.

6-(3-endo-{[2-(2,4-dichlorophenoxy)-2-methylpropanoyl]amino}-8-azabicyclo[3.2.1]oct-8-yl)-N-[1-(hydroxymethyl)cyclopropyl]pyridine-3-carboxamide, 1H NMR (CDCl3, 400 MHz): d 8.53 (d, J=2.4 Hz, 1H), 7.87 (dd, J=8.8 Hz, 1H), 7.65 (d, J=7.2 Hz, 1H), 7.45 (d, J=2.4 Hz, 1H), 7.21 (dd, J=8.8 Hz, 1H), 7.05 (d, J=8.8 Hz, 1H), 6.62 (s, 1H), 6.50 (d, J=8.8 Hz, 1H), 4.58 (br s, 2H), 4.32 (t, J=2.4 Hz, 1H), 4.09 (q, J=6.8 Hz, 1H), 3.69 (d, J=4.0 Hz, 2H), 2.30-2.03 (m, 6H), 1.72 (d, J=14.4 Hz, 2H), 1.55 (s, 6H), 1.02-0.91 (m, 4H). MS (EI): 548 (MH+).

6-(3-endo-{[2-(1H-indazol-4-yloxy)-2-methylpropanoyl]amino}-8-azabicyclo[3.2.1]oct-8-yl)-N-(2,2,2-trifluoroethyl)pyridine-3-carboxamide, MS (EI): 531 (MH+).

6-(3-endo-{[2-(2,4-dichlorophenoxy)-2-methylpropanoyl]amino}-8-azabicyclo[3.2.1]oct-8-yl)-N-(isoxazol-3-yl)pyridine-3-carboxamide, MS (EI): 544 (MH+).

6-{3-endo-[(2-{4-chloro-2-[2-(1H-imidazol-1-yl)ethoxy]phenoxy}-2-methylpropanoyl)amino]-8-azabicyclo[3.2.1]oct-8-yl}-N-(2,2,2-trifluoroethyl)pyridine-3-carboxamide, MS (EI): 635 (MH+). The necessary fibrate is synthesized by treatment of ethyl 2-(4-chloro-2-(2-hydroxyethoxy)phenoxy)-2-methylpropanoate with methanesulfonyl chloride followed by reaction with imidazole.

6-(3-endo-{[2-(4-chloro-2-sulfamoylphenoxy)-2-methylpropanoyl]amino}-8-azabicyclo[3.2.1]oct-8-yl)-N-(2,2,2-trifluoroethyl)pyridine-3-carboxamide, MS (EI): 604 (MH+). The necessary phenol is synthesized by reaction of 5-chloro-2-methoxybenzene-1-sulfonyl chloride with ammonium hydroxide followed by deprotection of the methyl ether with boron tribromide.

6-[3-endo-({2-[4-chloro-2-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide, MS (EI): 585 (MH+). The requisite phenol is prepared by alkylation of catechol with 2-bromoethanol followed by chlorination according to a procedure in J. Org. Chem. 1985, 50, 2145-2148.

6-(3-endo-{[2-(1H-indol-7-yloxy)-2-methylpropanoyl]amino}-8-azabicyclo[3.2.1]oct-8-yl)-N-(2,2,2-trifluoroethyl)pyridine-3-carboxamide, MS (EI): 530 (MH+).

6-[3-endo-({2-[2-chloro-4-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide, MS (EI): 583 (MH+). The necessary phenol is prepared by treatment of 4-bromo-2-chlorophenol with sodium hydride, n-butyllithium, then acetone.

6-[3-endo-({2-[2,4-dichloro-5-(2-hydroxyethoxy)phenoxy]-2-methylpropanoyl}amino)-8-azabicyclo[3.2.1]oct-8-yl]-N-(2,2-difluorocyclopropyl)pyridine-3-carboxamide, MS (EI): 614 (MH+).

6-[3-endo-({2-[4-chloro-2-(difluoromethyl)phenoxy]-2-methylpropanoyl}amino)-8-azabicyclo[3.2.1]oct-8-yl]-N-(2,2-difluorocyclopropyl)pyridine-3-carboxamide, 1H NMR (CDCl$_3$, 400 MHz): d 8.54 (d, J=2.4 Hz, 1H), 7.87 (dd, J=9.2 Hz, 1H), 7.57 (d, J=2.4 Hz, 1H), 7.34 (dd, J=9.2 Hz, 1H), 6.95 (d, J=7.6 Hz, 1H), 6.87 (t, J=55.2 Hz, 1H), 6.85 (d, J=7.6 Hz, 1H), 6.48 (d, J=8.8 Hz, 1H), 6.18 (br s, 1H), 4.53 (br s, 2H), 4.90 (q, J=7.2 Hz, 1H), 3.61-3.41 (m, 1H), 2.28-2.21 (m, 2H), 2.10-2.07 (m, 2H), 1.95-1.82 (m, 1H), 1.71-1.57 (m, 10H), 1.43-4.12 (m, 1H). MS (EI): 569 (MH+).

6-[3-endo-({2-[4-chloro-2-(trifluoromethoxy)phenoxy]-2-methylpropanoyl}amino)-8-azabicyclo[3.2.1]oct-8-yl]-N-(2,2-difluorocyclopropyl)pyridine-3-carboxamide, 1H NMR (CDCl$_3$, 400 MHz): d 8.56 (d, J=2.4 Hz, 1H), 7.87 (dd, J=8.8 Hz, 1H), 7.32-7.22 (m, 4H), 7.02 (d, J=8.8 Hz, 1H), 6.50 (d, J=5.2 Hz, 1H), 6.18 (br s, 1H), 4.58 (br s, 1H), 4.07 (q, J=6.4 Hz, 1H), 3.54-3.45 (m, 1H), 2.30-2.14 (m, 4H), 1.94-1.84 (m, 3H), 1.71 (d, J=14.8 Hz, 2H), 1.50 (s, 6H), 1.47-1.40 (m, 1H). MS (EI): 603 (MH+).

6-(3-endo-{[2-(2,4-dichlorophenoxy)-2-methylpropanoyl]amino}-8-azabicyclo[3.2.1]oct-8-yl)-N-(1-hydroxy-2-methylpropan-2-yl)pyridine-3-carboxamide, MS (EI): 550 (MH+).

6-(3-endo-{[2-(2,4-dichlorophenoxy)-2-methylpropanoyl]amino}-8-azabicyclo[3.2.1]oct-8-yl)-n-(2-hydroxy-2-methylpropyl)pyridine-3-carboxamide, MS (EI): 550 (MH+).

6-(3-endo-{[2-(2,4-dichlorophenoxy)-2-methylpropanoyl]amino}-8-azabicyclo[3.2.1]oct-8-yl)-N-[(2S)-1-hydroxypropan-2-yl]pyridine-3-carboxamide, MS (EI): 536 (MH+).

6-(3-endo-{[2-(2,4-dichlorophenoxy)-2-methylpropanoyl]amino}-8-azabicyclo[3.2.1]oct-8-yl)-N-[(2R)-1-hydroxypropan-2-yl]pyridine-3-carboxamide, MS (EI): 536 (MH+).

6-(3-endo-(2-(3,5-dichloropyridin-2-yloxy)-2-methylpropanamido)-8-azabicyclo[3.2.1]octan-8-yl)-N-(2,2-difluorocyclopropyl)nicotinamide, MS (EI): 554 (MH+).

6-(3-endo-(2-(3,5-dichloropyridin-2-yloxy)-2-methylpropanamido)-8-azabicyclo[3.2.1]octan-8-yl)-N-isopropylnicotinamide, MS (EI): 521 (MH+).

6-(3-endo-(2-(4-chloro-2-(trifluoromethoxy)phenoxy)-2-methylpropanamido)-8-azabicyclo[3.2.1]octan-8-yl)-N-(2,2-difluoroethyl)nicotinamide, MS (EI): 591 (MH+).

6-(3-endo-(2-(2,4-dichloro-5-(2-hydroxyethoxy)phenoxy)-2-methylpropanamido)-8-azabicyclo[3.2.1]octan-8-yl)-N-(2,2-difluoroethyl)nicotinamide, MS (EI): 602 (MH+).

6-(3-endo-(2-(4-chloro-2-(difluoromethyl)phenoxy)-2-methylpropanamido)-8-azabicyclo[3.2.1]octan-8-yl)-N-(1-(hydroxymethyl)cyclopropyl)nicotinamide, 1H NMR (CDCl$_3$, 600 MHz): d 8.51 (d, J=2.4 Hz, 1H), 7.85 (dd, J=9.0 Hz, 1H), 7.57 (d, J=2.4 Hz, 1H), 7.34 (dd, J=6.6 Hz, 1H), 6.95 (s, 1H), 6.87 (t, J=51 Hz, 1H), 6.85 (d, J=7.2 Hz, 1H), 6.65 (s, 1H), 6.47 (d, J=9.0 Hz, 1H), 4.51 (br s, 2H), 4.34 (br s, 1H), 4.07 (q, J=7.2 Hz, 1H), 3.68 (s, 1H), 2.25-2.21 (m, 2H), 2.09-2.08 (m, 2H), 1.69 (d, J=6.6 Hz, 2H), 1.60-1.59 (m, 8H), 1.00-0.92 (m, 4H). MS (EI): 563 (MH+).

6-(3-endo-(2-(4-chloro-2-(difluoromethyl)phenoxy)-2-methylpropanamido)-8-azabicyclo[3.2.1]octan-8-yl)-N-(isoxazol-3-yl)nicotinamide, MS (EI): 560 (MH+).

6-(3-endo-(2-(2,4-dichloro-5-(2-(pyrrolidin-1-yl)ethoxy)phenoxy)-2-methylpropanamido)-8-azabicyclo[3.2.1]octan-8-yl)-N-(2,2,2-trifluoroethyl)nicotinamide, MS (EI): 673 (MH+). The pyrrolidinyl group was introduced by treatment of 6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide with methanesulfonyl chloride followed by pyrrolidine.

6-(3-endo-(2-(2,4-dichloro-5-(2-(4-methylpiperazin-1-yl)ethoxy)phenoxy)-2-methylpropanamido)-8-azabicyclo[3.2.1]octan-8-yl)-N-(2,2,2-trifluoroethyl)nicotinamide, MS (EI): 702 (MH+). The methylpiperazinyl group was introduced by treatment of 6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide with methanesulfonyl chloride followed by 1-methylpiperazine.

6-(3-endo-(2-(2,4-dichloro-5-(2-morpholinoethoxy)phenoxy)-2-methylpropanamido)-8-azabicyclo[3.2.1]octan-8-yl)-N-(2,2,2-trifluoroethyl)nicotinamide, MS (EI): 689 (MH+). The morpholino group was introduced by treatment of 6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide with methanesulfonyl chloride followed by morpholine.

6-(3-endo-(2-(3,5-dichloropyridin-2-yloxy)-2-methylpropanamido)-8-azabicyclo[3.2.1]octan-8-yl)-N-(2,2-difluoroethyl)nicotinamide, MS (EI): 542 (MH+).

6-(3-endo-(2-(5-chloro-3-fluoropyridin-2-yloxy)-2-methylpropanamido)-8-azabicyclo[3.2.1]octan-8-yl)-N-(2,2-difluoroethyl)nicotinamide, MS (EI): 526 (MH+).

6-(3-endo-(2-(4-chloro-2-(trifluoromethoxy)phenoxy)-2-methylpropanamido)-8-azabicyclo[3.2.1]octan-8-yl)-N—((S)-1,1,1-trifluoropropan-2-yl)nicotinamide, MS (EI): 623 (MH+).

6-(3-endo-(2-(4-chloro-2-(difluoromethyl)phenoxy)-2-methylpropanamido)-8-azabicyclo[3.2.1]octan-8-yl)-N—((R)-1,1,1-trifluoropropan-2-yl)nicotinamide, MS (EI): 589 (MH+).

6-(3-endo-(2-(4-chloro-2-(trifluoromethyl)phenoxy)-2-methylpropanamido)-8-azabicyclo[3.2.1]octan-8-yl)-N—((R)-1,1,1-trifluoropropan-2-yl)nicotinamide, MS (EI): 607 (MH+).

2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)acetic acid, MS (EI): 633 (MH+). The carboxylic acid was installed in the final step by oxidation of 6-[3-endo-({2-[2,4-dichloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide with H$_5$IO$_6$/CrO$_3$.

2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)-2-methylpropanoic acid, MS (EI): 662 (MH+). The title compound is prepared by hydrolysis of ethyl 2-(2,4-dichloro-5-(2-methyl-1-oxo-1-(8-(5-(2,2,2-trifluoroethylcarbamoyl)pyridin-2-yl)-8-azabicyclo[3.2.1]octan-3-ylamino)propan-2-yloxy)phenoxy)-2-methylpropanoate with 2N sodium hydroxide in methanol. The requisite fibrate is synthesized by alkylation of 4,6-dichlororesorcinol with ethyl 2-bromoisobutyrate followed by treatment 2N sodium hydroxide.

6-[3-endo-({2-[4-chloro-2-(trifluoromethoxy)phenoxy]-2-methylpropanoyl}amino)-8-azabicyclo[3.2.1]oct-8-yl]-N-[(2R)-1,1,1-trifluoropropan-2-yl]pyridine-3-carboxamide, MS (EI): 623 (MH+).

6-[3-endo-({2-[4-chloro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 607 (MH+).

6-[3-endo-({2-[(3,5-dichloropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 574 (MH+).

6-[3-endo-({2-[2-(difluoromethyl)-4-fluorophenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 573 (MH+).

6-[3-endo-({2-[(5-chloro-3-fluoropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 558 (MH+).

6-(3-endo-{[2-(4-chlorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 539 (MH+).

6-(3-endo-{[2-(2,4-dichlorophenoxy)-2-methylpropanoyl]amino}-8-azabicyclo[3.2.1]oct-8-yl)-N-(3,3,3-trifluoro-2-hydroxypropyl)pyridine-3-carboxamide, MS (EI): 589 (MH+).

6-[3-endo-({2-[4-chloro-2-(methylsulfonyl)phenoxy]-2-methylpropanoyl}amino)-8-azabicyclo[3.2.1]oct-8-yl]-N-(2,2-difluoroethyl)pyridine-3-carboxamide, MS (EI): 585 (MH+).

6-[3-endo-({2-[4-fluoro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 591 (MH+).

6-[3-endo-({2-[4-chloro-2-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 589 (MH+).

6-(3-endo-{[2-(2,4-dichloro-5-fluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 591 (MH+).

6-{3-endo-[(2-{5-[(1-amino-2-methyl-1-oxopropan-2-yl)oxy]-2,4-dichlorophenoxy}-2-methylpropanoyl)amino]-8-azabicyclo[3.2.1]oct-8-yl}-N-(2,2,2-trifluoroethyl)pyridine-3-carboxamide, MS (EI): 661 (MH+). The carbamoyl group is installed in the final step by treatment of ethyl 2-(2,4-dichloro-5-(2-methyl-1-oxo-1-(8-(5-(2,2,2-trifluoroethylcarbamoyl)pyridin-2-yl)-8-azabicyclo[3.2.1]octan-3-ylamino)propan-2-yloxy)phenoxy)-2-methylpropanoate with ammonia in methanol.

6-[3-endo-({2-[4-chloro-2-(trifluoromethoxy)phenoxy]-2-methylpropanoyl}amino)-8-azabicyclo[3.2.1]oct-8-yl]-N-[1-(hydroxymethyl)cyclopropyl]pyridine-3-carboxamide, MS (EI): 597 (MH+).

6-[3-endo-({2-[2,4-dichloro-5-(hydroxymethyl)phenoxy]-2-methylpropanoyl}amino)-8-azabicyclo[3.2.1]oct-8-yl]-N-(2,2-difluoroethyl)pyridine-3-carboxamide, MS (EI): 571 (MH+). The requisite fibrate is synthesized by reacting ethyl 2-(5-(bromomethyl)-2,4-dichlorophenoxy)-2-methylpropanoate with calcium carbonate in aqueous dioxane.

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, 1H NMR (CDCl$_3$, 400 MHz): d 8.61 (d, J=2.4 Hz, 1H), 7.91 (dd, J=8.8 Hz, 1H), 7.67 (d, J=7.2 Hz, 1H), 7.59 (s, 1H), 7.43 (s, 1H), 6.53-6.50 (m, 2H), 5.95 (t, J=55.2 Hz, 1H), 4.59 (br s, 2H), 4.12 (q, J=6.8 Hz, 1H), 3.83-3.76 (m, 2H), 2.61 (s, 1H), 2.30-2.24 (m, 2H), 2.18-2.16 (m, 2H), 2.06-2.02 (m, 2H), 1.77-1.70 (m, 8H), 1.56 (s, 6H). MS (EI): 600 (MH+). The requisite phenol can be prepared by borylation and oxidation of methyl 2,4-dichlorobenzoate (according to a procedure outlined in J. Am. Chem. Soc. 2003, 125, 7792-7793) followed by treatment with excess methyl magnesium bromide.

6-(3-endo-{[2-(2-chloro-4,5-difluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 575 (MH+).

6-(3-endo-{[2-(2,4-difluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 541 (MH+).

6-[3-endo-({2-[4-chloro-2-(methylsulfonyl)phenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 617 (MH+).

6-[3-endo-({2-[4-chloro-2-(difluoromethyl)phenoxy]-2-methylpropanoyl}amino)-8-azabicyclo[3.2.1]oct-8-yl]-N-(2,2-difluoroethyl)pyridine-3-carboxamide, MS (EI): 557 (MH+).

6-(3-endo-{[2-(2-chloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 557 (MH+).

6-(3-endo-{[2-(4-chloro-2-fluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 557 (MH+).

6-(3-endo-{[2-(2,4-dichloro-5-fluorophenoxy)-2-methylpropanoyl]amino}-8-azabicyclo[3.2.1]oct-8-yl)-N-(2,2-difluoroethyl)pyridine-3-carboxamide, MS (EI): 559 (MH+).

6-(3-endo-{[2-(2,3-dichloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide, MS (EI): 591 (MH+).

6-[3-endo-({2-[4-chloro-2-(trifluoromethoxy)phenoxy]-2-methylpropanoyl}amino)-8-azabicyclo[3.2.1]oct-8-yl]-N-(2-hydroxy-2-methylpropyl)pyridine-3-carboxamide, MS (EI): 599 (MH+).

6-{3-endo-[(2-{[3-(difluoromethyl)-5-fluoropyridin-2-yl]oxy}-2-methylpropanoyl)amino]-8-azabicyclo[3.2.1]oct-8-yl}-N-[(2S)-1,1,1-trifluoropropan-2-yl]pyridine-3-carboxamide, MS (EI): 574 (MH+). The necessary phenol is prepared by reaction of 5-fluoro-2-methoxynicotinaldehyde with DAST followed by methyl ether deprotection with trimethylsilyliodide.

N-(2,2-difluoroethyl)-6-{3-endo-[(2-{[3-(difluoromethyl)-5-fluoropyridin-2-yl]oxy}-2-methylpropanoyl)amino]-8-azabicyclo[3.2.1]oct-8-yl}pyridine-3-carboxamide, MS (EI): 542 (MH+).

6-(3-endo-{[2-(2,3-dichloro-4-fluorophenoxy)-2-methylpropanoyl]amino}-8-azabicyclo[3.2.1]oct-8-yl)-N-(2,2-difluoroethyl)pyridine-3-carboxamide, MS (EI): 559 (MH+).

6-(3-endo-{[2-(2-chloro-4,5-difluorophenoxy)-2-methylpropanoyl]amino}-8-azabicyclo[3.2.1]oct-8-yl)-N-(2,2-difluoroethyl)pyridine-3-carboxamide, MS (EI): 543 (MH+).

N-(2,2-difluoroethyl)-6-(3-endo-{[2-(2,4-difluorophenoxy)-2-methylpropanoyl]amino}-8-azabicyclo[3.2.1]oct-8-yl)pyridine-3-carboxamide, MS (EI): 509 (MH+).

[2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]acetic acid, MS (EI): 617 (MH+). The acid is installed by hydrolysis of the corresponding nitrile in the final step. The synthesis of the necessary phenol begins with chlorination of 2-chloro-5-methylphenol (according to a procedure in J. Org. Chem. 1985, 50, 2145-2148) followed by alkylation with ethyl 2-bromoisobutyrate. Bromination with NBS and benzoyl peroxide followed by treatment with sodium cyanide generates the appropriately substituted phenol.

2-[2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]-2-methylpropanoic acid, MS (EI): 646 (MH+). The carboxylic acid is installed in the final step by acid treatment of 6-(3-endo-(2-(2,4-dichloro-5-(2-cyanopropan-2-yl)phenoxy)-2-methylpropanamido)-8-azabicyclo[3.2.1]octan-8-yl)-N-(2,2,2-trifluoroethyl)nicotinamide. The necessary fibrate is prepared by treating ethyl 2-(2,4-dichloro-5-(cyanomethyl)phenoxy)-2-methylpropanoate with sodium hydride and iodomethane.

6-[3-endo-({2-[5-(1-amino-2-methyl-1-oxopropan-2-yl)-2,4-dichlorophenoxy]-2-methylpropanoyl}amino)-8-azabicyclo[3.2.1]oct-8-yl]-N-(2,2,2-trifluoroethyl)pyridine-3-carboxamide, MS (EI): 645 (MH+). The carbamoyl group is installed in the final step by treatment of 6-(3-endo-(2-(2,4-dichloro-5-(2-cyanopropan-2-yl)phenoxy)-2-methylpropanamido)-8-azabicyclo[3.2.1]octan-8-yl)-N-(2,2,2-trifluoroethyl)nicotinamide with hydrogen peroxide in the presence of potassium carbonate.

6-(3-endo-{[2-(4-chloro-2-fluorophenoxy)-2-methylpropanoyl]amino}-8-azabicyclo[3.2.1]oct-8-yl)-N-(2,2-difluoroethyl)pyridine-3-carboxamide, MS (EI): 525 (MH+).

6-[3-endo-({2-[4-chloro-2-(trifluoromethoxy)phenoxy]-2-methylpropanoyl}amino)-8-azabicyclo[3.2.1]oct-8-yl]-N-(3,3,3-trifluoro-2-hydroxypropyl)pyridine-3-carboxamide, MS (EI): 639 (MH+).

6-[3-endo-({2-[4-chloro-2-(difluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide, MS (EI): 605 (MH+).

6-(3-endo-{[2-(2,4-dichloro-5-fluorophenoxy)-2-methylpropanoyl]amino}-8-azabicyclo[3.2.1]oct-8-yl)-N-[(2R)-1,1,1-trifluoropropan-2-yl]pyridine-3-carboxamide, MS (EI): 591 (MH+).

6-(3-endo-{[2-(2-chloro-4,5-difluorophenoxy)-2-methylpropanoyl]amino}-8-azabicyclo[3.2.1]oct-8-yl)-N-[(2R)-1,1,1-trifluoropropan-2-yl]pyridine-3-carboxamide, MS (EI): 575 (MH+).

6-(3-endo-{[2-(2-chloro-4-fluorophenoxy)-2-methylpropanoyl]amino}-8-azabicyclo[3.2.1]oct-8-yl)-N-[(2R)-1,1,1-trifluoropropan-2-yl]pyridine-3-carboxamide, MS (EI): 557 (MH+).

6-[3-endo-({2-[2-chloro-4-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide, MS (EI): 589 (MH+).

2-[4-chloro-2-(trifluoromethoxy)phenoxy]-n-(8-{5-[(3-hydroxypyrrolidin-1-yl)carbonyl]pyridin-2-yl}-8-azabicyclo[3.2.1]oct-3-endo-yl)-2-methylpropanamide, MS (EI): 597 (MH+).

2-[4-chloro-2-(trifluoromethoxy)phenoxy]-n-[8-(5-{[(2s)-2-(hydroxymethyl)pyrrolidin-1-yl]carbonyl}pyridin-2-yl)-8-azabicyclo[3.2.1]oct-3-endo-yl]-2-methylpropanamide, MS (EI): 611 (MH+).

6-(3-endo-{[2-(2,4-dichlorophenoxy)-2-methylpropanoyl]amino}-8-azabicyclo[3.2.1]oct-8-yl)-N-[(2S)-3,3,3-trifluoro-2-hydroxypropyl]pyridine-3-carboxamide, MS (EI): 589 (MH+).

6-(3-endo-{[2-(2-chloro-4-fluorophenoxy)-2-methylpropanoyl]amino}-8-azabicyclo[3.2.1]oct-8-yl)-N-(3,3,3-trifluoro-2-hydroxypropyl)pyridine-3-carboxamide, MS (EI): 573 (MH+).

6-[3-endo-({2-[4-chloro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide, MS (EI): 623 (MH+).

6-[3-endo-({2-[4-fluoro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide, MS (EI): 607 (MH+).

[2,4-dichloro-5-({1-[(8-{5-[(2,2-difluoroethyl)carbamoyl]pyridin-2-yl}-8-azabicyclo[3.2.1]oct-3-endo-yl)amino]-2-methyl-1-oxopropan-2-yl}oxy)phenyl]acetic acid, MS (EI): 600 (MH+). The carboxylic acid is installed in the final step by hydrolysis of 6-(3-endo-(2-(2,4-dichloro-5-(cyanomethyl)phenoxy)-2-methylpropanamido)-8-azabicyclo[3.2.1]octan-8-yl)-N-(2,2-difluoroethyl)nicotinamide with 3N NaOH in MeOH. The necessary fibrate is synthesized by bromination of ethyl 2-(2,4-dichloro-5-methylphenoxy)-2-methylpropanoate with NBS and benzoyl peroxide in carbon tetrachloride followed by treatment with sodium cyanide in DMF.

2-(2,4-dichlorophenoxy)-n-[8-(5-{[(3r)-3-hydroxypyrrolidin-1-yl]carbonyl}pyridin-2-yl)-8-azabicyclo[3.2.1]oct-3-endo-yl]-2-methylpropanamide, MS (EI): 548 (MH+).

2-(2,4-dichlorophenoxy)-N-[8-(5-{[(3s)-3-hydroxypyrrolidin-1-yl]carbonyl}pyridin-2-yl)-8-azabicyclo[3.2.1]oct-3-endo-yl]-2-methylpropanamide, MS (EI): 548 (MH+).

6-(3-endo-{[2-(2,4-dichlorophenoxy)-2-methylpropanoyl]amino}-8-azabicyclo[3.2.1]oct-8-yl)-N-(1,1,1-trifluoro-3-hydroxypropan-2-yl)pyridine-3-carboxamide, MS (EI): 589 (MH+). The necessary amine is prepared by treatment of ethyl trifluoropyruvate with 4-methylbenzenesulfinamide, diethylazodicarboxylate and triphenylphosphine followed by reduction with lithium aluminum hydride. (See: Eur. J. Org. Chem., 2001, 1449.)

6-[3-endo-({2-[2,5-dichloro-4-(hydroxymethyl)phenoxy]-2-methylpropanoyl}amino)-8-azabicyclo[3.2.1]oct-8-yl]-N-(2,2-difluoroethyl)pyridine-3-carboxamide, MS (EI): 571 (MH+). The necessary phenol is prepared by chlorination of 3-chloro-4-methylphenol with HCl and hydrogen peroxide followed by alkylation with ethyl 2-bromoisobutyrate. Bromination with NBS and benzoyl peroxide and subsequent treatment with calcium carbonate produces the desired hydroxymethyl group.

6-[3-endo-({2-[4-chloro-2-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, MS (EI): 565 (MH+). The necessary phenol is prepared by TBDMS protection of 2-bromo-4-chlorophenol, followed by treatment with isopropylmagnesium bromide and acetone, then TBAF deprotection.

6-(3-endo-(2-(4-chloro-2-fluoro-5-(2-hydroxypropan-2-yl)phenoxy)-2-methylpropanamido)-8-azabicyclo[3.2.1]octan-8-yl)-N-(2,2-difluoroethyl)nicotinamide, MS (EI): 583 (MH+).

N-(2,2-difluoroethyl)-6-(3-endo-(2-(4-fluoro-2-(2-hydroxypropan-2-yl)phenoxy)-2-methylpropanamido)-8-azabicyclo[3.2.1]octan-8-yl)nicotinamide, MS (EI): 549 (MH+).

N-(2,2-difluoroethyl)-6-[3-endo-({2-[2,4-difluoro-5-(2-hydroxypropan-2-yl)phenoxy]-2-methylpropanoyl}amino)-8-azabicyclo[3.2.1]oct-8-yl]pyridine-3-carboxamide, MS (EI): 567 (MH+).

6-[3-endo-({2-[4-chloro-2-(difluoromethoxy)phenoxy]-2-methylpropanoyl}amino)-8-azabicyclo[3.2.1]oct-8-yl]-N-(2,2-difluoroethyl)pyridine-3-carboxamide, MS (EI): 573 (MH+). The requisite phenol is synthesized by Dakin rearrangement of 2-(difluoromethoxy)benzaldehyde followed by chlorination according to a procedure in J. Org. Chem. 1985, 50, 2145-2148.

6-(3-endo-{[2-(2,4-dichlorophenoxy)-2-methylpropanoyl]amino}-8-azabicyclo[3.2.1]oct-8-yl)-N-[3,3,3-trifluoro-2-(morpholin-4-yl)propyl]pyridine-3-carboxamide, MS (EI): 659 (MH+). The necessary amine is prepared by treatment of 1,1,1-trifluoro-3-nitropropan-2-ol with methanesulfonyl chloride and morpholine followed by hydrogenolysis over palladium on carbon.

6-[3-endo-({2-[2-chloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, MS (EI): 565 (MH+). The phenol is prepared by TBDMS protection of 4-bromo-3-chlorophenol, metal-halogen exchange with tert-butyllithium, followed by addition of acetone, then TBAF deprotection.

6-[3-endo-({2-[2-chloro-4-fluoro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, 1H NMR (CDCl$_3$, 400 MHz): d 8.61 (d, J=2.4 Hz, 1H), 7.91 (dd, J=9.2 Hz, 1H), 7.75 (d, J=7.6 Hz, 1H), 7.44 (d, J=7.2 Hz, 1H), 7.13 (d, J=10.8 Hz, 1H), 6.52-6.50 (m, 2H), 5.95 (tt, J=56 Hz, 1H), 4.95 (br s, 2H), 4.11 (q, J=6.8 Hz, 1H), 3.84-3.74 (m, 2H), 2.34-2.06 (m, 7H), 1.80-1.73 (m, 2H), 1.61 (s, 6H), 1.54 (s, 6H). MS (EI): 583 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxamide, MS (EI): 536 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxylic acid, MS (EI): 537 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide, MS (EI): 618 (MH+).

6-(3-endo-{[2-(2,4-dichlorophenoxy)-2-methylpropanoyl]amino}-8-azabicyclo[3.2.1]oct-8-yl)-N-(3,3,3-trifluoro-2-oxopropyl)pyridine-3-carboxamide, MS (EI): 587 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]-N-(propan-2-yl)pyridine-3-carboxamide, 1H NMR (CDCl$_3$, 600 MHz): d 8.54 (d, J=2.4 Hz, 1H), 7.88 (dd, J=6.0 Hz, 1H), 7.65 (d, J=7.8 Hz, 1H), 7.58 (s, 1H), 7.43 (s, 1H), 6.51 (d, J=9.6 Hz, 1H), 5.78 (d, J=7.8 Hz, 1H), 4.57 (br s, 2H), 4.27-4.26 (m, 1H), 4.10 (q, J=6.6 Hz, 1H), 2.52 (br s, 1H), 2.30-2.26 (m, 2H), 2.17-2.15 (m, 2H), 2.03 (q, J=6.6 Hz, 2H), 1.75-1.71 (m, 7H), 1.24 (d, J=6.0 Hz, 6H), 1.56 (s, 6H). MS (EI): 578 (MH+).

6-[3-endo-({2-[2,4-dichloro-5-(prop-1-en-2-yl)phenoxy]-2-methylpropanoyl}amino)-8-azabicyclo[3.2.1]oct-8-yl]-N-(2,2-difluoroethyl)pyridine-3-carboxamide, MS (EI): 582 (MH+). The requisite fibric acid is prepared by treatment of 2-(2,4-dichloro-5-(2-hydroxypropan-2-yl)phenoxy)-2-methylpropanoic acid with methanesulfonyl chloride and triethylamine.

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide 1-oxide, MS (EI): 616 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]-N-(3,3,3-trifluoro-2-hydroxypropyl)pyridine-3-carboxamide, MS (EI): 648 (MH+).

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2-hydroxy-2-methylpropyl)pyridine-3-carboxamide, MS (EI): 608 (MH+).

N-(2,2-difluoroethyl)-6-[3-endo-({2-[2-fluoro-4-(2-hydroxypropan-2-yl)phenoxy]-2-methylpropanoyl}amino)-8-azabicyclo[3.2.1]oct-8-yl]pyridine-3-carboxamide, MS (EI): 549 (MH+).

6-[3-endo-({2-[2-chloro-5-fluoro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, MS (EI): 583 (MH+). The phenol is prepared by TBDMS protection of methyl 2-fluoro-4-hydroxybenzoate, followed by NCS chlorination, methyl magnesium bromide addition and TBAF deprotection.

6-[3-endo-({2-[2,5-dichloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide, MS (EI): 600 (MH+).

11 βHSD1 Inhibition Assays

11 βHSD1 SPA Assay

Inhibition of 11 βHSD1 by test compounds was assessed in vitro by a Scintillation Proximity Assay (SPA). The assay was carried out in a 384-well assay plate in a total well volume of 26 μl and contained a mixture of tritiated cortisone substrate (40 nM), NADPH cofactor (1 mM), inhibitor in serial dilutions (38 μM to 10 μM), and purified E. coli-expressed recombinant human 11 βHSD1 (30-100 nM) in assay buffer (50 mM HEPES, 100 mM KCl, 5 mM NaCl, and 2 mM MgCl$_2$, pH7.4). Following mixing, the plate was incubated for 2 hours at room temperature. Reactions were stopped by addition of 30 μl of protein A YSi SPA beads (10 mg/ml) that had been pre-incubated with glycyrrhetinic acid (1 mM) and a monoclonal cortisol antibody (3 μg/ml). The plate was then incubated overnight at room temperature prior to reading on a Microbeta counter. Percent inhibition of each compound was calculated based on the background and the maximal signals. Wells that contained substrate without compound or enzyme were used as the background signal, while the wells that contained substrate and enzyme without any compound were used as the maximal signal. The calculation of the IC$_{50}$ values for the inhibitors was performed by Activity Base. Test compounds with IC$_{50}$ values less than 1 μM were considered active.

Ex vivo 11βHSD1 Assay

Inhibition of 11βHSD1 in liver and white adipose tissue of mice treated by test compounds was assessed in an ex vivo manner using the Scintillation Proximity Assay (SPA). Liver and white adipose tissue from mice treated with compounds or vehicle were frozen immediately and stored at −80 C until analysis. Frozen tissue (~100 mg/piece) was transferred to the well of a 48-well tissue culture plate containing 500 μl assay buffer (15 mM HEPES, 1 mM NADPH, 5% FCS, penicillin-streptomycin, and protease inhibitor in RPMI 1640 media) and minced to 10-15 slices. The reaction was initiated by addition of 5 μl of 2 μM tritiated cortisone (final concentration=20 nM). Following mixing, the plate was incubated at 37° C. in a 5% $CO_2$ atmosphere for 10 minutes (liver) or 2 hours (adipose). After incubation, the reaction mixture was transferred to a 1.7 ml tube and centrifuged for 2 minutes at full speed in a table-top centrifuge. The liquid portion of the reaction (100 μl×3 wells) was then transferred to a 96-well assay plate and the reaction was stopped by addition of 100 μl of anti-mouse YSi SPA beads (10 mg/ml) that had been pre-incubated with glycyrrhetinic acid (1 mM) and a monoclonal cortisol antibody (3 μg/ml). The plate was then incubated for 1 hour at room temperature with light shaking prior to reading on a Microbeta counter. Percent inhibition of compound was calculated based on the background and the maximal signals. Wells that contained vehicle sample were used as the maximal signal, while wells that contained a second set of vehicle sample treated with 100 μM glycyrrhetinic acid in vitro were used as the background signal. Test compounds showing >25% inhibition of 11 βHSD1 at the doses tested were considered active.

11 β-HSD1 Inhibition Assays

11 β-HSD1 SPA Assay

Inhibition of 11 β-HSD1 by test compounds was assessed in vitro by a Scintillation Proximity Assay (SPA). The assay was carried out in a 384-well assay plate in a total well volume of 26 μl and contained a mixture of tritiated cortisone substrate (40 nM), NADPH cofactor (1 mM), inhibitor in serial dilutions (38 μM to 10 μM), and purified E. coli-expressed recombinant human 11 β-HSD1 (30-100 nM) in assay buffer (50 mM HEPES, 100 mM KCl, 5 mM NaCl, and 2 mM $MgCl_2$, pH7.4). Following mixing, the plate was incubated for 2 hours at room temperature. Reactions were stopped by addition of 30 μl of protein A YSi SPA beads (10 mg/ml) that had been pre-incubated with glycyrrhetinic acid (1 mM) and a monoclonal cortisol antibody (3 μg/ml). The plate was then incubated overnight at room temperature prior to reading on a Microbeta counter. Percent inhibition of each compound was calculated based on the background and the maximal signals. Wells that contained substrate without compound or enzyme were used as the background signal, while the wells that contained substrate and enzyme without any compound were used as the maximal signal. The calculation of the $IC_{50}$ values for the inhibitors was performed by Activity Base. Test compounds with $IC_{50}$ values less than 1 μM were considered active.

Ex vivo 11 β-HSD1 Assay

Inhibition of 11 β-HSD1 in liver and white adipose tissue of mice treated by test compounds was assessed in an ex vivo manner using the Scintillation Proximity Assay (SPA). Liver and white adipose tissue from mice treated with compounds or vehicle were frozen immediately and stored at −80° C. until analysis. Frozen tissue (~100 mg/piece) was transferred to the well of a 48-well tissue culture plate containing 500 μl assay buffer (15 mM HEPES, 1 mM NADPH, 5% FCS, penicillin-streptomycin, and protease inhibitor in RPMI 1640 media) and minced to 10-15 slices. The reaction was initiated by addition of 5 μl of 2 μM tritiated cortisone (final concentration=20 nM). Following mixing, the plate was incubated at 37° C. in a 5% $CO_2$ atmosphere for 10 minutes (liver) or 2 hours (adipose). After incubation, the reaction mixture was transferred to a 1.7 ml tube and centrifuged for 2 minutes at full speed in a table-top centrifuge. The liquid portion of the reaction (100 μl×3 wells) was then transferred to a 96-well assay plate and the reaction was stopped by addition of 100 μl of anti-mouse YSi SPA beads (10 mg/ml) that had been pre-incubated with glycyrrhetinic acid (1 mM) and a monoclonal cortisol antibody (3 μg/ml). The plate was then incubated for 1 hour at room temperature with light shaking prior to reading on a Microbeta counter. Percent inhibition of compound was calculated based on the background and the maximal signals. Wells that contained vehicle sample were used as the maximal signal, while wells that contained a second set of vehicle sample treated with 100 μM glycyrrhetinic acid in vitro were used as the background signal. Test compounds showing >25% inhibition of 11 β-HSD1 at the doses tested were considered active.

The compounds in Table I have been tested for their 11 β-HSD1 inhibitory activity ($IC_{50}$ values), and these compounds have 11 β-HSD1 $IC_{50}$ values of less than 10,000 nM. A preferred group of compounds of Table I have 11 β-HSD1 $IC_{50}$ values of less than 5,000 nM. Another preferred group of compounds of Table I have 11 β-HSD1 $IC_{50}$ values of less than 2,000 nM. Another preferred group of compounds of Table I have 11 β-HSD1 $IC_{50}$ values of less than 1,000 nM. Another preferred group of compounds of Table I have 11 β-HSD 1 values of less than 500 nM. Another preferred group of compounds of Table I have 11 β-HSD1 $IC_{50}$ values of less than 200 nM. Another preferred group of compounds of Table I have 11 β-HSD1 $IC_{50}$ values of less than 100 nM. Another preferred group of compounds of Table I have 11 β-HSD1 $IC_{50}$ values of less than 50 nM. Another preferred group of compounds of Table I have 11 β-HSD1 $IC_{50}$ values of less than 25 nM.

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| Formula I | 400 |
| Cornstarch | 50 |
| croscarmellose sodium | 25 |
| Lactose | 120 |
| Magnesium stearate | 5 |

Capsule Formulation

The following ingredients are mixed intimately and loaded into a hard-shell gelatin capsule.

| Ingredient | Quantity per tablet, mg |
| --- | --- |
| Formula I | 200 |
| lactose, spray-dried | 148 |
| magnesium stearate | 2 |

Suspension Formulation

The following ingredients are mixed to form a suspension for oral administration.

| Ingredient | Amount |
|---|---|
| Formula I | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation

The following ingredients are mixed to form an injectable formulation.

| Ingredient | Amount |
|---|---|
| Formula I | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60°-70° with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of disclosed herein (compound of Formula I) with Witepsol® H-15 (triglycerides of saturated vegetable fatty acid; Riches-Nelson, Inc., New York), and has the following composition:

| Ingredient | Quantity per tablet, mg |
|---|---|
| Formula I | 500 |
| Witepsol ® H-15 | Balance |

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:
1. A compound according to Formula I:

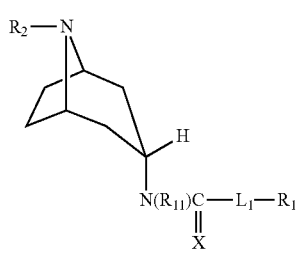

or a pharmaceutically acceptable salt thereof, wherein $R_1$ is selected from:

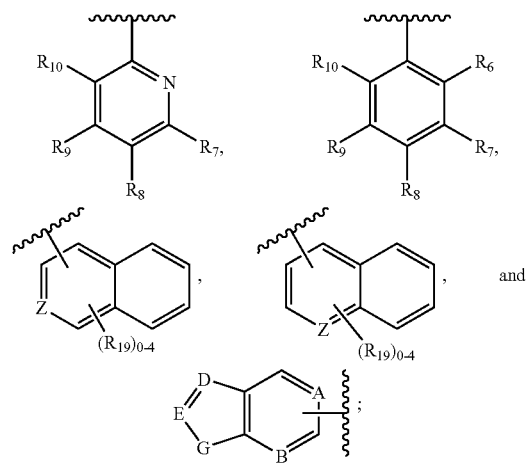

$R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl and 5-6 membered heteroaryl can each be unsubstituted or substituted with 1, 2, 3 or 4 groups selected from —C(O)—N(H)-$L_2$, —C(O)—(O)-$L_3$, —C(O)-$L_7$, —$CF_3$, —CN, —$NH_2$, —N(H)S(O)$_2$-alkyl, —S(O)2-alkyl, —S(O)$_2$—N($L_5$)$L_6$, —N(H)C(O)-$L_4$, heteroaryl optionally substituted with halo or —$CF_3$, —N(H)C(O)N(H)-alkyl-$CF_3$, —OH, alkoxy, and halo; wherein the alkyl portion of —N(H)S(O)$_2$-alkyl, —S(O)$_2$-alkyl, and —N(H)C(O)N(H)-alkyl-$CF_3$ is optionally substituted with 1, 2, 3, 4 or 5 halo, and wherein any alkyl portion of any $R_2$ group described above is optionally substituted with hydroxyalkyl, aminoalkyl, alkoxyalkyl or alkoxyalkoxy;

$R_6$, $R_7$, $R_8$, $R_9$, and $R_{10}$ are each independently selected from H, halo, alkyl optionally substituted with 1-5 halo, alkynyl, —OH, —$NH_2$, alkenyl optionally substituted with 1-5 halo, phenyl, aminocarbonylalkoxy, aminocarbonylalkyl, carboxyalkoxy, carboxyalkyl, aminocarbonyl, —S(O)$_2$-alkyl, —S(O)$_2$—$NH_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—$NH_2$, —C(O)(O)-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —$CF_3$, —($C_1$-$C_3$)alkyl, OH and alkoxy, and wherein any alkyl portion of any $R_6$, $R_7$, $R_8$, $R_9$ and $R_{10}$ group described above is optionally substituted with hydroxyl, hydroxyalkyl, aminoalkyl, alkoxyalkyl or alkoxyalkoxy;

$R_{11}$ is hydrogen, alkyl, alkenyl or alkynyl;

$R_{12}$ is selected from hydrogen, alkenyl, alkynyl, halo or alkyl;

$R_{13}$ is halo, alkyl, alkenyl or alkynyl;

or $R_{12}$ and $R_{13}$, together with the carbon atom to which they are both attached, join to form a 3-6 membered cycloalkyl;

$R_{19}$, when $R_{19}$ is present, is selected from H, halo, alkyl optionally substituted with 1-5 halo, alkenyl, alkynyl —OH, —$NH_2$, alkenyl optionally substituted with 1-5 halo, phenyl, —$S(O)_2$-alkyl, —$S(O)_2$—$NH_2$, —$S(O)_2$—N(H)-alkyl, —$S(O)_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—$NH_2$, —C(O)(O)-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —$CF_3$, OH and alkoxy, and wherein any alkyl portion of $R_{19}$ described above is optionally substituted with hydroxyalkyl, aminoalkyl, alkoxyalkyl or alkoxyalkoxy;

A is N or CH;

B is N or CH;

D and E are each selected from CH and N, and G is selected from NH and $CH_2$, wherein one of D, E and G is optionally substituted with —N(H)—$R^{15}$, provided that no more than two of D, E and G are nitrogen;

$L_1$ is selected from —C($R_{12}$)($R_{13}$)—, —C($R_{12}$)($R_{13}$)—(O)—, —C($R_{12}$)($R_{13}$)—$CH_2$—(O)—, —C($R_{12}$)($R_{13}$)—S— and —C($R_{12}$)($R_{13}$)—$S(O)_2$—;

$L_2$ is selected from alkyl optionally substituted with 1-5 halo, alkyl optionally substituted with 1-2 hydroxyl, alkyl optionally substituted with 1-2 alkoxy, halo alkenyl, alkynyl. cycloalkyl optionally substituted with 1-5 halo, heterocycloalkyl, heterocycloalkylalkyl optionally substituted with 1-2 oxo, heteroarylalkyl, hydroxyalkyl, dialkylaminoalkyl, hydrogen, alkoxyalkyl, and —$CF_3$, wherein any alkyl portion of $L_2$ can be substituted with hydroxyl;

$L_3$ is selected from hydrogen, alkyl optionally substituted with hydroxyalkyl, aminoalkyl, alkoxyalkyl or alkoxyalkoxy, alkenyl and alkynyl;

$L_4$ is selected from —$CF_3$, alkyl optionally substituted with 1-5 halo, alkenyl and alkynyl, wherein any alkyl portion of $L_4$ is optionally substituted with hydroxyalkyl, aminoalkyl, alkoxyalkyl or alkoxyalkoxy;

$L_5$ is selected from hydrogen, alkyl, alkenyl and alkynyl, wherein any alkyl portion of $L_5$ is optionally substituted with hydroxyalkyl, aminoalkyl, alkoxyalkyl or alkoxyalkoxy;

$L_6$ is selected from hydrogen, —$CF_3$, alkyl optionally substituted with 1-5 halo, alkenyl and alkynyl, wherein any alkyl portion of $L_6$ is optionally substituted with hydroxyalkyl, aminoalkyl, alkoxyalkyl or alkoxyalkoxy;

$L_7$ is selected from hydrogen, heterocycloalkyl optionally substituted with 1-2 groups selected from hydroxyl and hydroxyalkyl, alkyl, alkenyl and alkynyl, wherein any alkyl portion of $L_7$ is optionally substituted with hydroxyalkyl, aminoalkyl, alkoxyalkyl or alkoxyalkoxy;

X is O or S; and

Z is N or CH.

2. The compound according to claim 1, wherein $R_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-$L_2$, —C(O)—(O)-$L_3$, —C(O)-$L_7$, —$CF_3$, —CN, —N(H)$S(O)_2$-alkyl, —$S(O)_2$-alkyl, —$S(O)_2$—N($L_5$)$L_6$, —N(H)C(O)-$L_4$, heteroaryl optionally substituted with halo or —$CF_3$, —N(H)C(O)N(H)-alkyl-$CF_3$, —OH, alkoxy, and halo; wherein the alkyl portion of —N(H)$S(O)_2$-alkyl, —$S(O)_2$-alkyl, and —N(H)C(O)N(H)-alkyl-$CF_3$ is optionally substituted with 1, 2, 3, 4 or 5 halo, and wherein any alkyl portion of any $R_2$ group desribed above is optionally substituted with hydroxyalkyl, aminoalkyl, alkoxyalkyl or alkoxyalkoxy;

$R_6$, $R_7$, $R_8$, $R_9$, and $R_{10}$ are each independently selected from H, halo, alkyl optionally substituted with 1-5 halo, —OH, —$NH_2$, alkenyl optionally substituted with 1-5 halo, phenyl, —$S(O)_2$-alkyl, —$S(O)_2$—$NH_2$, —$S(O)_2$—N(H)-alkyl, —$S(O)_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—$NH_2$, —C(O)(O)-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, al kylaminoalkoxy, and dialkylaminoalkoxy, wherein each phenyl, cycloalkyl, cycloalkylalkoxy, heterocycloalkyl, heterocycloalkylalkoxy, heteroaryl, and heteroar8ylalkoxy is optionally substituted with 1, 2 or 3 groups selected from halo, —$CF_3$, OH and alkoxy, and wherein any alkyl portion of any $R_6$, $R_7$, $R_8$, $R_9$ and $R_{10}$ group described above is optionally substituted with hydroxyl, hydroxyalkyl, aminoalkyl, alkoxyalkyl or alkoxyalkoxy;

$R_{11}$ is hydrogen or alkyl;

$R_{12}$ is selected from hydrogen, halo or alkyl;

$R_{13}$ is halo or alkyl;

or $R_{12}$ and $R_{13}$, together with the carbon atom to which they are both attached, join to form a 3-6 membered cycloalkyl;

$R_{19}$, when $R_{19}$ is present, is selected from H, halo, alkyl optionally substituted with 1-5 halo, —OH, —$NH_2$, alkenyl optionally substituted with 1-5 halo, phenyl, —$S(O)_2$-alkyl, —$S(O)_2$—$NH_2$, —$S(O)_2$—N(H)-alkyl, —$S(O)_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—$NH_2$, —C(O)(O)-alkyl, —$CF_3$, —$OCF_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of R$_{19}$ described above is optionally substituted with hydroxyalkyl, aminoalkyl, alkoxyalkyl or alkoxyalkoxy;

A is N or CH;

B is N or CH;

L$_1$ is selected from —C(R$_{12}$)(R$_{13}$)—, —C(R$_{12}$)(R$_{13}$)—(O)—, —C(R$_{12}$)(R$_{13}$)—CH$_2$—(O)—, —C(R$_{12}$)(R$_{13}$)—S— and —C(R$_{12}$)(R$_{13}$)—S(O)$_2$—, L$_2$ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF$_3$;

L$_3$ is selected from hydrogen and alkyl optionally substituted with hydroxyalkyl, aminoalkyl, alkoxyalkyl or alkoxyalkoxy;

L$_4$ is selected from —CF$_3$ and alkyl optionally substituted with 1-5 halo, wherein any alkyl portion of L$_4$ is optionally substituted with hydroxyalkyl, aminoalkyl, alkoxyalkyl or alkoxyalkoxy;

L$_5$ is selected from hydrogen and alkyl optionally substituted with hydroxyalkyl, aminoalkyl, alkoxyalkyl or alkoxyalkoxy;

L$_6$ is selected from hydrogen, —CF$_3$, and alkyl optionally substituted with 1-5 halo, wherein any alkyl portion of L$_6$ is optionally substituted with hydroxyalkyl, aminoalkyl, alkoxyalkyl or alkoxyalkoxy;

L$_7$ is selected from hydrogen and alkyl optionally substituted with hydroxyalkyl, aminoalkyl, alkoxyalkyl or alkoxyalkoxy;

X is O or S; and

Z is N or CH.

3. The compound according to claim 1, wherein

R$_2$ is selected from phenyl, —C(O)-phenyl, benzyl, and a 5-6 membered heteroaryl that can contain 1, 2 or 3 heteroatoms, wherein the phenyl, —C(O)-phenyl, benzyl or 5-6 membered heteroaryl can each be unsubstituted or substituted with 1, 2, 3 or 4 groups selected from —C(O)—N(H)-L$_2$, —C(O)—(O)-L$_3$, —C(O)-L$_7$, —CF$_3$, —CN, —NH$_2$, —N(H)S(O)$_2$-alkyl, —S(O)$_2$-alkyl, —S(O)$_2$—N(L$_5$)L$_6$, —N(H)C(O)-L$_4$, heteroaryl optionally substituted with halo or —CF$_3$, —N(H)C(O)N(H)-alkyl-CF$_3$, —OH, alkoxy, and halo, wherein the alkyl portion of —N(H)S(O)$_2$-alkyl, —S(O)$_2$-alkyl, and —N(H)C(O)N(H)-alkyl-CF$_3$ is optionally substituted with 1, 2, 3, 4 or 5 halo, and wherein any alkyl portion of any R$_2$ group desribed above is optionally substituted with hydroxyalkyl, aminoalkyl, alkoxyalkyl or alkoxyalkoxy;

R$_6$, R$_7$, R$_8$, R$_9$, and R$_{10}$ are each independently selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—NH$_2$, —C(O)(O)-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of any R$_6$, R$_7$, R$_8$, R$_9$ and R$_{10}$ group described above is optionally substituted with hydroxyl, hydroxyalkyl, aminoalkyl, alkoxyalkyl or alkoxyalkoxy;

R$_{11}$ is hydrogen or alkyl;

R$_{12}$ is selected from hydrogen, halo or alkyl;

R$_{13}$ is halo or alkyl;

or R$_{12}$ and R$_{13}$, together with the carbon atom to which they are both attached, join to form a 3-6 membered cycloalkyl;

R$_{19}$, when R$_{19}$ is present, is selected from H, halo, alkyl optionally substituted with 1-5 halo, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—NH$_2$, —C(O)(O)-alkyl, —CF$_3$, —OCF$_3$, —CN, alkoxy, alkoxyalkyl, alkoxyalkoxy, hydroxyalkoxy, heteroaryl, heteroarylalkoxy, aminoalkoxy, alkylaminoalkoxy, and dialkylaminoalkoxy, wherein each phenyl, cycloalkyl, cycloalkylalkoxy, heterocycloalkyl, heterocycloalkylalkoxy, heteroaryl, and heteroarylalkoxy is optionally substituted with 1, 2 or 3 groups selected from halo, —CF$_3$, OH and alkoxy, and wherein any alkyl portion of R$_{19}$ described above is optionally substituted with hydroxyalkyl, aminoalkyl, alkoxyalkyl or alkoxyalkoxy;

A is N or CH;

B is N or CH;

L$_1$ is selected from —C(R$_{12}$)(R$_{13}$)—(O)—, —C(R$_{12}$)(R$_{13}$)—CH$_2$—(O)—, —C(R$_{12}$)(R$_{13}$)—S— and —C(R$_{12}$)(R$_{13}$)—S(O)$_2$—;

L$_2$ is selected from alkyl optionally substituted with 1-5 halo, alkyl optionally substituted with 1-2 hydroxyl, alkyl optionally substituted with 1-2 alkoxy, cycloalkyl optionally substituted with 1-5 halo, heterocycloalkyl, hydrogen, alkoxyalkyl, and —CF$_3$;

L$_3$ is selected from hydrogen and alkyl optionally substituted with hydroxyalkyl, aminoalkyl, alkoxyalkyl or alkoxyalkoxy, L$_4$ is selected from —CF$_3$ and alkyl optionally substituted with 1-5 halo, wherein any alkyl portion of L$_4$ is optionally substituted with hydroxyalkyl, aminoalkyl, alkoxyalkyl or alkoxyalkoxy;

L$_5$ is selected from hydrogen and alkyl optionally substituted with hydroxyalkyl, aminoalkyl, alkoxyalkyl or alkoxyalkoxy;

L$_6$ is selected from hydrogen, —CF$_3$, and alkyl optionally substituted with 1-5 halo, wherein any alkyl portion of L$_6$ is optionally substituted with hydroxyalkyl, aminoalkyl, alkoxyalkyl or alkoxyalkoxy;

L$_7$ is selected from hydrogen and alkyl optionally substituted with hydroxyalkyl, aminoalkyl, alkoxyalkyl or alkoxyalkoxy;

X is O or S; and

Z is N or CH.

4. The compound according to claim 1, wherein R$_2$ is pyridinyl or phenyl, wherein the pyridinyl or phenyl is substituted with one or two groups selected from —C(O)NH$_2$, —C(O)N(H)-cyclopropyl optionally substituted with 1 or 2 halo at any position on the cyclopropyl ring, —N(H)—S(O)$_2$—CH$_3$, —S(O)$_2$—NH$_2$, —S(O)$_2$—CH$_3$, —C(O)N(H)(C$_1$-C$_3$)alkyl-CF$_3$, and —C(O)N(H)(C$_1$-C$_3$)alkyl-OCH$_3$.

5. The compound according to claim 1, wherein

R$_1$ is selected from 2,4-dichlorophenyl, 3,4-dichlorophenyl, 4-fluorophenyl, 4-chlorophenyl, 4-methylphenyl, 2-chlorophenyl, 3-chlorophenyl, 3,4-difluorophenyl, 2,4-difluorophenyl, trifluoromethylphenyl, 4-cyanophenyl, 3-fluorophenyl, 4-chloro-2-fluorophenyl, 3,4-dichlorophenyl, 4-chloro-3-fluorophenyl, 4-(methyloxy)phenyl, 2-chloro-4-fluorophenyl, 2-chloro-5-fluorophenyl, 2,5-dichlorophenyl, 2-chloro-4,5-difluorophenyl, 2,4-dichloro-5-fluorophenyl, 3-chloro-4-fluorophenyl, 2,3-dichloro-4-fluorophenyl, 2,5-dichloro-4-fluorophenyl, 3,5-dichloropyridin-2-yl, 5-chloropyridin-2-yl, 5-fluoropyridin-2-yl, 4-(trifluoromethyl)phenyl, 2-(trifluoromethyl)phenyl, 5-chloro-3-fluoropyridin-2-yl, 4-[(trifluoromethyl)oxy]phenyl, 4-chloro-2-(trifluoromethyl)phenyl, 4-fluoro-2-(trifluoromethyl) phenyl, 3-chloro-5-(trifluoromethyl)pyridin-2-yl, 5-(trifluoromethyl)pyridin-2-yl, 2,5-dichloro-4-fluorophenyl, 2-chloro-4-fluorophenyl, 2,6-dichloro-4-fluorophenyl, 2-chloro-4-fluoro-6-(trifluoromethyl) phenyl, 2-chloro-4-(trifluoromethyl) phenyl, 4-chloro-3-(trifluoromethyl)phenyl, 2-fluoro-5-(trifluoromethyl)phenyl, 2,4,5-trichlorophenyl, 2-chloro-4-methylphenyl, 2,4,5-trifluorophenyl, 4-fluoro-2-methylphenyl, 4-fluoro-2-(methyloxy)phenyl, 2-chloro-4-(methyloxy) phenyl, 2,4,6-trifluorophenyl, 5-fluoro-2-(trifluoromethyl) phenyl, 1-chloronaphthalen-2-yl, 4-fluoro-3-(trifluoromethyl)phenyl, 5-chloro-3-(trifluoromethyl)pyridin-2-yl, 4-chloronaphthalen-1-yl, quinolin-2-yl, quinolin-4-yl, 4-chloro-2-(1-methylethyl)phenyl, phenyl, 3-chlorobiphenyl-4-yl, 4-fluoro-2-(methylsulfonyl)phenyl, 5-chloro-4'-fluorobiphenyl-2-yl, 4-chloro-2-cyclohexylphenyl, 2-(methylsulfonyl)phenyl, 4-chloro-2-(methylsulfonyl)phenyl, 2-[(3-chloro-4'-fluorobiphenyl-4-yl, 3-(methylsulfonyl)phenyl, 2-(methylsulfonyl)phenyl, 4-chloro-2-cyclopentylphenyl, and 5-chlorobiphenyl-2-yl; and R₂ is selected from N-cyclopropylpyridine-3-carboxamide, pyridine-3-carboxamide, 1-methylethyl)pyridine-3-carboxamide, 2,2,2-trifluoroethylpyridine-3-carboxamide, 2,2,2-trifluoroethylbenzamide, 3-chloro-2,2,2-trifluoroethylbenzamide, 3-fluoro-2,2,2-trifluoroethylbenzamide5-[(methylsulfonyl)amino] pyridin-2-yl, 5-aminopyridin-2-yl, 2-(methyloxy) ethylpyridine-3-carboxamide, (trifluoroacetyl)aminophenyl, {[1-(4-chlorophenyl)cyclopropyl] carbonyl}amino, cyclopropylbenzamide, 3-chloro-cyclopropylbenzamide, cyclopropyl-2-fluorobenzamide, 4-(methylsulfonyl)phenyl, 2,2,3,3,3-pentafluoropropyl)pyridine-3-carboxamide, 3-fluoro-(2,2,2-trifluoroethyl)benzamide, 2-choro-(2,2,2-trifluoroethyl)benzamide, cyclopropyl-3-fluorobenzamide, 5-(aminosulfonyl)pyridin-2-yl, 5-fluoro-(2,2,2-trifluoroethyl)pyridine-3-carboxamide, 5-(methylsulfonyl) pyridin-2-yl, oxetan-3-ylpyridine-3-carboxamide, 2,2-difluorocyclopropyl)pyridine-3-carboxamide, pyridine-3-carboxylate, 5-cyanopyridin-2-yl, 4-cyanopyridin-2-yl, pyridine-3-carboxylic acid, 5-acetylpyridin-2-yl, 5-(acetylamino)pyridin-2-yl, 8-pyrazin-2-yl, 8-pyridin-3-yl, 5-(1H-tetrazol-5-yl, acetylamino)phenyl, 2-chloro-4-({[(2,2,2-trifluoroethyl)amino] carbonyl}amino)phenyl, 5-({[(2,2,2-trifluoroethyl) amino]carbonyl}amino)pyridin-2-yl, 4-({[(2,2,2-trifluoroethyl)amino]carbonyl}amino)phenyl, 2-chloro-4-({[(2,2,2-trifluoroethyl)amino]carbonyl}amino)phenyl, 2-fluoro-4-({[(2,2,2-trifluoroethyl)amino] carbonyl}amino)phenyl, 3-(methylsulfonyl)phenyl, (methylsulfonyl)amino]pyridin-2-yl, 6-(1H-tetrazol-5-yl)pyridin-3-yl, 5-(trifluoromethyl)-1,2,4-oxadiazol-3-yl]pyridin-2-yl and 5-[3-(trifluoromethyl)-1H-1,2,4-triazol-5-yl]pyridin-2-yl.

6. The compound according to claim 1, wherein X is O.

7. The compound according to claim 1, wherein L₁ is selected from —CH(CH₃)—, —CH(CH₃)—(O)—, —C(CH₃)₂—, —C(CH₃)₂—(O)—, —C(CH₃)₂—CH₂—O—, —C(CH₃)₂—S—, —C(CH₃)₂—S(O)₂—,

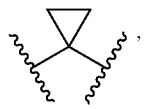

and

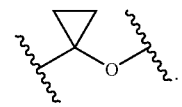

8. The compound according to claim 1, wherein R₂ is

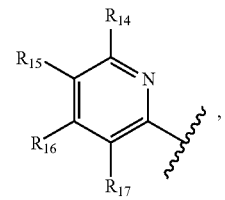

wherein R₁₄, R₁₅, R₁₆ and R₁₇ are each selected from hydrogen, —C(O)—N(H)-L₂, —C(O)—(O)-L₃, —CF₃, —CN, —NH₂, —N(H)S(O)₂-alkyl, —S(O)₂-alkyl, —S(O)₂—N(L₅)L₆, —N(H)C(O)L₄, heteroaryl, —N(H)C(O)N(H)-alkyl-CF₃, —OH, alkoxy, and halo, wherein the alkyl portion of —N(H)S(O)₂-alkyl, —S(O)₂-alkyl, and —N(H)C(O)N(H)-alkyl-CF₃ is optionally substituted with 1, 2, 3, 4 or 5 halo, and L₂, L₃, L₄, L₅, L₆ and L₇ are as defined above in claim 1.

9. The compound according to claim 1, wherein R₂ is

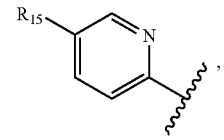

wherein R₁₅ is selected from —C(O)NH₂, —C(O)N(H)-cyclopropyl optionally substituted with 1 or 2 halo at any position on the cyclopropyl ring, —N(H)—S(O)₂—CH₃, —S(O)₂—CH₃, —S(O)₂—NH₂, —C(O)N(H) (C₁-C₃)alkyl-C(H)F₂, —C(O)N(H)(C₁-C₃)alkyl-CF₃, and —C(O)N(H)(C₁-C₃)alkyl-OCH₃.

10. The compound according to claim 1, wherein, R₂ is

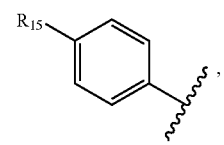

wherein R₁₅ is selected from —C(O)NH₂, —C(O)N(H)-cyclopropyl optionally substituted with 1 or 2 halo at any position on the cyclopropyl ring, —N(H)—S(O)₂—CH₃, —S(O)₂—CH₃, —S(O)₂—NH₂, —C(O)N(H)(C₁-C₃)alkyl-C(H)F₂, —C(O)N(H)(C₁-C₃)alkyl-CF₃, and —C(O)N(H)(C₁-C₃)alkyl-OCH₃.
11. A compound according to claim 1 selected from
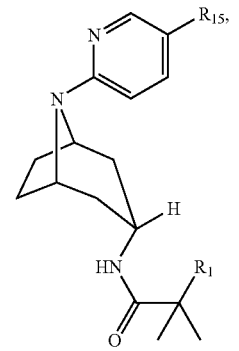
I(A)
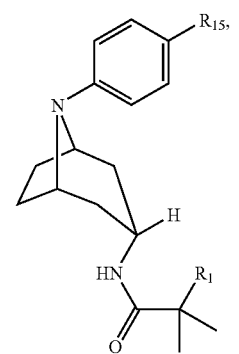
I(B)
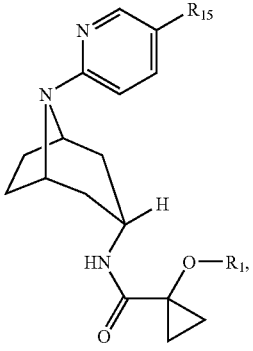
I(C)
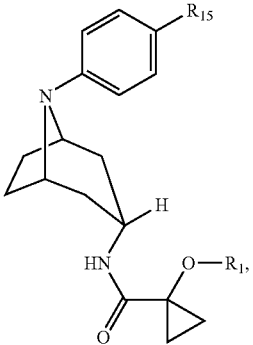
I(D)
-continued
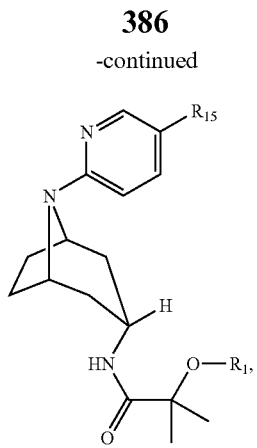
I(E)
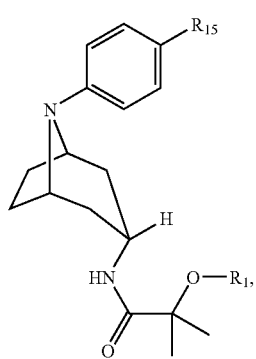
I(F)
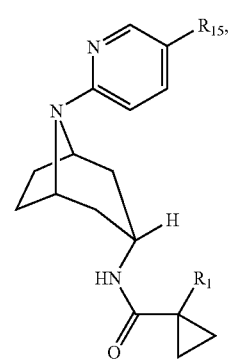
I(G)
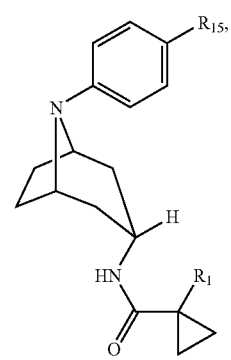
I(H)

387
-continued

I(I)
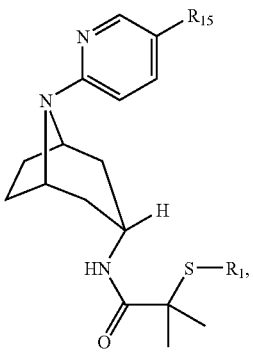

I(J)
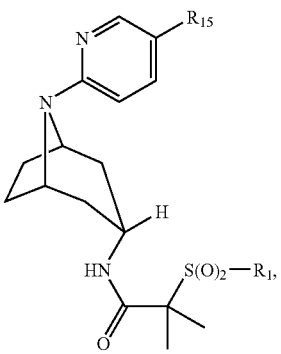

I(K)
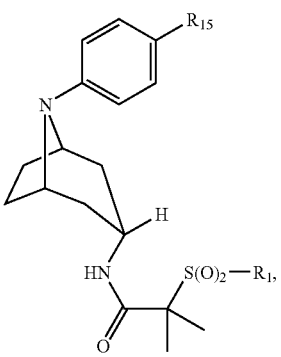

I(L)
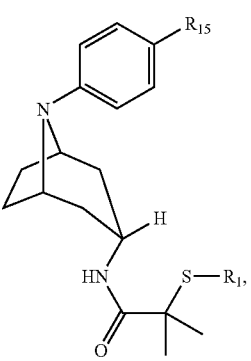

388
-continued

I(M)
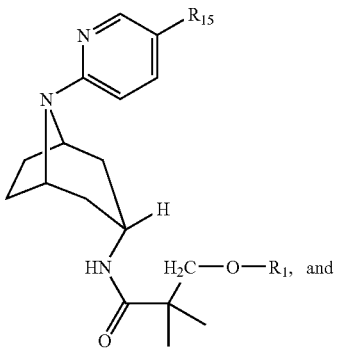

I(N)
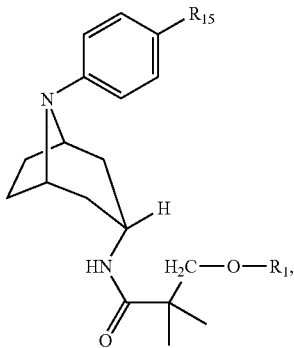

or a pharmaceutically acceptable salt thereof,
wherein $R_{15}$ is selected from —C(O)NH$_2$, —C(O)—CH$_3$, —C(O)N(H)-cyclopropyl optionally substituted with 1 or 2 halo at any position on the cyclopropyl ring, —N(H)—S(O)$_2$—CH$_3$, —S(O)$_2$—CH$_3$, —S(O)$_2$—NH$_2$, —C(O)N(H)(C$_1$-C$_3$)alkyl-C(H)F$_2$, —C(O)N(H)(C$_1$-C$_3$)alkyl-CF$_3$, and —C(O)N(H)(C$_1$-C$_3$)alkyl-OCH$_3$; and $R_1$ is selected from

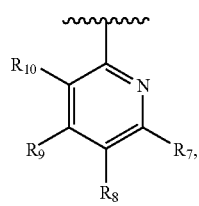 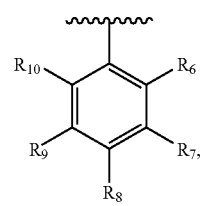

1-naphthyl optionally substituted with 1-4 $R_{19}$ groups, 2-quinolinyl optionally substituted with 1-4 $R_{19}$ groups, 2-naphthyl optionally substituted with 1-4 $R_{19}$ groups, and 4-quinolinyl optionally substituted with 1-4 $R_{19}$ groups, wherein $R_6$, $R_7$, $R_8$, $R_9$, $R_{10}$ and $R_{19}$ are each independently selected from H, halo, alkyl optionally substituted with 1-5 halo, alkyl optionally substituted with 1-2 —OH, —OH, —NH$_2$, alkenyl optionally substituted with 1-5 halo, phenyl, —S(O)$_2$-alkyl, —S(O)$_2$—NH$_2$, —S(O)$_2$—N(H)-alkyl, —S(O)$_2$—N(alkyl)$_2$, cycloalkyl, cycloalkylalkoxy, heterocycloalkyl, heterocycloalkylalkoxy, alkynyl optionally substituted with 1-5 halo, —C(O)OH, —C(O)(O)—NH$_2$, —C(O)(O)-alkyl, —CF$_3$, —OCF$_3$, —CN, alkoxy, alkoxyalkyl, alkoxyalkoxy, hydroxyalkoxy, heteroaryl, heteroaryl alkoxy, aminoalkoxy, alkylaminoalkoxy, and dialkylaminoalkoxy, wherein each phenyl, cycloalkyl cycloalkylalkoxy, heterocycloalkyl, heterocycloalkylalkoxy, heteroaryl, and heteroarylalkoxy is optionally substituted with 1, 2 or 3 groups selected from halo, —CF$_3$, —OH and alkoxy.

12. The compound according to claim 11, or a pharmaceutically acceptable salt thereof, wherein $R_{15}$ is —C(O)NH$_2$; and
$R_1$ is

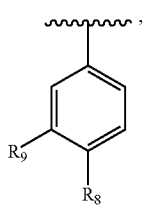

wherein $R_8$ and $R_9$ are each independently selected from Cl, F, hydroxyalkyl and —CF$_3$.

13. The compound according to claim 11, or a pharmaceutically acceptable salt thereof, wherein $R_{15}$ is —C(O)NH$_2$; and
$R_1$ is

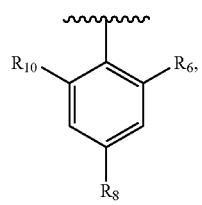

wherein $R_6$, $R_8$ and $R_{10}$ are each independently selected from Cl, F, hydroxyalkyl and —CF$_3$.

14. The compound according to claim 11, or a pharmaceutically acceptable salt thereof, wherein $R_{15}$ is —C(O)NH$_2$; and
$R_1$ is

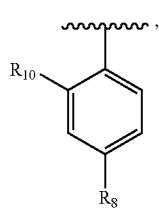

wherein $R_8$ and $R_{10}$ are each independently selected from Cl, F, hydroxyalkyl and —CF$_3$.

15. The compound according to claim 11, or a pharmaceutically acceptable salt thereof, wherein $R_{15}$ is —C(O)NH$_2$; and
$R_1$ is

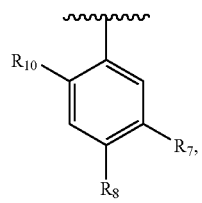

wherein $R_7$, $R_8$ and $R_{10}$ are each independently selected from Cl, F, hydroxyalkyl and —CF$_3$.

16. The compound according to claim 11, or a pharmaceutically acceptable salt thereof, wherein $R_{15}$ is —C(O)NH$_2$; and
$R_1$ is

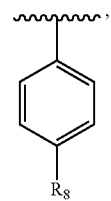

wherein $R_8$ is selected from Cl, F, hydroxyalkyl and —CF$_3$.

17. The compound according to claim 11, or a pharmaceutically acceptable salt thereof, wherein $R_{15}$ is —C(O)N(H)-cylopropyl optionally substituted with 1 or 2 halo at any position on the cyclopropyl ring; and
$R_1$ is

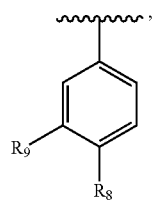

wherein $R_8$ and $R_9$ are each independently selected from Cl, F, hydroxyalkyl and —CF$_3$.

18. The compound according to claim 11, or a pharmaceutically acceptable salt thereof, wherein $R_{15}$ is —C(O)N(H)-cylopropyl optionally substituted with 1 or 2 halo at any position on the cyclopropyl ring; and
$R_1$ is

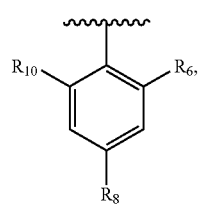

wherein $R_6$, $R_8$, and $R_{10}$ are each independently selected from Cl, F, hydroxyalkyl and —CF$_3$.

19. The compound according to claim 11, or a pharmaceutically acceptable salt thereof, wherein $R_{15}$ is —C(O)N(H)-cylopropyl optionally substituted with 1 or 2 halo at any position on the cyclopropyl ring; and $R_1$ is

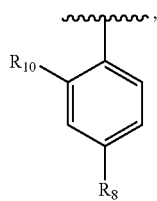

wherein $R_8$ and $R_{10}$ are each independently selected from Cl, F, hydroxyalkyl and —$CF_3$.

20. The compound according to claim 11, or a pharmaceutically acceptable salt thereof, wherein $R_{15}$ is —C(O)N(H)-cylopropyl optionally substituted with 1 or 2 halo at any position on the cyclopropyl ring; and
$R_1$ is

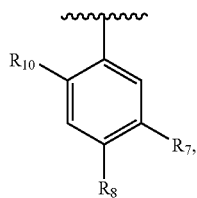

wherein $R_7$, $R_8$ and $R_{10}$ are each independently selected from Cl, F, hydroxyalkyl and —$CF_3$.

21. The compound according to claim 11, or a pharmaceutically acceptable salt thereof, wherein $R_{15}$ is —C(O)N(H)-cylopropyl optionally substituted with 1 or 2 halo at any position on the cyclopropyl ring, and
$R_1$ is

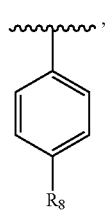

wherein $R_8$ is selected from Cl, F, hydroxyalkyl and —$CF_3$.

22. The compound according to claim 11, or a pharmaceutically acceptable salt thereof, wherein $R_{15}$ is —S(O)$_2$CH$_3$; and
$R_1$ is

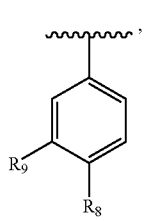

wherein $R_8$ and $R_9$ are each independently selected from Cl, F, hydroxyalkyl and —$CF_3$.

23. The compound according to claim 11, or a pharmaceutically acceptable salt thereof, wherein $R_{15}$ is —S(O)$_2$CH$_3$; and
$R_1$ is

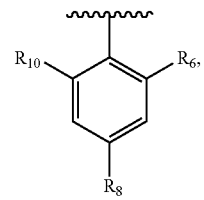

wherein $R_6$, $R_8$ and $R_{10}$ are each independently selected from Cl, F, hydroxyalkyl and —$CF_3$.

24. The compound according to claim 11, or a pharmaceutically acceptable salt thereof, wherein $R_{15}$ is —S(O)$_2$CH$_3$; and
$R_1$ is

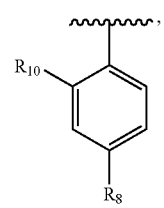

wherein $R_8$ and $R_{10}$ are each independently selected from Cl, F, hydroxyalkyl and —$CF_3$.

25. The compound according to claim 11, or a pharmaceutically acceptable salt thereof, wherein $R_{15}$ is —S(O)$_2$CH$_3$; and
$R_1$ is

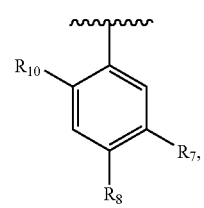

wherein $R_7$, $R_8$ and $R_{10}$ are each independently selected from Cl, F, hydroxyalkyl and —$CF_3$.

26. The compound according to claim 11, or a pharmaceutically acceptable salt thereof, wherein $R_{15}$ is —S(O)$_2$CH$_3$; and
$R_1$ is

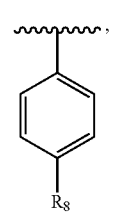

wherein $R_8$ is selected from Cl, F, hydroxyalkyl and —$CF_3$.

27. The compound according to claim 11, or a pharmaceutically acceptable salt thereof, wherein $R_{13}$ is —S(O)$_2$—NH$_2$, and
$R_1$ is

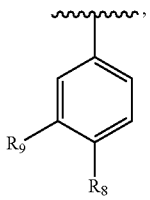

wherein $R_8$ and $R_9$ are each independently selected from Cl, F, hydroxyalkyl and —CF$_3$.

28. The compound according to claim 11, or a pharmaceutically acceptable salt thereof, wherein $R_{15}$ is —S(O)$_2$—NH$_2$; and
$R_1$ is

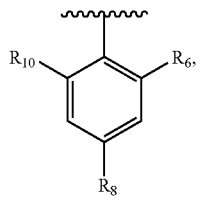

wherein $R_6$, $R_8$ and $R_{10}$ are each independently selected from Cl, F, hydroxyalkyl and —CF$_3$.

29. The compound according to claim 11, or a pharmaceutically acceptable salt thereof, wherein $R_{15}$ is —S(O)$_2$—NH$_2$; and
$R_1$ is

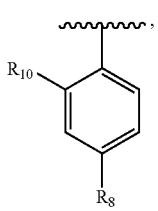

wherein $R_8$ and $R_{10}$ are each independently selected from Cl, F, hydroxyalkyl and —CF$_3$.

30. The compound according to claim 11 or a pharmaceutically acceptable salt thereof, wherein $R_{15}$ is —S(O)$_2$—NH$_2$; and
$R_1$ is

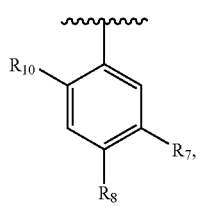

wherein $R_7$, $R_8$ and $R_{10}$ are each independently selected from Cl, F, hydroxyalkyl and —CF$_3$.

31. The compound according to claim 11, or a pharmaceutically acceptable salt thereof, wherein $R_{15}$ is —S(O)$_2$—NH$_2$; and
$R_1$ is

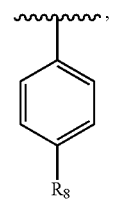

wherein $R_8$ is selected from Cl, F, hydroxyalkyl and —CF$_3$.

32. The compound according to claim 11, or a pharmaceutically acceptable salt thereof, wherein $R_{15}$ is —C(O)N(H)(C$_1$-C$_3$)alkyl-C(H)F$_2$ or —C(O)N(H)(C$_1$-C$_3$)alkyl-CF$_3$; and
$R_1$ is

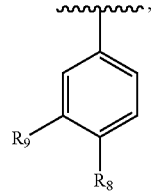

wherein $R_8$ and $R_9$ are each independently selected from Cl, F, hydroxyalkyl and —CF$_3$.

33. The compound according to claim 11, or a pharmaceutically acceptable salt thereof, wherein $R_{15}$ is —C(O)N(H)(C$_1$-C$_3$)alkyl-C(H)F$_2$ or —C(O)N(H)(C$_1$-C$_3$)alkyl-CF$_3$; and
$R_1$ is

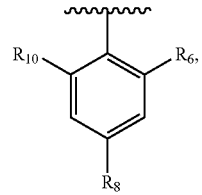

wherein $R_6$, $R_8$ and $R_{10}$ are each independently selected from Cl, F, hydroxyalkyl and —CF$_3$.

34. The compound according to claim 11, or a pharmaceutically acceptable salt thereof, wherein $R_{15}$ is —C(O)N(H)(C$_1$-C$_3$)alkyl-C(H)F$_2$ or —C(O)N(H)(C$_1$-C$_3$)alkyl-CF$_3$; and
$R_1$ is

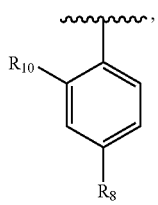

wherein $R_8$ and $R_{10}$ are each independently selected from Cl, F, hydroxyalkyl and —CF$_3$.

35. The compound according to claim 11, or a pharmaceutically acceptable salt thereof, wherein $R_{15}$ is —C(O)N(H)($C_1$-$C_3$)alkyl-C(H)$F_2$ or —C(O)N(H)($C_1$-$C_3$)alkyl-$CF_3$; and $R_1$ is

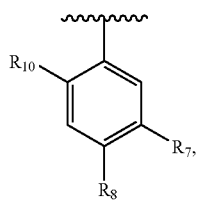

wherein $R_7$, $R_8$ and $R_{10}$ are each independently selected from Cl, F, hydroxyalkyl and —$CF_3$.

36. The compound according to claim 11, or a pharmaceutically acceptable salt thereof, wherein $R_{15}$ is —C(O)N(H)($C_1$-$C_3$)alkyl-C(H)$F_2$ or —C(O)N(H)($C_1$-$C_3$)alkyl-$CF_3$; and $R_1$ is

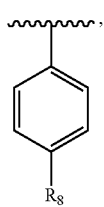

wherein $R_8$ is selected from Cl, F, hydroxyalkyl and —$CF_3$.

37. The compound according to claim 1, or a pharmaceutically acceptable salt thereof, wherein $R_2$ is

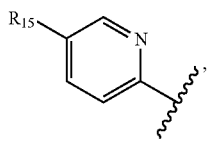

wherein $R_{15}$ is —N(H)C(O)-3-oxetane or —N(H)C(O)-2,2-difluorocyclopropyl.

38. The compound according to claim 12, or a pharmaceutically acceptable salt thereof, wherein $R_{15}$ is —C(O)$NH_2$; and $R_1$ is selected from 1-naphthyl optionally substituted with 1-2 $R_{19}$ groups, 2-quinolinyl optionally substituted with 1-2 $R_{19}$ groups, 2-naphthyl optionally substituted with 1-2 $R_{19}$ groups, and 4-quinolinyl optionally substituted with 1-2 $R_{19}$ groups, wherein each $R_{19}$, when $R_{19}$ is present, is independently selected from halo, alkyl optionally substituted with 1-5 halo, —OH, —$NH_2$, alkenyl optionally substituted with 1-5 halo, phenyl optionally substituted with 1, 2, or 3 groups selected from halo and —CF;, —S(O)$_2$-alkyl, —S(O)$_2$—$NH_2$, —S(O)$_2$—N(H)-alkyl, —S(O)$_2$—N(alkyl)$_2$, cycloalkyl, heterocycloalkyl, alkynyl optionally substituted with 1-5 halo, —C(O)OH, —C(O)(O)—$NH_2$, —C(O)(O)-alkyl, —$CF_3$, —(O)$CF_3$, —CN, alkoxy, alkoxyalkyl, alkoxyalkoxy, hydroxyalkoxy, heteroarylalkoxy, aminoalkoxy, alkylaminoalkoxy, and dialkylaminoalkoxy.

39. A compound selected from:
6-[3-({[1-(4-chlorophenyl)cyclopentyl]carbonyl}amino)-8-azabicyclo[3.2.1]oct-8-yl]-N-cyclopropylpyridine-3-carboxamide;
N-cyclopropyl-6[3-endo-({[1-(2,4-dichlorophenyl)cyclopropyl]carbonyl}amino)-8-azabicyclo[3.2.1]oct-8-yl]pyridine-3-carboxamide;
N-cyclopropyl-6-(3-endo-{[(1-phenylcyclopropyl)carbonyl]amino}-8-azabicyclo[3.2.1]oct-8-yl)pyridine-3-carboxamide;
N-cyclopropyl-6-[3-endo-({[1-(3,4-dichlorophenyl)cyclopropyl]carbonyl}amino)-8-azabicyclo[3.2.1]oct-8-yl]pyridine-3-carboxamide;
N-cyclopropyl-6-[3-endo-({[1-(4-fluorophenyl)cyclopropyl]carbonyl}amino)-8-azabicyclo[3.2.1]oct-8-yl]pyridine-3-carboxamide;
6-[3-endo-({[1-(4-chlorophenyl)cyclopropyl]carbonyl}amino)-8-azabicyclo[3.2.1]oct-8-yl]-N-(1-methylethyl)pyridine-3-carboxamide;
6-[3-endo-({2-[(4-chlorophenyl)oxy]-2-methylpropanoyl}amino)-8-azabicyclo[3.2.1]oct-8-yl]-N-cyclopropylpyridine-3-carboxamide;
6-[3-endo-({2-[(3-chlorophenyl)oxy]-2-methylpropanoyl}amino)-8-azabicyclo[3.2.1]oct-8-yl]-N-cyclopropylpyridine-3-carboxamide;
N-cyclopropyl-6-(3-endo-{[(2-methyl-2-(phenyloxy)propanoyl]amino}-8-azabicyclo[3.2.1]oct-8-yl)pyridine-3-carboxamide;
6-[3-endo-({[1-(3-chlorophenyl)cyclopropyl]carbonyl}amino)-8-azabicyclo[3.2.1]oct-8yl]-N-cyclopropylpyridine-3-carboxamide;
6-[3-endo-({[1-(2-chlorophenyl)cyclopropyl]carbonyl}amino)-8-azabicyclo[3.2.1]oct-8-yl]-N-cyclopropylpyridine-3-carboxamide;
1-(4-chlorophenyl)-N-[8-(4-cyanopyridin-2-yl)-8-azabicyclo[3.2.1]oct-3-endo-yl]cyclopropanecarboxamide;
6-[3-endo-({[1-(4-chlorophenyl)cyclopropyl]carbonyl}amino)-8-azabicyclo[3.2.1]oct-8-yl]pyridine-3-carboxylic acid;
6-(3-endo-{[2(4-chlorophenyl)-2-methylpropanoyl]amino}-8-azabicyclo[3.2.1]oct-8-yl)-N-cyclopropylpyridine-3-carboxamide;
N-cyclopropyl-6-{3-endo-[(2-methyl-2-phenylpropanoyl)amino]-8-azabicyclo[3.2.1]oct-8-yl}pyridine-3-carboxamide;
6-[3-endo-({[1-(4-chlorophenyl)cyclopropyl]carbonyl}amino)-8-azabicyclo[3.2.1]oct-8-yl]-N-(2,2,2-trifluoroethyl)pyridine-3-carboxamide;
N-cyclopropyl-6-[3-endo-({[1-(4-methylphenyl)cyclopropyl]carbonyl}amino)-8-azabicyclo[3.2.1]oct-8-yl]pyridine-3-carboxamide;
6-[3-endo-({2-[(2-chlorophenyl)oxy]-2-methylpropanoyl}amino)-8-azabicyclo[3.2.1]oct-8-yl]-N-cyclopropylpyridine-3-carboxamide;
6-(3-endo-{[2(3-chlorophenyl)-2-methylpropanoyl]amino}-8-azabicyclo[3.2.1]oct-8-yl)-N-cyclopropylpyridine-3-carboxamide;
6-(3-endo-{[2-(4-chlorophenyl)-2-methylpropanoyl]amino}-8-azabicyclo[3.2.1]oct-8-yl)-N-(2,2,2-trifluoroethyl)pyridine-3-carboxamide;
6-[3-endo-({2-[(4-chlorophenyl)oxy]-2-methylpropanoyl}amino)-8-azabicyclo[3.2.1]oct-8-yl]-N-(2,2,2-trifluoroethyl)pyridine-3-carboxamide;
N-cyclopropyl-6-[3-endo-({[1-(3,4-difluorophenyl)cyclopropyl]carbonyl}amino)-8-azabicyclo[3.2.1]oct-8-yl]pyridine-3-carboxamide;

6-[3-endo-({2-[(2-chlorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(4-chlorophenyl)oxy]-2-methylpropanoyl}amino)-8-azabicyclo[3.2.1]oct-8-yl]-N-(1-methylethyl)pyridine-3-carboxamide;
N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide;
2-[(4-chlorophenyl)oxy]-N-[8-(5-cyanopyridin-2-yl)-8-azabicyclo[3.2.1]oct-3-endo-yl]-2-methylpropanamide;
N-cyclopropyl-6-[3-endo-({2-[(3,4-difluorophenyl)oxy]-2-methylpropanoyl}amino)-8-azabicyclo[3.2.1]oct-8-yl]pyridine-3-carboxamide;
6-(3-endo-{[2-(2-chlorophenyl)-2-methylpropanoyl]amino}-8-azabicyclo[3.2.1]oct-8-yl)-N-cyclopropylpyridine-3-carboxamide;
N-cyclopropyl-6-[3-endo-({2-[(2,4-difluorophenyl)oxy]-2-methylpropanoyl}amino)-8-azabicyclo[3.2.1]oct-8-yl]pyridine-3-carboxamide;
2-[3-endo-({2-[(4-chlorophenyl)oxy]-2-methylpropanoyl}amino)-8-azabicyclo[3.2.1]oct-8-yl]-N-cyclopropylpyrimidine-5-carboxamide;
N-cyclopropyl-6-{3-endo-[(2-methyl-2-{[4-(trifluoromethyl)phenyl]oxy}propanoyl)amino]-8-azabicyclo[3.2.1]oct-8-yl}pyridine-3-carboxamide;
6-[3-endo-({2-[(4-cyanophenyl)oxy]-2-methylpropanoyl}amino)-8-azabicyclo[3.2.1]oct-8yl]-N-cyclopropylpyridine-3-carboxamide;
N-cyclopropyl-6-[3-endo-({[1-(3-fluorophenyl)cyclopropyl]carbonyl}amino)-8-azabicyclo[3.2.1]oct-8-yl]pyridine-3-carboxamide;
6-[3-endo-({2-[(4-chlorophenyl)oxy]-2-methylpropanoyl}amino)-8-azabicyclo[3.2.1]oct-8-yl]-N-cyclopropyl-5-methylpyridine-3-carboxamide;
6-[3-endo-({2-[(4-chloro-2-fluorophenyl)oxy]-2-methylpropanoyl}amino)-8-azabicyclo[3.2.1]oct-8-yl]-N-cyclopropylpyridine-3-carboxamide;
N-cyclopropyl-6-[3-endo-({2-[(3,4-dichlorophenyl)oxy]-2-methylpropanoyl}amino)-8-azabicyclo[3.2.1]oct-8-yl]pyridine-3-carboxamide;
6-[3-endo-({2-[(4-chloro-3-fluorophenyl)oxy]-2-methylpropanoyl}amino)-8-azabicyclo[3.2.1]oct-8-yl]-N-cyclopropylpyridine-3-carboxamide;
N-cyclopropyl-6-{3-endo-[(2-methyl-2-{[4-(methyloxy)phenyl]oxy}propanoyl)amino]-8-azabicyclo[3.2.1]oct-8-yl}pyridine-3-carboxamide;
N-cyclopropyl-6-[3-endo-({[1-(phenyloxy)cyclopropyl]carbonyl}amino)-8-azabicyclo[3.2.1]oct-8-yl]pyridine-3-carboxamide;
N-cyclopropyl-6-[3-endo-({[1-(phenyloxy)cyclobutyl]carbonyl}amino)-8-azabicyclo[3.2.1]oct-8-yl]pyridine-3-carboxamide;
6-{3-endo-[({1-[(4-chlorophenyl)oxy]cyclobutyl}carbonyl)amino]-8-azabicyclo[3.2.1]oct-8-yl}-N-cyclopropylpyridine-3-carboxamide;
N-cyclopropyl-6-(3-endo-{[2-(phenyloxy)propanoyl]amino}-8-azabicyclo[3.2.1]oct-8-yl)pyridine-3-carboxamide;
6-[3-endo-({2-[(4-chlorophenyl)oxy]propanoyl}amino)-8-azabicyclo[3.2.1]oct-8-yl]-N-cyclopropylpyridine-3-carboxamide;
6-[3-endo-({[1-(4-chlorophenyl)cyclobutyl]carbonyl}amino)-8-azabicyclo[3.2.1]oct-8-yl]-N-cyclopropylpyridine-3-carboxamide;
6-[3-endo-({2-[(4-chlorophenyl)oxy]-2-methylpropanoyl}amino)-8-azabicyclo[3.2.1]oct-8yl]-N-cyclopropyl-2-methylpyridine-3-carboxamide;
6-[3-endo-({2-[(2-chloro-4-fluorophenyl)oxy]-2-methylpropanoyl}amino)-8-azabicyclo[3.2.1]oct-8-yl]-N-(2,2,2-trifluoroethyl)pyridine-3-carboxamide;
2-[(2,4-dichlorophenyl)oxy]-N-{8-[5-(1-hydroxy-1-methylethyl)pyridin-2-yl]-8-azabicyclo[3.2.1]oct-3-endo-yl}-2-methylpropanamide;
6-[3-endo-({2-[(2,4-dichlorophenyl)oxy]-2-methylpropanoyl}amino)-8-azabicyclo[3.2.1]oct-8-yl]-N-(1-methylethyl)pyridine-3-carboxamide;
N-[8-(5-cyanopyridin-2-yl)-8-azabicyclo[3.2.1]oct-3-endo-yl]-2-[(2,4-dichlorophenyl)oxy]-2-methylpropanamide;
6-[3-endo-({2-[(2,4-dichlorophenyl)oxy]-2-methylpropanoyl}amino)-8-azabicyclo[3.2.1]oct-8-yl]pyridine-3-carboxamide;
N-[8-(5-acetylpyridin-2-yl)-8-azabicyclo[3.2.1]oct-3-endo-yl]-1-(4-chlorophenyl)cyclopropanecarboxamide;
N-{8-[5-(acetylamino)pyridin-2-yl]-8-azabicyclo[3.2.1]oct-3-endo-yl}-1-(4-chlorophenyl)cyclopropanecarboxamide;
1-(4-chlorophenyl)-N-(8-{5-[(cyclopropylcarbonyl)amino]pyridin-2-yl}-8-azabicyclo[3.2.1]oct-3-endo-yl)cyclopropanecarboxamide;
1-(4-chlorophenyl)-N-(8-{5-[(methylsulfonyl)amino]pyridin-2-yl}-8-azabicyclo[3.2.1]oct-3-endo-yl)cyclopropanecarboxamide;
N-[8-(5-aminopyridin-2-yl)-8-azabicyclo[3.2.1]oct-3-endo-yl]-1-(4-chlorophenyl)cyclopropanecarboxamide:
4-[3-endo-({[1-(4-chlorophenyl)cyclopropyl]carbonyl}amino)-8-azabicyclo[3.2.1]oct-8-yl]-N-cyclopropyl benzamide;
2-chloro-4-[3-endo-({[1-(4-chlorophenyl)cyclopropyl]carbonyl}amino)-8-azabicyclo[3.2.1]oct-8-yl]-N-cyclopropylbenzamide;
6-{3-endo-[({1-[(4-chlorophenyl)oxy]cyclopropyl}carbonyl)amino]-8-azabicyclo[3.2.1]oct-8-yl}-N-cyclopropylpyridine-3-carboxamide;
6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide;
2-[(4-chlorophenyl)oxy]-2-methyl-N-(8-pyrazin-2-yl-8-azabicyclo[3.2.1]oct-3-endo-yl)propanamide;
6-[3-endo-({2-[(4-chlorophenyl)oxy]propanoyl}amino)-8-azabicyclo[3.2.1]oct-8-yl]-N-[2-(methyloxy)ethyl]pyridine-3-carboxamide;
6-[3-endo-({2-[(2,4-dichlorophenyl)oxy]propanoyl}amino)-8-azabicyclo[3.2.1]oct-8-yl]-N-[2-(methyloxy)ethyl]pyridine-3-carboxamide;
6-[3-endo-({2-[(2-chloro-5-fluorophenyl)oxy]-2-methylpropanoyl}amino)-8-azabicyclo[3.2.1]oct-8-yl]-N-cyclopropylpyridine-3-carboxamide;
6-[3-endo-({2-[(2-chloro-4-fluorophenyl)oxy]-2-methylpropanoyl}amino)-8-azabicyclo[3.2.1]oct-8-yl]-N-(1-methylethyl)pyridine-3-carboxamide;
N-cyclopropyl-6-[3-endo-({2-[(2,5-dichlorophenyl)oxy]-2-methylpropanoyl}amino)-8-azabicyclo[3.2.1]oct-8-yl]pyridine-3-carboxamide;
6-[3-endo-({2-[(2,5-dichlorophenyl)oxy]-2-methylpropanoyl}amino)-8-azabicyclo[3.2.1]oct-8-yl]-N-(2,2,2-trifluoroethyl)pyridine-3-carboxamide;

6-[3-endo-({2-[(2-chloro-5-fluorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(2-chloro-4-fluorophenyl)oxy]-2-methylpropanoyl}amino)-8-azabicyclo[3.2.1]oct-8-yl]pyridine-3-carboxamide;
6-[3-endo-({2-[(2-chloro-4,5-difluorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(2,4-dichloro-5-fluorophenyl)oxy]-2-methylpropanoyl}amino)-8-azabicyclo[3.2.1]oct-8-yl]pyridine-3-carboxamide;
6-[3-endo-({2-[(4-chloro-3-fluorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(3,4-difluorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(3,4-dichlorophenyl)oxy]-2-methylpropanoyl}amino)-8-azabicyclo[3.2.1]oct-8-yl]-N-(1-methylethyl)pyridine-3-carboxamide;
6-[3-endo-({2-[(2,4-dichlorophenyl)oxy]-2-methylpropanoyl}amino)-8-azabicyclo[3.2.1]oct-8-yl]-N-[2-(methyloxy)ethyl]pyridine-3-carboxamide;
6-[3-endo-({2-[(4-chlorophenyl)oxy]butanoyl}amino)-8-azabicyclo[3.2.1]oct-8-yl]-N-[2-(methyloxy)ethyl]pyridine-3-carboxamide;
N-cyclopropyl-6-[3-endo-({2-[(2,4-dichlorophenyl)oxy]propanoyl}amino)-8-azabicyclo[3.2.1]oct-8-yl]pyridine-3-carboxamide;
6-[3-endo-({2-[(3,4-dichlorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(4-chloro-3-fluorophenyl)oxy]-2-methylpropanoyl}amino)-8-azabicyclo[3.2.1]oct-8-yl]-N-(1-methylethyl)pyridine-3-carboxamide;
6-[3-endo-({2-[(3,4-difluorophenyl)oxy]-2-methylpropanoyl}amino)-8-azabicyclo[3.2.1]oct-8-yl]-N-(1-methylethyl)pyridine-3-carboxamide;
5-chloro-N-cyclopropyl-6-[3-endo-({2-[(2,4-dichlorophenyl)oxy]-2-methylpropanoyl}amino)-8-azabicyclo[3.2.1]oct-8-yl]pyridine-3-carboxamide;
N-[8-(5-acetylpyridin-2-yl)-8-azabicyclo[3.2.1]oct-3-endo-yl]-2-[(2,4-dichlorophenyl)oxy]-2-methylpropanamide;
N-[8-(5-aminopyridin-2-yl)-8-azabicyclo[3.2.1]oct-3-endo-yl]--2-[(2,4-dichlorophenyl)oxy]-2-methylpropanamide;
6-[3-endo-({2-[(4-chlorophenyl)oxy]-2-methylpropanoyl}amino)-8-azabicyclo[3.2.1]oct-8-yl]-N-[2-(methyloxy)ethyl]pyridine-3-carboxamide;
6-[3-endo-({2-[(2,4-dichloro-5-fluorophenyl)oxy]-2-methylpropanoyl}amino)-8-azabicyclo[3.2.1]oct-8-yl]-N-(2,2,2-trifluoroethyl)pyridine-3-carboxamide;
N-cyclopropyl-6-[3-endo-({2-[(2,4-dichloro-5-fluorophenyl)oxy]-2-methylpropanoyl}amino)-8-azabicyclo[3.2.1]oct-8-yl]pyridine-3-carboxamide;
N-{6-[3-endo-({2[(2,4-dichlorophenyl)oxy]-2-methylpropanoyl}amino)-8-azabicyclo[3.2.1]oct-8-yl]pyridin-3-yl}cyclopropanecarboxamide;
6-[3-endo-({2-[(3-chloro-4-fluorophenyl)oxy]-2-methylpropanoyl}amino)-8-azabicyclo[3.2.1]oct-8-yl]-N-(2,2,2-trifluoroethyl)pyridine-3-carboxamide;
N-{8[5-(acetylamino)pyridin-2-yl]-8-azabicyclo[3.2.1]oct-3-endo-yl}-2-[(2,4-dichlorophenyl)oxy]-2-methyl-propanamide;
6-[3-endo-({2-[(3-chloro-4-fluorophenyl)oxy]-2-methylpropanoyl}amino)-8-azabicyclo[3.2.1]oct-8-yl]-N-(1-methylethyl)pyridine-3-carboxamide;
6-[3-endo-({2-[(2-chloro-4,5-difluorophenyl)oxy]-2-methylpropanoyl}amino)-8-azabicyclo[3.2.1]oct-8-yl]pyridine-3-carboxamide;
6-[3-endo-({2-[(2,3-dichloro-4-fluorophenyl)oxy]-2-methylpropanoyl}amino)-8-azabicyclo[3.2.1]oct-8-yl]pyridine-3-carboxamide;
6-[3-endo-({2-[(2,5-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(2,5-dichloro-4-fluorophenyl)oxy]-2-methylpropanoyl}amino)-8-azabicyclo[3.2.1]oct-8-yl]pyridine-3-carboxamide;
6-[3-endo-({2-[(2,3-dichloro-4-fluorophenyl)oxy]-2-methylpropanoyl}amino)-8-azabicyclo[3.2.1]oct-8-yl]-N-(2,2,2-trifluoroethyl)pyridine-3-carboxamide;
2-[(2,4-dichlorophenyl)oxy]-2-methyl-N-(8-{1 5-[(methylsulfonyl)amino]pyridin-2-yl}-8-azabicyclo[3.2.1]oct-3-endo-yl)propanamide;
6-[3-endo-({[1-(3-chlorophenyl)cyclopropyl]carbonyl}amino)-8-azabicyclo[3.2.1]oct-8-yl]pyridine-3-carboxamide;
6-[3-endo-({[1-(3,4-dichlorophenyl)cyclopropyl]carbonyl}amino)-8-azabicyclo[3.2.1]oct-8-yl]pyridine-3-carboxamide;
6-[3-endo-({[1-(3-fluorophenyl)cyclopropyl]carbonyl}amino)-8-azabicyclo[3.2.1]oct-8-yl]pyridine-3-carboxamide;
6-[3-endo-({2-[(4-chloro-2-fluorophenyl)oxy]-2-methylpropanoyl}amino)-8-azabicyclo[3.2.1]oct-8-yl]-N-(2,2,2-trifluoroethyl)pyridine-3-carboxamide;
2-[(2,4-dichlorophenyl)oxy]-2-methyl-N-(8-pyridin-3-yl-8-azabicyclo[3.2.1]oct-3-endo-yl)propanamide;
6-[3-endo-({2-[(3,5-dichloropyridin-2-yl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(5-chloropyridin-2-yl)oxy]-2-methylpropanoyl}amino)-8-azabicyclo[3.2.1]oct-8-yl]-N-(2,2,2-trifluoroethyl)pyridine-3-carboxamide;
6-[3-endo-({2-[(5-fluoropyridin-2-yl)oxy]-2-methylpropanoyl}amino)-8-azabicyclo[3.2.1]oct-8-yl]-N-(2,2,2-trifluoroethyl)pyridine-3-carboxamide;
4-[3-endo-({2-[(2,4-dichlorophenyl)oxy]-2-methylpropanoyl}amino)-8-azabicyclo[3.2.1]oct-8-yl]-N-(2,2,2-trifluoroethyl)benzamide;
6-{3-endo-[(2-methyl-2-{[4-(trifluoromethyl)phenyl]oxy}propanoyl)amino]-8-azabicyclo[3.2.1]oct-8-yl}-N-(2,2,2-trifluoroethyl)pyridine-3-carboxamide;
6-{3-endo-[(2-methyl-2-{[2-(trifluoromethyl)phenyl]oxy}propanoyl)amino]-8-azabicyclo[3.2.1]oct-8-yl}-N-(2,2,2-trifluoroethyl)pyridine-3-carboxamide;
N-cyclopropyl-6-{3-endo-[(2-methyl-2-{[2-trifluoromethyl)phenyl]oxy}propanoyl)amino]-8-azabicyclo[3.2.1]oct-8-yl}pyridine-3-carboxamide;
2-[(2,4-dichlorophenyl)oxy]-2-methyl-N-{8-[5-(1H-tetrazol-5-yl)pyridin-2-yl]-8-azabicyclo[3.2.1]oct-3-endo-yl}propanamide;
N-{8[4-(acetylamino)phenyl]-8-azabicyclo[3.2.1]oct-3-endo-yl]-24(2,4-dichlorophenyl)oxy]-2-methylpropanamide;
2-[(2,4-dichlorophenyl)oxy]-2-methyl-N-(8-{4-[(trifluoroacetyl)amino]phenyl}-8-azabicyclo[3.2.1]oct-3-endo-yl)propanamide;

3-chloro-4-[3-endo-({2-[(2,4-dichlorophenyl)oxy]-2-methylpropanoyl}amino)-8-azabicyclo[3.2.1]oct-8-yl]-N-(2,2,2-trifluoroethyl)benzamide;
3-chloro-4-[3-endo-({[1-(4-chlorophenyl)cyclopropyl]carbonyl}amino)-8-azabicyclo[3.2.1]oct-8-yl]-N-cyclopropylbenzamide;
4-[3-endo-({[1-(4-chlorophenyl)cyclopropyl]carbonyl}amino)-8-azabicyclo[3.2.1]oct-8-yl]-N-cyclopropyl-2-fluorobenzamide;
2-[(2,4-dichlorophenyl)oxy]-2-methyl-N-{8-[4-(methylsulfonyl)phenyl]-8-azabicyclo[3.2.1]oct-3-endo-yl}propanamide;
6-[3-endo-({[1-(3,4-difluorophenyl)cyclopropyl]carbonyl}amino)-8-azabicyclo[3.2.1]oct-8-yl]-N-(2,2,2-trifluoroethyl)pyridine-3-carboxamide;
6-[3-endo-({[1-(3-chlorophenyl)cyclopropyl]carbonyl}amino)-8-azabicyclo[3.2.1]oct-8-yl]-N-(2,2,2-trifluoroethyl)pyridine-3-carboxamide;
6-[3-endo-({[1-(3-fluorophenyl)cyclopropyl]carbonyl}amino)-8-azabicyclo[3.2.1]oct-8yl]-N-(2,2,2-trifluoroethyl)pyridine-3-carboxamide;
6-[3-endo-({2-[(3,5-dichloropyridin-2-yl)oxy]-2-methylpropanoyl}amino)-8-azabicyclo[3.2.1]oct-8-yl]pyridine-3-carboxamide;
N-{8-[5-(aminosulfonyl)pyridin-2-yl]-8-azabicyclo[3.2.1]oct-3-endo-yl}-2-[(2,4-dichlorophenyl)oxy]-2-methylpropanamide;
6-[3-endo-({2-[(2,4-dichlorophenyl)oxy]-2-methylpropanoyl}amino)-8-azabicyclo[3.2.1]oct-8-yl]-N-(2,2,3,3,3-pentafluoropropyl)pyridine-3-carboxamide;
6-[3-endo-({2-[(5-chloro-3-fluoropyridin-2-yl)oxy]-2-methylpropanoyl}amino)-8-azabicyclo[3.2.1]oct-8-yl]-N-(2,2,2-trifluoroethyl)pyridine-3-carboxamide;
6-(3-endo-{[2-methyl-2-({4-[(trifluoromethyl)oxy]phenyl}oxy)propanoyl]amino}-8-azabicyclo[3.2.1]oct-8-yl)-N-(2,2,2-trifluoroethyl)pyridine-3-carboxamide;
4-[3-endo-({2-[(2,4-dichlorophenyl)oxy]-2-methylpropanoyl}amino)-8-azabicyclo[3.2.1]oct-8-yl]-3-fluoro-N-(2,2,2-trifluoroethyl)benzamide;
N-cyclopropyl-4[3-endo-({2-[(2,4-dichlorophenyl)oxy]-2-methylpropanoyl}amino)-8-azabicyclo[3.2.1]oct-8-yl]-2-fluorobenzamide;
5-chloro-6-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-3-carboxamide;
N-cyclopropyl-4-[3-endo-({2-[(2,4-dichlorophenyl)oxy]-2-methylpropanoyl}amino)-8-azabicyclo[3.2.1]oct-8-yl]benzamide;
N-{4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide;
2-[(2,4-dichlorophenyl)oxy]-2-methyl-N-{8-[5-({[(2,2,2-trifluoroethyl)amino]carbonyl}amino)pyridin-2-yl]-8-azabicyclo[3.2.1]oct-3-endo-yl}propanamide;
2-[(2,4-dichlorophenyl)oxy]-2-methyl-N-{8-[4-({[(2,2,2-trifluoroethyl)amino]carbonyl}amino)phenyl]-8-azabicyclo[3.2.1]oct-3-endo-yl}propanamide;
N-{8-[2-chloro-4-({[(2,2,2-trifluoroethyl)amino]carbonyl}amino)phenyl]-8-azabicyclo[3.2.1]oct-3-endo-yl}-2-[(2,4-dichlorophenyl)oxy]-2-methylpropanamide;
2-[(2,4-dichlorophenyl)oxy]-N-{8-[2-fluoro-4-({[(2,2,2-trifluoroethyl)amino]carbonyl}amino)phenyl]-8-azabicyclo[3.2.1]oct-3-endo-yl}-2-methylpropanamide;
N-{3-chloro-4-[3-endo-({2-[(2,4-dichlorophenyl)oxy]-2-methylpropanoyl}amino)-8-azabicyclo[3.2.1]oct-8-yl]phenyl}-3,3,3-trifluoropropanamide;
N-{4-[3-endo-({2-[(2,4-dichlorophenyl)oxy]-2-methylpropanoyl}amino)-8-azabicyclo[3.2.1]oct-8-yl]-3-fluorophenyl}-3,3,3-trifluoropropanamide;
2-[(2,4-dichlorophenyl)oxy]-2-methyl-N-{8-[5-(methylsulfonyl)pyridin-2-yl]-8-azabicyclo[3.2.1]oct-3-endo-yl}propanamide;
6-[3-endo-({[1-(3,4-difluorophenyl)cyclopropyl]carbonyl}amino)-8-azabicyclo[3.2.1]oct-8-yl]pyridine-3-carboxamide;
6-[3-endo-({2-[(5-chloro-3-fluoropyridin-2-yl)oxy]-2-methylpropanoyl}amino)-8-azabicyclo[3.2.1]oct-8-yl]pyridine-3-carboxamide;
N-cyclopropyl-2-[3-endo-({2-[(2,4-dichlorophenyl)oxy]-2-methylpropanoyl}amino)-8-azabicyclo[3.2.1]oct-8-yl]pyridine-4-carboxamide;
6-{3-endo-[(2-{[4-chloro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
6-{3-endo-[(2-{[4-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
2-[(2,4-dichlorophenyl)oxy]-2-methyl-N-(8-{5-[(trifluoroacetyl)amino]pyridin-2-yl}-8-azabicyclo[3.2.1]oct-3-endo-yl)propanamide;
N-{6-[3-endo-({2-[(2,4-dichlorophenyl)oxy]-2-methylpropanoyl}amino)-8-azabicyclo[3.2.1]oct-8-yl]pyridin-3-yl}-3,3,3-trifluoropropanamide;
4-[3-endo-({[1-(4-chlorophenyl)cyclopropyl]carbonyl}amino)-8-azabicyclo[3.2.1]oct-8yl]-N-cyclopropyl-3-fluorobenzamide;
6-{3-endo-[(2-{[3-chloro-5-(trifluoromethyl)pyridin-2-yl]oxy}-2-methylpropanoyl)amino]-8-azabicyclo[3.2.1]oct-8-yl}pyridine-3-carboxamide;
6-{3-endo-(2-methyl-2-{[5-(trifluoromethyl)pyridin-2-yl]oxy}propanoyl)amino]-8-azabicyclo[3.2.1]oct-8-yl}pyridine-3-carboxamide;
6-{3-endo-[(2-{[3-chloro-5-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide;
6-{3-endo-[(2-methyl-2-{[5-(trifluoromethyl)pyridin-2-yl]oxy}propanoyl)amino]-8-azabicyclo[3.2.1]oct-8-yl}-N-(2,2,2-trifluoroethyppyridine-3-carboxamide;
2-[(2,3-dichloro-4-fluorophenyl)oxy]-2-methyl-N-{8-[5-(methylsulfonyl)pyridin-2-yl]-8-azabicyclo[3.2.1]oct-3-endo-yl}propanamide;
2-[(2,5-dichloro-4-fluorophenyl)oxy]-2-methyl-N-{8-[5-(methylsulfonyl)pyridin-2-yl]-8-azabicyclo[3.2.1]oct-3-endo-yl}propanamide;
2-[(2-chloro-4-fluorophenyl)oxy]-2-methyl-N-{8-[5-(methylsulfonyl)pyridin-2-yl]-8-azabicyclo[3.2.1]oct-3-endo-yl}propanamide;
2-[(2,4-dichlorophenyl)oxy]-2-methyl-N-{8-[3-(methylsulfonyl)phenyl]-8-azabicyclo[3.2.1]oct-3-endo-yl}propanamide;
N-{8-[5-(aminosulfonyl)pyridin-2-yl]-8-azabicyclo[3.2.1]oct-3-endo-yl}-2-[(2,5-dichloro-4-fluorophenyl)oxy]-2-methylpropanamide;
N-{8-[5-(aminosulfonyl)pyridin-2-yl]-8-azabicyclo[3.2.1]oct-3-endo-yl}-2-[(2-chloro-4-fluorophenyl)oxy]-2-methylpropanamide;

6-[3-endo-({2-[(2-chloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide;
6-[3-endo-({2-[(2,4-dichlorophenyl)oxy]-2-methylpropanoyl}amino)-8-azabicyclo[3.2.1]oct-8-yl]-5-fluoro-N-(2,2,2-trifluoroethyl)pyridine-3-carboxamide;
6-[3-endo-({2-[(3,5-dichloropyridin-2-yl)oxy]-2-methylpropanoyl}amino)-8-azabicyclo[3.2.1]oct-8-yl]-5-fluoro-N-(2,2,2-trifluoroethyl)pyridine-3-carboxamide;
6-[3-endo-({2-[(2,5-dichloro-4-fluorophenyl)oxy]-2-methylpropanoyl}amino)-8-azabicyclo[3.2.1]oct-8-yl]-5-fluoro-N-(2,2,2-trifluoroethyl)pyridine-3-carboxamide;
N-cyclopropyl-5-[3-endo-({2-[(2,4-dichlorophenyl)oxy]-2-methylpropanoyl}amino)-8-azabicyclo[3.2.1]oct-8-yl]pyridine-2-carboxamide;
6-{3-endo-[(2-methyl-2-{[2-(trifluoromethyl)phenyl]oxy}propanoyl)amino]-8-azabicyclo[3.2.1]oct-8-yl}pyridine-3-carboxamide;
6-(3-endo-{[2-(3,4-difluorophenyl)-2-methylpropanoyl]amino}-8-azabicyclo[3.2.1]oct-8-yl)pyridine-3-carboxamide;
4-[3-endo-({2-[(3,4-dichlorophenyl)oxy]-2-methylpropanoyl}amino)-8-azabicyclo[3.2.1]oct-8-yl]-N-(2,2,2-trifluoroethyl)benzamide;
4-[3-endo-({2-[(4-chloro-3-fluorophenyl)oxy]-2-methylpropanoyl}amino)-8-azabicyclo[3.2.1]oct-8-yl]N-(2,2,2-trifluoroethyl)benzamide;
6-{3-endo-[(2-{[4-fluoro-2-(trifluoromethyl)phenyl]oxy}-2-methylpropanoyl)amino]-8-azabicyclo[3.2.1]oct-8-yl}pyridine-3-carboxamide;
6-{3-endo-[(2-{[4-chloro-2-(trifluoromethyl)phenyl]oxy}-2-methylpropanoyl)amino]-8-azabicyclo[3.2.1]oct-8-yl}pyridine-3-carboxamide;
5-[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-2-carboxamide;
2[3-endo-({2-[(2,4-dichlorophenyl)oxy]-2-methylpropanoyl}amino)-8-azabicyclo[3.2.1]oct-8-yl]-N-(2,2,2-trifluoroethyl)pyridine-4-carboxamide;
6-{3-endo-[(2-methyl-2-{[4-(trifluoromethyl)phenyl]oxy}propanoyl)amino]-8-azabicyclo[3.2.1]oct-8-yl}pyridine-3-carboxamide;
2-[(2-chloro-4-fluorophenyl)oxy]-2-methyl-N-{8-[4-(methylsulfonyl)phenyl]-8-azabicyclo[3.2.1]oct-3-endo-yl}propanamide;
2-[(2,5-dichloro-4-fluorophenyl)oxy]-2-methyl-N-{8-[4-(methylsulfonyl)phenyl]-8-azabicyclo[3.2.1]oct-3-endo-yl}propanamide;
2[(3,5-dichloropyridin-2-yl)oxy]-2-methyl-N-{8-[4-(methylsulfonyl)phenyl]-8-azabicyclo[3.2.1]oct-3-endo-yl}propanamide;
2-{[4-fluoro-2-(trifluoromethyl)phenyl]oxy}-2-methyl-N-{8-[5-(methylsulfonyl)pyridin-2yl]-8-azabicyclo[3.2.1]oct-3-endo-yl}propanamide;
N-{8-[5-(aminosulfonyl)pyridin-2-yl]-8-azabicyclo[3.2.1]oct-3-endo-yl}-2-{[4-fluoro-2-(trifluoromethyl)phenyl]oxy}-2-methylpropanamide;
2-[(2,6-dichloro-4-fluorophenyl)oxy]-2-methyl-N-{8-[5-(methylsulfonyl)pyridin-2-yl]-8-azabicyclo[3.2.1]oct-3-endo-yl}propanamide;
2-{[2-chloro-4-fluoro-6-(trifluoromethyl)phenyl]oxy}-2-methyl-N-{8-[5-(methylsulfonyl)pyridin-2-yl]-8-azabicyclo[3.2.1]oct-3-endo-yl}propanamide;
2-methyl-2-{[4-(methyloxy)phenyl]oxy}-N-{8-[5-(methylsulfonyl)pyridin-2-yl]-8-azabicyclo[3.2.1]oct-3-endo-yl}propanamide;
N-{8-[5-(aminosulfonyl)pyridin-2-yl]-8-azabicyclo[3.2.1]oct-3-endo-yl}-2-methyl-2-{[4-(methyloxy)phenyl]oxy}propanamide;
2-methyl-2-{[4-(methyloxy)phenyl]oxy}-N-{8-[4-(methylsulfonyl)phenyl]-8-azabicyclo[3.2.1]oct-3-endo-yl}propanamide;
6-{3-endo-[(2-{[2-chloro-4-(trifluoromethyl)phenyl]oxy}-2-methylpropanoyl)amino]-8-azabicyclo[3.2.1]oct-8-yl}pyridine-3-carboxamide;
6-{3-endo-[(2-{[2-chloro-4-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
6-{3-endo-[(2-{[4-chloro-3-(trifluoromethyl)phenyl]oxy}-2-methylpropanoyl)amino]-8-azabicyclo[3.2.1]oct-8-yl}pyridine-3-carboxamide;
6-{3-endo-[(2-{[4-chloro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
6-{3-endo-[(2-{[4-fluoro-3-(trifluoromethyl)phenyl]oxy}-2-methylpropanoyl)amino]-8-azabicyclo[3.2.1]oct-8-yl}pyridine-3-carboxamide;
6-{3-endo-[(2-{[4-fluoro-3-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
6-{3-endo-[(2-{[2-fluoro-5-(trifluoromethyl)phenyl]oxy}-2-methylpropanoyl)amino]-8-azabicyclo[3.2.1]oct-8-yl}pyridine-3-carboxamide;
6-{3-endo-[(2-{[2-fluoro-5-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;
N-{8-[5-(aminosulfonyl)pyridin-2-yl]-8-azabicyclo[3.2.1]oct-3-endo-yl}-2-[(3,5-dichloropyridin-2-yl)oxy]-2-methylpropanamide;
N-{8-[4-(aminosulfonyl)phenyl]-8-azabicyclo[3.2.1]oct-3-endo-yl}-2-methyl-2-{[5-(trifluoromethyl)pyridin-2-yl]oxy}propanamide;
2[(3,5-dichloropyridin-2-yl)oxy]-2-methyl-N-{8-[5-(methylsulfonyl)pyridin-2-yl]-8-azabicyclo[3.2.1]oct-3-endo-yl}propanamide;
2-[(5-chloro-3-fluoropyridin-2-yl)oxy]-2-methyl-N-{8-[5-(methylsulfonyl)pyridin-2-yl]-8-azabicyclo[3.2.1]oct-3-endo-yl}propanamide;
2-[(5-chloro-3-fluoropyridin-2-yl)oxy]-2-methyl-N-{8-[5-(methylsulfonyl)phenyl]-8-azabicyclo[3.2.1]oct-3-endo-yl}propanamide;
2-methyl-N-{8-[4-(methylsulfonyl)phenyl]-8-azabicyclo[3.2.1]oct-3-endo-yl}-2-{[5-(trifluoromethyl)pyridin-2-yl]oxy}propanamide;
2-methyl-N-{8-[5-(methylsulfonyl)pyridin-2-yl]-8-azabicyclo[3.2.1]oct-3-endo-yl}-2-[(2,4,5-trichlorophenyl)oxy]propanamide;
N-{8-[5-(aminosulfonyl)pyridin-2-yl]-8-azabicyclo[3.2.1]oct-3-endo-yl}-2-methyl-2-[(2,4,5-trichlorophenyl)oxy]propanamide;
2-methyl-N-{8-[4-(methylsulfonyl)phenyl]-8-azabicyclo[3.2.1]oct-3-endo-yl}-2-[(2,4,5-trichlorophenyl)oxy]propanamide;
2-[(2,4-difluorophenyl)oxy]-2-methyl-N-{8-[5-(methylsulfonyl)pyridin-2-yl]-8-azabicyclo[3.2.1]oct-3-endo-yl}propanamide;

2-[(4-chlorophenyl)oxy]-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(4-chlorophenyl)oxy]-2-methylpropanamide;

2-[(4-chlorophenyl)oxy]-2-methyl-N-{8-[4-(methylsulfonyl)phenyl]-8-azabicyclo[3.2.1]oct-3-endo-yl}propanamide;

2-[(3,4-dichlorophenyl)oxy]-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2[(3,4-dichlorophenyl)oxy]-2-methylpropanamide;

2-[(3,4-dichlorophenyl)oxy]-2-methyl-N-{8-[4-(methylsulfonyl)phenyl]-8-azabicyclo[3.2.1]oct-3-endo-yl}propanamide;

2-[(3,4-difluorophenyl)oxy]-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(3,4-difluorophenyl)oxy]-2-methylpropanamide;

2-[(3,4-difluorophenyl)oxy]-2-methyl-N-{8-[4-(methylsulfonyl)phenyl]-8-azabicyclo[3.2.1]oct-3-endo-yl}propanamide;

4-[3-endo-({2-[(3,4-difluorophenyl)oxy]-2-methylpropanoyl}amino)-8-azabicyclo[3.2.1]oct-8-yl]-N-(2,2,2-trifluoroethyl)benzamide;

N-{8-[5-(aminosulfonyl)pyridin-2-yl]-8-azabicyclo[3.2.1]oct-3-endo-yl}-2-{[4-chloro-2-(trifluoromethyl)phenyl]oxy}-2-methylpropanamide;

2-[(2-chloro-4-methylphenyl)oxy]-2-methyl-N-{8-[5-(methylsulfonyl)pyridin-2-yl]-8-azabicyclo[3.2.1]oct-3-endo-yl}propanamide;

N-{8[5-(aminosulfonyl)pyridin-2-yl]-8-azabicyclo[3.2.1]oct-3-endo-yl}-2-[(2-chloro-4-methylphenyl)oxy]-2-methylpropanamide;

2-[(2-chloro-4-methylphenyl)oxy]-2-methyl-N-{8-[4-(methylsulfonyl)phenyl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(2,3-dichloro-4-fluorophenyl)oxy]-2-methylpropanamide;

N-{8-[5-(aminosulfonyl)pyridin-2-yl]-8-azabicyclo[3.2.1]oct-3-endo-yl}-2-methyl-2-[(2,4, 5-trifluorophenyl)oxy]propanamide;

2-[(4-fluoro-2-methylphenyl)oxy]-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(4-fluoro-2-methylphenyl)oxy]-2-methylpropanamide;

2-[(4-fluoro-2-methylphenyl)oxy]-2-methyl-N-{8-[4-(methylsulfonyl)phenyl]-8-azabicyclo[3.2.1]oct-3-endo-yl}propanamide;

2-{[4-fluoro-2-(methyloxy)phenyl]oxy}-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-{[4-fluoro-2-(methyloxy)phenyl]oxy}-2-methylpropanamide;

2-{[4-fluoro-2-(methyloxy)phenyl]oxy}-2-methyl-N-{8-[4-(methylsulfonyl)phenyl]-8-azabicyclo[3.2.1]oct-3-endo-yl}propanamide;

2-[(4-chloro-2-fluorophenyl)oxy]-2-methyl-N-{8-[4-(methylsulfonyl)phenyl]-8-azabicyclo[3.2.1]oct-3-endo-yl}propanamide;

2-[(2,4-difluorophenyl)oxy]-2-methyl-N-{8-[4-(methylsulfonyl)phenyl]-8-azabicyclo[3.2.1]oct-3-endo-yl}propanamide;

2-[(2-chloro-4,5-difluorophenyl)oxy]-2-methyl-N-{8-[4-(methylsulfonyl)phenyl]-8-azabicyclo[3.2.1]oct-3-endo-yl}propanamide;

2-[(3-chloro-4-fluorophenyl)oxy]-2-methyl-N-{8-[5-(methylsulfonyl)pyridin-2-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(3-chloro-4-fluorophenyl)oxy]-2-methylpropanamide;

2-[(3-chloro-4-fluorophenyl)oxy]-2-methyl-N-{8-[4-(methylsulfonyl)phenyl]-8-azabicyclo[3.2.1]oct-3-endo-yl}propanamide;

2-[(4-chloro-2-fluorophenyl)oxy]-2-methyl-N-{8-[5-(methylsulfonyl)pyridin-2-yl]-8-azabicyclo[3.2.1]oct-3-endo-yl}propanamide;

2[(4-fluorophenyl)oxy]-2-methyl-N-{8-[5-(methylsulfonyl)pyridin-2-yl]-8-azabicyclo[3.2.1]oct-3-endo-yl}propanamide;

2-[(2-chloro-4,5-difluorophenyl)oxy]-2-methyl-N-{8-[5-(methylsulfonyl)pyridin-2-yl]-8-azabicyclo[3.2.1]oct-3-endo-yl}propanamide;

2-methyl-N-{8-[5-(methylsulfonyl)pyridin-2-yl]-8-azabicyclo[3.2.1]oct-3-endo-yl}-2-[(2,4,5-trifluorophenyl)oxy]propanamide;

2-[(4-fluorophenyl)oxy]-2-methyl-N-{8-[4-(methylsulfonyl)phenyl]-8-azabicyclo[3.2.1]oct-3-endo-yl}propanamide;

2-methyl-N-{8-[4-(methylsulfonyl)phenyl]-8-azabicyclo[3.2.1]oct-3-endo-yl}-2-[(2,4,5-trifluorophenyl)oxy]propanamide;

2-[(2,3-dichloro-4-fluorophenyl)oxy]-2-methyl-N-{8-[4-(methylsulfonyl)phenyl]-8-azabicyclo[3.2.1]oct-3-endo-yl}propanamide;

2-[(2,4-dichloro-5-fluorophenyl)oxy]-2-methyl-N-{8-[5-(methylsulfonyl)pyridin-2-yl]-8-azabicyclo[3.2.1]oct-3-endo-yl}propanamide;

2-[(2,4-dichloro-5-fluorophenyl)oxy]-2-methyl-N-{8-[4-(methylsulfonyl)phenyl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(2,6-dichloro-4-fluorophenyl)oxy]-2-methylpropanamide;

2-[(2,6-dichloro-4-fluorophenyl)oxy]-2-methyl-N-{8-[4-(methylsulfonyl)phenyl]-8-azabicyclo[3.2.1]oct-3-endo-yl}propanamide;

2-[(4-chloro-3-fluorophenyl)oxy]-2-methyl-N-{8-[5-(methylsulfonyl)pyridin-2-yl]-8-azabicyclo[3.2.1]oct-3-endo-yl}propanamide;

2-[(4-chloro-3-fluorophenyl)oxy]-2-methyl-N-{8-[4-(methylsulfonyl)phenyl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-[(4-chloro-3-fluorophenyl)oxy]-2-methylpropanamide;

2-methyl-N-{8-[5-(methylsulfonyl)pyridin-2-yl]-8-azabicyclo[3.2.1]oct-3-endo-yl}-2-{[4-(trifluoromethyl)phenyl]oxy}propanamide;

N-{8-[5-(aminosulfonyl)pyridin-2-yl]-8-azabicyclo[3.2.1]oct-3-endo-yl}-2-methyl-2-{[4-(trifluoromethyl)phenyl]oxy}propanamide;

2-methyl-N-{8-[4-(methylsulfonyl)phenyl]-8-azabicyclo[3.2.1]oct-3-endo-yl}-2-{[4-(trifluoromethyl)phenyl]oxy}propanamide;

N-{8-[5-(aminosulfonyl)pyridin-2-yl]-8-azabicyclo[3.2.1]oct-3-endo-yl}-2-{[3-chloro-5-(trifluoromethyl)pyridin-2-yl]oxy}-2-methylpropanamide;

N-{8[5-(aminosulfonyl)pyridin-2-yl]-8-azabicyclo[3.2.1]oct-3-endo-yl}-2-[(5-chloro-3-fluoropyridin-2-)oxy]-2-methylpropanamide;

2-{[3-chloro-5-(trifluoromethyl)pyridin-2-yl]oxy}-2-methyl-N-{8[5-(methylsulfonyl)pyridin-2-yl]-8-azabicyclo[3.2.1]oct-3-endo-yl}propanamide;

2-{[3-chloro-5-(trifluoromethyl)pyridin-2-yl]oxy}-2-methyl-N-{8-[4-(methylsulfonyl)phenyl]-8-azabicyclo[3.2.1]oct-3-endo-yl}propanamide;

2-{[4-fluoro-2-(trifluoromethyl)phenyl]oxy}-2-methyl-N-{8-[4-(methylsulfonyl)phenyl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-{[2-chloro-4-fluoro-6-(trifluoromethyl)phenyl]oxy}-2-methylpropanamide;

2-{[2-chloro-4-fluoro-6-(triuoromethyl)phenyl]oxy}-2-methyl-N-{8-[4-(methylsulfonyl)phenyl]-8-azabicyclo[3.2.1]oct-3-endo-yl}propanamide;

2-{[2-chloro-4-(methyloxy)phenyl]oxy}-2-methyl-N-{8-[5-(methylsulfonyl)pyridin-2-yl]-8-azabicyclo[3.2.1]oct-3-endo-yl}propanamide;

2-{[2-chloro-4-(methyloxy)phenyl]oxy}-2-methyl-N-{8-[4-(methylsulfonyl)phenyl]-8-azabicyclo[3.2.1]oct-3-endo-yl}propanamide;

2-methyl-N-{8-[5-(methylsulfonyl)pyridin-2-yl]-8-azabicyclo[3.2.1]oct-3-endo-yl}-2-{[2-(trifluoromethyl)phenyl]oxy}propanamide;

N-{8-[5-(aminosulfonyl)pyridin-2-yl]-8-azabicyclo[3.2.1]oct-3-endo-yl}-2-methyl-2-{[2-(trifluoromethyl)phenyl]oxy}propanamide;

2-methyl-N-{8-[4-(methylsulfonyl)phenyl]-8-azabicyclo[3.2.1]oct-3-endo-yl}-2-{[2-(trifluoromethyl)phenyl]oxy}propanamide;

2-methyl-N-{8-[5-(methylsulfonyl)pyridin-2-yl]-8-azabicyclo[3.2.1]oct-3-endo-yl}-2-[(2,4,6-trifluorophenyl)oxy]propanamide;

N-{8[5-(aminosulfonyl)pyridin-2-yl]-8-azabicyclo[3.2.1]oct-3-endo-yl}-2-methyl-2-[(2,4,6-trifluorophenyl)oxy]propanamide;

2-methyl-N-{8-[4-(methylsulfonyl)phenyl]-8-azabicyclo[3.2.1]oct-3-endo-yl}-2-[(2,4,6-trifluorophenyl)oxy]propanamide;

N-{8[5-(aminosulfonyl)pyridin-2-yl]-8-azabicyclo[3.2.1]oct-3-endo-yl}-2-[(2,4-dichloro-5-fluorophenyl)oxy]-2-methylpropanamide;

N-{8-[5-(aminosulfonyl)pyridin-2-yl]-8-azabicyclo[3.2.1]oct-3-endo-yl}-2-[(2-chloro-4,5-difluorophenyl)oxy]-2-methylpropanamide;

2-{[4-chloro-2-(trifluoromethyl)phenyl]oxy}-2-methyl-N-{8-[5-(methylsulfonyl)pyridin-2-yl]-8-azabicyclo[3.2.1]oct-3-endo-yl}propanamide;

N-{8-[5-(aminosulfonyppyridin-2-yl]-8-azabicyclo[3.2.1]oct-3-endo-yl}-2-[(4-fluorophenyl)oxy]-2-methylpropanamide;

6-[3-endo-({2-[(2-chloro-4-fluorophenyl)oxy]-2-methylpropanoyl}amino)-8-azabicyclo[3.2.1]oct-8-yl]-N-cyclopropylpyridine-3-carboxamide;

6-[3-endo-({2-[(3-chlorobiphenyl-4-yl)oxy]-2-methylpropanoyl}amino)-8-azabicyclo[3.2.1]oct-8-yl]pyridine-3-carboxamide;

2-{[5-fluoro-2-(trifluoromethyl)phenyl]oxy}-2-methyl-N-{8-[5-(methylsulfonyl)pyridin-2-yl]-8-azabicyclo[3.2.1]oct-3-endo-yl}propanamide;

6-[3-endo-({2-[(2,4-dichlorophenyl)oxy]-2-methylpropanoyl}amino)-8-azabicyclo[3.2.1]oct-8-yl]-N-(2,2-difluorocyclopropyl)pyridine-3-carboxamide;

6-{3-endo-[(2-{[4-fluoro-2-(methylsulfonyl)phenyl]oxy}-2-methylpropanoyl)amino]-8-azabicyclo[3.2.1]oct-8-yl}pyridine-3-carboxamide;

2-[(2,5-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide;

6-[3-endo-({2-[(1-chloronaphthalen-2-yl)oxy]-2-methylpropanoyl}amino)-8-azabicyclo[3.2.1]oct-8-yl]pyridine-3-carboxamide;

2-{[4-fluoro-3-(trifluoromethyl)phenyl]oxy}-2-methyl-N-{8-[5-(methylsulfonyl)pyridin-2-yl]-8-azabicyclo[3.2.1]oct-3-endo-yl}propanamide;

6-{3-endo-[(2-{[5-chloro-3-(trifluoromethyl)pyridin-2-yl]oxy}-2-methylpropanoyl)amino]-8-azabicyclo[3.2.1]oct-8-yl}-N-(2,2,2-trifluoroethyl)pyridine-3-carboxamide;

6-[3-endo-({2-[(2,4-dichlorophenyl)sulfonyl]-2-methylpropanoyl}amino)-8-azabicyclo[3.2.1]oct-8-yl]pyridine-3-carboxamide;

2-[(2-chloro-4-fluorophenyl)oxy]-2-methyl-N-{8-[6-(methylsulfonyl)pyridin-3-yl]-8-azabicyclo[3.2.1]oct-3-endo-yl}propanamide;

2-[(2-chloro-4-fluorophenyl)oxy]-2-methyl-N-(8-{5-[5-(trifluoromethyl)-1,2,4-oxadiazol-3-yl]pyridin-2-yl}-8-azabicyclo[3.2.1]oct-3-endo-yl)propanamide;

6-[3-endo-({2-[(5-chloro-4'-fluorobiphenyl-2-yl)oxy]-2-methylpropanoyl}amino)-8-azabicyclo[3.2.1]oct-8-yl]pyridine-3-carboxamide;

N-{5-chloro-6-[3-endo-({2-[(2,4-dichlorophenyl)oxy]-2-methylpropanoyl}amino)-8-azabicyclo[3.2.1]oct-8-yl]pyridin-3-yl}-3,3,3-trifluoropropanamide;

4-{[3-endo-({2-[(2,4-dichlorophenyl)oxy]-2-methylpropanoyl}amino)-8-azabicyclo[3.2.1]oct-8-yl]carbonyl}benzamide;

1-[4-fluoro-3-(trifluoromethyl)phenyl]-N-{8-[5-(methylsulfonyl)pyridin-2-yl]-8-azabicyclo[3.2.1]oct-3-endo-yl}cyclopropanecarboxamide;

1-(3,4-difluorophenyl)-N-{8-[5-(methylsulfonyl)pyridin-2-yl]-8-azabicyclo[3.2.1]oct-3-endo-yl}cyclopropanecarboxamide;

6-[3-endo-({2-[(3-chloro4'-fluorobiphenyl-4-yl)oxy]-2-methylpropanoyl}amino)-8-azabicyclo[3.2.1]oct-8-yl]pyridine-3-carboxamide;

2-{[4-fluoro-2-(trifluoromethyl)phenyl]oxy}-2-methyl-N-(8-{4-[(methylsulfonyl)amino]phenyl}-8-azabicyclo[3.2.1]oct-3-endo-yl)propanamide;

2-{[4-chloro-2-(trifluoromethyl)phenyl]oxy}-2-methyl-N-{8-[4-(methylsulfonyl)phenyl]-8-azabicyclo[3.2.1]oct-3-endo-yl}propanamide;

6-[3-endo-({2-[(4-chloro-2-cyclohexylphenyl)oxy]-2-methylpropanoyl}amino)-8-azabicyclo[3.2.1]oct-8-yl]pyridine-3-carboxamide;

6-[3-endo-({2-[(2,4-dichlorophenyl)thio]-2-methylpropanoyl}amino)-8-azabicyclo[3.2.1]oct-8-yl]pyridine-3-carboxamide;

6-[3-endo-({2-[(2,4-dichlorophenyl)oxy]-2-methylpropanoyl}amino)-8-azabicyclo[3.2.1]oct-8-yl]pyridine-3-carboxylic acid;

2-{[4-fluoro-2-(trifluoromethyl)phenyl]oxy}-2-methyl-N-{8-[6-(methylsulfonyl)pyridin-3yl]-8-azabicyclo[3.2.1]oct-3-endo-yl}propanamide;

6-{3-endo-[({1-[3-(methylsulfonyl)phenyl]cyclopropyl}carbonyl)amino]-8-azabicyclo[3.2.1]oct-8-yl}-N-(2,2,2-trifluoroethyl)pyridine-3-carboxamide;

2-[(2,3-dichloro-4-fluorophenyl)oxy]-2-methyl-N-(8-{5-[(methylsulfonyl)amino]pyridin-2-yl}-8-azabicyclo[3.2.1]oct-3-endo-yl)propanamide;

3-{[3-endo-({2-[(2,4-dichlorophenyl)oxy]-2-methylpropanoyl}amino)-8-azabicyclo[3.2.1]oct-8-yl]methyl}benzamide;

2-{[4-fluoro-2-(trifluoromethyl)phenyl]oxy}-2-methyl-N-{8-[6-(1H-tetrazol-5-yl)pyridin-3-yl]-8-azabicyclo[3.2.1]oct-3-endo-yl}propanamide;

N-{8-[5-(aminosulfonyl)pyridin-2-yl]-8-azabicyclo[3.2.1]oct-3-endo-yl}-2-{[4-chloro-2-(methylsulfonyl)phenyl]oxy}-2-methylpropanamide;

N-{8-[5-(aminosulfonyl)pyridin-2-yl]-8-azabicyclo[3.2.1]oct-3-endo-yl}-2-[(2,4-difluorophenyl)oxy]-2-methylpropanamide;

4-{[3-endo-({2-[(2,4-dichlorophenyl)oxy]-2-methylpropanoyl}amino)-8-azabicyclo[3.2.1]oct-8-yl]methyl}benzamide;

6-{3-endo-[(2-{[4-fluoro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide;

6-[3-endo-({2-[(4-chloronaphthalen-1-yl)oxy]-2-methylpropanoyl}amino)-8-azabicyclo[3.2.1]oct-8-yl]pyridine-3-carboxamide;

N-{8[5-(aminosulfonyl)pyridin-2-yl]-8-azabicyclo[3.2.1]oct-3-endo-yl}-2-{[4-fluoro-2-(methylsulfonyl)phenyl]oxy}-2-methylpropanamide;

2-{[4-chloro-2-(trifluoromethyl)phenyl]oxy}-2-methyl-N-{8-[6-(methylsulfonyl)pyridin-3-yl]-8-azabicyclo[3.2.1]oct-3-endo-yl}propanamide;

6-{3-endo-[(2-methyl-2-{[2-(methylsulfonyl)phenyl]oxy}propanoyl)amino]-8-azabicyclo[3.2.1]oct-8-yl}-N-(2,2,2-trifluoroethyl)pyridine-3-carboxamide;

3-{[4-chloro-2-(trifluoromethyl)phenyl]oxy}-2,2-dimethyl-N-{8-[5-(methylsulfonyl)pyridin-2-yl]-8-azabicyclo[3.2.1]oct-3-endo-yl}propanamide;

6-[(8-{2-[(2,4-dichlorophenyl)oxy]-2-methylpropanoyl}-8-azabicyclo[3.2.1]oct-3-endo-yl)amino]pyridine-3-carboxamide;

2-{[4-chloro-2-(trifluoromethyl)phenyl]oxy}-2-methyl-N-{8-[6-(1 H-tetrazol-5-yl)pyridin-3-yl]-8-azabicyclo[3.2.1]oct-3-endo-yl}propanamide;

2-[(2,4-dichlorophenyl)oxy]-2-methyl-N-{8-[6-(methylsulfonyl)pyridin-3-yl]-8-azabicyclo[3.2.1]oct-3-endo-yl}propanamide;

2-[(2,4-dichlorophenyl)sulfonyl]-2-methyl-N-{8-[5-(methylsulfonyl)pyridin-2-yl]-8-azabicyclo[3.2.1]oct-3-endo-yl}propanamide;

6-{3-endo-[(2-{[5-fluoro-2-(trifluoromethyl)phenyl]oxy}-2-methylpropanoyl)amino]-8-azabicyclo[3.2.1]oct-8-yl}pyridine-3-carboxamide;

6-(3-endo-{[2-methyl-2-(quinolin-2-yloxy)propanoyl]amino}-8-azabicyclo[3.2.1]oct-8-yl)pyridine-3-carboxamide;

6-{3-endo-[({1-[3-(methylsulfonyl)phenyl]cyclopropyl}carbonyl)amino]-8-azabicyclo[3.2.1]oct-8-yl}pyridine-3-carboxamide;

6-{3-endo-[(3-{[4-chloro-2-(trifluoromethyl)phenyl]oxy}-2,2-dimethylpropanoyl)amino]-8-azabicyclo[3.2.1]oct-8-yl}-N-(2,2,2-trifluoroethyl)pyridine-3-carboxamide;

N-{8[5-(aminosulfonyl)pyridin-2-yl]-8-azabicyclo[3.2.1]oct-3-endo-yl}-1-[3-(methylsulfonyl)phenyl]cyclopropanecarboxamide;

2-{[5-chloro-3-(trifluoromethyl)pyridin-2-yl]oxy}-2-methyl-N-{8-[5-(methylsulfonyl)pyridin-2-yl]-8-azabicyclo[3.2.1]oct-3-endo-yl}propanamide;

2-[(2-chloro-4-fluorophenyl)oxy]-2-methyl-N-(8-{4-[(methylsulfonyl)amino]phenyl}-8-azabicyclo[3.2.1]oct-3-endo-yl)propanamide;

6-(3-endo-{[2-methyl-2-(naphthalen-2-yloxy)propanoyl]amino}-8-azabicyclo[3.2.1]oct-8-yl)pyridine-3-carboxamide;

6-{3-endo-({2-[(2,4-dichlorophenyl)oxy]-2-methylpropanoyl}amino)-8-azabicyclo[3.2.1]oct-8-yl]-N-oxetan-3-ylpyridine-3-carboxamide;

6-(3-endo-{[2-methyl-2-(quinolin-4-yloxy)propanoyl]amino}-8-azabicyclo[3.2.1]oct-8-yl)pyridine-3-carboxamide;

6-{3-endo-[(2-{[5-fluoro-2-(trifluoromethyl)phenyl]oxy}-2-methylpropanoyl)amino]-8-azabicyclo[3.2.1]oct-8-yl}-N-(2,2,2-trifluoroethyl)pyridine-3-carboxamide;

6-[3-endo-({2-[(4-chloro-2-cyclopentylphenyl)oxy]-2-methylpropanoyl}amino)-8-azabicyclo[3.2.1]oct-8-yl]pyridine-3-carboxamide;

6-{3-endo-[(2-{[4-chloro-2-(methylsulfonyl)phenyl]oxy}-2-methylpropanoyl)amino]-8-azabicyclo[3.2.1]oct-8-yl}-N-(2,2,2-trifluoroethyl)pyridine-3-carboxamide;

6-[3-endo-({2-[(5-chlorobiphenyl-2-yl)oxy]-2-methylpropanoyl}amino)-8-azabicyclo[3.2.1]oct-8-yl]pyridine-3-carboxamide;

6-{[3-endo-({2-[(2,4-dichlorophenyl)oxy]-2-methylpropanoyl}amino)-8-azabicyclo[3.2.1]oct-8-yl]methyl}pyridine-3-carboxamide;

2-{[4-chloro-2-(methylsulfonyl)phenyl]oxy}-2-methyl-N-{8-[5-(methylsulfonyl)pyridin-2yl]-8-azabicyclo[3.2.1]oct-3-endo-yl}propanamide;

2-{[5-chloro-3-(trifluoromethyl)pyridin-2-yl]oxy}-2-methyl-N-{8-[4-(methylsulfonyl)phenyl]-8-azabicyclo[3.2.1]oct-3-endo-yl}propanamide;

6-{3-endo-[(2-methyl-2-{[2-(methylsulfonyl)phenyl]oxy}propanoyl)amino]-8-azabicyclo[3.2.1]oct-8-yl}pyridine-3-carboxamide;

3-{[3-endo-({2-[(2,4-dichlorophenyl)oxy]-2-methylpropanoyl}amino)-8-azabicyclo[3.2.1]oct-8-yl]carbonyl}benzamide;

2-[(2,4-dichlorophenyl)thio]-2-methyl-N-{8-[5-(methylsulfonyl)pyridin-2-yl]-8-azabicyclo[3.2.1]oct-3-endo-yl}propanamide;

2-[(3,4-dichlorophenyl)oxy]-2-methyl-N-(8-{4-[(methylsulfonyl)amino]phenyl}-8-azabicyclo[3.2.1]oct-3-endo-yl)propanamide;

2-[(2-chloro-4-fluorophenyl)oxy]-2-methyl-N-(8-{5-[3-(trifluoromethyl)-1H-1,2,4-triazol-5-yl]pyridin-2-yl}-8-azabicyclo[3.2.1]oct-3-endo-yl)propanamide;

6-{3-endo-[(2-{[4-chloro-2-(1-methylethyl)phenyl]oxy}-2-methylpropanoyl)amino]-8-azabicyclo[3.2.1]oct-8-yl}pyridine-3-carboxamide;

1-(3-chloro-4-fluorophenyl)-N-{8-[5-(methylsulfonyl)pyridin-2-yl]-8-azabicyclo[3.2.1]oct-3-endo-yl}cyclopropanecarboxamide;

2-{[4-chloro-2-(trifluoromethyl)phenyl]oxy}-2-methyl-N-(8-{5-[(methylsulfonyl)amino]pyridin-2-yl}-8-azabicyclo[3.2.1]oct-3-endo-yl)propanamide;

6-{3-endo-[(2-{[4-chloro-2-(methylsulfonyl)phenyl]oxy}-2-methylpropanoyl)amino]-8-azabicyclo[3.2.1]oct-8-yl}pyridine-3-carboxamide;

2-{[2-fluoro-5-(trifluoromethyl)phenyl]oxy}-2-methyl-N-{8-[5-(methylsulfonyl)pyridin-2yl]-8-azabicyclo[3]oct-3-endo-yl}propanainide, 6-(3-endo-{[2-(2-bromo-4-chlorophenoxy)-2-methylpropanoyl]amino}-8-azabicyclo[3.2.1]oct-8-yl)-N-(2,2,2-trifluoroethyl)pyridine-3-carboxamide;

6-(3-endo-{[2-methyl-2-(naphthalen-2-yloxy)propanoyl]amino}-8-azabicyclo[3.2.1]oct-8-yl)-N-(2,2,2-trifluoroethyl)pyridine-3-carboxamide;

6-(3-endo-{[2-(isoquinolin-1-yloxy)-2-methylpropanoyl]amino}-8-azabicyclo[3.2.1]oct-8-yl)pyridine-3-carboxamide;

6-(3-endo-{[2-(2,4-dichlorophenoxy)-2-methylpropanoyl]amino}-8-azabicyclo[3.2.1]oct-8-yl)-N-[2-(pyrrolidin-1-yl)ethyl]pyridine-3-carboxamide;

6-(3-endo-{[2-(2,4-dichlorophenoxy)-2-methylpropanoyl]amino}-8-azabicyclo[3.2.1]oct-8-yl)-N-[3-(1h-imidazol-1-yl)propyl]pyridine-3-carboxamide;

6-(3-endo-{[2-(2,4-dichlorophenoxy)-2-methylpropanoyl]amino}-8-azabicyclo[3.2.1]oct-8-yl)-N-(pyridin-4-ylmethyl)pyridine-3-carboxamide;

6-[3-endo-({2-[4-chloro-2-(trifluoromethyl)phenoxy]-2-methylpropanoyl}amino)-8-azabicyclo[3.2.1]oct-8-yl]-N-(2,2-difluoroethyl)pyridine-3-carboxamide;

6-[3-endo-({2-[(4-chlorobiphenyl-3-yl)oxy]-2-methylpropanoyl}amino)-8-azabicyclo[3.2.1]oct-8-yl]pyridine-3-carboxamide;

6-[3-endo-({2-[4-chloro-2-(trifluoromethyl)phenoxy]-2-methylpropanoyl}amino)-8-azabicyclo[3.2.1]oct-8-yl]-N-(2,2-difluorocyclopropyl)pyridine-3-carboxamide;

6-[3-endo-({2-[(4-chloro-4'-fluorobiphenyl-3-yl)oxy]-2-methylpropanoyl}amino)-8-azabicyclo[3.2.1]oct-8-yl]pyridine-3-carboxamide;

6-[3-endo-({2-methyl-2-[2-(trifluoromethoxy)phenoxy]propanoyl}amino)-8-azabicyclo[3.2.1]oct-8-yl]-N-(2,2,2-trifluoroethyl)pyridine-3-carboxamide;

6-[3-endo-({2-[(1-chloronaphthalen-2-yl)oxy]-2-methylpropanoyl}amino)-8-azabicyclo[3.2.1]oct-8-yl]-N-(2,2,2-trifluoroethyl)pyridine-3-carboxamide;

6-(3-endo-{[2-(2-chloro-4-fluorophenoxy)-2-methylpropanoyl]amino}-8-azabicyclo[3.2.1]oct-8-yl)-N-(2,2-difluorocyclopropyl)pyridine-3-carboxamide;

6-(3-endo-{[2-(2,4-dichlorophenoxy)-2-methylpropanoyl]amino}-8-azabicyclo[3.2.1]oct-8-yl)-N-[2-methyl-1-(pyrrolidin-1-yl)propan-2-yl]pyridine-3-carboxamide;

6-[3-endo-({2-[4-chloro-2-(dimethylsulfamoyl)phenoxy]-2-methylpropanoyl}amino)-8-azabicyclo[3.2.1]oct-8-yl]-n-(2,2,2-trifluoroethyl)pylidine-3-carboxamide;

6-[3-endo-({2-[4-chloro-2-(2-methoxyethoxy)phenoxy]-2-methylpropanoyl}amino)-8-azabicyclo[3.2.1]oct-8-yl]-N-(2,2,2-trifluoroethyl)pyridine-3-carboxamide;

6-[3-endo-({2-[4-chloro-2-(propan-2-yl)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(isoquinolin-1-yloxy)-2-methylpropanoyl]amino}-8-azabicyclo[3.2.1]oct-8-y1)-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-(2,2-difluoroethyl)pyridine-3-carboxamide;

6-[3-endo-({2-[2-chloro-4-(hydroxymethyl)phenoxy]-2-methylpropanoyl}amino)-8-azabicyclo[3.2.1]oct-8-yl]-N-(2,2,2-trifluoroethyl)pyridine-3-carboxamide;

6-[3-endo-({2-[4-chloro-2-(methylsulfonyl)phenoxy]-2-methylpropanoyl}amino)-8-azabicyclo[3.2.1]oct-8-yl]-N-(2,2-difluorocyclopropyl)pyridine-3-carboxamide;

6-(3-endo-{[2-(4-chloro-2-cyclopentylphenoxy)-2-methylpropanoyl]amino}-8-azabicyclo[3.2.1]oct-8-yl)-N-(2,2,2-trifluoroethyl)pyridine-3-carboxamide;

6-[3-endo-({2-[4-chloro-2-(morpholin-4-yl)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(2-carbamoyl-4-chlorophenoxy)-2-methylpropanoyl]amino}-8-azabicyclo[3.2.1]oct-8-yl)-N-(2,2,2-trifluoroethyl)pyridine-3-carboxamide;

6-[3-endo-({2-[2,4-dichiloro-5-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-[2-(morpholin-4-yl)ethyl]pyridine-3-carboxamide;

6-[3-endo-({2-[4-chloro-2-(trifluoromethoxy)phenoxy]-2-methylpropanoyl}amino)-8-azabicyclo[3.2.1]oct-8-yl]-N-(2,2,2-trifluoroethyl)pyridine-3-carboxamide;

6-[3-endo-({2-[4-chloro-2-(difluoromethyl)phenoxy]-2-methylpropanoyl}amino)-8-azabicyclo[3.2.1]oct-8-yl]-N-(2,2,2-trifluoroethyl)pyridine-3-carboxamide;

2-[4-chloro-2-(difluoromethyl)phenoxy]-2-methyl-N-{8-[5-(methylsulfonyl)pyridin-2-yl]-8-azabicyclo[3.2.1]oct-3-endo-yl}propanamide;

6-(3-endo-{[2-(1h-indol-4-yloxy)-2-methylpropanoyl]amino}-8-azabicyclo[3.2.1]oct-8-yl)-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-(2-hydroxyethyl)pyridine-3-carboxamide;

6-[3-endo-({2-[4-chloro-2-(methylsulfonyl)phenoxy]-2-methylpropanoyl}amino)-8-azabicyclo[3.2.1]oct-8-yl]-N-(propan-2-yl)pyridine-3-carboxamide;

N-(2,2-difluorocyclopropyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide;

6-[3-endo-({2-[4-chloro-2-(trifluoromethyl)phenoxy]-2-methylpropanoyl}amino)-8-azabicyclo[3.2.1]oct-8-yl]-N-(propan-2-yl)pyridine-3-carboxamide;

6-(3-endo-{[2-(2-chloro-4-fluorophenoxy)-2-methylpropanoyl]amino}-8-azabicyclo[3.2.1]oct-8-yl)-N-(2,2-difluoroethyl)pyridine-3-carboxamide;

N-(2,2-difluoroethyl)-6-[3-endo-({2-[4-fluoro-2-(trifluoromethyl)phenoxy]-2-methylpropanoyl}amino)-8-azabicyclo[3.2.1]oct-8-yl]pyridine-3-carboxamide;

6-(3-endo-{[2-(2,4-dichlorophenoxy)-2-methylpropanoyl]amino}-8-azabicyclo[3.2.1]oct-8-yl)-N-[(2R)-1,1,1-trifluoropropan-2-yl]pyridine-3-carboxamide;

6-(3-endo-{[2-(2,4-dichlorophenoxy)-2-methylpropanoyl]amino}-8-azabicyclo[3.2.1]oct-8-yl)-N-[(2S)-1,1,1-trifluoropropan-2-yl]-pyridine-3-carboxamide;

5-chloro-2-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)benzoicacid;

6-[3-endo-({2-[4-chloro-2-(hydroxymethyl)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-[2-(diethylamino)ethyl]pyridine-3-carboxamide;

6-(3-endo-{[2-(2,4-dichlorophenoxy)-2-methylpropanoyl]amino}-8-azabicyclo[3.2.1]oct-8-yl)-N-(tetrahydro-2h-pyran-4-yl)pyridine-3-carboxamide;

6-(3-endo-{[2-(2,4-dichlorophenoxy)-2-methylpropanoyl]amino}-8-azabicyclo[3.2.1]oct-8-yl)-N-(1,1-dioxidotetrahydro-2h-thiopyran-4-yl)pyridine-3-carboxamide;

6-(3-endo-{[2-(2,4-dichlorophenoxy)-2-methylpropanoyl]amino}-8-azabicyclo[3.2.1]oct-8-yl)-N-(tetrahydro-2H-thiopyran-4-yl)pyridine-3-carboxamide;

6-[3-endo-({2-[2,4-dichloro-5-(2-methoxyethoxy)phenoxy]-2-methylpropanoyl}amino)-8-azabicyclo[3.2.1]oct-8-yl]-N-(2,2,2-trifluoroethyl)pyridine-3-carboxamide;

6-[3-endo-({2[4-chloro-2-(2-hydroxyethyl)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-[1-(hydroxymethyl)cyclopropyl]pyridine-3-carboxamide;

6-(3-endo-{[2-(1H-indazol-4-yloxy)-2-methylpropanoyl]amino}-8-azabicyclo[3.2.1]oct-8-yl)-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-(isoxazol-3-yl)pyridine-3-carboxamide;

6-{3-endo-[(2-{4-chloro-2-[2-(1H-imidazol-1-yl)ethoxy]phenoxy}-2-methylpropanoyl)amino]-8-azabicyclo[3.2.1]oct-8-yl}-N-(2,2,2-trifluoroethyl)pyridine-3-carboxamide;

6-(3-endo-{[2-(4-chloro-2-sulfamoylphenoxy)-2-methylpropanoyl]amino}-8-azabicyclo[3.2.1]oct-8-yl)-N-(2,2,2-trifluoroethyl)pyridine-3-carboxamide;

6-[3-endo-({2-[4-chloro-2-(2-hydroxyethoxy)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(1H-indol-7-yloxy)-2-methylpropanoyl]amino}-8-azabicyclo[3.2.1]oct-8-yl)-N-(2,2,2-trifluoroethyl)pyridine-3-carboxamide;

6-[3-endo-({1-[2-chloro-4-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide;

6-[3-endo-({2-[2,4-dichloro-5-(2-hydroxyethoxy)phenoxy]-2-methylpropanoyl}amino)-8-azabicyclo[3.2.1]oct-8-yl]-N-(2,2-difluorocyclopropyl)pyridine-3-carboxamide;

6-[3-endo-({2-[4-chloro-2-(difluoromethyl)phenoxy]-2-methylpropanoyl}amino)-8-azabicyclo[3.2.1]oct-8-yl]-N-(2,2-difluorocyclopropyl)pyridine-3-carboxamide;

6-[3-endo-({2-[4-chloro-2-(trifluoromethoxy)phenoxy]-2-methylpropanoyl}amino)-8-azabicyclo[3.2.1]oct-8-yl]-N-(2,2-difluorocyclopropyl)pyridine-3-carboxamide;

6-(3-endo-{[2-(2,4-dichlorophenoxy)-2-methylpropanoyl]amino}-8-azabicyclo[3.2.1]oct-8-yl)-N-(1-hydroxy-2-methylpropan-2-yl)pyridine-3-carboxamide;

6-(3-endo-{[2-(2,4-dichlorophenoxy)-2-methylpropanoyl]amino}-8-azabicyclo[3.2.1]oct-8-yl)-n-(2-hydroxy-2-methylpropyl)pyridine-3-carboxamide;

6-(3-endo-{[2-(2,4-dichlorophenoxy)-2-methylpropanoyl]amino}-8-azabicyclo[3.2.1]oct-8-yl)-N-[(2S)-1-hydroxypropan-2-yl]pyridine-3-carboxamide;

6-(3-endo-{[2-(2,4-dichlorophenoxy)-2-methylpropanoyl]amino}-8-azabicyclo[3.2.1]oct-8-yl)-N-[(2R)-1-hydroxypropan-2-yl]pyridine-3-carboxamide;

6-(3-endo-(2-(3,5-dichloropyridin-2-yloxy)-2-methylpropanamido)-8-azabicyclo[3.2.1]octan-8-yl)-N-(2,2-difluorocyclopropyl)nicotinamide;

6-(3-endo-(2-(3,5-dichloropyridin-2-yloxy)-2-methylpropanamido)-8-azabicyclo[3.2.1]octan-8-yl)-N-isopropylnicotinamide;

6-(3-endo-(2-(4-chloro-2-(trifluoromethoxy)phenoxy)-2-methylpropanamido)-8-azabicyclo[3.2.1]octan-8-yl)-N-(2,2-difluoroethyl)nicotinamide;

6-(3-endo-(2-(2,4-dichloro-5-(2-hydroxyethoxy)phenoxy)-2-methylpropanamido)-8-azabicyclo[3.2.1]octan-8-yl)-N-(2,2-difluoroethyl)nicotinamide;

6-(3-endo-(2-(4-chloro-2-(difluoromethyl)phenoxy)-2-methylpropanamido)-8-azabicyclo[3.2.1]octan-8-yl)-N-(1-(hydroxymethyl)cyclopropyl)nicotinamide;

6-(3-endo-(2-(4-chloro-2-(difluoromethyl)phenoxy)-2-methylpropanamido)-8-azabicyclo[3.2.1]octan-8-yl)-N-(isoxazol-3-yl)nicotinamide;

6-(3-endo-(2-(2,4-dichloro-5-(2-(pyrrolidin-1-yl)ethoxy)phenoxy)-2-methylpropanamido)-8-azabicyclo[3.2.1]octan-8-yl)-N-(2,2,2-trifluoroethyl)nicotinamide;

6-(3-endo-(2-(2,4-dichloro-5-(2-(4-methylpiperazin-1-yl)ethoxy)phenoxy)-2-methylpropanamido)-8-azabicyclo[3.2.1]octan-8-yl)-N-(2,2,2-tiifluoroethyl)nicotinamide;

6-(3-endo-(2-(2,4-dichloro-5-(2-morpholinoethoxy)phenoxy)-2-methylpropanamido)-8-azabicyclo[3.2.1]octan-8-yl)-N-(2,2,2-trifluoroethypnicotinamide;

6-(3-endo-(2-(3,5-dichloropyridin-2-yloxy)-2-methylpropanamido)-8-azabicyclo[3.2.1]octan-8-yl)-N-(2,2-difluoroethyl)nicotinamide;

6-(3-endo-(2-(5-chloro-3-fluoropyridin-2-yloxy)-2-methylpropanamido)-8-azabicyclo[3.2.1]octan-8-yl)-N-(2,2-difluoroethyl)nicotinamide;

6-(3-endo-(2-(4-chloro-2-(trifluoromethoxy)phenoxy)-2-methylpropanamido)-8-azabicyclo[3.2.1]octan-8-yl)-N-((S)-1,1,1-trifluoropropan-2-yl)nicotinamide;

6-(3-endo-(2-(4-chloro-2-(difluoromethyl)phenoxy)-2-methylpropanamido)-8-azabicyclo[3.2.1]octan-8-yl)-N-((R)-1,1,1-trifluoropropan-2-yl)nicotinamide;

6-(3-endo-(2-(4-chloro-2-(trifluoromethyl)phenoxy)-2-methylpropanamido)-8-azabicyclo[3.2.1]octan-8-yl)-N-((R)-1,1,1-trifluoropropan-2-yl)nicotinamide;

2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)acetic acid;

2-(2,4-dichloro-5-(2-methyl-1-oxo-1-(8-(5-(2,2,2-trifluoroethylcarbamoyl)pyridin-2-yl)-8-azabicyclo[3.2.1]octan-3-endo-ylamino)propan-2-yloxy)phenoxy)-2-methylpropanoic acid;

6-[3-endo-({2-[4-chloro-2-(trifluoromethoxy)phenoxy]-2-methylpropanoyl}amino)-8-azabicyclo[3.2.1]oct-8-yl]-N-[(2R)-1,1,1-trifluoropropan-2-yl]pyridine-3-carboxamide;

6-[3-endo-({2-[4-chloro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide;

6-[3-endo-({2-[(3,5-dichloropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide;

6-[3-endo-({2-[2-(difluoromethyl)-4-fluorophenoxy]-2-methylpropanoyl}amino)-8-azabicyclo[3.2.1]oct-8-yl]-N-[(2S)-1,1,1-trifluoropropan-2-yl]pyridine-3-carboxamide;

6-[3-endo-({2-[(5-chloro-3-fluoropyridin-2-yl)oxy]-2-methylpropanoyl}amino)-8-azabicyclo[3.2.1]oct-8-yl]-N-[(2S)-1,1,1-trifluoropropan-2-yl]pyridine-3-carboxamide;

6-(3-endo-{[2-(4-chlorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-(3-endo-{[2(2,4-dichlorophenoxy)-2-methylpropanoyl]amino}-8-azabicyclo[3.2.1]oct-8-yl)-N-(3,3,3-trifluoro-2-hydroxypropyl)pyridine-3-carboxamide;

6-[3-endo-({2-[4-chloro-2-(methylsulfonyl)phenoxy]-2-methylpropanoyl}amino)-8-azabicyclo[3.2.1]oct-8-yl]-N-(2,2-difluoroethyl)pyridine-3-carboxamide;

6-[3-endo-({2-[4-fluoro-2-(trifluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide;

6-[3-endo-({2-[4-chloro-2-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide;

6-(3-endo-{[2-(2,4-dichloro-5-fluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-{3-endo-[(2-{5-[(1-amino-2-methyl-1-oxopropan-2-yl)oxy]-2,4-dichlorophenoxy}-2-methylpropanoyl)amino]-8-azabicyclo[3.2.1]oct-8-yl}-N-(2,2,2-trifluoroethyl)pyridine-3-carboxamide;

6-[3-endo-({2-[4-chloro-2-(uifluoromethoxy)phenoxy]-2-methylpropanoyl}amino)-8-azabicyclo[3.2.1]oct-8-yl)-N1-(hydroxymethyl)cyclopropyl]pyridine-3-calboxamide;

6-[3-endo-({2-[2,4-dichloro-5-(hydroxymethyl)phenoxy]-2-methylpropanoyl}amino)-8-azabicyclo[3.2.1]oct-8-yl]-N-(2,2-difluoroethyppyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide;

6-(3-endo-{[2-(2-chloro-4,5-difluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-(3-endo-{[2-(2,4-difluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-[3-endo-({2-[4-chloro-2-(methylsulfonyl)phenoxy]-2-methylpropanoyl}amino)-8-azabicyclo[3.2.1]oct-8-yl]-N-[(2S)-1,1,1-trifluoropropan-2-yl]pyridine-3-carboxamide;

6-[3-endo-({2-[4-chloro-2-(difluoromethyl)phenoxy]-2-methylpropanoyl}amino)-8-azabicyclo[3.2.1]oct-8-yl]-N-(2,2-difluoroethyl)pyridine-3-carboxamide;

6-(3-endo-{[2-(2-chloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-(3-endo-{[2-(4-chloro-2-fluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-(3-endo-{[2-(2,4-dichloro-5-fluorophenoxy)-2-methylpropanoyl]amino}-8-azabicyclo[3.2.1]oct-8-yl)-N-(2,2-difluoroethyl)pyridine-3-carboxamide;

6-(3-endo-{[2-(2,3-dichloro-4-fluorophenoxy)-2-methylpropanoyl]amino}-8-azabicyclo[3.2.1]oct-8-yl)-N-[(2S)-1,1,1-trifluoropropan-2-yl]pyridine-3-carboxamide;

6-[3-endo-({2-[4-chloro-2-(trifluoromethoxy)phenoxy]-2-methylpropanoyl}amino)-8-azabicyclo[3.2.1]oct-8-yl]-N-(2-hydroxy-2-methylpropyl)pyridine-3-carboxamide;

6-{3-endo-[2-{[3-(difluoromethyl)-5-fluoropyridin-2-yl]oxy}-2-methylpropanoyl)amino]-8-azabicyclo[3.2.1]oct-8-yl}-N-[(2S)-1,1,1-trifluoropropan-2-yl]pyridine-3-carboxamide;

N-(2,2-difluoroethyl)-6-{3-endo-[(2-{[3-(difluoromethyl)-5-fluoropyridin-2-yl]oxy}-2-methylpropanoyl)amino]-8-azabicyclo[3.2.1]oct-8-yl}pyridine-3-carboxamide;

6-(3-endo-{[2-(2,3-dichloro-4-fluorophenoxy)-2-methylpropanoyl]amino}-8-azabicyclo[3.2.1]oct-8-yl)-N-(2,2-difluoroethyl)pyridine-3-carboxamide;

6-(3-endo-{[2-(2-chloro-4,5-difluorophenoxy)-2-methylpropanoyl]amino}-8-azabicyclo[3.2.1]oct-8-yl)-N-(2,2-difluoroethyl)pyridine-3-carboxamide;

N-(2,2-difluoroethyl)-6-(3-endo-{[2-(2,4-difluorophenoxy)-2-methylpropanoyl]amino}-8-azabicyclo[3.2.1]oct-8-yl)pyridine-3-carboxamide;

[2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]acetic acid;

2-[2,4-dichloro-5-({2-methyl-1-oxo-1-[(8-{5-[(2,2,2-trifluoroethyl)carbamoyl]pyridin-2-yl}-8-azabicyclo[3.2.1]oct-3-endo-yl)amino]propan-2-yl}oxy)phenyl]-2-methylpropanoic acid;

6-[3-endo-({2-[5-(1-amino-2-methyl-1-oxopropan-2-yl)-2,4-dichlorophenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(4-chloro-2-fluorophenoxy)-2-methylpropanoyl]amino}-8-azabicyclo[3.2.1]oct-8-yl)-N-(2,2-difluoroethyl)pyridine-3-carboxamide;

6-[3-endo-({2-[4-chloro-2-(trifluoromethoxy)phenoxy]-2-methylpropanoyl}amino)-8-azabicyclo[3.2.1]oct-8-yl]-N-(3,3,3-trifluoro-2-hydroxypropyl)pyridine-3-carboxamide;

6-[3-endo-({2-[4-chloro-2-(difluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide;

6-(3-endo-{[2-(2,4-dichloro-5-fluorophenoxy)-2-methylpropanoyl]amino}-8-azabicyclo[3.2.1]oct-8-yl)-N-[(2R)-1,1,1-trifluoropropan-2-yl]pyridine-3-carboxamide;

6-(3-endo-{[2-(2-chloro-4,5-difluorophenoxy)-2-methylpropanoylamino }-8-azabicyclo[3.2.1]oct-8-yl)-N-[(2R)-1,1,1-trifluoropropan-2-yl]pyridine-3-carboxamide;

6-(3-endo-{[2-(2-chloro-4-fluorophenoxy)-2-methylpropanoyl]amino}-8-azabicyclo[3.2.1]oct-8-yl)-N-[(2R)-1,1,1-trifluoropropan-2-yl]pyridine-3-carboxamide;

6-[3-endo-({2-[2-chloro-4-(difluoromethyl)phenoxy]-2-methylpropanoyl}amino)-8-azabicyclo[3.2.1]oct-8-yl]-N-[(2S)-1,1,1-trifluoropropan-2-yl]pyridine-3-carboxamide;

2-[4-chloro-2-(trifluoromethoxy)phenoxy]-n-(8-{5-[(3-hydroxypyrrolidin-1-yl)carbonyl]pyridin-2-yl}-8-azabicyclo[3.2.1]oct-3-endo-yl)-2-methylpropanamide;

2-[4-chloro-2-(trifluoromethoxy)phenoxy]-n-[8-(5-{[(2s)-2-(hydroxymethyl)pyrrolidin-1-yl]carbonyl}pyridin-2-yl)-8-azabicyclo[3.2.1]oct-3-endo-yl]-2-methylpropanamide;

6-(3-endo-{[2-(2,4-dichlorophenoxy)-2-methylpropanoyl]amino}-8-azabicyclo[3.2.1]oct-8-yl)-N-[(2S)-3,3,3-trifluoro-2-hydroxypropyl]pyridine-3-carboxamide;

6-(3-endo-{[2-(2-chloro-4-fluorophenoxy)-2-methylpropanoyl]amino}-8-azabicyclo[3.2.1]oct-8-yl)-N-(3,3,3-trifluoro-2-hydroxypropyl)pyridine-3-carboxamide;

6-[3-endo-({2-[4-chloro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide;

6-[3-endo-({2-[4-fluoro-2-(trifluoromethyl)phenoxy]-2-methylpropanoyl}amino)-8-azabicyclo[3.2.1]oct-8-yl]-N-(3,3,3-trifluoro-2-hydroxypropyl)pyridine-3-carboxamide;

[2,4-dichloro-5-({1-[(8-{5-[(2,2-difluoroethyl)carbamoyl]pyridin-2-yl}-8-azabicyclo[3.2.1]oct-3-endo-yl)amino]-2-methyl-1-oxopropan-2-yl}oxy)phenyl]acetic acid;

2-(2,4-dichlorophenoxy)-n-[8-(5-{[(3r)-3-hydroxypyrrolidin-1-yl]carbonyl}pyridin-2-yl)-8-azabicyclo[3.2.1]oct-3-endo-yl]-2-methylpropanamide;

2-(2,4-dichlorophenoxy)-N-[8-(5-{[(3s)-3-hydroxypyrrolidin-1-yl]carbonyl}pyridin-2-yl)-8-azabicyclo[3.2.1]oct-3-endo-yl]-2-methylpropanamide;

6-(3-endo-{[2-(2,4-dichlorophenoxy)-2-methylpropanoyl]amino}-8-azabicyclo[3.2.1]oct-8-yl)-N-(1,1,1-trifluoro-3-hydroxypropan-2-yl)pyridine-3-carboxamide;

6-[3-endo-({2-[2,5-dichloro-4-(hydroxymethyl)phenoxy]-2-methylpropanoyl}amino)-8-azabicyclo[3.2.1]oct-8-yl]-N-(2,2-difluoroethyl)pyridine-3-carboxamide;

6-[3-endo-({2-[4-chloro-2-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide;

6-(3-endo-(2-(4-chloro-2-fluoro-5-(2-hydroxypropan-2-yl)phenoxy)-2-methylpropanamido)-8-azabicyclo[3.2.1]octan-8-yl)-N-(2,2-difluoroethyl)nicotinamide;

N-(2,2-difluoroethyl)-6-(3-endo-(2-(4-fluoro-2-(2-hydroxypropan-2-yl)phenoxy)-2-methylpropanamido)-8-azabicyclo[3.2.1]octan-8-yl)nicotinamide;

N-(2,2-difluoroethyl)-6-[3-endo-({2-[2,4-difluoro-5-(2-hydroxypropan-2-yl)phenoxy]-2-methylpropanoyl}amino)-8-azabicyclo[3.2.1]oct-8-yl]pyridine-3-carboxamide;

6-[3-endo-({2-[4-chloro-2-(difluoromethoxy)phenoxy]-2-methylpropanoyl}amino)-8-azabicyclo[3.2.1]oct-8-yl]-N-(2,2-difluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-[3,3,3-trifluoro-2-(morpholin-4-yl)propyl]pyridine-3-carboxamide;

6-[3-endo-({2-[2-chloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide;

6-[3-endo-({2-[2-chloro-4-fluoro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]pyridine-3-carboxylic acid;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2,2-trifluoroethyl)pyridine-3-carboxamide;

6-(3-endo-{[2-(2,4-dichlorophenoxy)-2-methylpropanoyl]amino}-8-azabicyclo[3.2.1]oct-8-yl)-N-(3,3,3-trifluoro-2-oxopropyl)pyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(propan-2-yl)pyridine-3-carboxamide;

6-[3-endo-({2-[2,4-dichloro-5-(prop-1-en-2-yl)phenoxy]-2-methylpropanoyl}amino)-8-azabicyclo[3.2.1]oct-8-yl]-N-(2,2-difluoroethyl)pyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide 1-oxide;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(3,3,3-trifluoro-2-hydroxypropyl)pyridine-3-carboxamide;

6-[3-endo-({2-[2,4-dichloro-5-(2-hydroxypropan-2-yl)phenoxy]-2-methylpropanoyl}amino)-8-azabicyclo[3.2.1]oct-8-yl]-N-(2-hydroxy-2-methylpropyl)pyridine-3-carboxamide;

N-(2,2-difluoroethyl)-6-[3-endo-({2-[2-fluoro-4-(2-hydroxypropan-2-yl)phenoxy]-2-methylpropanoyl}amino)-8-azabicyclo[3.2.1]oct-8-yl]pyridine-3-carboxamide;

6-[3-endo-({2-[2-chloro-5-fluoro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide and 6-[3-endo-({2-[2,5-dichloro-4-(2-hydroxypropan-2-yl)phenoxy]-2-methylpropanoyl}amino)-8-azabicyclo[3.2.1]oct-8-yl]-N-(2,2-difluoroethyl)pyridine-3-carboxamide;

or a pharmaceutically acceptable salt of any of the above compounds.

40. A pharmaceutical composition, comprising the compound according to claim 1, or pharmaceutically acceptable salt thereof, and a pharmaceutically acceptable carrier, excipient, or diluent.

* * * * *